United States Patent
Burns et al.

(10) Patent No.: US 10,370,697 B2
(45) Date of Patent: Aug. 6, 2019

(54) PROPEPTIDE-LUCIFERASE FUSION PROTEINS AND METHODS OF USE THEREOF

(71) Applicants: THE BROAD INSTITUTE, INC., Cambridge, MA (US); The General Hospital Corporation, Boston, MA (US); INSTITUTO CARLOS SLIM DE LA SALUD, A.C., Granada, Mexico City (MX)

(72) Inventors: Sean Burns, Hingham, MA (US); David Altshuler, Brookline, MA (US); Amedeo Vetere, Cambridge, MA (US)

(73) Assignees: THE BROAD INSTITUE, INC., Cambridge, MA (US); THE GENERAL HOSPITAL CORPORATION, Boston, MA (US); INSTITUTO CARLOS SLIM DE LA SALUD, A.C., Mexico City (MX)

( * ) Notice: Subject to any disclaimer, the term of this patent is extended or adjusted under 35 U.S.C. 154(b) by 0 days.

(21) Appl. No.: 15/600,475

(22) Filed: May 19, 2017

(65) Prior Publication Data
US 2017/0260565 A1    Sep. 14, 2017

Related U.S. Application Data

(62) Division of application No. 14/356,864, filed as application No. PCT/US2012/063982 on Nov. 7, 2012, now Pat. No. 9,657,329.

(60) Provisional application No. 61/576,530, filed on Dec. 16, 2011, provisional application No. 61/556,619, filed on Nov. 7, 2011.

(51) Int. Cl.
| | |
|---|---|
| *C12N 9/02* | (2006.01) |
| *C12Q 1/66* | (2006.01) |
| *C07K 14/62* | (2006.01) |
| *G01N 33/50* | (2006.01) |
| *G01N 33/58* | (2006.01) |
| *C07K 14/575* | (2006.01) |
| *C07K 14/605* | (2006.01) |
| *C12Q 1/6897* | (2018.01) |

(52) U.S. Cl.
CPC .............. *C12Q 1/66* (2013.01); *C07K 14/575* (2013.01); *C07K 14/605* (2013.01); *C07K 14/62* (2013.01); *C12N 9/0069* (2013.01); *C12Q 1/6897* (2013.01); *G01N 33/5008* (2013.01); *G01N 33/5035* (2013.01); *G01N 33/5073* (2013.01); *G01N 33/581* (2013.01); *C07K 2319/00* (2013.01); *C07K 2319/50* (2013.01); *C07K 2319/60* (2013.01)

(58) Field of Classification Search
None
See application file for complete search history.

(56) References Cited

U.S. PATENT DOCUMENTS

| | | | |
|---|---|---|---|
| 9,181,318 B2 | 11/2015 | Satoshi | |
| 2011/0159529 A1 | 6/2011 | Inouye et al. | |
| 2013/0243741 A1 | 9/2013 | Bossmann | |

FOREIGN PATENT DOCUMENTS

GB    2 468 757 A    9/2010

OTHER PUBLICATIONS

Pouli et al., "Insulin targeting to the regulated secretory pathway after fusion with green fluorescent protein and firefly luciferase", Biochemical Journal, 331(2):669-675 (1998).
Suzuki, T. et al., "Video rate bioluminescence imaging of secretory proteins in living cells: Localization, secretory frequency and quantification", Analytical Biochemistry, Academic Press Inc., NY, 415(2):182-189 (2011).
Watkins, S. et al., "Imaging Secretory Vesicles by Fluorescent Protein Insertion in Propeptide Rather Than Mature Secreted Peptide", Traffic, 3(7):461-471 (2002).
Liu et al., Proinsulin maturation, Misfolding, and Proteotoxicity, PNAS, Oct. 2, 2007, vol. 104, No. 40, 15841-15846.
Promega, pTARGET Mammalian Expression Vector System, published and revised in Feb. 2006, Promega Corporation.
Promega, Dual-Luciferase® Reporter 1000 Assay System, published and revised in Mar. 2009, Promega Corporation.

*Primary Examiner* — Nancy J Leith
(74) *Attorney, Agent, or Firm* — Burns & Levinson LLP; Christopher R. Cowles, J.D.

(57) ABSTRACT

The present invention provides nucleic acid constructs that encode fusion peptides comprising a bioluminescent protein and a precursor of a secreted peptide or protein expressed at the cell surface and high throughput screening assays using same.

27 Claims, 14 Drawing Sheets
Specification includes a Sequence Listing.

PROPEPTIDE-LUCIFERASE FUSION PROTEINS AND METHODS OF USE THEREOF

RELATED APPLICATION

This application is a Divisional of application Ser. No. 14/356,864 filed May 7, 2014, which application is a U.S. National Phase application of International application No. PCT/US2012/063982 filed on Nov. 7, 2012, which claims the benefit of, priority to U.S. provisional application No. 61/556,619 filed on Nov. 7, 2011 and U.S. provisional application No. 61/576,530 filed on Dec. 16, 2011, the contents of each of which are incorporated herein by references in its entireties.

INCORPORATION-BY-REFERENCE OF SEQUENCE LISTING

The contents of the text file named "BRDI-016_N01US_ST25.txt", which was created on Oct. 3, 2014 and is 717 KB in size, are hereby incorporated by reference in their entireties.

FIELD OF THE INVENTION

The present invention provides methods and compositions relating to detecting peptide secretion or cell surface expression of a peptide by a cell.

BACKGROUND OF THE INVENTION

Peptide hormones, cytokines and neuropeptides are signaling molecules that play key roles in normal physiology and disease states. Traditional immunoassays for these secreted proteins, such as the enzyme-linked immunosorbant assay (ELISA) and radioimmunoassay, have enabled limited investigation into the pathways regulating their secretion, yet these assays are too expensive and time-consuming to be useful for large-scale chemical and genetic screening. Thus, a need exists for a high-throughput method of tracking peptide secretion or cell surface expression of a peptide.

A particular secreted peptide of interest is insulin. Failure to maintain adequate insulin secretion is central to the pathogenesis of both type 1 and type 2 diabetes. Determining the genetic pathways that regulate insulin secretion and finding small molecule probes of these pathways would greatly advance our understanding of the beta cell and bring us closer to a cure for both forms of diabetes. However, high throughput screens of insulin secretion using genetic (e.g., RNAi) or chemical perturbations are currently impracticable due to the lack of an amenable assay for measuring secreted insulin. Insulin ELISA kits and radioimmunoassays are not well suited to this application due to their expense, complicated handling requirements and restriction to 96-well format. Thus, a need exists for a high-throughput method of tracking peptide secretion, in particular, insulin hormone secretion.

SUMMARY OF THE INVENTION

The invention is based upon the discovery of methods and compositions relating to detecting peptide secretion from a cell or peptide expression at the cell surface, including but not limited to peptide hormones, cytokines and neuropeptides.

In one aspect the invention provides a nucleic acid construct encoding a fusion protein comprising a peptide hormone or peptide precursor linked to a bioluminescent protein, wherein the bioluminescent protein is flanked by two cleavage sites such that wherein the fusion protein is expressed by a cell the bioluminescent protein is cleaved from the peptide precursor and the bioluminescent protein is secreted simultaneously with the secretion or cell surface expression of the mature form of the propeptide. The propeptide is a prohormone, a preprohormone, a cytokine precursor or a neuropeptide precursor.

Exemplary propeptides that can be used in the present invention include, but are not limited to, the precursor proteins of amylin, insulin, glucagon (includes GRPP, glucagon, GLP-1, GLP-2), peptide YY, neuropeptide Y, pancreatic polypeptide, somatostatin, growth hormone-releasing hormone (GHRH), proopiomelanocortin (POMC, including ACTH, MSH), oxytocin, vasopressin-neurophysin-2, gonadotropin-releasing hormone (GnRH), thyroid-stimulating hormone, beta subunit (TSHB), cortisol-releasing factor (CRF), atrial natriuretic peptide (ANP), brain natriuretic peptide (BNP), renin, galanin, orexin, ghrelin-obestatin, cholecystokinin, gastrin, protachykinin-1 (substance P, neurokinin A, neuropeptide K, neuropeptide gamma), proenkephalin-A, proenkephalin-B, insulin-like growth hormone 1 (IGF-1), insulin-like growth hormone 2 (IGF-2), parathyroid hormone (PTH), parathyroid hormone-related protein (PTHrP), osteocalcin, urocortin-3, urocortin-2, urocortin-1, fibroblast growth factor 23 (FGF23), interleukin-1-beta (IL1B), tumor necrosis factor (TNF), interferon-gamma (IFNG), sortilin (SORT1), neuropeptide W, cocaine and amphetamine-related transcript (CART), transforming growth factor-beta-1 (TGFB1), transforming growth factor-beta-2 (TGFB2), transforming growth factor-beta-3 (TGFB3), platelet-derived growth factor-alpha (PDGFA), brain-derived neurotrophic factor (BDNF), nerve growth factor (NGF), albumin, calcitonin, cortistatin (CORT), ADAM-10, -11, -12, -15, -17, -22, -23, -28, -33, ADAMTS-1, -3-10, -12 through -20, BMP-1 through -6, -10, MMP-11, -14 through -17, -21, -23, -24, -25, -28, beta-defensins and mesothelin.

Preferably, the peptide precursor is encoded by any one of the nucleotide sequences of SEQ ID NOs: 5-100. Optionally the nucleic acid construct contains a promoter.

In some embodiments the peptide precursor is preproinsulin and the bioluminescent protein is within the C-peptide component of preproinsulin. In other embodiments, the peptide precursor is preproamylin and the N-terminal end of the bioluminescent protein is inserted between the regions encoding the signal peptide and the mature amylin hormone or between the mature amylin hormone and the C-terminus of the molecule. In another embodiment, the peptide precursor is preproglucagon and the bioluminescent protein is inserted between the regions encoding the GRPP and glucagon, glucagon and GLP-1, or GLP-1 and GLP-2. The nucleic acid construct further comprises an additional cleavage site at the N-terminal and C-terminal ends of the bioluminescent protein. Optionally, there is an additional cleavage site at the C-terminal end of the bioluminescent protein. Optionally, there are at least 3 additional nucleotides flanking at least one cleavage site to enhance cleavage.

Exemplary cleavage sites that can be used for the constructs of the present invention include, but are not limited to, aagagg (SEQ ID NO: 101); aagcgt (SEQ ID NO: 102); aagcgc (SEQ ID NO: 103); aaaaga (SEQ ID NO: 104); aagaggagg (SEQ ID NO: 105); aagaga (SEQ ID NO: 106); cgcaaa (SEQ ID NO: 107); cggcgg (SEQ ID NO: 108);

tatctg (SEQ ID NO: 109); aggcgg (SEQ ID NO: 110); cggagc (SEQ ID NO: 111); cggtct (SEQ ID NO: 112); cgaagc (SEQ ID NO: 113); aaacgg (SEQ ID NO: 114); aagagaggt (SEQ ID NO: 115); aaacgaggc (SEQ ID NO: 116); gggccgccgc (SEQ ID NO: 117); ccacgagct (SEQ ID NO: 118); ccccgagct (SEQ ID NO: 119); cgaaggcagct-gcgggct (SEQ ID NO: 120); cgtaggcagctgagggta (SEQ ID NO: 121); cgccgcagt (SEQ ID NO: 122); cgaaga (SEQ ID NO: 123); cggaga (SEQ ID NO: 124); agaagg (SEQ ID NO: 125); aaacgc (SEQ ID NO: 126); tccagcattcggagg (SEQ ID NO: 127); agcagtcggagg (SEQ ID NO: 128); gagagggac (SEQ ID NO: 129); cggcgc (SEQ ID NO: 130); aggcgc (SEQ ID NO: 131); cggggcaccaag (SEQ ID NO: 132); caccgc (SEQ ID NO: 133); acccgtgtc (SEQ ID NO: 134); tcgcgcatt (SEQ ID NO: 135): cgacgg (SEQ ID NO: 136); aagagaaga (SEQ ID NO: 137); and ggccgccgc (SEQ ID NO: 138).

The bioluminescent protein is luciferase, such as for example, *Gaussia* luciferase or *Cypridina* luciferase. In some embodiments, the bioluminescent protein is truncated, for example, the *Gaussia* or the *Cypridina* luciferase lacks a native signal sequence. The invention also includes a cell comprising a nucleic acid construct of the invention and a fusion protein encoded by the nucleic acid construct of the invention. The cell is capable of expressing the encoded fusion protein. The cell is, for example, a pancreatic cell, an immune cell, a neuron, a hepatocyte, a myocyte, a kidney cell, an adipocyte, an osteocyte or a cell line derived therefrom. The cell is for example, a peptide-secreting cell such as a beta cell, an alpha cell, an L-cell, a K-cell, a neuron or a cell line derived therefrom. The cell is for example, an immune cell such as a B cell, a T cell, a monocyte, a macrophage, a dendritic cell, a mast cell, a neutrophil or a cell line derived therefrom. Alternatively, the cell is an embryonic stem cell or an iPS cell. The invention also includes a cell comprising at least two nucleic acid constructs of the invention, wherein the cell is capable of expressing the encoded fusion proteins and wherein the bioluminescent proteins of the nucleic acid constructs are different. For example, the first nucleic acid construct comprises *Gaussia* luciferase and the second nucleic acid construct comprises *Cypridina* luciferase. Optionally, the cell also comprises a control nucleic acid construct encoding a control luciferase different from the luciferase of the fusion proteins to be used as an internal reference.

The invention further provides an assay for screening for compounds that modulate peptide secretion or cell surface expression of a peptide by a cell by contacting the cell culture comprising the cell of the invention with a test compound and determining bioluminescence in the cell culture. A difference in bioluminescence from the cell culture that has been contacted with the test compound compared to bioluminescence from a control cell culture indicates that the test compound modulates peptide secretion or expression at the cell surface.

The invention further provides an assay for screening for compounds that modulate peptide secretion or cell surface expression of the peptide bu a cell by contacting the cell culture comprising the cell of the invention with a test compound, separating the population of cells into single cells, and determining bioluminescence in the cell culture. A difference in bioluminescence from the cell culture that has been contacted with the test compound compared to bioluminescence from a control cell culture indicates that the test compound modulates peptide secretion or cell surface expression. The separation of the population of cells into single cells can be performed by, for example, a microfluidic device. In some embodiments, the test compound is a test nucleic acid and further comprising determining the identity of the test nucleic acid using single cell nucleic acid amplification methods.

The invention also provides a method of screening for compounds that differentiate embryonic stem cells or induced pluripotent stem (iPS) cells into mature cell types of interest, such as pancreatic beta cells, by contacting a cell culture comprising the cells of the invention with a test compound and determining bioluminescence in the cell culture. An increase in bioluminescence from the cell culture that has been contacted with the test compound compared to bioluminescence from a control cell culture indicates that the test compound induced differentiation of embryonic stem cells or iPS cells into the cell type of interest.

The invention also provides a method of screening for compounds that differentiate embryonic stem cells or iPS cells into glucose responsive beta cells by contacting a cell culture comprising the cells of the invention with a test compound and determining bioluminescence in the cell culture. An increase of bioluminescence from the cell culture that has been contacted with the test compound compared to bioluminescence from a control cell culture indicates that the test compound differentiates embryonic stem cells or iPS cells into glucose responsive beta cells.

The test compound is for example a nucleic acid or a small molecule. The nucleic acid is for example an RNAi or gene overexpression sequence.

The present invention also provides a nucleic acid expression vector comprising a nucleic acid sequence encoding a bioluminescent protein, wherein the bioluminescent protein lacks a native signal peptide; a nucleic acid sequence encoding two cleavage sites, wherein the cleavage sites flank the bioluminescent protein such that when the vector is expressed by a cell, the bioluminescent protein is cleaved from the remaining peptide; and at least one insertion site for insertion of a nucleic acid sequence encoding a propeptide such that the inserted nucleic acid sequence is in-frame with the bioluminescent protein. The insertion site is a restriction enzyme site, multiple cloning site containing multiple restriction enzyme sites, or a site recognized by a recombinase. Optionally, the nucleic acid expression vector comprises a promoter, wherein the promoter is operatively linked to the nucleic acid sequence encoding the bioluminescent protein. Optionally, the nucleic acid expression vector comprises a selective marker operatively linked to a second promoter. The selective marker can be an antibiotic resistance gene, drug resistance gene, toxin resistance gene or a cell surface marker.

Alternatively, a nucleic acid expression vector may comprise any nucleic acid construct described herein operatively linked to a promoter and a selective marker operatively linked to a second promoter.

The present invention further provides a kit. The kit includes any or at least one of the nucleic acid expression vectors described herein, at least one luciferase substrate and instructions for use. The luciferase substrate will be selected according to the nucleic acid expression vector of the kit, such that the luciferase of the expression vector will dictate the luciferase substrate included in the kit. The present invention further provides a kit that contains any one of the cells that express a propeptide-luciferase fusion protein as described herein. Any kit of the present invention further comprises a control nucleic acid construct that encodes a control luciferase or cells expressing the control luciferase for use as an internal control.

Unless otherwise defined, all technical and scientific terms used herein have the same meaning as commonly understood by one of ordinary skill in the art to which this invention pertains. Although methods and materials similar or equivalent to those described herein can be used in the practice of the present invention, suitable methods and materials are described below. All publications, patent applications, patents, and other references mentioned herein are expressly incorporated by reference in their entirety. In cases of conflict, the present specification, including definitions, will control. In addition, the materials, methods, and examples described herein are illustrative only and are not intended to be limiting.

Other features and advantages of the invention will be apparent from and encompassed by the following detailed description and claims.

DETAILED DESCRIPTION OF THE INVENTION

Figure 1A:
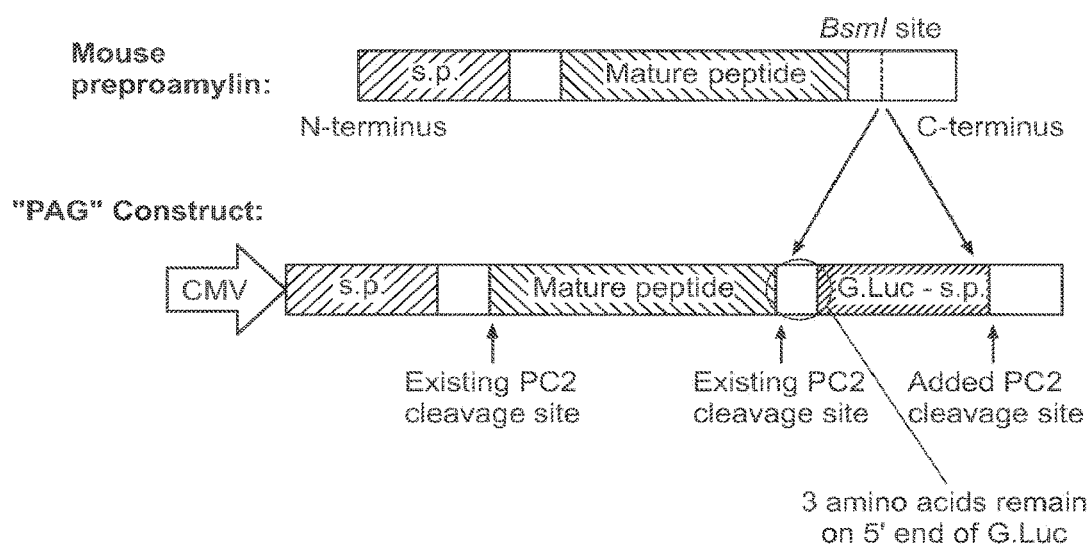
FIG. 1A-1B depicts the structure of the preproamylin-Gaussia luciferase (PAG) construct and its expression in MIN6 cells. (A) The luciferase was placed near the C-terminal end of the proamylin peptide, adjacent to an existing "prohormone convertase 2" (PC2) cleavage site. An additional PC2 cleavage site was inserted to the 3'-end of the luciferase sequence. s.p. stands for signal peptide. (B) Immunohistochemistry of MIN6 cells expressing pre-proamylin-luciferase reporter showing co-localization of luciferase and insulin.

The invention is based in part upon methods and compositions relating to detecting peptide secretion or cell surface expression of the peptide by a cell, including but not limited to that of peptide hormones, cytokines, neuropeptides and transmembrane proteins. Examples of such peptides include but are not limited to, insulin, amylin, glucagon, glucagon-like peptide-1 (GLP-1), glucagon-like peptide-2 (GLP-2), gastric inhibitory peptide (GIP), growth hormone (GH), proopiomelanocortin (POMC)-derived hormones, growth hormone releasing hormone (GHRH), parathyroid hormone (PTH), gonadotropin releasing hormone (GnRH), peptide YY, neuropeptide Y, protachykinin-1 (Substance P, Neurokinin A, Neuropeptide K, Neuropeptide gamma), proenkephalin-A, proenkephalin-B, oxytocin, vasopressin-neurophysin-2, thyroid-stimulating hormone, beta subunit (TSHB), cortisol-releasing factor (CRF), atrial natriuretic peptide (ANP), brain natriuretic peptide (BNP), renin, galanin, orexin, ghrelin-obestatin, cholecystokinin, gastrin, insulin-like growth hormone 1 (IGF-1), insulin-like growth hormone 2 (IGF-2), parathyroid hormone (PTH), parathyroid hormone-related protein (PTHrP), osteocalcin, urocortin-3, urocortin-2, urocortin-1, fibroblast growth factor 23 (FGF23), interleukin-1-beta (IL1B), tumor necrosis factor (TNF), interferon-gamma (IFNG), sortilin (SORT1), neuropeptide W, cocaine and amphetamine-related transcript (CART), transforming growth factor-beta-1 (TGFB1), transforming growth factor-beta-2 (TGFB2), transforming growth factor-beta-3 (TGFB3), platelet-derived growth factor-alpha (PDGFA), brain-derived neurotrophic factor (BDNF), nerve growth factor (NGF), albumin, calcitonin, cortistatin (CORT), ADAM-10, -11, -12, -15, -17, -22, -23, -28, -33, ADAMTS-1, -3-10, -12 through -20, BMP-1 through -6, -10, MMP-11, -14 through -17, -21, -23, -24, -25, -28, beta-defensins and mesothelin. The methods are useful in screening for compounds or genes that modulate peptide secretion or cell surface expression. Specifically, the invention provides for the high throughput measurement of peptide secretion or cell surface expression in the setting of genetic and chemical perturbations, and as such is well suited to screens for genes and compounds impacting physiologic processes. Additionally, the methods are useful in screening for compounds that are capable of differentiating one cell type (e.g., embryonic stem cells or iPS cells) into mature cell type, such as a peptide-secreting cell type (e.g., glucose-responsive pancreatic beta cell).

The present invention provides novel tools and methods for measuring peptide secretion or expression at the cell surface. In some embodiments, the peptide is a hormone peptide, prohormone, or precursor thereof. In some embodiments, the peptide is a neuropeptide or precursor thereof. In other embodiments, the peptide is a cytokine or precursor thereof. Specifically, the present invention provides a fusion protein comprising a propeptide and a bioluminescent protein, nucleic acid constructs encoding the fusion proteins, vectors and host cells containing the nucleic acid constructs. The fusion gene constructs may also contain promoters and other transcriptional and/or translational regulatory sequences to drive expression of the fusion gene.

Propeptide Fusion Protein Constructs

Fusion proteins comprise a single continuous linear polymer of amino acids which comprise the full or partial sequence of two or more distinct proteins. The construction of fusion proteins is well-known in the art. Two or more amino acids sequences may be joined chemically, for instance, through the intermediacy of a crosslinking agent. In a preferred embodiment, a fusion protein is generated by expression of a fusion gene construct in a cell. A fusion gene construct comprises a single continuous linear polymer of nucleotides which encodes the full or partial sequences of two or more distinct proteins. Fusion gene constructs of the present invention contain a reporter gene in addition to other genes or fragments thereof that encode at least one propeptide. Fusion gene constructs generally also contain replication origins active in eukaryotic and/or prokaryotic cells and one or more selectable markers encoding, for example, drug resistance. They may also contain viral packaging signals as well as transcriptional and/or translational regulatory sequences and RNA processing signals.

Reporter genes for use in the invention encode detectable proteins, include, but are by no means limited to, Luciferase, Thalassicolin, Aequorin, Mitrocomin, Clytin (synonymous with Phialidin, Obelin, Mnemiopsin) and Berovin. For example, the detectable protein is a bioluminescent protein. An exemplary bioluminescent protein is the *Gaussia* luciferase, which is utilized for its unique properties of being small in size and with increased luminescence in comparison to other more commonly used luciferases (1000 times brighter than Firefly or *Renilla* luciferase). Another exemplary bioluminescent protein is the *Cypridina* luciferase. In some embodiments, the bioluminescent protein is truncated or a fragment thereof such that the bioluminescent protein retains its luminescent characteristics. The bioluminescent protein may have a native signal peptide that controls its secretion. Preferably, the bioluminescent protein lacks the native signal peptide. An exemplary modified luciferase is the *Gaussia* luciferase wherein the luciferase lacks the N-terminal signal peptide that controls the secretion of the luciferase (e.g., SEQ ID NO: 1). An exemplary modified luciferase is the *Cypridina* luciferase wherein the luciferase lacks the N-terminal signal peptide (e.g., SEQ ID NO: 3).

The configuration of the propeptide fusion proteins of the present invention is unique. Early studies and attempts for hormone-reporter fusion proteins have had limited success. Early hormone-reporter constructs caused varying levels of toxicity to the host cells. Other constructs were improperly processed, for example the fusion proteins were sequestered in the endoplasmic reticulum or other secretory pathway organelles rather than appropriately secreted. Other prohormone reporters were constructed such that the mature hormone was fused to the reporter protein, which could potentially result in misfolding and retention of the fusion proteins, as well as alteration of the function and activity of the mature hormone. As described above, these early hormone-reporter fusion proteins had limitations in their use for accurately tracking hormone secretion and amenability for high throughput screening assays. The fusion proteins of the present invention were specifically designed to address the difficulties and limitations of the previous generation of hormone-receptor fusion proteins.

Three modifications were made to an early preproinsulin fusion protein to reduce toxicity to host cells and increase accuracy of secretion for peptide tracking. (1) The bioluminescent protein utilized is small, comprised of less than 200 amino acids. For example, the bioluminescent protein is a *Gaussia* luciferase. The *Gaussia* luciferase is additionally modified such that it is lacking its native secretion signal peptide. (2) The prohormone gene of the fusion protein and the host cell are of the same species. The early preproinsulin fusion protein utilized a human preproinsulin gene and was expressed in a mouse cell line. It would be well within the knowledge of the skilled artisan to use the present disclosure to construct propeptide fusion proteins for expression in mouse, rat, or hamster pancreatic cell lines (i.e., beta-cell lines) with mouse, rat or hamster prohormone genes, which are known in the art. Similarly, the skilled artisan would be able to construct a human prohormone fusion protein using the present disclosure for expression in a human pancreatic cell line (i.e., beta-cell line) upon availability of said cell line. (3) Cleavage sites were introduced into the fusion protein such that there is minimal intervening sequence between the cleavage site and the bioluminescent protein that may interfere with proper processing. For example, for the proinsulin-luciferase fusion construct, no extra amino acids are present between the cleavage site and the bioluminescent protein, such that the luciferase will have no extra amino acids after it is cleaved out of proinsulin. Together, these modifications produced prohormone fusion proteins useful for tracking peptide hormone secretion, as described herein.

An important distinction between the fusion proteins of the present invention and other hormone reporter proteins is that the fusion protein of the present invention is processed normally to produce a mature hormone peptide that is fully intact, unmodified, does not contain additional amino acids, and therefore, should be fully functional. Furthermore, the mature hormone peptide is predicted to be fully competent for endogenous interactions, signaling, and function. The bioluminescent protein is processed and secreted simultaneously and in parallel to secretion of the mature hormone, thereby providing an accurate readout of secretion or expression at the cell surface of the mature hormone. In contrast, other hormone-reporter constructs irreversibly join the mature hormone with the bioluminescent or reporter protein, thereby significantly altering the processing, secretion and downstream function of both the mature hormone and the luciferase protein.

The inventors also discovered that this strategy is useful for other propeptides that are processed prior to secretion or cell surface expression. The nucleic acid constructs and fusion proteins described herein are useful for the tracking peptide secretion and expression at the cell surface.

The present invention provides fusion proteins that comprise a propeptide and a bioluminescent protein. The bioluminescent protein is inserted into the propeptide such that there is at least one cleavage site at the N-terminal end and at least one cleavage site at the C-terminal end of the bioluminescent protein. Any one of the cleavage sites can be native to the propeptide or can be introduced through recombinant DNA techniques known in the art. Exemplary cleavage sites for prohormone fusion proteins, include but are not limited to, prohormone convertase 1/3 (PC1/3), prohormone convertase 2 (PC2), and caspase-1 cleavage sites. Preferably, the cleavage sites are the same cleavages sites that are normally used to process the endogenous propeptide. Utilizing the same cleavage sites at the N and C-terminal ends of the bioluminescent protein that are normally used to process the propeptide allows the cleavage of the bioluminescent protein upon processing of the propeptide for secretion of the mature protein. Importantly, the cleaved bioluminescent protein is free (e.g., separated or non-covalently linked) from the mature peptide(s), and therefore, serves as an accurate readout of peptide secretion or expression of the peptide at the cell surface. In some embodiments, the cleavage sites can be selected and introduced by the skilled artisan such that the bioluminescent protein is cleaved only under specific circumstances determined by the skilled artisan (e.g., cellular context). For example, the skilled artisan could control fusion protein processing and bioluminescent protein secretion by introducing PC2 cleavage sites at the N and C-terminal ends of the bioluminescent protein and expressing the fusion protein in cells that only express PC2 at a certain time or under a specific condition.

The nucleic acid sequences listed in SEQ ID NO: 139 through SEQ ID NO: 330 encode fusion proteins in which a bioluminescent protein is incorporated into a propeptide, flanked by cleavage sites required for the maturation of the propeptide into a mature protein. Whereas the original propeptide cleavage site is maintained on the 5' end of the bioluminescent protein in each fusion protein, an additional cleavage site is added at the 3' end of the bioluminescent protein in each fusion protein to allow for release of the bioluminescent protein after proper cleavage. Both the native and added cleavage sites are underlined in the nucleic acid sequences. While most constructs were designed with the minimal required sequence (i.e., beginning of proprotein-cleavage site #1-bioluminescent protein-cleavage site #2-end of proprotein), in some cases extra flanking nucleotides were included around each cleavage site to create the optimal context for cleavage at these locations, as predicted by the available scientific literature on each protein.

These additional nucleotides encode additional amino acids that enhance cleavage at the cleavage site are referred to herein as "additional cleavage sequence" or ACS. Cleavage sites in which cleavage can be enhanced through additional amino acids can be readily determined by one of ordinary skill in the art through available scientific literature. Some cleavage sites do not require presence of an ACS. ACS can comprise 3 or more nucleotides, wherein the total number of nucleotides is a multiple of 3. For example, the ACS may be 3, 6, 9, 12, or more nucleotides. The ACS encodes amino acids that do not interfere with the function of the fusion protein. For example, the ACS encodes 1, 2, 3, 4, or more additional amino acids.

Optionally, restriction enzyme sites can be added on either side of the bioluminescent protein to allow for construction of the fusion protein. These restriction enzyme sites do not alter the function or expression of the bioluminescent protein and the propeptide.

The present invention provides a nucleic acid construct encoding a fusion protein comprising a peptide precursor linked to a bioluminescent protein, wherein the bioluminescent protein is flanked by two cleavage sites such that wherein the fusion protein is expressed by a cell the bioluminescent protein is cleaved from the peptide precursor and secreted simultaneously with the mature protein.

The present invention provides a nucleic acid construct encoding a fusion protein comprising a peptide precursor linked to a bioluminescent protein, wherein the bioluminescent protein is flanked by two cleavage sites such that wherein the fusion protein is expressed by a cell the bioluminescent protein is cleaved from the peptide precursor simultaneously upon expression of the mature peptide at the cell surface.

The present invention encompasses fusion proteins encoded by the nucleic acid constructs described herein. The fusion proteins have at least 70%, 75%, 80%, 85%, 90%, or 95% sequence identity to the fusion proteins encoded by the nucleic acid constructs of the present invention, such that the resulting fusion protein retains the ability to be cleaved to separate the bioluminescent protein and the mature peptide such that the bioluminescent protein is secreted and the mature form of the propeptide is either secreted or expressed on the cell surface. In some embodiments, the fusion proteins have at least 90%, 91%, 92%, 93%, 94%, 95%, 96%, 97%, 98%, or 99% sequence identity to the fusion proteins encoded by the nucleic acid constructs of the present invention, such that the resulting fusion protein retains the ability to be cleaved to separate the bioluminescent protein and the mature peptide such that the bioluminescent protein is secreted and the mature form of the propeptide is either secreted or expressed on the cell surface. Additionally, the mature peptide produced by the fusion protein having 70%, 75%, 80%, 85%, 90%, or 95% sequence identity to the fusion proteins encoded by the nucleic acid constructs of the present invention has activities substantially similar to the native (e.g., endogenous) mature peptide.

The present invention provides a preproinsulin fusion protein. Preproinsulin consists of a B-peptide, a C-peptide, and an A-peptide (from N to C-terminus). The bioluminescent protein is inserted within the C-peptide component of preproinsulin. A native PC1/3 cleavage sites exists between the B-peptide and the C-peptide, and a native PC2 cleavage site exists between the C-peptide and the A-peptide. In some embodiments, the bioluminescent protein replaces all or some portion of the C-peptide. In some embodiments, the bioluminescent protein is flanked at the N and C terminus by the native cleavage cites. Optionally, an additional cleavage site is added at the N or C-terminal end of the bioluminescent protein. In some embodiments, the bioluminescent protein two cleavage sites are added at the N and C terminus of the bioluminescent protein, i.e., PC2 cleavage sites.

The present invention provides a preproamylin fusion protein. Native PC2 cleavage sites exist at the N and C-terminal ends of the mature amylin peptide. The bioluminescent protein is located at the C-terminus of the preproamylin, adjacent to the native prohormone convertase enzyme 2 (PC2) cleavage site at the C-terminus of the mature amylin peptide. Optionally, an additional cleavage site is added at the C-terminal end of the bioluminescent protein, i.e. PC2. Optionally, an additional cleavage site is inserted at the N and C-terminal end of the bioluminescent protein. Optionally, restriction enzyme sites can be added on either side of the bioluminescent protein to allow for construction of the fusion protein (e.g., aatgca in SEQ ID NO: 139 and SEQ ID NO: 140). These restriction sites are dispensable for the function of the fusion protein.

The present invention provides a preproglucagon fusion protein. The preproglucagon comprises four distinct peptides GRPP, glucagon, GLP-1 (glucagon-like protein 1), and GLP-2 (glucagon-like protein 2), in order from N to C-terminus. Native PC2 sites exist between GRPP and glucagon, two PC2 sites exist between glucagon and Glp-1, a PC1 site exists between glucagon and Glp-1 (in between the existing PC2 sites), and a PC1 site exists between Glp-1 and Glp-2. The bioluminescent protein is inserted between the GLP-1 and GLP-2 encoding regions. Optionally, an additional cleavage site is added at the C-terminal end of the bioluminescent protein, i.e., PC2. In some embodiments, the cellular context in which the preproglucagon fusion protein is expressed determines which peptide is tracked by the bioluminescent protein. In one embodiment, the preproglucagon fusion protein is expressed in L cells which express PC1 and therefore would cause cleavage of the Glp-1 peptide and the bioluminescent protein such that the luminescence would accurately reflect Glp-1 secretion. In one embodiment, the preproglucagon fusion protein is expressed in alpha cells which express PC2 and therefore would cause cleavage of the glucagon peptide and the bioluminescent protein such that the luminescence would accurately reflect glucagon secretion.

Additionally, the present invention provides a fusion protein comprising one propeptide selected from the group consisting of: peptide YY, neuropeptide Y, pancreatic polypeptide, somatostatin, growth hormone-releasing hormone (GHRH), proopiomelanocortin (POMC, including ACTH, MSH), oxytocin, vasopressin-neurophysin-2, gonadotropin-releasing hormone (GnRH), thyroid-stimulating hormone, beta subunit (TSHB), cortisol-releasing factor (CRF), atrial natriuretic peptide (ANP), brain natriuretic peptide (BNP), renin, galanin, orexin, ghrelin-obestatin, cholecystokinin, gastrin, protachykinin-1 (substance P, neurokinin A, neuropeptide K, neuropeptide gamma), proenkephalin-A, proenkephalin-B, insulin-like growth hormone 1 (IGF-1), insulin-like growth hormone 2 (IGF-2), parathyroid hormone (PTH), parathyroid hormone-related protein (PTHrP), osteocalcin, urocortin-3, urocortin-2, urocortin-1, fibroblast growth factor 23 (FGF23), interleukin-1-beta (IL1B), tumor necrosis factor (TNF), interferon-gamma (IFNG), sortilin (SORT1), neuropeptide W, cocaine and amphetamine-related transcript (CART), transforming growth factor-beta-1 (TGFB1), transforming growth factor-beta-2 (TGFB2), transforming growth factor-beta-3 (TGFB3), platelet-derived growth factor-alpha (PDGFA), brain-derived neurotrophic factor (BDNF), nerve growth factor (NGF), albumin, calcitonin, cortistatin (CORT), ADAM-10, -11, -12, -15, -17, -22, -23, -28, -33, ADAMTS-1, -3-10, -12 through -20, BMP-1 through -6, -10, MMP-11, -14 through -17, -21, -23, -24, -25, -28, beta-defensins and mesothelin.

The fusion gene constructs of the invention are introduced into cells to assay for peptide secretion. The fusion gene constructs may also contain promoters and other transcriptional and/or translational regulatory sequences that are normally associated with the gene encoding propeptide. The fusion gene constructs may be introduced into cells by any method of nucleic acid transfer known in the art, including, but not limited to, viral vectors, transformation, co-precipitation, electroporation, neutral or cationic liposome-mediated transfer, microinjection or gene gun. Viral vectors include retroviruses, poxviruses, herpes viruses, adenoviruses, and adeno-associated viruses. Particularly preferred in the present invention are retroviral vectors, which are capable of stable integration into the genome of the host cell. For example, retroviral constructs encoding integration and packaging signals, drug resistance markers and one or more fusion genes of interest are useful in the practice of the invention.

The fusion gene constructs or fusion proteins of the invention may be introduced into cultured cells, animal cells in vivo, animal cells ex vivo, or any other type of cell in which it is desired to study peptide secretion. Preferably, the fusion gene construct is introduced into a cell in which the peptide is secreted or a precursor cell thereof. For example, the fusion gene construct comprising preproinsulin or preproamylin is introduced into beta cells to measure insulin secretion. In some embodiments the beta cell is a beta cell line, such as the murine MIN6 beta cell line or the rat INS-1E beta cell line. The beta cell may be a mouse, rat or hamster beta cell. To measure glucagon or GLP-1 secretion, the fusion construct comprising preproglucagon is introduced into alpha cells or L-cells, respectively. Although a human beta cell line is not yet available in the art, the skilled artisan would be able to use and apply the methods described herein to expressing the fusion proteins of the invention in such a human beta cell line upon its availability.

The recombinant cells of the invention that express the fusion constructs of the invention provide for development of screening assays, particularly for high throughput screening of molecules that up- or down-regulate the activity of peptide secretion.

Exemplary luciferase nucleic acid sequences include, but are not limited to:

Gaussia luciferase without signal peptide or stop codon (nucleic acid sequence):
(SEQ ID NO: 1)
Aagcccaccgagaacaacgaagacttcaacatcgtggccgtggccagcaacttcgcgaccacggatctcgatgctgaccgcgggaa gttgcccggcaagaagctgccgctggaggtgctcaaagagatggaagcaatgcccggaaagctggctgcaccaggggctgtctga -continued tctgcctgtcccacatcaagtgcacgcccaagatgaagaagttcatcccaggacgctgccacacctacgaaggcgacaaagagtccg cacagggcggcataggcgaggcgatcgtcgacattcctgagattcctgggttcaaggacttggagcccatggagcagttcatcgcaca ggtcgatctgtgtgtggactgcacaactggctgcctcaaagggcttgccaacgtgcagtgttctgacctgctcaagaagtggctgccgc aacgctgtgcgacctttgccagcaagatccagggccaggtggacaagatcaaggggccggtggtgac Gaussia luciferase with signal peptide and stop codon (nucleic acid sequence):
(SEQ ID NO: 2)
Atgggagtcaaagttctgtttgccctgatctgcatcgctgtggccgaggccaagcccaccgagaacaacgaagacttcaacatcgtgg ccgtggccagcaacttcgcgaccacggatctcgatgctgaccgctttaagttgcccggcaagaagctgccgctggaggtgctcaaa gagatggaagccaatgcccggaaagctggctgcaccaggggctgtctgatctgcctgtcccacatcaagtgcacgcccaagatgaag aagttcatcccaggacgctgccacacctacgaaggcgacaaagagtccgcacagggcggcataggcgaggcgatcgtcgacattcc tgagattcctgggttcaaggacttggagcccatggagcagttcatcgcacaggtcgatctgtgtgtggactgcacaactggctgcctcaa agggcttgccaacgtgcagtgttctgacctgctcaagaagtggctgccgcaacgctgtgcgacctttgccagcaagatccagggccag gtggacaagatcaaggggccggtggtgactaa Cypridina luciferase without signal peptide or stop codon (nucleic acid sequence):
(SEQ ID NO: 3)
Tactgcgccactgttcattgccaggactgtccttacgaacctgatccaccaaacacagttccaacttcctgtgaagctaaagaaggagaa tgtattgatagcagctgtggcacctgcacgagagacatactatcagatggactgtgtgaaaataaaccaggaaaaacatgttgccgaatg tgtcagtatgtaattgaatgcagagtagaggccgcaggatggtttagaacattctatggaaagagattccagttccaggaacctggtacat acgtgttgggtcaaggaaccaagggcggcgactggaaggtgtccatcaccctggagaacctggatggaaccaaggggctgtgctg accaagacaagactggaagtggctggagacatcattgacatcgctcaagctactgagaatcccatcactgtaaacggtggagctgacc ctatcatcgccaacccgtacaccatcggcgaggtcaccatcgctgttgttgagatgccaggcttcaacatcaccgtcattgagttcttcaa actgatcgtgatcgacatcctcggaggaagatctgtaagaatcgccccagacacagcaaacaaaggaatgatctctggcctctgtgga gatcttaaaatgatggaagatacagacttcacttcagatccagaacaactcgctattcagcctaagatcaaccaggagtttgacggttgtc cactctatggaaatcctgatgacgttgcatactgcaaagtcttctggagccgtacaaggacagctgccgcaaccccatcaacttctacta ctacaccatctcctgcgccttcgcccgctgtatgggtggagacgagcgagcctcacacgtgctgcttgactacagggagacgtgcgct gctcccgaaactagaggaacctgcgtttgtctggacatactttctacgatacatttgacaaagcaagataccaattccagggtccctgca aggagattcttatgccgccgactgtttctggaacacttgggatgtgaaggtttcacacaggaatgttgactcttacactgaagtagagaa agtacgaatcaggaaacaatcgactgtagtagaactcattgttgatggaaaacagattctggttggaggagaagccgtgtccgtcccgta cagctctcagaacacttccatctactggcaagatggtgacatactgactacagccatcctacctgaagctctggtggtcaagttcaacttc aagcaactgctcgtcgtacatattagagatccattcgatggtaagacttgcggtatttgcggtaactacaaccaggatttcagtgatgattct tttgatgctgaaggagcctgtgatctgaccccaacccaccgggatgcaccgaagaacagaaacctgaagctgaacgactctgcaata gtctcttcgccggtcaaagtgatcttgatcagaaatgtaacgtgtgccacaagcctgaccgtgtcgaacgatgcatgtacgagtattgcct gaggggacaacagggtttctgtgaccacgcatgggagttcaagaaagaatgctacataaagcatggagacaccctagaagtaccaga tgaatgcaaa Cypridina luciferase with signal peptide and stop codon (nucleic acid sequence):
(SEQ ID NO: 4)
atgaagaccttaattcttgccgttgcattagtctactgcgccactgttcattgccaggactgtccttacgaacctgatccaccaaacacagtt ccaacttcctgtgaagctaaagaaggagaatgtattgatagcagctgtggcacctgcacgagagacatactatcagatggactgtgtga aaataaaccaggaaaaacatgttgccgaatgtgtcagtatgtaattgaatgcagagtagaggccgcaggatggtttagaacattctatgg aaagagattccagttccaggaacctggtacatacgtgttgggtcaaggaaccaagggcggcgactggaaggtgtccatcaccctgga gaacctggatggaaccaaggggctgtgctgaccaagacaagactggaagtggctggagacatcattgacatcgctcaagctactga gaatcccatcactgtaaacggtggagctgaccctatcatcgccaacccgtacaccatcggcgaggtcaccatcgctgttgttgagatgc caggcttcaacatcaccgtcattgagttcttcaaactgatcgtgatcgacatcctcggaggaagatctgtaagaatcgccccagacacag -continued

```
caaacaaaggaatgatctctggcctctgtggagatcttaaaatgatggaagatacagacttcacttcagatccagaacaactcgctattca gcctaagatcaaccaggagtttgacggttgtccactctatggaaatcctgatgacgttgcatactgcaaaggtcttctggagccgtacaag gacagctgccgcaacccatcaacttctactactacaccatctcctgcgccttcgcccgctgtatgggtggagacgagcgagcctcaca cgtgctgcttgactacagggagacgtgcgctgctcccgaaactagaggaacctgcgttttgtctggacatacttctacgatacatttgac aaagcaagataccaattccagggtcctgcaaggagattcttatggccgccgactgtttctggaacacttgggatgtgaaggtttcacac aggaatgttgactcttacactgaagtagagaaagtacgaatcaggaaacaatcgactgtagtagaactcattgttgatggaaaacagattc tggttggaggagaagccgtgtccgtcccgtacagctctcagaacacttccatctactggcaagatggtgacatactgactacagccatcc tacctgaagctctggtggtcaagttcaacttcaagcaactgctcgtcgtacatattagagatccattcgatggtaagacttgcggtatttgcg gtaactacaaccaggatttcagtgatgattcttttgatgctgaaggagcctgtgatctgaccccaacccaccgggatgcaccgaagaac agaaacctgaagctgaacgactctgcaatagtctcttcgccggtcaaagtgatcttgatcagaaatgtaacgtgtgccacaagcctgacc gtgtcgaacgatgcatgtacgagtattgcctgaggggacaacagggtttctgtgaccacgcatgggagttcaagaaagaatgctacata aagcatggagacaccctagaagtaccagatgaatgcaaatag
```

Exemplary nucleic acid sequences of the propeptides of the present invention include, but are not limited to, those listed below.

```
Proamylin Mouse (nucleic acid sequence):
                                                                      (SEQ ID NO: 5)
atgatgtgcatctccaaactgccagctgtcctcctcatcctctctgtggcactgaaccacttgagagctacacctgtcagaagtggtagca accctcagatggacaaacgaagtgcaacacggccacgtgtgccacacaacgcctggcaaacttttttggttcgttccagcaacaaccttt ggtccagtcctcccaccaaccaacgtgggatcgaatacatatggcaagaggaatgcggcagggggatccaaatagggaatccttggatt tcttactcgtttaa
Proamylin Human (nucleic acid sequence):
                                                                      (SEQ ID NO: 6)
atgggcatcctgaagctgcaagtatttctcattgtgctctctgttgcattgaaccatctgaaagctacaccattgaaagtcatcaggtggaa aagcggaaatgcaacactgccacatgtgcaacgcagcgcctggcaaatttttttagttcattccagcaacaactttggtgccattctctcatc taccaacgtgggatccaatacatatggcaagaggaatgcagtagaggttttaaagagagagccactgaattacttgcccctttag
Proinsulin 2 Mouse (nucleic acid sequence):
                                                                      (SEQ ID NO: 7)
atggccctgtggatgcgcttcctgcccctgctggccctgctcttcctctgggagtcccaccccaccaggctttgtcaagcagcacctttt gtggttcccacctggtggaggctctctacctggtgtgtggggagcgtggcttcttctacacacccatgtcccgccgtgaagtggaggac ccacaagtggcacaactggagctgggtggaggcccgggagcaggtgacctttcagaccttggcactggaggtggcccagcagaagc gtggcattgtagatcagtgctgcaccagcatctgctccctctaccagctggagaactactgcaactag
Proinsulin Human (nucleic acid sequence):
                                                                      (SEQ ID NO: 8)
atggccctgtggatgcgcctcctgcccctgctggcgctgctggccctctggggacctgacccagccgcagcctttgtgaaccaacacct gtgcggctcacacctggtggaagctctctacctagtgtgcggggaacgaggcttcttctacacacccaagacccgccggggaggcaga ggacctgcaggtggggcaggtggagctgggcgggggccctggtgcaggcagcctgcagcccttggccctggagggtccctgca gaagcgtggcattgtggaacaatgctgtaccagcatctgctccctctaccagctggagaactactgcaactag
Proglucagon (includes GRPP, glucagon, GLP-1, GLP-2) Mouse (nucleic acid sequence):
                                                                      (SEQ ID NO: 9)
atgaagaccatttactttgtggctggattgcttataatgctggtgcaaggcagctggcagcacgcccttcaagacacagaggagaaccc cagatcattcccagcttcccagacagaagcgcatgaggaccctgatgagatgaatgaagacaaacgccactcacagggcacattcac cagcgactacagcaaatacctggactcccgccgtgcccaagattttgtgcagtggtgatgaacaccaagaggaaccggaacaacatt gccaaacgtcatgatgaatttgagaggcatgctgaagggaccttaccagtgatgtgagttcttacttggagggccaggcagcaaagga attcattgcttggctggtgaaaggccgaggaaggcgagacttcccagaagaagtcgccattgccgaggaactcggccgcaggcacgc
```

-continued tgatggctccttctctgacgagatgagcaccattctggataatcttgccaccagggacttcatcaactggctgattcaaaccaagatcactg acaagaaatag Proglucagon (includes GRPP, glucagon, GLP-1, GLP-2) Human (nucleic acid sequence):
(SEQ ID NO: 10)
atgaaaagcatttactttgtggctggattatttgtaatgctggtacaaggcagctggcaacgttcccttcaagacacagaggagaaatcca gatcattctcagcttcccaggcagacccactcagtgatcctgatcagatgaacgaggacaagcgccattcacagggcacattcaccagt gactacagcaagtatctggactccaggcgtgcccaagattttgtgcagtggttgatgaataccaagaggaacaggaataacattgccaa acgtcacgatgaatttgagagacatgctgaagggacctttaccagtgatgtaagttcttatttggaaggccaagctgccaaggaattcatt gcttggctggtgaaaggccgaggaaggcgagatttcccagaagaggtcgccattgttgaagaacttggccgcagacatgctgatggtt ctttctctgatgagatgaacaccattcttgataatcttgccgccagggactttataaactggttgattcagaccaaaatcactgacaggaaat aa Peptide YY Mouse (nucleic acid sequence):
(SEQ ID NO: 11)
atggtggcggtgcgcaggccttggcccgtcacggtcgcaatgctgctaatcctgctcgcctgtctgggagccctggtggacgcctacc ctgccaaaccagaggctcccggcgaagacgcctcccggaggagctgagccgctactacgcctccctgcgccactacctcaacctg gtcacccggcagcggtatggaaaaagagatgtccccgcagctctgttctccaaactgctcttcacagacgacagcgacagcgagaac ctcccccttcaggccagaaggtttggaccagtggtga Peptide YY Human (nucleic acid sequence):
(SEQ ID NO: 12)
atggtgttcgtgcgcaggccgtggcccgccttgaccacagtgcttctggccctgctcgtctgcctaggggcgctggtcgacgcctaccc catcaaacccgaggctcccggcgaagacgcctcgccggaggagctgaaccgctactacgcctccctgcgccactacctcaacctggt cacccggcagcggtatgggaaaagagacgcccggacacgcttctttccaaaacgttcttccccgacggcgaggaccgccccgtca ggtcgcggtcggagggcccagacctgtggtga Neuropeptide Y Mouse (nucleic acid sequence):
(SEQ ID NO: 13)
atgctaggtaacaagcgaatggggctgtgtggactgaccctcgctctatctctgctcgtgtgtttgggcattctggctgaggggtaccct ccaagccggacaatccgggcgaggacgcgccagcagaggacatggccagatactactccgctctgcgacactacatcaatctcatca ccagacagagatatggcaagagatccagccctgagacactgatttcagacctcttaatgaaggaaagcacagaaaacgcccccagaa caaggcttgaagacccttccatgtggtga Neuropeptide Y Human (nucleic acid sequence):
(SEQ ID NO: 14)
atgctaggtaacaagcgactggggctgtccggactgaccctcgccctgtccctgctcgtgtgcctgggtgcgctggccgaggcgtacc cctccaagccggacaacccgggcgaggacgcaccagcggaggacatggccagatactactcggcgctgcgacactacatcaacct catcaccaggcagagatatggaaaacgatccagcccagagacactgatttcagacctcttgatgagagaaagcacagaaaatgttccc agaactcggcttgaagaccctgcaatgtggtga Pancreatic polypeptide Mouse (nucleic acid sequence):
(SEQ ID NO: 15)
atggccgtcgcatactgctgcctctccctgtttctcgtatccacttgggtggctctgctgctgcagcccctgcaggggacctggggagcc cccctggagccaatgtacccaggcgactatgcgacacctgagcgatggcacaatatgaaactcagctccgcagatacatcaacacac tgaccaggcctaggtatgggaagagagccgaggaggagaacacaggtggacttcctggagtgcagctctcccctgcaccagcccc ccagttggcttgattccctgctctgcgccctggagctga Pancreatic polypeptide Human (nucleic acid sequence):
(SEQ ID NO: 16)
atggctgccgcacgcctctgcctctccctgctgctcctgtccacctgcttggctctgttactacagccactgctgggtgcccagggagcc ccactggagccagtgtacccaggggacaatgccacaccagagcagatggcccagtatgcagctgatctccgtagatacatcaacatg ctgaccaggcctaggtatgggaaaagacacaaagaggacacgctggccttctcggagtgggggtccccgcatgctgctgtccccagg gagctcagcccgctggacttataa -continued Somatostatin Mouse (nucleic acid sequence):
(SEQ ID NO: 17)
atgctgtcctgccgtctccagtgcgccctggctgcgctctgcatcgtcctggctttgggcggtgtcaccggcgcgccctcggaccccag actccgtcagtttctgcagaagtctctggcggctgccaccgggaaacaggaactggccaagtacttcttggcagagctgctgtccgagc ccaaccagacagagaatgatgccctggagcccgaggatttgccccaggcagctgagcaggacgagatgaggctggagctgcagag gtctgccaactcgaacccagcaatggcaccccgggaacgcaaagctggctgcaagaacttcttctggaagacattcacatcctgttag Somatostatin Human (nucleic acid sequence):
(SEQ ID NO: 18)
atgctgtcctgccgcctccagtgcgcgctggctgcgctgtccatcgtcctggccctgggctgtgtcaccggcgctccctcggaccccag actccgtcagtttctgcagaagtccctggctgctgccgcggggaagcaggaactggccaagtacttcttggcagagctgctgtctgaac ccaaccagacggagaatgatgccctggaacctgaagatctgtcccaggctgctgagcaggatgaaatgaggcttgagctgcagagat ctgctaactcaaacccggctatggcaccccgagaacgcaaagctggctgcaagaatttcttctggaagactttcacatcctgttag GHRH Mouse (nucleic acid sequence):
(SEQ ID NO: 19)
atgctgctctgggtgctctttgtgatcctcatcctcaccagtggctcccactgctcactgcccccctcacctcccttcaggatgcagcgaca cgtagatgccatcttcaccaccaactacaggaaactcctgagccagctgtatgcccggaaagtgatccaggacatcatgaacaagcaa ggggagaggatccaggaacaaagggccaggctcagccgccaggaagacagcatgtggacagaggacaagcagatgaccctgga gagcatcttgcagggattcccaaggatgaagccttcagcggacgcttga GHRH Human (nucleic acid sequence):
(SEQ ID NO: 20)
atgccactctgggtgttcttctttgtgatcctcaccctcagcaacagctcccactgctcccacctccccctttgaccctcaggatgcggcg gtatgcagatgccatcttcaccaacagctaccggaaggtgctgggccagctgtccgcccgcaagctgctccaggacatcatgagcag gcagcagggagagagcaaccaagagcgaggagcaagggcacggcttggtcgtcaggtagacagcatgtgggcagaacaaaagca aatggaattggagagcatcctggtggccctgctgcagaagcacaggaactcccagggatga POMC (ACTH, MSH) Mouse (nucleic acid sequence):
(SEQ ID NO: 21)
atgccgagattctgctacagtcgctcaggggccctgttgctggccctcctgcttcagacctccatagatgtgtggagctggtgcctggag agcagccagtgccaggacctcaccacggagagcaacctgctggcttgcatccgggcttgcaaactcgacctctcgctggagacgcc gtgtttcctggcaacggagatgaacagcccctgactgaaaaccccggaagtacgtcatgggtcacttccgctgggaccgcttcggcc ccaggaacagcagcagtgctggcagcgcggcgcagagggcgtgcggaggaagaggcggtgtggggagatggcagtccagagccg agtccacgcgagggcaagcgctcctactccatggagcacttccgctggggcaagccggtgggcaagaaacggcgcccggtgaagg tgtaccccaacgttgctgagaacgagtcggcggaggccttttcccctagagttcaagagggagctggaaggcgagcggccattaggctt ggagcaggtcctggagtccgacgcggagaaggacgacgggccctaccgggtggagcacttccgctggagcaacccgcccaagga caagcgttacggtggcttcatgacctccgagaagagccagacgcccctggtgacgctcttcaagaacgccatcatcaagaacgcgca caagaagggccagtga POMC (ACTH, MSH) Human (nucleic acid sequence):
(SEQ ID NO: 22)
atgccgagatcgtgctgcagccgctcggggggccctgrtgctggccttgctgcttcaggcctccatggaagtgcgtggctggtgcctgga gagcagccagtgtcaggacctcaccacggaaagcaacctgctggagtgcatccgggcctgcaagcccgacctctcggccgagactc ccatgttcccgggaaatggcgacgagcagcctctgaccgagaaccccggaagtacgtcatgggccacttccgctgggaccgattcg gccgccaacagcagcagcagcggcagcagcggcgcagggcagaagcgcgaggacgtctcagcgggcgaagactgcggccc gctgcctgagggcggccccgagcccgcagcgatggtgccaagcggcccgcgcgagggcaagcgctcctactccatggagca cttccgctggggcaagccggtgggcaagaagcggcgcccagtgaaggtgtaccctaacggcgccgaggacgagtcggccgaggc cttccccctggagttcaagagggagctgactggccagcgactccgggagggatggccccgacggccctgccgatgacggcgca ggggcccaggccgacctggagcacagcctgctggtggcggccgagaagaaggacgagggcccctacaggatggagcacttccgc -continued tggggcagcccgcccaaggacaagcgctacggcggtttcatgacctccgagaagagccagacgcccctggtgacgctgttcaaaaa cgccatcatcaagaacgcctacaagaagggcgagtga Oxytocin Mouse (nucleic acid sequence):
(SEQ ID NO: 23)

atggcctgccccagtctcgcttgctgcctgcttggcttactggctctgacctcggcctgctacatccagaactgcccctgggcggcaag agggctgtgctggacctggatatgcgcaagtgtctccccctgcgggcccggggcggcaaaggacgctgcttcggaccaagcatctgctgc gcggacgagctgggctgcttcgtgggcaccgccgaggcgctgcgctgccaggaggagaactacctgccttcgccctgccagtctgg ccagaagccctgcgggagcggaggccgctgcgccgccacaggcatctgctgcagcccggatggctgccgcacagaccccgcctg cgaccctgagtctgccttctcggagcgctga Oxytocin Human (nucleic acid sequence):
(SEQ ID NO: 24)

atggccggccccagcctcgcttgctgtctgctcggcctcctggcgctgacctccgcctgctacatccagaactgcccctgggaggca agagggccgcgccggacctcgacgtgcgcaagtgcctccccctgcggccccgggggcaaaggccgctgcttcgggcccaatatctg ctgcgcggaagagctgggctgcttcgtgggcaccgccgaagcgctgcgctgccaggaggagaactacctgccgtcgccctgccagt ccggccagaaggcgtgcgggagcggggggccgctgcgcggtcttgggcctctgctgcagcccggacggctgccacgccgaccctg cctgcgacgcggaagccaccttctcccagcgctga Vasopressin-Neurophysin-2 Mouse (nucleic acid sequence):
(SEQ ID NO: 25)

atgctcgccaggatgctcaacactacgctctccgcttgtttcctgagcctgctggccttctcctccgcctgctacttccagaactgcccaag aggcggcaagagggccatctctgacatggagctgagacagtgtctccccctgcggcccgggcggcaaaggacgctgcttcggaccaa gcatctgctgcgcggacgagctgggctgcttcgtgggcaccgccgaggcgctgcgctgccaggaggagaactacctgccctcgccc tgccagtccggccagaagccctgcgggagcggggggccgctgcgccgccgtgggcatctgctgcagcgacgagagctgcgtggcc gagcccgagtgccacgacggttttttccgcctcaccgcgctcgggagccaagcaacgccacacagctggacggccctgctcgggc gctgctgctaaggctggtacagctggctgggacacgggagtccgtggattctgccaagcccgggtctactga Vasopressin-Neurophysin-2 Human (nucleic acid sequence):
(SEQ ID NO: 26)

atgcctgacaccatgctgccgcctgcttcctcggcctactggccttctcctccgcgtgctacttccagaactgcccgaggggcggcaa gagggccatgtccgacctggagctgagacagtgcctcccctgcggccccggggcaaaggccgctgcttcgggcccagcatctgct gcgcggacgagctgggctgcttcgtgggcacggctgaggcgctgcgctgccaggaggagaactacctgccgtcgccctgccagtcc ggccagaaggcgtgcgggagcggggggccgctgcgccgccttcggcgtttgctgcaacgacgagagctgcgtgaccgagcccgagt gccgcgagggctttcaccgccgcgcccgcgccagcgaccggagcaacgccacgcagctggacgggccggccggggccttgctgc tgcggctggtgcagctggccggggcgcccgagcccttcgagcccgcccagcccgacgcctactga Gonadotropin-releasing hormone (GnRH) Mouse (nucleic acid sequence):
(SEQ ID NO: 27)

atgatcctcaaactgatggccggcattctactgctgactgtgtgtttggaaggctgctccagccagcactggtcctatgggttgcgccctg ggggaaagagaaacactgaacacttggttgagtctttccaagagatgggcaaggaggtggatcaaatggcagaaccccagcacttcg aatgtactgtccactggccccgttcaccccctcagggatctgcgaggagctctggaaagtctgattgaagaggaagccaggcagaagaa gatgtag Gonadotropin-releasing hormone (GnRH) Human (nucleic acid sequence):
(SEQ ID NO: 28)

atgaagccaattcaaaaactcctagctggccttattctactgacttggtgcgtggaaggctgctccagccagcactggtcctatggactgc gccctggaggaaagagagatgccgaaaatttgattgattctttccaagagatagtcaaagaggttggtcaactggcagaaacccaacgc ttcgaatgcaccacgcaccagccacgttctcccctccgagacctgaaaggagctctggaaagtctgattgaagaggaaactgggcaga agaagatttaa -continued Thyroid-stimulating hormone, beta subunit (TSHB) Mouse (nucleic acid sequence):

(SEQ ID NO: 29)

atgagtgctgccgtcctcctctccgtgcttttgtgctcttgcttgtgggcaagcagcatcctttgtattcccactgagtatacaatgtacgtgga taggagagagtgtgcctactgcctgaccatcaacaccaccatctgtgctgggtattgtatgacacgggatatcaatggcaaactgtttcttc ccaaatatgcactctctcaggatgtctgtacatacagagacttcatctacagaacggtggaaataccaggatgcccgcaccatgttactcc ttatttctccttccctgtcgccataagctgcaagtgtggcaagtgtaatactgacaacagtgactgcatacacgaggctgtcagaaccaact actgcaccaagccgcagtctttctatctgggggattttctgtttaa Thyroid-stimulating hormone, beta subunit (TSHB) Human (nucleic acid sequence):

(SEQ ID NO: 30)

atgactgctctcttctgatgtccatgcttttggccttacatgtgggcaagcgatgtcttttgtattccaactgagtatacaatgcacatcgaa aggagagagtgtgcttattgcctaaccatcaacaccaccatctgtgctggatattgtatgacacgggatatcaatggcaaactgtttcttcc caaatatgctctgtcccaggatgtttgcacatatagagacttcatctacaggactgtagaaataccaggatgcccactccatgttgctccct attttcctatcctgttgctttaagctgtaagtgtggcaagtgcaatactgactatagtgactgcatacatgaagccatcaagacaaactactg taccaaacctcagaagtcttatctggtaggattttctgtctaa Cortisol-releasing factor (CRF) Mouse (nucleic acid sequence):

(SEQ ID NO: 31)

atgcggctgcggctgctggtgtccgcgggcatgctgctggtggctctgtcgtcctgcctgccttgcagggccctgctcagcaggggatc cgtccccgagcgccgcgggccccgcagcccttgaatttcttgcagccggagcagccccagcaacctcagccggttctgatccgcat gggtgaagaatacttcctccgcctggggaatctcaacagaagtcccgctgctcggctgtccccaactccacgcccctcaccgcggt cgcggcagccgcccctcgcacgaccaggctgcggctaacttttttccgcgtgttgctgcagcagctgcagatgcctcagcgctcgctcg acagccgcgcggagccggccgaacgcggcgccgaggatgccctcggtggccaccaggggcgctggagagggagaggcggtc ggaggagccgcccatctctctggatctcaccttccaccttctgcgggaagtcttggaaatggcccgggcagagcagttagctcagcaa gctcacagcaacaggaaactgatggagattatcgggaaatga Cortisol-releasing factor (CRF) Human (nucleic acid sequence):

(SEQ ID NO: 32)

atgcggctgccgctgcttgtgtccgcgggagtcctgctggtggctctcctgccctgcccgccatgcagggcgctcctgagccgcgggc cggtcccgggagctcggcaggcgccgcagcaccctcagcccttggatttcttccagccgccgccgcagtccgagcagccccagcag ccgcaggctcggccggtcctgctccgcatgggagaggagtacttcctccgcctggggaacctcaacaagagcccggccgctcccctt tcgcccgcctcctcgctcctcgccggaggcagcggcagccgcccttcgccgaacaggcgaccgccaactttttccgcgtgttgctgc agcagctgctgctgcctcggcgctcgctcgacagccccgcgggctctcgcggagcgcggcgctaggaatgccctcggcggccacca ggaggcaccggagagagaaaggcggtccgaggagcctcccatctccctggatctcaccttccacctcctccgggaagtcttggaaat ggccagggccgagcagttagcacagcaagctcacagcaacaggaaactcatggagattattgggaaataa Atrial natriuretic peptide (ANP) Mouse (nucleic acid sequence):

(SEQ ID NO: 33)

atgggctccttctccatcaccctgggcttcttcctcgtcttggccttttggcttccaggccatattggagcaaatcctgtgtacagtgcggtgt ccaacacagatctgatggatttcaagaacctgctagaccacctggaggagaagatgccggtagaagatgaggtcatgccccgcagg ccctgagtgagcagactgaggaagcaggggccgcacttagctcccctccccgaggtgcctccctggactggggaggtcaacccacct ctgagagacggcagtgctctagggcgcagcccctgggaccctccgatagatctgccctcttgaaaagcaaactgagggctctgctcg ctggccctcggagcctacgaagatccagctgcttcgggggtaggattgacaggattggagcccagagtggactaggctgcaacagctt ccggtaccgaagataa Atrial natriuretic peptide (ANP) Human (nucleic acid sequence):

(SEQ ID NO: 34)

atgagctccttctccaccaccaccgtgagcttcctccttttactggcattccagctcctaggtcagaccagagctaatcccatgtacaatgc cgtgtccaacgcagacctgatggatttcaagaatttgctggaccatttggaagaaaagatgcctttagaagatgaggtcgtgccccaca agtgctcagtgagccgaatgaagaagcgggggctgctctcagccccctccctgaggtgcctccctggaccggggaagtcagcccag cccagagagatggaggtgcccctcgggcggggcccctgggactcctctgatcgatctgccctcctaaaaagcaagctgagggcgctgc -continued tcactgcccctcggagcctgcggagatccagctgcttcggggcaggatggacaggattggagcccagagcggactgggctgtaac agcttccggtactga Brain natriuretic peptide (BNP) Mouse (nucleic acid sequence):

(SEQ ID NO: 35)

atggatctcctgaaggtgctgtcccagatgattctgtttctgcttttcctttatctgtcaccgctgggaggtcactcctatcctctgggaagtcc tagccagtctccagagcaattcaagatgcagaagctgctggagctgataagagaaaagtcggaggaaatggcccagagacagctctt gaaggaccaaggcctcacaaaagaacacccaaaaagagtccttcggtctcaaggcagcaccctccgggtccagcagagacctcaaa attccaaggtgacacatatctcaagctgctttgggcacaagatagaccggatcggatccgtcagtcgtttgggctgtaacgcactgaagtt gttgtag Brain natriuretic peptide (BNP) Human (nucleic acid sequence):

(SEQ ID NO: 36)

atggatccccagacagcaccttcccgggcgctcctgctcctgctcttcttgcatctggctttcctgggaggtcgttcccaccgctgggca gccccggttcagcctcggacttggaaacgtccgggttacaggagcagcgcaaccatttgcagggcaaactgtcggagctgcaggtgg agcagacatccctggagcccctccaggagagcccccgtcccacaggtgtctggaagtcccgggaggtagccaccgagggcatccgt gggcaccgcaaaatggtcctctacaccctgcgggcaccacgaagcccaagatggtgcaagggtctggctgctttgggaggaagatg gaccggatcagctcctccagtggcctgggctgcaaagtgctgaggcggcattaa Renin Mouse (nucleic acid sequence):

(SEQ ID NO: 37)

atggacagaaggaggatgcctctctgggcactcttgttgctctggagtccttgcaccttcagtctcccaacacgcaccgctacctttgaac gaatcccgctcaagaaaatgccttctgtccgggaaatcctggaggagcggggagtggacatgaccaggctcagtgctgaatgggcg tattcacaaagaggccttccttgaccaatcttacctcccccgtggtcctcaccaactacctgaatacccagtactacggcgagattggcat cggtaccccaccccagaccttcaaagtcatctttgacacgggttcagccaacctctgggtgccctccaccaagtgcagccgcctctacct tgcttgtgggattcacagcctctatgagtcctctgactcctccagctacatggagaacgggtccgacttcaccatccactacggatcagg gagagtcaaaggtttcctcagccaggactcggtgactgtgggtgaatcactgtgacacagaccttggagaggtcaccgagctgccc ctgatcccttttcatgctggccaagtttgacggtgttctaggcatgggctttcccgctcaggccgttggcggggttaccctgtctttgacca cattctctcccagggggtgctaaaggaggaagtgttctctgtctactacaacaggggttcccacctgctgggggcgaggtggtgctag gaggtagcgacccgcagcattatcaaggcaattttcactatgtgagcatcagcaagactgactcctggcagatcacgatgaagggggt gtctgtggggtcttccaccctgctatgtgaagaaggctgtgcggtagtggtggacactggttcatcctttatctcggctcctacgagctccc tgaagttgatcatgcaagccctgggagccaaggagaagagaatagaagaatatgttgtgaactgtagccaggtgcccacccctccccga catttcctttgacctgggaggcagggcctacacactcagcagtacggactacgtgctacagtatcccaacaggagagacaagctgtgc acactggctctccatgccatggacatcccaccacccactgggcctgtctgggtcctgggtgccaccttcatccgcaagttctatacagag tttgatcggcataacaatcgcattggattcgccttggcccgctaa Renin Human (nucleic acid sequence):

(SEQ ID NO: 38)

atggatggatggagaaggatgcctcgctggggactgctgctgctgctctggggctcctgtacctttggtctcccgacagacaccaccac ctttaaacggatcttcctcaagagaatgcccctcaatccgagaaagcctgaaggaacgaggtgtggacatggccaggcttggtcccgagt ggagccaacccatgaagaggctgacacttggcaacaccacctcccgtgatcctcaccaactacatggacacccagtactatggcga gattggcatcggcacccaccccagaccttcaaagtcgtctttgacactggttcgtccaatgtttgggtgccctcctccaagtgcagccgt ctctacactgcctgtgtgtatcacaagctcttcgatgcttcggattcctccagctacaagcacaatggaacagaactcaccctccgctattc aacagggacagtcagtggctttctcagccaggacatcatcaccgtgggtggaatcacggtgacacagatgtttgagaggtcacggag atgcccgccttacccttcatgctggccgagtttgatggggttgtgggcatgggcttcattgaacaggccattggcagggtcacccctatct tcgacaacatcatctcccaaggggtgctaaaagaggacgtcttctctttctactacaacagagattccgagaattcccaatcgctgggag gacagattgtgctgggaggcagcgaccccccagcattacgaagggaatttccactatatcaacctcatcaagactggtgtctggcagattc aaaatgaaggggtgtctgtggggtcatccaccttgctctgtgaagacggctgcctggcattggtagacaccggtgcatcctacatctcag gttctaccagctccatagagaagctcatggaggccttgggagccaagaagaggctgtttgattatgtcgtgaagtgtaacgagggccct -continued acactccccgacatctctttccacctgggaggcaaagaatacacgctcaccagcgcggactatgtatttcaggaatcctacagtagtaaa aagctgtgcacactggccatccacgccatggatatcccgccacccactggacccacctgggccctgggggccaccttcatccgaaagt tctacacagagtttgatcggcgtaacaaccgcattggcttcgccttggcccgctga Galanin Mouse (nucleic acid sequence):

(SEQ ID NO: 39)

atggccagaggcagcgttatcctgctaggctggctcctgttggttgtgaccctgtcagccactctgggacttgggatgcctgcaaagga gaagagaggttggaccctgaacagcgctggctaccttctgggcccacatgccattgacaaccacagatcatttagcgacaagcatggc ctcacaggcaagagggagttacaactggaggtggaggaaaggagaccaggaagtgttgatgtgcccctgcctgagagcaacattgtc cgcactataatggagtttctcagtttcttgcaccttaaagaggccggggccctcgacagcctgcctggcatcccttggccacctcctcag aagacctagagaagtcctga Galanin Human (nucleic acid sequence):

(SEQ ID NO: 40)

atggcccgaggcagcgccctcctgctcgcctccctcctcctcgccgcggcccttctgcctctgcggggctctggtcgccggccaagg aaaaacgaggctggaccctgaacagcgcgggctacctgctgggcccacatgccgttggcaaccacaggtcattcagcgacaagaat ggcctcaccagcaagcgggagctgcggcccgaagatgacatgaaaccaggaagctttgacaggtccatacctgaaaacaatatcatg cgcacaatcattgagtttctgtctttcttgcatctcaaagaggccggtgccctcgaccgcctcctggatctccccgccgcagcctcctcag aagacatcgagcggtcctga Orexin Mouse (nucleic acid sequence):

(SEQ ID NO: 41)

atgaactttccttctacaaaggttccctgggccgccgtgacgctgctgctgctgctactgctgccgccggcgctgctgtcgcttggggtg gacgcacagcctctgcccgactgctgtcgccagaagacgtgttcctgccgtctctacgaactgttgcacggagctggcaaccacgctg cgggtatcctgactctgggaaagcggcggcctggacctccaggcctccagggacggctgcagcgcctccttcaggccaacggtaac cacgcagctggcatcctgaccatgggccgccgcgcaggcgcagagctagagccacatccctgctctggtcgcggctgtccgaccgt aactaccaccgctttagcaccccggggagggtccggagtctga Orexin Human (nucleic acid sequence):

(SEQ ID NO: 42)

atgaaccttccttccacaaaggtctcctgggccgccgtgacgctactgctgctgctgctgctgccgcccgcgctgttgtcgtccggg gcggctgcacagcccctgcccgactgctgtcgtcaaaagacttgctcttgccgcctctacgagctgctgcacggcgcgggcaatcacg cggccggcatcctcacgctgggcaagcggaggtccgggcccccgggcctccagggtcggctgcagcgcctcctgcaggcagcg gcaaccacgccgcgggcatcctgaccatgggccgccgcgcaggcgcagagccagcgccgcgccctgcctcgggcgccgctgtt ccgcccggccgccgcctccgtcgcgcccggaggacagtccgggatctga Ghrelin-Obestatin Mouse (nucleic acid sequence):

(SEQ ID NO: 43)

atgctgtcttcaggcaccatctgcagtttgctgctactcagcatgctctggatggacatggccatggcaggctccagcttcctgagcccag agcaccagaaagcccagcagagaaaggaatccaagaagccaccagctaaactgcagccacgagctctggaaggctggctccaccc agaggacagaggacaagcagaagagacagaggaggagctggagatcaggttcaatgctcccttcgatgttggcatcaagctgtcag gagctcagtatcagcagcatggccgggccctggggaagtttcttcaggatatcctctgggaagaggtcaaagaggcgccagctgaca agtaa Ghrelin-Obestatin Human (nucleic acid sequence):

(SEQ ID NO: 44)

atgccctccccagggaccgtctgcagcctcctgctcctcggcatgctctggctggacttggccatggcaggctccagcttcctgagccc tgaacaccagagagtccagagaaaggagtcgaagaagccaccagccaagctgcagccccgagctctagcaggctggctccgcccg gaagatggaggtcaagcagaaggggcagaggatgaactggaagtccggttcaacgccccctttgatgttggaatcaagctgtcaggg gttcagtaccagcagcacagccaggccctggggaagtttcttcaggacatcctctgggaagaggccaaagaggccccagccgacaa gtga -continued Cholecystokinin Mouse (nucleic acid sequence):

(SEQ ID NO: 45)

atgaagagcggcgtatgtctgtgcgtggtgatggcagtcctagctgctggcgccctggcgcagccggtagtccctgcagaagctacgg accccgtggagcagcgggcgcaagaggcgccccgaaggcagctgcgggctgtgctccggacggacggcgagccccgagcgcg cctgggcgcactgctagcgcgatacatccagcaggtccgcaaagctccttctggccgcatgtccgttcttaagaacctgcagagcctgg accccagccatagaataagtgaccgggactacatgggctggatggattttggccggcgcagtgccgaggactacgaatacccatcgta g Cholecystokinin Human (nucleic acid sequence):

(SEQ ID NO: 46)

atgaacagcggcgtgtgcctgtgcgtgctgatggcggtactggcggctggcgccctgacgcagccggtgcctcccgcagatcccgc gggctccgggctgcagcgggcagaggaggcgccccgtaggcagctgagggtatcgcagagaacggatggcgagtcccgagcgc acctgggcgccctgctggcaagatacatccagcaggcccggaaagctccttctggacgaatgtccatcgttaagaacctgcagaacct ggaccccagccacaggataagtgaccgggactacatgggctggatggattttggccgtcgcagtgccgaggagtatgagtacccctc ctag Gastrin Mouse (nucleic acid sequence):

(SEQ ID NO: 47)

atgcctcgactgtgtgtgtacatgctggtcttagtgctggctctagctaccttctcggaagcttcttggaagccccgctcccagctacagga tgcatcatctggaccagggaccaatgaggacctggaacagcgccagttcaacaagctgggctcagcctctcaccatcgaaggcagct ggggccccagggtcctcaacacttcatagcagacctgtccaagaagcagaggccacgaatggaggaagaagaagaggcctacgga tggatggactttggccgccgcagtgctgaggaagaccagtag Gastrin Human (nucleic acid sequence):

(SEQ ID NO: 48)

atgcagcgactatgtgtgtatgtgctgatctttgcactggctctggccgccttctctgaagcttcttggaagccccgctccagcagccag atgcacccttaggtacaggggccaacagggacctggagctaccctggctggagcagcagggcccagcctctcatcatcgaaggcag ctgggaccccagggtcccccacacctcgtggcagaccccgtccaagaagcagggaccatggctggaggaagaagaagaagcctatg gatgatggacttcggccgccgcagtgctgaggatgagaactaa Protachykinin-1 (Substance P, Neurokinin A, Neuropeptide K, Neuropeptide gamma) Mouse
(nucleic acid sequence):

(SEQ ID NO: 49)

atgaaaatcctcgtggccgtggcggtctttttttctcgtttccactcaactgtttgcagaggaaatcgatgccaacgatgatctaaattattggt ccgactggtccgacagtgaccagatcaaggaggcaatgccggagccctttgagcatcttctgcagagaatcgcccgaagacccaagc ctcagcagttctttggattaatgggcaagcgggatgctgattcctcagttgaaaaacaagtgggccctgttaaaggctctttatggacatggc cagatctctcacaaaaggcataaaacagattcctttgttggactaatgggcaaaagagctttaaattctgtggcttatgaaagaagcgcga tgcagaactacgaaagaagacgtaaataa Protachykinin-1 (Substance P, Neurokinin A, Neuropeptide K, Neuropeptide gamma) Human
(nucleic acid sequence):

(SEQ ID NO: 50)

atgaaaatcctcgtggccttggcagtctttttttcttgtctccactcagctgtttgcagaagaaataggagccaatgatgatctgaattactggt ccgactggtacgacagcgaccagatcaaggaggaactgccggagccctttgagcatcttctgcagagaatcgcccggagacccaag cctcagcagttctttggattaatgggcaaacgggatgctgattcctcaattgaaaaacaagtgggccctgttaaaggctctttatggacatgg ccagatctctcacaaagacataaaacagattcctttgttggactaatgggcaaaagagctttaaattctgtggcttatgaaaggagtgcaa tgcagaattatgaaagaagacgttaa Proenkephalin-A Mouse (nucleic acid sequence):

(SEQ ID NO: 51)

atggcgcggttcctgaggctttgcacctggctgctggcgcttgggtcctgcctcctggctacagtgcaggcggaatgcagccaggact gcgctaaatgcagctaccgcctggttcgcccaggcgacatcaatttcctggcgtgcacactggaatgtgaaggacagctgccttctttca aaatctgggagacctgcaaggatctcctgcaggtgtccaggcccgagttcccttgggataacatcgacatgtacaaagacagcagcaa acaggatgagagccacttgctagccaagaagtacggaggcttcatgaaacggtacggaggcttcatgaagaagatggacgagctatat -continued cccatggagccagaagaagaagcgaacggaggagagatccttgccaagaggtatggcggcttcatgaagaaggatgcagatgagg gagacaccttggccaactcctccgatctgctgaaagagctactgggaacgggagacaaccgtgcgaaagacagccaccaacaagag agcaccaacaatgacgaagacatgagcaagaggtatgggggcttcatgagaagcctcaaaagaagcccccaactggaagatgaagc aaaagagctgcagaagcgctacggggcttcatgagaagggtgggacgccccgagtggtggatggactaccagaagaggtatggg ggcttcctgaagcgctttgctgagtctctgccctccgatgaagaaggcgaaaattactcgaaagaagttcctgagatagaaaagatac gggggctttatgcggttctga Proenkephalin-A Human (nucleic acid sequence):

(SEQ ID NO: 52)

atggcgcggttcctgacactttgcacttggctgctgttgctcggccccgggctcctggcgaccgtgcgggccgaatgcagccaggattg cgcgacgtgcagctaccgcctagtgcgcccggccgacatcaacttcctggcttgcgtaatggaatgtgaaggtaaactgccttctctga aaatttgggaaacctgcaaggagctcctgcagctgtccaaaccagagcttcctcaagatggcaccagcaccctcagagaaaatagcaa accggaagaaagccatttgctagccaaaaggtatgggggcttcatgaaaaggtatggaggcttcatgaagaaaatggatgagctttatc ccatggagccagaagaagaggccaatggaagtgagatcctcgccaagcggtatgggggcttcatgaagaaggatgcagaggagga cgactcgctggccaattcctcagacctgctaaaagagcttctggaaacaggggacaaccgagagcgtagccaccaccaggatggca gtgataatgaggaagaagtgagcaagagatatgggcttcatgagaggcttaaagagaagccccaactggaagatgaagccaaa gagctgcagaagcgatatgggggcttcatgagaagagtaggtcgcccagagtggtggatggactaccagaaacggtatggaggtttc ctgaagcgctttgccgaggctctgccctccgacgaagaaggcgaaagttactccaaagaagttcctgaaatggaaaaaagatacggag gatttatgagattttaa Proenkephalin-B Mouse (nucleic acid sequence):

(SEQ ID NO: 53)

atggcgtggtccaggctgatgctggcagcttgcctcctcgtgatgccctctaatgttatggcggactgcctgtccctgtgctccctgtgtgc agtgaggattcaggatgggccccgtcccatcaaccccctgatttgctccctggagtgccaggacctggtgccgcccctcagaggagtgg gagacatgccggggcttctcatctttttctcaccctgacggtctctgggctccgtggcaaggatgacttggaagatgaggttgctttggaag aaggctacagtgcactagccaagctcttggaacccgtcctgaaggagctggagaaaagccgactccttaccagcgtcccagaggaaa agttcaggggtctctccagcagctttggcaacggaaaagaatctgagctggcgggtgctgaccggatgaatgatgaagccgcacagg cgggcacgctccatttaatgaggaggacttgagaaaacaggccaaacgctatggcggcttttttgcgcaaatacccccaagaggagttcc gagatggccgggatgaggacgggggccaggatgggatcaggtagggcatgaggacctgtacaaacgctatggggcttcctgc ggcgcattcgccccaagctgaagtgggacaaccagaagcgctatggtggtttcctgcggcgtcagttcaaggtggtgacgcggtccca ggagaaccccaatacctattctgaagatttagatgtttga Proenkephalin-B Human (nucleic acid sequence):

(SEQ ID NO: 54)

atggcctggcagggctggtcctggctgcctgcctcctcatgttcccctccaccacagcggactgcctgtcgcggtgctccttgtgtgct gtaaagacccaggatggtcccaaacctatcaatcccctgatttgctccctgcaatgccaggctgcctgctgccctctgaggaatggga gagatgccagagctttctgtctttttcaccccctccaccctttgggctcaatgacaaggaggacttggggagcaagtcggttggggaagg gccctacagtgagctggccaagctctctgggtcattcctgaaggagctggagaaaagcaagtttctcccaagtatctcaacaaaggaga acactctgagcaagagcctggaggagaagctcaggggtctctctgacgggtttagggagggagcagagtctgagctgatgagggatg cccagctgaacgatggtgccatggagactggcacactctatctcgctgaggaggaccccaaggagcaggtcaaacgctatggggct ttttgcgcaaataccccaagaggagctcagaggtggctggggagggggacgggatagcatgggccatgaggacctgtacaaacgc tatggggcttcttgcggcgcattcgtcccaagctcaagtgggacaaccagaagcgctatggcggttttctccggcgccagttcaaggt ggtgactcggtctcaggaagatccgaatgcttactctggagagctttttgatgcataa Insulin-like growth hormone 1 (IGF-1) Mouse (nucleic acid sequence):

(SEQ ID NO: 55)

atggggaaaatcagcagccttccaactcaattatttaagatctgcctctgtgacttcttgaagataaagatacacatcatgtcgtcttcacac ctcttctacctggcgctctgcttgctcaccttcaccagctccaccacagctggaccagagacccttgcggggctgagctggtggatgct cttcagttcgtgtgtggaccgaggggcttttacttcaacaagcccacaggctatggctccagcattcggagggcacctcagacaggcatt -continued

```
gtggatgagtgttgcttccggagctgtgatctgaggagactggagatgtactgtgcccactgaagcctacaaaagcagcccgctctat ccgtgcccagcgccacactgacatgcccaagactcagaagtccccgtccctatcgacaaacaagaaaacgaagctgcaaaggagaa ggaaaggaagtacatttgaagaacacaagtag
```

Insulin-like growth hormone 1 (IGF-1) Human (nucleic acid sequence):

(SEQ ID NO: 56)

```
atgggaaaaatcagcagtcttccaacccaattatttaagtgctgcttttgtgatttcttgaaggtgaagatgcacaccatgtcctcctcgcatc tcttctacctggcgctgtgcctgctcaccttcaccagctctgccacggctggaccggagacgctctgcggggctgagctggtggatgct cttcagttcgtgtgtggagacaggggctttttatttcaacaagcccacagggtatggctccagcagtcggagggcgcctcagacaggcat cgtggatgagtgctgcttccggagctgtgatctaaggaggctggagatgtattgcgcaccctcaagcctgccaagtcagctcgctctgt ccgtgcccagcgccacaccgacatgcccaagacccagaagtatcagcccccatctaccaacaagaacacgaagtctcagagaagga aaggaagtacatttgaagaacgcaagtag
```

Insulin-like growth hormone 2 (IGF-2) Mouse (nucleic acid sequence):

(SEQ ID NO: 57)

```
atgggcggcagcgtcgccggcttccaggtaccaatggggatcccagtggggaagtcgatgttggtgcttctcatctctttggccttcgcc ttgtgctgcatcgctgcttacggccccggagagactctgtgcggaggggagcttgttgacacgcttcagtttgtctgttcggaccgcggc ttctacttcagcaggccttcaagccgtgccaaccgtcgcagccgtggcatcgtggaagagtgctgcttccgcagctgcgacctggccct cctggagacatactgtgccacccccgccaagtccgagagggacgtgtctacctctcaggccgtacttccggacgacttccccagatac cccgtgggcaagttcttccaatatgacacctggagacagtccgcgggacgcctgcgcagaggcctgcctgccctcctgcgtgcccgc cggggtcgcatgcttgccaaagagctcaaagagttcagagaggccaaacgtcatcgtccctgatcgtgttaccaccccaaagaccccg cccacggggagcctcttcggagatgtccagcaaccatcagtga
```

Insulin-like growth hormone 2 (IGF-2) Human (nucleic acid sequence):

(SEQ ID NO: 58)

```
atgggaatcccaatggggaagtcgatgctggtgcttctcaccttcttggccttcgcctcgtgctgcattgctgcttaccgccccagtgaga ccctgtgcggcggggagctggtggacaccctccagttcgtctgtggggaccgcgcggcttctacttcagcaggcccgcaagccgtgtga gccgtcgcagccgtggcatcgttgaggagtgctgtttccgcagctgtgacctggccctcctggagacgtactgtgctaccccccgccaag tccgagagggacgtgtcgaccccctccgaccgtgcttccggacaacttccccagatacccccgtgggcaagttcttccaaatatgacacctg gaagcagtccacccagcgcctgcgcagggcctgcctgccctcctgcgtgcccgccggggtcacgtgctcgccaaggagctcgag gcgttcagggaggccaaacgtcaccgtcccctgattgctctaccacccaagaccccgcccacggggcgcccccccagagatggc cagcaatcggaagtga
```

Parathyroid hormone (PTH) Mouse (nucleic acid sequence):

(SEQ ID NO: 59)

```
atgatgtctgcaaacaccgtggctaaagtgatgatcatcatgctggcagtctgtcttcttacccaaacggatgggaaacccgtgaggaag agagctgtcagtgaaatacagcttatgcacaacctgggcaaacacctggcctccatggagaggatgcaatggctgagaaggaagctg caagatatgcacaattttgttagtcttggagtccaaatggctgccagagatggcagtcaccagaagcccaccaagaaggaggaaaatgt ccttgttgatggcaatccaaaaagtcttggtgagggagacaaagctgatgtggatgtattagttaaatcaaaatctcagtaa
```

Parathyroid hormone (PTH) Human (nucleic acid sequence):

(SEQ ID NO: 60)

```
atgatacctgcaaaagacatggctaaagtgatgattgtcatgttggcaatttgttttcttacaaaatcggatgggaaatctgttaagaagagat ctgtgagtgaaatacagcttatgcataacctgggaaaacatctgaactcgatggagagagtagaatggctgcgtaagaagctgcaggat gtgcacaattttgttgcccttggagctcctctagctcccagagatgctggttcccagaggccccgaaaaaaggaagacaatgtcttggttg agagccatgaaaaaagtcttggagaggcagacaaagctgatgtgaatgtattaactaaagctaaatcccagtga
```

Parathyroid hormone-related protein (PTHrP) Mouse (nucleic acid sequence):

(SEQ ID NO: 61)

```
atgctgcggaggctggttcagcagtggagtgtcctggtattcctgctcagctactccgtgccctcccgcgggcgttcggtggaggggct tggccgcaggctcaaacgcgctgtgtctgaacatcagctactgcatgacaagggcaagtccatccaagacttgcgccgccgtttcttcct ccaccatctgatcgcggagatccacacagccgaaatcagagctacctcggaggtgtcccccaactccaaacctgctcccaacaccaaa
```

-continued aaccacccgtgcggtttgggtcagacgatgagggcagatacctaactcaggaaaccaacaaggtggagacgtacaaagaacagcc actcaagacacccgggaagaagaagaaaggcaagcctgggaaacgcagagaacaggagaaaaagaagcgaaggactcggtctg cctggccaagcacagctgcgagtggcctgcttgaggaccccctgccccacacctccaggccctcgctggagcccagcttaaggacg cattga Parathyroid hormone-related protein (PTHrP) Human (nucleic acid sequence):

(SEQ ID NO: 62)

atgcagcggagactggttcagcagtggagcgtcgcggtgttcctgctgagctacgcggtgccctcctgcgggcgctcggtggaggt ctcagccgccgcctcaaaagagctgtgtctgaacatcagctcctccatgacaaggggaagtccatccaagatttacggcgacgattcttc cttcaccatctgatcgcagaaatccacacagctgaaatcagagctacctcggaggtgtccctaactccaagccctctccaacacaaa gaaccacccgtccgatttgggtctgatgatgagggcagatacctaactcaggaaactaacaaggtggagacgtacaaagagcagcc gctcaagacacctgggaagaaaagaaaggcaagcccgggaaacgcaaggagcaggaaaagaaaaaacggcgaactcgctctgc ctggttagactctggagtgactgggagtgggctagaaggggaccacctgtctgacacctccacaacgtcgctggagctcgattcacgg aggcattga Osteocalcin Mouse (nucleic acid sequence):

(SEQ ID NO: 63)

atgaggaccatctttctgctcactctgctgaccctggctgcgctctgtctctctgacctcacagatgccaagcccagcggccctgagtctg acaaagccttcatgtccaagcaggagggcaataaggtagtgaacagactccggcgctaccttggagcctcagtccccagcccagatc ccctggagcccaccgggagcagtgtgagcttaaccctgcttgtgacgagctatcagaccagtatggcttgaagaccgcctacaaacg catctatggtatcactatttag Osteocalcin Human (nucleic acid sequence):

(SEQ ID NO: 64)

atgagagccctcacactcctcgccctattggccctggccgcactttgcatcgctggccaggcaggtgcgaagcccagcggtgcagagt ccagcaaaggtgcagcctttgtgtccaagcaggagggcagcgaggtagtgaagagacccaggcgctacctgtatcaatggctggga gccccagtcccctacccggatcccctggagcccaggaggaggtgtgtgagctcaatccggactgtgacgagttggctgaccacatc ggctttcaggaggcctatcggcgcttctacggcccggtctag Urocortin-3 Mouse (nucleic acid sequence):

(SEQ ID NO: 65)

atgctgatgcccacctacttcctgctgccacttctgctgctcctaggaggtccaaggacaagcctctcccacaagttctacaacactggac cagtcttcagctgcctcaacacagccctatctgaggtcaagaagaacaagctggaagatgtgcccttgctgagcaagaagagctttggc cacctgcccacacaagaccctcaggggaagaagatgacaaccaaacgcacctccagatcaaaagaactttctcaggtgccgcgggt gggaatggagctgggagcaccggtacagataccaatcccaggcacagcacaaggggaagctgtacccagacaagcccaaaagc gaccggggcaccaagttcaccctttcccttgatgttcccactaacatcatgaacatcctcttcaacatcgacaaggccaagaatttgcgag ccaaggcagctgccaatgctcagctcatggcacagattgggaagaagaagtaa Urocortin-3 Human (nucleic acid sequence):

(SEQ ID NO: 66)

atgctgatgccggtccacttcctgctgctcctgctgctgctcctgggggcccaggacaggcctcccccacaagttctacaaagccaa gcccattcttcagctgcctcaacaccgccctgtctgaggctgagaagggccagtgggaggatgcatccctgctgagcaagaggagcttc cactacctgcgcagcagagacgcctcttcgggagaggaggagggcaaagagaaaaagactttccccatctctggggccaggg gtggagccagaggcacccggtacagatacgtgtcccaagcacagcccaggggaaagccacgccaggacacggccaagagtcccc accgcaccaagttcaccctgtccctcgacgtcccaccaacatcatgaacctcctcttcaacatcgccaaggccaagaacctgcgtgcc caggcggccgccaatgcccacctgatggcgcaaattgggaggaagaagtag Urocortin-2 Mouse (nucleic acid sequence):

(SEQ ID NO: 67)

atgatgaccaggtgggcactggtggtgttcgtggtcctgatgttggataggatcctatttgtcccaggaactcctatccccaccttccagct cctccctcagaactctctggagacaactcctagctctgtgacctcagagagctcctcaggtaccaccacaggaccctcagcttcctgga gcaactctaaagccagcccttacctagacacccgtgtcatactctccctggatgttcccattggcctcctacggatcttactggaacaggc tcgttacaaggctgccaggaatcaggctgccactaatgctcaaatactagcccatgttggccgccgctga Urocortin-2 Human (nucleic acid sequence):
(SEQ ID NO: 68)
atgaccaggtgtgctctgctgttgctgatggtcctgatgttgggcagagtcctggttgtcccagtgaccccctatcccaaccttccagctccg ccctcagaattctccccagaccactccccgacctgcggcctcagagagcccctcagctgctcccacatggccgtgggctgcccagag ccactgcagccccaccgccacctggctcgcgcattgtcctatcgctggatgtccccatcggcctcttgcagatcttactggagcaagc ccgggccagggctgccaggagcaggccaccaccaacgcccgcatcctggcccgtgtcggccactgctga Urocortin-1 Mouse (nucleic acid sequence):
(SEQ ID NO: 69)
atgatacagaggggacgcgctacgctcctggtggcgttgctgctcttggcacagcttcgcccggagagcagccagtggagcccagcg gctgcggcggcaactggggtccaggatccgaatctgcgatggagccctggagtgcggaatcagggcggcggcgtccgcgcgctcc tcttgctgttagcggagcgcttcccgcgccgcgcaggatctgagcctgcgggcgagcggcagcgacgggacgaccctccactgtcc atcgacctcaccttccacctgctgcggaccctgctggagctagctcggacacagagccagcgcgagcgcgcagagcagaaccgcat catattcgattcggtgggcaagtga Urocortin-1 Human (nucleic acid sequence):
(SEQ ID NO: 70)
atgaggcaggcgggacgcgcagcgctgctggccgcgctgctgctcctggtacagctgtgccctgggagcagccagaggagccccg aggcggccggggtccaggaccgagtctgcgctggagccccggggcacggaaccagggtggcggggcccgcgcgctcctcttgc tgctggcggagcgcttcccgcgccgcgcggggcccggccgattgggactcgggacggcaggcgagcggccgcgcggcgggacaac ccttctctgtccattgacctcaccttccacctgctgcggaccctgctggagctggcgcggacgcagagccagcgggagcgcgccgagc agaaccgcatcatattcgactcggtgggcaagtga FGF23 Mouse (nucleic acid sequence):
(SEQ ID NO: 71)
Atgctagggacctgccttagactcctggtgggcgtgctctgcactgtctgcagcttgggcactgctagagcctatccggacacttcccc attgcttggctccaactggggaagcctgacccacctgtacacggctacagccaggaccagctatcacctacagatccatagggatggtc atgtagatggcaccccccatcagaccatctacagtgccctgatgattacatcagaggacgccggctctgtggtgataacaggagccatg actcgaaggttcctttgtatggatctccacggcaacattttggatcgcttcacttcagcccagagaattgcaagttccgccagtggacgct ggagaatggctatgacgtctacttgtcgcagaagcatcactacctggtgagcctgggccgcgccaagcgcatcttccagccgggcacc aacccgccgcccttctcccagttcctggctcgcaggaacgaggtcccgctgctgcatttctacactgttcgcccacggcgccacacgcg cagcgccgaggaccaccggagcgcgacccactgaacgtgctcaagccgcggccccgcgccacgcctgtgcctgtatcctgctctc gcgagctgccgagcgcagaggaaggtggccccgcagccagcgatcctctgggggtgctgcgcagaggccgtggagatgctcgcg ggggcgcggggagcgcggataggtgtcgccccctttcccaggttcgtctag FGF23 Human (nucleic acid sequence):
(SEQ ID NO: 72)
Atgttgggggcccgcctcaggctctgggtctgtgccttgtgcagcgtctgcagcatgagcgtcctcagagcctatcccaatgcctcccc actgctcggctccagctggggtggcctgatccacctgtacacagccacagccaggaacagctaccacctgcagatccacaagaatgg ccatgtggatggcgcacccccatcagaccatctacagtgccctgatgatcagatcagaggatgctggctttgtggtgattacaggtgtgat gagcagaagatacctctgcatggatttcagaggcaacattttggatcacactatttcgacccggagaactgcaggttccaacaccagac gctggaaaacgggtacgacgtctaccactctcctcagtatcacttcctggtcagtctgggccgggcgaagagagccttcctgccaggca tgaacccacccccgtactcccagttcctgtcccggaggaacgagatcccctattcacttcaacacccccataccacggcggcacac ccggagcgccgaggacgactcggagcgggaccccctgaacgtgctgaagcccgggcccggatgaccccggcccggcctcctg ttcacaggagctcccgagcgccgaggacaacagcccgatggccagtgacccattaggggtggtcaggggcggtcgagtgaacacg cacgctgggggaacgggcccggaaggctgccgccccttcgccaagttcatctag IL1B Mouse (nucleic acid sequence):
(SEQ ID NO: 73)
Atggcaactgttcctgaactcaactgtgaaatgccaccttttgacagtgatgagaatgacctgttctttgaagttgacggacccccaaaaga tgaagggctgcttccaaacctttgacctgggctgtcctgatgagagcatccagcttcaaatctcgcagcagcacatcaacaagagcttca

```
ggcaggcagtatcactcattgtggctgtggagaagctgtggcagctacctgtgtctttcccgtggaccttccaggatgaggacatgagca
ccttctttccttcatctttgaagaagagcccatcctctgtgactcatgggatgatgatgataacctgctggtgtgtgacgttcccattagaca
actgcactacaggctccgagatgaacaacaaaaaagcctcgtgctgtcggacccatatgagctgaaagctctccacctcaatggacag
aatatcaaccaacaagtgatattctccatgagctttgtacaaggagaaccaagcaacgacaaaatacctgtggccttgggcctcaagg
aaagaatctatacctgtcctgtgtaatgaaagacggcacacccaccctgcagctggagagtgtggatcccaagcaatacccaaagaag
aagatggaaaaacggtttgtcttcaacaagatagaagtcaagagcaaagtggagtttgagtctgcagagttccccaactggtacatcagc
acctcacaagcagagcacaagcctgtcttcctgggaaacaacagtggtcaggacataattgacttcaccatggaatccgtgtcttcctaa
```

IL1B Human (nucleic acid sequence):
(SEQ ID NO: 74)
```
Atggcagaagtacctgagctcgccagtgaaatgatggcttattacagtggcaatgaggatgacttgttctttgaagctgatggccctaaa
cagatgaagtgctccttccaggacctggacctctgccctctggatggcggcatccagctacgaatctccgaccaccactacagcaagg
gcttcaggcaggccgcgtcagttgttgtggccatggacaagctgaggaagatgctggttccctgcccacagaccttccaggagaatga
cctgagcaccttctttcccttcatctttgaagaagaacctatcttcttcgacacatgggataacgaggcttatgtgcacgatgcacctgtacg
atcactgaactgcacgctccgggactcacagcaaaaaagcttggtgatgtctggtccatatgaactgaaagctctccacctccagggac
aggatatggagcaacaagtggtgttctccatgtcctttgtacaaggagaagaaagtaatgacaaaatacctgtggccttgggcctcaagg
aaaagaatctgtacctgtcctgcgtgttgaaagatgataagcccactctacagctggagagtgtagatcccaaaaattacccaaagaaga
agatggaaaagcgatttgtcttcaacaagatagaaatcaataacaagctggaatttgagtctgcccagttccccaactggtacatcagcac
ctctcaagcagaaaacatgcccgtcttcctgggagggaccaaaggcggccaggatataactgacttcaccatgcaatttgtgtcttccta
a
```

TNFA Mouse (nucleic acid sequence):
(SEQ ID NO: 75)
```
Atgagcacagaaagcatgatccgcgacgtggaactggcagaagaggcactcccccaaaagatggggggcttccagaactccaggc
ggtgcctatgtctcagcctcttctcattcctgcttgtggcaggggccaccacgctcttctgtctactgaacttcggggtgatcggtccccaa
agggatgagaagttcccaaatggcctccctctcatcagttctatggcccagaccctcacactcagatcatcttctcaaaattcgagtgaca
agcctgtagcccacgtcgtagcaaaccaccaagtggaggagcagctggagtggctgagccagcgcgccaacgccctcctggccaa
cggcatggatctcaaagacaaccaactagtggtgccagccgatgggttgtaccttgtctactcccaggttctcttcaagggacaaggctg
ccccgactacgtgctcctcacccacaccgtcagccgatttgctatctcataccaggagaaagtcaacctcctctctgccgtcaagagccc
ctgccccaaggacacccctgaggggctgagctcaaaccctggtatgagcccatatacctgggaggagtcttccagctggagaaggg
ggaccaactcagcgctgaggtcaatctgcccaagtacttagactttgcggagtccgggcaggtctactttggagtcattgctctgtga
```

TNFA Human (nucleic acid sequence):
(SEQ ID NO: 76)
```
Atgagcactgaaagcatgatccgggacgtggagctggccgaggaggcgctccccaagaagacaggggggccccagggctccag
gcggtgcttgttcctcagcctcttctccttcctgatcgtggcaggcgccaccacgctcttctgcctgctgcactttggagtgatcggcccc
agagggaagagttccccagggacctctctctaatcagccctctggcccaggcagtcagatcatcttctcgaaccccgagtgacaagcct
gtagcccatgttgtagcaaaccctcaagctgaggggcagctccagtggctgaaccgccgggccaatgccctcctggccaatggcgtg
gagctgagagataaccagctggtggtgccatcagagggcctgtacctcatctactcccaggtcctcttcaagggccaaggctgcccctc
cacccatgtgctcctcacccacaccatcagccgcatcgccgtctcctaccagaccaaggtcaacctcctctctgccatcaagagcccct
gccagggggagacccccagggggctgaggccaagccctggtatgagcccatctatctgggaggggtcttccagctggagaaggt
gaccgactcagcgctgagatcaatcggcccgactatctcgactttgccgagtctgggcaggtctactttgggatcattgccctgtga
```

IFNG Mouse (nucleic acid sequence):
(SEQ ID NO: 77)
```
Atgaacgctacacactgcatcttggctttgcagctcttcctcatggctgtttctggctgttactgccacggcacagtcattgaaagcctaga
aagtctgaataactattttaactcaagtggcatagatgtggaagaaaagagtctcttcttggatatctggaggactggcaaaaggatggt
gacatgaaaatcctgcagagccagattatctctttctacctcagactcttttgaagtcttgaaagacaatcaggccatcagcaacaacataa
gcgtcattgaatcacacctgattactaccttcttcagcaacagcaaggcgaaaaaggatgcattcatgagtattgccaagtttgaggtcaa
```

-continued caacccacaggtccagcgccaagcattcaatgagctcatccgagtggtccaccagctgttgccggaatccagcctc<u>aggaagcggaa</u>
<u>a</u>aggagtcgctgctga IFNG Human (nucleic acid sequence):

(SEQ ID NO: 78)

Atgaaatatacaagttatatcttggcttttcagctctgcatcgttttgggttctcttggctgttactgccaggacccatatgtaaaagaagcag aaaaccttaagaaatattttaatgcaggtcattcagatgtagcggataatggaactcttttcttaggcattttgaagaattggaaagaggaga gtgacagaaaaataatgcagagccaaattgtctccttttacttcaaacttttaaaaactttaaagatgaccagagcatccaaaagagtgtg gagaccatcaaggaagacatgaatgtcaagttttcaatagcaacaaaaagaaacgagatgacttcgaaaagctgactaattattcggta actgacttgaatgtccaacgcaaagcaatacatgaactcatccaagtgatggctgaactgtcgccagcagctaaaacagggaagcgaa aaaggagtcagatgctgtttcgaggt<u>cgaagag</u>catcccagtaa Sortilin Mouse (nucleic acid sequence):

(SEQ ID NO: 79)

Atggagcggccccggggagctgcggacggccttttgcgctggcccctcggcctcctcctgctccttcaactgctgcctcctgccgccg tcggccaggaccggctggacgcgccgccgccgccgcgcctcctctgctgcgctgggccggtccggtcggggtgagctgggggct gcgcgccgccgcgcccgggggccccgtcccccgcgctggccgttgg<u>cgccgc</u>ggcgcgcccgccgaggaccaagactgcggcc gcctcccggacttcatcgccaagctgaccaacaatacgcaccagcatgtctttgatgacctcagtggctcagtgtccttgtcctgggttgg agacagcactggggttattctcgtcctgaccactttccaagtgcctctggtaattgtgagctttggacagtccaagttgtatcgaagtgagg attatggaaagaactttaaggatattacaaatctcatcaataacaccttcattcggacggaatttggcatggctattggtcctgagaactctg gaaaggtgatactaacagcggaggtgtccgggggaagccgaggcggaagagtgttcaggtcatcagactttgccaagaactttgtgc aaacagatctccccttttcatcctctgacgcagatgatgtacagccctcagaattctgattacctgttagctctcagcaccgaaaatggcctg tgggtgtccaagaattttggggaaaaatgggaagaaatccacaaagcagtatgtttggccaaatggggaccaaacaacatcatcttcttt accacccatgtgaatggctcctgcaaagctgatcttggtgccctggaattatggagaacatccgacttgggaaaaaccttcaaaaccatt ggtgtgaaaatctactcctttggtcttgggggccgtttccttttttgcctctgtgatggctgataaggacacaacaagaaggatccatgtgtca acagaccaggggacacatggagcatggcacaacttccttctgtgggacaggaacagttctactccatcctggcagccaatgaggaca tggtcttcatgcatgtagatgaacctggagataccgggtttggcaccatctttacctctgatgatcgaggcattgtctactccaagtctctgg acagacatctctataccaccacaggcggggagacggactttaccaacgtgacttccctccgtggggtctatataacaagcacgctctca gaagataactctattcagagcatgatcacttttgaccagggaggacggtgggagcacctgcggaagccggagaacagcaagtgcgac gctaccgcaaagaacaagaacgagtgcagccttcatatccatgcttcttatagcatctcccagaagctaaacgttccaatggccccacttt ccgagcccaatgctgtgggcatagtcatcgctcacgtagtgtgggagatgccatctcggtgatggtcccagatgtgtacatctcagatg atgggggttactcctgggcgaagatgctagaaggaccacattactataccatcctggactctggaggcatcattgtggccattgagcaca gcaaccgtcctatcaatgtgattaagttctccacagatgaaggccagtgctggcagagctatgtgttcacacaggagcccatctacttcac tgggcttgcttccgagcctggagccaggtccatgaacatcagcatctggggattcacagagtctttcattacccgccagtgggtctcctac acagtcgatttcaaagacatccttgagcggaattgtgaagaggatgactataccacgtggctggcacactccacagaccctggagatta caaagacggctgcattttgggctataaagaacagttcctacggctacggaagtcatccgtctgtcagaatggtcgagactatgttgtggc caagcagccatccgtctgtccgtgttccctggaggacttcctctgtgactttggctacttccgtccggagaacgcctcagagtgcgtgga gcagcctgaactgaaggggcatgagttagagttctgtctgtacggcaaggaggagcacctgacaacaaatgggtaccggaaaatccc aggagacaaatgccaaggtgggatgaatcccgccagagaagtaaaagacttgaaaaagaaatgcacaagcaacttcttgaaccccac aaagcaggactcccgcccacagggacacagcttgtcccagaatccagctccgcctcctcttggatacactgaaaacacacacttcctat ctcctacccagaagcagaattccaagtcaaattctgtccctattatcctggccatcgtgggactgatgcttgtcacagtcgtagcaggagt cctcattgtgaagaaatatgtctgtggcggaaaggttcctggtgcaccggtactcggtgctacagcagcacgcagaggctgacggcgta gaggctttggattcaacctcccacgctaaaagcggatatcacgacgactcagatgaggacctcctggaatag -continued Sortilin Human (nucleic acid sequence):
(SEQ ID NO: 80)
Atggagcggccctggggagctgcggacggcctctcgcgctggccccatggcctcggcctcctcctcctcctgcagctgctgccgcc gtcgaccctcagccaggaccggctggacgcgccgccgccgcccgctgcgccgctgccgcgctggtctggccccatcggggtgagc tgggggctgcgggcggccgcagccgggggcgcgtttccccgcggcggccgttgg*cgtcgc*agcgcgccgggcgaggacgagga gtgcggccgggtccgggacttcgtcgccaagctggccaacaacacgcaccagcatgtgtttgatgatctcagaggctcagtatccttgt cctgggttggagatagcactggggtcattctagtcttgactaccttccatgtaccactggtaattatgacttttggacagtccaagctatatc gaagtgaggattatgggaagaactttaaggatattacagatctcatcaataacacctttattcggactgaatttggcatggctattggtcctg agaactctggaaaggtggtgttaacagcagaggtgtctggaggaagtcgtggaggaagaatctttagatcatcagattttgcgaagaatt ttgtgcaaacagatctcccttttcatcctctcactcagatgatgtatagccctcagaattctgattatcttttagctctcagcactgaaaatggc ctgtgggtgtccaagaattttgggggaaaatgggaagaaatccacaaagcagtatgtttggccaaatggggatcagacaacaccatctt ctttacaacctatgcaaatggctcctgcaaagctgaccttggggctctggaattatggagaacttcagacttgggaaaaagcttcaaaact attggtgtgaaaatctactcatttggtcttggggacgtttcctttttgcctctgtgatggctgataaggatacaacaagaaggatccacgttt caacagatcaaggggacacatggagcatggcccagctcccctccgtgggacaggaacagttctattctattctggcagcaaatgatga catggtattcatgcatgtagatgaacctggagacactggggtttggcacaatctttacctcagatgatcgaggcattgtctattccaagtctttt ggaccgacatctctacactaccacaggcggagagacggactttaccaacgtgacctcctccgcggcgtctacataacaagcgtgctc tccgaagataattctatccagaccatgatcacttttgaccaaggaggaaggtggacgcacctgaggaagcctgaaaacagtgaatgtga tgtacagcaaaaaacaagaatgagtgcagccttcatattcatgcttcctacagcatctcccagaaactgaatgttccaatggccccactc tcagagccgaatgccgtaggcattgtcattgctcatggtagcgtgggggatgccatctcagtgatggttccagatgtgtacatctcagatg atgggggttactcctggacaaagatgctggaaggaccccactattacaccatcctggattctggaggcatcattgtggccattgagcaca gcagccgtcctatcaatgtgattaagttctccacagacgaaggtcaatgctggcaaacctacacgttcaccagggacccccatctatttcac tggcctagcttcagaacctggagctaggtccatgaatatcagcatttggggcttcacagaatctttcctgaccagccagtgggtctcctac accattgattttaaagatatccttgaaaggaactgtgaagagaaggactataccatggctggcacactccacagaccctgaagattatg aagatggctgcattttgggctacaaagaacagtttctgcggctacgcaagtcatccgtgtgtcagaatggtcgagactatgttgtgaccaa gcagccctccatctgcctctgttccctggaggactttctctgtgattttggctactaccgtccagaaaatgactccaagtgtgtggaacagc cagaactgaagggccacgacctggagttttgtctgtacgaagagaagaacacctaacaacaaatgggtaccggaaaattccagggg acaaatgccagggtggggtaaatccagttcgagaagtaaaagacttgaaaaagaaatgcacaagcaacttttgagtccggaaaaaca gaattccaagtcaaattctgttccaattatcctggccatcgtgggattgatgctggtcacagtcgtagcaggagtgctcattgtgaagaat atgtctgtggggaaggttcctggtgcatcgatactctgtgctgcagcagcatgcagaggccaatggtgtggatggtgtggatgctttgg acacagcctcccacactaataaaagtggttatcatgatgactcagatgaggacctcttggaatag Neuropeptide W Mouse (nucleic acid sequence):
(SEQ ID NO: 81)
Ctggcgtctaacagagaagtgcggggccctgggcccgggactccaggaaccggcccctgctgccctgctgctgcttctgctcttg ctaccgctgccgccagcgcctggtataagcacgtggcgagtcccgctatcacacagtgggtcgtgcctccgggctgctcatgggg ctgcgccgctcgccctaccagtgg*cgccgt*gccctgggcggggctgctggaccctctcccggctcccaggaccggtcgcccgcgg cgctctcctgcttccttcctcagggcaggagctgtgggaggtacgaagcaggagctcacctgcagggcttcccgtccatgcaccctgg agtccgcgggacctggagggagtccgccaaccggagcagtcgctaagccttcactcctggatctcagaggagcccgctgctagagc cttcggagagacgcttcgtgcccagccatggttcctgcagcaagtcatctttgccgatcctgtcaggcccaagaaccgatggcgccccc atgcttga Neuropeptide W Human (nucleic acid sequence):
(SEQ ID NO: 82)
Ctggcgtggcgcccaggggagcggggggctcccgcgagccggccgcggctggcactgctgctgcttctgctcctgctgccgctgc cctccggcgcgtggtacaagcacgtggcgagtccccgctaccacacggtgggccgcgccgctggcctgctcatggggctgcgtcgc -continued tcaccctatctgtggcgccgcgcgctgcgcgcggccgccgggcccctggccagggacaccctctcccccgaacccgcagcccgcg aggctcctctcctgctgccctcgtgggttcaggagctgtgggagacgcgacgcaggagctcccaggcagggatcccgtccgtgcgc cccggagcccgcgcgccccagagcctgcgctggaaccggagtccctggacttcagcggagctggccagagacttcggagagacgt ctcccgcccagcggtggaccccgcagcaaaccgccttggcctgccctgcctggccccggaccgttctga CART Mouse (nucleic acid sequence):

(SEQ ID NO: 83)

Atggagagctcccgcctgcggctgctaccctcctgggcgccgccctgctgctactgctaccttgctgggtgcccgtgcccaggagg acgccgagctgcagccccgagccctggacatctactctgccgtggatgatgcgtcccacgagaaggagctgatcgaagcgttgcaag aagtcctgaagaagctcaagagtaaacgcattccgatctacgagaagaagtacggccaagtccccatgtgtgacgctggagagcagt gcgcagtgaggaaaggggccaggatcgggaagctgtgtgactgtccccgaggaacttcctgcaattctttcctcttgaagtgcttgtga CART Human (nucleic acid sequence):

(SEQ ID NO: 84)

Atggagagctcccgcgtgaggctgctgcccctcctgggcgccgccctgctgctgatgctacctctgttgggtacccgtgcccaggag gacgccgagctccagccccgagccctggacatctactctgccgtggatgatgcctcccacgagaaggagctgatcgaagcgctgcaa gaagtcttgaagaagctcaagagtaaacgtgttcccatctatgagaagaagtatggccaagtccccatgtgtgacgccggtgagcagtg tgcagtgaggaaaggggcaaggatcgggaagctgtgtgactgtccccgaggaacctcctgcaattccttcctcctgaagtgcttatga TGFB1 Mouse (nucleic acid sequence):

(SEQ ID NO: 85)

Atgccgccctcggggctgcggctactgccgcttctgctcccactcccgtggcttctagtgctgacgcccggaggccagccgcggga ctctccacctgcaagaccatcgacatggagctggtgaaacgcgaagcgcatcgaagccatccgtggccagatcctgtccaaactaagg ctcgccagtcccccaagccaggggaggtaccgcccggcccgctgcccgaggcggtgctcgctttgtacaacagcacccgcgacc gggtggcaggcgagagcgccgacccagagccggagcccgaagcggactactatgctaaagaggtcacccgcgtgctaatggtgga ccgcaacaacgccatctatgagaaaaccaaagacatctcacacagtatatatatgttcttcaatacgtcagacattcgggaagcagtgcc cgaaccccattgctgtcccgtgcagagctgcgcttgcagagattaaaatcaagtgtggagcaacatgtggaactctaccagaaatata gcaacaattcctggcgttaccttggtaaccggctgctgaccccactgatacgcctgagtggctgtcttttgacgtcactggagttgtacg gcagtggctgaaccaaggagacggaatacagggctttcgattcagcgctcactgctcttgtgacagcaaagataacaaactccacgtg gaaatcaacgggatcagccccaaacgtcggggcgacctgggcaccatccatgacatgaaccggcccttcctgctcctcatggccacc cccctggaaagggcccagcacctgcacagctcacggcaccggagagccctggataccaactattgcttcagctccacagagaagaa ctgctgtgtgcggcagctgtacattgactttaggaaggacctgggttggaagtggatccacgagcccaagggctaccatgccaacttct gtctgggaccctgcccctatatttggagcctggacacacagtacagcaaggtccttgccctctacaaccaacacaacccgggcgcttcg gcgtcaccgtgctgcgtgccgcaggctttggagccactgcccatcgtctactacgtgggtcgcaagcccaaggtggagcagttgtcca acatgattgtgcgctcctgcaagtgcagctga TGFB1 Human (nucleic acid sequence):

(SEQ ID NO: 86)

Atgccgccctccgggctgcggctgctgccgctgctgctaccgctgctgtggctactggtgctgacgcctggccggcggccgcggg actatccacctgcaagactatcgacatggagctggtgaagcggaagcgcatcgaggccatccgcggccagatcctgtccaagctgcg gctcgccagccccccgagccaggggaggtgccgccggccgctgcccgaggccgtgctcgccctgtacaacagcacccgcga ccgggtggccggggagagtgcagaaccggagcccgagcctgaggccgactactacgcaaggaggtcacccgcgtgctaatggtg gaaacccacaacgaaatctatgacaagttcaagcagagtacacacagcatatatatgttcttcaacacatcagagctccgagaagcggt acctgaaccccgtgttgctctcccggggcagagctgcgtctgctgaggctcaagttaaaagtggagcagcacgtggagctgtaccgaaa tacagcaacaattcctggcgatacctcagcaaccggctgctggcacccagcgactcgccagagtggttatcttttgatgtcaccggagtt gtgcggcagtggttgagccgtggaggggaaattgagggctttcgccttagcgcccactgctcctgtgacagcaggataacacactgc aagtggacatcaacgggttcactaccggccgccgaggtgacctggccaccattcatggcatgaaccggcctttcctgcttctcatggcc acccccgctggagagggcccagcatctgcaaagctcccggcaccgccgagccctggacaccaactattgcttcagctccacgagaa gaactgctgcgtgcggcagctgtacattgacttccgcaaggacctcggctggaagtggatccacgagcccaagggctaccatgccaa -continued cttctgcctcgggccctgcccctacatttggagcctggacacgcagtacagcaaggtcctggccctgtacaaccagcataacccgggc gcctcggcggcgccgtgctgcgtgccgcaggcgctggagccgctgcccatcgtgtactacgtgggccgcaagcccaaggtggagc agctgtccaacatgatcgtgcgctcctgcaagtgcagctga TGFB2 Mouse (nucleic acid sequence):

(SEQ ID NO: 87)

Atgcactactgtgtgctgagcacctttttgctcctgcatctggtcccggtggcgctcagtctgtctacctgcagcaccctcgacatggatc agtttatgcgcaagaggatcgaggccatccgcgggcagatcctgagcaagctgaagctcaccagccccccggaagactatccggag ccggatgaggtccccccggaggtgatttccatctacaacagtaccagggacttactgcaggagaaggcaagccggaggcagccgc ctgcgagcgcgagcggagcgacgaggagtactacgccaaggaggtttataaaatcgacatgccgtcccacctcccctccgaaaatgc catcccgcccactttctacagaccctacttcagaatcgtccgctttgatgtctcaacaatggagaaaaatgcttcgaatctggtgaaggca gagttcagggtcttccgcttgcaaaaccccaaagccagagtggccgagcagcggattgaactgtatcagatccttaaatccaaagactt aacatctcccacccagcgctacatcgatagcaaggttgtgaaaaccagagcggagggtgaatggctctccttcgacgtgacagacgct gtgcaggagtggcttcaccacaaagacaggaacctgggggtttaaaataagtttacactgcccctgctgtaccttcgtgccgtctaataatt acatcatcccgaataaaagcgaagagctcgaggcgagatttgcaggtattgatggcacctctacatatgccagtggtgatcagaaaact ataaagtccactaggaaaaaaaccagtgggaagaccccacatctcctgctaatgttgttgccctcctacagactggagtcacaacagtcc agccggcggaagaagcgcgctttggatgctgcctactgctttagaaatgtgcaggataattgctgccttcgccctctttacattgatttttaa gagggatcttggatggaaatggatccatgaacccaaagggtacaatgctaacttctgtgctggggcatgcccatatctatggagttcaga cactcaacacaccaaagtcctcagcctgtacaacaccataaatcccgaagcttccgcttccccttgctgtgtgtcccaggatctggaacc actgaccattctctattacattggaaatacgcccaagatcgaacagctttccaatatgattgtcaagtcttgtaaatgcagctaa TGFB2 Human (nucleic acid sequence):

(SEQ ID NO: 88)

Atgcactactgtgtgctgagcgcttttctgatcctgcatctggtcacggtcgcgctcagcctgtctacctgcagcacactcgatatggacc agttcatgcgcaagaggatcgaggcgatccgcgggcagatcctgagcaagctgaagctcaccagtccccagaagactatcctgagc ccgaggaagtccccccggaggtgatttccatctacaacagcaccaggggacttgctccaggagaaggcgagccggagggcggccgc ctgcgagcgcgagaggagcgacgaagagtactacgccaaggaggtttacaaaatagacatgccgcccttcttcccctccgaaactgtc tgcccagttgttacaacaccctctggctcagtgggcagcttgtgctccagacagtcccaggtgctctgtgggtaccttgatgccatcccgc ccactttctacagaccctacttcagaattgttcgatttgacgtctcagcaatggagaagaatgcttccaatttggtgaaagcagagttcaga gtctttcgtttgcagaacccaaaagccagagtgcctgaacaacggattgagctatatcagattctcaagtccaaagatttaacatctccaac ccagcgctacatcgacagcaaagttgtgaaaacaagagcgaaggcgaatggctctccttcgatgtaactgatgctgttcatgaatggct tcaccataaagacaggaacctgggatttaaaataagcttacactgtccctgctgcactttgtaccatctaataattacatcatcccaaataa aagtgaagaactagaagcaagatttgcaggtattgatggcacctccacatataccagtggtgatcagaaaactataaagtccactaggaa aaaaaacagtgggaagaccccacatctcctgctaatgttattgccctcctacagacttgagtcacaacagaccaaccggcggaagaag cgtgctttggatgcggcctattgctttagaaatgtgcaggataattgctgcctacgtccactttacattgattcaagagggatctagggtgg aaatggatacacgaacccaaagggtacaatgccaacttctgtgctggagcatgcccgtatttatggagttcagacactcagcacagcag ggtcctgagcttatataataccataaatccgaagcatctgcttctccttgctgcgtgtcccaagatttagaacctctaaccattctctactac attggcaaaacacccaagattgaacagctttctaatatgattgtaaagtcttgcaaatgcagctaa TGFB3 Mouse (nucleic acid sequence):

(SEQ ID NO: 89)

Atgaagatgcacttgcaaagggctctggtagtcctggccctgctgaacttggccacaatcagcctctctctgtccacttgcaccacgttg gacttcggccacatcaagaagaagagggtggaagccattagggggacagatcttgagcaagctcaggctcaccagccccctgagcc atcggtgatgacccacgtccctatcaggtcctggcactttacaacagcacccgggagttgctggaagagatgcacggggagaggga ggaaggctgcactcaggagacctcggagtctgagtactatgccaaagagatccataaattcgacatgatccagggactggcggagca caatgaactggccgtctgcccccaaaggaattacctctaaggttttttcgtttcaatgtgtcctcagtggagaaaaatggaaccaatctgttcc -continued gggcagagttccgggtcttgcgggtgcccaaccccagctccaagcgcacagagcagagaattgagctcttccagatacttcgaccgg atgagcacatagccaagcagcgctacataggtggcaagaatctgcccacaaggggcaccgctgaatggctgtctttcgatgtcactga cactgtgcgcgagtggctgttgaggagagagtccaacttgggtctggaaatcagcatccatgtccatgtcacacctttcagcccaatgg agacatactggaaaatgttcatgaggtgatggaaatcaaattcaaaggagtggacaatgaagatgaccatggccgtggagacctgggg cgtctcaagaagcaaaaggatcaccacaacccacacctgatcctcatgatgatcccccacaccgactggacagcccaggccagggc agtcag<u>aggaag</u>aagagggccctggacaccaattactgcttccgcaacctggaggagaactgctgtgtacgcccccttttatattgacttc cggcaggatctaggctggaaatgggtccacgaacctaagggttactatgccaacttctgctcaggcccttgcccatacctccgcagcgc agacacaacccatagcacggtgcttggactatacaacaccctgaacccagaggcgtctgcctcgccatgctgcgtccccaggacctg gagcccctgaccatcttgtactatgtgggcagaaccccaaggtggagcagctgtccaacatggtggtgaagtcgtgtaagtgcagctg a TGFB3 Human (nucleic acid sequence):

(SEQ ID NO: 90)

Atgaagatgcacttgcaaagggctctggtggtcctggccctgctgaactttgccacggtcagcctctctctgtccacttgcaccaccttg gacttcggccacatcaagaagaagagggtggaagccattaggggacagatcttgagcaagctcaggctcaccagcccccctgagcc aacggtgatgacccacgtccctatcaggtcctggccctttacaacagcacccgggagctgctggaggagatgcatggggagaggga ggaaggctgcacccaggaaaacaccgagtcggaatactatgccaaagaaatccataaaattcgacatgatccaggggctggcggagc acaacgaactggctgtctgccctaaaggaattacctccaaggttttccgcttcaatgtgtcctcagtggagaaaaatagaaccaacctatt ccgagcagaattccgggtcttgcgggtgcccaaccccagctctaagcggaatgagcagaggatcgagctcttccagatccttcggcca gatgagcacattgccaaacagcgctatatcggtggcaagaatctgcccacacggggcactgccgagtggctgtgtctttgatgtcactga cactgtgcgtgagtggctgttgagaagagagtccaacttaggtctagaaatcagcattcactgtccatgtcacacctttcagcccaatgga gatatcctggaaaacattcacgaggtgatggaaatcaaattcaaaggcgtggacaatgaggatgaccatggccgtggagatctgggc gcctcaagaagcagaaggatcaccacaaccctcatctaatcctcatgatgattcccccacaccggctcgacaacccgggccagggg gtcag<u>aggaag</u>aagcgggctttggacaccaattactgcttccgcaacttggaggagaactgctgtgtgcgcccctctacattgacttcc gacaggatctgggctggaagtgggtccatgaacctaagggctactatgccaacttctgctcaggcccttgcccatacctccgcagtgca gacacaacccacagcacggtgctgggactgtacaacactctgaaccctgaagcatctgcctcgccttgctgcgtgccccaggacctgg agcccctgaccatcctgtactatgttgggaggaccccccaaagtggagcagctctccaacatggtggtgaagtcttgtaaatgtagctga PDGF alpha Mouse (nucleic acid sequence):

(SEQ ID NO: 91)

Atgaggacctgggcttgcctgctgctcctcggctgcggatacctcgcccatgccctggccgaggaagccgagataccccgggagttg atcgagcggctggctcgaagtcagatccacagcatccggaccctccagcgactcttggagatagactccgtaggggctgaggatgcc ttggagacaagtctgagagcccatgggtcccatgccattaaccatgtgcccgagaagcggcctgtgcccatt<u>cgcagg</u>aagagaagta ttgaggaagccattcctgcagtttgcaagaccaggacggtcatttacgagatacctcggagccaggtggaccccacatcggccaacttc ctgatctggcccccatgtgtggaggtgaagcgctgcactggctgttgtaacaccagcagcgtcaagtgccagccttcacgggtccacc accgcagtgtcaaggtggccaaagtggagtatgtcaggaagaagccaaaattgaaagaggtccaggtgaggttagaggaacacctg gagtgtgcatgtgcgacctccaacctgaacccagaccatcgggaggaggagacagatgtgaggtga PDGF alpha Human (nucleic acid sequence):

(SEQ ID NO: 92)

Atgaggaccttggcttgcctgctgctcctcggctgcggataccctcgcccatgttctggccgaggaagccgagatccccgcgaggtga tcgagaggctggcccgcagtcagatccacagcatccgggacctccagcgactcctggagatagactccgtagggagtgaggattcttt ggacaccagcctgagagctcacgggtccatgccactaagcatgtgcccgagaagcggcccctgcccatt<u>cggagg</u>aagagaagc atcgaggaagctgtccccgctgtctgcaagaccaggacggtcatttacgagattcctcggagtcaggtcgaccccacgtccgccaactt cctgatctggccccgtgcgtggaggtgaaacgctgcaccggctgctgcaacacgagcagtgtcaagtgccagccctcccgcgtcca ccaccgcagcgtcaaggtggccaaggtggaatacgtcaggaagaagccaaaattaaaagaagtccaggtgaggttagaggagcattt ggagtgcgcctgcgcgaccacaagcctgaatccggattatcgggaagaggacacgggaaggcctagggagtcaggtaaaaaacgg
aaaagaaaaaggttaaaacccacctaa Brain derived neurotrophic factor (BDNF) Mouse (nucleic acid sequence):

(SEQ ID NO: 93)

Atgttccaccaggtgagaagagtgatgaccatccttttccttactatggttatttcatacttcggttgcatgaaggcggcgcccatgaaaga
agtaaacgtccacggacaaggcaacttggcctacccaggtgtgcggacccatgggactctggagagcgtgaatgggcccagggcag
gttcgagaggtctgacgacgacatcactggctgacacttttgagcacgtcatcgaagagctgctggatgaggaccagaaggttcggcc
caacgaagaaaaccataaggacgcggacttgtacacttcccgggtgatgctcagcagtcaagtgcctttggagcctcctctactctttctg
ctggaggaatacaaaaattacctggatgccgcaaacatgtctatgagggttcggcgccactccgaccctgcccgccgtggggagctga
gcgtgtgtgacagtattagcgagtgggtcacagcggcagataaaaagactgcagtggacatgtctggcgggacggtcacagtcctag
agaaagtcccggtatccaaaggccaactgaagcagtatttctacgagaccaagtgtaatcccatgggttacaccaaggaaggctgcag
gggcatagacaaaaggcactggaactcgcaatgccgaactacccaatcgtatgttcgggcccttactatggatagcaaaaagagaattg
gctggcgattcataaggatagacacttcctgtgtatgtacactgaccattaaaaggggaagatag Brain derived neurotrophic factor (BDNF) Human (nucleic acid sequence):

(SEQ ID NO: 94)

Atgaccatccttttccttactatggttatttcatactttggttgcatgaagctgcccccatgaaagaagcaaacatccgaggacaaggtgg
cttggcctacccaggtgtgcggacccatgggactctggagagcgtgaatgggcccaaggcaggttcaagaggcttgacatcattggct
gacactttcgaacacgtgatagaagagctgttggatgaggaccagaaagttcggcccaatgaagaaaacaataaggacgcagacttgt
acacgtccagggtgatgctcagtagtcaagtgcctttggagcctcctcttctctttctgctggaggaatacaaaaattacctagatgctgca
aacatgtccatgagggtccggcgccactctgaccctgcccgccgagggagctgagcgtgtgtgacagtattagtgagtgggtaacg
gcggcagacaaaaagactgcagtggacatgtcgggcgggacggtcacagtccttgaaaaggtccctgtatcaaaaggccaactgaa
gcaatacttctacgagaccaagtgcaatcccatgggttacacaaaagaaggctgcaggggcatagacaaaaggcattggaactccca
gtgccgaactacccagtcgtacgtgcgggcccttaccatggatagcaaaaagagaattggctggcgattcataaggatagacacttctt
gtgtatgtacattgaccattaaaaggggaagatag Beta nerve growth factor Mouse (nucleic acid sequence):

(SEQ ID NO: 95)

Atgtccatgttgttctacactctgatcactgcgttttttgatcggcgtacaggcagaaccgtacacagatagcaatgtcccagaaggagact
ctgtccctgaagcccactggactaaacttcagcattcccttgacacagccctccgcagagcccgcagtgcccctactgcaccaatagct
gcccgagtgacagggcagacccgcaacatcactgtagaccccagactgtttaagaaacggagactccactcaccccgtgtgctgttca
gcacccagcctccaccacctcttcagacactctggatctagacttccaggcccatggtacaatcctttcaacaggactcaccggagc
aagcgctcatccacccacccagtcttccacatgggggagttctcagtgtgtgacagtgtcagtgtgtgggttggagataagaccacagc
cacagacatcaagggcaaggaggtgacagtgctggccgaggtgaacattaacaacagtgtattcagacagtacttttttgagaccaagt
gccgagcctccaatcctgttgagagtgggtgccggggcatcgactccaaacactggaactcatactgcaccacgactcacaccttcgtc
aaggcgttgacaacagatgagaagcaggctgcctggaggttcatccggatagacacagcctgtgtgtgtgtgctcagcaggaaggcta
caagaagaggctga Beta nerve growth factor Human (nucleic acid sequence):

(SEQ ID NO: 96)

Atgtccatgttgttctacactctgatcacagcttttctgatcggcatacaggcggaaccacactcagagagcaatgtcctgcaggacac
accatcccccaagcccactggactaaacttcagcattcccttgacactgcccttcgcagagcccgcagcgccccggcagcggcgata
gctgcacgcgtggcggggcagacccgcaacattactgtggaccccaggctgtttaaaaagcggcgactccgttcacccgtgtgctgt
ttagcacccagcctccccgtgaagctgcagacactcaggatctggacttcgaggtcggtggtgctgcccccttcaacaggactcacag
gagcaagcggtcatcatcccatcccatcttccacaggggcgaattctcggtgtgtgacagtgtcagcgtgtgggttggggataagacca
ccgccacagacatcaagggcaaggaggtgatggtgttgggagaggtgaacattaacaacagtgtattcaaacagtactttttttgagacc
aagtgccgggacccaaatcccgttgacagcgggtgccggggcattgactcaaagcactggaactcatattgtaccacgactcacacctt -continued tgtcaaggcgctgaccatggatggcaagcaggctgcctggcggtttatccggatagatacggcctgtgtgtgtgctcagcaggaag gctgtgagaagagcctga Albumin Mouse (nucleic acid sequence):

(SEQ ID NO: 97)

Atgaagtgggtaacctttctcctcctcctcttcgtctccggctctgcttttttccaggggtgtgttt<u>cgccg</u>agaagcacacaagagtgagat cgcccatcggtataatgatttgggagaacaacatttcaaaggcctagcctgattgccttttcccagtatctccagaaatgctcatacgatg agcatgccaaattagtgcaggaagtaacagacttttgcaaagacgtgtgttgccgatgagtctgccgccaactgtgacaaatcccttcaca ctcttttttggagataagttgtgtgccattccaaacctccgtgaaaactatggtgaactggctgactgctgtacaaaacaagagcccgaaag aaacgaatgtttcctgcaacacaaagatgacaacccccagcctgccaccatttgaaaggccagaggctgaggccatgtgcacctccttta aggaaaacccaaccaccttttatgggacactatttgcatgaagttgccagaagacatccttattctatgccccagaacttctttactatgctg agcagtacaatgagattctgacccagtgttgtgcagaggctgacaaggaaagctgcctgaccccgaagcttgatggtgtgaaggagaa agcattggtctcatctgtccgtcagagaatgaagtgctccagtatgcagaagtttggagagagagcttttaaagcatgggcagtagctcgt ctgagccagacattccccaatgctgactttgcagaaatcaccaaattggcaacagacctgaccaaagtcaacaaggagtgctgccatgg tgacctgctggaatgcgcagatgacagggcggaacttgccaagtacatgtgtgaaaaccaggcgactatctccagcaaactgcagact tgctgcgataaaccactgttgaagaaagcccactgtcttagtgaggtggagcatgacaccatgcctgctgatctgcctgccattgctgctg attttgttgaggaccaggaagtgtgcaagaactatgctgaggccaaggatgtcttcctgggcacgttcttgtatgaatattcaagaagaca ccctgattactctgtatccctgttgctgagacttgctaagaaatatgaagccactctggaaaagtgctgcgctgaagccaatcctcccgcat gctacggcacagtgcttgctgaatttcagcctcttgtagaagagcctaagaacttggtcaaaaccaactgtgatctttacgagaagcttgg agaatatggattccaaaatgccattctagttcgctacacccagaaagcacctcaggtgtcaaccccaactctcgtggaggctgcaagaa acctaggaagagtgggcaccaagtgttgtacacttcctgaagatcagagactgccttgtgtggaagactatctgtctgcaatcctgaacc gtgtgtgtctgctgcatgagaagacccccagtgagtgagcatgttaccaagtgctgtagtggatccctggtggaaaggcggccatgcttct ctgctctgacagttgatgaaacatatgtccccaaagagtttaaagctgagaccttcaccttccactctgatatctgcacacttccagagaag gagaagcagattaagaaacaaacggctcttgctgagctggtgaagcacaagcccaaggctacagcggagcaactgaagactgtcatg gatgactttgcacagttcctggatacatgttgcaaggctgctgacaaggacacctgcttctcgactgagggtccaaaccttgtcactagat gcaaagacgccttagcctaa Albumin Human (nucleic acid sequence):

(SEQ ID NO: 98)

atgaagtgggtaacctttatttccccttcttttttctctttagctcggcttattccaggggtgtgttt<u>cgtcg</u>agatgcacacaagagtgaggttgc tcatcggtttaaagatttgggagaagaaaatttcaaagccttggtgttgattgcctttgctcagtatcttcagcagtgtccatttgaagatcatg taaaattagtgaatgaagtaactgaatttgcaaaaacatgtgttgctgatgagtcagctgaaaattgtgacaaatcacttcataccttttttgg agacaaattatgcacagttgcaactcttcgtgaaacctatggtgaaatggctgactgctgtgcaaaacaagaacctgagagaaatgaatg cttcttgcaacacaaagatgacaacccaaacctccccccgattggtgagaccagaggttgatgtgatgtgcactgcttttcatgacaatgaa gagacatttttgaaaaaatacttatatgaaattgccagaagacatccttacttttatgccccggaactccttttctttgctaaaaggtataaagc tgcttttacagaatgttgccaagctgctgataaagctgcctgcctgttgccaaagctcgatgaacttcgggatgaagggaaggcttcgtct gccaaacagagactcaagtgtgccagtctccaaaaatttggagaaagagctttcaaagcatgggcagtagctcgcctgagccagagat ttcccaaagctgagtttgcagaagtttccaagttagtgacagatcttaccaaagtccacacggaatgctgccatggagatctgcttgaatgt gctgatgacagggcggaccttgccaagtatatctgtgaaaatcaagattcgatctccagtaaactgaaggaatgctgtgaaaaacctctg ttggaaaaatcccactgcattgccgaagtggaaaatgatgagatgcctgctgacttgccttcattagctgctgattttgttgaaagtaaggat gtttgcaaaaactatgctgaggcaaaggatgtcttcctgggcatgtttttgtatgaatatgcaagaaggcatcctgattactctgtcgtgctg ctgctgagacttgccaagacatatgaaaccactctagagaagtgctgtgccgctgcagatcctcatgaatgctatgccaaagtgttcgat gaatttaaacctcttgtggaagagcctcagaatttaatcaaacaaaattgtgagcttttttgagcagcttggagagtacaaattccagaatgc gctattagttcgttacaccaagaaagtaccccaagtgtcaactccaactcttgtagaggtctcaagaaacctaggaaaagtgggcagcaa atgttgtaaacatcctgaagcaaaaagaatgccctgtgcagaagactatctatccgtggtcctgaaccagttatgtgtgttgcatgagaaa -continued

```
acgccagtaagtgacagagtcaccaaatgctgcacagaatccttggtgaacaggcgaccatgcttttcagctctggaagtcgatgaaac atacgttcccaaagagtttaatgctgaaacattcaccttccatgcagatatatgcacactttctgagaaggagagacaaatcaagaaacaa actgcacttgttgagctcgtgaaacacaagcccaaggcaacaaaagagcaactgaaagctgttatggatgatttcgcagcttttgtagag aagtgctgcaaggctgacgataaggagacctgctttgccgaggagggtaaaaaacttgttgctgcaagtcaagctgccttaggcttataa
```

Calcitonin Mouse (nucleic acid sequence):

(SEQ ID NO: 99)
```
Atgggcttcctgaagttctccccttttcctggttgtcagcatcttgctcctgtaccaggcatgcagcctccaggcagtgcctttgaggtcaat cttggaaagcagcccaggcatggccactctcagtgaagaagaagttcgcctgctggctgcactggtgcaggactatatgcagatgaaa gccagggagctggagcaggaggaagagcaggaggctgagggctctagcttggacagcccagatctaagcggtgtgggaatctga gtacctgcatgctgggcacgtacacacaagacctcaacaagtttcacaccttcccccaaacttcaattggggttgaagcacctggcaag aaaagggatgtggccaaggacttggagacaaaccaccaatcccattttggcaactaa
```

Calcitonin Human (nucleic acid sequence):

(SEQ ID NO: 100)
```
Atgggcttccaaaagttctccccccttcctggctctcagcatcttggtcctgttgcaggcaggcagcctccatgcagcaccattcaggtctg ccctggagagcagcccagcagacccggccacgctcagtgaggacgaagcgcgcctcctgctggctgcactggtgcaggactatgtg cagatgaaggccagtgagctggagcaggagcaagagagagagggctccagcctggacagcccagatctaagcggtgcggtaatc tgagtacttgcatgctgggcacatacacgcaggacttcaacaagtttcacacgttcccccaaactgcaattggggttggagcacctggaa agaaaagggatatgtccagcgacttggagagagaccatcgccctcatgttagcatgccccagaatgccaactaa
```

Exemplary cleavage sites that can be used for the constructs of the present invention include, but are not limited to, aagagg (SEQ ID NO: 101); aagcgt (SEQ ID NO: 102); aagcgc (SEQ ID NO: 103); aaaaga (SEQ ID NO: 104); aagaggagg (SEQ ID NO: 105); aagaga (SEQ ID NO: 106); cgcaaa (SEQ ID NO: 107); cggcgg (SEQ ID NO: 108); tatctg (SEQ ID NO: 109); aggcgg (SEQ ID NO: 110); cggagc (SEQ ID NO: 111); cggtct (SEQ ID NO: 112); cgaagc (SEQ ID NO: 113); aaacgg (SEQ ID NO: 114); aagagaggt (SEQ ID NO: 115); aaacgaggc (SEQ ID NO: 116); gggccgccgc (SEQ ID NO: 117); ccacgagct (SEQ ID NO: 118); ccccgagct (SEQ ID NO: 119); cgaaggcagctgcgggct (SEQ ID NO: 120); cgtaggcagctgagggta (SEQ ID NO: 121); cgccgcagt (SEQ ID NO: 122); cgaaga (SEQ ID NO: 123); cggaga (SEQ ID NO: 124); agaagg (SEQ ID NO: 125); aaacgc (SEQ ID NO: 126); tccagcattcggagg (SEQ ID NO: 127); agcagtcggagg (SEQ ID NO: 128); gagagggac (SEQ ID NO: 129); cggcgc (SEQ ID NO: 130); aggcgc (SEQ ID NO: 131); cggggcaccaag (SEQ ID NO: 132); caccgc (SEQ ID NO: 133); acccgtgtc (SEQ ID NO: 134); tcgcgcatt (SEQ ID NO: 135); cgacgg (SEQ ID NO: 136); aagagaaga (SEQ ID NO: 137); and ggccgccgc (SEQ ID NO: 138).

One skilled in the art would know how to design a cleavage site, so the propeptide and bioluminescent protein will separate and function normally.

Any luciferase known in the art, any propeptide known in the art and any cleavage site known in the art can be used to make a fusion protein according to the method of the present invention.

Exemplary luciferase fusion proteins (their nucleic acid sequences) include, but are not limited to, the sequences below. Underline indicates the putative cleavage sites. Italics indicates *Gaussia* luciferase without its signal peptide.

Proamylin Mouse (nucleic acid sequence):

(SEQ ID NO: 139)
```
Atgatgtgcatctccaaactgccagctgtcctcctcatcctctctgtggcactgaaccacttgagagctacacctgtcagaagtggtagca accctcagatggacaaacggaagtgcaacacggccacgtgtgccacacaacgcctggcaaactttttggttcgttccagcaacaaccTT ggtccagtcctcccaccaaccaacgtgggatcgaatacatatggcaagaggaatgcgaagcccaccgagaacaacgaagacttca acatcgtggccgtggccagcaacttcgcgaccacggatctcgatgctgaccgcgggaagttgcccggcaagaagctgccgctgg aggtgctcaaagagatggaagccaatgcccggaaagctggctgcaccaggggctgtctgatctgcctgtcccacatcaagtgcac gcccaagatgaagaagttcatcccaggacgctgccacacctacgaaggcgacaaagagtccgcacagggcggcataggcgag gcgatcgtcgacattcctgagattcctggggttcaaggacttggagcccatggagcagttcatcgcacaggtcgatctgtgtgtggact gcacaactggctgcctcaaaggggcttgccaacgtgcagtgttctgacctgctcaagaagtggctgccgcaacgctgtgcgacctttg ccagcaagatccagggccaggtggacaagatcaaggggggccggtggtgacaagaggaatgcggcaggggatccaaataggga atccttggatttcttactcgtttaa
```

-continued

Proamylin Human (nucleic acid sequence):
(SEQ ID NO: 140)
Atgggcatcctgaagctgcaagtatttctcattgtgctctctgttgcattgaaccatctgaaagctacacccattgaaagtcatcaggtgga aaagcggaaatgcaacactgccacatgtgcaacgcagcgcctggcaaatttttagttcattccagcaacaactttggtgccattctctcat ctaccaacgtgggatccaatacatatggc<u>aagagg</u>aatgcaaagccaccgagaacaacgaagacttcaacatcgtggccgtggc cagcaacttcgcgaccacggatctcgatgctgaccgcgggaagttgcccggcaagaagctgccgctggaggtgctcaaagagat ggaagccaatgcccggaaagctggctgcaccaggggctgtctgatctgcctgtcccacatcaagtgcacgcccaagatgaagaa gttcatcccaggacgctgccacacctacgaaggcgacaaagagtccgcacagggcggcataggcgaggcgatcgtcgacattc ctgagattcctgggttcaaggacttggagcccatggagcagttcatcgcacaggtcgatctgtgtgtggactgcacaactggctgcct caaagggcttgccaacgtgcagtgttctgacctgctcaagaagtggctgccgcaacgctgtgcgacctttgccagcaagatccagg gccaggtggacaagatcaaggggccggtggtgaca<u>aagagg</u>aatgcggtagaggttttaaagagagagccactgaattacttgccc ctttag Proinsulin Mouse (nucleic acid sequence):
(SEQ ID NO: 141)
Atggccctgtggatgcgcttcctgcccctgctggccctgctcttcctctgggagtcccacccacccaggcttttgtcaagcagcacctttt gtggttcccacctggtggaggctctctacctggtgtgtggggagcgtggcttcttctacacacccatgtcccgccgtgaagtggaggac ccacaagtggcacaactggagctgggtggaggcccggagcaggtgaccttcagaccttggcactggaggtggcccagcag<u>aaga</u>

<u>gg</u>aagcccaccgagaacaacgaagacttcaacatcgtggccgtggccagcaacttcgcgaccacggatctcgatgctgaccgc gggaagttgcccggcaagaagctgccgctggaggtgctcaaagagatggaagccaatgcccggaaagctggctgcaccaggg gctgtctgatctgcctgtcccacatcaagtgcacgcccaagatgaagaagttcatcccaggacgctgccacacctacgaaggcga caaagagtccgcacagggcggcataggcgaggcgatcgtcgacattcctgagattcctgggttcaaggacttggagcccatgga gcagttcatcgcacaggtcgatctgtgtgtggactgcacaactggctgcctcaaagggcttgccaacgtgcagtgttctgacctgctc aagaagtggctgccgcaacgctgtgcgacctttgccagcaagatccagggccaggtggacaagatcaaggggccggtggtga <u>caagcgt</u>ggcattgtagatcagtgctgcaccagcatctgctccctctaccagctggagaactactgcaactag Proinsulin Human (nucleic acid sequence):
(SEQ ID NO: 142)
Atggccctgtggatgcgcctcctgcccctgctggcgctgctggccctctggggacctgacccagccgcagcctttgtgaaccaacacc tgtgcggctcacacctggtggaagctctctacctagtgtgcggggaacgaggcttcttctacacacccaagacccgccgggaggcaga ggacctgcaggtggggcaggtggagctgggcgggggccctggtgcaggcagcctgcagcccttggccctggaggggtccctgca g<u>aagagg</u>aagcccaccgagaacaacgaagacttcaacatcgtggccgtggccagcaacttcgcgaccacggatctcgatgctg accgcgggaagttgcccggcaagaagctgccgctggaggtgctcaaagagatggaagccaatgcccggaaagctggctgcac caggggctgtctgatctgcctgtcccacatcaagtgcacgcccaagatgaagaagttcatcccaggacgctgccacacctacgaa ggcgacaaagagtccgcacagggcggcataggcgaggcgatcgtcgacattcctgagattcctgggttcaaggacttggagccc atggagcagttcatcgcacaggtcgatctgtgtgtggactgcacaactggctgcctcaaagggcttgccaacgtgcagtgttctgac ctgctcaagaagtggctgccgcaacgctgtgcgacctttgccagcaagatccagggccaggtggacaagatcaaggggcggt ggtgac<u>aagcgt</u>ggcattgtgaacaatgctgtaccagcatctgctccctctaccagctggagaactactgcaactag Proglucagon (includes GRPP, glucagon, GLP-1, GLP-2) Mouse (nucleic acid sequence):
(SEQ ID NO: 143)
Atgaagaccatttactttgtggctggattgcttataatgctggtgcaaggcagctggcagcacgcccttcaagcacacagaggagaaccc cagatcattcccagcttcccagacagaagcgcatgaggaccctgatgagatgaatgaagacaaacgccactcacagggcacattcac cagcgactacagcaaatacctggactcccgccgtgcccaagattttgtgcagtggttgatgaacaccaagaggaaccggaacaacatt gccaaacgtcatgatgaatttgagaggcatgctgaagggacctttaccagtgatgtgagttcttacttggagggccaggcagcaaagga attcattgcttggctggtgaaaggccgaggaaggcgagacttcccagaagaagtcgccattgccgaggaactc<u>ggccgaaagagaa</u>

<u>ga</u>aagcccaccgagaacaacgaagacttcaacatcgtggccgtggccagcaacttcgcgaccacggatctcgatgctgaccgc -continued gggaagttgcccggcaagaagctgccgctggaggtgctcaaagagatggaagccaatgcccggaaagctggctgcaccaggg gctgtctgatctgcctgtcccacatcaagtgcacgcccaagatgaagaagttcatcccaggacgctgccacacctacgaaggcga caaagagtccgcacagggcggcataggcgaggcgatcgtcgacattcctgagattcctgggttcaaggacttggagcccatgga gcagttcatcgcacaggtcgatctgtgtgtggactgcacaactggctgcctcaaagggcttgccaacgtgcagtgttctgacctgctc aagaagtggctgccgcaacgctgtgcgacctttgccagcaagatccagggccaggtggacaagatcaaggggccggtggtga c<u>aagcgcg</u>gccgcaggcacgctgatggctccttctctgacgagatgagcaccattctggataatcttgccaccagggacttcatcaact ggctgattcaaaccaagatcactgacaagaaatag Proglucagon (includes GRPP, glucagon, GLP-1, GLP-2) Human (nucleic acid sequence):

(SEQ ID NO: 144)

atgaaaagcatttactttgtggctggattatttgtaatgctggtacaaggcagctggcaacgttcccttcaagacacagaggagaaatcca gatcattctcagcttcccaggcagacccactcagtgatcctgatcagatgaacgaggacaagcgccattcacagggcacattcaccagt gactacagcaagtatctggactccaggcgtgcccaagattttgtgcagtggttgatgaataccaagaggaacaggaataacattgccaa acgtcacgatgaatttgagagacatgctgaagggaccctttaccagtgatgtaagttcttatttggaaggccaagctgccaaggaattcatt gcttggctggtgaaaggccgaggaaggcgagatttcccagaagaggtcgccattgttgaagaacttggccga<u>aagagaaga</u>aagc ccaccgagaacaacgaagacttcaacatcgtggccgtggccagcaacttcgcgaccacggatctcgatgctgaccgcgggaagt tgcccggcaagaagctgccgctggaggtgctcaaagagatggaagccaatgcccggaaagctggctgcaccaggggctgtctg atctgcctgtcccacatcaagtgcacgcccaagatgaagaagttcatcccaggacgctgccacacctacgaaggcgacaaagag tccgcacagggcggcataggcgaggcgatcgtcgtcgacattcctgagattcctgggttcaaggacttggagcccatggagcagttcat cgcacaggtcgatctgtgtgtggactgcacaactggctgcctcaaagggcttgccaacgtgcagtgttctgacctgctcaagaagtg gctgccgcaacgctgtgcgacctttgccagcaagatccagggccaggtggacaagatcaaggggccggtggtgac<u>aagcgcg</u> gccgcagacatgctgatggttctttctctgatgagatgaacaccattcttgataatcttgccgccagggactttataaactggttgattcaga ccaaaatcactgacaggaaataa Peptide YY Mouse (nucleic acid sequence):

(SEQ ID NO: 145)

atggtggcggtgcgcaggccttggcccgtcacggtcgcaatgctgctaatcctgctcgcctgtctgggagccctggtggacgcctacc ctgccaaaccagaggctcccggcgaagacgcctcccggaggagctgagccgctactacgcctccctgcgccactacctcaacctg gtcacccggcagcggtatgga<u>aaaaga</u>aagcccaccgagaacaacgaagacttcaacatcgtggccgtggccagcaacttcgcg accacggatctcgatgctgaccgcgggaagttgcccggcaagaagctgccgctggaggtgctcaaagagatggaagccaatgc ccggaaagctggctgcaccaggggctgtctgatctgcctgtcccacatcaagtgcacgcccaagatgaagaagttcatcccagga cgctgccacacctacgaaggcgacaaagagtccgcacagggcggcataggcgaggcgatcgtcgacattcctgagattcctggg ttcaaggacttggagcccatggagcagttcatcgcacaggtcgatctgtgtgtggactgcacaactggctgcctcaaagggcttgcc aacgtgcagtgttctgacctgctcaagaagtggctgccgcaacgctgtgcgacctttgccagcaagatccagggccaggtggaca agatcaaggggccggtggtgac<u>aagaggagg</u>gatgtccccgcagctctgttctccaaactgctcttcacagacgacagcgacagc gagaacctccccttcaggccagaagg tttggaccagtggtga Peptide YY Human (nucleic acid sequence):

(SEQ ID NO: 146)

Atggtgttcgtgcgcaggccgtggcccgccttgaccacagtgcttctggccctgctcgtctgcctaggggcgctggtcgacgcctacc ccatcaaacccgaggctcccggcgaagacgcctcgcggaggagctgaaccgctactactgcctccctgcgccactacctcaacctg gtcacccggcagcggtatggg<u>aaaaga</u>aagcccaccgagaacaacgaagacttcaacatcgtggccgtggccagcaacttcgcg accacggatctcgatgctgaccgcgggaagttgcccggcaagaagctgccgctggaggtgctcaaagagatggaagccaatgc ccggaaagctggctgcaccaggggctgtctgatctgcctgtcccacatcaagtgcacgcccaagatgaagaagttcatcccagga cgctgccacacctacgaaggcgacaaagagtccgcacagggcggcataggcgaggcgatcgtcgacattcctgagattcctggg ttcaaggacttggagcccatggagcagttcatcgcacaggtcgatctgtgtgtggactgcacaactggctgcctcaaagggcttgcc aacgtgcagtgttctgacctgctcaagaagtggctgccgcaacgctgtgcgacctttgccagcaagatccagggccaggtggaca -continued agatcaaggggccggtggtgaca<u>aagaggaggg</u>acggcccggacacgcttctttccaaaacgttcttccccgacggcgaggaccg ccccgtcaggtcgcggtcggagggcccagacctgtggtga Neuropeptide Y Mouse (nucleic acid sequence):

(SEQ ID NO: 147)

Atgctaggtaacaagcgaatggggctgtgtggactgaccctcgctctatctctgctcgtgtgtttgggcattctggctgaggggtacccc tccaagccggacaatccgggcgaggacgcgccagcagaggacatggccagatactactccgctctgcgacactacatcaatctcatc accagacagagatatggc<u>aagaga</u>aagcccaccgagaacaacgaagacttcaacatcgtggccgtggccagcaacttcgcgac cacggatctcgatgctgaccgcgggaagttgcccggcaagaagctgccgctggaggtgctcaaagagatggaagccaatgccc ggaaagctggctgcaccaggggctgtctgatctgcctgtcccacatcaagtgcacgcccaagatgaagaagttcatcccaggacg ctgccacacctacgaaggcgacaaagagtccgcacagggcggcataggcgaggcgatcgtcgacattcctgagattcctgggtt caaggactggagcccatggagcagttcatcgcacaggtcgatctgtgtgtggactgcacaactggctgcctcaaagggcttgcca acgtgcagtgttctgacctgctcaagaagtggctgccgcaacgctgtgcgacctttgccagcaagatccagggccaggtggacaa gatcaaggggccggtggtgaca<u>aagaggaggt</u>ccagccctgagacactgatttcagacctcttaatgaaggaaagcacagaaaacg ccccagaacaaggcttgaagacccttccatgtggtga Neuropeptide Y Human (nucleic acid sequence):

(SEQ ID NO: 148)

Atgctaggtaacaagcgactggggctgtccggactgaccctcgccctgtccctgctcgtgtgcctgggtgcgctggccgaggcgtac ccctccaagccggacaacccgggcgaggacgcaccagcgcgaggacatggccagatactactcggcgctgcgacactacatcaacc tcatcaccaggcagagatatggaaaacgaaagcccaccgagaacaacgaagacttcaacatcgtggccgtggccagcaacttcg cgaccacggatctcgatgctgaccgcgggaagttgcccggcaagaagctgccgctggaggtgctcaaagagatggaagccaat gcccggaaagctggctgcaccaggggctgtctgatctgcctgtcccacatcaagtgcacgcccaagatgaagaagttcatcccag gacgctgccacacctacgaaggcgacaaagagtccgcacagggcggcataggcgaggcgatcgtcgacattcctgagattcctg ggttcaaggacttggagcccatggagcagttcatcgcacaggtcgatctgtgtgtggactgcacaactggctgcctcaaagggcttg ccaacgtgcagtgttctgacctgctcaagaagtggctgccgcaacgctgtgcgacctttgccagcaagatccagggccaggtgga caagatcaaggggccggtggtgaca<u>aagaggaggt</u>ccagcccagagacactgatttcagacctcttgatgagagaaagcacagaa aatgttcccagaactcggcttgaagaccctgcaatgtggtga Pancreatic polypeptide Mouse (nucleic acid sequence):

(SEQ ID NO: 149)

Atggccgtcgcatactgctgcctctccctgttttctcgtatccacttgggtggctctgctgctgcagcccctgcaggggacctggggagcc cccctggagccaatgtacccaggcgactatgcgacacctgagcagatggcacaatatgaaactcagctccgcagatacatcaacacac tgaccaggcctaggtatgggaagagaaagcccaccgagaacaacgaagacttcaacatcgtggccgtggccagcaacttcgcga ccacggatctcgatgctgaccgcgggaagttgcccggcaagaagctgccgctggaggtgctcaaagagatggaagccaatgcc cggaaagctggctgcaccaggggctgtctgatctgcctgtcccacatcaagtgcacgcccaagatgaagaagttcatcccaggac gctgccacacctacgaaggcgacaaagagtccgcacagggcggcataggcgaggcgatcgtcgacattcctgagattcctgggt tcaaggacttggagcccatggagcagttcatcgcacaggtcgatctgtgtgtggactgcacaactggctgcctcaaagggcttgcc aacgtgcagtgttctgacctgctcaagaagtggctgccgcaacgctgtgcgacctttgccagcaagatccagggccaggtggaca agatcaaggggcggtggtgaca<u>aagaggaggg</u>ccgaggaggagaacacaggtggacttcctggagtgcagctctcccctgca ccagcccccagttggcttgattccctgctctgcgccctggagctga Pancreatic polypeptide Human (nucleic acid sequence):

(SEQ ID NO: 150)

Atggctgccgcacgcctctgcctctccctgctgctcctgtccacctgcgtggctctgttactacagccactgctgggtgcccagggagc cccactggagccagtgtacccaggggacaatgccacaccagagcagatggcccagtatgcagctgatctccgtagatacatcaacat gctgaccaggcctaggtatgggaaaagaaagcccaccgagaacaacgaagacttcaacatcgtggccgtggccagcaacttcgc gaccacggatctcgatgctgaccgcgggaagttgcccggcaagaagctgccgctggaggtgctcaaagagatggaagccaatg -continued cccggaaagctggctgcaccaggggctgtctgatctgcctgtcccacatcaagtgcacgcccaagatgaagaagttcatcccagg acgctgccacacctacgaaggcgacaaagagtccgcacagggcggcataggcgaggcgatcgtcgacattcctgagattcctgg gttcaaggacttggagcccatggagcagttcatcgcacaggtcgatctgtgtgtggactgcacaactggctgcctcaaagggcttgc caacgtgcagtgttctgacctgctcaagaagtggctgccgcaacgctgtgcgacctttgccagcaagatccagggccaggtggac aagatcaaggggccggtggtgacaagaggaggcacaaagaggacacgctggccttctcggagtgggggtccccgcatgctgct gtccccagggagctcagcccgctggacttataa Somatostatin Mouse (nucleic acid sequence):

(SEQ ID NO: 151)

Atgctgtcctgccgtctccagtgcgccctggctgcgctctgcatcgtcctggctttgggcggtgtcaccggcgcgccctcggacccca gactccgtcagtttctgcagaagtctctggcggctgccaccgggaaacaggaactggccaagtacttcttggcagagctgcgcaaaaa gcccaccgagaacaacgaagacttcaacatcgtggccgtggccagcaacttcgcgaccacggatctcgatgctgaccgcggga agttgcccggcaagaagctgccgctggaggtgctcaaagagatggaagccaatgcccggaaagctggctgcaccaggggctgt ctgatctgcctgtcccacatcaagtgcacgcccaagatgaagaagttcatcccaggacgctgccacacctacgaaggcgacaaa gagtccgcacagggcggcataggcgaggcgatcgtcgacattcctgagattcctgggttcaaggacttggagcccatggagcagt tcatcgcacaggtcgatctgtgtgtggactgcacaactggctgcctcaaagggcttgccaacgtgcagtgttctgacctgctcaaga agtggctgccgcaacgctgtgcgacctttgccagcaagatccagggccaggtggacaagatcaaggggccggtggtgaccgc aaactgtccgagcccaaccagacagagaatgatgccctggagcccgaggatttgccccaggcagctgagcaggacgagatgaggct ggagctgcagaggtctgccaactcgaacccagcaatggcaccccgggaacgcaaagctggctgcaagaacttcttctggaagacatt cacatcctgttag Somatostatin Human (nucleic acid sequence):

(SEQ ID NO: 152)

Atgctgtcctgccgcctccagtgcgcgctggctgcgctgtccatcgtcctggccctgggctgtgtcaccggcgctccctcggacccca gactccgtcagtttctgcagaagtccctggctgctgccgcggggaagcaggaactggccaagtacttcttggcagagctgcgcaaaaa gcccaccgagaacaacgaagacttcaacatcgtggccgtggccagcaacttcgcgaccacggatctcgatgctgaccgcggga agttgcccggcaagaagctgccgctggaggtgctcaaagagatggaagccaatgcccggaaagctggctgcaccaggggctgt ctgatctgcctgtcccacatcaagtgcacgcccaagatgaagaagttcatcccaggacgctgccacacctacgaaggcgacaaa gagtccgcacagggcggcataggcgaggcgatcgtcgacattcctgagattcctgggttcaaggacttggagcccatggagcagt tcatcgcacaggtcgatctgtgtgtggactgcacaactggctgcctcaaagggcttgccaacgtgcagtgttctgacctgctcaaga agtggctgccgcaacgctgtgcgacctttgccagcaagatccagggccaggtggacaagatcaaggggccggtggtgaccgc aaactgtctgaacccaaccagacggagaatgatgccctggaacctgaagatctgtcccaggctgctgagcaggatgaaatgaggcttg agctgcagagatctgctaactcaaacccggctatggcaccccgagaacgcaaagctggctgcaagaatttcttctggaagactttcacat cctgttag GHRH Mouse (nucleic acid sequence):

(SEQ ID NO: 153)

Atgctgctctgggtgctctttgtgatcctcatcctcaccagtggctcccactgctcactgccccctcacctcccttcaggatgcagcgac acgtagatgccatcttcaccaccaactacaggaaactcctgagccagctgtatgcccggaaagtgatccaggacatcatgaacaagca aggggagaggatccaggaacaaagggccaggctcagccgccaggaagacagcatgtggacagaggacaagcagatgacccctgg agagcatccggcggaagcccaccgagaacaacgaagacttcaacatcgtggccgtggccagcaacttcgcgaccacggatctc gatgctgaccgcgggaagttgcccggcaagaagctgccgctggaggtgctcaaagagatggaagccaatgcccggaaagctg gctgcaccaggggctgtctgatctgcctgtcccacatcaagtgcacgcccaagatgaagaagttcatcccaggacgctgccacac ctacgaaggcgacaaagagtccgcacagggcggcataggcgaggcgatcgtcgacattcctgagattcctgggttcaaggactt ggagcccatggagcagttcatcgcacaggtcgatctgtgtgtggactgcacaactggctgcctcaaagggcttgccaacgtgcagt gttctgacctgctcaagaagtggctgccgcaacgctgtgcgacctttgccagcaagatccagggccaggtggacaagatcaaggg ggccggtggtgaccgcggttgcagggattcccaaggatgaagccttcagcggacgcttga -continued GHRH Human (nucleic acid sequence):
(SEQ ID NO: 154)
Atgccactctgggtgttcttctttgtgatcctcaccctcagcaacagctcccactgctcccacctccccctttgaccctcaggatgcggc
ggtatgcagatgccatcttcaccaacagctaccggaaggtgctgggccagctgtccgcccgcaagctgctccaggacatcatgagca
ggcagcagggagagagcaaccaagagcgaggagcaagggcacggcttggtcgtcaggtagacagcatgtgggcagaacaaaag
caaatggaattggagagcatcctggtggccctgcggcggaagcccaccgagaacaacgaagacttcaacatcgtggccgtggcc
agcaacttcgcgaccacggatctcgatgctgaccgcgggaagttgcccggcaagaagctgccgctggaggtgctcaaagagatg
gaagccaatgcccggaaagctggctgcaccaggggctgtctgatctgcctgtcccacatcaagtgcacgcccaagatgaagaag
ttcatcccaggacgctgccacacctacgaaggcgacaaagagtccgcacagggcggcataggcgaggcgatcgtcgacattcct
gagattcctgggttcaaggacttggagcccatggagcagttcatcgcacaggtcgatctgtgtgtggactgcacaactggctgcctc
aaagggcttgccaacgtgcagtgttctgacctgctcaagaagtggctgccgcaacgctgtgcgacctttgccagcaagatccaggg
ccaggtggacaagatcaaggggccggtggtgaccggcggctgcagaagcacaggaactcccagggatga POMC (ACTH, MSH) Mouse (nucleic acid sequence):
(SEQ ID NO: 155)
Atgccgagattctgctacagtcgctcaggggccctgttgctggccctcctgcttcagacctccatagatgtgtggagctggtgcctgga
gagcagccagtgccaggacctcaccacggagagcaacctgctggcttgcatccgggcttgcaaactcgacctctcgctggagacgcc
cgtgtttcctggcaacggagatgaacagcccctgactgaaaaccccggaagtacgtcatgggtcacttccgctgggaccgcttcggc
cccaggaacagcagcagtgctggcagcgcggcgcagaggcgtgcggaggaagaggcggtgtggggagatggcagtccagagcc
gagtccacgcgagggcaagcgcaagcccaccgagaacaacgaagacttcaacatcgtggccgtggccagcaacttcgcgacca
cggatctcgatgctgaccgcgggaagttgcccggcaagaagctgccgctggaggtgctcaaagagatggaagccaatgcccgg
aaagctggctgcaccaggggctgtctgatctgcctgtcccacatcaagtgcaacgcccaagatgaagaagttcatcccaggacgct
gccacacctacgaaggcgacaaagagtccgcacagggcggcataggcgaggcgatcgtcgacattcctgagattcctgggttca
aggacttggagcccatggagcagttcatcgcacaggtcgatctgtgtgtggactgcacaactggctgcctcaaagggcttgccaac
gtgcagtgttctgacctgctcaagaagtggctgccgcaacgctgtgcgacctttgccagcaagatccagggccaggtggacaagat
caaggggccggtggtgacaagcgctcctactccatggagcacttccgctggggcaagccggtgggcaagaaacggcgcccggtg
aaggtgtaccccaacgttgctgagaacgagtcggcggaggccttcccctagagttcaagagggagctggaaggcgagcggccatta
ggcttggagcaggtcctggagtccgacgcggagaaggacgacgggccctaccgggtggagcacttccgctggagcaacccgccca
aggacaagcgttacggtggcttcatgacctccgagaagagccagacgccctggtgacgctcttcaagaacgccatcatcaagaacg
cgcacaagaaggggccagtga POMC (ACTH, MSH) Human (nucleic acid sequence):
(SEQ ID NO: 156)
Atgccgagatcgtgctgcagccgctcgggggccctgttgctggccttgctgcttcaggcctccatggaagtgcgtggctggtgcctgg
agagcagccagtgtcaggacctcaccacggaaagcaacctgctggagtgcatccgggcctgcaagcccgacctctcggccgagact
cccatgttcccgggaaatggcgacgagcagcctctgaccgagaaccccggaagtacgtcatgggccacttccgctgggaccgattc
ggccgccgcaacagcagcagcggcagcagcggcgcagggcagaagcgcgaggacgtctcagcgggcgaagactgcggcc
cgctgcctgagggcggccccgagccccgcagcgatggtgccaagccgggccccgcgcgaggcaagcgcaagcccaccgagaa
caacgaagacttcaacatcgtggccgtggccagcaacttcgcgaccacggatctcgatgctgaccgcgggaagttgcccggcaa
gaagctgccgctggaggtgctcaaagagatggaagccaatgcccggaaagctggctgcaccaggggctgtctgatctgcctgtcc
cacatcaagtgcacgcccaagatgaagaagttcatcccaggacgctgccacacctacgaaggcgacaaagagtccgcacagg
gcggcataggcgaggcgatcgtcgacattcctgagattcctgggttcaaggacttggagcccatggagcagttcatcgcacaggtc
gatctgtgtgtggactgcacaactggctgcctcaaagggcttgccaacgtgcagtgttctgacctgctcaagaagtggctgccgcaa
cgctgtgcgacctttgccagcaagatccagggccaggtggacaagatcaaggggccggtggtgacaagcgctcctactccatgg
agcacttccgctggggcaagccggtgggcaagaagcggcgcccagtgaaggtgtaccctaacggcgccgaggacgagtcggccg -continued aggccttcccccctggagttcaagagggagctgactggccagcgactccgggagggagatggccccgacggccctgccgatgacgg cgcaggggcccaggccgacctggagcacagcctgctggtggcggccgagaagaaggacgagggcccctacaggatggagcactt ccgctggggcagcccgcccaaggacaagcgctacggcggtttcatgacctccgagaagagccagacgcccctggtgacgctgttca aaaacgccatcatcaagaacgcctacaagaagggcgagtga Oxytocin Mouse (nucleic acid sequence):

(SEQ ID NO: 157)

Atggcctgccccagtctcgcttgctgcctgcttggcttactggctctgacctcggcctgctacatccagaactgcccccctgggcggc<u>aa</u>
<u>gagg</u>aagcccaccgagaacaacgaagacttcaacatcgtggccgtggccagcaacttcgcgaccacggatctcgatgctgacc
gcgggaagttgcccggcaagaagctgccgctggaggtgctcaaagagatggaagccaatgcccggaaagctggctgcaccag
gggctgtctgatctgcctgtcccacatcaagtgcacgcccaagatgaagaagttcatcccaggacgctgccacacctacgaaggc
gacaaagagtccgcacagggcggcataggcgaggcgatcgtcgacattcctgagattcctggggttcaaggacttggagcccatg
gagcagttcatcgcacaggtcgatctgtgtgtggactgcacaactggctgcctcaaagggcttgccaacgtgcagtgttctgacctg
ctcaagaagtggctgccgcaacgctgtgcgacctttgccagcaagatccagggccaggtggacaagatcaaggggccggtggt
gaca<u>aagcg</u>cgctgtgctggacctggatatgcgcaagtgtctccctgcggcccgggcggcaaaggacgctgcttcggaccaagcat
ctgctgcgcggacgagctgggctgcttcgtgggcaccgccgaggcgctgcgctgccaggaggagaactacctgccttcgccctgcc
agtctggccagaagccctgcgggagcggaggccgctgcgccgccacaggcatctgctgcagcccggatggctgccgcacagaccc
cgcctgcgaccctgagtctgccttctcggagcgctga Oxytocin Human (nucleic acid sequence):

(SEQ ID NO: 158)

Atggccggccccagcctcgcttgctgtctgctcggcctcctggcgctgacctccgcctgctacatccagaactgcccccctgggaggc<u>a</u>
<u>agagg</u>aagcccaccgagaacaacgaagacttcaacatcgtggccgtggccagcaacttcgcgaccacggatctcgatgctgacc
gcgggaagttgcccggcaagaagctgccgctggaggtgctcaaagagatggaagccaatgcccggaaagctggctgcaccag
gggctgtctgatctgcctgtcccacatcaagtgcacgcccaagatgaagaagttcatcccaggacgctgccacacctacgaaggc
gacaaagagtccgcacagggcggcataggcgaggcgatcgtcgacattcctgagattcctggggttcaaggacttggagcccatg
gagcagttcatcgcacaggtcgatctgtgtgtggactgcacaactggctgcctcaaagggcttgccaacgtgcagtgttctgacctg
ctcaagaagtggctgccgcaacgctgtgcgacctttgccagcaagatccagggccaggtggacaagatcaaggggccggtggt
gaca<u>aagcg</u>cgccgcgccggacctcgacgtgcgcaagtgcctccctgcggcccgggggcaaaggccgctgcttcgggcccaata
tctgctgcgcggaagagctgggctgcttcgtgggcaccgccgaagcgctgcgctgccaggaggagaactacctgccgtcgccctgc
cagtccggccagaaggcgtgcgggagcggggccgctgcgcggtcttgggcctctgctgcagcccggacggctgccacgccgac
cctgcctgcgacgcggaagccaccttctcccagcgctga Vasopressin-Neurophysin-2 Mouse (nucleic acid sequence):

(SEQ ID NO: 159)

atgctcgccaggatgctcaacactacgctctccgcttgtttcctgagcctgctggccttctcctccgcctgctacttccagaactgcccaag
aggcgg<u>aagagg</u>aagcccaccgagaacaacgaagacttcaacatcgtggccgtggccagcaacttcgcgaccacggatctcg
atgctgaccgcgggaagttgcccggcaagaagctgccgctggaggtgctcaaagagatggaagccaatgcccggaaagctggc
tgcaccaggggctgtctgatctgcctgtcccacatcaagtgcacgcccaagatgaagaagttcatcccaggacgctgccacaccta
cgaaggcgacaaagagtccgcacagggcggcataggcgaggcgatcgtcgacattcctgagattcctgggttcaaggacttgga
gcccatggagcagttcatcgcacaggtcgatctgtgtgtggactgcacaactggctgcctcaaagggcttgccaacgtgcagtgttc
tgacctgctcaagaagtggctgccgcaacgctgtgcgacctttgccagcaagatccagggccaggtggacaagatcaaggggc
cggtggtgaca<u>aagcg</u>cgccatctctgacatggagctgagacagtgtctccctgcgggcccgggcggcaaaggacgctgcttcggac
caagcatctgctgcgcggacgagctgggctgcttcgtgggcaccgccgaggcgctgcgctgccaggaggagaactacctgccctcg
ccctgccagtccggccagaagccctgcgggagcggggccgctgcgccgccgtgggcatctgctgcagcgacgagagctgcgtg
gccgagcccgagtgccacgacggttttttccgcctcacccgcgctcgggagccaagcaacgccacacagctggacgcccctgctcg
ggcgctgctgctaaggctggtacagctggctgggacacgggagtccgtggattctgccaagcccgggtctactga -continued Vasopressin-Neurophysin-2 Human (nucleic acid sequence):
(SEQ ID NO: 160)
Atgcctgacaccatgctgcccgcctgcttcctcggcctactggccttctcctccgcgtgctacttccagaactgcccgagggggcggc<u>aa</u>
<u>gagg</u>aagcccaccgagaacaacgaagacttcaacatcgtggccgtggccagcaacttcgcgaccacggatctcgatgctgacc
gcggaagttgcccggcaagaagctgccgctggaggtgctcaaagagatggaagccaatgcccggaaagctggctgcaccag
gggctgtctgatctgcctgtcccacatcaagtgcacgcccaagatgaagaagttcatcccaggacgctgccacacctacgaaggc
gacaaagagtccgcacagggcggcataggcgaggcgatcgtcgacattcctgagattcctggttcaaggacttggagcccatg
gagcagttcatcgcacaggtcgatctgtgtgtggactgcacaactggctgcctcaaagggcttgccaacgtgcagtgttctgacctg
ctcaagaagtggctgccgcaacgctgtgcgacctttgccagcaagatccagggccaggtggacaagatcaagggggccggtggt
gacaag<u>cgc</u>gccatgtccgacctggagctgagacagtgcctccctgcggccccgggggcaaaggccgctgcttcgggcccagca
tctgctgcgcggacgagctggctgcttcgtgggcacggctgaggcgctgcgctgccaggaggagaactacctgccgtcgccctgc
cagtccggccagaaggcgtgcgggagcggggccgctgcgccgccttcggcgtttgctgcaacgacgagagctgcgtgaccgagc
ccgagtgccgcgagggcttcaccgccgcgcccgcgccagcgaccggagcaacgccacgcagctggacgggccggccggggcc
ttgctgctgcggctggtgcagctggccggggcgcccgagcccttcgagcccgcccagcccgacgcctactga Gonadotropin-releasing hormone (GnRH) Mouse (nucleic acid sequence):
(SEQ ID NO: 161)
Atgatcctcaaactgatggccggcattctactgctgactgtgtgtttggaaggctgctccagccagcactggtcctatgggttgcgccct
gggggga<u>aagaga</u>aagcccaccgagaacaacgaagacttcaacatcgtggccgtggccagcaacttcgcgaccacggatctcga
tgctgaccgcggggaagttgcccggcaagaagctgccgctggaggtgctcaaagagatggaagccaatgcccggaaagctggct
gcaccaggggctgtctgatctgcctgtcccacatcaagtgcacgcccaagatgaagaagttcatcccaggacgctgccacaccta
cgaaggcgacaaagagtccgcacagggcggcataggcgaggcgatcgtcgacattcctgagattcctgggttcaaggacttgga
gcccatggagcagttcatcgcacaggtcgatctgtgtgtggactgcacaactggctgcctcaaagggcttgccaacgtgcagtgttc
tgacctgctcaagaagtggctgccgcaacgctgtgcgacctttgccagcaagatccagggccaggtggacaagatcaagggggc
cggtggtgac<u>aagcgc</u>aacactgaacacttggttgagtctttccaagagatgggcaaggaggtggatcaaatggcagaaccccagca
cttcgaatgtactgtccactggccccgttcacccctcagggatctgcgaggagctctggaaagtctgattgaagaggaagccaggcag
aagaagatgtag Gonadotropin-releasing hormone (GnRH) Human (nucleic acid sequence):
(SEQ ID NO: 162)
Atgaagccaattcaaaaactcctagctggccttattctactgacttggtgcgtggaaggctgctccagccagcactggtcctatggactg
cgccctggagga<u>aagaga</u>aagcccaccgagaacaacgaagacttcaacatcgtggccgtggccagcaacttcgcgaccacgga
tctcgatgctgaccgcggggaagttgcccggcaagaagctgccgctggaggtgctcaaagagatggaagccaatgcccggaaag
ctggctgcaccaggggctgtctgatctgcctgtcccacatcaagtgcacgcccaagatgaagaagttcatcccaggacgctgccac
acctacgaaggcgacaaagagtccgcacagggcggcataggcgaggcgatcgtcgacattcctgagattcctgggttcaaggac
ttggagcccatggagcagttcatcgcacaggtcgatctgtgtgtggactgcacaactgctgcctcaaagggcttgccaacgtgca
gtgttctgacctgctcaagaagtggctgccgcaacgctgtgcgacctttgccagcaagatccagggccaggtggacaagatcaag
ggggccggtggtgac<u>aagcgc</u>gatgccgaaaatttgattgattcttttccaagagatagtcaaagaggttggtcaactggcagaaaccca
acgcttcgaatgcaccacgcaccagccacgttctcccctccgagacctgaaaggagctctggaaagtctgattgaagaggaaactggg
cagaagaagatttaa Thyroid-stimulating hormone, beta subunit (TSHB) Mouse (nucleic acid sequence):
(SEQ ID NO: 163)
Atgagtgctgccgtcctcctctccgtgcttttttgctcttgcttgtgggcaagcagcatcctttttgtattcccactgagtatacaatgtacgtgg
ataggagagagtgtgcctactgcctgaccatcaacaccaccatctgtgctgggtattgtatgacacgggatatcaatggcaaactgtttcttc
ccaaatatgcactctctcaggatgtctgtacatacagagacttcatctacagaacggtggaaataccaggatgcccgcaccatgttactc
cttatttctccttccctgtcgccataagctgcaagtgtggcaagtgtaatactgacaacagtgactgcatacacgaggctgtcagaaccaa -continued ctactgcaccaagccgcagtctttc<u>tatctg</u>aagcccaccgagaacaacgaagacttcaacatcgtggccgtggccagcaacttcgc gaccacggatctcgatgctgaccgcgggaagttgcccggcaagaagctgccgctggaggtgctcaaagagatggaagccaatg cccggaaagctggctgcaccaggggctgtctgatctgcctgtcccacatcaagtgcacgcccaagatgaagaagttcatcccagg acgctgccacacctacgaaggcgacaaagagtccgcacagggcggcataggcgaggcgatcgtcgacattcctgagattcctgg gttcaaggacttggagcccatggagcagttcatcgcacaggtcgatctgtgtgtggactgcacaactggctgcctcaaagggcttgc caacgtgcagtgttctgacctgctcaagaagtggctgccgcaacgctgtgcgacctttgccagcaagatccagggccaggtggac aagatcaaggggccggtggtgac<u>tatctg</u>ggggattttctgtttaa Thyroid-stimulating hormone, beta subunit (TSHB) Human (nucleic acid sequence):

(SEQ ID NO: 164)

Atgactgctctctttctgatgtccatgcttttggccttacatgtgggcaagcgatgtcttttgtattccaactgagtatacaatgcacatcga aaggagagagtgtgcttattgcctaaccatcaacaccaccatctgtgctggatattgtatgacacgggatatcaatggcaaactgtttcttc ccaaatatgctctgtcccaggatgtttgcacatatagagacttcatctacaggactgtagaaataccaggatgcccactccatgttgctccc tattttcctatcctgttgctttaagctgtaagtgtggcaagtgcaatactgactatagtgactgcatacatgaagccatcaagacaaactact gtaccaaacctcagaagtctt<u>tatctg</u>aagcccaccgagaacaacgaagacttcaacatcgtggccgtggccagcaacttcgcgacc acggatctcgatgctgaccgcgggaagttgcccggcaagaagctgccgctggaggtgctcaaagagatggaagccaatgcccg gaaagctggctgcaccaggggctgtctgatctgcctgtcccacatcaagtgcacgcccaagatgaagaagttcatcccaggacgc tgccacacctacgaaggcgacaaagagtccgcacagggcggcataggcgaggcgatcgtcgacattcctgagattcctgggttc aaggacttggagcccatggagcagttcatcgcacaggtcgatctgtgtgtggactgcacaactggctgcctcaaagggcttgccaa cgtgcagtgttctgacctgctcaagaagtggctgccgcaacgctgtgcgacctttgccagcaagatccagggccaggtggacaag atcaaggggccggtggtgac<u>tatctg</u>gtaggattttctgtctaa Cortisol-releasing factor (CRF) Mouse (nucleic acid sequence):

(SEQ ID NO: 165)

Atgcggctgcggctgctggtgtccgcgggcatgctgctggtggctctgtcgtcctgcctgccttgcagggccctgctcagcaggggat ccgtcccccgagcgccgcgggccccgcagcccttgaatttcttgcagccggagcagcccagcaacctcagccggttctgatccgca tgggtgaagaatacttcctccgcctggggaatctcaacagaagtcccgctgctcggctgtccccaactccacgcccctcaccgcgggt cgcggcagccgcccctcgcacgaccaggctgcggctaacttttttccgcgtgttgctgcagcagctgcagatgcctcagcgctcgctcg acagccgcgcggagccggccgaacgcggcgccgaggatgccctcggtggccaccaggggggcgctggagagggag<u>aggcgga</u>

<u>agcccaccgagaacaacgaagacttcaacatcgtggccgtggccagcaacttcgcgaccacggatctcgatgctgaccgcggg</u>

<u>aagttgcccggcaagaagctgccgctggaggtgctcaaagagatggaagccaatgcccggaaagctggctgcaccaggggctg</u>

<u>tctgatctgcctgtcccacatcaagtgcacgcccaagatgaagaagttcatcccaggacgctgccacacctacgaaggcgacaaa</u>

<u>gagtccgcacagggcggcataggcgaggcgatcgtcgacattcctgagattcctgggttcaaggacttggagcccatggagcagt</u>

<u>tcatcgcacaggtcgatctgtgtgtggactgcacaactggctgcctcaaagggcttgccaacgtgcagtgttctgacctgctcaaga</u>

<u>agtggctgccgcaacgctgtgcgacctttgccagcaagatccagggccaggtggacaagatcaaggggccggtggtgac</u>tgg cggtcggaggagccgcccatctctctggatctcaccttccaccttctgcgggaagtcttggaaatggcccgggcagagcagttagctca gcaagctcacagcaacaggaaactgatggagattatcgggaaatga Cortisol-releasing factor (CRF) Human (nucleic acid sequence):

(SEQ ID NO: 166)

Atgcggctgccgctgctgtgtccgcgggagtcctgctggtggctctcctgccctgcccgccatgcaggcgctcctgagccgcggg ccggtcccgggagctcggcaggcgccgcagcaccctcagcccttggatttcttccagccgccgccgcagtccgagcagccccagca gccgcaggctcggccggtcctgctccgcatggagaggagtacttcctccgcctggggaacctcaacaagagcccggccgctcccc tttcgcccgcctcctcgctcctcgccggaggcagcggcagccgcccttcgccggaacaggcgaccgccaacttttttccgcgtgttgctg cagcagctgctgctgcctcggcgctcgctcgacagccccgcggctctcgcggagcgcggcgctaggaatgccctcggcggccacc aggaggcaccggagagagaa<u>aggcggaagcccaccgagaacaacgaagacttcaacatcgtggccgtggccagcaacttcgc</u>

-continued gaccacggatctcgatgctgaccgcgggaagttgcccggcaagaagctgccgctggaggtgctcaaagagatggaagccaatg cccggaaagctggctgcaccaggggctgtctgatctgcctgtcccacatcaagtgcacgcccaagatgaagaagttcatcccagg acgctgccacacctacgaaggcgacaaagagtccgcacagggcggcataggcgaggcgatcgtcgacattcctgagattcctgg gttcaaggacttggagcccatggagcagttcatcgcacaggtcgatctgtgtgtggactgcacaactggctgcctcaaagggcttgc caacgtgcagtgttctgacctgctcaagaagtggctgccgcaacgctgtgcgacctttgccagcaagatccagggccaggtggac aagatcaaggggccggtggtgacaggcggtccgaggagcctcccatctccctggatctcaccttccacctcctccgggaagtcttg gaaatggccagggccgagcagttagcacagcaagctcacagcaacaggaaactcatggagattattgggaaataa Atrial natriuretic peptide (ANP) Mouse (nucleic acid sequence):
(SEQ ID NO: 167)

Atgggctccttctccatcaccctgggcttcttcctcgtcttggccttttggcttccaggccatattggagcaaatcctgtgtacagtgcggtg tccaacacagatctgatggatttcaagaacctgctagaccacctggaggagaagatgccggtagaagatgaggtcatgcccccgcag gccctgagtgagcagactgaggaagcaggggccgcacttagctcccctccccgaggtgcctccctggactggggaggtcaacccacc tctgagagacggcagtgctctagggcgcagcccctgggacccctccgatagatctgccctcttgaaaagcaaactgagggctctgctc gctggccctcggagcaagcccaccgagaacaacgaagacttcaacatcgtggccgtggccagcaacttcgcgaccacggatctc gatgctgaccgcgggaagttgcccggcaagaagctgccgctggaggtgctcaaagagatggaagccaatgccggaaagctg gctgcaccaggggctgtctgatctgcctgtcccacatcaagtgcacgcccaagatgaagaagttcatcccaggacgctgccacac ctacgaaggcgacaaagagtccgcacagggcggcataggcgaggcgatcgtcgacattcctgagattcctgggttcaaggactt ggagcccatggagcagttcatcgcacaggtcgatctgtgtgtggactgcacaactggctgcctcaaagggcttgccaacgtgcagt gttctgacctgctcaagaagtggctgccgcaacgctgtgcgacctttgccagcaagatccagggccaggtggacaagatcaaggg ggccggtggtgaccggagcctacgaagatccagctgcttcggggtaggattgacaggattggagcccagagtggactaggctgca acagcttccggtaccgaagataa Atrial natriuretic peptide (ANP) Human (nucleic acid sequence):
(SEQ ID NO: 168)

atgagctccttctccaccaccaccgtgagcttcctcctttttactggcattccagctcctaggtcagaccagagctaatcccatgtacaatgc cgtgtccaacgcagacctgatggatttcaagaatttgctggaccatttggaagaaaagatgcctttagaagatgaggtcgtgcccccaca agtgctcagtgagccgaatgaagaagcgggggctgctctcagcccctccctgaggtgcctccctggaccggggaagtcagcccag cccagagagatggaggtgcccctcgggcggggcccctgggactcctctgatcgatctgccctcctaaaaagcaagctgagggcgctgc tcactgcccctcggagcaagcccaccgagaacaacgaagacttcaacatcgtggccgtggccagcaacttcgcgaccacggatc tcgatgctgaccgcgggaagttgcccggcaagaagctgccgctggaggtgctcaaagagatggaagccaatgccggaaagct ggctgcaccaggggctgtctgatctgcctgtcccacatcaagtgcacgcccaagatgaagaagttcatcccaggacgctgccaca cctacgaaggcgacaaagagtccgcacagggcggcataggcgaggcgatcgtcgacattcctgagattcctgggttcaaggact tggagcccatggagcagttcatcgcacaggtcgatctgtgtgtggactgcacaactggctgcctcaaagggcttgccaacgtgcag tgttctgacctgctcaagaagtggctgccgcaacgctgtgcgacctttgccagcaagatccagggccaggtggacaagatcaagg gggccggtggtgaccggagcctgcggagatccagctgcttcggggcaggatggacaggattggagcccagagcggactgggct gtaacagcttccggtactga Brain natriuretic peptide (BNP) Mouse (nucleic acid sequence):
(SEQ ID NO: 169)

atggatctcctgaaggtgctgtcccagatgattctgtttctgcttttcctttatctgtcaccgctgggaggtcactcctatcctctgggaagtcc tagccagtctccagagcaattcaagatgcagaagctgctggagctgataagagaaaagtcggaggaaatggcccagagacagctctt gaaggaccaaggcctcacaaaagaacacccaaaaagagtccttcggtctaagcccaccgagaacaacgaagacttcaacatcgtg gccgtggccagcaacttcgcgaccacggatctcgatgctgaccgcgggaagttgcccggcaagaagctgccgctggaggtgctc aaagagatggaagccaatgcccggaaagctggctgcaccaggggctgtctgatctgcctgtcccacatcaagtgcacgcccaag atgaagaagttcatcccaggacgctgccacacctacgaaggcgacaaagagtccgcacagggcggcataggcgaggcgatcg tcgacattcctgagattcctgggttcaaggacttggagcccatggagcagttcatcgcacaggtcgatctgtgtgtggactgcacaac -continued tggctgcctcaaagggcttgccaacgtgcagtgttctgacctgctcaagaagtggctgccgcaacgctgtgcgacctttgccagcaa gatccagggccaggtggacaagatcaaggggggccggtggtgacc<u>cggtct</u>caaggcagcaccctccgggtccagcagagacctca aaattccaaggtgacacatatctcaagctgctttgggcacaagatagaccggatcggatccgtcagtcgtttgggctgtaacgcactgaa gttgttgtag Brain natriuretic peptide (BNP) Human (nucleic acid sequence):

(SEQ ID NO: 170)

Atggatccccagacagcaccttcccgggcgctcctgctcctgctcttcttgcatctggctttcctgggaggtcgttcccacccgctgggc agccccggttcagcctcggacttggaaacgtccggttacaggagcagcgcaaccatttgcagggcaaactgtcggagctgcaggtg gagcagacatccctggagcccctccaggagagcccccgtcccacaggtgtctggaagtcccggggggtagccaccgagggcatcc gtgggcaccgcaaaatggtcctctacaccctgcgggcacca<u>cgaag</u>caagcccaccgagaacaacgaagacttcaacatcgtgg ccgtggccagcaacttcgcgaccacggatctcgatgctgaccgcggggaagttgcccggcaagaagctgccgctggaggtgctca aagagatggaagccaatgcccggaaagctggctgcaccaggggctgtctgatctgcctgtcccacatcaagtgcacgcccaaga tgaagaagttcatcccaggacgctgccacacctacgaaggcgacaaagagtccgcacaggggcggcataggcgaggcgatcgtc gacattcctgagattcctgggttcaaggacttggagcccatggagcagttcatcgcacaggtcgatctgtgtgtggactgcacaact ggctgcctcaaagggcttgccaacgtgcagtgttctgacctgctcaagaagtggctgccgcaacgctgtgcgacctttgccagcaa gatccagggccaggtggacaagatcaaggggggccggtggtgacc<u>cgaagc</u>cgaagcccaagatggtgcaagggtctggctgctt tgggaggaagatggaccggatcagctcctccagtggcctgggctgcaaagtgctgaggcggcattaa Renin Mouse (nucleic acid sequence):

(SEQ ID NO: 171)

Atggacagaaggaggatgcctctctgggcactcttgttgctctggagtccttgcaccttcagtctcccaacacgcaccgctacctttgaa cgaatcccgctcaagaaaatgccttctgtccgggaaatcctggaggagcggggagtggacatgaccaggctcagtgctgaatggggc gtattcaca<u>aagagg</u>aagcccaccgagaacaacgaagacttcaacatcgtggccgtggccagcaacttcgcgaccacggatctc gatgctgaccgcggggaagttgcccggcaagaagctgccgctggaggtgctcaaagagatggaagccaatgcccggaaagctg gctgcaccaggggctgtctgatctgcctgtcccacatcaagtgcacgcccaagatgaagaagttcatcccaggacgctgccacac ctacgaaggcgacaaagagtccgcacaggggcggcataggcgaggcgatcgtcgacattcctgagattcctgggttcaaggactt ggagcccatggagcagttcatcgcacaggtcgatctgtgtgtggactgcacaactggctgcctcaaagggcttgccaacgtgcagt gttctgacctgctcaagaagtggctgccgcaacgctgtgcgacctttgccagcaagatccagggccaggtggacaagatcaaggg ggccggtggtgac<u>aagagg</u>ccttccttgaccaatcttacctcccccgtggtcctcaccaactacctgaatacccagtactacggcgaga ttggcatcggtaccccaccccagaccttcaaagtcatctttgacacgggttcagccaacctctgggtgccctccaccaagtgcagccgc ctctaccttgcttgtgggattcacagcctctatgagtcctctgactcctccagctacatggagaacgggtccgacttcaccatccactacgg atcagggagagtcaaaggtttcctcagccaggactcggtgactgtgggtggaatcactgtgacacagaccctttgagaggtcaccgag ctgcccctgatcccttctcatgctggccaagtttgacggtgttctaggcatgggctttcccgctcaggccgttggcggggttacccctgtctttt gaccacattctctcccaggggtgctaaaggaggaagtgttctctgtctactacaacaggggttcccacctgctgggggcgaggtggt gctaggaggtagcgacccgcagcattatcaaggcaattttcactatgtgagcatcagcaagactgactcctggcagatcacgatgaagg gggtgtctgtggggtcttccaccctgctatgtgaagaaggctgtgcggtagtggtggacactggttcatcctttatctcggctcctacgag ctccctgaagttgatcatgcaagccctgggagccaaggagaagagaatagaagaatatgttgtgaactgtagccaggtgcccaccctc cccgacatttcctttgacctgggaggcagggcctacacactcagcagtacggactacgtgctacagtatcccaacaggagagacaagc tgtgcacactggctctccatgccatggacatcccaccacccactgggcctgtctgggtcctgggtgccaccttcatccgcaagttctatac agagtttgatcggcataacaatcgcattggattcgccttggcccgctaa Renin Human (nucleic acid sequence):

(SEQ ID NO: 172)

Atggatggatggagaaggatgcctcgctggggactgctgctgctgctctggggctcctgtacctttggtctcccgacagacaccacca cctttt<u>aaacgg</u>aagcccaccgagaacaacgaagacttcaacatcgtggccgtggccagcaacttcgcgaccacggatctcgatgc -continued

```
tgaccgcgggaagttgcccggcaagaagctgccgctggaggtgctcaaagagatggaagccaatgcccggaaagctggctgca
ccaggggctgtctgatctgcctgtcccacatcaagtgcacgcccaagatgaagaagttcatcccaggacgctgccacacctacga
aggcgacaaagagtccgcacagggcggcataggcgaggcgatcgtcgacattcctgagattcctgggttcaaggacttggagcc
catggagcagttcatcgcacaggtcgatctgtgtgtggactgcacaactggctgcctcaaagggcttgccaacgtgcagtgttctga
ctgctcaagaagtggctgccgcaacgctgtgcgacctttgccagcaagatccagggccaggtggacaagatcaaggggccg
gtggtgacaaacggatcttcctcaagagaatgccctcaatccgagaaagcctgaaggaacgaggtgtggacatggccaggcttggtc
ccgagtggagccaacccatgaagaggctgacacttggcaacaccacctcctccgtgatcctcaccaactacatggacaccagtacta
tggcgagattggcatcggcaccccaccccagaccttcaaagtcgtctttgacactggttcgtccaatgtttgggtgccctcctccaagtgc
agccgtctctacactgcctgtgtgtatcacaagctcttcgatgcttcggattcctccagctacaagcacaatggaacagaactcaccctcc
gctattcaacagggacagtcagtggctttctcagccaggacatcatcaccgtgggtggaatcacggtgacacagatgtttggagaggtc
acggagatgcccgccttacccttcatgctggccgagtttgatggggttgtgggcatgggcttcattgaacaggccattggcagggtcac
ccctatcttcgacaacatcatctcccaaggggtgctaaaagaggacgtcttctctttctactacaacagagattccgagaattcccaatcgc
tgggaggacagattgtgctgggaggcagcgaccccccagcattacgaagggaatttccactatatcaacctcatcaagactggtgtctgg
cagattcaaatgaaggggtgtctgtgggtcatccaccttgctctgtgaagacggctgcctggcattggtagacaccggtgcatcctac
atctcaggttctaccagctccatagagaagctcatggaggccttgggagccaagaagaggctgtttgattatgtcgtgaagtgtaacgag
ggccctacactccccgacatctctttccacctgggaggcaaagaatacacgctcaccagcgcggactatgtatttcaggaatcctacagt
agtaaaaagctgtgcacactggccatccacgccatggatatcccgccacccactggacccacctgggccctgggggccaccttcatcc
gaaagttctacacagagtttgatcggcgtaacaaccgcattggcttcgccttggcccgctga
```

Galanin Mouse (nucleic acid sequence):

(SEQ ID NO: 173)

```
Atggccagaggcagcgttatcctgctaggctggctcctgttggttgtgaccctgtcagccactctgggacttgggatgcctgcaaagga
gaagagaggtaagcccaccgagaacaacgaagacttcaacatcgtggccgtggccagcaacttcgcgaccacggatctcgatgc
tgaccgcgggaagttgcccggcaagaagctgccgctggaggtgctcaaagagatggaagccaatgcccggaaagctggctgca
ccaggggctgtctgatctgcctgtcccacatcaagtgcacgcccaagatgaagaagttcatcccaggacgctgccacacctacga
aggcgacaaagagtccgcacagggcggcataggcgaggcgatcgtcgacattcctgagattcctgggttcaaggacttggagcc
catggagcagttcatcgcacaggtcgatctgtgtgtggactgcacaactggctgcctcaaagggcttgccaacgtgcagtgttctga
cctgctcaagaagtggctgccgcaacgctgtgcgacctttgccagcaagatccagggccaggtggacaagatcaaggggccg
gtggtgacaagagaggttggaccctgaacagcgctggctaccttctgggcccacatgccattgacaaccacagatcatttagcgacaa
gcatggcctcacaggcaagaggagttacaactggaggtggaggaaaggagaccaggaagtgttgatgtgccccctgcctgagagca
acattgtccgcactataatggagtttctcagtttcttgcaccttaaagaggccggggccctcgacagcctgcctggcatccccttggccac
ctcctcagaagacctagagaagtcctga
```

Galanin Human (nucleic acid sequence):

(SEQ ID NO: 174)

```
Atggcccgaggcagcgcccctcctgctcgcctccctcctcctcgccgcggcccttcctgcctctgcggggctctggtcgccggccaag
gaaaaacgaggcaagcccaccgagaacaacgaagacttcaacatcgtggccgtggccagcaacttcgcgaccacggatctcga
tgctgaccgcgggaagttgcccggcaagaagctgccgctggaggtgctcaaagagatggaagccaatgcccggaaagctggct
gcaccaggggctgtctgatctgcctgtcccacatcaagtgcacgcccaagatgaagaagttcatcccaggacgctgccacaccta
cgaaggcgacaaagagtccgcacagggcggcataggcgaggcgatcgtcgaacattcctgagattcctgggttcaaggacttgga
gcccatggagcagttcatcgcacaggtcgatctgtgtgtggactgcacaactggctgcctcaaagggcttgccaacgtgcagtgttc
tgacctgctcaagaagtggctgccgcaacgctgtgcgacctttgccagcaagatccagggccaggtggacaagatcaaggggc
cggtggtgacaaacgaggctggaccctgaacagcgcgggctacctgctgggcccacatgccgttggcaaccacaggtcattcagcg
```

-continued acaagaatggcctcaccagcaagcgggagctgcggcccgaagatgacatgaaaccaggaagctttgacaggtccatacctgaaaac aatatcatgcgcacaatcattgagtttctgtcttttcttgcatctcaaagaggccggtgccctcgaccgcctcctggatctccccgccgcagc ctcctcagaagacatcgagcggtcctga Orexin Mouse (nucleic acid sequence):

(SEQ ID NO: 175)

Atgaactttccttctacaaaggttccctgggccgccgtgacgctgctgctgctgctactgctgccgccggcgctgctgtcgcttggggtg gacgcacagcctctgcccgactgctgtcgccagaagacgtgttcctgccgtctctacgaactgttgcacggagctggcaaccacgctg cgggtatcctgactctgggaaagcggcggcctggacctccaggcctccagggacggctgcagcgcctccttcaggccaacggtaac cacgcagctggcatcctgaccatgggccgccgcaagcccaccgagaacaacgaagacttcaacatcgtggccgtggccagcaa cttcgcgaccacggatctcgatgctgaccgcgggaagttgcccggcaagaagctgccgctggaggtgctcaaagagatggaagc caatgcccggaaagctggctgcaccaggggctgtctgatctgcctgtcccacatcaagtgcacgcccaagatgaagaagttcatcc caggacgctgccacacctacgaaggcgacaaagagtccgcacagggcggcataggcgaggcgatcgtcgacattcctgagatt cctgggttcaaggacttggagcccatggagcagttcatcgcacaggtcgatctgtgtgtggactgcacaactggctgcctcaaagg gcttgccaacgtgcagtgttctgacctgctcaagaagtggctgccgcaacgctgtgcgacctttgccagcaagatccagggccagg tggacaagatcaaggggggccggtggtgacggccgccgcgcaggcgcagagctagagccacatccctgctctggtcgcggctgtcc gaccgtaactaccaccgctttagcaccccggggagggtccggagtctga Orexin Human (nucleic acid sequence):

(SEQ ID NO: 176)

Atgaaccttccttccacaaaggtctcctgggccgccgtgacgctactgctgctgctgctgctgccgcccgcgctgttgtcgtccgg ggcggctgcacagcccctgcccgactgctgtcgtcaaaagacttgctcttgccgcctctacgagctgctgcacgcgcgggcaatcac gcggccggcatcctcacgctgggcaagcggaggtccgggcccccgggcctccagggtcggctgcagcgcctcctgcaggccagc ggcaaccacgccgcgggcatcctgaccatgggccgccgcaagcccaccgagaacaacgaagacttcaacatcgtggccgtggc cagcaacttcgcgaccacggatctcgatgctgaccgcgggaagttgcccggcaagaagctgccgctggaggtgctcaaagagat ggaagccaatgcccggaaagctggctgcaccaggggctgtctgatctgcctgtcccacatcaagtgcacgcccaagatgaagaa gttcatcccaggacgctgccacacctacgaaggcgacaaagagtccgcacagggcggcataggcgaggcgatcgtcgacattc ctgagattcctgggttcaaggacttggagcccatggagcagttcatcgcacaggtcgatctgtgtgtggactgcacaactggctgcct caaagggcttgccaacgtgcagtgttctgacctgctcaagaagtggctgccgcaacgctgtgcgacctttgccagcaagatcccagg gccaggtggacaagatcaaggggggccggtggtgacggccgccgcgcaggcgcagagccagcgccgcgcccctgcctcgggcg ccgctgttccgccccggccgccgcctccgtcgcgcccggaggacagtccgggatctga Ghrelin-Obestatin Mouse (nucleic acid sequence):

(SEQ ID NO: 177)

Atgctgtcttcaggcaccatctgcagtttgctgctactcagcatgctctggatggacatggccatggcaggctccagcttcctgagccca gagcaccagaaagcccagcagagaaaggaatccaagaagccaccagctaaactgcagccacgagctaagcccaccgagaacaa cgaagacttcaacatcgtggccgtggccagcaacttcgcgaccacggatctcgatgctgaccgcgggaagttgcccggcaagaa gctgccgctggaggtgctcaaagagatggaagccaatgcccggaaagctggctgcaccaggggctgtctgatctgcctgtcccac atcaagtgcacgcccaagatgaagaagttcatcccaggacgctgccacacctacgaaggcgacaaagagtccgcacagggcg gcataggcgaggcgatcgtcgacattcctgagattcctgggttcaaggacttggagcccatggagcagttcatcgcacaggtcgat ctgtgtgtggactgcacaactggctgcctcaaagggcttgccaacgtgcagtgttctgacctgctcaagaagtggctgccgcaacgc tgtgcgacctttgccagcaagatccagggccaggtggacaagatcaaggggggccggtggtgaccacgagctctggaaggctgg ctccacccagaggacagaggacaagcagaagagacagaggaggagctggagatcaggttcaatgctcccttcgatgttggcatcaa gctgtcaggagctcagtatcagcagcatggccgggccctggggaagtttcttcaggatatcctctgggaagaggtcaaagaggcgcca gctgacaagtaa -continued Ghrelin-Obestatin Human (nucleic acid sequence):
(SEQ ID NO: 178)
Atgccctccccagggaccgtctgcagcctcctgctcctcggcatgctctggctggacttggccatggcaggctccagcttcctgagcc ctgaacaccagagagtccagagaaaggagtcgaagaagccaccagccaagctgcag<u>ccccgagct</u>aagcccaccgagaacaac gaagacttcaacatcgtggccgtggccagcaacttcgcgaccacggatctcgatgctgaccgcgggaagttgcccggcaagaaag ctgccgctggaggtgctcaaagagatggaagccaatgcccggaaagctggctgcaccagggGctgtctgatctgcctgtcccaca tcaagtgcacgccaagatgaagaagttcatcccaggacgctgccacacctacgaaggcgacaaagagtccgcacagggcgg cataggcgaggcgatcgtcgacattcctgagattcctgggttcaaggacttggagcccatggagcagttcatcgcacaggtcgatct gtgtgtggactgcacaactggctgcctcaaagggcttgccaacgtgcagtgttctgacctgctcaagaagtggctgccgcaacgctg tgcgacctttgccagcaagatccagggccaggtggacaagatcaagggggccggtggtgac<u>ccccgagct</u>ctagcaggctggct ccgcccggaagatggaggtcaagcagaaggggcagaggatgaactggaagtccggttcaacgcccccttttgatgttggaatcaagct gtcaggggttcagtaccagcagcacagccaggccctggggaagtttcttcaggacatcctctggggaagaggccaaagaggccccag ccgacaagtga Cholecystokinin Mouse (nucieic acid sequence):
(SEQ ID NO: 179)
Atgaagagcggcgtatgtctgtgcgtggtgatggcagtcctagctgctggcgccctggcgcagccggtagtccctgcagaagctacg gaccccgtggagcagcgggcgcaagaggcgccc<u>cgaaggcagctgcgggct</u>aagcccaccgagaacaacgaagacttcaaca tcgtggccgtggccagcaacttcgcgaccacggatctcgatgctgaccgcgggaagttgcccggcaagaagctgccgctggaggt gctcaaagagatggaagccaatgcccggaaagctggctgcaccagggGctgtctgatctgcctgtcccacatcaagtgcacgccc aagatgaagaagttcatcccaggacgctgccacacctacgaaggcgacaaagagtccgcacagggcggcataggcgaggcg atcgtcgacattcctgagattcctgggttcaaggacttggagcccatggagcagttcatcgcacaggtcgatctgtgtgtggactgca caactggctgcctcaaagggcttgccaacgtgcagtgttctgacctgctcaagaagtggctgccgcaagctgtgcgacctttgcca gcaagatccagggccaggtggacaagatcaaggggGccggtggtgac<u>cgaaggcagctgcgggct</u>gtgctccggacggacgg cgagccccgagcgcgcctgggcgcactgctagcgcgatacatccagcaggtccgcaaagctccttctggccgcatgtccgttcttaag aacctgcagagcctggaccccagccatagaataagtgaccgggactacatgggctggatggattttggccggcgcagtgccgaggac tacgaataccccatcgtag Cholecystokinin Human (nucleic acid sequence):
(SEQ ID NO: 180)
atgaacagcggcgtgtgcctgtgcgtgctgatggcggtactggcggctggcgccctgacgcagccggtgcctcccgcagatcccgc gggctccgggctgcagcgggcagaggaggcgccc<u>cgtaggcagctgagggta</u>aagcccaccgagaacaacgaagacttcaac atcgtggccgtggccagcaacttcgcgaccacggatctcgatgctgaccgcgggaagttgcccggcaagaagctgccgctggag gtgctcaaagagatggaagccaatgcccggaaagctggctgcaccagggGctgtctgatctgcctgtcccacatcaagtgcacgc ccaagatgaagaagttcatcccaggacgctgccacacctacgaaggcgacaaagagtccgcacagggcggcataggcgaggc gatcgtcgacattcctgagattcctgggttcaaggacttggagcccatggagcagttcatcgcacaggtcgatctgtgtgtggactgc acaactggctgcctcaaagggcttgccaacgtgcagtgttctgacctgctcaagaagtggctgccgcaacgctgtgcgacctttgcc agcaagatccagggccaggtggacaagatcaaggggGccggtggtgac<u>cgtaggcagctgagggta</u>tcgcagagaacggatgg cgagtcccgagcgcacctgggcgccctgctggcaagatacatccagcaggcccgaaagctccttctggacgaatgtccatcgttaa gaacctgcagaacctggaccccagccacaggataagtgaccgggactacatgggctggatggattttggccgtcgcagtgccgagga gtatgagtacccctcctag Gastrin Mouse (nucleic acid sequence):
(SEQ ID NO: 181)
Atgcctcgactgtgtgtgacatgctggtcttagtgctggctctagctaccttctcggaagcttcttggaagcccgctcccagctacagg atgcatcatctggaccaggaccaatgaggacctggaacagcgccagttcaacaagctgggctcagcctctcaccatcgaaggcagc tggggcCccagggtCCtcaacacttcatagcagacctgtccaagaagcagaggccacgaatggaggaagaagaagaggcctacgg -continued atggatggactttggc<u>cgccgcagt</u>aagcccaccgagaacaacgaagacttcaacatcgtggccgtggccagcaacttcgcgacc acggatctcgatgctgaccgcgggaagttgcccggcaagaagctgccgctggaggtgctcaaagagatggaagccaatgcccg gaaagctggctgcaccaggggctgtctgatctgcctgtcccacatcaagtgcacgcccaagatgaagaagttcatcccaggacgc tgccacacctacgaaggcgacaaagagtccgcacagggcggcataggcgaggcgatcgtcgacattcctgagattcctgggttc aaggacttggagcccatggagcagttcatcgcacaggtcgatctgtgtgtggactgcacaactggctgcctcaaagggcttgccaa cgtgcagtgttctgacctgctcaagaagtggctgccgcaacgctgtgcgacctttgccagcaagatccagggccaggtggacaag atcaaggggccggtggtgac<u>cgccgcagt</u>gctgaggaagaccagtag Gastrin Human (nucleic acid sequence):

(SEQ ID NO: 182)

Atgcagcgactatgtgtgtatgtgctgatctttgcactggctctggccgccttctctgaagcttcttggaagcccgctcccagcagccag atgcacccttaggtacaggggccaacagggacctggagctaccctggctggagcagcagggcccagcctctcatcatcgaaggcag ctgggaccccagggtcccccacacctcgtggcagacccgtccaagaagcagggaccatggctggaggaagaagaagaagcctatg gatgatggacttcggc<u>cgccgcagt</u>aagcccaccgagaacaacgaagacttcaacatcgtggccgtggccagcaacttcgcga ccacggatctcgatgctgaccgcgggaagttgcccggcaagaagctgccgctggaggtgctcaaagagatggaagccaatgcc cggaaagctggctgcaccaggggctgtctgatctgcctgtcccacatcaagtgcacgcccaagatgaagaagttcatcccaggac gctgccacacctacgaaggcgacaaagagtccgcacagggcggcataggcgaggcgatcgtcgacattcctgagattcctgggt tcaaggacttggagcccatggagcagttcatcgcacaggtcgatctgtgtgtggactgcacaactggctgcctcaaagggcttgcc aacgtgcagtgttctgacctgctcaagaagtggctgccgcaacgctgtgcgacctttgccagcaagatccagggccaggtggaca agatcaaggggccggtggtgac<u>cgccgcagt</u>gctgaggatgagaactaa Protachykinin-1 (Substance P, Neurokinin A, Neuropeptide K, Neuropeptide gamma) Mouse (nucleic acid sequence):

(SEQ ID NO: 183)

atgaaaatcctcgtggccgtgcggtctttttttctcgtttccactcaactgtttgcagaggaaatcgatgccaacgatgatctaaattattggt ccgactggtccgacagtgaccagatcaaggaggcaatgccggagccctttgagcatcttctgcagagaatcgc<u>cgaaga</u>aagccc accgagaacaacgaagacttcaacatcgtggccgtggccagcaacttcgcgaccacggatctcgatgctgaccgcgggaagttg cccggcaagaagctgccgctggaggtgctcaaagagatggaagccaatgcccggaaagctggctgcaccaggggctgtctgat ctgcctgtcccacatcaagtgcacgcccaagatgaagaagttcatcccaggacgctgccacacctacgaaggcgacaaagagtc cgcacagggcggcataggcgaggcgatcgtcgacattcctgagattcctgggttcaaggacttggagcccatggagcagttcatc gcacaggtcgatctgtgtgtggactgcacaactggctgcctcaaagggcttgccaacgtgcagtgttctgacctgctcaagaagtgg ctgccgcaacgctgtgcgacctttgccagcaagatccagggccaggtggacaagatcaaggggccggtggtgac<u>cgaaga</u>cc caagcctcagcagttctttggattaatgggcaagcgggatgctgattcctcagttgaaaaacaagtggccctgttaaaggctctttatgga catggccagatctctcacaaaaggcataaaacagattcctttgttggactaatgggcaaaagagctttaaattctgtggcttatgaaagaa gcgcgatgcagaactacgaaagaagacgtaaataa Protachykinin-1 (Substance P, Neurokinin A, Neuropeptide K, Neuropeptide gamma) Human (nucleic acid sequence):

(SEQ ID NO: 184)

atgaaaatcctcgtggccttggcagtcttttttcttgtctccactcagctgtttgcagaagaaataggagccaatgatgatctgaattactggt ccgactggtacgacagcgaccagatcaaggaggaactgccggagccctttgagcatcttctgcagagaatcgc<u>cggaga</u>aagccc accgagaacaacgaagacttcaacatcgtggccgtggccagcaacttcgcgaccacggatctcgatgctgaccgcgggaagttg cccggcaagaagctgccgctggaggtgctcaaagagatggaagccaatgcccggaaagctggctgcaccaggggctgtctgat ctgcctgtcccacatcaagtgcacgcccaagatgaagaagttcatcccaggacgctgccacacctacgaaggcgacaaagagtc cgcacagggcggcataggcgaggcgatcgtcgacattcctgagattcctgggttcaaggacttggagcccatggagcagttcatc gcacaggtcgatctgtgtgtggactgcacaactggctgcctcaaagggcttgccaacgtgcagtgttctgacctgctcaagaagtgg ctgccgcaacgctgtgcgacctttgccagcaagatccagggccaggtggacaagatcaaggggccggtggtgac<u>cggaga</u>cc caagcctcagcagttctttggattaatgggcaaacgggatgctgattcctcaattgaaaaacaagtggccctgttaaaggctctttatggac atggccagatctctcacaaaagacataaaacagattcctttgttggactaatgggcaaaagagctttaaattctgtggcttatgaaaggagt gcaatgcagaattatgaaagaagacgttaa Proenkephalin-A Mouse (nucleic acid sequence):

(SEQ ID NO: 185)

atggcgcggttcctgaggctttgcacctggctgctggcgcttgggtcctgcctcctggctacagtgcaggcggaatgcagccaggact gcgctaaatgcagctaccgcctggttcgcccaggcgacatcaatttcctggcgtgcacactggaatgtgaaggacagctgccttctttca aaatctgggagacctgcaaggatctcctgcaggtgtccaggcccgagttcccttgggataacatcgacatgtacaaagacagcagcaa acaggatgagagccacttgctagccaagaagtacggaggcttcatgaaacggtacggaggcttcatgaagaagatggacgagctatat cccatggagccagaagaagaagcgaacggaggagagatccttgccaagaggtatggcggcttcatgaagaaggatgcagatgagg gagacaccttggccaactcctccgatctgctgaaagagctactgggaacgggagacaaccgtgcgaaagacagccaccaacaagag agcaccaacaatgacgaagacatgagcaagaggtatgggggcttcatgagaagcctcaaaagaagcccccaactggaagatgaagc aaaagagctgcagaagcgctacgggggcttcatgagaaggaagcccaccgagaacaacgaagacttcaacatcgtggccgtggc cagcaacttcgcgaccacggatctcgatgctgaccgcgggaagttgcccggcaagaagctgccgctggaggtgctcaaagagat ggaagccaatgcccggaaagctggctgcaccagggctgtctgatctgcctgtcccacatcaagtgcacgcccaagatgaagaa gttcatccaggacgctgccacacctacgaaggcgacaaagagtccgcacagggcggcataggcgaggcgatcgtcgacattc ctgagattcctgggttcaaggacttggagcccatggagcagttcatcgcacaggtcgatctgtgtgtggactgcacaactggctgcct caaagggcttgccaacgtgcagtgttctgacctgctcaagaagtggctgccgcaacgctgtgcgacctttgccagcaagatccagg gccaggtggacaagatcaaggggggccggtggtgacagaagggtgggacgccccgagtggtggatggactaccagaagaggtat ggggggcttcctgaagcgctttgctgagtctctgccctccgatgaagaaggcgaaaattactcgaaagaagttcctgagatagagaaaag atacgggggctttatgcggttctga Proenkephalin-A Human (nucleic acid sequence):

(SEQ ID NO: 186)

atggcgcgcggttcctgacactttgcacttggctgctgttgctcggccccgggctcctggcgaccgtgcgggccgaatgcagccaggattg cgcgacgtgcagctaccgcctagtgcgcccggccgacatcaacttcctggcttgcgtaatggaatgtgaaggtaaactgccttctctga aaatttgggaaacctgcaaggagctcctgcagctgtccaaaccagagcttcctcaagatggcaccagcaccctcagagaaaatagcaa accggaagaaagccatttgctagccaaaaggtatgggggcttcatgaaaaggtatggaggcttcatgaagaaatggatgagctttatc ccatggagccagaagaagaggccaatggaagtgagatcctcgccaagcggtatgggggcttcatgaagaaggatgcagaggagga cgactcgctggccaattcctcagacctgctaaaagagcttctggaaacaggggacaaccgagagcgtagccaccaccaggatggca gtgataatgaggaagaagtgagcaagagatatgggggcttcatgagaggcttaaagagaagcccccaactggaagatgaagccaaa gagctgcagaagcgatatgggggcttcatgagaagaaagcccaccgagaacaacgaagacttcaacatcgtggccgtggccagc aacttcgcgaccacggatctcgatgctgaccgcgggaagttgcccggcaagaagctgccgctggaggtgctcaaagagatggaa gccaatgcccggaaagctggctgcaccagggctgtctgatctgcctgtcccacatcaagtgcacgcccaagatgaagaagttca tccaggacgctgccacacctacgaaggcgacaaagagtccgcacagggcggcataggcgaggcgatcgtcgacattcctgag attcctgggttcaaggacttggagcccatggagcagttcatcgcacaggtcgatctgtgtgtggactgcacaactggctgcctcaaa gggcttgccaacgtgcagtgttctgacctgctcaagaagtggctgccgcaacgctgtgcgacctttgccagcaagatccagggcca ggtggacaagatcaaggggggccggtggtgacagaagagtaggtcgcccagagtggtggatggactaccagaaacggtatggagg tttcctgaagcgctttgccgaggctctgccctccgacgaagaaggcgaaagttactccaaagaagttcctgaaatggaaaaaagatacg gaggatttatgagattttttaa Proenkephalin-B Mouse (nucleic acid sequence):

(SEQ ID NO: 187)

atggcgtggtccaggctgatgctggcagcttgcctcctcgtgatgccctctaatgttatggcggactgcctgtccctgtgctccctgtgtgc agtgaggattcaggatgggccccgtcccatcaaccccctgatttgctccctggagtgccaggacctggtgccgccctcagaggagtgg gagacatgccgggcttctcatcttttctcaccctgacggtctctgggctccgtggcaaggatgacttggaagatgaggttgctttggaag -continued aaggctacagtgcactagccaagctcttggaacccgtcctgaaggagctggagaaaagccgactccttaccagcgtcccagaggaaa
agttcaggggtctctccagcagctttggcaacggaaaagaatctgagctggcgggtgctgaccggatgaatgatgaagccgcacagg
cgggcacgctccattttaatgaggaggacttgagaaaacaggccaaacgctatggcggttttttgcgcaaatacccc<u>aagagg</u>aagcc
caccgagaacaacgaagacttcaacatcgtggccgtggccagcaacttcgcgaccacggatctcgatgctgaccgcgggaagtt
gcccggcaagaagctgccgctggaggtgctcaaagagatggaagccaatgcccggaaagctggctgcaccaggggctgtctga
tctgcctgtcccacatcaagtgcacgcccaagatgaagaagttcatcccaggacgctgccacacctacgaaggcgacaaagagt
ccgcacagggcggcataggcgaggcgatcgtcgacattcctgagattcctgggttcaaggacttggagcccatggagcagttcatc
gcacaggtcgatctgtgtgtggactgcacaactggctgcctcaaagggcttgccaacgtgcagtgttctgacctgctcaagaagtgg
ctgccgcaacgctgtgcgacctttgccagcaagatccagggccaggtggacaagatcaaggggccggtggtgac<u>aagagg</u>agt
tccgagatggcccgggatgaggacgggggccaggatgggatcaggtagggcatgaggacctgtacaaacgctatggggcttcct
gcggcgcattcgccccaagctgaagtgggacaaccagaagcgctatggtggtttcctgcggcgtcagttcaaggtggtgacgcggtc
ccaggagaaccccaataccctattctgaagatttagatgtttga Proenkephalin-B Human (nucleic acid sequence):

(SEQ ID NO: 188)
atggcctggcaggggctggtcctggctgcctgcctcctcatgttcccctccaccacagcggactgcctgtcgcggtgctccttgtgtgct
gtaaagacccaggatggtcccaaacctatcaatcccctgatttgctccctgcaatgccaggctgcctgctgccctctgaggaatggga
gagatgccagagctttctgtctttttttcaccccctccacccttgggctcaatgacaaggaggacttggggagcaagtcggttggggaagg
gcctacagtgagctggccaagctctctgggtcattcctgaaggagctggagaaaagcaagtttctcccaagtatctcaacaaaggaga
acactctgagcaagagcctggaggagaagctcaggggtctctctgacgggtttagggagggagcagagtctgagctgatgagggatg
cccagctgaacgatggtgccatggagactggcacactctatctcgctgaggaggaccccaaggagcaggtc<u>aaacgc</u>aagcccacc
gagaacaacgaagacttcaacatcgtggccgtggccagcaacttcgcgaccacggatctcgatgctgaccgcgggaagttgccc
ggcaagaagctgccgctggaggtgctcaaagagatggaagccaatgccggaaagctggctgcaccaggggctgtctgatctg
cctgtcccacatcaagtgcacgcccaagatgaagaagttcatcccaggacgctgccacacctacgaaggcgacaaagagtccgc
acagggcggcataggcgaggcgatcgtcgacattcctgagattcctgggttcaaggacttggagcccatggagcagttcatcgca
caggtcgatctgtgtgtggactgcacaactggctgcctcaaagggcttgccaacgtgcagtgttctgacctgctcaagaagtggctg
ccgcaacgctgtgcgacctttgccagcaagatccagggccaggtggacaagatcaaggggccggtggtgac<u>aaacgc</u>tatggg
ggcttttttgcgcaaataccccaagaggagctcagaggtggctggggagggggacggggatagcatgggccatgaggacctgtacaa
acgctatggggcttcttgcggcgcattcgtcccaagctcaagtgggacaaccagaagcgctatggcggttttctcccggcgccagttca
aggtggtgactcggtctcaggaagatccgaatgcttactctggagagcttttgatgcataa Insulin-like growth hormone 1 (IGF-1) Mouse (nucleic acid sequence):

(SEQ ID NO: 189)
atggggaaaatcagcagccttccaactcaattatttaagatctgcctctgtgacttcttgaagataaagatacacatcatgtcgtcttcacac
ctcttctacctggcgctctgcttgctcaccttccagctccaccacagctggaccagagacccttttgcggggctgagctggtggatgct
cttcagttcgtgtgtggaccgaggggcttttacttcaacaagcccacaggctatggc<u>tccagcattcggagg</u>aagcccaccgagaaca
acgaagacttcaacatcgtggccgtggccagcaacttcgcgaccacggatctcgatgctgaccgcgggaagttgcccggcaaga
agctgccgctggaggtgctcaaagagatggaagccaatgcccggaaagctggctgcaccaggggctgtctgatctgcctgtccca
catcaagtgcacgcccaagatgaagaagttcatcccaggacgctgccacacctacgaaggcgacaaagagtccgcacagggc
ggcataggcgaggcgatcgtcgacattcctgagattcctgggttcaaggacttggagcccatggagcagttcatcgcacaggtcga
tctgtgtgtggactgcacaactggctgcctcaaagggcttgccaacgtgcagtgttctgacctgctcaagaagtggctgccgcaacg
ctgtgcgacctttgccagcaagatccagggccaggtggacaagatcaaggggccggtggtgac<u>tccagcattcggaggg</u>cacct
cagacaggcattgtggatgagtgttgcttccggagctgtgatctgaggagactggagatgtactgtgccccactgaagcctacaaaagc
agcccgctctatccgtgcccagcgccacactgacatgcccaagactcagaagtccccgtccctatcgacaaacaagaaaacgaagct
gcaaaggagaaggaaaggaagtacatttgaagaacacaagtag -continued Insulin-like growth hormone 1 (IGF-1) Human (nucleic acid sequence):
(SEQ ID NO: 190)
atgggaaaaatcagcagtcttccaacccaattatttaagtgctgcttttgtgatttcttgaaggtgaagatgcacaccatgtctcctcgcatct cttctacctggcgctgtgcctgctcaccttcaccagctctgccacggctggaccggagacgctctgcggggctgagctggtggatgctc ttcagttcgtgtgtggagacagggggcttttatttcaacaagcccacagggtatggctccagcagtcggaggaagcccaccgagaaca acgaagacttcaacatcgtggccgtggccagcaacttcgcgaccacggatctcgatgctgaccgcgggaagttgcccggcaaga agctgccgctggaggtgctcaaagagatggaagccaatgcccggaaagctggctgcaccaggggctgtctgatctgcctgtccca catcaagtgcacgcccaagatgaagaagttcatcccaggacgctgccacacctacgaaggcgacaaagagtccgcacagggc ggcataggcgaggcgatcgtcgacattcctgagattcctgggttcaaggacttggagcccatggagcagttcatcgcacaggtcga tctgtgtgtggactgcacaactggctgcctcaaagggcttgccaacgtgcagtgttctgacctgctcaagaagtggctgccgcaacg ctgtgcgacctttgccagcaagatccagggccaggtggacaagatcaaggggccggtggtgacagcagtcggagggcgcctca gacaggcatcgtggatgagtgctgcttccggagctgtgatctaaggaggctggagatgtattgcgcacccctcaagcctgccaagtca gctcgctctgtccgtgcccagcgccacaccgacatgcccaagacccagaagtatcagcccccatctaccaacaagaacacgaagtct cagagaaggaaaggaagtacatttgaagaacgcaagtag Insulin-like growth hormone 2 (IGF-2) Mouse (nucleic acid sequence):
(SEQ ID NO: 191)
atgggcggcagcgtcgccggcttccaggtaccaatggggatcccagtggggaagtcgatgttggtgcttctcatctctttggccttcgcc ttgtgctgcatcgctgcttacggccccggagagactctgtgcggaggggagcttgttgacacgcttcagtttgtctgttcggaccgcggc ttctacttcagcaggccttcaagccgtgccaaccgtcgcagccgtggcatcgtggaagagtgctgcttccgcagctgcgacctggccct cctggagacatactgtgccacccccgccaagtccgagagggacaagcccaccgagaacaacgaagacttcaacatcgtggccgt ggccagcaacttcgcgaccacggatctcgatgctgaccgcgggaagttgcccggcaagaagctgccgctggaggtgctcaaaga gatggaagccaatgcccggaaagctggctgcaccaggggctgtctgatctgcctgtcccacatcaagtgcacgcccaagatgaa gaagttcatcccaggacgctgccacacctacgaaggcgacaaagagtccgcacagggcggcataggcgaggcgatcgtcgac attcctgagattcctgggttcaaggacttggagcccatggagcagttcatcgcacaggtcgatctgtgtgtggactgcacaactggct gcctcaaagggcttgccaacgtgcagtgttctgacctgctcaagaagtggctgccgcaacgctgtgcgacctttgccagcaagatc cagggccaggtggacaagatcaagggggccggtggtgacgagagggacgtgtctacctctcaggccgtacttccggacgacttcc ccagataccccgtgggcaagttcttccaatatgacacctggaagcagtccgcgggacgcctgcgcagaggcctgcctgccctcctgc gtgcccgccggggtcgcatgcttgccaaagagctcaaagagttcagagaggccaaacgtcatcgtcccctgatcgtgttaccacccaa agaccccgcccacggggagcctcttcggagatgtccagcaaccatcagtga Insulin-like growth hormone 2 (IGF-2) Human (nucleic acid sequence):
(SEQ ID NO: 192)
atgggaatcccaatggggaagtcgatgctggtgcttctcaccttcttggccttcgcctcgtgctgcattgctgcttaccgccccagtgaga ccctgtgcggcggggagctggtggacaccctccagtcgtctctgtggggaccgcggcttctacttcagcaggcccgcaagccgtgtga gccgtcgcagccgtggcatcgttgaggagtgctgtttccgcagctgtgacctggccctcctggagacgtactgtgctaccccccgccaag tccgagagggacaagcccaccgagaacaacgaagacttcaacatcgtggccgtggccagcaacttcgcgaccacggatctcgat gctgaccgcgggaagttgcccggcaagaagctgccgctggaggtgctcaaagagatggaagccaatgcccggaaagctggctg caccaggggctgtctgatctgcctgtcccacatcaagtgcacgcccaagatgaagaagttcatcccaggacgctgccacacctac gaaggcgacaaagagtccgcacagggcggcataggcgaggcgatcgtcgacattcctgagattcctgggttcaaggacttggag cccatggagcagttcatcgcacaggtcgatctgtgtgtggactgcacaactggctgcctcaaagggcttgccaacgtgcagtgttct gacctgctcaagaagtggctgccgcaacgctgtgcgacctttgccagcaagatccagggccaggtggacaagatcaaggggc cggtggtgacgagagggacgtgtcgacccctccgaccgtgcttccggacaacttccccagataccccgtgggcaagttcttccaatat gacacctggaagcagtccacccagcgcctgcgcagggggcctgcctgccctcctgcgtgcccgccggggtcacgtgctcgccaagga -continued gctcgaggcgttcagggaggccaaacgtcaccgtccctgattgctctaccacccaagaccccgcccacggggcgccccccag agatggccagcaatcggaagtga Parathyroid hormone (PTH) Mouse (nucleic acid sequence):

(SEQ ID NO: 193)

atgatgtctgcaaacaccgtggctaaagtgatgatcatcatgctggcagtctgtcttcttacccaaacggatgggaaacccgtgagg<u>aag</u>

<u>aga</u>aagcccaccgagaacaacgaagacttcaacatcgtggccgtggccagcaacttcgcgaccacggatctcgatgctgaccgc gggaagttgcccggcaagaagctgccgctggaggtgctcaaagagatggaagccaatgcccggaaagctggctgcaccaggg gctgtctgatctgcctgtcccacatcaagtgcacgcccaagatgaagaagttcatcccaggacgctgccacacctacgaaggcga caaagagtccgcacagggcggcataggcgaggcgatcgtcgacattcctgagattcctgggttcaaggacttggagcccatgga gcagttcatcgcacaggtcgatctgtgtgtggactgcacaactggctgcctcaaagggcttgccaacgtgcagtgttctgacctgctc aagaagtggctgccgcaacgctgtgcgacctttgccagcaagatccagggccaggtggacaagatcaaggggccggtggtga c<u>aagagag</u>ctgtcagtgaaatacagcttatgcacaacctgggcaaacacctggcctccatggagaggatgcaatggctgagaaggaa gctgcaagatatgcacaattttgttagtcttggagtccaaatggctgccagagatggcagtcaccagaagcccaccaagaaggaggaa aatgtccttgttgatggcaatccaaaaagtcttggtgagggagacaaagctgatgtggatgtattagttaaatcaaaatctcagtaa Parathyroid hormone (PTH) Human (nucleic acid sequence):

(SEQ ID NO: 194)

atgatacctgcaaaagacatggctaaagttatgattgtcatgttggcaatttgttttcttacaaaaatcggatgggaaatctgttaag<u>aagaga</u> aagcccaccgagaacaacgaagacttcaacatcgtggccgtggccagcaacttcgcgaccacggatctcgatgctgaccgcgg gaagttgcccggcaagaagctgccgctggaggtgctcaaagagatggaagccaatgcccggaaagctggctgcaccaggggct gtctgatctgcctgtcccacatcaagtgcacgcccaagatgaagaagttcatcccaggacgctgccacacctacgaaggcgacaa agagtccgcacagggcggcataggcgaggcgatcgtcgacattcctgagattcctgggttcaaggacttggagcccatggagca gttcatcgcacaggtcgatctgtgtgtggactgcacaactggctgcctcaaagggcttgccaacgtgcagtgttctgacctgctcaag aagtggctgccgcaacgctgtgcgacctttgccagcaagatccagggccaggtggacaagatcaaggggccggtggtgac<u>aa</u>

<u>gaga</u>tctgtgagtgaaatacagcttatgcataacctgggaaaacatctgaactcgatggagagagtagaatggctgcgtaagaagctgc aggatgtgcacaattttgttgcccttggagctcctctagctcccagagatgctggtcccagaggccccgaaaaaaggaagacaatgtct tggttgagagccatgaaaaaagtcttggagaggcagacaaagctgatgtgaatgtattaactaaagctaaatcccagtga Parathyroid hormone-related protein (PTHrP) Mouse (nucleic acid sequence):

(SEQ ID NO: 195)

atgctgcggaggctggttcagcagtggagtgtcctggtattcctgctcagctactccgtgccctcccgcgggcgttcggtggaggggct tggccgcaggctc<u>aaacgc</u>aagcccaccgagaacaacgaagacttcaacatcgtggccgtggccagcaacttcgcgaccacgg atctcgatgctgaccgcggggaagttgcccggcaagaagctgccgctggaggtgctcaaagagatggaagccaatgcccggaaa gctggctgcaccaggggctgtctgatctgcctgtcccacatcaagtgcacgcccaagatgaagaagttcatcccaggacgctgcca cacctacgaaggcgacaaagagtccgcacagggcggcataggcgaggcgatcgtcgacattcctgagattcctgggttcaagga cttggagcccatggagcagttcatcgcacaggtcgatctgtgtgtggactgcacaactggctgcctcaaagggcttgccaacgtgca gtgttctgacctgctcaagaagtggctgccgcaacgctgtgcgacctttgccagcaagatccagggccaggtggacaagatcaag ggggccggtggtgac<u>aaacgc</u>gctgtgtctgaacatcagctactgcatgacaagggcaagtccatccaagacttgcgccgccgtttctt cctccaccatctgatcgcggagatccacacagccgaaatcagagctacctcggaggtgtcccccaactccaaacctgctcccaacacc aaaaaccacccgtgcggtttgggtcagacgatgagggcagatacctaactcaggaaaccaacaaggtggagacgtacaaagaaca gccactcaagacacccgggaagaagaagaaaggcaagcctgggaaacgcagagaacaggagaaaaagaagcgaaggactcggt ctgcctggccaagcacagctgcgagtggcctgcttgaggaccccctgccccacacctccaggccctcgctggagcccagcttaagga cgcattga Parathyroid hormone-related protein (PTHrP) Human (nucleic acid sequence):

(SEQ ID NO: 196)
atgcagcggagactggttcagcagtggagcgtcgcggtgttcctgctgagctacgcggtgccctcctgcgggcgctcggtggagggt ctcagccgccgcctcaaaagaaagcccaccgagaacaacgaagacttcaacatcgtggccgtggccagcaacttcgcgaccacg gatctcgatgctgaccgcggggaagttgcccggcaagaagctgccgctggaggtgctcaaagagatggaagccaatgcccggaa agctggctgcaccaggggctgtctgatctgcctgtcccacatcaagtgcacgcccaagatgaagaagttcatcccaggacgctgcc acacctacgaaggcgacaaagagtccgcacagggcggcataggcgaggcgatcgtcgacattcctgagattcctgggttcaagg acttggagcccatggagcagttcatcgcacaggtcgatctgtgtgtggactgcacaactggctgcctcaaagggcttgccaacgtgc agtgttctgacctgctcaagaagtggctgccgcaacgctgtgcgacctttgccagcaagatccagggccaggtggacaagatcaa gggggccggtggtgacaaaagagctgtgtctgaacatcagctcctccatgacaaggggaagtccatccaagatttacggcgacgattc ttccttcaccatctgatcgcagaaatccacacagctgaaatcagagctacctcggaggtgtcccctaactccaagccctctcccaacaca aagaaccaccccgtccgatttgggtctgatgatgagggcagataccctaactcaggaaactaacaaggtggagacgtacaaagagcag ccgctcaagacacctgggaagaaaaagaaaggcaagcccgggaaacgcaaggagcaggaaaagaaaaaacggcgaactcgctct gcctggttagactctggagtgactgggagtgggctagaaggggaccacctgtctgacacctccacaacgtcgctggagctcgattcac ggaggcattga Osteocalcin Mouse (nucleic acid sequence):

(SEQ ID NO: 197)
atgaggaccatctttctgctcactctgctgaccctggctgcgctctgtctctctgacctcacagatgccaagcccagcggccctgagtctg acaaagccttcatgtccaagcaggagggcaataaggtagtgaacagactccggcgcaagcccaccgagaacaacgaagacttca acatcgtggccgtggccagcaacttcgcgaccacggatctcgatgctgaccgcggggaagttgcccggcaagaagctgccgctgg aggtgctcaaagagatggaagccaatgcccggaaagctggctgcaccaggggctgtctgatctgcctgtcccacatcaagtgcac gcccaagatgaagaagttcatcccaggacgctgccacacctacgaaggcgacaaagagtccgcacagggcggcataggcgag gcgatcgtcgacattcctgagattcctgggttcaaggacttggagcccatggagcagttcatcgcacaggtcgatctgtgtgtggact gcacaactggctgcctcaaagggcttgccaacgtgcagtgttctgacctgctcaagaagtggctgccgcaacgctgtgcgacctttg ccagcaagatccagggccaggtggacaagatcaaggggccggtggtgaccggcgctaccttggagcctcagtccccagccca gatcccctggagcccacccgggagcagtgtgagcttaaccctgcttgtgacgagctatcagaccagtatggcttgaagaccgcctaca aacgcatctatggtatcactatttag Osteocalcin Human (nucleic acid sequence):

(SEQ ID NO: 198)
atgagagccctcacactcctcgccctattggccctggccgcactttgcatcgctggccaggcaggtgcgaagcccagcggtgcagagt ccagcaaaggtgcagcctttgtgtccaagcaggaggcagcgaggtagtgaagagacccaggcgcaagcccaccgagaacaac gaagacttcaacatctgtggccgtggccagcaacttcgcgaccacggatctcgatgctgaccgcggggaagttgcccggcaagaag ctgccgctggaggtgctcaaagagatggaagccaatgcccggaaagctggctgcaccaggggctgtctgatctgcctgtcccaca tcaagtgcacgcccaagatgaagaagttcatcccaggacgctgccacacctacgaaggcgacaaagagtccgcacagggcgg cataggcgaggcgatcgtcgacattcctgagattcctgggttcaaggacttggagcccatggagcagttcatcgcacaggtcgatct gtgtgtggactgcacaactggctgcctcaaagggcttgccaacgtgcagtgttctgacctgctcaagaagtggctgccgcaacgctg tgcgacctttgccagcaagatccagggccaggtggacaagatcaaggggccggtggtgacaggcgctacctgtatcaatggctg ggagcccccaagtcccctacccggatcccctggagcccaggagggaggtgtgtgagctcaatccggactgtgacgagttggctgaccac atcggctttcaggaggcctatcggcgcttctacggcccggtctag Urocortin-3 Mouse (nucleic acid sequence):

(SEQ ID NO: 199)
atgctgatgcccacctacttcctgctgccacttctgctgctcctaggaggtccaaggacaagcctctcccacaagttctacaacactggac cagtcttcagctgcctcaacacagccctatctgaggtcaagaagaacaagctggaagatgtgcccttgctgagcaagaagagctttggc cacctgcccacacaagaccctcaggggaagaagatgacaaccaaacgcacctccagatcaaaagaactttctcaggtgccgcgggt -continued gggaatggagctgggagcacccggtacagataccaatcccaggcacagcacaaggggaagctgtacccagacaagcccaaaagc gacc<u>ggggcaccaag</u>aagcccaccgagaacaacgaagacttcaacatcgtggccgtggccagcaacttcgcgaccacggatct cgatgctgaccgcgggaagttgcccggcaagaagctgccgctggaggtgctcaaagagatggaagccaatgcccggaaagctg gctgcaccaggggctgtctgatctgcctgtcccacatcaagtgcacgcccaagatgaagaagttcatcccaggacgctgccacac ctacgaaggcgacaaagagtccgcacagggcggcataggcgaggcgatcgtcgacattcctgagattcctgggttcaaggactt ggagcccatggagcagttcatcgcacaggtcgatctgtgtgtggactgcacaactggctgcctcaaagggcttgccaacgtgcagt gttctgacctgctcaagaagtggctgccgcaacgctgtgcgacctttgccagcaagatccagggccaggtggacaagatcaaggg ggccggtggtgac<u>cggggcaccaag</u>ttcaccctttcccttgatgttcccactaacatcatgaacatcctcttcaacatcgacaaggccaa gaatttgcgagccaaggcagctgccaatgctcagctcatggcacagattgggaagaagaagtaa Urocortin-3 Human (nucleic acid sequence):
(SEQ ID NO: 200)
Atgctgatgccggtccacttcctgctgctcctgctgctgctcctgggggggccccaggacaggcctcccccacaagttctacaaagcca agcccatcttcagctgcctcaacaccgccctgtctgaggctgagaagggccagtgggaggatgcatccctgctgagcaagaggagctt ccactacctgcgcagcagagacgcctcttcggagaggaggaggagggcaaagagaaaaagactttccccatctctggggccagg ggtggagccagaggcacccggtacagatacgtgtcccaagcacagcccaggggaaagccacgccaggacacggccaagagtccc <u>caccgc</u>aagcccaccgagaacaacgaagacttcaacatcgtggccgtggccagcaacttcgcgaccacggatctcgatgctgac cgcgggaagttgcccggcaagaagctgccgctggaggtgctcaaagagatggaagccaatgcccggaaagctggctgcacca ggggctgtctgatctgcctgtcccacatcaagtgcacgcccaagatgaagaagttcatcccaggacgctgccacacctacgaagg cgacaaagagtccgcacagggcggcataggcgaggcgatcgtcgacattcctgagattcctgggttcaaggacttggagcccat ggagcagttcatcgcacaggtcgatctgtgtgtggactgcacaactggctgcctcaaagggcttgccaacgtgcagtgttctgacct gctcaagaagtggctgccgcaacgctgtgcgacctttgccagcaagatccagggccaggtggacaagatcaaggggccggtg gtgac<u>caccgc</u>accaagttcaccctgtccctcgacgtccccaccaacatcatgaacctcctcttcaacatcgccaaggccaagaacctg cgtgcccaggcggccgccaatgcccacctgatggcgcaaattgggaggaagaagtag Urocortin-2 Mouse (nucleic acid sequence):
(SEQ ID NO: 201)
Atgatgaccaggtgggcactggtggtgttcgtggtcctgatgttggataggatcctatttgtcccaggaactcctatccccaccttccagc tcctccctcagaactctctggagacaactcctagctctgtgacctcagagagctcctcaggtaccaccacaggaccctcagcttcctgga gcaactctaaagccagcccttacctagac<u>acccgtgtc</u>aagcccaccgagaacaacgaagacttcaacatcgtggccgtggccag caacttcgcgaccacggatctcgatgctgaccgcgggaagttgcccggcaagaagctgccgctggaggtgctcaaagagatgga agccaatgcccggaaagctggctgcaccaggggctgtctgatctgcctgtcccacatcaagtgcacgcccaagatgaagaagttc atcccaggacgctgccacacctacgaaggcgacaaagagtccgcacagggcggcataggcgaggcgatcgtcgacattcctga gattcctgggttcaaggacttggagcccatggagcagttcatcgcacaggtcgatctgtgtgtggactgcacaactggctgcctcaa agggcttgccaacgtgcagtgttctgacctgctcaagaagtggctgccgcaacgctgtgcgacctttgccagcaagatcagggcc aggtggacaagatcaaggggccggtggtgac<u>acccgtgtc</u>atactctccctggatgttcccattggcctcctacggatcttactggaa caggctcgttacaaggctgccaggaatcaggctgccactaatgctcaaatactagcccatgttggccgccgctga Urocortin-2 Human (nucleic acid sequence):
(SEQ ID NO: 202)
atgaccaggtgtgctctgctgttgctgatggtcctgatgttgggcagagtcctggttgtcccagtgaccctatcccaaccttccagctccg ccctcagaattctccccagaccactccccgacctgcggcctcagagagccctcagctgctcccacatggccgtgggctgcccagag ccactgcagcccaccgcccacctggc<u>tcgcgcatt</u>aagcccaccgagaacaacgaagacttcaacatcgtggccgtggccag caacttcgcgaccacggatctcgatgctgaccgcgggaagttgcccggcaagaagctgccgctggaggtgctcaaagagatgga agccaatgcccggaaagctggctgcaccaggggctgtctgatctgcctgtcccacatcaagtgcacgcccaagatgaagaattc atcccaggacgctgccacacctacgaaggcgacaaagagtccgcacagggcggcataggcgaggcgatcgtcgacattcctga gattcctgggttcaaggacttggagcccatggagcagttcatcgcacaggtcgatctgtgtgtggactgcacaactggctgcctcaa -continued agggcttgccaacgtgcagtgttctgacctgctcaagaagtggctgccgcaacgctgtgcgacctttgccagcaagatccagggcc aggtggacaagatcaagggggccggtggtgactcgcgcattgtcctatcgctggatgtccccatcggcctcttgcagatcttactgga gcaagcccgggccagggctgccagggagcaggccaccaccaacgcccgcatcctggcccgtgtcggccactgctga Urocortin-1 Mouse (nucleic acid sequence):

(SEQ ID NO: 203)

Atgatacagaggggacgcgctacgctcctggtggcgttgctgctcttggcacagcttcgcccggagagcagccagtggagcccagc ggctgcggcggcaactggggtccaggatccgaatctgcgatggagccctggagtgcggaatcagggcggcggcgtccgcgcgctc ctcttgctgttagcggagcgcttcccgcgccgcgcaggatctgagcctgcgggcgagcggcagcgacggaagcccaccgagaac aacgaagacttcaacatcgtggccgtggccagcaacttcgcgaccacggatctcgatgctgaccgcgggaagttgcccggcaag aagctgccgctggaggtgctcaaagagatggaagccaatgcccggaaagctggctgcaccaggggctgtctgatctgcctgtccc acatcaagtgcaacgcccaagatgaagaagttcatcccaggacgctgccacacctacgaaggcgacaaagagtccgcacaggg cggcataggcgaggcgatcgtcgacattcctgagattcctgggttcaaggacttggagcccatggagcagttcatcgcacaggtcg atctgtgtgtggactgcacaactggctgcctcaaagggcttgccaacgtgcagtgttctgacctgctcaagaagtggctgccgcaac gctgtgcgacctttgccagcaagatccagggccaggtggacaagatcaagggggccggtggtgaccgacgggacgaccctccac tgtccatcgacctcaccttccacctgctgcggaccctgctggagctagctcggacacagagccagcgcgagcgcgcagagcagaac cgcatcatattcgattcggtgggcaagtga Urocortin-1 Human (nucleic acid sequence):

(SEQ ID NO: 204)

atgaggcaggcgggacgcgcagcgctgctggccgcgctgctgctcctggtacagctgtgccctgggagcagccagaggagccccg aggcggccggggtccaggaccgagtctgcgctggagccccggggcacggaaccagggtggcggggcccgcgcgctcctcttgc tgctggcggagcgcttcccgcgccgcgcggggcccggccgattgggactcgggacggcaggcgagcggccgcggcggaagccc accgagaacaacgaagacttcaacatcgtggccgtggccagcaacttcgcgaccacggatctcgatgctgaccgcgggaagttg cccggcaagaagctgccgctggaggtgctcaaagagatggaagccaatgcccggaaagctggctgcaccaggggctgtctgat ctgcctgtcccacatcaagtgcacgcccaagatgaagaagttcatcccaggacgctgccacacctacgaaggcgacaaagagtc cgcacagggcggcataggcgaggcgatcgtcgacattcctgagattcctgggttcaaggacttggagcccatggagcagttcatc gcacaggtcgatctgtgtgtggactgcacaactggctgcctcaaagggcttgccaacgtgcagtgttctgacctgctcaagaagtgg ctgccgcaacgctgtgcgacctttgccagcaagatccagggccaggtggacaagatcaagggggccggtggtgaccggcggga caaccctctctgtccattgacctcacctttcacctgctgcggaccctgctggagctggcgcggacgcagagccagcgggagcgcgcc gagcagaaccgcatcatattcgactcggtgggcaagtga FGF23 Mouse (nucleic acid sequence):

(SEQ ID NO: 205)

Atgctagggacctgccttagactcctggtgggcgtgctctgcactgtctgcagcttgggcactgctagagcctatccggacacttcccc attgcttggctccaactggggaagcctgacccacctgtacacggctacagccaggaccagctatcacctacagatccatagggatggtc atgtagatggcacccccatcagaccatctacagtgccctgatgattacatcagaggacgccggctctgtggtgataacaggagccatg actcgaaggttcctttgtatggatctccacggcaacattttggatcgcttcacttcagcccagagaattgcaagttccgccagtggacgct ggagaatggctatgacgtctacttgtcgcagaagcatcactacctggtgagcctgggccgcgccaagcgcatcttccagcccgggcacc aacccgccgcccttctcccagttcctggctcgcaggaacgaggtcccgctgctgcatttctacactgttcgcccacggcgccacacggcg cagcaagcccaccgagaacaacgaagacttcaacatcgtggccgtggccagcaacttcgcgaccacggatctcgatgctgaccg cgggaagttgcccggcaagaagctgccgctggaggtgctcaaagagatggaagccaatgcccggaaagctggctgcaccagg ggctgtctgatctgcctgtcccacatcaagtgcacgcccaagatgaagaagttcatcccaggacgctgccacacctacgaaggcg acaaagagtccgcacagggcggcataggcgaggcgatcgtcgacattcctgagattcctgggttcaaggacttggagcccatgg agcagttcatcgcacaggtcgatctgtgtgtggactgcacaactggctgcctcaaagggcttgccaacgtgcagtgttctgacctgct caagaagtggctgccgcaacgctgtgcgacctttgccagcaagatccagggccaggtggacaagatcaagggggccggtggtg -continued accgcagcgccgaggacccaccggagcgcgacccactgaacgtgctcaagccgcggccccgcgccacgcctgtgcctgtatcctg ctctcgcgagctgccgagcgcagaggaaggtggcccgcagccagcgatcctctgggggtgctgcgcagaggccgtggagatgct cgcggggcgcgggaggcgcggataggtgtcgccccttcccaggttcgtctag Human (nucleic acid sequence):

(SEQ ID NO: 206)

Atgttgggggcccgcctcaggctctgggtctgtgccttgtgcagcgtctgcagcatgagcgtcctcagagcctatcccaatgcctcccc actgctcggctccagctggggtggcctgatccacctgtacacagccacagccaggaacagctaccacctgcagatccacaagaatgg ccatgtggatggcgcaccccatcagaccatctacagtgccctgatgatcagatcagaggatgctggctttgtggtgattacaggtgtgat gagcagaagatacctctgcatggatttcagaggcaacatttttggatcacactatttcgacccggagaactgcaggttccaacaccagac gctggaaaacgggtacgacgtctaccactctcctcagtatcacttcctggtcagtctgggccgggcgaagagagccttcctgccaggca tgaaccaccccgtactcccagttcctgtcccggaggaacgagatcccctaattcacttcaacaccccatacccacggcggcacac ccggagcaagcccaccgagaacaacgaagacttcaacatcgtggccgtggccagcaacttcgcgaccacggatctcgatgctga ccgcgggaagttgccccggcaagaagctgccgctggaggtgctcaaagagatggaagccaatgcccggaaagctggctgcacc aggggctgtctgatctgcctgtcccacatcaagtgcacgcccaagatgaagaagttcatcccaggacgctgccacacctacgaag gcgacaaagagtccgcacagggcggcataggcgaggcgatcgtcgacattcctgagattcctgggttcaaggacttggagccca tggagcagttcatcgcacaggtcgatctgtgtgtggactgcacaactggctgcctcaaagggcttgccaacgtgcagtgttctgacct gctcaagaagtggctgccgcaacgctgtgcgacctttgccagcaagatccagggccaggtggacaagatcaaggggccggtg gtgaccggagcgccgaggacgactcggagcgggacccccgaacgtgctgaagcccgggcccgatgacccgccccggcct cctgttcacaggagctcccgagcgccgaggacaacagcccgatggccagtgacccattagggggtggtcaggggcggtcgagtgaac acgcacgctgggggacgggcccggaaggctgccgcccccttcgccaagttcatctag IL1B Mouse (nucleic acid sequence):

(SEQ ID NO: 207)

Atggcaactgttcctgaactcaactgtgaaatgccacctttttgacagtgatgagaatgacctgttctttgaagttgacggacccccaaaaga tgaagggctgcttccaaacctttgacctgggctgtcctgatgagagcatccagcttcaaatctcgcagcagcacatcaacaagagcttca ggcaggcagtatcactcattgtggctgtgagaagctgtggcagctacctgtgtctttcccgtggaccttccaggatgaggacatgagca ccttcttttccttcatctttgaagaagagcccatcctctgtgactcatgggatgatgatgataacctgctggtgtg<u>gacgtt</u>cccaagccca ccgagaacaacgaagacttcaacatcgtggccgtggccagcaacttcgcgaccacggatctcgatgctgaccgcgggaagttgc ccggcaagaagctgccgctggaggtgctcaaagagatggaagccaatgcccggaaagctggctgcaccaggggctgtctgatct gcctgtcccacatcaagtgcacgcccaagatgaagaagttcatcccaggacgctgccacacctacgaaggcgacaaagagtcc gcacagggcggcataggcgaggcgatcgtcgacattcctgagattcctgggttcaaggacttggagcccatggagcagttcatcg cacaggtcgatctgtgtgtggactgcacaaactggctgcctcaaagggcttgccaacgtgcagtgttctgacctgctcaagaagtggc tgccgcaacgctgtgcgacctttgccagcaagatccagggccaggtggacaagatcaaggggccggtggtgacctggtgtgtg<u>a</u>

<u>acgtt</u>cccgttcccattagacaactgcactacaggctccgagatgaacaacaaaaaagcctcgtgctgtcggacccatatgagctgaaa gctctccacctcaatggacagaatatcaaccaacaagtgatattctccatgagctttgtacaaggagaaccaagcaacgacaaaatacct gtggcctttgggcctcaaaggaaagaatctatacctgtcctgtgtaatgaaagacggcacacccaccctgcagctggagagtgtggatcc caagcaatacccaaagaagaagatggaaaaacggtttgtcttcaacaagatagaagtcaagagcaaagtggagtttgagtctgcagag ttccccaactggtacatcagcacctcacaagcagagcacaagcctgtcttcctgggaaacaacagtggtcaggacataattgacttcacc atggaatccgtgtcttcctaa IL1B Human (nucleic acid sequence):

(SEQ ID NO: 208)

Atggcagaagtacctgagctcgccagtgaaatgatggcttattacagtggcaatgaggatgacttgttctttgaagctgatggccctaaa cagatgaagtgctccttccaggacctggacctctgccctctggatggcggcatccagctacgaatctccgaccaccactacagcaagg gcttcaggcaggccgcgtcagttgttgtggccatggacaagctgaggaagatgctggttcctgcccacagaccttccaggagaatga cctgagcaccttctttccttcatctttgaagaagaacctatcttcttcgacacatgggataacgaggcttatgtgcac<u>gatgca</u>ccta<i>agc</i>

-continued ccaccgagaacaacgaagacttcaacatcgtggccgtggccagcaacttcgcgaccacggatctcgatgctgaccgcgggaagt tgcccggcaagaagctgccgctggaggtgctcaaagagatggaagccaatgcccggaaagctggctgcaccaggggctgctg atctgcctgtcccacatcaagtgcacgcccaagatgaagaagttcatcccaggacgctgccacacctacgaaggcgacaaagag tccgcacagggcggcataggcgaggcgatcgtcgacattcctgagattcctgggttcaaggacttggagcccatggagcagttcat cgcacaggtcgatctgtgtgtggactgcacaaactggctgcctcaaagggcttgccaacgtgcagtgttctgacctgctcaagaagtg gctgccgcaacgctgtgcgacctttgccagcaagatccagggccaggtggacaagatcaaggggggccggtggtgactatgtgca c<u>gatgca</u>cctgtacgatcactgaactgcacgctccgggactcacagcaaaaaagcttggtgatgtctggtccatatgaactgaaagctct ccacctccagggacaggatatggagcaacaagtggtgttctccatgtcctttgtacaaggagaagaaagtaatgacaaaatacctgtgg ccttgggcctcaaggaaaagaatctgtacctgtcctgcgtgttgaaagatgataagcccactctacagctggagagtgtagatcccaaaa attacccaaagaagaagatggaaaagcgatttgtcttcaacaagatagaaatcaataacaagctggaatttgagtctgcccagttcccca actggtacatcagcacctctcaagcagaaaacatgcccgtcttcctgggagggaccaaaggcggccaggatataactgacttcaccat gcaatttgtgtcttcctaa TNFA Mouse (nucleic acid sequence):

(SEQ ID NO: 209)

Atgagcacagaaagcatgatccgcgacgtggaactggcagaagaggcactccccccaaaagatggggggcttccagaactccaggc ggtgcctatgtctcagcctcttctcattcctgcttgtggcaggggccaccacgctcttctgtctactgaacttcggggtgatcggtccccaa agggatgagaagttccccaaatggcctccctctcatcagttctatggcccagaccctcaca<u>ctcaga</u>aagccaccgagaacaacgaa gacttcaacatcgtggccgtggccagcaacttcgcgaccacggatctcgatgctgaccgcgggaagttgcccggcaagaagctgcc cgctggaggtgctcaaagagatggaagccaatgcccggaaagctggctgcaccaggggctgtctgatctgcctgtcccacatcaa gtgcacgcccaagatgaagaagttcatcccaggacgctgccacacctacgaaggcgacaaagagtccgcacagggcggcata ggcgaggcgatcgtcgacattcctgagattcctgggttcaaggacttggagcccatggagcagttcatcgcacaggtcgatctgtgt gtggactgcacaactggctgcctcaaagggcttgccaacgtgcagtgttctgacctgctcaagaagtggctgccgcaacgctgtgc gacctttgccagcaagatccagggccaggtggacaagatcaaggggggccggtggtgac<u>ctcagat</u>catcttctcaaaattcgagtg acaagcctgtagcccacgtcgtagcaaaccaccaagtggaggagcagctggagtggctgagccagcgcgccaacgccctcctggc caacggcatggatctcaaagacaaccaactagtggtgccagccgatgggttgtaccttgtctactcccaggttctcttcaagggacaagg ctgccccgactacgtgctcctcacccacaccgtcagccgatttgctatctcataccaggagaaagtcaacctcctctctgccgtcaagag cccctgccccaaggacacccctgagggggctgagctcaaaccctggtatgagcccatatacctgggaggagtcttccagctggagaa gggggaccaactcagcgctgaggtcaatctgcccaagtacttagactttgcggagtccgggcaggtctactttggagtcattgctctgtg a TNFA Human (nucleic acid sequence):

(SEQ ID NO: 210)

Atgagcactgaaagcatgatccgggacgtggagctggccgaggaggcgctccccaagaagacaggggggccccagggctccag gcggtgcttgttcctcagcctcttctccttcctgatcgtggcaggcgccaccacgctcttctgcctgctgcactttggagtgatcggccccc agagggaagagttccccagggacctctctctaatcagccctctggcccaggca<u>gtcaga</u>aagccaccgagaacaacgaagactt caacatcgtggccgtggccagcaacttcgcgaccacggatctcgatgctgaccgcgggaagttgcccggcaagaagctgccgct ggaggtgctcaaagagatggaagccaatgcccggaaagctggctgcaccaggggctgtctgatctgcctgtcccacatcaagtgc acgcccaagatgaagaagttcatcccaggacgctgccacacctacgaaggcgacaaagagtccgcacagggcggcataggcg aggcgatcgtcgacattcctgagattcctgggttcaaggacttggagcccatggagcagttcatcgcacaggtcgatctgtgtgtgg actgcacaactggctgcctcaaagggcttgccaacgtgcagtgttctgacctgctcaagaagtggctgccgcaacgctgtgcgacc tttgccagcaagatccagggccaggtggacaagatcaaggggggccggtggtgacg<u>tcagat</u>catcttctcgaaccccgagtgacaa gcctgtagcccatgttgtagcaaaccctcaagctgaggggcagctccagtggctgaaccgccgggccaatgccctcctggccaatgg cgtggagctgagagataaccagctggtggtgccatcagagggcctgtacctcatctactcccaggtcctcttcaagggccaaggctgc -continued cctccacccatgtgctcctcacccacaccatcagccgcatcgccgtctcctaccagaccaaggtcaacctcctctctgccatcaagag ccctgccagagggagaccccagagggggctgaggccaagccctggtatgagcccatctatctgggaggggtcttccagctggaga agggtgaccgactcagcgctgagatcaatcggcccgactatctcgactttgccgagtctgggcaggtctactttgggatcattgccctgt ga IFNG Mouse (nucleic acid sequence):

(SEQ ID NO: 211)

Atgaacgctacacactgcatcttggctttgcagctcttcctcatggctgtttctggctgttactgccacggcacagtcattgaaagcctaga aagtctgaataactattttaactcaagtggcatagatgtggaagaaaagagtctcttcttggatatctggaggaactggcaaaaggatggt gacatgaaaatcctgcagagccagattatctcttttctacctcagactctttgaagtcttgaaagacaatcaggccatcagcaacaacataa gcgtcattgaatcacacctgattactaccttcttcagcaacagcaaggcgaaaaaggatgcattcatgagtattgccaagtttgaggtcaa caacccacaggtccagcgccaagcattcaatgagctcatccgagtggtccaccagctgttgccgaatccagcctc<u>aggaag</u>aagcc caccgagaacaacgaagacttcaacatcgtggccgtggccagcaacttcgcgaccacggatctcgatgctgaccgcgggaagtt gcccggcaagaagctgccgctggaggtgctcaaagagatggaagccaatgcccggaaagctggctgcaccaggggctgtctga tctgcctgtcccacatcaagtgcacgcccaagatgaagaagttcatcccaggacgctgccacacctacgaaggcgacaaagagt ccgcacagggcggcataggcgaggcgatcgtcgacattcctgagattcctgggttcaaggacttggagcccatggagcagttcatc gcacaggtcgatctgtgtgtggactgcacaactggctgcctcaaagggcttgccaacgtgcagtgttctgacctgctcaagaagtgg ctgccgcaacgctgtgcgacctttgccagcaagatccagggccaggtggacaagatcaaggggggcggtggtgac<u>cggaaa</u>ag gagtcgctgctga IFNG Human (nucleic acid sequence):

(SEQ ID NO: 212)

Atgaaatatacaagttatatcttggcttttcagctctgcatcgttttgggttctcttggctgttactgccaggaccatatgtaaaagaagcag aaaaccttaagaaatattttaatgcaggtcattcagatgtagcggataatggaactcttttcttaggcattttgaagaattggaaagaggaga gtgacagaaaaataatgcagagccaaattgtctccttttacttcaaacttttttaaaaactttaaagatgaccagagcatccaaaagagtgtg gagaccatcaaggaagacatgaatgtcaagttttttcaatagcaacaaaaagaaacgagatgacttcgaaaagctgactaattattcggta actgacttgaatgtccaacgcaaagcaatacatgaactcatccaagtgatggctgaactgtcgccagcagctaaaacagggaagcgaa aaaggagtcagatgctgtttcgaggt<u>cgaaga</u>aagcccaccgagaacaacgaagacttcaacatcgtggccgtggccagcaactt cgcgaccacggatctcgatgctgaccgcgggaagttgcccggcaagaagctgccgctggaggtgctcaaagagatggaagcca atgcccggaaagctggctgcaccaggggctgtctgatctgcctgtcccacatcaagtgcacgcccaagatgaagaagttcatccca ggacgctgccacacctacgaaggcgacaaagagtccgcacagggcggcataggcgaggcgatcgtcgacattcctgagattcct gggttcaaggacttggagcccatggagcagttcatcgcacagtcgatctgtgtgtggactgcacaactggctgcctcaaagggctt gccaacgtgcagtgttctgacctgctcaagaagtggctgccgcaacgctgtgcgacctttgccagcaagatccagggccaggtgg acaagatcaaggggggccggtggtgacggt<u>cgaagag</u>catcccagtaa Sortilin Mouse (nucleic acid sequence):

(SEQ ID NO: 213)

Atggagcggccccggggagctgcggacggccttttgcgctggcccctcggcctcctcctgctccttcaactgctgcctcctgccgccg tcggccaggaccggctggacgcgccgccgccgccgcgcctcctctgctgcgctgggccggtccggtcggggtgagcgggggct gcgcgccgccgcgcccggggccccgtcccccgcgctggccgttgg<u>cgccgc</u>aagcccaccgagaacaacgaagacttcaac atcgtggccgtggccagcaacttcgcgaccacggatctcgatgctgaccgcgggaagttgcccggcaagaagctgccgctggag gtgctcaaagagatggaagccaatgcccggaaagctggctgcaccaggggctgtctgatctgcctgtcccacatcaagtgcacgc ccaagatgaagaagttcatcccaggacgctgccacacctacgaaggcgacaaagagtccgcacagggcggcataggcgaggc gatcgtcgacattcctgagattcctggttcaaggacttggagcccatggagcagttcatcgcacaggtcgatctgtgtgtggactgc acaactggctgcctcaaagggcttgccaacgtgcagtgttctgacctgctcaagaagtggctgccgcaacgctgtgcgacctttgcc agcaagatccagggccaggtggacaagatcaaggggggccggtggtgac<u>cgccgc</u>ggcgcgcccgccgaggaccaagactgc ggccgcctcccggacttcatcgccaagctgaccaacaatacgcaccagcatgtctttgatgacctcagtggctcagtgtccttgtcctgg -continued gttggagacagcactgggggttattctcgtcctgaccacttttccaagtgcctctggtaattgtgagctttggacagtccaagttgtatcgaagt
gaggattatgggaaagaactttaaggatattacaaatctcatcaataacaccttcattcggacggaatttggcatggctattggtcctgagaa
ctctggaaaggtgatactaacagcggaggtgtccgggggaagccgaggcggaagagtgttcaggtcatcagactttgccaagaacttt
gtgcaaacagatctcccctttcatcctctgacgcagatgatgtacagccctcagaattctgattacctgttagctctcagcaccgaaaatgg
cctgtgggtgtccaagaattttggggaaaaatgggaagaaatccacaaagcagtatgtttggccaaatggggaccaaacaacatcatctt
ctttaccacccatgtgaatggctcctgcaaagctgatcttggtgccctggaattatggagaacatccgacttgggaaaaaccttcaaacc
attggtgtgaaaatctactcctttggtcttgggggccgtttccttttttgcctctgtgatggctgataaggacacaacaagaaggatccatgtg
tcaacagaccaggggggacacatggagcatggcacaacttccttctgtgggacaggaacagttctactccatcctggcagccaatgagg
acatggtcttcatgcatgtagatgaacctggagataccgggtttggcaccatctttacctctgatgatcgaggcattgtctactccaagtctc
tggacagacatctctataccaccacaggcggggagacggactttaccaacgtgacttccctccgtggggtctatataacaagcacgctc
tcagaagataactctattcagagcatgatcacttttgaccagggaggacggtgggagcacctgcggaagccggagaacagcaagtgc
gacgctaccgcaaagaacgagtgcagccttcatatccatgcttcttatagcatctcccagaagctaaacgttccaatggcccca
ctttccgagcccaatgctgtgggcatagtcatcgctcacggtagtgtgggagatgccatctcggtgatggtcccagatgtgtacatctcag
atgatgggggttactcctgggcgaagatgctagaaggaccacattactataccatcctggactctggaggcatcattgtggccattgagc
acagcaaccgtcctatcaatgtgattaagttctccacagatgaaggccagtgctggcagagctatgtgttcacacaggagcccatctactt
cactgggcttgcttccgagcctggagccaggtccatgaacatcagcatctggggattcacagagtctttcattacccgccagtgggtctc
ctacacagtcgatttcaaagacatccttgagcggaattgtgaagaggatgactataccacgtggctggcacactccacagaccctggag
attacaaagacggctgcatttgggctataagaacagttcctacggctacggaagtcatccgtctgtcagaatggtcgagactatgttgt
ggccaagcagccatccgtctgtccgtgttccctggaggacttcctctgtgactttggctacttccgtccggagaacgcctcagagtgcgt
ggagcagcctgaactgaaggggcatgagttagagttctgtctgtacggcaaggaggagcacctgacaacaaatgggtaccggaaaat
cccaggagacaaatgccaaggtgggatgaatcccgccagagaagtaaaagacttgaaaaagaaatgcacaagcaacttcttgaaccc
cacaaagcaggactcccgcccacagggacacagcttgtcccagaatccagctccgcctcctcttggatacactgaaaacacacacttc
ctatctcctacccagaagcagaattccaagtcaaattctgtccctattatcctggccatcgtgggactgatgcttgtcacagtcgtagcagg
agtcctcattgtgaagaaatatgtctgtggcggaaggttcctggtgcaccggtactcggtgctacagcagcacgcagaggctgacggc
gtagaggctttggattcaacctcccacgctaaaagcggatatcacgacgactcagatgaggacctcctggaatag Sortilin Human (nucleic acid sequence):

(SEQ ID NO: 214)
Atggagcggccctggggagctgcggacggcctctcgcgctggccccatggcctcggcctcctcctcctgcagctgctgccgcc
gtcgaccctcagccaggaccggctggacgcgccgccgccgccgctgcgccgctgccgcgctggtctggccccatcggggtgagc
tgggggctgcggcggccgcagccggggcgcgtttcccgcggcggccgttgg*cgtcgc*aagccaccgagaacaacgaag
acttcaacatcgtggccgtggccagcaacttcgcgaccacggatctcgatgcctgaccgcgggaagttgcccggcaagaagctgcc
gctggaggtgctcaaagagatggaagccaatgcccggaaagctggctgcaccaggggctgtctgatctgcctgtcccacatcaag
tgcacgcccaagatgaagaagttcatcccaggacgctgccacacctacgaaggcgacaaagagtccgcacagggcggcatag
gcgaggcgatcgtcgacattcctgagattcctgggttcaaggacttggagccatggagcagttcatcgcacaggtcgatctgtgtg
tggactgcacaactggctgcctcaaagggcttgccaacgtgcagtgttctgacctgctcaagaagtggctgccgcaacgctgtgcg
acctttgccagcaagatccagggccaggtggacaagatcaagggggccggtggtgac*cgtcgc*agcgcgccgggcgaggacg
aggagtgcggccgggtccgggacttcgtcgccaagctggccaacaacacgcaccagcatgtgtttgatgatctcagaggctcagtatc
cttgtcctgggttggagatagcactggggtcattctagtcttgactaccttccatgtaccactggtaattatgacttttggacagtccaagcta
tatcgaagtgaggattatgggaagaactttaaggatattacagatctcatcaataacacctttattcggactgaatttggcatggctattggtc
ctgagaactctggaaaggtggtgttaacagcagaggtgtctggaggaagtcgtggaggaagaatctttagatcatcagattttgcgaag
aatttttgtgcaaacagatctccccttttcatcctctcactcagatgatgtatagccctcagaattctgattatcttttagctctcagcactgaaaat -continued ggcctgtgggtgtccaagaattttgggggaaaatgggaagaaatccacaaagcagtatgtttggccaaatggggatcagacaacacca
tcttctttacaacctatgcaaatggctcctgcaaagctgaccttggggctctggaattatggagaacttcagacttgggaaaaagcttcaaa
actattggtgtgaaaatctactcatttggtcttggggacgtttccttttttgcctctgtgatggctgataaggatacaacaagaaggatccac
gtttcaacagatcaaggggacacatggagcatggcccagctcccctccgtgggacaggaacagttctattctattctggcagcaaatgat
gacatggtattcatgcatgtagatgaacctggagacactgggtttggcacaatcttttacctcagatgatcgaggcattgtctattccaagtct
ttggaccgacatctctacactaccacaggcggagagacggacttaccaacgtgacctcctccgcggcgtctacataacaagcgtgct
ctccgaagataattctatccagaccatgatcacttttgaccaaggaggaaggtggacgcacctgaggaagcctgaaaacagtgaatgtg
atgctacagcaaaaaacaagaatgagtgcagccttcatattcatgcttcctacagcatctcccagaaactgaatgttccaatggccccact
ctcagagccgaatgccgtaggcattgtcattgctcatggtagcgtgggggatgccatctcagtgatggttccagatgtgtacatctcagat
gatggggttactcctggacaaagatgctggaaggaccccactattacaccatcctggattctggaggcatcattgtggccattgagcac
agcagccgtcctatcaatgtgattaagttctccacagacgaaggtcaatgctggcaaacctacacgttcaccagggaccccatctatttca
ctggcctagcttcagaacctggagctaggtccatgaatatcagcatttggggcttcacagaatctttcctgaccagccagtgggtctccta
caccattgattttaaagatatccttgaaaggaactgtgaagagaaggactataccatatggctggcacactccacagaccctgaagattat
gaagatggctgcattttgggctacaaagaacagtttctgcggctacgcaagtcatccgtgtgtcagaatggtcgagactatgttgtgacca
agcagccctccatctgcctctgttccctggaggactttctctgtgattttggctactaccgtccagaaaatgactccaagtgtgtggaacag
ccagaactgaagggccacgacctggagttttgtctgtacggaagagaagaacacctaacaacaaatgggtaccggaaaattccaggg
gacaaatgccagggtggggtaaatccagttcgagaagtaaaagacttgaaaaagaaatgcacaagcaactttttgagtccggaaaaac
agaattccaagtcaaattctgttccaattatcctggccatcgtgggattgatgctggtcacagtcgtagcaggagtgctcattgtgaagaaa
tatgtctgtgggggaaggttcctggtgcatcgatactctgtgctgcagcagcatgcagaggccaatggtgtggatggtgtggatgctttg
gacacagcctcccacactaataaaagtggttatcatgatgactcagatgaggacctcttggaatag Neuropeptide W Mouse (nucleic acid sequence):

(SEQ ID NO: 215)

Ctggcgtctaacagagaagtgcggggccctgggcccgggactcccaggaaccggcccctgctgcccctgctgctgcttctgctccttg
ctaccgctgcccgccagcgcctggtataagcacgtggcgagtccccgctatcacacagtgggtcgtgcctccgggctgctcatgggg
ctgcgccgctcgccctaccagtgg*cgccgt*aagcccaccgagaacaacgaagacttcaacatcgtggccgtggccagcaacttcg
cgaccacggatctcgatgctgaccgcgggaagttgcccggcaagaagctgccgctggaggtgctcaaagagatggaagccaat
gcccggaaagctggctgcaccaggggctgtctgatctgcctgtcccacatcaagtgcacgcccaagatgaagaagttcatcccag
gacgctgccacacctacgaaggcgacaaagagtccgcacagggcggcataggcgaggcgatcgtcgacattcctgagattcctg
ggttcaaggacttggagcccatggagcagttcatcgcacaggtcgatctgtgtgtggactgcacaactggctgcctcaaagggcttg
ccaacgtgcagtgttctgacctgctcaagaagtggctgcgcaacgctgtgcgacctttgccagcaagatccagggccaggtgga
caagatcaagggggccggtggtgac*cgccgt*gccctgggcggggctgctggacccctctcccggctcccaggaccggtcgcccg
cggcgctctcctgcttccttcctcagggcaggagctgtgggaggtacgaagcaggagctcacctgcagggcttcccgtccatgcaccc
tggagtccgcggacctggaggagtccgccaaccggagcagtcgctaagccttcactcctggatctcagaggagcccgctgctaga
gccttcggagagacgcttcgtgcccagccatggttcctgcagcaagtcatctttgccgatcctgtcaggcccaagaaccgatggcgccc
ccatgcttga Neuropeptide W Human (nucleic acid sequence):

(SEQ ID NO: 216)

Ctggcgtggcgcccaggggagcgggggctcccgcgagccggccgcggctggcactgctgctgcttctgctcctgctgccgctgc
cctccggcgcgtggtacaagcacgtggcgagtccccgctaccacacggtgggccgcgccgctggcctgctcatgggcgctgcgtcgc
tcacccctatctgtgg*cgccgc*aagcccaccgagaacaacgaagacttcaacatcgtggccgtggccagcaacttcgcgaccacg
gatctcgatgctgaccgcgggaagttgcccggcaagaagctgccgctggaggtgctcaaagatgatggaagcccaatgcccggaa
agctggctgcaccaggggctgtctgatctgcctgtcccacatcaagtgcacgcccaagatgaagaagttcatcccaggacgctgcc
acacctacgaaggcgacaaagagtccgcacagggcggcataggcgaggcgatcgtcgacattcctgagattcctgggttcaagg -continued acttggagcccatggagcagttcatcgcacaggtcgatctgtgtgtggactgcacaactggctgcctcaaagggcttgccaacgtgc agtgttctgacctgctcaagaagtggctgccgcaacgctgtgcgaccttttgccagcaagatccagggccaggtggacaagatcaa gggggccggtggtgaccgccgcgcgctgcgcgcggccgccggcccctggccagggacaccctctcccccgaacccgcagccc gcgaggctcctctcctgctgccctcgtgggttcaggagctgtgggagacgcgacgcaggagctcccaggcagggatcccgtccgtg cgccccggagcccgcgcgcccagagcctgcgctggaaccggagtccctggacttcagcggagctggccagagacttcggagaga cgtctcccgcccagcggtggacccgcagcaaaccgccttggcctgccctgcctggcccccggaccgttctga CART Mouse (nucleic acid sequence):
(SEQ ID NO: 217)
Atggagagctcccgcctgcggctgctacccctcctgggcgccgccctgctgctactgctaccttttgctgggtgcccgtgcccaggagg acgccgagctgcagccccgagccctggacatctactctgccgtggatgatgcgtcccacgagaaggagctgatcgaagcgttgcaag aagtcctgaagaagctcaagagtaaacgcaaagcccaccgagaacaacgaagacttcaacatcgtggccgtggccagcaacttcg cgaccacggatctcgatgctgaccgcgggaagttgcccggcaagaagctgccgctggaggtgctcaaagagatggaagccaat gcccggaaagctggctgcaccaggggctgtctgatctgcctgtcccacatcaagtgcacgcccaagatgaagaagttcatcccag gacgctgccacacctacgaaggcgacaaagagtccgcacagggcggcataggcgaggcgatcgtcgacattcctgagattcctg ggttcaaggacttggagcccatggagcagttcatcgcacaggtcgatctgtgtgtggactgcacaactggctgcctcaaagggcttg ccaacgtgcagtgttctgacctgctcaagaagtggctgccgcaacgctgtgcgacctttgccagcaagatccagggccaggtgga caagatcaaggggcggtggtgac*aaacgc*attccgatctacgagaagaagtacggccaagtcccatgtgtgacgctggagagc agtgcgcagtgaggaaaggggccaggatcgggaagctgtgtgactgtccccgaggaacttcctgcaattctttcctcttgaagtgcttgt ga CART Human (nucleic acid sequence):
(SEQ ID NO: 218)
Atggagagctcccgcgtgaggctgctgccctcctgggcgccgccctgctgctgatgctacctctgttgggtacccgtgcccaggag gacgccgagctccagccccgagccctggacatctactctgccgtggatgatgcctcccacgagaaggagctgatcgaagcgctgcaa gaagtcttgaagaagctcaagagtaaacgtaagcccaccgagaacaacgaagacttcaacatcgtggccgtggccagcaacttcg cgaccacggatctcgatgctgaccgcgggaagttgcccggcaagaagctgccgctggaggtgctcaaagagatggaagccaat gcccggaaagctggctgcaccaggggctgtctgatctgcctgtcccacatcaagtgcacgcccaagatgaagaagttcatcccag gacgctgccacacctacgaaggcgacaaagagtccgcacagggcggcataggcgaggcgatcgtcgacattcctgagattcctg ggttcaaggacttggagcccatggagcagttcatcgcacaggtcgatctgtgtgtggactgcacaactggctgcctcaaagggcttg ccaacgtgcagtgttctgacctgctcaagaagtggctgccgcaacgctgtgcgacctttgccagcaagatccagggccaggtgga caagatcaaggggcggtggtgac*aaacgt*gttcccatctatgagaagaagtatggccaagtcccatgtgtgacgccggtgagca gtgtgcagtgaggaaagggcaaggatcgggaagctgtgtgactgtccccgaggaacctcctgcaattccttcctcctgaagtgcttatga TGFB1 Mouse (nucleic acid sequence):
(SEQ ID NO: 219)
Atgccgccctcggggctgcggctactgccgcttctgctcccactcccgtggcttctagtgctgacgcccggggaggccagccgcggga ctctccacctgcaagaccatcgacatggagctggtgaaacggaagcgcatcgaagccatccgtggccagatcctgtccaaactaagg ctcgccagtcccccaagccagggggaggtaccgcccggcccgctgcccgaggcggtgctcgctttgtacaacagcacccgcgacc gggtggcaggcgagagcgccgacccagagccggagcccgaagcggactactatgctaaagaggtcacccgcgtgctaatggtgga ccgcaacaacgccatctatgagaaaaccaaagacatctcacacagtatatatatgttcttcaatacgtcagacattcgggaagcagtgcc cgaacccccattgctgtcccgtgcagagctgcgcttgcagagattaaaatcaagtgtgggagcaacatgtggaactctaccagaaatata gcaacaattcctggcgttaccttggtaaccggctgctgaccccactgatacgcctgagtggctgtcttttgacgtcactggagttgtacg gcagtggctgaaccaaggagacggaatacaggctttcgattcagcgctcactgctcttgtgacagcaaagataacaaactccacgtg gaaatcaacgggatcagccccaaacgtcggggcgacctgggcaccatccatgacatgaaccggcccttcctgctcctcatggccacc -continued cccctggaaagggcccagcacctgcacagctcacggcaccggagaaagcccaccgagaacaacgaagacttcaacatcgtggc cgtggccagcaacttcgcgaccacggatctcgatgctgaccgcgggaagttgcccggcaagaagctgccgctggaggtgctcaa agagatggaagccaatgcccggaaagctggctgcaccaggggctgtctgatctgcctgtcccacatcaagtgcacgcccaagat gaagaagttcatcccaggacgctgccacacctacgaaggcgacaaagagtccgcacagggcggcataggcgaggcgatcgtc gacattcctgagattcctgggttcaaggacttggagcccatggagcagttcatcgcacaggtcgatctgtgtgtggactgcacaact ggctgcctcaaaggggcttgccaacgtgcagtgttctgacctgctcaagaagtggctgccgcaacgctgtgcgacctttgccagcaa gatccagggccaggtggacaagatcaagggggccggtggtgaccggagagccctggataccaactattgcttcagctccacagag aagaactgctgtgtgcggcagctgtacattgactttaggaaggacctgggttggaagtggatccacgagcccaagggctaccatgcca acttctgtctgggaccctgcccctatatttggagcctggacacacagtacagcaaggtccttgccctctacaaccaacacaacccgggc gcttcggcgtcaccgtgctgcgtgccgcaggcttttggagccactgcccatcgtctactacgtgggtcgcaagcccaaggtggagcagt tgtccaacatgattgtgcgctcctgcaagtgcagctga TGFB1 Human (nucleic acid sequence):
(SEQ ID NO: 220)
Atgccgccctccgggctgcggctgctgccgctgctgctaccgctgctgtggctactggtgctgacgcctggccggccggccgcggg actatccacctgcaagactatcgacatggagctggtgaagcggaagcgcatcgaggccatccgcggccagatcctgtccaagctgcg gctcgccagccccccgagccaggggggaggtgccgcccggccgctgcccgaggccgtgctcgccctgtacaacagcacccgcga ccgggtggccggggagagtgcagaaccggagcccgagcctgaggccgactactacgccaaggaggtcacccgcgtgctaatggtg gaaacccacaacgaaatctatgacaagttcaagcagagtacacacagcatatatatgttcttcaacacatcagagctccgagaagcggt acctgaacccgtgttgcctctcccgggcagagctgcgtctgctgaggctcaagttaaaagtggagcagcacgtggagctgtaccagaaa tacagcaacaattcctggcgatacctcagcaaccggctgctggcacccagcgactcgccagagtggttatcttttgatgtcaccggagtt gtgcggcagtggttgagccgtggagggggaaattgagggctttcgccttagcgcccactgctcctgtgacagcagggataacacactgc aagtggacatcaacgggttcactaccggccgccgaggtgacctggccaccattcatggcatgaaccggccttcctgcttctcatggcc accccgctggagagggcccagcatctgcaaagctcccggcaccgccgaaagcccaccgagaacaacgaagacttcaacatcgtg gccgtggccagcaacttcgcgaccacggatctcgatgctgaccgcgggaagttgcccggcaagaagctgccgctggaggtgctc aaagagatggaagccaatgcccggaaagctggctgcaccaggggctgtctgatctgcctgtcccacatcaagtgcacgcccaag atgaagaagttcatcccaggacgctgccacacctacgaaggcgacaaagagtccgcacagggcggcataggcgaggcgatcg tcgacattcctgagattcctgggttcaaggacttggagcccatggagcagttcatcgcacaggtcgatctgtgtgtggactgcacaac tggctgcctcaaaggggcttgccaacgtgcagtgttctgacctgctcaagaagtggctgccgcaacgctgtgcgacctttgccagcaa gatccagggccaggtggacaagatcaagggggccggtggtgaccgccgagccctggacaccaactattgcttcagctccacggag aagaactgctgcgtgcggcagctgtacattgacttccgcaaggacctcggctggaagtggatccacgagcccaagggctaccatgcc aacttctgcctcgggccctgcccctacatttggagcctggacacgcagtacagcaaggtcctggccctgtacaaccagcatgaacccgg gcgcctcggcggcgccgtgctgcgtgccgcaggcgctggagccgctgcccatcgtgtactacgtgggccgcaagcccaaggtgga gcagctgtccaacatgatcgtgcgctcctgcaagtgcagctga TGFB2 Mouse (nucleic acid sequence):
(SEQ ID NO: 221)
Atgcactactgtgtgctgagcaccttttgctcctgcatctggtcccgtggcgctcagtctgtctacctgcagcaccctcgacatggatc agtttatgcgcaagaggatcgaggccatccgcgggcagatcctgagcaagctgaagctcaccagcccccggaagactatccggag ccggatgaggtcccccggaggtgatttccatctacaacagtaccagggacttactgcaggagaaggcaagccggagggcagccgc ctgcgagcgcgagcggagcgacgaggagtactacgccaaggaggtttataaaatcgacatgccgtcccacctcccctccgaaatgc catcccgcccactttctacagaccctacttcagaatcgtccgctttgatgtctcaacaatggagaaaatgcttcgaatctggtgaaggca gagttcagggtcttccgcttgcaaaaccccaaagccagagtggccgagcagcggattgaactgtatcagatccttaaatccaaagactt aacatctcccacccagcgctacatcgatagcaaggttgtgaaaaccagagcggagggtgaatggctctccttcgacgtgacagacgct gtgcaggagtggcttcaccacaaagacaggaacctggggtttaaaataagtttacactgccctgctgtaccttcgtgccgtctaataatt -continued acatcatcccgaataaaagcgaagagctcgaggcgagatttgcaggtattgatggcacctctacatatgccagtggtgatcagaaaact ataaagtccactaggaaaaaaaccagtgggaagaccccacatctcctgctaatgttgttgccctcctacagactggagtcacaacagtcc agc<u>cggcgg</u>aagcccaccgagaacaacgaagacttcaacatcgtggccgtggccagcaacttcgcgaccacggatctcgatgct

*gaccgcgggaagttgcccggcaagaagctgccgctggaggtgctcaaagagatggaagccaatgcccggaaagctggctgca*

*ccaggggctgtctgatctgcctgtcccacatcaagtgcacgcccaagatgaagaagttcatcccaggacgctgccacacctacga*

*aggcgacaaagagtccgcacagggcggcataggcgaggcgatcgtcgacattcctgagattcctgggttcaaggacttggagcc*

*catggagcagttcatcgcacaggtcgatctgtgtgtggactgcacaactggctgcctcaaagggcttgccaacgtgcagtgttctga*

*cctgctcaagaagtggctgccgcaacgctgtgcgacctttgccagcaagatccagggccaggtggacaagatcaaggggccg*

*gtggtgacc<u>cggcgg</u>aagaagcgcgctttggatgctgcctactgctttagaaatgtgcaggataattgctgccttcgccctctttacattgat* tttaagagggatcttggatggaaatggatccatgaacccaaagggtacaatgctaacttctgtgctggggcatgcccatatctatggagtt cagacactcaacacaccaaagtcctcagcctgtacaacaccataaatcccgaagcttccgcttcccttgctgtgtgtcccaggatctgg aaccactgaccattctctattacattggaaatacgcccaagatcgaacagctttccaatatgattgtcaagtcttgtaaatgcagctaa TGFB2 Human (nucleic acid sequence):

(SEQ ID NO: 222)

Atgcactactgtgtgctgagcgcttttctgatcctgcatctggtcacggtcgcgctcagcctgtctacctgcagcacactcgatatggacc agttcatgcgcaagaggatcgaggcgatccgcgggcagatcctgagcaagctgaagctcaccagtcccccagaagactatcctgagc ccgaggaagtccccccggaggtgatttccatctacaacagcaccagggacttgctccaggagaaggcgagcggagggcggccgc ctgcgagcgcgagaggagcgacgaagagtactacgccaaggaggtttacaaaatagacatgccgcccttcttcccctccgaaactgtc tgcccagttgttacaacaccctctggctcagtgggcagcttgtgctccagacagtcccaggtgctctgtgggtaccttgatgccatcccgc ccactttctacagaccctacttcagaattgttcgatttgacgtctcagcaatggagaagaatgcttccaatttggtgaaagcagagttcaga gtctttgctttgcagaacccaaaagccagagtgcctgaacaacggattgagctatatcagattctcaagtccaaagatttaacatctccaac ccagcgctacatcgacagcaaagttgtgaaaacaagagcagaaggcgaatggctctccttcgatgtaactgatgctgttcatgaatggct tcaccataaagacaggaacctgggatttaaaataagcttacactgtccctgctgcacttttgtaccatctaataattacatcatcccaaataa aagtgaagaactagaagcaagatttgcaggtattgatggcacctccacatataccagtggtgatcagaaaactataaagtccactaggaa aaaaaacagtgggaagaccccacatctcctgctaatgttattgccctcctacagacttgagtcacaacagaccaac<u>cggcgg</u>aagcc

*accgagaacaacgaagacttcaacatcgtggccgtggccagcaacttcgcgaccacggatctcgatgctgaccgcgggaagttg*

*cccggcaagaagctgccgctggaggtgctcaaagagatggaagccaatgcccggaaagctggctgcaccaggggctgtctgat*

*ctgcctgtcccacatcaagtgcacgcccaagatgaagaagttcatcccaggacgctgccacacctacgaaggcgacaaagagtc*

*cgcacagggcggcataggcgaggcgatcgtcgacattcctgagattcctgggttcaaggacttggagcccatggagcagttcatc*

*gcacaggtcgatctgtgtgtggactgcacaactggctgcctcaaagggcttgccaacgtgcagtgttctgacctgctcaagaagtgg*

*ctgccgcaacgctgtgcgacctttgccagcaagatccagggccaggtggacaagatcaaggggccggtggtgacc<u>cggcgg</u>aa* gaagcgtgctttggatgcggcctattgctttagaaatgtgcaggataattgctgcctacgtccactttacattgatttcaagagggatctagg gtggaaatggatacacgaacccaaagggtacaatgccaacttctgtgctggagcatgcccgtatttatggagttcagacactcagcaca gcagggtcctgagcttatataataccataaatccagaagcatctgcttctccttgctgcgtgtcccaagatttagaacctctaaccattctcta ctacattggcaaaacacccaagattgaacagctttctaatatgattgtaaagtcttgcaaatgcagctaa TGFB3 Mouse (nucleic acid sequence):

(SEQ ID NO: 223)

Atgaagatgcacttgcaaagggctctggtagtcctggccctgctgaacttggccacaatcagcctctctctgtccacttgcaccacgttg gacttcggccacatcaagaagaagagggtggaagccattaggggacagatcttgagcaagctcaggctcaccagcccccctgagcc atcggtgatgacccacgtccctatcaggtcctggcactttacaacagcacccgggagttgctggaagagatgcacggggagaggga ggaaggctgcactcaggagacctcggagtctgagtactatgccaaagagatcctaaatttcgacatgatccaggactggcggagca caatgaactggccgtctgccccaaaggaattacctctaaggttttttcgtttcaatgtgtcctcagtggagaaaaatggaaccaatctgttcc -continued gggcagagttccgggtcttgcgggtgcccaaccccagctccaagcgcacagagcagagaattgagctcttccagatacttcgaccgg atgagcacatagccaagcagcgctacataggtggcaagaatctgcccacaaggggcaccgctgaatggctgtctttcgatgtcactga cactgtgcgcgagtggctgttgaggagagagtccaacttgggtctggaaatcagcatccactgtccatgtcacacctttcagcccaatgg agacatactggaaaatgttcatgaggtgatggaaatcaaattcaaaggagtggacaatgaagatgaccatggccgtggagacctgggg cgtctcaagaagcaaaaggatcaccacaacccacacctgatcctcatgatgatcccccacaccgactggacagcccaggccagggc agtcag<u>aggaag</u>aagcccaccgagaacaacgaagacttcaacatcgtggccgtggccagcaacttcgcgaccacggatctcgat

*gctgaccgcgggaagttgcccggcaagaagctgccgctggaggtgctcaaagagatggaagccaatgcccggaaagctggctg*

*caccaggggctgtctgatctgcctgtcccacatcaagtgcacgcccaagatgaagaagttcatcccaggacgctgccacacctac*

*gaaggcgacaaagagtccgcacagggcggcataggcgaggcgatcgtcgacattcctgagattcctgggttcaaggacttggag*

*cccatggagcagttcatcgcacaggtcgatctgtgtgtggactgcacaactggctgcctcaaagggcttgccaacgtgcagtgttct*

*gacctgctcaagaagtggctgccgcaacgctgtgcgacctttgccagcaagatccagggccaggtggacaagatcaaggggc*

*cggtggtgac<u>aggaag</u>aagagggccctggacaccaattactgcttccgcaacctggaggagaactgctgtgtacgcccccttatattg* acttccggcaggatctaggctggaaatgggtccacgaacctaaggggttactatgccaacttctgctcaggcccttgcccatacctccgca gcgcagacacaaccccatagcacggtgcttggactatacaacaccctgaacccagaggcgtctgcctcgccatgctgcgtcccccagg acctggagcccctgaccatcttgtactatgtgggcagaacccccaaggtggagcagctgtccaacatggtggtgaagtcgtgtaagtgc agctga TGFB3 Human (nucleic acid sequence):

(SEQ ID NO: 224)

Atgaagatgcacttgcaaagggctctggtggtcctggccctgctgaactttgccacggtcagcctctctctgtccacttgcaccaccttg gacttcggccacatcaagaagaagagggtggaagccattaggggacagatcttgagcaagctcaggctcaccagcccccctgagcc aacggtgatgacccacgtccctatcaggtcctggccctttacaacagcacccgggagctgctggaggagatgcatggggagaggga ggaaggctgcacccaggaaaacaccgagtcggaatactatgccaaagaaatccataaaattcgacatgatccaggggctggcggagc acaacgaactggctgtctgccctaaaggaattacctccaaggttttccgcttcaatgtgtcctcagtggagaaaaatagaaccaacctatt ccgagcagaattccgggtcttgcgggtgcccaaccccagctctaagcggaatgagcagaggatcgagctcttccagatccttcggcca gatgagcacattgccaaacagcgctatatcggtggcaagaatctgcccacacggggcactgccgagtggctgtcctttgatgtcactga cactgtgcgtgagtggctgttgagaagagagtccaacttaggtctagaaatcagcattcactgtccatgtcacacctttcagcccaatgga gatatcctggaaaacattcacgaggtgatggaaatcaaattcaaaggcgtggacaatgaggatgaccatggccgtggagatctggggc gcctcaagaagcagaaggatcaccacaaccctcatctaatcctcatgatgattccccacaccggctcgacaacccgggccaggggg gtcag<u>aggaag</u>aagcccaccgagaacaacgaagacttcaacatcgtggccgtggccagcaacttcgcgaccacggatctcgatg

*ctgaccgcgggaagttgcccggcaagaagctgccgctggaggtgctcaaagagatggaagccaatgcccggaaagctggctgc*

*accaggggctgtctgatctgcctgtcccacatcaagtgcacgcccaagatgaagaagttcatcccaggacgctgccacacctacg*

*aaggcgacaaagagtccgcacagggcggcataggcgaggcgatcgtcgacattcctgagattcctgggttcaaggacttggagc*

*ccatggagcagttcatcgcacaggtcgatctgtgtgtggactgcacaactggctgcctcaaagggcttgccaacgtgcagtgttctg*

*acctgctcaagaagtggctgccgcaacgctgtgcgacctttgccagcaagatccagggccaggtggacaagatcaaggggccgg*

*ggtggtgac<u>aggaag</u>aagcgggctttggacaccaattactgcttccgcaacttggaggagaactgctgtgtgcgcccccctctacattga* cttccggacaggatctgggctggaagtgggtccatgaacctaagggctactatgccaacttctgctcaggcccttgcccatacctccgcag tgcagacacaacccacagcacggtgctgggactgtacaacactctgaaccctgaagcatctgcctcgccttgctgcgtgcccccaggac ctggagcccctgaccatcctgtactatgttgggaggacccccaaagtggagcagctctccaacatggtggtgaagtcttgtaaatgtagc tga PDGFA Mouse (nucleic acid sequence):

(SEQ ID NO: 225)

Atgaggacctgggcttgcctgctgctcctcggctgcggatacctcgcccatgccctggccgaggaagccgagataccccgggagttg atcgagcggctggctcgaagtcagatccacagcatccgggacctccagcgactcttggagatagactccgtagggggctgaggatgcc -continued ttggagacaagtctgagagcccatgggtcccatgccattaaccatgtgcccgagaagcggcctgtgcccatt<u>cgcagg</u>aagcccacc
gagaacaacgaagacttcaacatcgtggccgtggccagcaacttcgcgaccacggatctcgatgctgaccgcgggaagttgccc
ggcaagaagctgccgctggaggtgctcaaagagatggaagccaatgcccggaaagctggctgcaccaggggctgtctgatctg
cctgtcccacatcaagtgcacgcccaagatgaagaagttcatcccaggacgctgccacacctacgaaggcgacaaagagtccgc
acagggcggcataggcgaggcgatcgtcgacattcctgagattcctgggttcaaggacttggagcccatggagcagttcatcgca
caggtcgatctgtgtgtggactgcacaactggctgcctcaaagggcttgccaacgtgcagtgttctgacctgctcaagaagtggctg
ccgcaacgctgtgcgacctttgccagcaagatccagggccaggtggacaagatcaaggggccggtggtgac<u>cgcagg</u>aagag
aagtattgaggaagccattcctgcagtttgcaagaccaggacggtcatttacgagatacctcggagccaggtggaccccacatcggcc
aacttcctgatctggcccccatgtgtggaggtgaagcgctgcactggctgttgtaacaccagcagcgtcaagtgccagccttcacgggt
ccaccaccgcagtgtcaaggtggccaaagtggagtatgtcaggaagaagccaaaattgaaagaggtccaggtgaggttagaggaac
acctggagtgtgcatgtgcgacctccaacctgaacccagaccatcgggaggaggagacagatgtgaggtga PDGFA Human (nucleic acid sequence):
(SEQ ID NO: 226)
Atgaggaccttggcttgcctgctgctcctcggctgcggatacctcgcccatgttctggccgaggaagccgagatcccccgcgaggtga
tcgagaggctggcccgcagtcagatccacagcatccgggaccctccagcgactcctggagatagactccgtagggagtgaggattcttt
ggacaccagcctgagagctcacggggtccatgccactaagcatgtgcccgagaagcggccctgcccatt<u>cggagg</u>aagcccacc
gagaacaacgaagacttcaacatcgtggccgtggccagcaacttcgcgaccacggatctcgatgctgaccgcgggaagttgccc
ggcaagaagctgccgctggaggtgctcaaagagatggaagccaatgcccggaaagctggctgcaccaggggctgtctgatctg
cctgtcccacatcaagtgcacgcccaagatgaagaagttcatcccaggacgctgccacacctacgaaggcgacaaagagtccgc
acagggcggcataggcgaggcgatcgtcgacattcctgagattcctgggttcaaggacttggagcccatggagcagttcatcgca
caggtcgatctgtgtgtggactgcacaactggctgcctcaaagggcttgccaacgtgcagtgttctgacctgctcaagaagtggctg
ccgcaacgctgtgcgacctttgccagcaagatccagggccaggtggacaagatcaaggggccggtggtgac<u>cggagg</u>aagag
aagcatcgaggaagctgtccccgctgtctgcaagaccaggacggtcatttacgagattcctcggagtcaggtcgaccccacgtccgcc
aacttcctgatctggcccccgtgcgtggaggtgaaacgctgcaccggctgctgcaacacgagcagtgtcaagtgccagccctcccgc
gtccaccaccgcagcgtcaaggtggccaaggtggaatacgtcaggaagaagccaaaattaaaagaagtccaggtgaggttagagga
gcatttggagtgcgcctgcgcgaccacaagcctgaatccggattatcgggaagaggacacgggaaggcctagggagtcaggtaaaa
aacgaaaagaaaaaggttaaaacccacctaa BDNF Mouse (nucleic acid sequence):
(SEQ ID NO: 227)
Atgttccaccaggtgagaagagtgatgaccatccttttccttactatggttatttcatacttcggttgcatgaaggcggcgcccatgaaaga
agtaaacgtccacggacaaggcaacttggcctacccaggtgtgcggacccatgggactctggagagcgtgaatgggcccagggcag
gttcgagaggtctgacgacgacatcactggctgacacttttgagcacgtcatcgaagagctgctggatgaggaccagaaggttcggcc
caacgaagaaaaccataaggacgcggacttgtacacttcccgggtgatgctcagcagtcaagtgcctttggagcctcctctactctttctg
ctggaggaatacaaaaattacctggatgccgcaaacatgtctatgaggtt<u>cggcgc</u>aagcccaccgagaacaacgaagacttcaa
catcgtggccgtggccagcaacttcgcgaccacggatctcgatgctgaccgcgggaagttgcccggcaagaagctgccgctgga
ggtgctcaaagagatggaagccaatgcccggaaagctggctgcaccaggggctgtctgatctgcctgtcccacatcaagtgcacg
cccaagatgaagaagttcatcccaggacgctgccacacctacgaaggcgacaaagagtccgcacagggcggcataggcgagg
cgatcgtcgacattcctgagattcctgggttcaaggacttggagcccatggagcagttcatcgcacaggtcgatctgtgtgtggactg
cacaactggctgcctcaaagggcttgccaacgtgcagtgttctgacctgctcaagaagtggctgccgcaacgctgtgcgacctttgc
cagcaagatccagggccaggtggacaagatcaaggggccggtggtgac<u>cggcgc</u>cactccgaccctgcccgccgtggggag
ctgagcgtgtgtgacagtattagcgagtgggcacagcggcagataaaaagactgcagtggacatgtctggcgggacggtcacagtc
ctagagaaagtcccggtatccaaaggccaactgaagcagtatttctacgagaccaagtgtaatcccatggggttacaccaaggaaggctg -continued caggggcatagacaaaaggcactggaactcgcaatgccgaactacccaatcgtatgttcgggcccttactatggatagcaaaaagaga attggctggcgattcataaggatagacacttcctgtgtatgtacactgaccattaaaaggggaagatag BDNF Human (nucleic acid sequence):

(SEQ ID NO: 228)

Atgaccatcctttccttactatggttatttcatactttggttgcatgaaggctgccccccatgaaagaagcaaacatccgaggacaaggtgg cttggcctacccaggtgtgcggacccatgggactctggagagcgtgaatgggcccaaggcaggttcaagaggcttgacatcattggct gacactttcgaacacgtgatagaagagctgttggatgaggaccagaaagttcggcccaatgaagaaaacaataaggacgcagacttgt acacgtccagggtgatgctcagtagtcaagtgccttggagcctcctcttctctttctgctggaggaatacaaaaattacctagatgctgca aacatgtccatgagggtccggcgccactctgaccctgcccgccgaaagcccaccgagaacaacgaagacttcaacatcgtggccg tggccagcaacttcgcgaccacggatctcgatgctgaccgcgggaagttgccggaagaagctgccgctggaggtgctcaaag agatggaagccaatgcccggaaagctggctgcaccagggctgtctgatctgcctgtcccacatcaagtgcacgcccaagatga agaagttcatcccaggacgctgccacacctacgaaggcgacaaagagtccgcacaggcggcataggcgaggcgatcgtcga cattcctgagattcctgggttcaaggacttggagcccatggagcagttcatcgcacaggtcgatctgtgtgtggactgcacaactggc tgcctcaaagggcttgccaacgtgcagtgttctgacctgctcaagaagtggctgccgcaacgctgtgcgacctttgccagcaagatc cagggccaggtggacaagatcaaggggccggtggtgaccgccgaggggagctgagcgtgtgtgacagtattagtgagtgggta acggcggcagacaaaaagactgcagtggacatgtcggcgggacggtcacagtccttgaaaaggtccctgtatcaaaaggccaact gaagcaatacttctacgagaccaagtgcaatcccatgggttacacaaaagaaggctgcaggggcatagacaaaaggcattggaactc ccagtgccgaactacccagtcgtacgtgcgggcccttaccatggatagcaaaaagagaattggctggcgattcataaggatagacactt cttgtgtatgtacattgaccattaaaaggggaagatag NGF Mouse (nucleic acid sequence):

(SEQ ID NO: 229)

Atgtccatgttgttctacactctgatcactgcgttttgatcggcgtacaggcagaaccgtacacagatagcaatgtcccagaaggagact ctgtccctgaagcccactggactaaacttcagcattcccttgacacagccctccgcagagcccgcagtgcccctactgcaccaatagct gcccgagtgacagggcagaccccgcaacatcactgtagaccccagactgtttaagaaacggagactccactcaccccgtgtgctgttca gcacccagcctccacccacctcttcagacactctggatctagacttccaggcccatggtacaatccctttcaacaggactcaccggagc aagcgcaagcccaccgagaacaacgaagacttcaacatcgtggccgtggccagcaacttcgcgaccacggatctcgatgctgac cgcgggaagttgccggcaagaagctgccgctggaggtgctcaaagagatggaagccaatgcccggaaagctggctgcacca gggctgtctgatctgcctgtcccacatcaagtgcacgcccaagatgaagaagttcatcccaggacgctgccacacctacgaagg cgacaaagagtccgcacaggcggcataggcgaggcgatcgtcgacattcctgagattcctgggttcaaggaacttggagcccat ggagcagttcatcgcacaggtcgatctgtgtgtggactgcacaactggctgcctcaaagggctgccaacgtgcagtgttctgacct gctcaagaagtggctgccgcaacgctgtgcgacctttgccagcaagatccagggccaggtggacaagatcaaggggccggtg gtgacaagcgctcatccacccaccagtcttccacatggggagttctcagtgtgtgacagtgtcagtgtgtgggttggagataagacc acagccacagacatcaagggcaaggaggtgacagtgctggccgaggtgaacattaacaacagtgtattcagacagtactttttttgagac caagtgccgagcctccaatcctgttgagagtgggtgccggggcatcgactccaaacactggaactcatactgcaccacgactcacacc ttcgtcaaggcgttgacaacagatgagaagcaggctgcctggaggttcatccggatagacacagcctgtgtgtgtgtgctcagcagga aggctacaagaagaggctga NGF Human (nucleic acid sequence):

(SEQ ID NO: 230)

Atgtccatgttgttctacactctgatcacagcttttctgatcggcatacaggcggaaccacactcagagagcaatgtccctgcaggacac accatcccccaagcccactggactaaacttcagcattcccttgacactgccttcgcagagcccgcagcgcccggcagcggcgata gctgcacgcgtggcggggcagaccccgcaacattactgtggaccccaggctgtttaaaaagcggcgactccgttcaccccgtgtgctgt ttagcacccagcctccccgtgaagctgcagacactcaggatctggacttcgaggtcggtggtgctgcccccttcaacaggactcacag gagcaagccggaagcccaccgagaacaacgaagacttcaacatcgtggccgtggccagcaacttcgcgaccacggatctcgatg ctgaccgcgggaagttgccggcaagaagctgccgctggaggtgctcaaagagatggaagccaatgccggaaagctggctgc -continued accaggggctgtctgatctgcctgtcccacatcaagtgcacgcccaagatgaagaagttcatcccaggacgtctgccacacctacg aaggcgacaaagagtccgcacagggcggcataggcgaggcgatcgtcgacattcctgagattcctggggttcaaggacttggagc ccatggagcagttcatcgcacaggtcgatctgtgtgtggactgcacaactggctgcctcaaagggcttgccaacgtgcagtgttctg acctgctcaagaagtggctgccgcaacgctgtgcgacctttgccagcaagatccagggccaggtggacaagatcaaggggggcc ggtggtgaca<u>aagcggt</u>catcatccatcccatcttccacaggggcgaattctcggtgtgtgacagtgtcagcgtgtgggttggggataa gaccaccgccacagacatcaagggcaaggaggtgatggtgttgggagaggtgaacattaacaacagtgtattcaaacagtactttttg agaccaagtgccgggacccaaatcccgttgacagcgggtgccggggcattgactcaaagcactggaactcatattgtaccacgactca cacctttgtcaaggcgctgaccatggatggcaagcaggctgcctggcggtttatccggatagatacggcctgtgtgtgtgtgctcagca ggaaggctgtgagaagagcctga Albumin Mouse (nucleic acid sequence):
(SEQ ID NO: 231)

Atgaagtgggtaacctttctcctcctcctcttcgtctccggctctgcttttttccaggggtgtgttt<u>cgccga</u>aaagcccaccgagaacaac gaagacttcaacatcgtggccgtggccagcaacttcgcgaccacggatctcgatgctgaccgcgggaagttgcccggcaagaag ctgccgctggaggtgctcaaagagatggaagccaatgcccggaaagctggctgcaccaggggctgtctgatctgcctgtcccaca tcaagtgcacgcccaagatgaagaagttcatcccaggacgctgccacacctacgaaggcgacaaagagtccgcacagggcgg cataggcgaggcgatcgtcgacattcctgagattcctggggttcaaggacttggagcccatggagcagttcatcgcacaggtcgatct gtgtgtggactgcacaactggctgcctcaaagggcttgccaacgtgcagtgttctgacctgctcaagaagtggctgccgcaacgctg tgcgacctttgccagcaagatccagggccaggtggacaagatcaaggggggccggtggtgac<u>acgccga</u>gaagcacacaagagtg agatcgcccatcggtataatgatttgggagaacaacatttcaaaggcctagtcctgattgccttttcccagtatctccagaaatgctcatac gatgagcatgccaaattagtgcaggaagtaacagactttgcaaagacgtgtgttgccgatgagtctgccgccaactgtgacaaatcccttt cacactcttttgtggagataagttgtgtgccattccaaacctccgtgaaaactatggtgaactggctgactgctgtacaaaacaagagcccg aaagaaacgaatgtttcctgcaacacaaagatgacaaccccagcctgccaccatttgaaaggccagaggctgaggccatgtgcacctc ctttaaggaaaacccaaccacctttatgggacactatttgcatgaagttgccagaagacatccttatttctatgccccagaacttctttactat gctgagcagtacaatgagattctgacccagtgttgtgcagaggctgacaaggaaagctgcctgaccccgaagcttgatggtgtgaagg agaaagcattggtctcatctgtccgtcagagaatgaagtgctccagtatgcagaagtttggagagagagccttttaaagcatgggcagtag ctcgtctgagccagacattccccaatgctgactttgcagaaatcaccaaattggcaacagacctgaccaaagtcaacaaggagtgctgc catggtgacctgctggaatgcgcagatgacagggcggaacttgccaagtacatgtgtgaaaaccaggcgactatctccagcaaactgc agacttgctgcgataaaccactgttgaagaaagcccactgtcttagtgaggtggagcatgacaccatgcctgctgatctgcctgccattg ctgctgattttgttgaggaccaggaagtgtgcaagaactatgctgaggccaaggatgtcttcctgggcacgttcttgtatgaatattcaaga agacaccctgattactctgtatccctgttgctgagacttgctaagaaatatgaagccactctggaaaagtgctgcgctgaagccaatcctc ccgcatgctacggcacagtgcttgctgaatttcagcctcttgtagaagagcctaagaacttggtcaaaaccaactgtgatctttacgagaa gcttggagaatatgattccaaaatgccattctagttcgctacacccagaaagcacctcaggtgtcaaccccaactctcgtggaggctgc aagaaacctaggaagagtgggcaccaagtgttgtacacttcctgaagatcagagactgccttgtgtggaagactatctgtctgcaatcct gaaccgtgtgtgtctgctgcatgagaagacccccagtgagtgagcatgttaccaagtgctgtagtggatccctggtggaaaggcggccat gcttctctgctctgacagttgatgaaacatatgtccccaaagagtttaaagctgagaccttcaccttccactctgatatctgcacacttccag agaaggagaagcagattaagaaacaaacggctcttgctgagctggtgaagcacaagcccaaggctacagcggagcaactgaagact gtcatggatgactttgcacagttcctggatacatgttgcaaggctgctgacaaggacaccttgcttctcgactgagggtccaaaccttgtca ctagatgcaaagacgccttagcctaa Albumin Human (nucleic acid sequence):
(SEQ ID NO: 232)

atgaagtgggtaacctttatttcccttcttttttctctttagctcggcttattccaggggtgtgttt<u>cgtcga</u>aaagcccaccgagaacaacgaa gacttcaacatcgtggccgtggccagcaacttcgcgaccacggatctcgatgctgaccgcgggaagttgcccggcaagaagctgc -continued cgctggaggtgctcaaagagatggaagccaatgcccggaaagctggctgcaccagggggctgtctgatctgcctgtcccacatcaa gtgcacgcccaagatgaagaagttcatcccaggacgctgccacacctacgaaggcgacaaagagtccgcacagggcggcata ggcgaggcgatcgtcgacattcctgagattcctgggttcaaggacttggagcccatggagcagttcatcgcacaggtcgatctgtgt gtggactgcacaactggctgcctcaaagggcttgccaacgtgcagtgttctgacctgctcaagaagtggctgccgcaacgctgtgc gacctttgccagcaagatccagggccaggtggacaagatcaagggggccggtggtgac<u>cgtcga</u>gatgcacacaagagtgaggt tgctcatcggtttaaagatttgggagaagaaatttcaaagccttggtgttgattgcctttgctcagtatcttcagcagtgtccatttgaagatc atgtaaaattagtgaatgaagtaactgaatttgcaaaaacatgtgttgctgatgagtcagctgaaaattgtgacaaatcacttcatacccttt tggagacaaattatgcacagttgcaactcttcgtgaaacctatggtgaaatggctgactgctgtgcaaaacaagaacctgagagaaatga atgcttcttgcaacacaaagatgacaacccaaacctccccgattggtgagaccagaggttgatgtgatgtgcactgcttttcatgacaat gaagagacattttgaaaaaatacttatatgaaattgccagaagacatccttacttttatgccccggaactccttttctttgctaaaaggtataa agctgcttttacagaatgttgccaagctgctgataaagctgcctgcctgttgccaaagctcgatgaacttcgggatgaagggaaggcttc gtctgccaaacagagactcaagtgtgccagtctccaaaaatttggagaaagagctttcaaagcatgggcagtagctcgcctgagccag agatttcccaaagctgagtttgcagaagtttccaagttagtgacagatcttaccaaagtcccacacggaatgctgccatggagatctgcttg aatgtgctgatgacagggcggaccttgccaagtatatctgtgaaaatcaagattcgatctccagtaaactgaaggaatgctgtgaaaaac ctctgttggaaaaatcccactgcattgccgaagtggaaaatgatgagatgcctgctgacttgccttcattagctgctgattttgttgaaagta aggatgtttgcaaaaactatgctgaggcaaaggatgtcttcctgggcatgtttttgtatgaatatgcaagaaggcatcctgattactctgtcg tgctgctgctgagacttgccaagacatatgaaaccactctagagaagtgctgtgccgctgcagatcctcatgaatgctatgccaaagtgtt cgatgaatttaaacctcttgtggaagagcctcagaatttaatcaaacaaaattgtgagctttttgagcagcttggagagtacaaattccaga atgcgctattagttcgttacaccaagaaagtaccccaagtgtcaactccaactcttgtagaggtctcaagaaacctaggaaaagtgggca gcaaatgttgtaaacatcctgaagcaaaagaatgccctgtgcagaagactatctatccgtggtcctgaaccagttatgtgtgttgcatga gaaaacgccagtaagtgacagagtcaccaaatgctgcacagaatcctggtgaacaggcgaccatgcttttcagctctggaagtcgatg aaacatacgttcccaaagagtttaatgctgaaacattcaccttccatgcagatatatgcacactttctgagaaggagagacaaatcaagaa acaaactgcacttgttgagctcgtgaaacacaagcccaaggcaacaaaagagcaactgaaagctgttatggatgatttcgcagcttttgt agagaagtgctgcaaggctgacgataaggagacctgctttgccgaggagggtaaaaaacttgttgctgcaagtcaagctgccttaggct tataa Calcitonin Mouse (nucleic acid sequence):

(SEQ ID NO: 233)

Atgggcttcctgaagttctccccctttcctggttgtcagcatcttgctcctgtaccaggcatgcagcctccaggcagtgcctttgaggtcaat cttggaaagcagcccaggcatggccactctcagtgaagaagaagttcgcctgctggctgcactggtgcaggactatatgcagatgaaa gccagggagctggagcaggaggaagagcaggaggctgagggctctagcttggacagccccagatct<u>aagcgg</u>aagcccaccga gaacaacgaagacttcaacatcgtggccgtggccagcaacttcgcgaccacggatctcgatgctgaccgcggaagttgcccgg caagaagctgccgctggaggtgctcaaagagatggaagccaatgcccggaaagctggctgcaccaggggctgtctgatctgcct gtcccacatcaagtgcacgcccaagatgaagaagttcatcccaggacgctgccacacctacgaaggcgacaaagagtccgcac agggcggcataggcgaggcgatcgtcgacattcctgagattcctgggttcaaggacttggagcccatggagcagttcatcgcaca ggtcgatctgtgtgtggactgcacaactggctgcctcaaagggcttgccaacgtgcagtgttctgacctgctcaagaagtggctgcc gcaacgctgtgcgacctttgccagcaagatccagggccaggtggacaagatcaaggggccggtggtgac<u>aagcgg</u>tgtggga atctgagtacctgcatgctgggcacgtacacacaagacctcaacaagtttcacaccttccccccaaacttcaattggggttgaagcacctg gcaagaaagggatgtggcaaggacttggagacaaaccaccaatcccatttttggcaactaa Calcitonin Human (nucleic acid sequence):

(SEQ ID NO: 234)

Atgggcttccaaaagttctccccccttcctggctctcagcatcttggtcctgttgcaggcaggcagcctccatgcagcaccattcaggtctg ccctggagagcagcccagcagacccgccacgctcagtgaggacgaagcgcgcctcctgctggctgcactggtgcaggactatgtg cagatgaaggccagtgagctggagcaggagcaagagagagagggctccagcctggacagccccagatct<u>aagcgg</u>aagcccacc

```
gagaacaacgaagacttcaacatcgtggccgtggccagcaacttcgcgaccacggatctcgatgctgaccgcgggaagttgccc ggcaagaagctgccgctggaggtgctcaaagagatggaagccaatgcccggaaagctggctgcaccaggggctgtctgatctg cctgtcccacatcaagtgcacgcccaagatgaagaagttcatcccaggacgctgccacacctacgaaggcgacaaagagtccgc acagggcggcataggcgaggcgatcgtcgacattcctgagattcctgggttcaaggacttggagcccatggagcagttcatcgca caggtcgatctgtgtgtggactgcacaactggctgcctcaaagggcttgccaacgtgcagtgttctgacctgctcaagaagtggctg ccgcaacgctgtgcgacctttgccagcaagatccaggggccaggtggacaagatcaaggggggccggtggtgacaagcggtgcgg taatctgagtacttgcatgctgggcacatacacgcaggacttcaacaagtttcacacgttcccccaaactgcaattggggttggagcacct ggaaagaaaagggatatgtccagcgacttggagagagaccatcgccctcatgttagcatgccccagaatgccaactaa
```
15

Further exemplary luciferase fusion proteins (their nucleic acid sequences) include, but are not limited to, the sequences below. The portions italicized correspond to inserted nucleotides encoding *Cypridina* luciferase without its signal peptide. Underline indicates the putative cleavage sites.

Proamylin-luciferase Mouse (nucleic acid sequence):

(SEQ ID NO: 235)

*Atgatgtgcatctccaaactgccagctgtcctcctcatcctctctgtggcactgaaccacttgagagctacacctgtcagaagtggtagca*

*acccctcagatggacaaacggaagtgcaacacggccacgtgtgccacacaacgcctggcaaacttttttggttcgttccagcaacaaccttt*

*ggtccagtcctcccaccaaccaacgtgggatcgaatacatatggc*<u>aagagg</u>*aatgcg*Tactgcgccactgttcattgccaggactgtc cttacgaacctgatccaccaaacacagttccaacttcctgtgaagctaaagaaggagaatgtattgatagcagctgtggcacctgc acgagagacatactatcagatggactgtgtgaaaataaaccaggaaaaacatgttgccgaatgtgtcagtatgtaattgaatgcag agtagaggccgcaggatggtttagaacattctatggaaagagattccagttccaggaacctggtacatacgtgtttgggtcaaggaa ccaagggcggcgactggaaggtgtccatcaccctggagaacctggatgaaccaagggggctgtgctgaccaagacaagactg gaagtggctggagacatcattgacatcgctcaagctactgagaatcccatcactgtaaacggtggagctgaccctatcatcgccaa cccgtacaccatcggcgaggtcaccatcgctgttgttgagatgccaggcttcaacatcaccgtcattgagttcttcaaactgatcgtga tcgacatcctcggaggaagatctgtaagaatcgcccagacacagcaaacaaaggaatgatctctggcctctgtggagatcttaa aatgatggaagatacagacttcacttcagatccagaacaactcgctattcagcctaagatcaaccaggagtttgacggttgtccact ctatggaaatcctgatgacgttgcatactgcaaaggtcttctggagccgtacaaggacagctgccgcaacccccatcaacttctacta ctacaccatctcctgcgccttcgcccgctgtatgggtggagacgagcgagcctcacacgtgctgcttgactacagggagacgtgcg ctgctcccgaaactagaggaacctgcgttttgtctggacatactttctacgatacatttgacaaagcaagataccaattccagggtcc ctgcaaggagattcttatggccgccgactgtttctggaacacttgggatgtgaaggtttcacacaggaatgttgactcttacactgaa gtagagaaagtacgaatcaggaaacaatcgactgtagtagaactcattgttgatggaaacagattctggttggaggagaagccg tgtccgtcccgtacagctctcagaacacttccatctactggcaagatggtgacatactgactacagccatcctacctgaagctctggt ggtcaagttcaacttcaagcaactgctcgtcgtacatattagagatccattcgatggtaagacttgcggtatttgcggtaactacaacc aggatttcagtgatgattcttttgatgctgaaggagcctgtgatctgaccccaacccaccgggatgcaccgaagaacagaaacct gaagctgaacgactctgcaatagtctcttcgccggtcaaagtgatcttgatcagaaatgtaacgtgtgccacaagcctgaccgtgtc gaacgatgcatgtacgagtattgcctgaggggacaacagggtttctgtgaccacgcatgggagttcaagaaagaatgctacataa* agcatggagacaccctagaagtaccagatgaatgcaaa<u>aagagg</u>aatgcggcagggatccaaatagggaatccttggatttctta ctcgttaa Proamylin-luciferase Human (nucleic acid sequence):

(SEQ ID NO: 236)

*Atgggcatcctgaagctgcaagtatttctcattgtgctctctgttgcattgaaccatctgaaagctacacccattgaaagtcatcaggt*

*ggaaaagcggaaatgcaacactgccacatgtgcaacgcagcgcctggcaaatttttagttcattccagcaacaactttggtgccat*

*tctctcatctaccaacgtgggatccaatacatggc*<u>aagagg</u>*aatgcaT*actgcgccactgttcattgccaggactgtccttacga acctgatccaccaaacacagttccaacttcctgtgaagctaaagaaggagaatgtattgatagcagctgtggcacctgcacgaga -continued gacatactatcagatggactgtgtgaaaataaaccaggaaaaacatgttgccgaatgtgtcagtatgtaattgaatgcagagtaga
ggccgcaggatggtttagaacattctatggaaagagattccagttccaggaacctggtacatacgtgttgggtcaaggaaccaagg
gcggcgactggaaggtgtccatcaccctggagaacctggatggaaccaaggggctgtgctgaccaagacaagactggaagtg
gctggagacatcattgacatcgctcaagctactgagaatcccatcactgtaaacggtggagctgaccctatcatcgccaacccgta
caccatcggcgaggtcaccatcgctgttgttgagatgccaggcttcaacatcaccgtcattgagttcttcaaactgatcgtgatcgac
atcctcggaggaagatctgtaagaatcgccccagacacagcaaacaaaggaatgatctctggcctctgtggagatcttaaaatga
tggaagatacagacttcacttcagatccagaacaactcgctattcagcctaagatcaaccaggagtttgacggttgtccactctatgg
aaatcctgatgacgttgcatactgcaaaggtcttctggagccgtacaaggacagctgccgcaacccccatcaacttctactactacac
catctcctgcgccttcgcccgctgtatgggtggagacgagcgagcctcacacgtgctgcttgactacagggagacgtgcgctgctcc
cgaaactagaggaacctgcgtttgtgtctggacatactttctacgatacatttgacaaagcaagataccaattccagggtccctgcaa
ggagattcttatggccgccgactgtttctggaacacttgggatgtgaaggtttcacacaggaatgttgactcttacactgaagtagag
aaagtacgaatcaggaaacaatcgactgtagtagaactcattgttgatggaaaacagattctggttggaggagaagccgtgtccgt
cccgtacagctctcagaacacttccatctactggcaagatggtgacatactgactacagccatcctacctgaagctctggtggtcaa
gttcaacttcaagcaactgctcgtcgtacatattagagatccattcgatggtaagacttgcggtatttgcggtaactacaaccaggatt
tcagtgatgattcttttgatgctgaaggagcctgtgatctgacccccaacccaccgggatgcaccgaagaacagaaacctgaagct
gaacgactctgcaatagtctcttcgccggtcaaagtgatcttgatcagaaatgtaacgtgtgccacaagcctgaccgtgtcgaacga
tgcatgtacgagtattgctgaggggacaacagggtttctgtgaccacgcatgggagttcaagaaagaatgctacataaagcatg
gagacaccctagaagtaccagatgaatgcaaa<u>aagagg</u>aatgcggtagaggttttaaagagagagccactgaattacttgccccttt
ag Proinsulin-luciferase Mouse (nucleic acid sequence):
(SEQ ID NO: 237)
Atggccctgtggatgcgcttcctgccctgctggccctgctcttcctctgggagtcccaccccacccaggcttttgtcaagcagcacctttt
gtggttcccacctggtggaggctctctacctggtgtgtggggagcgtggcttcttctacacacccatgtcccgccgtgaagtggaggac
ccacaagtggcacaactggagctgggtggaggcccggagcaggtgaccttcagaccttggcactggaggtggcccagcag<u>aaga</u>
<u>gg</u>Tactgcgccactgttcattgccaggactgtccttacgaacctgatccaccaaacacagttccaacttcctgtgaagctaaagaag
gagaatgtattgatagcagctgtggcacctgcacgagagacatactatcagatggactgtgtgaaaataaaccaggaaaaacat
gttgccgaatgtgtcagtatgtaattgaatgcagagtagaggccgcaggatggtttagaacattctatggaaagagattccagttcc
aggaacctggtacatacgtgttgggtcaaggaaccaagggcggcgactggaaggtgtccatcaccctggagaacctggatggaa
ccaaggggctgtgctgaccaagacaagactggaagtggctggagacatcattgacatcgctcaagctactgagaatcccatca
ctgtaaacggtggagctgaccctatcatcgccaacccgtacaccatcggcgaggtcaccatcgctgttgttgagatgccaggcttca
acatcaccgtcattgagttcttcaaactgatcgtgatcgacatcctcggaggaagatctgtaagaatcgccccagacacagcaaac
aaaggaatgatctctggcctctgtggagatcttaaaatgatggaagatacagacttcacttcagatccagaacaactcgctattcag
cctaagatcaaccaggagtttgacggttgtccactctatggaaatcctgatgacgttgcatactgcaaaggtcttctggagccgtaca
aggacagctgccgcaacccatcaacttctactactacaccatctcctgcgccttcgcccgctgtatgggtggagacgagcgagcct
cacacgtgctgcttgactacagggagacgtgcgctgctcccgaaactagaggaacctgcgttttgtctggacatactttctacgatac
atttgacaaagcaagataccaattccagggtccctgcaaggagattcttatggccgccgactgtttctggaacacttgggatgtgaa
ggtttcacacaggaatgttgactcttacactgaagtagagaaagtacgaatcaggaaacaatcgactgtagtagaactcattgttga
tggaaaacagattctggttggaggagaagccgtgtccgtcccgtacagctctcagaacacttccatctactggcaagatggtgacat
actgactacagccatcctacctgaagctctggtggtcaagttcaacttcaagcaactgctcgtcgtacatattagagatccattcgatg
gtaagacttgcggtatttgcggtaactacaaccaggatttcagtgatgattcttttgatgctgaaggagcctgtgatctgacccccaac
ccaccgggatgcaccgaagaacagaaacctgaagctgaacgactctgcaatagtctcttcgccggtcaaagtgatcttgatcaga -continued aatgtaacgtgtgccacaagcctgaccgtgtcgaacgatgcatgtacgagtattgcctgaggggacaacagggtttctgtgaccac gcatgggagttcaagaaagaatgctacataaagcatggagacaccctagaagtaccagatgaatgcaaaaagcgtggcattgta gatcagtgctgcaccagcatctgctccctctaccagctggagaactactgcaactag Proinsulin-luciferase Human (nucleic acid sequence) (nucleic acid sequence):
(SEQ ID NO: 238)
Atggccctgtggatgcgcctcctgcccctgctggcgctgctggccctctggggacctgacccagccgcagcctttgtgaaccaacacc tgtgcggctcacacctggtggaagctctctacctagtgtgcggggaacgaggcttcttctacacacccaagacccgccgggaggcaga ggacctgcaggtggggcaggtggagctgggcgggggccctggtgcaggcagcctgcagcccttggccctggagggcctgca gaagaggTactgcgccactgttcattgccaggactgtccttacgaacctgatccaccaaacacagttccaacttcctgtgaagctaa agaaggagaatgtattgatagcagctgtggcacctgcacgagagacatactatcagatggactgtgtgaaaataaaccaggaaa aacatgttgccgaatgtgtcagtatgtaattgaatgcagagtagaggccgcaggatggtttagaacattctatggaaagagattcca gttccaggaacctggtacatacgtgttgggtcaaggaaccaagggcggcgactggaaggtgtccatcaccctggagaacctggat ggaaccaaggggctgtgctgaccaagacaagactggaagtggctggagacatcattgacatcgctcaagctactgagaatccc atcactgtaaacggtggagctgacccctatcatcgccaacccgtacaccatcggcgaggtcaccatcgctgttgttgagatgccagg cttcaacatcaccgtcattgagttcttcaaactgatcgtgatcgacatcctcggaggaagatctgtaagaatcgccccagacacagc aaacaaggaatgatctctggcctctgtggagatcttaaaatgatggaagatacagacttcacttcagatccagaacaactcgctat tcagcctaagatcaaccaggagtttgacggttgtccactctatggaaatcctgatgacgttgcatactgcaaaggtcttctggagccg tacaaggacagctgccgcaacccatcaacttctactactacaccatctcctgcgccttcgccgctgtatgggtggagacgagcg agcctcacacgtgctgcttgactacagggagacgtgcgctgctcccgaaactagaggaacctgcgttttgtctggacatactttctac gatacatttgacaaagcaagataccaattccagggtccctgcaaggagattcttatggccgccgactgtttctggaacacttgggat gtgaaggtttcacacaggaatgttgactcttacactgaagtagagaaagtacgaatcaggaaacaatcgactgtagtagaactcat tgttgatggaaaacagattctggttggaggagaagccgtgtccgtcccgtacagctctcagaacacttccatctactggcaagatgg tgacatactgactacagccatcctacctgaagctctggtggtcaagttcaacttcaagcaactgctcgtcgtacatattagagatccat tcgatggtaagacttgcggtatttgcggtaactacaaccaggatttcagtgatgattcttttgatgctgaaggagcctgtgatctgaccc ccaacccaccgggatgcaccgaagaacagaaacctgaagctgaacgactctgcaatagtctcttcgccggtcaaagtgatcttga tcagaaatgtaacgtgtgccacaagcctgaccgtgtcgaacgatgcatgtacgagtattgcctgaggggacaacagggtttctgtg accacgcatgggagttcaagaaagaatgctacataaagcatggagacaccctagaagtaccagatgaatgcaaaaagcgtggc attgtggaacaatgctgtaccagcatctgctccctctaccagctggagaactactgcaactag Proglucagon (includes GRPP, glucagon, GLP-1, GLP-2) Mouse (nucleic acid sequence):
(SEQ ID NO: 239)
Atgaagaccatttactttgtggctggattgcttataatgctggtgcaaggcagctggcagcacgcccttcaagacacagaggagaaccc cagatcattcccagcttcccagacagaagcgcatgaggaccctgatgagatgaatgaagacaaacgccactcacagggcacattcac cagcgactacagcaaatacctggactcccgccgtgcccaagattttgtgcagtggttgatgaacaccaagaggaaccggaacaacatt gccaaacgtcatgatgaatttgagaggcatgctgaagggacctttaccagtgatgtgagttcttacttggagggccaggcagcaaagga attcattgcttggctggtgaaaggccgaggaaggcgagacttcccagaagaagtcgccattgccgaggaactcggccgaaaagagaag aTactgcgccactgttcattgccaggactgtccttacgaacctgatccaccaaacacagttccaacttcctgtgaagctaaagaagg agaatgtattgatagcagctgtggcacctgcacgagagacatactatcagatggactgtgtgaaaataaaccaggaaaaacatgt tgccgaatgtgtcagtatgtaattgaatgcagagtagaggccgcaggatggtttagaacattctatggaaagagattccagttccag gaacctggtacatacgtgttgggtcaaggaaccaagggcggcgactggaaggtgtccatcaccctggagaacctggatggaacc aagggggctgtgctgaccaagacaagactggaagtggctggagacatcattgacatcgctcaagctactgagaatccctcactg taaacggtggagctgacccctatcatcgccaacccgtacaccatcggcgaggtcaccatcgctgttgttgagatgccaggcttcaac atcaccgtcattgagttcttcaaactgatcgtgatcgacatcctcggaggaagatctgtaagaatcgccccagacacagcaaacaa aggaatgatctctggcctctgtggagatcttaaaatgatggaagatacagacttcacttcagatccagaacaactcgctattcagcct -continued

```
aagatcaaccaggagtttgacggttgtccactctatggaaatcctgatgacgttgcatactgcaaaggtcttctggagccgtacaag gacagctgccgcaaccccatcaacttctactactacaccatctcctgcgccttcgcccgctgtatgggtggagacgagcgagcctca cacgtgctgcttgactacagggagacgtgcgctgctcccgaaactagaggaacctgcgttttgtctggacatactttctacgatacatt tgacaaagcaagataccaattccagggtccctgcaaggagattcttatggccgccgactgtttctgaacacttgggatgtgaaggt ttcacacaggaatgttgactcttacactgaagtagagaaagtacgaatcaggaaacaatcgactgtagtagaactcattgttgatgg aaaacagattctggttggaggagaagccgtgtccgtcccgtacagctctcagaacacttccatctactggcaagatggtgacatact gactacagccatcctacctgaagctctggtggtcaagttcaacttcaagcaactgctcgtcgtacatattagagatccattcgatggta agacttgcggtatttgcggtaactacaaccaggatttcagtgatgattcttttgatgctgaaggagcctgtgatctgaccccccaaccca ccgggatgcaccgaagaacagaaacctgaagctgaacgactctgcaatagtctcttcgccggtcaaagtgatcttgatcagaaat gtaacgtgtgccacaagcctgaccgtgtcgaacgatgcatgtacgagtattgcctgaggggacaacagggtttctgtgaccacgca tgggagttcaagaaagaatgctacataaagcatggagacaccctagaagtaccagatgaatgcaaaaagcgcggccgcaggca cgctgatggctccttctctgacgagatgagcaccattctggataatcttgccaccagggacttcatcaactggctgattcaaaccaagatc actgacaagaaatag
```

Proglucagon (includes GRPP, glucagon, GLP-1, GLP-2) Human (nucleic acid sequence)
(nucleic acid sequence):

(SEQ ID NO: 240)

```
atgaaaagcatttactttgtggctggattatttgtaatgctggtacaaggcagctggcaacgttcccttcaagacacagaggagaaatcca gatcattctcagcttcccaggcagacccactcagtgatcctgatcagatgaacgaggacaagcgccattcacagggcacattcaccagt gactacagcaagtatctggactccaggcgtgcccaagatttttgtgcagtggttgatgaataccaagaggaacaggaataacattgccaa acgtcacgatgaatttgagagacatgctgaagggaccttaccagtgatgtaagttcttatttggaaggccaagctgccaaggaattcatt gcttggctggtgaaaggccgaggaaggcgagatttcccagaagaggtcgccattgttgaagaacttggccgaaagagaagaTactg cgccactgttcattgccaggactgtccttacgaacctgatccaccaaacacagttccaacttcctgtgaagctaaagaaggagaatg tattgatagcagctgtggcacctgcacgagagacatactatcagatggactgtgtgaaaataaaccaggaaaaacatgttgccga atgtgtcagtatgtaattgaatgcagagtagaggccgcaggatggtttagaacattctatggaaagagattccagttccaggaacct ggtacatacgtgttgggtcaaggaaccaagggcggcgactggaaggtgtccatcaccctggagaacctggatggaaccaaggg ggctgtgctgaccaagacaagactggaagtggctggagacatcattgacatcgctcaagctactgagaatcccatcactgtaaac ggtggagctgacccatcatcgccaacccgtacaccatcggcgaggtcaccatcgctgttgttgagatgccaggcttcaacatcacc gtcattgagttcttcaaactgatcgtgatcgacatcctcggaggaagatctgtaagaatcgcccagacacagcaaacaaaggaat gatctctggcctctgtggagatcttaaaatgatggaagatacagacttcacttcagatccagaacaactcgctattcagcctaagatc aaccaggagtttgacggttgtccactctatggaaatcctgatgacgttgcatactgcaaaggtcttctggagccgtacaaggacagc tgccgcaaccccatcaacttctactactacaccatctcctgcgccttcgcccgctgtatgggtggagacgagcgagcctcacacgtg ctgcttgactacagggagacgtgcgctgctcccgaaactagaggaacctgcgttttgtctggacatactttctacgatacatttgaca agcaagataccaattccagggtccctgcaaggagattcttatggccgccgactgtttctggaacacttgggatgtgaaggtttcac acaggaatgttgactcttacactgaagtagagaaagtacgaatcaggaaacaatcgactgtagtagaactcattgttgatgaaaa cagattctggttggaggagaagccgtgtccgtcccgtacagctctcagaacacttccatctactggcaagatggtgacatactgact acagccatcctacctgaagctctggtggtcaagttcaacttcaagcaactgctcgtcgtacatattagagatccattcgatggtaaga cttgcggtatttgcggtaactacaaccaggatttcagtgatgattcttttgatgctgaaggagcctgtgatctgaccccccaacccaccg gatgcaccgaagaacagaaacctgaagctgaacgactctgcaatagtctcttcgccggtcaaagtgatcttgatcagaaatgta acgtgtgccacaagcctgaccgtgtcgaacgatgcatgtacgagtattgcctgaggggacaacagggtttctgtgaccacgcatgg gagttcaagaaagaatgctacataaagcatggagacaccctagaagtaccagatgaatgcaaaaagcgcggccgcagacatgc tgatggttctttctctgatgagatgaacaccattcttgataatcttgccgccagggacttttataaactggttgattcagaccaaaatcactgac aggaaataa
```

-continued

Peptide YY Mouse (nucleic acid sequence):

(SEQ ID NO: 241)

atggtggcggtgcgcaggccttggcccgtcacggtcgcaatgctgctaatcctgctcgcctgtctgggagccctggtggacgcctac cctgccaaccagaggctcccggcgaagacgcctccccggaggagctgagccgctactacgcctccctgcgccactacctcaac ctggtcacccggcagcggtatgga<u>aaaaga</u>Tactgcgccactgttcattgccaggactgtccttacgaacctgatccaccaaaca cagttccaacttcctgtgaagctaaagaaggagaatgtattgatagcagctgtggcacctgcacgagagacatactatcagatgga ctgtgtgaaaataaaccaggaaaaacatgttgccgaatgtgtcagtatgtaattgaatgcagagtagaggccgcaggatggtttag aacattctatggaaagagattccagttccaggaacctggtacatacgtgtgggtcaaggaaccaagggcggcgactggaaggtg tccatcaccctggagaacctggatgaaccaaggggggctgtgctgaccaagacaagactggaagtggctggagacatcattgac atcgctcaagctactgagaatcccatcactgtaaacggtggagctgaccctatcatcgccaacccgtacaccatcggcgaggtcac catcgctgttgttgagatgccaggcttcaacatcaccgtcattgagttcttcaaactgatcgtgatcgacatcctcggaggaagatctg taagaatcgccccagacacagcaaacaaggaatgatctctggcctctgtggagatcttaaaatgatggaagatacagacttcac ttcagatccagaacaactcgctattcagcctaagatcaaccaggagtttgacggttgtccactctatggaaatcctgatgacgttgca tactgcaaaggtcttctggagccgtacaaggacagctgccgcaacccatcaacttctactactacaccatctcctgcgccttcgccc gctgtatggtggagacgagcgagcctcacacgtgctgcttgactacagggagacgtgcgctgctcccgaaactagaggaacct gcgttttgtctggacatactttctacgatacatttgacaaagcaagataccaattccagggtccctgcaaggagattcttatggccgcc gactgtttctggaacacttgggatgtgaaggtttcacacaggaatgttgactcttacactgaagtagagaaagtacgaatcaggaaa caatcgactgtagtagaactcattgttgatggaaaacagattctggttggaggagaagccgtgtccgtcccgtacagctctcagaac acttccatctactggcaagatggtgacatactgactacagccatcctacctgaagctctggtggtcaagttcaacttcaagcaactgc tcgtcgtacatattagagatccattcgatggtaagacttgcggtatttgcggtaactacaaccaggatttcagtgatgattcttttgatgc tgaaggagcctgtgatctgaccccaaccccaccgggatgcaccgaagaacagaaacctgaagctgaacgactctgcaatagtct cttcgccggtcaaagtgatcttgatcagaaatgtaacgtgtgccacaagcctgaccgtgtcgaacgatgcatgtacgagtattgcct gaggggacaacagggtttctgtgaccacgcatgggagttcaagaaagaatgctataaagcatggagacaccctagaagtac cagatgaatgcaaa<u>aagaggaggg</u>gatgtccccgcagctctgttctccaaactgctcttcacagacgacagcgacagcgagaacctcc ccttcaggccagaaggtttggaccagtggtga Peptide YY Human (nucleic acid sequence):

(SEQ ID NO: 242)

Atggtgttcgtgcgcaggccgtggcccgccttgaccacagtgcttctggccctgctcgtctgcctaggggcgctggtcgacgcctacc ccatcaaacccgaggctcccggcgaagacgcctcgccggaggagctgaaccgctactacgcctccctgcgccactacctcaacctg gtcacccggcagcggtatggg<u>aaaaga</u>Tactgcgccactgttcattgccaggactgtccttacgaacctgatccaccaaacacagtt ccaacttcctgtgaagctaaagaaggagaatgtattgatagcagctgtggcacctgcacgagagacatactatcagatggactgtg tgaaaataaaccaggaaaaacatgttgccgaatgtgtcagtatgtaattgaatgcagagtagaggccgcaggatggtttagaaca ttctatggaaagagattccagttccaggaacctggtacatacgtgtgggtcaaggaaccaagggcggcgactggaaggtgtccat caccctggagaacctggatgaaccaaggggggctgtgctgaccaagacaagactggaagtggctggagacatcattgacatcg ctcaagctactgagaatcccatcactgtaaacggtggagctgaccctatcatcgccaacccgtacaccatcggcgaggtcaccatc gctgttgttgagatgccaggcttcaacatcaccgtcattgagttcttcaaactgatcgtgatcgacatcctcggaggaagatctgtaag aatcgccccagacacagcaaacaaggaatgatctctggcctctgtggagatcttaaaatgatggaagatacagacttcacttcag atccagaacaactcgctattcagcctaagatcaaccaggagtttgacggttgtccactctatggaaatcctgatgacgttgcatactg caaaggtcttctggagccgtacaaggacagctgccgcaacccatcaacttctactactacaccatctcctgcgccttcgcccgctgt atgggtggagacgagcgagcctcacacgtgctgcttgactacagggagacgtgcgctgctcccgaaactagaggaacctgcgttt tgtctggacatactttctacgatacatttgacaaagcaagataccaattccagggtccctgcaaggagattcttatggccgccgactg tttctggaacacttgggatgtgaaggtttcacacaggaatgttgactcttacactgaagtagagaaagtacgaatcaggaaacaatc -continued gactgtagtagaactcattgttgatggaaaacagattctggttggaggagaagccgtgtccgtcccgtacagctctcagaacacttc catctactggcaagatggtgacatactgactacagccatcctacctgaagctctggtggtcaagttcaacttcaagcaactgctcgtc gtacatattagagatccattcgatggtaagacttgcggtatttgcggtaactacaaccaggatttcagtgatgattcttttgatgctgaa ggagcctgtgatctgaccccaaccaccgggatgcaccgaagaacagaaacctgaagctgaacgactctgcaatagtctcttcg ccggtcaaagtgatcttgatcagaaatgtaacgtgtgccacaagcctgaccgtgtcgaacgatgcatgtacgagtattgcctgagg ggacaacagggtttctgtgaccacgcatgggagttcaagaaagaatgctacataaagcatggagacaccctagaagtaccagat gaatgcaaa<u>aagaggaggg</u>acggcccggacacgcttctttccaaaacgttcttccccgacggcgaggaccgcccccgtcaggtcgcg gtcggagggcccagacctgtggtga Neuropeptide Y Mouse (nucleic acid sequence):

(SEQ ID NO: 243)

*Atgctaggtaacaagcgaatggggctgtgtggactgaccctcgctctatctctgctcgtgtgtttgggcattctggctgaggggtaccc*

*ctccaagccggacaatccgggcgaggacgcgccagcagaggacatggccagatactactccgctctgcgacactacatcaatct*

*catcaccagacagagatatggc<u>aagaga</u>Tactgcgccactgttcattgccaggactgtccttacgaacctgatccaccaaacaca*

*gttccaacttcctgtgaagctaaagaaggagaatgtattgatagcagctgtggcacctgcacgagagacatactatcagatggact*

*gtgtgaaaataaaccaggaaaaacatgttgccgaatgtgtcagtatgtaattgaatgcagagtagaggccgcaggatggtttaga*

*acattctatggaaagagattccagttccaggaacctggtacatacgtgttgggtcaaggaaccaagggcggcgactggaaggtgt*

*ccatcaccctggagaacctggatggaaccaaggggctgtgctgaccaagacaagactggaagtggctggagacatcattgac*

*atcgctcaagctactgagaatcccatcactgtaaacggtggagctgaccctatcatcgccaacccgtacaccatcggcgaggtcac*

*catcgctgttgttgagatgccaggcttcaacatcaccgtcattgagttcttcaaactgatcgtgatcgacatcctcggaggaagatctg*

*taagaatcgccccagacacagcaaacaaggaatgatctctggcctctgtggagatcttaaaatgatggaagatacagacttcac*

*ttcagatccagaacaactcgctattcagcctaagatcaaccaggagtttgacggttgtccactctatggaaatcctgatgacgttgca*

*tactgcaaaggtcttctggagccgtacaaggacagctgccgcaaccccatcaacttctactactacaccatctcctgcgccttcgccc*

*gctgtatgggtggagacgagcgagcctcacacgtgctgcttgactacaggagacgtgcgctgctcccgaaactagaggaacct*

*gcgttttgtctggacatactttctacgatacatttgacaaagcaagataccaattccagggtccctgcaaggagattcttatggccgcc*

*gactgtttctggaacacttgggatgtgaaggttttcacacaggaatgttgactcttacactgaagtagagaaagtacgaatcaggaaa*

*caatcgactgtagtagaactcattgttgatggaaaacagattctggttggaggagaagccgtgtccgtcccgtacagctctcagaac*

*acttccatctactggcaagatggtgacatactgactacagccatcctacctgaagctctggtggtcaagttcaacttcaagcaactgc*

*tcgtcgtacatattagagatccattcgatggtaagacttgcggtatttgcggtaactacaaccaggatttcagtgatgattcttttgatgc*

*tgaaggagcctgtgatctgaccccaacccaccgggatgcaccgaagaacagaaacctgaagctgaacgactctgcaatagtctc*

*ttcgccggtcaaagtgatcttgatcagaaatgtaacgtgtgccacaagcctgaccgtgtcgaacgatgcatgtacgagtattgcct*

*gagggggacaacagggtttctgtgaccacgcatgggagttcaagaaagaatgctacataaagcatggagacaccctagaagtac*

*cagatgaatgcaaa<u>aagaggaggt</u>ccagccctgagacactgatttcagacctcttaatgaaggaaagcacagaaaacgcccccaga*

*acaaggcttgaagacccttccatgtggtga*

Neuropeptide Y Human (nucleic acid sequence):

(SEQ ID NO: 244)

*Atgctaggtaacaagcgactggggctgtccggactgaccctcgccctgtccctgctcgtgtgcctgggtgcgctggccgaggcgtac*

*ccctccaagccggacaaccgggcgaggacgcaccagcgcaggacatggccagatactactcggcgctgcgacactacatcaacc*

*tcatcaccaggcagagatatggaaaacgaTactgcgccactgttcattgccaggactgtccttacgaacctgatccaccaaacacag*

*ttccaacttcctgtgaagctaaagaaggagaatgtattgatagcagctgtggcacctgcacgagagacatactatcagatggactgt*

*gtgaaaataaaccaggaaaaacatgttgccgaatgtgtcagtatgtaattgaatgcagagtagaggccgcaggatggtttagaac*

*attctatggaaagagattccagttccaggaacctggtacatacgtgttgggtcaaggaaccaagggcggcgactggaaggtgtcc*

*atcaccctggagaacctggatggaaccaaggggctgtgctgaccaagacaagactggaagtggctggagacatcattgacatc*

*gctcaagctactgagaatcccatcactgtaaacggtggagctgaccctatcatcgccaacccgtacaccatcggcgaggtcaccat*

-continued cgctgttgttgagatgccaggcttcaacatcaccgtcattgagttcttcaaactgatcgtgatcgacatcctcggaggaagatctgtaa gaatcgccccagacacagcaaacaaaggaatgatctctggcctctgtggagatcttaaaatgatggaagatacagacttcacttca gatccagaacaactcgctattcagcctaagatcaaccaggagtttgacggttgtccactctatggaaatcctgatgacgttgcatact gcaaaggtcttctggagccgtacaaggacagctgccgcaacccatcaacttctactactacaccatctcctgcgccttcgcccgct gtatgggtggagacgagcgagcctcacacgtgctgcttgactacagggagacgtgcgctgctcccgaaactagaggaacctgcg ttttgtctggacatactttctacgatacatttgacaaagcaagataccaattccagggtccctgcaaggagattcttatggccgccgac tgtttctggaacacttgggatgtgaaggtttcacacaggaatgttgactcttacactgaagtagagaaagtacgaatcaggaaacaa tcgactgtagtagaactcattgttgatggaaaacagattctggttggaggagaagccgtgtccgtcccgtacagctctcagaacactt ccatctactggcaagatggtgacatactgactacagccatcctacctgaagctctggtggtcaagttcaacttcaagcaactgctcgt cgtacatattagagatccattcgatggtaagacttgcggtatttgcggtaactacaaccaggatttcagtgatgattcttttgatgctga aggagcctgtgatctgaccccaacccaccgggatgcaccgaagaacagaaacctgaagctgaacgactctgcaatagtctcttc gccggtcaaagtgatcttgatcagaaatgtaacgtgtgccacaagcctgaccgtgtcgaacgatgcatgtacgagtattgcctgag gggacaacagggtttctgtgaccacgcatgggagttcaagaaagaatgctacataaagcatggagacacctagaagtaccag atgaatgcaaa<u>aagaggaggt</u>ccagcccagagacactgatttcagacctcttgatgagagaaagcacagaaaatgttcccagaactc ggcttgaagaccctgcaatgtggtga Pancreatic polypeptide Mouse (nucleic acid sequence):

(SEQ ID NO: 245)

Atggccgtcgcatactgctgcctctccctgtttctcgtatccacttgggtggctctgctgctgcagccctgcaggggacctggggagcc cccctggagccaatgtaccaggcgactatgcgacacctgagcagatggcacaatatgaaactcagctccgcagatacatcaacacac tgaccaggcctaggtatgggaagagaTactcgcgccactgttcattgccaggactgtccttacgaacctgatccaccaaacacagttc caacttcctgtgaagctaaagaaggagaatgtattgatagcagctgtggcacctgcacgagagacatactatcagatggactgtgt gaaaataaaccaggaaaaacatgttgccgaatgtgtcagtatgtaattgaatgcagagtagaggccgcaggatggtttagaacat tctatggaaagagattccagttccaggaacctggtacatacgtgtttgggtcaaggaaccaagggcggcgactggaaggtgtccat cacccctggagaacctggatggaaccaaggggctgtgctgaccaagacaagactggaagtggctggagacatcattgacatcg ctcaagctactgagaatcccatcactgtaaacggtggagctgaccctatcatcgccaacccgtacaccatcggcgaggtcaccatc gctgttgttgagatgccaggcttcaacatcaccgtcattgagttcttcaaactgatcgtgatcgacatcctcggaggaagatctgtaag aatcgccccagacacagcaaacaaaggaatgatctctggcctctgtggagatcttaaaatgatggaagatacagacttcacttcag atccagaacaactcgctattcagcctaagatcaaccaggagtttgacggttgtccactctatggaaatcctgatgacgttgcatactg caaaggtcttctggagccgtacaaggacagctgccgcaacccatcaacttctactactacaccatctcctgcgccttcgcccgctgt atgggtggagacgagcgagcctcacacgtgctgcttgactacagggagacgtgcgctgctcccgaaactagaggaacctgcgttt tgtctggacatactttctacgatacatttgacaaagcaagataccaattccagggtccctgcaaggagattcttatggccgccgactg tttctggaacacttgggatgtgaaggtttcacacaggaatgttgactcttacactgaagtagagaaagtacgaatcaggaaacaatc gactgtagtagaactcattgttgatggaaaacagattctggttggaggagaagccgtgtccgtcccgtacagctctcagaacacttc catctactggcaagatggtgacatactgactacagccatcctacctgaagctctggtggtcaagttcaacttcaagcaactgctcgtc gtacatattagagatccattcgatggtaagacttgcggtatttgcggtaactacaaccaggatttcagtgatgattcttttgatgctgaa ggagcctgtgatctgaccccaacccaccgggatgcaccgaagaacagaaacctgaagctgaacgactctgcaatagtctcttcg ccggtcaaagtgatcttgatcagaaatgtaacgtgtgccacaagcctgaccgtgtcgaacgatgcatgtacgagtattgcctgagg ggacaacagggtttctgtgaccacgcatgggagttcaagaaagaatgctacataaagcatggagacacctagaagtaccagat gaatgcaaa<u>aagaggaggg</u>gccgaggaggagaacacaggtggacttcctggagtgcagctctcccctgcaccagcccccagttg gcttgattccctgctctgcgccctggagctga -continued Pancreatic polypeptide Human (nucleic acid sequence):

(SEQ ID NO: 246)

Atggctgccgcacgcctctgcctctccctgctgctcctgtccacctgcgtggctctgttactacagccactgctgggtgcccagggag
ccccactggagccagtgtacccaggggacaatgccacaccagagcagatggcccagtatgcagctgatctccgtagatacatca
acatgctgaccaggcctaggtatgggaaaagaTactgcgccactgttcattgccaggactgtccttacgaacctgatccaccaaac
acagttccaacttcctgtgaagctaaagaaggagaatgtattgatagcagctgtggcacctgcacgagagacatactatcagatgg
actgtgtgaaaataaaccaggaaaaacatgttgccgaatgtgtcagtatgtaattgaatgcagagtagaggccgcaggatggttta
gaacattctatggaaagagattccagttccaggaacctggtacatacgtgttgggtcaaggaaccaagggcggcgactggaaggt
gtccatcaccctggagaacctggatgaaccaaggggggctgtgctgaccaagacaagactggaagtggctggagacatcattga
catcgctcaagctactgagaatcccatcactgtaaacggtggagctgacctatcatcgccaacccgtacaccatcggcgaggtca
ccatcgctgttgttgagatgccaggcttcaacatcaccgtcattgagttcttcaaactgatcgtgatcgacatcctcggaggaagatct
gtaagaatcgccccagacacagcaaacaaaggaatgatctctggcctctgtggagatcttaaaatgatggaagatacagacttca
cttcagatccagaacaactcgctattcagcctaagatcaaccaggagtttgacggttgtccactctatggaaatcctgatgacgttgc
atactgcaaaggtcttctggagccgtacaaggacagctgccgcaacccccatcaacttctactactacaccatctcctgcgccttcgcc
cgctgtatgggtggagacgagcgagcctcacacgtgctgcttgactacagggagacgtgcgctgctcccgaaactagaggaacct
gcgttttgtctggacatactttctacgatacatttgacaaagcaagataccaattccagggtccctgcaaggagattcttatggccgcc
gactgtttctggaacacttgggatgtgaaggtttcacacaggaatgttgactcttacactgaagtagagaaagtacgaatcaggaaa
caatcgactgtagtagaactcattgttgatggaaaacagattctggttggaggagaagccgtgtccgtcccgtacagctctcagaac
acttccatctactggcaagatggtgacatactgactacagccatcctacctgaagctctggtggtcaagttcaacttcaagcaactgc
tcgtcgtacatattagagatccattcgatggtaagacttgcggtatttgcggtaactacaaccaggatttcagtgatgattcttttgatgc
tgaaggagcctgtgatctgaccccccaaccccaccgggatgcaccgaagaacagaaacctgaagctgaacgactctgcaatagtct
cttcgccggtcaaagtgatcttgatcagaaatgtaacgtgtgccacaagcctgaccgtgtcgaacgatgcatgtacgagtattgcct
gaggggacaacagggtttctgtgaccacgcatgggagttcaagaaagaatgctacataaagcatggagacaccctagaagtac
cagatgaatgcaaaaagaggaggcacaaagaggacacgctggccttctcggagtgggggtccccgcatgctgctgtccccaggga
gctcagcccgctggacttataa Somatostatin Mouse (nucleic acid sequence):

(SEQ ID NO: 247)

Atgctgtcctgccgtctccagtgcgccctggctgcgctctgcatcgtcctggctttgggcggtgtcaccggcgcgccctcggacccca
gactccgtcagtttctgcagagtctctggcggctgccaccgggaaacaggaactggccaagtacttcttggcagagctgcgcaaaTa
ctgcgccactgttcattgccaggactgtccttacgaacctgatccaccaaacacagttccaacttcctgtgaagctaaagaaggaga
atgtattgatagcagctgtggcacctgcacgagagacatactatcagatggactgtgtgaaaataaaccaggaaaaacatgttgcc
gaatgtgtcagtatgtaattgaatgcagagtagaggccgcaggatggtttagaacattctatggaaagagattccagttccaggaa
cctggtacatacgtgttgggtcaaggaaccaagggcggcgactggaaggtgtccatcaccctggagaacctggatgaaccaag
ggggctgtgctgaccaagacaagactggaagtggctggagacatcattgacatcgctcaagctactgagaatcccatcactgtaa
acggtggagctgacctatcatcgccaacccgtacaccatcggcgaggtcaccatcgctgttgttgagatgccaggcttcaacatca
ccgtcattgagttcttcaaactgatcgtgatcgacatcctcggaggaagatctgtaagaatcgccccagacacagcaaacaaagg
aatgatctctggcctctgtggagatcttaaaatgatggaagatacagacttcacttcagatccagaacaactcgctattcagcctaag
atcaaccaggagtttgacggttgtccactctatggaaatcctgatgacgttgcatactgcaaaggtcttctggagccgtacaaggac
agctgccgcaacccccatcaacttctactactacaccatctcctgcgccttcgcccgctgtatgggtggagacgagcgagcctcacac
gtgctgcttgactacagggagacgtgcgctgctcccgaaactagaggaacctgcgttttgtctggacatactttctacgatacatttga
caaagcaagataccaattccagggtccctgcaaggagattcttatggccgccgactgtttctggaacacttgggatgtgaaggtttc
acacaggaatgttgactcttacactgaagtagagaaagtacgaatcaggaaacaatcgactgtagtagaactcattgttgatggaa -continued aacagattctggttggaggagaagccgtgtccgtcccgtacagctctcagaacacttccatctactggcaagatggtgacatactga
ctacagccatcctacctgaagctctggtggtcaagttcaacttcaagcaactgctcgtcgtacatattagagatccattcgatggtaag
acttgcggtatttgcggtaactacaaccaggatttcagtgatgattcttttgatgctgaaggagcctgtgatctgaccccaacccacc
gggatgcaccgaagaacagaaacctgaagctgaacgactctgcaatagtctcttcgccggtcaaagtgatcttgatcagaaatgt
aacgtgtgccacaagcctgaccgtgtcgaacgatgcatgtacgagtattgcctgaggggacaacagggtttctgtgaccacgcatg
ggagttcaagaaagaatgctacataaagcatggagacaccctagaagtaccagatgaatgcaaa<u>cgcaaa</u>ctgtccgagcccaa
ccagacagagaatgatgccctggagcccgaggatttgccccaggcagctgagcaggacgagatgaggctggagctgcagaggtct
gccaactcgaacccagcaatggcaccccgggaacgcaaagctggctgcaagaacttcttctggaagacattcacatcctgttag Somatostatin Human (nucleic acid sequence):
(SEQ ID NO: 248)
Atgctgtcctgccgcctccagtgcgcgctggctgcgctgtccatcgtcctggccctgggctgtgtcaccggcgctccctcggacccca
gactccgtcagtttctgcagaagtccctggctgctgccgcggggaagcaggaactggccaagtacttcttggcagagctg<u>cgcaaaTa</u>
ctgcgccactgttcattgccaggactgtccttacgaacctgatccaccaaacacagttccaacttcctgtgaagctaaagaaggaga
atgtattgatagcagctgtggcacctgcacgagagacatactatcagatggactgtgtgaaaataaaccaggaaaaacatgttgcc
gaatgtgtcagtatgtaattgaatgcagagtagaggccgcaggatggtttagaacattctatggaaagagattccagttccaggaa
cctggtacatacgtgtgggtcaaggaaccaagggcggcgactggaaggtgtccatcaccctggagaacctggatgaaccaag
ggggctgtgctgaccaagacaagactggaagtggctggagacatcattgacatcgctcaagctactgagaatcccatcactgtaa
acggtggagctgaccctatcatcgccaacccgtacaccatcggcgaggtcaccatcgctgttgttgagatgccaggcttcaacatca
ccgtcattgagttcttcaaactgatcgtgatcgacatcctcggaggaagatctgtaagaatcgcccagacacagcaaacaaagg
aatgatctctggcctctgtggagatcttaaaatgatggaagatacagacttcacttcagatccagaacaactcgctattcagcctaag
atcaaccaggagttttgacggttgtccactctatggaaatcctgatgacgttgcatactgcaaaggtcttctggagccgtacaaggac
agctgccgcaacccccatcaacttctactactacaccatctcctgcgccttcgcccgctgtatgggtggagacgagcgagcctcacac
gtgctgcttgactacagggagacgtgcgctgctcccgaaactagaggaacctgcgttttgtctggacatactttctacgatacatttga
caaagcaagataccaattccagggtccctgcaaggagattcttatggccgccgactgtttctggaacacttgggatgtgaaggtttc
acacaggaatgttgactcttacactgaagtagagaaagtacgaatcaggaaacaatcgactgtagtagaactcattgttgatggaa
aacagattctggttggaggagaagccgtgtccgtcccgtacagctctcagaacacttccatctactggcaagatggtgacatactga
ctacagccatcctacctgaagctctggtggtcaagttcaacttcaagcaactgctcgtcgtacatattagagatccattcgatggtaag
acttgcggtatttgcggtaactacaaccaggatttcagtgatgattcttttgatgctgaaggagcctgtgatctgaccccaacccacc
gggatgcaccgaagaacagaaacctgaagctgaacgactctgcaatagtctcttcgccggtcaaagtgatcttgatcagaaatgt
aacgtgtgccacaagcctgaccgtgtcgaacgatgcatgtacgagtattgcctgaggggacaacagggtttctgtgaccacgcatg
ggagttcaagaaagaatgctacataaagcatggagacaccctagaagtaccagatgaatgcaaa<u>cgcaaa</u>ctgtctgaacccaa
ccagacggagaatgatgccctggaacctgaagatctgtcccaggctgctgagcaggatgaaatgaggcttgagctgcagagatctgct
aactcaaacccggctatggcaccccgagaacgcaaagctggctgcaagaatttcttctggaagactttcacatcctgttag GHRH Mouse (nucleic acid sequence):
(SEQ ID NO: 249)
Atgctgctctgggtgctctttgtgatcctcatcctcaccagtggctcccactgctcactgcccccctcacctcccttcaggatgcagcgac
acgtagatgccatcttccaccaactacaggaaactcctgagccagctgtatgcccggaaagtgatccaggacatcatgaacaagca
aggggagaggatccaggaacaaagggccaggctcagccgccaggaagacagcatgtggacagaggacaagcagatgacccctgg
agagcatc<u>cggcgg</u>Tactgcgccactgttcattgccaggactgtccttacgaacctgatccaccaaacacagttccaacttcctgtg
aagctaaagaaggagaatgtattgatagcagctgtggcacctgcacgagagacatactatcagatggactgtgtgaaaataaac
caggaaaaacatgttgccgaatgtgtcagtatgtaattgaatgcagagtagaggccgcaggatggtttagaacattctatggaaag
agattccagttccaggaacctggtacatacgtgtgggtcaaggaaccaagggcggcgactggaaggtgtccatcaccctggaga
acctggatgaaccaaggggggctgtgctgaccaagacaagactggaagtggctggagacatcattgacatcgctcaagctactg -continued

```
agaatcccatcactgtaaacggtggagctgaccctatcatcgccaacccgtacaccatcggcgaggtcaccatcgctgttgttgag
atgccaggcttcaacatcaccgtcattgagttcttcaaactgatcgtgatcgacatcctcggaggaagatctgtaagaatcgcccca
gacacagcaaacaaaggaatgatctctggcctctgtggagatcttaaaatgatggaagatacagacttcacttcagatccagaac
aactcgctattcagcctaagatcaaccaggagtttgacggttgtccactctatggaaatcctgatgacgttgcatactgcaaaggtctt
ctggagccgtacaaggacagctgccgcaaccccatcaacttctactactacaccatctcctgcgccttcgcccgctgtatgggtgga
gacgagcgagcctcacacgtgctgcttgactacagggagacgtgcgctgctcccgaaactagaggaacctgcgttttgtctggaca
tactttctacgatacatttgacaaagcaagataccaattccagggtcctgcaaggagattcttatggccgccgactgtttctggaac
acttgggatgtgaaggtttcacacaggaatgttgactcttacactgaagtagagaaagtacgaatcaggaaacaatcgactgtagt
agaactcattgttgatggaaaacagattctggttggaggagaagccgtgtccgtcccgtacagctctcagaacacttccatctactg
gcaagatggtgacatactgactacagccatcctacctgaagctctggtggtcaagttcaacttcaagcaactgctcgtcgtacatatt
agagatccattcgatggtaagacttgcggtatttgcggtaactacaaccaggatttcagtgatgattcttttgatgctgaaggagcctg
tgatctgaccccaacccaccgggatgcaccgaagaacagaaacctgaagctgaacgactctgcaatagtctcttcgccggtcaa
agtgatcttgatcagaaatgtaacgtgtgccacaagcctgaccgtgtcgaacgatgcatgtacgagtattgcctgaggggacaaca
gggtttctgtgaccacgcatgggagttcaagaaagaatgctacataaagcatggagacaccctagaagtaccagatgaatgcaa
ac<u>cggcgg</u>ttgcagggattcccaaggatgaagccttcagcggacgcttga
```

GHRH Human (nucleic acid sequence):
(SEQ ID NO: 250)
```
Atgccactctgggtgttcttcttttgtgatcctcaccctcagcaacagctcccactgctcccacctccccctttgaccctcaggatgcggc
ggtatgcagatgccatcttcaccaacagctaccggaaggtgctgggccagctgtccgcccgcaagctgctccaggacatcatgagca
ggcagcagggagagagcaaccaagagcgaggagcaagggcacggcttggtcgtcaggtagacagcatgtgggcagaacaaaag
caaatggaattggagagcatcctggtggccctg<u>cggcgg</u>Tactgcgccactgttcattgccaggactgtccttacgaacctgatccac
caaacacagttccaacttcctgtgaagctaaagaaggagaatgtattgatagcagctgtggcacctgcacgagagacatactatc
agatggactgtgtgaaaataaaccaggaaaaacatgttgccgaatgtgtcagtatgtaattgaatgcagagtagaggccgcagga
tggtttagaacattctatggaaagagattccagttccaggaacctggtacatacgtgttgggtcaaggaaccaagggcggcgactg
gaaggtgtccatcaccctggagaacctggatggaaccaaggggggctgtgctgaccaagacaagactggaagtggctggagaca
tcattgacatcgctcaagctactgagaatcccatcactgtaaacggtggagctgaccctatcatcgccaacccgtacaccatcggcg
aggtcaccatcgctgttgttgagatgccaggcttcaacatcaccgtcattgagttcttcaaactgatcgtgatcgacatcctcggagga
agatctgtaagaatcgccccagacacagcaaacaaaggaatgatctctggcctctgtggagatcttaaaatgatggaagatacag
acttcacttcagatccagaacaactcgctattcagcctaagatcaaccaggagtttgacggttgtccactctatggaaatcctgatga
cgttgcatactgcaaaggtcttctggagccgtacaaggacagctgccgcaaccccatcaacttctactactacaccatctcctgcgc
cttcgcccgctgtatgggtggagacgagcgagcctcacacgtgctgcttgactacagggagacgtgcgctgctcccgaaactaga
ggaacctgcgttttgtctggacatactttctacgatacatttgacaaagcaagataccaattccagggtcctgcaaggagattcttat
ggccgccgactgtttctggaacacttgggatgtgaaggtttcacacaggaatgttgactcttacactgaagtagagaaagtacgaat
caggaaacaatcgactgtagtagaactcattgttgatggaaaacagattctggttggaggagaagccgtgtccgtcccgtacagct
ctcagaacacttccatctactggcaagatggtgacatactgactacagccatcctacctgaagctctggtggtcaagttcaacttcaa
gcaactgctcgtcgtacatattagagatccattcgatggtaagacttgcggtatttgcggtaactacaaccaggatttcagtgatgatt
cttttgatgctgaaggagcctgtgatctgaccccaacccaccgggatgcaccgaagaacagaaacctgaagctgaacgactctg
caatagtctcttcgccggtcaaagtgatcttgatcagaaatgtaacgtgtgccacaagcctgaccgtgtcgaacgatgcatgtacga
gtattgcctgaggggacaacagggtttctgtgaccacgcatgggagttcaagaaagaatgctacataaagcatggagacaccctag
aagtaccagatgaatgcaaa<u>cggcgg</u>ctgcagaagcacaggaactcccagggatga
```

-continued

POMC (ACTH, MSH) Mouse (nucleic acid sequence):

(SEQ ID NO: 251)

Atgccgagattctgctacagtcgctcaggggccctgttgctggccctcctgcttcagacctccatagatgtgtggagctggtgcctgga gagcagccagtgccaggacctcaccacggagagcaacctgctggcttgcatccgggcttgcaaactcgacctctcgctggagacgcc cgtgtttcctggcaacggagatgaacagcccctgactgaaaaccccggaagtacgtcatggtgcacttccgctgggaccgcttcggc cccaggaacagcagcagtgctggcagcgcggcgcagaggcgtgcggaggaagaggcggtgtggggagatggcagtccagagcc gagtccacgcgagggc<u>aagcgc</u>Tactgcgccactgttcattgccaggactgtccttacgaacctgatccaccaaacacagttccaa cttcctgtgaagctaaagaaggagaatgtattgatagcagctgtggcacctgcacgagagacatactatcagatggactgtgtgaa aataaaccaggaaaaacatgttgccgaatgtgtcagtatgtaattgaatgcagagtagaggccgcaggatggtttagaacattcta tggaaagagattccagttccaggaacctggtacatacgtgttgggtcaaggaaccaagggcggcgactggaaggtgtccatcacc ctggagaacctggatggaaccaagggggctgtgctgaccaagacaagactggaagtggctggagacatcattgacatcgctcaa gctactgagaatcccatcactgtaaacggtggagctgacctatcatcgccaacccgtacaccatcggcgaggtcaccatcgctgtt gttgagatgccaggcttcaacatcaccgtcattgagttcttcaaactgatcgtgatcgacatcctcggaggaagatctgtaagaatcg ccccagacacagcaaacaaggaatgatctctggcctctgtggagatcttaaaatgatggaagatacagacttcacttcagatcca gaacaactcgctattcagcctaagatcaaccaggagtttgacggttgtccactctatggaaatcctgatgacgttgcatactgcaaa ggtcttctggagccgtacaaggacagctgccgcaacccccatcaacttctactactacaccatctcctgcgccttcgcccgctgtatgg gtggagacgagcgagcctcacacgtgctgcttgactacagggagacgtgcgctgctcccgaaactagaggaacctgcgttttgtct ggacatactttctacgatacatttgacaaagcaagataccaattccagggtccctgcaaggagattcttatggccgccgactgtttct ggaacacttgggatgtgaaggtttcacacaggaatgttgactcttacactgaagtagagaaagtacgaatcaggaaacaatcgac tgtagtagaactcattgttgatggaaaacagattctggttggaggagaagccgtgtccgtcccgtacagctctcagaacacttccatc tactggcaagatggtgacatactgactacagccatcctacctgaagctctggtggtcaagttcaacttcaagcaactgctcgtcgtac atattagagatccattcgatggtaagacttgcggtatttgcggtaactacaaccaggatttcagtgatgattcttttgatgctgaaggag cctgtgatctgaccccccaacccaccgggatgcaccgaagaacagaaacctgaagctgaacgactctgcaatagtctcttcgccgg tcaaagtgatcttgatcagaaatgtaacgtgtgccacaagcctgaccgtgtcgaacgatgcatgtacgagtattgcctgaggggac aacagggtttctgtgaccacgcatgggagttcaagaaagaatgctacataaagcatggagacaccctagaagtaccagatgaat gcaaa<u>aagcgc</u>tcctactccatggagcacttccgctggggcaagccggtgggcaagaaacggcgcccggtgaaggtgtaccccaa cgttgctgagaacgagtcggcggaggccttccctagagttcaagagggagctggaaggcgagcggccattaggcttggagcaggt cctggagtccgacgcggagaaggacgacgggccctaccgggtggagcacttccgctggagcaacccgcccaaggacaagcgttac ggtggcttcatgacctccgagaagagccagacgcccctggtgacgctcttcaagaacgccatcatcaagaacgcgcacaagaaggg ccagtga POMC (ACTH, MSH) Human (nucleic acid sequence):

(SEQ ID NO: 252)

Atgccgagatcgtgctgcagccgctcgggggccctgttgctggccttgctgcttcaggcctccatggaagtgcgtggctggtgcctgg agagcagccagtgtcaggacctcaccacggaaagcaacctgctggagtgcatccgggcctgcaagcccgacctctcggccgagact cccatgttcccgggaaatggcgacgagcagcctctgaccgagaaccccggaagtacgtcatgggccacttccgctgggaccgattc ggccgccgcaacagcagcagcagcggcagcagcggcgcagggcagaagcgcgaggacgtctcagcgggcgaagactgcggcc cgctgcctgagggcggccccgagcccgcagcgatggtgccaagccgggcccgcgcgagggc<u>aagcgc</u>Tactgcgccactgttc attgccaggactgtccttacgaacctgatccaccaaacacagttccaacttcctgtgaagctaaagaaggagaatgtattgatagca gctgtggcacctgcacgagagacatactatcagatggactgtgtgaaaataaaccaggaaaaacatgttgccgaatgtgtcagtat gtaattgaatgcagagtagaggccgcaggatggtttagaacattctatggaaagagattccagttccaggaacctggtacatacgt gttgggtcaaggaaccaagggcggcgactggaaggtgtccatcaccctggagaacctggatggaaccaagggggctgtgctga ccaagacaagactggagtggctggagacatcattgacatcgctcaagctactgagaatcccatcactgtaaacggtggagctga -continued ccctatcatcgccaacccgtacaccatcggcgaggtcaccatcgctgttgttgagatgccaggcttcaacatcaccgtcattgagttct tcaaactgatcgtgatcgacatcctcggaggaagatctgtaagaatcgcccagacacagcaaacaaaggaatgatctctggcct ctgtggagatcttaaaatgatggaagatacagacttcacttcagatccagaacaactcgctattcagcctaagatcaaccaggagtt tgacggttgtccactctatggaaatcctgatgacgttgcatactgcaaaggtcttctggagccgtacaaggacagctgccgcaaccc catcaacttctactactacaccatctcctgcgccttcgcccgctgtatgggtgggagacgagcgagcctcacacgtgctgcttgactac agggagacgtgcgctgctcccgaaactagaggaacctgcgttttgtctggacatactttctacgatacatttgacaaagcaagatac caattccagggtccctgcaaggagattcttatggccgccgactgtttctggaacacttgggatgtgaaggtttcacacaggaatgttg actcttacactgaagtagagaaagtacgaatcaggaaacaatcgactgtagtagaactcattgttgatggaaaacagattctggttg gaggagaagccgtgtccgtcccgtacagctctcagaacacttccatctactggcaagatggtgacatactgactacagccatccta cctgaagctctggtggtcaagttcaacttcaagcaactgctcgtcgtacatattagagatccattcgatggtaagacttgcggtatttgc ggtaactacaaccaggatttcagtgatgattcttttgatgctgaaggagcctgtgatctgaccccccaacccaccgggatgcaccgaa gaacagaaacctgaagctgaacgactctgcaatagtctcttcgccggtcaaagtgatcttgatcagaaatgtaacgtgtgccacaa gcctgaccgtgtcgaacgatgcatgtacgagtattgcctgaggggacaacagggtttctgtgaccacgcatgggagttcaagaaa gaatgctacataaagcatggagacaccctagaagtaccagatgaatgcaaa<u>aagcgct</u>cctactccatggagcacttccgctggg gcaagccggtgggcaagaagcggcgcccagtgaaggtgtaccctaacggcgccgaggacgagtcggccgaggccttcccccctgg agttcaagagggagctgactggccagcgactccgggaggagatggccccgacggccctgccgatgacggcgcaggggcccagg ccgacctggagcacagcctgctggtggcggccgagaagaaggacgagggcccctacaggatggagcacttccgctggggcagcc cgcccaaggacaagcgctacggcggtttcatgacctccgagaagagccagacgcccctggtgacgctgttcaaaaacgccatcatca agaacgcctacaagaagggcgagtga Oxytocin Mouse (nucleic acid sequence):

(SEQ ID NO: 253)

Atggcctgccccagtctcgcttgctgcctgcttggcttactggctctgacctcggcctgctacatccagaactgcccccctgggcggc<u>aa</u>
<u>gagg</u>Tactgcgccactgttcattgccaggactgtccttacgaacctgatccaccaaacacagttccaacttcctgtgaagctaaga aggagaatgtattgatagcagctgtggcacctgcacgagagacatactatcagatggactgtgtgaaaataaaccaggaaaaac atgttgccgaatgtgtcagtatgtaattgaatgcagagtagaggccgcaggatggtttagaacattctatggaaagagattccagttc caggaacctggtacatacgtgttgggtcaaggaaccaagggcggcgactggaaggtgtccatcaccctggagaacctggatgga accaaggggctgtgctgaccaagacaagactggaagtggctggagacatcattgacatcgctcaagctactgagaatcccatc actgtaaacggtggagctgaccctatcatcgccaaacccgtacaccatcggcgaggtcaccatcgctgttgttgagatgccaggcttc aacatcaccgtcattgagttcttcaaactgatcgtgatcgacatcctcggaggaagatctgtaagaatcgccccagacacagcaaa caaaggaatgatctctggcctctgtggagatcttaaaatgatggaagatacagacttcacttcagatccagaacaactcgctattca gcctaagatcaaccaggagtttgacggttgtccactctatggaaatcctgatgacgttgcatactgcaaaggtcttctggagccgtac aaggacagctgccgcaacccccatcaacttctactactacaccatctcctgcgccttcgcccgctgtatgggtgggagacgagcgagc ctcacacgtgctgcttgactacagggagacgtgcgctgctcccgaaactagaggaacctgcgttttgtctggacatactttctacgat acatttgacaaagcaagataccaattccagggtccctgcaaggagattcttatggccgccgactgtttctggaacacttgggatgtg aaggtttcacacaggaatgttgactcttacactgaagtagagaaagtacgaatcaggaaacaatcgactgtagtagaactcattgtt gatggaaaacagattctggttggaggagaagccgtgtccgtcccgtacagctctcagaacacttccatctactggcaagatggtga catactgactacagccatcctacctgaagctctggtggtcaagttcaacttcaagcaactgctcgtcgtacatattagagatccattcg atggtaagacttgcggtatttgcggtaactacaaccaggatttcagtgatgattcttttgatgctgaaggagcctgtgatctgacccc aacccaccgggatgcaccgaagaacagaaacctgaagctgaacgactctgcaatagtctcttcgccggtcaaagtgatcttgatc agaaatgtaacgtgtgccacaagcctgaccgtgtcgaacgatgcatgtacgagtattgcctgaggggacaacagggtttctgtgac cacgcatgggagttcaagaaagaatgctacataaagcatggagacaccctagaagtaccagatgaatgcaaa<u>aagcgc</u>gctgt gctggacctggatatgcgcaagtgtctcccctgcggccccggcggcaaaggacgctgcttcggaccaagcatctgctgcgcggacg agctgggctgcttcgtgggcaccgccgaggcgctgcgctgccaggaggagaactacctgccttcgccctgccagtctggccagaag ccctgcgggagcggaggccgctgcgccgccacaggcatctgctgcagcccggatggctgccgcacagaccccgcctgcgaccctg agtctgccttctcggagcgctga Oxytocin Human (nucleic acid sequence):

(SEQ ID NO: 254)

Atggccggccccagcctcgcttgctgtctgctcggcctcctggcgctgacctccgcctgctacatccagaactgcccctgggaggc<u>a</u>

<u>agagg</u>Tactgcgccactgttcattgccaggactgtccttacgaacctgatccacaccaaacacagttccaacttcctgtgaagctaaag aaggagaatgtattgatagcagctgtggcacctgcacgagagacatactatcagatggactgtgtgaaaataaaccaggaaaaa catgttgccgaatgtgtcagtatgtaattgaatgcagagtagaggccgcaggatggtttagaacattctatggaaagagattccagtt ccaggaacctggtacatacgtgttgggtcaaggaaccaagggcggcgactggaaggtgtccatcaccctggagaacctggatgg aaccaagggggctgtgctgaccaagacaagactggaagtggctggagacatcattgacatcgctcaagctactgagaatcccat cactgtaaacggtggagctgaccctatcatcgccaacccgtacaccatcggcgaggtcaccatcgctgttgttgagatgccaggctt caacatcaccgtcattgagttcttcaaactgatcgtgatcgacatcctcggaggaagatctgtaagaatcgcccagacacagcaa acaaaggaatgatctctggcctgtgtggagatcttaaaatgatggaagatacagacttcacttcagatccagaacaactcgctattc agcctaagatcaaccaggagtttgacggttgtccactctatggaaatcctgatgacgttgcatactgcaaaggtcttctggagccgta caaggacagctgccgcaacccatcaacttctactactacaccatctcctgcgccttcgcccgctgtatgggtggagacgagcgag cctcacacgtgctgcttgactacagggagacgtgcgctgctcccgaaactagaggaacctgcgttttgtctggacatactttctacga tacatttgacaaagcaagataccaattccagggtccctgcaaggagattcttatggccgccgactgtttctggaacacttgggatgtg aaggtttcacacaggaatgttgactcttacactgaagtagagaaagtacgaatcaggaaacaatcgactgtagtagaactcattgtt gatggaaaacagattctggttggaggagaagcctgtccgtcccgtacagctctcagaacacttccatctactggcaagatggtga catactgactacagccatcctacctgaagctctggtggtcaagttcaacttcaagcaactgctcgtcgtacatattagagatccattcg atggtaagacttgcggtatttgcggtaactacaaccaggatttcagtgatgattcttttgatgctgaaggagcctgtgatctgaccccc aacccaccgggatgcaccgaagaacagaaacctgaagctgaacgactctgcaatagtctcttcgccggtcaaagtgatcttgatc agaaatgtaacgtgtgccacaagcctgaccgtgtcgaacgatgcatgtacgagtattgcctgagggggacaacaggggtttctgtgac cacgcatgggagttcaagaaagaatgctacataaagcatggagacaccctagaagtaccagatgaatgcaaa<u>aagcgc</u>gccgc gccggacctcgacgtgcgcaagtgcctcccctgcggccccggggcaaaggccgctgcttcgggcccaatatctgctgcgcggaag agctgggctgcttcgtgggcaccgccgaagcgctgcgctgccaggaggagaactacctgccgtcgccctgccagtccggccagaag gcgtgcgggagcggggccgctgcgcggtcttgggcctctgctgcagcccggacggctgccacgccgaccctgcctgcgacgcgg aagccaccttctcccagcgctga Vasopressin-Neurophysin-2 Mouse (nucleic acid sequence):

(SEQ ID NO: 255)

atgctcgccaggatgctcaacactacgctctccgcttgtttcctgagcctgctggccttctcctccgcctgctacttccagaactgcccaag aggcggc<u>aagagg</u>Tactgcgccactgttcattgccaggactgtccttacgaacctgatccacaccaaacacagttccaacttcctgtga agctaaagaaggagaatgtattgatagcagctgtggcacctgcacgagagacatactatcagatggactgtgtgaaaataaacc aggaaaaacatgttgccgaatgtgtcagtatgtaattgaatgcagagtagaggccgcaggatggtttagaacattctatggaaaga gattccagttccaggaacctggtacatacgtgttgggtcaaggaaccaagggcggcgactggaaggtgtccatcaccctggagaa cctggatggaaccaagggggctgtgctgaccaagacaagactggaagtggctggagacatcattgacatcgctcaagctactga gaatcccatcactgtaaacggtggagctgaccctatcatcgccaacccgtacaccatcggcgaggtcaccatcgctgttgttgagat gccaggcttcaacatcaccgtcattgagttcttcaaactgatcgtgatcgacatcctcggaggaagatctgtaagaatcgcccaga cacagcaaacaaaggaatgatctctggcctctgtggagatcttaaaatgatggaagatacagacttcacttcagatccagaacaa ctcgctattcagcctaagatcaaccaggagtttgacggttgtccactctatggaaatcctgatgacgttgcatactgcaaaggtcttct ggagccgtacaaggacagctgccgcaacccatcaacttctactactacaccatctcctgcgccttcgcccgctgtatgggtggag -continued acgagcgagcctcacacgtgctgcttgactacagggagacgtgcgctgctcccgaaactagaggaacctgcgttttgtctggacat actttctacgatacatttgacaaagcaagataccaattccagggtccctgcaaggagattcttatggccgccgactgtttctggaaca cttgggatgtgaaggtttcacacaggaatgttgactcttacactgaagtagagaaagtacgaatcaggaaacaatcgactgtagta gaactcattgttgatgaaaacagattctggttggaggagaagccgtgtccgtcccgtacagctctcagaacacttccatctactggc aagatggtgacatactgactacagccatcctacctgaagctctggtggtcaagttcaacttcaagcaactgctcgtcgtacatattag agatccattcgatggtaagacttgcggtatttgcggtaactacaaccaggatttcagtgatgattcttttgatgctgaaggagcctgtg atctgaccccaacccaccgggatgcaccgaagaacagaaacctgaagctgaacgactctgcaatagtctcttcgccggtcaaa gtgatcttgatcagaaatgtaacgtgtgccacaagcctgaccgtgtcgaacgatgcatgtacgagtattgcctgagggacaacag ggtttctgtgaccacgcatgggagttcaagaaagaatgctacataaagcatggagacaccctagaagtaccagatgaatgcaaa <u>aagcgcg</u>ccatctctgacatggagctgagacagtgtctcccctgcggcccgggcggcaaaggacgctgcttcggaccaagcatctgc tgcgcggacgagctgggctgcttcgtgggcaccgccgaggcgctgcgctgccaggaggagaactacctgcctcgccctgccagtc cggccagaagccctgcgggagcggggccgctgcgccgccgtgggcatctgctgcagcgacgagagctgcgtggccgagcccg agtgccacgacggttttttccgcctcacccgcgctcgggagccaagcaacgccacacagctggacgccctgctcgggcgctgctgc taaggctggtacagctggctgggacacgggagtccgtggattctgccaagccccgggtctactga Vasopressin-Neurophysin-2 Human (nucleic acid sequence):

(SEQ ID NO: 256)

Atgcctgacaccatgctgcccgcctgcttcctcggcctactggccttctcctccgcgtgctacttccagaactgcccgaggggcggc<u>aa
gagg</u>Tactgcgccactgttcattgccaggactgtccttacgaacctgatccaccaaacacagttccaacttcctgtgaagctaaaga aggagaatgtattgatagcagctgtggcacctgcacgagagacatactatcagatggactgtgtgaaaataaaccaggaaaaac atgttgccgaatgtgtcagtatgtaattgaatgcagagtagaggccgcaggatggtttagaacattctatggaaagagattccagttc caggaacctggtacatacgtgttgggtcaaggaaccaagggcggcgactggaaggtgtccatcaccctggagaacctggatgga accaaggggctgtgctgaccaagacaagactggaagtggctggagacatcattgacatcgctcaagctactgagaatcccatc actgtaaacggtggagctgaccctatcatcgccaacccgtacaccatcggcgaggtcaccatcgctgttgttgagatgccaggcttc aacataccgtcattgagttcttcaaactgatcgtgatcgacatcctcggaggaagatctgtaagaatcgccccagacacagcaaa caaaggaatgatctctggcctctgtggagatcttaaaatgatggaagatacagacttcacttcagatccagaacaactcgctattca gcctaagatcaaccaggagtttgacggttgtccactctatggaaatcctgatgacgttgcatactgcaaaggtcttctggagccgtac aaggacagctgccgcaaccccatcaacttctactactacaccatctcctgcgccttcgcccgctgtatgggtggagacgagcgagc ctcacacgtgctgcttgactacagggagacgtgcgctgctcccgaaactagaggaacctgcgttttgtctggacatactttctacgat acatttgacaaagcaagataccaattccagggtccctgcaaggagattcttatggccgccgactgtttctggaacacttgggatgtg aaggtttcacacaggaatgttgactcttacactgaagtagagaaagtacgaatcaggaaacaatcgactgtagtagaactcattgtt gatgaaaacagattctggttggaggagaagccgtgtccgtcccgttacagctctcagaacacttccatctactggcaagatggtga catactgactacagccatcctacctgaagctctggtggtcaagttcaacttcaagcaactgctcgtcgtacatattagagatccattcg atggtaagacttgcggtatttgcggtaactacaaccaggatttcagtgatgattcttttgatgctgaaggagcctgtgatctgaccccc aacccaccgggatgcaccgaagaacagaaacctgaagctgaacgactctgcaatagtctcttcgccggtcaaagtgatcttgatc agaaatgtaacgtgtgccacaagcctgaccgtgtcgaacgatgcatgtacgagtattgcctgagggacaacagggtttctgtgac cacgcatgggagttcaagaaagaatgctacataaagcatggagacaccctagaagtaccagatgaatgcaaa<u>aagcgcg</u>ccat gtccgacctggagctgagacagtgcctcccctgcggccccgggcaaaggccgctgcttcgggcccagcatctgctgcgcggacg agctgggctgcttcgtgggcacggctgaggcgctgcgctgccaggaggagaactacctgccgtcgccctgccagtccggccagaag gcgtgcgggagcggggccgctgcgccgccttcggcgtttgctgcaacgacgagagctgcgtgaccgagcccgagtgccgcgag ggctttcaccgccgcgcccgccagcgaccggagcaacgccacgcagctggacgggccggccggggccttgctgctgcggctg gtgcagctggccggggcgcccgagcccttcgagcccgcccagcccgacgcctactga -continued Gonadotropin-releasing hormone (GnRH) Mouse (nucleic acid sequence):

(SEQ ID NO: 257)

Atgatcctcaaactgatggccggcattctactgctgactgtgtgtttggaaggctgctccagccagcactggtcctatgggttgcgccc tggggga*aagaga*Tactgcgccactgttcattgccaggactgtccttacgaacctgatccaccaaacacagttccaacttcctgtga agctaaagaaggagaatgtattgatagcagctgtggcacctgcacgagagacatactatcagatggactgtgtgaaaataaacc aggaaaaacatgttgccgaatgtgtcagtatgtaattgaatgcagagtagaggccgcaggatggtttagaacattctatggaaaga gattccagttccaggaacctggtacatacgtgttgggtcaaggaaccaagggcggcgactggaaggtgtccatcaccctggagaa cctggatggaaccaaggggctgtgctgaccaagacaagactggaagtggctggagacatcattgacatcgctcaagctactga gaatcccatcactgtaaacggtggagctgaccctatcatcgccaacccgtacaccatcggcgaggtcaccatcgctgttgttgagat gccaggcttcaacatcaccgtcattgagttcttcaaactgatcgtgatcgacatcctcggaggaagatctgtaagaatcgccccaga cacagcaaacaaaggaatgatctctggcctctgtggagatcttaaaatgatggaagatacagacttcacttcagatccagaacaa ctcgctattcagcctaagatcaaccaggagtttgacggttgtccactctatggaaatcctgatgacgttgcatactgcaaaggtcttct ggagccgtacaaggacagctgccgcaacccatcaacttctactactacaccatctcctgcgccttcgcccgctgtatgggtggag acgagcgagcctcacacgtgctgcttgactacagggagacgtgcgctgctcccgaaactagaggaacctgcgttttgtctggacat actttctacgatacatttgacaaagcaagataccaattccagggtccctgcaaggagattcttatggccgccgactgtttctggaaca cttgggatgtgaaggtttcacacaggaatgttgactcttacactgaagtagagaaagtacgaatcaggaaacaatcgactgtagta gaactcattgttgatgaaaacagattctggttggaggagaagccgtgtccgtcccgtacagctctcagaacacttccatctactggc aagatggtgacatactgactacagccatcctacctgaagctctggtggtcaagttcaacttcaagcaactgctcgtcgtacatattag agatccattcgatggtaagacttgcggtatttgcggtaactacaaccaggatttcagtgatgattcttttgatgctgaaggagcctgtg atctgaccccaacccaccgggatgcaccgaagaacagaaacctgaagctgaacgactctgcaatagtctcttcgccggtcaaa gtgatcttgatcagaaatgtaacgtgtgccacaagcctgaccgtgtcgaacgatgcatgtacgagtattgcctgaggggacaacag ggtttctgtgaccacgcatgggagttcaagaaagaatgctacataaagcatggagacaccctagaagtaccagatgaatgcaaa

*aagcgc*aacactgaacacttggttgagtctttccaagagatgggcaaggaggtggatcaaatggcagaaccccagcacttcgaatgta ctgtccactggccccgttcacccctcagggatctgcgaggagctctggaaagtctgattgaagaggaagccaggcagaagaagatgta g Gonadotropin-releasing hormone (GnRH) Human (nucleic acid sequence):

(SEQ ID NO: 258)

Atgaagccaattcaaaaactcctagctggccttattctactgacttggtgcgtggaaggctgctccagccagcactggtcctatggac tgcgccctggagga*aagaga*Tactgcgccactgttcattgccaggactgtccttacgaacctgatccaccaaacacagttccaact tcctgtgaagctaaagaaggagaatgtattgatagcagctgtggcacctgcacgagagacatactatcagatggactgtgtgaaa ataaaccaggaaaaacatgttgccgaatgtgtcagtatgtaattgaatgcagagtagaggccgcaggatggtttagaacattctat ggaaagagattccagttccaggaacctggtacatacgtgttgggtcaaggaaccaagggcggcgactggaaggtgtccatcacc ctggagaacctggatggaaccaaggggctgtgctgaccaagacaagactggaagtggctggagacatcattgacatcgctcaa gctactgagaatcccatcactgtaaacggtggagctgaccctatcatcgccaacccgtacaccatcggcgaggtcaccatcgctgtt gttgagatgccaggcttcaacatcaccgtcattgagttcttcaaactgatcgtgatcgacatcctcggaggaagatctgtaagaatcg ccccagacacagcaaacaaaggaatgatctctggcctctgtggagatcttaaaatgatggaagatacagacttcacttcagatcca gaacaactcgctattcagcctaagatcaaccaggagtttgacggttgtccactctatggaaatcctgatgacgttgcatactgcaaa ggtcttctggagccgtacaaggacagctgccgcaacccatcaacttctactactacaccatctcctgcgccttcgcccgctgtatgg gtggagacgagcgagcctcacacgtgctgcttgactacagggagacgtgcgctgctcccgaaactagaggaacctgcgttttgtct ggacatactttctacgatacatttgacaaagcaagataccaattccagggtccctgcaaggagattcttatggccgccgactgtttct ggaacacttgggatgtgaaggtttcacacaggaatgttgactcttacactgaagtagagaaagtacgaatcaggaaacaatcgac tgtagtagaactcattgttgatggaaaacagattctggttggaggagaagccgtgtccgtcccgtacagctctcagaacacttccatc -continued tactggcaagatggtgacatactgactacagccatcctacctgaagctctggtggtcaagttcaacttcaagcaactgctcgtcgtac atattagagatccattcgatggtaagacttgcggtatttgcggtaactacaaccaggatttcagtgatgattcttttgatgctgaaggag cctgtgatctgaccccaacccaccgggatgcaccgaagaacagaaacctgaagctgaacgactctgcaatagtctcttcgccgg tcaaagtgatcttgatcagaaatgtaacgtgtgccacaagcctgaccgtgtcgaacgatgcatgtacgagtattgcctgaggggac aacagggtttctgtgaccacgcatgggagttcaagaaagaatgctacataaagcatggagacaccctagaagtaccagatgaat gcaaa<u>aagcgc</u>gatgccgaaaatttgattgattcttttccaagagatagtcaaagaggttggtcaactggcagaaacccaacgcttcgaa tgcaccacgccaccagccacgttctcccctccgagacctgaaaggagctctggaaagtctgattgagaggaaactgggcagaagaag atttaa Thyroid-stimulating hormone, beta subunit (TSHB) Mouse (nucleic acid sequence):
(SEQ ID NO: 259)
Atgagtgctgccgtcctcctctccgtgcttttttgctcttgcttgtgggcaagcagcatccttttgtattcccactgagtatacaatgtacgtg gataggagagagtgtgcctactgcctgaccatcaacaccaccatctgtgctgggtattgtatgacacgggatatcaatggcaaact gtttcttcccaaatatgcactctctcaggatgtctgtacatacagagacttcatctacagaacggtggaaataccaggatgcccgcac catgttactcctttatttctccttccctgtcgccataagctgcaagtgtggcaagtgtaatactgacaacagtgactgcatacacgaggct gtcagaaccaactactgcaccaagccgcagtcttt<u>ctatctg</u>Tactgcgccactgttcattgccaggactgtccttacgaacctgatc caccaaacacagttccaacttcctgtgaagctaaagaaggagaatgtattgatagcagctgtggcacctgcacgagagacatact atcagatggactgtgtgaaaataaaccaggaaaaacatgttgccgaatgtgtcagtatgtaattgaatgcagagtagaggccgca ggatggtttagaacattctatggaaagagattccagttccaggaacctggtacatacgtgtttgggtcaaggaaccaagggcggcg actggaaggtgtccatcaccctggagaacctggatggaaccaaggggctgtgctgaccaagacaagactggaagtggctgga gacatcattgacatcgctaagctactgagaatcccatcactgtaaacggtggagctgaccctatcatcgccaacccgtacaccatc ggcgaggtcaccatcgctgttgttgagatgccaggcttcaacatcaccgtcattgagttcttcaaactgatcgtgatcgacatcctcgg aggaagatctgtaagaatcgcccagacacagcaaacaaaggaatgatctctggcctctgtggagatcttaaaatgatggaagat acagacttcacttcagatccagaacaactcgctattcagcctaagatcaaccaggagtttgacggttgtccactctatggaaatcctg atgacgttgcatactgcaaaggtcttctggagccgtacaaggacagctgccgcaacccatcaacttctactactacaccatctcctg cgccttcgcccgctgtatgggtggagacgagcgagcctcacacgtgctgcttgactacagggagacgtgcgctgctcccgaaacta gaggaacctgcgttttgtctggacatactttctacgatacatttgacaaagcaagataccaattccagggtccctgcaaggagattctt atggccgccgactgtttctggaacacttgggatgtgaaggtttcacacaggaatgttgactcttacactgaagtagagaaagtacga atcaggaaacaatcgactgtagtagaactcattgttgatggaaaacagattctggttggaggagaagccgtgtccgtcccgtacag ctctcagaacacttccatctactggcaagatggtgacatactgactacagccatcctacctgaagctctggtggtcaagttcaacttca agcaactgctcgtcgtacatattagagatccattcgatggtaagacttgcggtatttgcggtaactacaaccaggatttcagtgatgat tcttttgatgctgaaggagcctgtgatctgaccccaacccaccgggatgcaccgaagaacagaaacctgaagctgaacgactct gcaatagtctcttcgccggtcaaagtgatcttgatcagaaatgtaacgtgtgccacaagcctgaccgtgtcgaacgatgcatgtacg agtattgcctgaggggacaacagggtttctgtgaccacgcatgggagttcaagaaagaatgctacataaagcatggagacaccct agaagtaccagatgaatgcaaa<u>tatctg</u>gggggattttctgtttaa Thyroid-stimulating hormone, beta subunit (TSHB) Human (nucleic acid sequence):
(SEQ ID NO: 260)
Atgactgctctcttctgatgtccatgctttttggccttacatgtgggcaagcgatgtcttttgtattccaactgagtatacaatgcacatcga aaggagagagtgtgcttattgcctaaccatcaacaccaccatctgtgctggatattgtatgacacggggatatcaatggcaaactgtttcttc ccaaatatgctctgtcccaggatgtttgcacatatagagacttcatctacaggactgtagaaataccaggatgcccactccatgttgctccc tattttcctatcctgttgctttaagctgtaagtgtggcaagtgcaatactgactatagtgactgcatacatgaagccatcaagacaaactact gtaccaaacctcagaagtct<u>tatctg</u>Tactgcgccactgttcattgccaggactgtccttacgaacctgatccaccaaacacagttcca acttcctgtgaagctaaagaaggagaatgtattgatagcagctgtggcacctgcacgagagacatactatcagatggactgtgtga aaataaaccaggaaaaacatgttgccgaatgtgtcagtatgtaattgaatgcagagtagaggccgcaggatggtttagaacattct

```
atggaaagagattccagttccaggaacctggtacatacgtgttgggtcaaggaaccaagggcggcgactggaaggtgtccatca
ccctggagaacctggatggaaccaaggggggctgtgctgaccaagacaagactggaagtggctggagacatcattgacatcgctc
aagctactgagaatcccatcactgtaaacggtggagctgaccctatcatcgccaacccgtacaccatcggcgaggtcaccatcgct
gttgttgagatgccaggcttcaacatcaccgtcattgagttcttcaaactgatcgtgatcgacatcctcggaggaagatctgtaagaat
cgccccagacacagcaaacaaaggaatgatctctggcctctgtggagatcttaaaatgatggaagatacagacttcacttcagatc
cagaacaactcgctattcagcctaagatcaaccaggagtttgacggttgtccactctatggaaatcctgatgacgttgcatactgcaa
aggtcttctggagccgtacaaggacagctgccgcaacccccatcaacttctactactacaccatctcctgcgccttcgcccgctgtatg
ggtggagacgagcgagcctcacacgtgctgcttgactacaggagacgtgcgctgctcccgaaactagaggaacctgcgttttgtc
tggacatactttctacgatacatttgacaaagcaagataccaattccagggtccctgcaaggagattcttatggccgccgactgtttct
ggaacacttgggatgtgaaggtttcacacaggaatgttgactcttacactgaagtagagaaagtacgaatcaggaaacaatcgac
tgtagtagaactcattgttgatggaaaacagattctggttggaggagaagccgtgtccgtcccgtacagctctcagaacacttccatc
tactggcaagatggtgacatactgactacagccatcctacctgaagctctggtggtcaagttcaacttcaagcaactgctcgtcgtac
atattagagatccattcgatggtaagacttgcggtatttgcggtaactacaaccaggatttcagtgatgattcttttgatgctgaaggag
cctgtgatctgaccccaacccaccgggatgcaccgaagaacagaaacctgaagctgaacgactctgcaatagtctcttcgccgg
tcaaagtgatcttgatcagaaatgtaacgtgtgccacaagcctgaccgtgtcgaacgatgcatgtacgagtattgcctgaggggac
aacagggtttctgtgaccacgcatgggagttcaagaaagaatgctacataaagcatggagacaccctagaagtaccagatgaat
gcaaatatctggtaggattttctgtctaa
```

Cortisol-releasing factor (CRF) Mouse (nucleic acid sequence):

(SEQ ID NO: 261)

```
Atgcggctgcgctgctggtgtccgcgggcatgctgctggtggctctgtcgtcctgcctgccttgcagggccctgctcagcaggggat
ccgtcccccgagcgccgcgggccccgcagcccttgaatttcttgcagccggagcagcccagcaacctcagccggttctgatccgca
tgggtgaagaatacttcctccgcctggggaatctcaacagaagtcccgctgctcggctgtccccaactccacgcccctcaccgcggt
cgcggcagccgcccctcgcacgaccaggctgcggctaacttttttccgcgtgttgctgcagcagctgcagatgcctcagcgctcgctcg
acagccgcgcggagccggccgaacgcggcgccgaggatgccctcggtggccaccaggggggcgctggagagggagaggcggT
actgcgccactgttcattgccaggactgtccttacgaacctgatccaccaaacacagttccaacttcctgtgaagctaaagaaggag
aatgtattgatagcagctgtggcacctgcacgagagacatactatcagatggactgtgtgaaaataaaccaggaaaaacatgttg
ccgaatgtgtcagtatgtaattgaatgcagagtagaggccgcaggatggtttagaacattctatggaaagagattccagttccagga
acctggtacatacgtgttgggtcaaggaaccaagggcggcgactggaagtgtccatcaccctggagaacctggatggaaccaa
gggggctgtgctgaccaagacaagactggaagtggctggagacatcattgacatcgctcaagctactgagaatcccatcactgta
aacggtggagctgaccctatcatcgccaacccgtacaccatcggcgaggtcaccatcgctgttgttgagatgccaggcttcaacatc
accgtcattgagttcttcaaactgatcgtgatcgacatcctcggaggaagatctgtaagaatcgccccagacacagcaaacaaag
gaatgatctctggcctctgtggagatcttaaaatgatggaagatacagacttcacttcagatccagaacaactcgctattcagcctaa
gatcaaccaggagtttgacggttgtccactctatggaaatcctgatgacgttgcatactgcaaaggtcttctggagccgtacaagga
cagctgccgcaacccatcaacttctactactacaccatctcctgcgccttcgcccgctgtatgggtggagacgagcgagcctcaca
cgtgctgcttgactacaggagacgtgcgctgctcccgaaactagaggaacctgcgttttgtctggacatactttctacgatacatttg
acaaagcaagataccaattccagggtccctgcaaggagattcttatggccgccgactgtttctggaacacttgggatgtgaaggttt
cacacaggaatgttgactcttacactgaagtagagaaagtacgaatcaggaaacaatcgactgtagtagaactcattgttgatgga
aaacagattctggttggaggagaagccgtgtccgtcccgtacagctctcagaacacttccatctactggcaagatggtgacatactg
actacagccatcctacctgaagctctggtggtcaagttcaacttcaagcaactgctcgtcgtacatattagagatccattcgatggtaa
gacttgcggtatttgcggtaactacaaccaggatttcagtgatgattcttttgatgctgaaggagcctgtgatctgaccccaacccac
cgggatgcaccgaagaacagaaacctgaagctgaacgactctgcaatagtctcttcgccggtcaaagtgatcttgatcagaaatgt
```

-continued aacgtgtgccacaagcctgaccgtgtcgaacgatgcatgtacgagtattgcctgaggggacaacagggtttctgtgaccacgcatg ggagttcaagaaagaatgctacataaagcatggagacaccctagaagtaccagatgaatgcaaa*aggcgg*tcggaggagccg cccatctctctggatctcaccttccaccttctgcgggaagtcttggaaatggcccgggcagagcagttagctcagcaagctcacagcaa caggaaactgatggagattatcgggaaatga Cortisol-releasing factor (CRF) Human (nucleic acid sequence):

(SEQ ID NO: 262)

Atgcggctgccgctgcttgtgtccgcgggagtcctgctggtggctctcctgccctgcccgccatgcagggcgctcctgagccgcggg ccggtcccgggagctcggcaggcgccgcagcaccctcagcccttggatttcttccagccgccgccgcagtccgagcagcccagca gccgcaggctcggccggtcctgctccgcatgggagaggagtacttcctccgcctggggaacctcaacaagagcccggccgctcccc tttcgcccgcctcctcgctcctcgccggaggcagcggcagccgcccttcgccggaacaggcgaccgccaactttttccgcgtgttgctg cagcagctgctgctgcctcggcgctcgctcgacagccccgcggctctcgcggagcgcggcgctaggaatgccctcggcggccacc aggaggcaccggagagagaa*aggcgg*Tactgcgccactgttcattgccaggactgtccttacgaacctgatccaccaaacacagt tccaacttcctgtgaagctaaagaaggagaatgtattgatagcagctgtggcacctgcacgagagacatactatcagatggactgt gtgaaaataaaccaggaaaaacatgttgccgaatgtgtcagtatgtaattgaatgcagagtagaggccgcaggatggtttagaac attctatggaaagagattccagttccaggaacctggtacatacgtgttgggtcaaggaaccaagggcggcgactggaaggtgtcc atcaccctggagaacctggatggaaccaagggggctgtgctgaccaagacaagactggaagtggctggagacatcattgacatc gctcaagctactgagaatcccatcactgtaaacggtggagctgaccctatcatcgccaacccgtacaccatcggcgaggtcaccat cgctgttgttgagatgccaggcttcaacatcaccgtcattgagttcttcaaactgatcgtgatcgacatcctcggaggaagatctgtaa gaatcgccccagacacagcaaacaaaggaatgatctctggcctctgtggagatcttaaaatgatggaagatacagacttcacttca gatccagaacaactcgctattcagcctaagatcaaccaggagtttgacggttgtccactctatggaaatcctgatgacgttgcatact gcaaaggtcttctggagccgtacaaggacagctgccgcaaccccatcaacttctactactacaccatctcctgcgccttcgcccgct gtatgggtggagacgagcgagcctcacacgtgctgcttgactacaggagacgtgcgctgctcccgaaactagaggaacctgcg ttttgtctggacatactttctacgatacatttgacaaagcaagataccaattccagggtccctgcaaggagattcttatggccgccgac tgtttctggaacacttgggatgtgaaggtttcacacaggaatgttgactcttacactgaagtagagaaagtacgaatcaggaaacaa tcgactgtagtagaactcattgttgatggaaaacagattctggttggaggagaagccgtgtccgtcccgtacagctctcagaacactt ccatctactggcaagatggtgacatactgactacagccatcctacctgaagctctggtggtcaagttcaacttcaagcaactgctcgt cgtacatattagagatccattcgatggtaagacttgcggtatttgcggtaactacaaccaggatttcagtgatgattcttttgatgctga vaggagcctgtgatctgaccccaacccaccgggatgcaccgaagaacagaaacctgaagctgaacgactctgcaatagtctcttc gccggtcaaagtgatcttgatcagaaatgtaacgtgtgccacaagcctgaccgtgtcgaacgatgcatgtacgagtattgcctgag gggacaacagggtttctgtgaccacgcatgggagttcaagaaagaatgctacataaagcatggagacaccctagaagtaccag atgaatgcaaa*aggcgg*tccgaggagcctcccatctccctggatctcaccttccacctcctccgggaagtcttggaaatggccagggc cgagcagttagcacagcaagctccagcaacaggaaactcatggagattattgggaataa Atrial natriuretic peptide (ANP) Mouse (nucleic acid sequence)

(SEQ ID NO: 263)

Atgggctccttctccatcaccctgggcttcttcctcgtcttggcttttggcttccaggccatattggagcaaatcctgtgtacagtgcggtg tccaacacagatctgatggatttcaagaacctgctagaccacctggaggagaagatgccggtagaagatgaggtcatgccccgcag gccctgagtgagcagactgaggaagcaggggccgcacttagctccctccccgaggtgcctccctggactggggaggtcaacccacc tctgagagacgcagtgctctagggcgcagcccctgggaccctccgatagatctgccctcttgaaaagcaaactgagggctctgctc gctggccctcggagcTactgcgccactgttcattgccaggactgtccttacgaacctgatccaccaaacacagttccaacttcctgtg aagctaaagaaggagaatgtattgatagcagctgtggcacctgcacgagagacatactatcagatggactgtgtgaaaataaac caggaaaaacatgttgccgaatgtgtcagtatgtaattgaatgcagagtagaggccgcaggatggtttagaacattctatggaaag agattccagttccaggaacctggtacatacgtgttgggtcaaggaaccaagggcggcgactggaaggtgtccatcaccctggaga acctggatggaaccaagggggctgtgctgaccaagacaagactggaagtggctggagacatcattgacatcgctcaagctactg -continued agaatcccatcactgtaaacggtggagctgaccctatcatcgccaacccgtacaccatcggcgaggtcaccatcgctgttgttgag atgccaggcttcaacatcaccgtcattgagttcttcaaactgatcgtgatcgacatcctcggaggaagatctgtaagaatcgcccca gacacagcaaacaaaggaatgatctctggcctctgtggagatcttaaaatgatggaagatacagacttcacttcagatccagaac aactcgctattcagcctaagatcaaccaggagtttgacggttgtccactctatggaaatcctgatgacgttgcatactgcaaaggtctt ctggagccgtacaaggacagctgccgcaaccccatcaacttctactactacaccatctcctgcgccttcgcccgctgtatgggtgga gacgagcgagcctcacacgtgctgcttgactacagggagacgtgcgctgctcccgaaactagaggaacctgcgttttgtctggaca tactttctacgatacatttgacaaagcaagataccaattccagggtcctgcaaggagattcttatggccgccgactgtttctggaac acttgggatgtgaaggtttcacacaggaatgttgactcttacactgaagtagagaaagtacgaatcaggaaacaatcgactgtagt agaactcattgttgatggaaaacagattctggttggaggagaagccgtgtccgtcccgtacagctctcagaacacttccatctactg gcaagatggtgacatactgactacagccatcctacctgaagctctggtggtcaagttcaacttcaagcaactgctcgtcgtacatatt agagatccattcgatggtaagacttgcggtatttgcggtaactacaaccaggatttcagtgatgattcttttgatgctgaaggagcctg tgatctgaccccccaacccaccgggatgcaccgaagaacagaaacctgaagctgaacgactctgcaatagtctcttcgccggtcaa agtgatcttgatcagaaatgtaacgtgtgccaacaagcctgaccgtgtcgaacgatgcatgtacgagtattgcctgaggggacaaca gggtttctgtaccacgcatgggagttcaagaaagaatgctacataaagcatggagacaccctagaagtaccagatgaatgcaa ac<u>cggagc</u>ctacgaagatccagctgcttcgggggtaggattgacaggattggagcccagagtggactaggctgcaacagcttccggta ccgaagataa Atrial natriuretic peptide (ANP) Human (nucleic acid sequence):

(SEQ ID NO: 264)

atgagctccttctccaccaccaccgtgagcttcctcctttttactggcattccagctcctaggtcagaccagagctaatcccatgtacaatgc cgtgtccaacgcagacctgatggatttcaagaatttgctggaccatttggaagaaaagatgcctttagaagatgaggtcgtgcccccaca agtgctcagtgagccgaatgaagaagcggggggctgctctcagcccctccctgaggtgcctccctggaccggggaagtcagcccag cccagagagatggaggtgcccctcgggcggggcccctgggactcctctgatcgatctgccctcctaaaaagcaagctgagggcgctgc tcactgcccct<u>cggagc</u>Tatgcgccactgttcattgccaggactgtccttacgaacctgatccaccaaacacagttccaacttcctgt gaagctaaagaaggagaatgtattgatagcagctgtggcacctgcacagagagacatactatcagatggactgtgaaaataaa ccaggaaaaacatgttgccgaatgtgtcagtatgtaattgaatgcagagtagaggccgcaggatggtttagaacattctatggaaa gagattccagttccaggaacctggtacatacgtgttgggtcaaggaaccaagggcggcgactggaaggtgtccatcaccctggag aacctggatggaaccaaggggctgtgctgaccaagacaagactggaagtggctggagacatcattgacatcgctcaagctact gagaatcccatcactgtaaacggtggagctgaccctatcatcgccaacccgtacaccatcggcgaggtcaccatcgctgttgttga gatgccaggcttcaacatcaccgtcattgagttcttcaaactgatcgtgatcgacatcctcggaggaagatctgtaagaatcgcccc agacacagcaaacaaaggaatgatctctggcctctgtggagatcttaaaatgatggaagatacagacttcacttcagatccagaa caactcgctattcagcctaagatcaaccaggagtttgacggttgtccactctatggaaatcctgatgacgttgcatactgcaaaggtc ttctggagccgtacaaggacagctgccgcaaccccatcaacttctactactacaccatctcctgcgccttcgcccgctgtatgggtgg agacgagcgagcctcacacgtgctgcttgactacagggagacgtgcgctgctcccgaaactagaggaacctgcgttttgtctggac atactttctacgatacatttgacaaagcaagataccaattccagggtcctgcaaggagattcttatggccgccgactgtttctggaa cacttgggatgtgaaggtttcacacaggaatgttgactcttacactgaagtagagaaagtacgaatcaggaaacaatcgactgtag tagaactcattgttgatggaaaacagattctggttggaggagaagccgtgtccgtcccgtacagctctcagaacacttccatctactg gcaagatggtgacatactgactacagccatcctacctgaagctctggtggtcaagttcaacttcaagcaactgctcgtcgtacatatt agagatccattcgatggtaagacttgcggtatttgcggtaactacaaccaggatttcagtgatgattcttttgatgctgaaggagcctg tgatctgaccccccaacccaccgggatgcaccgaagaacagaaacctgaagctgaacgactctgcaatagtctcttcgccggtcaa agtgatcttgatcagaaatgtaacgtgtgccaacaagcctgaccgtgtcgaacgatgcatgtacgagtattgcctgaggggacaaca gggtttctgtgaccacgcatgggagttcaagaaagaatgctacataaagcatggagacaccctagaagtaccagatgaatgcaa -continued acggagcctgcggagatccagctgcttcgggggcaggatggacaggattggagcccagagcggactgggctgtaacagcttccggt actga Brain natriuretic peptide (BNP) Mouse (nucleic acid sequence):

(SEQ ID NO: 265)

atggatctcctgaaggtgctgtcccagatgattctgtttctgcttttcctttatctgtcaccgctggaggtcactcctatcctctgggaagtcc tagccagtctccagagcaattcaagatgcagaagctgctggagctgataagagaaaagtcggaggaaatggcccagagacagctctt gaaggaccaaggcctcacaaaagaacacccaaaaagagtccttcggtctTactgcgccactgttcattgccaggactgtccttacga acctgatccaccaaacacagttccaacttcctgtgaagctaaagaaggagaatgtattgatagcagctgtggcacctgcacgaga gacatactatcagatggactgtgtgaaaataaaccaggaaaaacatgttgccgaatgtgtcagtatgtaattgaatgcagagtaga ggccgcaggatggtttagaacattctatggaaagagattccagttccaggaactggtacatacgtgtgggtcaaggaaccaagg gcggcgactggaaggtgtccatcaccctggagaacctggatggaaccaaggggggctgtgctgaccaagacaagactggaagtg gctggagacatcattgacatcgctcaagctactgagaatcccatcactgtaaacggtggagctgaccctatcatcgccaacccgta caccatcggcgaggtcaccatcgctgttgttgagatgccaggcttcaacatcaccgtcattgagttcttcaaactgatcgtgatcgac atcctcggaggaagatctgtaagaatcgcccagacacagcaaacaaaggaatgatctctggcctctgtggagatcttaaaatga tggaagatacagacttcacttcagatccagaacaactcgctattcagcctaagatcaaccaggagtttgacggttgtccactctatgg aaatcctgatgacgttgcatactgcaaaggtcttctggagccgtacaaggacagctgccgcaacccatcaacttctactactacac catctcctgcgccttcgcccgctgtatgggtggagacgagcgagcctcacacgtgctgcttgactacagggagacgtgcgctgctcc cgaaactagaggaacctgcgttttgtctggacatactttctacgatacatttgacaaagcaagataccaattccagggtccctgcaa ggagattcttatggccgccgactgtttctggaacacttgggatgtgaaggttttcacacaggaatgttgactcttacactgaagtagag aaagtacgaatcaggaaacaatcgactgtagtagaactcattgttgatggaaaacagattctggttggaggagaagccgtgtccgt cccgtacagctctcagaacacttccatctactggcaagatggtgacatactgactacagccatcctacctgaagctctggtggtcaa gttcaacttcaagcaactgctcgtcgtacatattagagatccattcgatggtaagacttgcggtatttgcggtaactacaaccaggatt tcagtgatgattcttttgatgctgaaggagcctgtgatctgaccccccaacccaccgggatgcaccgaagaacagaaacctgaagct gaacgactctgcaatagtctcttcgccggtcaaagtgatcttgatcagaaatgtaacgtgtgccacaagcctgaccgtgtcgaacga tgcatgtacgagtattgcctgaggggacaacagggtttctgtgaccacgcatgggagttcaagaaagaatgctacataaagcatg gagacacccctagaagtaccagatgaatgcaaacggtctcaaggcagcaccctccgggtccagcagagacctcaaaattccaaggt gacacatatctcaagctgcttttgggcacaagatagaccggatcggatccgtcagtcgtttgggctgtaacgcactgaagttgttgtag Brain natriuretic peptide (BNP) Human (nucleic acid sequence):

(SEQ ID NO: 266)

Atggatccccagacagcaccttcccgggcgctcctgctcctgctcttcttgcatctggctttcctgggaggtcgttcccacccgctgggc agccccggttcagcctcggacttggaaacgtccgggttacaggagcagcgcaaccaatttgcagggcaaactgtcggagctgcaggtg gagcagacatccctggagcccctccaggagagcccccgtcccacaggtgtctggaagtcccgggaggtagccaccgagggcatcc gtgggcaccgcaaaatggtcctctacaccctgcgggcaccacgaagcTactgcgccactgttcattgccaggactgtccttacgaac ctgatccaccaaacacagttccaacttcctgtgaagctaaagaaggagaatgtattgatagcagctgtggcacctgcacgagaga catactatcagatggactgtgtgaaaataaaccaggaaaaacatgttgccgaatgtgtcagtatgtaattgaatgcagagtagagg ccgcaggatggtttagaacattctatggaaagagattccagttccaggaacctggtacatacgtgtgggtcaaggaaccaagggc ggcgactggaaggtgtccatcaccctggagaacctggatggaaccaaggggggctgtgctgaccaagacaagactggaagtggc tggagacatcattgacatcgctcaagctactgagaatcccatcactgtaaacggtggagctgaccctatcatcgccaacccgtaca ccatcggcgaggtcaccatcgctgttgttgagatgccaggcttcaacatcaccgtcattgagttcttcaaactgatcgtgatcgacatc ctcggaggaagatctgtaagaatcgcccagacacagcaaacaaaggaatgatctctggcctctgtggagatcttaaaatgatgg aagatacagacttcacttcagatccagaacaactcgctattcagcctaagatcaaccaggagtttgacggttgtccactctatggaa atcctgatgacgttgcatactgcaaaggtcttctggagccgtacaaggacagctgccgcaacccatcaacttctactactacacca tctcctgcgccttcgcccgctgtatgggtggagacgagcgagcctcacacgtgctgcttgactacagggagacgtgcgctgctcccg -continued aaactagaggaacctgcgttttgtctggacatactttctacgatacatttgacaaagcaagataccaattccagggtccctgcaagg agattcttatggccgccgactgtttctggaacacttgggatgtgaaggtttcacacaggaatgttgactcttacactgaagtagagaa agtacgaatcaggaaacaatcgactgtagtagaactcattgttgatggaaaacagattctggttggaggagaagccgtgtccgtcc cgtacagctctcagaacacttccatctactggcaagatggtgacatactgactacagccatcctacctgaagctctggtggtcaagtt caacttcaagcaactgctcgtcgtacatattagagatccattcgatggtaagacttgcggtatttgcggtaactacaaccaggatttca gtgatgattcttttgatgctgaaggagcctgtgatctgaccccaacccaccgggatgcaccgaagaacagaaacctgaagctga acgactctgcaatagtctcttcgccggtcaaagtgatcttgatcagaaatgtaacgtgtgccacaagcctgaccgtgtcgaacgatg catgtacgagtattgcctgaggggacaacaggggtttctgtgaccacgcatggggttcaagaaagaatgctacataaagcatgga gacaccctagaagtaccagatgaatgcaaa*cgaagc*cgaagccccaagatggtgcaagggtctggctgctttgggaggaagatgg accggatcagctcctccagtggcctgggctgcaaagtgctgaggcggcattaa Renin Mouse (nucleic acid sequence):

(SEQ ID NO: 267)
Atggacagaaggaggatgcctctctgggcactcttgttgctctggagtccttgcaccttcagtctcccaacacgcaccgctacctttgaa cgaatcccgctcaagaaaatgccttctgtccgggaaatcctggaggagcggggagtggacatgaccaggctcagtgctgaatggggc gtattcaca*aagagg*Tactgcgccactgttcattgccaggactgtccttacgaacctgatccaccaaacacagttccaacttcctgtg aagctaaagaaggagaatgtattgatagcagctgtggcacctgcacgagagacatactatcagatggactgtgtgaaaataaac caggaaaaacatgttgccgaatgtgtcagtatgtaattgaatgcagagtagaggccgcaggatggtttagaacattctatggaaag agattccagttccaggaacctggtacatacgtgttgggtcaaggaaccaagggcggcgactggaaggtgtccatcaccctggaga acctggatggaaccaagggggctgtgctgaccaagacaagactggaagtggctgagacatcattgacatcgctcaagctactg agaatcccatcactgtaaacggtggagctgacccatcatcgccaacccgtacaccatcggcgaggtcaccatcgctgttgttgag atgccaggcttcaacatcaccgtcattgagttcttcaaactgatcgtgatcgacatcctcggaggaagatctgtaagaatcgcccca gacacagcaaacaaaggaatgatctctggcctctgtggagatcttaaaatgatggaagatacagacttcacttcagatccagaac aactcgctattcagcctaagatcaaccaggagtttgacggttgtccactctatggaaatcctgatgacgttgcatactgcaaaggtctt ctggagccgtacaaggacagctgccgcaaccccatcaacttctactactacaccatctcctgcgccttcgcccgctgtatgggtgga gacgagcgagcctcacacgtgctgcttgactacagggagacgtgcgctgctcccgaaactagaggaacctgcgttttgtctggaca tactttctacgatacatttgacaaagcaagataccaattccagggtccctgcaaggagattcttatggccgccgactgtttctggaac acttgggatgtgaaggtttcacacaggaatgttgactcttacactgaagtagagaaagtacgaatcaggaaacaatcgactgtagt agaactcattgttgatggaaaacagattctggttggaggagaagccgtgtccgtcccgtacagctctcagaacacttccatctactg gcaagatggtgacatactgactacagccatcctacctgaagctctggtggtcaagttcaacttcaagcaactgctcgtcgtacatatt agagatccattcgatggtaagacttgcggtatttgcggtaactacaaccaggatttcagtgatgattcttttgatgctgaaggagcctg tgatctgaccccaacccaccgggatgcaccgaagaacagaaacctgaagctgaacgactctgcaatagtctcttcgccggtcaa agtgatcttgatcagaaatgtaacgtgtgccacaagcctgaccgtgtcgaacgatgcatgtacgagtattgcctgaggggacaaca gggtttctgtgaccacgcatggggttcaagaaagaatgctacataaagcatggagacaccctagaagtaccagatgaatgcaa a*aagagg*ccttccttgaccaatcttacctcccccgtggtcctcaccaactacctgaatacccagtactacggcgagattggcatcggtac cccacccagaccttcaaagtcatctttgacacgggttcagccaacctctgggtgccctccaccaagtgcagccgcctctaccttgcttgt gggattcacagcctctatgagtcctctgactcctccagctacatggagaacgggtccgacttcaccatccactacggatcagggagagt caaaggtttcctcagccaggactcggtgactgtgggtggaatcactgtgacacagacctttggagaggtcaccgagctgccctgatcc ctttcatgctggccaagtttgacggtgttctaggcatgggctttcccgctcaggccgttggcggggttacccctgtctttgaccacattctct cccaggggggtgctaaaggaggaagtgttctctgtctactacaacagggggttcccacctgctgggggggcgaggtggtgctaggagta gcgaccgcagcattatcaaggcaattttcactatgtgagcatcagcaagactgactcctggcagatcacgatgaagggggtgtctgtg gggtcttccaccctgctatgtgaagaaggctgtgcggtagtggtggacactggttcatcctttatctcggctcctacgagctccctgaagtt -continued gatcatgcaagccctgggagccaaggagaagagaatagaagaatatgttgtgaactgtagccaggtgcccaccctccccgacatttcc
tttgacctggggaggcagggcctacacactcagcagtacggactacgtgctacagtatcccaacaggagagacaagctgtgcacactg
gctctccatgccatggacatcccaccacccactgggcctgtctgggtcctgggtgccaccttcatccgcaagttctatacagagtttgatc
ggcataacaatcgcattggattcgccttggcccgctaa Renin Human (nucleic acid sequence):

(SEQ ID NO: 268)

Atggatggatggagaaggatgcctcgctggggactgctgctgctgctctgggctcctgtacctttggtctcccgacagacaccacca
cctttaaacggTactgcgccactgttcattgccaggactgtccttacgaacctgatccaccaaacacagttccaacttcctgtgaagct
aaagaaggagaatgtattgatagcagctgtggcacctgcacgagagacatactatcagatggactgtgtgaaaataaaccagga
aaaacatgttgccgaatgtgtcagtatgtaattgaatgcagagtagaggccgcaggatggtttagaacattctatggaaagagattc
cagttccaggaacctggtacatacgtgttgggtcaaggaaccaagggcggcgactggaaggtgtccatcaccctggagaacctg
gatggaaccaaggggctgtgctgaccaagacaagactggaagtggctggagacatcattgacatcgctcaagctactgagaat
cccatcactgtaaacggtggagctgacctatcatcgccaacccgtacaccatcggcgaggtcaccatcgctgttgttgagatgcca
ggcttcaacatcaccgtcattgagttcttcaaactgatcgtgatcgacatcctcggaggaagatctgtaagaatcgcccccagacaca
gcaaacaaggaatgatctctggcctctgtggagatcttaaaatgatggaagatacagacttcacttcagatccagaacaactcgc
tattcagcctaagatcaaccaggagtttgacggttgtccactctatggaaatcctgatgacgttgcatactgcaaaggtcttctggagc
cgtacaaggacagctgccgcaaccccatcaacttctactactacaccatctcctgcgccttcgcccgctgtatgggtggagacgagc
gagcctcacacgtgctgcttgactacagggagacgtgcgctgctcccgaaactagaggaacctgcgttttgtctggacatactttcta
cgatacatttgacaaagcaagataccaattccagggtccctgcaaggagattcttatggccgccgactgtttctggaacacttggga
tgtgaaggttcacacaggaatgttgactcttacactgaagtagagaaagtacgaatcaggaaacaatcgactgtagtagaactca
ttgttgatggaaaacagattctggttggaggagaagccgtgtccgtcccgtacagctctcagaacacttccatctactggcaagatg
gtgacatactgactacagccatcctacctgaagctctggtggtcaagttcaacttcaagcaactgctcgtcgtacatattagagatcc
attcgatggtaagacttgcggtatttgcggtaactacaaccaggatttcagtgatgattcttttgatgctgaaggagcctgtgatctgac
ccccaacccaccgggatgcaccgaagaacagaaacctgaagctgaacgactctgcaatagtctcttcgccggtcaaagtgatctt
gatcagaaatgtaacgtgtgccacaagcctgaccgtgtcgaacgatgcatgtacgagtattgcctgagggggacaacagggtttctg
tgaccacgcatgggagttcaagaaagaatgctacataaagcatggagacaccctagaagtaccagatgaatgcaaaaaacgga
tcttcctcaagagaatgccctcaatccgagaaagcctgaaggaacgaggtgtggacatggccaggcttggtcccgagtggagccaac
ccatgaagaggctgacacttggcaacaccacctcctccgtgatcctcaccaactacatggacacccagtactatggcgagattggcatc
ggcaccccaccccagaccttcaaagtcgtctttgacactggttcgtccaatgtttgggtgccctcctccaagtgcagccgtctctacactg
cctgtgtgtatcacaagctcttcgatgcttcggattcctccagctcaagcacaatggaacagaactcaccctccgctattcaacagggac
agtcagtggctttctcagccaggacatcatcaccgtgggtggaatcacggtgacacagatgtttggagaggtcacggagatgcccgcct
taccccttcatgctggccgagtttgatggggttgtgggcatgggcttcattgaacaggccattggcagggtcaccccctatcttcgacaacat
catctcccaagggggtgctaaaagaggacgtcttctctttctactacaacagagattccgagaattcccaatcgctgggaggacagattgt
gctgggaggcagcgaccccagcattacgaagggaatttccactatatcaacctcatcaagactggtgtctggcagattcaaatgaagg
gggtgtctgtggggtcatccttccagctctgtgaagacggctgcctggcattggtagacaccggtgcatcctacatctcaggttctaccag
ctccatagaaagctcatggaggccttgggagccaagaagaggctgtttgattatgtcgtgaagtgtaacgagggccctacactccccg
acatctcttttccacctgggaggcaaagaatacacgctcaccagcgcggactatgtatttcaggaatcctacagtagtaaaaagctgtgca
cactggccatccacgccatggatatcccgccacccactggacccacctgggccctgggggccaccttcatccgaaagttctacacaga
gtttgatcggcgtaacaaccgcattggcttcgccttggcccgctga Galanin Mouse (nucleic acid sequence):

(SEQ ID NO: 269)

Atggccagaggcagcgttatcctgctaggctggctcctgttggttgtgaccctgtcagccactctgggacttgggatgcctgcaaagga
gaagagaggtTactgcgccactgttcattgccaggactgtccttacgaacctgatccaccaaacacagttccaacttcctgtgaagct -continued

```
aaagaaggagaatgtattgatagcagctgtggcacctgcacgagagacatactatcagatggactgtgtgaaaataaaccagga
aaaacatgttgccgaatgtgtcagtatgtaattgaatgcagagtagaggccgcaggatggtttagaacattctatggaaagagattc
cagttccaggaacctggtacatacgtgttgggtcaaggaaccaagggcggcgactggaaggtgtccatcaccctggagaacctg
gatggaaccaaggggctgtgctgaccaagacaagactggaagtggctggagacatcattgacatcgctcaagctactgagaat
cccatcactgtaaacggtggagctgaccctatcatcgccaacccgtacaccatcggcgaggtcaccatcgctgttgttgagatgcca
ggcttcaacatcaccgtcattgagttcttcaaactgatcgtgatcgacatcctcggaggaagatctgtaagaatcgccccagacaca
gcaaacaaggaatgatctctggcctctgtggagatcttaaaatgatggaagatacagacttcacttcagatccagaacaactcgc
tattcagcctaagatcaaccaggagtttgacggttgtccactctatggaaatcctgatgacgttgcatactgcaaaggtcttctggagc
cgtacaaggacagctgccgcaaccccatcaacttctactactacaccatctcctgcgccttcgcccgctgtatgggtggagacgagc
gagcctcacacgtgctgcttgactacaggagacgtgcgctgctcccgaaactagaggaacctgcgttttgtctggacatactttcta
cgatacatttgacaaagcaagataccaattccagggtcctgcaaggagattcttatggccgccgactgtttctggaacacttggga
tgtgaaggtttcacacaggaatgttgactcttacactgaagtagagaaagtacgaatcaggaaacaatcgactgtagtagaactca
ttgttgatggaaaacagattctggttggaggagaagccgtgtccgtcccgtacagctctcagaacacttccatctactggcaagatg
gtgacatactgactacagccatcctacctgaagctctggtggtcaagttcaacttcaagcaactgctcgtcgtacatattagagatcc
attcgatggtaagacttgcggtatttgcggtaactacaaccaggatttcagtgatgattcttttgatgctgaaggagcctgtgatctgac
ccccaacccaccgggatgcaccgaagaacagaaacctgaagctgaacgactctgcaatagtctcttcgccggtcaaagtgatctt
gatcagaaatgtaacgtgtgccacaagcctgaccgtgtcgaacgatgcatgtacgagtattgcctgaggggacaacagggtttctg
tgaccacgcatgggagttcaagaaagaatgctacataaagcatggagacaccctagaagtaccagatgaatgcaaaaagagag
gtt
ggaccctgaacagcgctggctaccttctgggcccacatgccattgacaaccacagatcatttagcgacaagcatggcctcacaggc
aagagggagttacaactggaggtggaggaaaggagaccaggaagtgttgatgtgcccctgcctgagagcaacattgtccgcactata
atggagtttctcagtttcttgcaccttaaagaggccggggccctcgacagcctgcctggcatccccttggccacctcctcagaagaccta
gagaagtcctga
```

Galanin Human (nucleic acid sequence):

(SEQ ID NO: 270)

```
Atggcccgaggcagcgccctcctgctcgcctccctcctcctcgccgcggccctttctgcctctgcggggctctggtcgccggccaag
gaaaaacgaggcTactgcgccactgttcattgccaggactgtccttacgaacctgatccaccaaacacagttccaacttcctgtgaa
gctaaagaaggagaatgtattgatagcagctgtggcacctgcacgagagacatactatcagatggactgtgtgaaaataaacca
ggaaaaacatgttgccgaatgtgtcagtatgtaattgaatgcagagtagaggccgcaggatggtttagaacattctatggaaagag
attccagttccaggaacctggtacatacgtgttgggtcaaggaaccaagggcggcgactggaaggtgtccatcaccctggagaac
ctggatggaaccaaggggctgtgctgaccaagacaagactggaagtggctggagacatcattgacatcgctcaagctactgag
aatcccatcactgtaaacggtggagctgaccctatcatcgccaacccgtacaccatcggcgaggtcaccatcgctgttgttgagatg
ccaggcttcaacatcaccgtcattgagttcttcaaactgatcgtgatcgacatcctcggaggaagatctgtaagaatcgccccagac
acagcaaacaaggaatgatctctggcctctgtggagatcttaaaatgatggaagatacagacttcacttcagatccagaacaact
cgctattcagcctaagatcaaccaggagtttgacggttgtccactctatggaaatcctgatgacgttgcatactgcaaaggtcttctgg
agccgtacaaggacagctgccgcaaccccatcaacttctactactacaccatctcctgcgccttcgcccgctgtatgggtggagacg
agcgagcctcacacgtgctgcttgactacaggagacgtgcgctgctcccgaaactagaggaacctgcgttttgtctggacatactt
tctacgatacatttgacaaagcaagataccaattccagggtcctgcaaggagattcttatggccgccgactgtttctggaacacttg
ggatgtgaaggtttcacacaggaatgttgactcttacactgaagtagagaaagtacgaatcaggaaacaatcgactgtagtagaa
ctcattgttgatggaaaacagattctggttggaggagaagccgtgtccgtcccgtacagctctcagaacacttccatctactggcaag
atggtgacatactgactacagccatcctacctgaagctctggtggtcaagttcaacttcaagcaactgctcgtcgtacatattagaga
tccattcgatggtaagacttgcggtatttgcggtaactacaaccaggatttcagtgatgattcttttgatgctgaaggagcctgtgatct
```

-continued gaccccaacccaccgggatgcaccgaagaacagaaacctgaagctgaacgactctgcaatagtctcttcgccggtcaaagtga
tcttgatcagaaatgtaacgtgtgccacaagcctgaccgtgtcgaacgatgcatgtacgagtattgcctgaggggacaacagggttt
ctgtgaccacgcatgggagttcaagaaagaatgctacataaagcatggagacaccctagaagtaccagatgaatgcaaaaaac
gaggctggaccctgaacagcgcgggctacctgctgggcccacatgccgttggcaaccacaggtcattcagcgacaagaatggcctca
ccagcaagcgggagctgcggcccgaagatgacatgaaaccaggaagctttgacaggtccatacctgaaaacaatatcatgcgcacaa
tcattgagtttctgtctttcttgcatctcaaagaggccggtgccctcgaccgcctcctggatctccccgccgcagcctcctcagaagacatc
gagcggtcctga Orexin Mouse (nucleic acid sequence):
(SEQ ID NO: 271)
Atgaactttccttctacaaaggttccctgggccgccgtgacgctgctgctgctgctactgctgccgccggcgctgctgtcgcttggggt
ggacgcacagcctctgcccgactgctgtcgccagaagacgtgttcctgccgtctctacgaactgttgcacggagctggcaaccacg
ctgcgggtatcctgactctgggaaagcggcggcctggacctccaggcctccaggacggctgcagcgcctccttcaggccaacgg
taaccacgcagctggcatcctgaccatgggccgccgcTactgcgccactgttcattgccaggactgtccttacgaacctgatccacc
aaaacacagttccaacttcctgtgaagctaaagaaggagaatgtattgatagcagctgtggcacctgcacgagagacatactatca
gatggactgtgtgaaaataaaccaggaaaaacatgttgccgaatgtgtcagtatgtaattgaatgcagagtagaggccgcaggat
ggtttagaacattctatggaaagagattccagttccaggaacctggtacatacgtgttgggtcaaggaaccaagggcggcgactgg
aaggtgtccatcaccctggagaacctggatggaaccaaggggggctgtgctgaccaagacaagactggaagtggctggagacat
cattgacatcgctaagctactgagaatcccatcactgtaaacggtggagctgaccctatcatcgccaacccgtacaccatcggcg
aggtcaccatcgctgttgttgagatgccaggcttcaacatcaccgtcattgagttcttcaaactgatcgtgatcgacatcctcggagga
agatctgtaagaatcgccccagacacagcaaacaaggaatgatctctggcctctgtggagatcttaaaatgatggaagatacag
acttcacttcagatccagaacaactcgctattcagcctaagatcaaccaggagtttgacggttgtccactctatggaaatcctgatga
cgttgcatactgcaaaggtcttctggagccgtacaaggacagctgccgcaacccccatcaacttctactactacaccatctcctgcgc
cttcgcccgctgtatgggtggagacgagcgagcctcacacgtgctgcttgactacagggagacgtgcgctgctcccgaaactaga
ggaacctgcgttttgtctggacatactttctacgatacatttgacaaagcaagataccaattccagggtccctgcaaggagattcttat
ggccgccgactgtttctggaacacttgggatgtgaaggtttcacacaggaatgttgactcttacactgaagtagagaaagtacgaat
caggaaacaatcgactgtagtagaactcattgttgatggaaaacagattctggttggaggagaagccgtgtccgtcccgtacagct
ctcagaacacttccatctactggcaagatggtgacatactgactacagccatcctacctgaagctctggtggtcaagttcaacttcaa
gcaactgctcgtcgtacatattagagatccattcgatggtaagacttgcggtatttgcggtaactacaaccaggatttcagtgatgatt
cttttgatgctgaaggagcctgtgatctgaccccaacccaccgggatgcaccgaagaacagaaacctgaagctgaacgactctg
caatagtctcttcgccggtcaaagtgatcttgatcagaaatgtaacgtgtgccacaagcctgaccgtgtcgaacgatgcatgtacga
gtattgcctgaggggacaacagggtttctgtgaccacgcatgggagttcaagaaagaatgctacataaagcatggagacaccta
gaagtaccagatgaatgcaaaggccgccgcgcaggcgcagagctagagccacatccctgctctggtcgcggctgtccgaccgtaa
ctaccaccgctttagcaccccggggagggtccggagtctga Orexin Human (nucleic acid sequence):
(SEQ ID NO: 272)
Atgaaccttccttccacaaaggtctcctgggccgccgtgacgctactgctgctgctgctgctgccgccgcgctgttgtcgtccgg
ggcggctgcacagcccctgcccgactgctgtcgtcaaaagacttgctcttgccgcctctacgagctgctgcacggcgcgggcaatcac
gcggccggcatcctcacgctgggcaagcggaggtccgggcccccgggcctccaggtcggctgcagcgcctcctgcaggccagc
ggcaaccacgccgcgggcatcctgaccatgggccgccgcTactgcgccactgttcattgccaggactgtccttacgaacctgatcc
accaaacacagttccaacttcctgtgaagctaaagaaggagaatgtattgatagcagctgtggcacctgcacgagagacatacta
tcagatggactgtgtgaaaataaaccaggaaaaacatgttgccgaatgtgtcagtatgtaattgaatgcagagtagaggccgcag
gatggtttagaacattctatggaaagagattccagttccaggaacctggtacatacgtgttgggtcaaggaaccaagggcggcgac
tggaaggtgtccatcaccctggagaacctggatggaaccaaggggggctgtgctgaccaagacaagactggaagtggctggaga catcattgacatcgctcaagctactgagaatcccatcactgtaaacggtggagctgaccctatcatcgccaacccgtacaccatcgg cgaggtcaccatcgctgttgttgagatgccaggcttcaacatcaccgtcattgagttcttcaaactgatcgtgatcgacatcctcggag gaagatctgtaagaatcgccccagacacagcaaacaaaggaatgatctctggcctctgtggagatcttaaaatgatggaagatac agacttcacttcagatccagaacaactcgctattcagcctaagatcaaccaggagtttgacggttgtccactctatggaaatcctgat gacgttgcatactgcaaaggtcttctggagccgtacaaggacagctgccgcaacccccatcaacttctactactacaccatctcctgc gccttcgcccgctgtatgggtggagacgagcgagcctcacacgtgctgcttgactacagggagacgtgcgctgctcccgaaacta gaggaacctgcgttttgtctggacatactttctacgatacatttgacaaagcaagataccaattccagggtcctgcaaggagattctt atggccgcgcgactgtttctggaacacttgggatgtgaaggtttcacacaggaatgttgactcttacactgaagtagagaaagtacga atcaggaaacaatcgactgtagtagaactcattgttgatggaaaacagattctggttggaggagaagccgtgtccgtcccgtacag ctctcagaacacttccatctactggcaagatggtgacatactgactacagccatcctacctgaagctctggtggtcaagttcaacttca agcaactgctcgtcgtacatattagagatccattcgatggtaagacttgcggtatttgcggtaactacaaccaggatttcagtgatgat tcttttgatgctgaaggagcctgtgatctgaccccccaacccaccgggatgcaccgaagaacagaaacctgaagctgaacgactct gcaatagtctcttcgccggtcaaagtgatcttgatcagaaatgtaacgtgtgccacaagcctgaccgtgtcgaacgatgcatgtacg agtattgcctgaggggacaacagggtttctgtgaccacgcatgggagttcaagaaagaatgctacataaagcatggagacaccct agaagtaccagatgaatgcaaa<u>ggccgccgcg</u>caggcgcagagccagcgccgcgcccctgcctcgggcgccgctgttccgccc cggccgccgcctccgtcgcgcccggaggacagtccgggatctga Ghrelin-Obestatin Mouse (nucleic acid sequence):

(SEQ ID NO: 273)

Atgctgtcttcaggcaccatctgcagtttgctgctactcagcatgctctggatggacatggccatggcaggctccagcttcctgagccca gagcaccagaaagcccagcagagaaaggaatccaagaagccaccagctaaactgcag<u>ccacgagct</u>Tactgcgccactgttcattg ccaggactgtccttacgaacctgatccaccaaacacagttccaacttcctgtgaagctaaagaaggagaatgtattgatagcagct gtggcacctgcacgagagacatactatcagatggactgtgtgaaaataaaccaggaaaaacatgttgccgaatgtgtcagtatgt aattgaatgcagagtagaggccgcaggatggtttagaacattctatggaaagagattccagttccaggaacctggtacatacgtgtt gggtcaaggaaccaagggcggcgactggaaggtgtccatcaccctggagaacctggatggaaccaaggggggctgtgctgacc aagacaagactggaagtggctggagacatcattgacatcgctcaagctactgagaatcccatcactgtaaacggtggagctgacc ctatcatcgccaacccgtacaccatcggcgaggtcaccatcgctgttgttgagatgccaggcttcaacatcaccgtcattgagttcttc aaactgatcgtgatcgacatcctcggaggaagatctgtaagaatcgccccagacacagcaaacaaaggaatgatctctggcctct gtggagatcttaaaatgatggaagatacagacttcacttcagatccagaacaactcgctattcagcctaagatcaaccaggagtttg acggttgtccactctatggaaatcctgatgacgttgcatactgcaaaggtcttctggagccgtacaaggacagctgccgcaaccccca tcaacttctactactacaccatctcctgcgccttcgcccgctgtatgggtggagacgagcgagcctcacacgtgctgcttgactacag ggagacgtgcgctgctcccgaaactagaggaacctgcgttttgtctggacatactttctacgatacatttgacaaagcaagatacca attccagggtcctgcaaggagattcttatggccgccgactgtttctggaacacttgggatgtgaaggtttcacacaggaatgttgact cttacactgaagtagagaagtacgaatcaggaaacaatcgactgtagtagaactcattgttgatggaaaacagattctggttgga ggagaagccgtgtccgtcccgtacagctctcagaacacttccatctactggcaagatggtgacatactgactacagccatcctacct gaagctctggtggtcaagttcaacttcaagcaactgctcgtcgtacatattagagatccattcgatggtaagacttgcggtatttgcgg taactacaaccaggatttcagtgatgattcttttgatgctgaaggagcctgtgatctgaccccccaacccaccgggatgcaccgaaga acagaaacctgaagctgaacgactctgcaatagtctcttcgccggtcaaagtgatcttgatcagaaatgtaacgtgtgccacaagc ctgaccgtgtcgaacgatgcatgtacgagtattgcctgaggggacaacagggtttctgtgaccacgcatgggagttcaagaaaga atgctacataaagcatggagacaccctagaagtaccagatgaatgcaaa<u>ccacgagct</u>ctggaaggctggctccacccagagga cagaggacaagcagaagagacagaggaggagctgagatcaggttcaatgctcccttcgatgttggcatcaagctgtcaggagctca gtatcagcagcatggccgggccctggggaagtttcttcaggatatcctctgggaagaggtcaaagaggcgccagctgacaagtaa Ghrelin-Obestatin Human (nucleic acid sequence):

(SEQ ID NO: 274)

Atgccctccccagggaccgtctgcagcctcctgctcctcggcatgctctggctggacttggccatggcaggctccagcttcctgagcc ctgaacaccagagagtccagagaaaggagtcgaagaagccaccagccaagctgcag*ccccgagct*Tactgcgccactgttcattgc caggactgtccttacgaacctgatccaccaaacacagttccaacttcctgtgaagctaaagaaggagaatgtattgatagcagctgt ggcacctgacgagagacatactatcagatggactgtgtgaaaataaaccaggaaaaacatgttgccgaatgtgtcagtatgtaa ttgaatgcagagtagaggccgcaggatggtttagaacattctatggaaagagattccagttccaggaacctggtacatacgtgttgg gtcaaggaaccaagggcggcgactggaaggtgtccatcaccctggagaacctggatggaaccaagggggctgtgctgaccaa gacaagactggaagtggctggagacatcattgacatcgctcaagctactgagaatcccatcactgtaaacggtggagctgacccct atcatcgccaacccgtacaccatcggcgaggtcaccatcgctgttgttgagatgccaggcttcaacatcaccgtcattgagttcttca aactgatcgtgatcgacatcctcggaggaagatctgtaagaatcgcccagacacagcaaacaaaggaatgatctctggcctctg tggagatcttaaaatgatggaagatacagacttcacttcagatccagaacaactcgctattcagcctaagatcaaccaggagtttga cggttgtccactctatggaaatcctgatgacgttgcatactgcaaaggtcttctggagccgtacaaggacagctgccgcaacccat caacttctactactacaccatctcctgcgccttcgcccgctgtatgggtggagacgagcgagcctcacacgtgctgcttgactacagg gagacgtgcgctgctcccgaaactagaggaacctgcgttttgtctggacatactttctacgatacatttgacaaagcaagataccaa ttccagggtccctgcaaggagattcttatggccgccgactgtttctggaacacttgggatgtgaaggtttcacacaggaatgttgactc ttacactgaagtagagaaagtacgaatcaggaaacaatcgactgtagtagaactcattgttgatggaaaacagattctggttggag gagaagccgtgtccgtcccgtacagctctcagaacacttccatctactggcaagatggtgacatactgactacagccatcctacctg aagctctggtggtcaagttcaacttcaagcaactgctcgtcgtacatattagagatccattcgatggtaagacttgcggtatttgcggt aactacaaccaggatttcagtgatgattcttttgatgctgaaggagcctgtgatctgaccccaacccaccgggatgcaccgaaga acagaaacctgaagctgaacgactctgcaatagtctcttcgccggtcaaagtgatcttgatcagaaatgtaacgtgtgccacaagc ctgaccgtgtcgaacgatgcatgtacgagtattgcctgagggacaacagggtttctgtgaccacgcatgggagttcaagaaaga atgctacataaagcatggagacaccctagaagtaccagatgaatgcaaa*ccccgagct*ctagcaggctggctccgcccggaagat ggaggtcaagcagaaggggcagaggatgaactggaagtccggttcaacgcccccttttgatgttggaatcaagctgtcaggggttcagt accagcagcacagccaggccctggggaagtttcttcaggacatcctctgggaagaggccaaagaggccccagccgacaagtga Cholecystokinin Mouse (nucleic acid sequence):

(SEQ ID NO: 275)

Atgaagagcggcgtatgtctgtgcgtggtgatggcagtcctagctgctggccgccctggcgcagccggtagtcctgcagaagctacg gaccccgtggagcagcgggcgcaagaggcgccc*cgaaggcagctgcgggct*Tactgcgccactgttcattgccaggactgtccttt acgaacctgatccaccaaacacagttccaacttcctgtgaagctaaagaaggagaatgtattgatagcagctgtggcacctgcac gagagacatactatcagatggactgtgtgaaaataaaccaggaaaaacatgttgccgaatgtgtcagtatgtaattgaatgcaga gtagaggccgcaggatggtttagaacattctatggaaagagattccagttccaggaacctggtacatacgtgttgggtcaaggaac caagggcggcgactggaaggtgtccatcaccctggagaacctggatggaaccaaggggggctgtgctgaccaagacaagactg gaagtggctggagacatcattgacatcgctcaagctactgagaatcccatcactgtaaacggtggagctgacccctatcatcgccaa cccgtacaccatcggcgaggtcaccatcgctgttgttgagatgccaggcttcaacatcaccgtcattgagttcttcaaactgatcgtga tcgacatcctcggaggaagatctgtaagaatcgcccagacacagcaaacaaaggaatgatctctggcctctgtggagatcttaa aatgatggaagatacagacttcacttcagatccaagaacaactcgctattcagcctaagatcaaccaggagtttgacggttgtccact ctatggaaatcctgatgacgttgcatactgcaaaggtcttctggagccgtacaaggacagctgccgcaacccatcaacttctacta ctacaccatctcctgcgccttcgcccgctgtatgggtggagacgagcgagcctcacacgtgctgcttgactacagggagacgtgcg ctgctcccgaaactagaggaacctgcgttttgtctggacatactttctacgatacatttgacaaagcaagataccaattccagggtcc ctgcaaggagattcttatggccgccgactgtttctggaacacttgggatgtgaaggtttcacacaggaatgttgactcttacactgaa gtagagaaagtacgaatcaggaaacaatcgactgtagtagaactcattgttgatggaaaacagattctggttggaggagaagccg tgtccgtcccgtacagctctcagaacacttccatctactggcaagatggtgacatactgactacagccatcctacctgaagctctggt ggtcaagttcaacttcaagcaactgctcgtcgtacatattagagatccattcgatggtaagacttgcggtatttgcggtaactacaacc
aggatttcagtgatgattcttttgatgctgaaggagcctgtgatctgaccccaacccaccgggatgcaccgaagaacagaaacct
gaagctgaacgactctgcaatagtctcttcgccggtcaaagtgatcttgatcagaaatgtaacgtgtgccacaagcctgaccgtgtc
gaacgatgcatgtacgagtattgcctgaggggacaacaggggtttctgtgaccacgcatgggagttcaagaaagaatgctacataa
agcatggagacaccctagaagtaccagatgaatgcaaacgaaggcagctgcgggctgtgctccggacggacggcgagccccga
gcgcgcctgggcgcactgctagcgcgatacatccagcaggtccgcaaagctccttctggccgcatgtccgttcttaagaacctgcaga
gcctggaccccagccatagaataagtgaccgggactacatgggctggatggattttggccggcgcagtgccgaggactacgaatacc
catcgtag Cholecystokinin Human (nucleic acid sequence):
(SEQ ID NO: 276)
atgaacagcggcgtgtgcctgtgcgtgctgatggcggtactggcggctggcgccctgacgcagccggtgcctcccgcagatcccgc
gggctccgggctgcagcgggcagaggaggcgccccgtaggcagctgagggtaTactgcgccactgttcattgccaggactgtcctt
acgaacctgatccaccaaacacagttccaacttcctgtgaagctaaagaaggagaatgtattgatagcagctgtggcacctgcac
gagagacatactatcagatggactgtgtgaaaataaaccaggaaaaacatgttgccgaatgtgtcagtatgtaattgaatgcaga
gtagaggccgcaggatggtttagaacattctatggaaagagattccagttccaggaacctggtacatacgtgttgggtcaaggaac
caagggcggcgactggaaggtgtccatcaccctggagaacctggatggaaccaagggggctgtgctgaccaagacaagactg
gaagtggctggagacatcattgacatcgctcaagctactgagaatcccatcactgtaaacggtggagctgaccctatcatcgccaa
cccgtacaccatcggcgaggtcaccatcgctgttgttgagatgccaggcttcaacatcaccgtcattgagttcttcaaactgatcgtga
tcgacatcctcggaggaagatctgtaagaatcgccccagacacagcaaacaaaggaatgatctctggcctctgtggagatcttaa
aatgatggaagatacagacttcacttcagatccagaacaactcgctattcagcctaagatcaaccaggagtttgacggttgtccact
ctatggaaatcctgatgacgttgcatactgcaaaggtcttctggagccgtacaaggacagctgccgcaacccatcaacttctacta
ctacaccatctcctgcgcccttcgcccgctgtatgggtggagaacgagcgagcctcacacgtgctgcttgactacagggagacgtgcg
ctgctcccgaaactagaggaacctgcgttttgtctggacatactttctacgatacatttgacaaagcaagataccaattccagggtcc
ctgcaaggagattcttatggccgccgactgtttctggaacacttgggatgtgaaggtttcacacaggaatgttgactcttacactgaa
gtagagaaagtacgaatcaggaaacaatcgactgtagtagaactcattgttgatggaaaacagattctggttggaggagaagccg
tgtccgtcccgtacagctctcagaacacttccatctactggcaagatggtgacatactgactacagccatcctacctgaagctctggt
ggtcaagttcaacttcaagcaactgctcgtcgtacatattagagatccattcgatggtaagacttgcggtatttgcggtaactacaacc
aggatttcagtgatgattcttttgatgctgaaggagcctgtgatctgaccccaacccaccgggatgcaccgaagaacagaaacct
gaagctgaacgactctgcaatagtctcttcgccggtcaaagtgatcttgatcagaaatgtaacgtgtgccacaagcctgaccgtgtc
gaacgatgcatgtacgagtattgcctgaggggacaacaggggtttctgtgaccacgcatgggagttcaagaaagaatgctacataa
agcatggagacaccctagaagtaccagtgaatgcaaacgtaggcagctgagggtatcgcagagaacggatggcgagtcccgag
cgcacctgggcgccctgctggcaagatacatccagcaggcccggaaagctccttctggacgaatgtccatcgttaagaacctgcagaa
cctggaccccagccacaggataagtgaccgggactacatgggctggatggattttggccgtcgcagtgccgaggagtatgagtaccc
ctcctag Gastrin Mouse (nucleic acid sequence):
(SEQ ID NO: 277)
Atgcctcgactgtgtgtgtacatgctggtcttagtgctggctctagctaccttctcggaagcttcttggaagcccccgctcccagctacagg
atgcatcatctggaccagggaccaatgaggacctggaacagcgccagttcaacaagctgggctcagcctctcaccatcgaaggcagc
tggggccccagggtcctcaacactttcatagcagacctgtccaagaagcagaggccacgaatggaggaagaagaagaggcctacgg
atggatggactttggccgccgcagtTactgcgccactgttcattgccaggactgtccttacgaacctgatccaccaaacacagttcca
acttcctgtgaagctaaagaaggagaatgtattgatagcagctgtggcacctgcacgagagacatactatcagatggactgtgtga
aaataaaccaggaaaaacatgttgccgaatgtgtcagtatgtaattgaatgcagagtagaggccgcaggatggtttagaacattct -continued atggaaagagattccagttccaggaacctggtacatacgtgttgggtcaaggaaccaagggcggcgactggaaggtgtccatca ccctggagaacctggatggaaccaaggggctgtgctgaccaagacaagactggaagtggctggagacatcattgacatcgctc aagctactgagaatcccatcactgtaaacggtggagctgaccctatcatcgccaacccgtacaccatcggcgaggtcaccatcgct gttgttgagatgccaggcttcaacatcaccgtcattgagttcttcaaactgatcgtgatcgacatcctcggaggaagatctgtaagaat cgccccagacacagcaaacaaaggaatgatctctggcctctgtggagatcttaaaatgatggaagatacagacttcacttcagatc cagaacaactcgctattcagcctaagatcaaccaggagtttgacggttgtccactctatggaaatcctgatgacgttgcatactgcaa aggtcttctggagccgtacaaggacagctgccgcaaccccatcaacttctactactacaccatctcctgcgccttcgcccgctgtatg ggtgagacgagcgagcctcacacgtgctgcttgactacaggagacgtgcgctgctcccgaaactagaggaacctgcgttttgtc tggacatactttctacgatacatttgacaaagcaagataccaattccagggtccctgcaaggagattcttatggccgccgactgtttct ggaacacttgggatgtgaaggtttcacacaggaatgttgactcttacactgaagtagagaaagtacgaatcaggaaacaatcgac tgtagtagaactcattgttgatggaaaacagattctggttggaggagaagccgtgtccgtcccgtacagctctcagaacacttccatc tactggcaagatggtgacatactgactacagccatcctacctgaagctctggtggtcaagttcaacttcaagcaactgctcgtcgtac atattagagatccattcgatggtaagacttgcggtatttgcggtaactacaaccaggatttcagtgatgattcttttgatgctgaaggag cctgtgatctgaccccaacccaccgggatgcaccgaagaacagaaacctgaagctgaacgactctgcaatagtctcttcgccgg tcaaagtgatcttgatcagaaatgtaacgtgtgccacaagcctgaccgtgtcgaacgatgcatgtacgagtattgcctgagggggac aacagggtttctgtgaccacgcatgggagttcaagaaagaatgctacataaagcatggagacaccctagaagtaccagatgaat gcaaacgccgcagtgctgaggaagaccagtag Gastrin Human (nucleic acid sequence):

(SEQ ID NO: 278)

Atgcagcgactatgtgtgtatgtgctgatctttgcactggctctggccgccttctctgaagcttcttggaagccccgctcccagcagccag atgcacccttaggtacaggggccaacagggacctggagctaccctggctggagcagcagggcccagcctctcatcatcgaaggcag ctgggacccagggtcccccacacctcgtggcagacccgtccaagaagcagggaccatggctggaggaagaagaagaagcctatg gatggatggacttcggccgccgcagtTactgcgccactgttcattgccaggactgtccttacgaacctgatccaccaaacacagttc caacttcctgtgaagctaaagaaggagaatgtattgatagcagctgtggcacctgcacgagagacatactatcagatggactgtgt gaaaatataaaccaggaaaaacatgttgccgaatgtgtcagtatgtaattgaatgcagagtagaggccgcaggatggtttagaacat tctatgaaagagattccagttccaggaacctggtacatacgtgttgggtcaaggaaccaagggcggcgactggaaggtgtccat caccctggagaacctggatggaaccaaggggctgtgctgaccaagacaagactggaagtggctggagacatcattgacatcg ctcaagctactgagaatcccatcactgtaaacggtggagctgaccctatcatcgccaacccgtacaccatcggcgaggtcaccatc gctgttgttgagatgccaggcttcaacatcaccgtcattgagttcttcaaactgatcgtgatcgacatcctcggaggaagatctgtaag aatcgccccagacacagcaaacaaaggaatgatctctggcctctgtggagatcttaaaatgatggaagatacagacttcacttcag atccagaacaactcgctattcagcctaagatcaaccaggagtttgacggttgtccactctatggaaatcctgatgacgttgcatactg caaaggtcttctggagccgtacaaggacagctgccgcaaccccatcaacttctactactacaccatctcctgcgccttcgcccgctgt atgggtgagacgagcgagcctcacacgtgctgcttgactacaggagacgtgcgctgctcccgaaactagaggaacctgcgttt tgtctggacatactttctacgatacatttgacaaagcaagataccaattccagggtccctgcaaggagattcttatggccgccgactg tttctggaacacttgggatgtgaaggtttcacacaggaatgttgactcttacactgaagtagagaaagtacgaatcaggaaacaatc gactgtagtagaactcattgttgatggaaaacagattctggttggaggagaagccgtgtccgtcccgtacagctctcagaacacttc catctactggcaagatggtgacatactgactacagccatcctacctgaagctctggtggtcaagttcaacttcaagcaactgctcgtc gtacatattagagatccattcgatggtaagacttgcggtatttgcggtaactacaaccaggatttcagtgatgattcttttgatgctgaa ggagcctgtgatctgaccccaacccaccgggatgcaccgaagaacagaaacctgaagctgaacgactctgcaatagtctcttcg ccggtcaaagtgatcttgatcagaaatgtaacgtgtgccacaagcctgaccgtgtcgaacgatgcatgtacgagtattgcctgagg ggacaacagggtttctgtgaccacgcatgggagttcaagaaagaatgctacataaagcatggagacaccctagaagtaccagat gaatgcaaacgccgcagtgctgaggatgagaactaa -continued Protachykinin-1 (Substance P, Neurokinin A, Neuropeptide K, Neuropeptide gamma) Mouse
(nucleic acid sequence):

(SEQ ID NO: 279)

atgaaaatcctcgtggccgtggcggtctttttctcgtttccactcaactgtttgcagaggaaatcgatgccaacgatgatctaaattattggt ccgactggtccgacagtgaccagatcaaggaggcaatgccggagccctttgagcatcttctgcagagaatcgcc*cgaagaTactgcg*

*ccactgttcattgccaggactgtccttacgaacctgatccaccaaacacagttccaacttcctgtgaagctaaagaaggagaatgta*

*ttgatagcagctgtggcacctgcacgagagacatactatcagatggactgtgtgaaaataaaccaggaaaaacatgttgccgaat*

*gtgtcagtatgtaattgaatgcagagtagaggccgcaggatggtttagaacattctatggaaagagattccagttccaggaacctgg*

*tacatacgtgttgggtcaaggaaccaagggcggcgactggaaggtgtccatcaccctggagaacctggatggaaccaagggg*

*ctgtgctgaccaagacaagactggaagtggctggagacatcattgacatcgctcaagctactgagaatcccatcactgtaaacggt*

*ggagctgaccctatcatcgccaacccgtacaccatcggcgaggtcaccatcgctgttgttgagatgccaggcttcaacatcaccgtc*

*attgagttcttcaaactgatcgtgatcgacatcctcggaggaagatctgtaagaatcgcccagacacagcaaacaaaggaatga*

*tctctggcctctgtggagatcttaaaatgatggaagatacagacttcacttcagatccagaacaactcgctattcagcctaagatcaa*

*ccaggagtttgacggttgtccactctatggaaatcctgatgacgttgcatactgcaaaggtcttctggagccgtacaaggacagctg*

*ccgcaacccatcaacttctactactacaccatctcctgcgccttcgcccgctgtatgggtggagacgagcgagcctcacacgtgct*

*gcttgactacagggagacgtgcgctgctcccgaaactagaggaacctgcgttttgtctggacatactttctacgatacatttgacaaa*

*gcaagataccaattccagggtccctgcaaggagattcttatggccgccgactgtttctggaacacttgggatgtgaaggtttcacac*

*aggaatgttgactcttacactgaagtagagaaagtacgaatcaggaaacaatcgactgtagtagaactcattgttgatgaaaaca*

*gattctggttggaggagaagccgtgtccgtcccgtacagctctcagaacacttccatctactggcaagatggtgacatactgactac*

*agccatcctacctgaagctctggtggtcaagttcaacttcaagcaactgctcgtcgtacatattagagatccattcgatggtaagactt*

*gcggtatttgcggtaactacaaccaggatttcagtgatgattcttttgatgctgaaggagcctgtgatctgaccccaacccaccggg*

*atgcaccgaagaacagaaacctgaagctgaacgactctgcaatagtctcttcgccggtcaaagtgatcttgatcagaaatgtaacg*

*tgtgccacaagcctgaccgtgtcgaacgatgcatgtacgagtattgcctgaggggacaacagggtttctgtgaccacgcatgggag*

*ttcaagaaagaatgctacataaagcatggagacaccctagaagtaccagatgaatgcaaa*cgaaga*cccaagcctcagcagttct*

*ttggattaatgggcaagcgggatgctgattcctcagttgaaaaacaagtggccctgttaaaggctctttatggacatggccagatctctca*

*caaaaggcataaaacagattcctttgttggactaatgggcaaaagagctttaaattctgtggcttatgaaagaagcgcgatgcagaactac*

*gaaagaagacgtaaataa*

Protachykinin-1 (Substance P, Neurokinin A, Neuropeptide K, Neuropeptide gamma) Human
(nucleic acid sequence):

(SEQ ID NO: 280)

atgaaaatcctcgtggccttggcagtcttttttcttgtctccactcagctgtttgcagaagaaataggagccaatgatgatctgaattactggt ccgactggtacgacagcgaccagatcaaggaggaactgccggagccctttgagcatcactgcagagaatcgcc*cggagaTactgc*

*gccactgttcattgccaggactgtccttacgaacctgatccaccaaacacagttccaacttcctgtgaagctaaagaaggagaatgt*

*attgatagcagctgtggcacctgcacgagagacatactatcagatggactgtgtgaaaataaaccaggaaaaacatgttgccgaa*

*tgtgtcagtatgtaattgaatgcagagtagaggccgcaggatggtttagaacattctatggaaagagattccagttccaggaacctg*

*gtacatacgtgttgggtcaaggaaccaagggcggcgactggaaggtgtccatcaccctggagaacctggatggaaccaagggg*

*gctgtgctgaccaagacaagactggaagtggctggagacatcattgacatcgctcaagctactgagaatcccatcactgtaaacg*

*gtggagctgaccctatcatcgccaacccgtacaccatcggcgaggtcaccatcgctgttgttgagatgccaggcttcaacatcaccg*

*tcattgagttcttcaaactgatcgtgatcgacatcctcggaggaagatctgtaagaatcgccccagacacagcaaacaaaggaatg*

*atctctggcctctgtggagatcttaaaatgatggaagatacagacttcacttcagatccagaacaactcgctattcagcctaagatca*

*accaggagtttgacggttgtccactctatggaaatcctgatgacgttgcatactgcaaaggtcttctggagccgtacaaggacagct*

*gccgcaacccatcaacttctactactacaccatctcctgcgccttcgcccgctgtatgggtggagacgagcgagcctcacacgtgc*

*tgcttgactacagggagacgtgcgctgctcccgaaactagaggaacctgcgttttgtctggacatactttctacgatacatttgacaa*

-continued agcaagataccaattccagggtccctgcaaggagattcttatggccgccgactgtttctggaacacttgggatgtgaaggtttcaca caggaatgttgactcttacactgaagtagagaaagtacgaatcaggaaacaatcgactgtagtagaactcattgttgatggaaaac agattctggttggaggagaagccgtgtccgtcccgtacagctctcagaacacttccatctactggcaagatggtgacatactgacta cagccatcctacctgaagctctggtggtcaagttcaacttcaagcaactgctcgtcgtacatattagagatccattcgatggtaagact tgcggtatttgcggtaactacaaccaggatttcagtgatgattcttttgatgctgaaggagcctgtgatctgacccccaacccaccgg gatgcaccgaagaacagaaacctgaagctgaacgactctgcaatagtctcttcgccggtcaaagtgatcttgatcagaaatgtaac gtgtgccacaagcctgaccgtgtcgaacgatgcatgtacgagtattgcctgaggggacaacaggggtttctgtgaccacgcatggga gttcaagaaagaatgctacataaagcatggagacaccctagaagtaccagatgaatgcaaa<u>cggaga</u>cccaagcctcagcagtt ctttggattaatgggcaaacgggatgctgattcctcaattgaaaaacaagtggccctgttaaaggctctttatggacatggccagatctctc acaaaagacataaaacagattcctttgttggactaatgggcaaaagagctttaaattctgtggcttatgaaaggagtgcaatgcagaattat gaaagaagacgttaa Proenkephalin-A Mouse (nucleic acid sequence):

(SEQ ID NO: 281)

atggcgcggttcctgaggctttgcacctggctgctggcgcttgggtcctgcctcctggctacagtgcaggcggaatgcagccaggact gcgctaaatgcagctaccgcctggttcgcccaggcgacatcaatttcctggcgtgcacactggaatgtgaaggacagctgccttctttca aaatctgggagacctgcaaggatctcctgcaggtgtccaggcccgagttcccttgggataacatcgacatgtacaaagacagcagcaa acaggatgagagccacttgctagccaagaagtacggaggcttcatgaaacggtacggaggcttcatgaagaagatggacgagctatat cccatggagccagaagaagaagcgaacgaggagagatccttgccaagaggtatggcggcttcatgaagaaggatgcagatgagg gagacaccttggccaactcctccgatctgctgaaagagctactgggaacgggagacaaccgtgcgaaagacagccaccaacaagag agcaccaacaatgacgaagacatgagcaagaggtatgggggcttcatgagaagcctcaaaagaagccccccaactggaagatgaagc aaaagagctgcagaagcgctacggggggcttcat<u>gagaagg</u>Tactgcgccactgttcattgccaggactgtccttacgaacctgatcc accaaacacagttccaacttcctgtgaagctaaagaaggagaatgtattgatagcagctgtggcacctgcacgagagacatacta tcagatggactgtgtgaaaataaaccaggaaaaacatgttgccgaatgtgtcagtatgtaattgaatgcagagtagaggccgcag gatggtttagaacattctatggaaagagattccagttccaggaacctggtacatacgtgttgggtcaaggaaccaagggcggcgac tggaaggtgtccatcaccctggagaacctggatggaaccaagggggctgtgctgaccaagacaagactggaagtggctggaga catcattgacatcgctcaagctactgagaatcccatcactgtaaacggtggagctgaccctatcatcgccaacccgtacaccatcgg cgaggtcaccatcgctgttgttgagatgccaggcttcaacatcaccgtcattgagttcttcaaactgatcgtgatcgacatcctcggag gaagatctgtaagaatcgccccagacacagcaaacaaaggaatgatctctggcctctgtggagatcttaaaatgatggaagatac agacttcacttcagatccagaacaactcgctattcagcctaagatcaaccaggagtttgacggttgtccactctatggaaatcctgat gacgttgcatactgcaaaggtcttctggagccgtacaaggacagctgccgcaacccatcaacttctactactacaccatctcctgc gccttcgcccgctgtatgggtggagacgagcgagcctcacacgtgctgcttgactacaggagacgtgcgctgctcccgaaacta gaggaacctgcgttttgtctggacatactttctacgatacatttgacaaagcaagataccaattccagggtccctgcaaggagattctt atggccgccgactgtttctggaacacttgggatgtgaaggtttcacacaggaatgttgactcttacactgaagtagagaaagtacga atcaggaaacaatcgactgtagtagaactcattgttgatggaaaacagattctggttggaggagaagccgtgtccgtcccgtacag ctctcagaacacttccatctactggcaagatggtgacatactgactacagccatcctacctgaagctctggtggtcaagttcaacttca agcaactgctcgtcgtacatattagagatccattcgatggtaagacttgcggtatttgcggtaactacaaccaggatttcagtgatgat tcttttgatgctgaaggagcctgtgatctgacccccaacccaccgggatgcaccgaagaacagaaacctgaagctgaacgactct gcaatagtctcttcgccggtcaaagtgatcttgatcagaaatgtaacgtgtgccacaagcctgaccgtgtcgaacgatgcatgtacg agtattgcctgaggggacaacaggggtttctgtgaccacgcatgggagttcaagaaagaatgctacataaagcatggagacaccct agaagtaccagatgaatgcaaa<u>agaaggg</u>tgggacgccccgagtggtggatggactaccagaagaggtatgggggcttcctgaa gcgctttgctgagtctctgccctccgatgaagaaggcgaaaattactcgaaagaagttcctgagatagagaaaagatacgggggctttat gcggttctga -continued Proenkephalin-A Human (nucleic acid sequence):

(SEQ ID NO: 282)

atggcgcggttcctgacactttgcacttggctgctgttgctcggccccgggctcctggcgaccgtgcgggccgaatgcagccaggattg cgcgacgtgcagctaccgcctagtgcgcccggccgacatcaacttcctggcttgcgtaatggaatgtgaaggtaaactgccttctctga aaatttgggaaacctgcaaggagctcctgcagctgtccaaaccagagcttcctcaagatggcaccagcaccctcagagaaaatagcaa accggaagaaagccatttgctagccaaaaggtatgggggcttcatgaaaaggtatggaggcttcatgaagaaatggatgagctttatc ccatggagccagaagaagaggccaatggaagtgagatcctcgccaagcggtatgggggcttcatgaagaaggatgcagaggagga cgactcgctggccaattcctcagacctgctaaaagagcttctggaaacaggggacaaccgagagcgtagccaccaccaggatggca gtgataatgaggaagaagtgagcaagagatatgggggcttcatgagaggcttaaagagaagcccccaactggaagatgaagccaaa gagctgcagaagcgatatgggggcttcat*gagaaga*Tactgcgccactgttcattgccaggactgtccttacgaacctgatccacca

*aacacagttccaacttcctgtgaagctaaagaaggagaatgtattgatagcagctgtggcacctgcacgagagacatactatcag*

*atggactgtgtgaaaataaaccaggaaaaacatgttgccgaatgtgtcagtatgtaattgaatgcagagtagaggccgcaggatg*

*gtttagaacattctatggaaagagattccagttccaggaacctggtacatacgtgtgggtcaaggaaccaagggcggcgactgga*

*aggtgtccatcaccctggagaacctggatggaaccaaggggctgtgctgaccaagacaagactggaagtggctggagacatc*

*attgacatcgctcaagctactgagaatccatcactgtaaacggtggagctgacccatcatcgccaacccgtacaccatcggcga*

*ggtcaccatcgctgttgttgagatgccaggcttcaacatcaccgtcattgagttcttcaaactgatcgtgatcgacatcctcggaggaa*

*gatctgtaagaatcgcccagacacagcaaacaaaggaatgatctctggcctctgtggagatcttaaaatgatggaagatacaga*

*cttacttcagatccagaacaactcgctattcagcctaagatcaaccaggagtttgacggttgtccactctatggaaatcctgatgac*

*gttgcatactgcaaaggtcttctggagccgtacaaggacagctgccgcaacccccatcaacttctactactacaccatctcctgcgcct*

*tcgcccgctgtatgggtggagacgagcgagcctcacacgtgctgcttgactacagggagacgtgcgctgctcccgaaactagagg*

*aacctgcgttttgtctggacatactttctacgatacatttgacaaagcaagataccaattccagggtccctgcaaggagattcttatgg*

*ccgccgactgtttctggaacacttgggatgtgaaggttttcacacaggaatgttgactcttacactgaagtagagaaagtacgaatca*

*ggaacaatcgactgtagtagaactacattgttgatgaaaacagattctggttggaggagaagccgtgtccgtcccgtacagctctc*

*agaacacttccatctactggcaagatggtgacatactgactacagccatcctacctgaagctctggtggtcaagttcaacttcaagc*

*aactgctcgtcgtacatattagagatccattcgatggtaagacttgcggtatttgcggtaactacaaccaggatttcagtgatgattctt*

*tgatgctgaaggagcctgtgatctgaccccccaacccaccgggatgcaccgaagaacagaaacctgaagctgaacgactctgcaa*

*tagtctcttcgccgttcaaagtgatcttgatcagaaatgtaacgtgtgccacaagcctgaccgtgtcgaacgtgcatgtacgagtat*

*tgcctgaggggacaacaggggtttctgtgaccacgcatgggagttcaagaaagaatgctacataaagcatggagacacccctagaa*

*gtaccagatgaatgcaaa*agaaga*gtaggtcgcccagagtggtggatggactaccagaaacggtatggaggtttcctgaagcgcttt* gccgaggctctgccctccgacgaagaaggcgaaagttactccaaagaagttcctgaaatggaaaaaagatacggaggatttatgagat tttaa Proenkephalin-B Mouse (nucleic acid sequence):

(SEQ ID NO: 283)

*atggcgtggtccaggctgatgctggcagcttgcctcctcgtgatgccctctaatgttatggcggactgcctgtccctgtgctccctgtgt*

*gcagtgaggattcaggatgggcccgtcccatcaaccccctgatttgctccctggagtgccaggacctggtgccgccctcagagga*

*gtgggagacatgccggggcttctcatctttctcacccctgacggtctctgggctccgtggcaaggatgacttggaagatgaggttgctt*

*tggaagaaggctacagtgcactagccaagctcttggaacccgtcctgaaggagctggagaaaagccgactccttaccagcgtcc*

*cagaggaaaagttcaggggtctctccagcagctttggcaacggaaaagaatctgagctggcgggtgctgaccggatgaatgatg*

*aagccgcacaggcgggcacgctccatttttaatgaggaggacttgagaaaacaggccaaacgctatgcggcttttttgcgcaaata*

*cccc*aagagg*Tactgcgccactgttcattgccaggactgtccttacgaacctgatccaccaaacacagttccaacttcctgtgaagc*

*taaagaaggagaatgtattgatagcagctgtggcacctgcacgagagacatactatcagatggactgtgtgaaaataaaccagg*

*aaaaacatgttgccgaatgtgtcagtatgtaattgaatgcagagtagaggccgcaggatggtttagaacattctatggaaagagatt*

-continued ccagttccaggaacctggtacatacgtgttgggtcaaggaaccaagggcggcgactggaaggtgtccatcaccctggagaacct
ggatgaaccaaggggctgtgctgaccaagacaagactggaagtggctggagacatcattgacatcgctcaagctactgaga
atcccatcactgtaaacggtggagctgaccctatcatcgccaacccgtacaccatcggcgaggtcaccatcgctgttgttgagatgc
caggcttcaacatcaccgtcattgagttcttcaaactgatcgtgatcgacatcctcggaggaagatctgtaagaatcgccccagaca
cagcaaacaaggaatgatctctggcctctgtggagatcttaaaatgatggaagatacagacttcacttcagatccagaacaactc
gctattcagcctaagatcaaccaggagtttgacggttgtccactctatggaaatcctgatgacgttgcatactgcaaaggtcttctgga
gccgtacaaggacagctgccgcaacccccatcaacttctactactacaccatctcctgcgccttcgcccgctgtatgggtggagacga
gcgagcctcacacgtgctgcttgactacagggagacgtgcgctgctcccgaaactagaggaacctgcgttttgtctggacatactttc
tacgatacatttgacaaagcaagataccaattccagggtccctgcaaggagattcttatggccgccgactgtttctggaacacttgg
gatgtgaaggtttcacacaggaatgttgactcttacactgaagtagagaaagtacgaatcaggaaacaatcgactgtagtagaact
cattgttgatgaaaacagattctggttggaggagaagccgtgtccgtcccgtacagctctcagaacacttccatctactggcaaga
tggtgacatactgactacagccatcctacctgaagctctggtggtcaagttcaacttcaagcaactgctcgtcgtacatattagagatc
cattcgatggtaagacttgcggtatttgcggtaactacaaccaggatttcagtgatgattcttttgatgctgaaggagcctgtgatctga
ccccccaacccaccgggatgcaccgaagaacagaaacctgaagctgaacgactctgcaatagtctcttcgccggtcaaagtgatct
tgatcagaaatgtaaacgtgtgccacaagcctgaccgtgtcgaacgatgcatgtacgagtattgcctgaggggacaacagggtttct
gtgaccacgcatgggagttcaagaaagaatgctacataaagcatggagacaccctagaagtaccagatgaatgcaaa<u>aagagg</u>
agttccgagatggcccgggatgaggacggggggccaggatggggatcaggtagggcatgaggacctgtacaaacgctatggggctt
cctgcggcgcattcgccccaagctgaagtgggacaaccagaagcgctatggtggtttcctgcggcgtcagttcaaggtggtgacgcg
gtcccaggagaaccccaatacctattctgaagatttagatgtttga Proenkephalin-B Human (nucleic acid sequence):

(SEQ ID NO: 284)

atggcctggcagggggctggtcctggctgcctgcctcctcatgttcccctccaccacagcggactgcctgtcgcggtgctccttgtgtgct
gtaaagacccaggatggtcccaaacctatcaatccctgatttgctccctgcaatgccaggctgccctgctgccctctgaggaatggga
gagatgccagagctttctgtctcttttttcaccccctccacccttgggctcaatgacaaggaggacttggggagcaagtcggttggggaagg
gccctacagtgagctggccaagctctctgggtcattcctgaaggagctggagaaaagcaagtttctcccaagtatctcaacaaggaga
acactctgagcaagagcctggaggagaagctcaggggtctctctgacgggtttagggagggagcagagtctgagctgatgagggatg
cccagctgaacgatggtgccatggagactggcacactctatctcgctgaggaggaccccaaggagcaggtc<u>aaacgc</u>Tactgcgcc
actgttcattgccaggactgtccttacgaacctgatccaccaaacacagttccaacttcctgtgaagctaaagaaggagaatgtattg
atagcagctgtggcacctgcacgagagacatactatcagatggactgtgtgaaaataaaccaggaaaaacatgttgccgaatgtg
tcagtatgtaattgaatgcagagtagaggccgcaggatggtttagaacattctatggaaagagattccagttccaggaacctggtac
atacgtgttgggtcaaggaaccaagggcggcgactggaaggtgtccatcaccctggagaacctggatggaaccaagggggctgt
gctgaccaagacaagactggaagtggctggagacatcattgacatcgctcaagctactgagaatcccatcactgtaaacggtgga
gctgaccctatcatcgccaacccgtacaccatcggcgaggtcaccatcgctgttgttgagatgccaggcttcaacatcaccgtcattg
agttcttcaaactgatcgtgatcgacatcctcggaggaagatctgtaagaatcgccccagacacagcaaacaaggaatgatctct
ggcctctgtggagatcttaaaatgatggaagtacagacttcacttcagatccagaacaactcgctattcagcctaagatcaaccag
gagtttgacggttgtccactctatggaaatcctgatgacgttgcatactgcaaaggtcttctggagccgtacaaggacagctgccgc
aacccccatcaacttctactactacaccatctcctgcgccttcgcccgctgtatgggtggagacgagcgagcctcacacgtgctgcttg
actacagggagacgtgcgctgctcccgaaactagaggaacctgcgttttgtctggacatactttctacgatacatttgacaaagcaa
gataccaattccagggtccctgcaaggagattcttatggccgccgactgtttctggaacacttgggatgtgaaggtttcacacagga
atgttgactcttacactgaagtagagaaagtacgaatcaggaaacaatcgactgtagtagaactcattgttgatgaaaacagattc
tggttggaggagaagccgtgtccgtcccgtacagctctcagaacacttccatctactggcaagatggtgacatactgactacagcca
tcctacctgaagctctggtggtcaagttcaacttcaagcaactgctcgtcgtacatattagagatccattcgatggtaagacttgcggt

```
atttgcggtaactacaaccaggatttcagtgatgattcttttgatgctgaaggagcctgtgatctgaccccaacccaccgggatgca ccgaagaacagaaacctgaagctgaacgactctgcaatagtctcttcgccggtcaaagtgatcttgatcagaaatgtaacgtgtgc cacaagcctgaccgtgtcgaacgatgcatgtacgagtattgcctgagggggacaacagggtttctgtgaccacgcatgggagttcaa gaaagaatgctacataaagcatggagacaccctagaagtaccagatgaatgcaaaaaacgctatgggggcttttttgcgcaaatac cccaagaggagctcagaggtggctggggaggggacggggatagcatgggccatgaggacctgtacaaacgctatgggggcttctt gcggcgcattcgtcccaagctcaagtgggacaaccagaagcgctatggcggttttctccggcgccagttcaaggtggtgactcggtctc aggaagatccgaatgcttactctggagagcttttttgatgcataa
```

Insulin-like growth hormone 1 (IGF-1) Mouse (nucleic acid sequence):

(SEQ ID NO: 285)

```
atggggaaaatcagcagccttccaactcaattatttaagatctgcctctgtgacttcttgaagataaagatacacatcatgtcgtcttcacac ctcttctacctggcgctctgcttgctcaccttcaccagctccaccacagctggaccagagacccttcgcggggctgagctggtggatgct cttcagttcgtgtgtggaccgaggggcttttacttcaacaagcccacaggctatggctccagcattcggaggTactgcgccactgttcat tgccaggactgtccttacgaacctgatccaccaaacacagttccaacttcctgtgaagctaaagaaggagaatgtattgatagcag ctgtggcacctgcacgagagacatactatcagatggactgtgtgaaaataaaccaggaaaaacatgttgccgaatgtgtcagtatg taattgaatgcagagtagaggccgcaggatggtttagaacattctatggaaagagattccagttccaggaacctggtacatacgtgt tgggtcaaggaaccaagggcggcgactggaaggtgtccatcaccctggagaacctggatggaaccaagggggctgtgctgacc aagacaagactggaagtggctggagacatcattgacatcgctcaagctactgagaatcccatcactgtaaacggtggagctgacc ctatcatcgccaacccgtacaccatcggcgaggtcaccatcgctgttgttgagatgccaggcttcaacatcaccgtcattgagttcttc aaactgatcgtgatcgacatcctcggaggaagatctgtaagaatcgcccagacacagcaaacaaggaatgatctctggcctct gtggagatcttaaaatgatggaagatacagacttcacttcagatccagaacaactcgctattcagcctaagatcaaccaggagtttg acggttgtccactctatggaaatcctgatgacgttgcatactgcaaaggtcttctggagccgtacaaggacagctgccgcaaccca tcaacttctactactacaccatctcctgcgccttcgcccgctgtatgggtggagacgagcgagcctcacacgtgctgcttgactacag ggagacgtgcgctgctcccgaaaactagaggaacctgcgttttgtctggacatactttctacgatacatttgacaaagcaagatacca attccagggtccctgcaaggagattcttatggccgccgactgtttctggaacacttgggatgtgaaggtttcacacaggaatgttgact cttacactgaagtagagaaagtacgaatcaggaaacaatcgactgtagtagaactcattgttgatggaaaacagattctggttgga gggagaagccgtgtccgtcccgtacagctctcagaacacttccatctactggcaagatggtgacatactgactacagccatcctacct gaagctctggtggtcaagttcaacttcaagcaactgctcgtcgtacatattagagatccattcgatggtaagacttgcggtatttgcgg taactacaaccaggatttcagtgatgattcttttgatgctgaaggagcctgtgatctgaccccaacccaccgggatgcaccgaaga acagaaacctgaagctgaacgactctgcaatagtctcttcgccggtcaaagtgatcttgatcagaaatgtaacgtgtgccacaagc ctgaccgtgtcgaacgatgcatgtacgagtattgcctgaggggacaacagggtttctgtgaccacgcatgggagttcaagaaaga atgctacataaagcatggagacaccctagaagtaccagatgaatgcaaatccagcattcggaggcacctcagacaggcattgtg gatgagtgttgcttccggagctgtgatctgaggagactggagatgtactgtgccccactgaagcctacaaaagcagcccgctctatccgt gcccagcgccacactgacatgcccaagactcagaagtccccgtccctatcgacaaacaagaaaacgaagctgcaaaggagaaggaa aggaagtacatttgaagaacacaagtag
```

Insulin-like growth hormone 1 (IGF-1) Human (nucleic acid sequence):

(SEQ ID NO: 286)

```
atggggaaaatcagcagtcttccaacccaattatttaagtgctgcttttgtgatttcttgaaggtgaagatgcacaccatgtcctcctcgcatc tcttctacctggcgctgtgcctgctcaccttcaccagctctgccacggctggaccggagacgctctgcggggctgagctggtggatgct cttcagttcgtgtgtggagacaggggcttttatttcaacaagcccacagggtatggctccagcagtcggaggTactgcgccactgttcat tgccaggactgtccttacgaacctgatccaccaaacacagttccaacttcctgtgaagctaaagaaggagaatgtattgatagcag ctgtggcacctgcacgagagacatactatcagatggactgtgtgaaaataaaccaggaaaaacatgttgccgaatgtgtcagtatg taattgaatgcagagtagaggccgcaggatggtttagaacattctatggaaagagattccagttccaggaacctggtacatacgtgt
```

-continued tgggtcaaggaaccaagggcggcgactggaaggtgtccatcaccctggagaacctggatggaaccaaggggctgtgctgacc aagacaagactggaagtggctggagacatcattgacatcgctcaagctactgagaatcccatcactgtaaacggtggagctgacc ctatcatcgccaacccgtacaccatcggcgaggtcaccatcgctgttgttgagatgccaggcttcaacatcaccgtcattgagttcttc aaactgatcgtgatcgacatcctcggaggaagatctgtaagaatcgcccagacacagcaaacaaaggaatgatctctggcctct gtggagatcttaaaatgatggaagatacagacttcacttcagatccagaacaactcgctattcagcctaagatcaaccaggagtttg acggttgtccactctatggaaatcctgatgacgttgcatactgcaaaggtcttctggagccgtacaaggacagctgccgcaaccca tcaacttctactactacaccatctcctgcgccttcgcccgctgtatgggtggagacgagcgagcctcacacgtgctgcttgactacag ggagacgtgcgctgctcccgaaactagaggaacctgcgttttgtctggacatactttctacgatacatttgacaaagcaagatacca attccagggtccctgcaaggagattcttatggccgccgactgtttctggaacacttgggatgtgaaggtttcacacaggaatgttgact cttacactgaagtagagaaagtacgaatcaggaaacaatcgactgtagtagaactcattgttgatgaaaacagattctggttgga ggagaagccgtgtccgtcccgtacagctctcagaacacttccatctactggcaagatggtgacatactgactacagccatcctacct gaagctctggtggtcaagttcaacttcaagcaactgctcgtcgtacatattagagatccattcgatggtaagacttgcggtatttgcgg taactacaaccaggatttcagtgatgattcttttgatgctgaaggagcctgtgatctgaccccaacccaccgggatgcaccgaaga acagaaacctgaagctgaacgactctgcaatagtctcttcgccggtcaaagtgatcttgatcagaaatgtaacgtgtgccacaagc ctgaccgtgtcgaacgatgcatgtacgagtattgcctgaggggacaacagggtttctgtgaccacgcatgggagttcaagaaaga atgctacataaagcatggagacaccctagaagtaccagatgaatgcaaa*agcagtcggagggcgcctcagacaggcatcgtgga* tgagtgctgcttccggagctgtgatctaaggaggctggagatgtattgcgcacccctcaagcctgccaagtcagctcgctctgtccgtgc ccagcgccacaccgacatgcccaagacccagaagtatcagcccccatctaccaacaagaacacgaagtctcagagaaggaaagga agtacatttgaagaacgcaagtag Insulin-like growth hormone 2 (IGF-2)Mouse (nucleic acid sequence):

(SEQ ID NO: 287)

atgggcggcagcgtcgccggcttccaggtaccaatggggatcccagtggggaagtcgatgttggtgcttctcatctcttttggccttcgcc ttgtgctgcatcgctgcttacggccccggagagactctgtgcggaggggagcttgagacacgcttcagtagtctgacggaccgcggc ttctacttcagcaggccttcaagccgtgccaaccgtcgcagccgtggcatcgtggaagagtgctgcttccgcagctgcgacctggccct cctggagacatactgtgccaccccgccaagtcc*gagagggac*Tactgcgccactgttcattgccaggactgtccttacgaacctga tccaccaaacacagttccaacttcctgtgaagctaaagaaggagaatgtattgatagcagctgtggcacctgcacgagagacata ctatcagatggactgtgtgaaaataaaccaggaaaaacatgttgccgaatgtgtcagtatgtaattgaatgcagagtagaggccgc aggatggtttagaacattctatggaaagagattccagttccaggaacctggtacatacgtgtttgggtcaaggaaccaagggcggc gactggaaggtgtccatcaccctggagaacctggatggaaccaaggggctgtgctgaccaagacaagactggaagtggctgg agacatcattgacatcgctcaagctactgagaatcccatcactgtaaacggtggagctgaccctatcatcgccaacccgtacaccat cggcgaggtcaccatcgctgttgttgagatgccaggcttcaacatcaccgtcattgagttcttcaaactgatcgtgatcgacatcctcg gaggaagatctgtaagaatcgcccagacacagcaaacaaaggaatgatctctggcctctgtggagatcttaaaatgatggaag atacagacttcacttcagatccagaacaactcgctattcagcctaagatcaaccaggagtttgacggttgtccactctatggaaatcc tgatgacgttgcatactgcaaaggtcttctggagccgtacaaggacagctgccgcaaccccatcaacttctactactacaccatctcc tgcgccttcgcccgctgtatgggtggagacgagcgagcctcacacgtgctgcttgactacagggagacgtgcgctgctcccgaaac tagaggaacctgcgttttgtctggacatactttctacgatacatttgacaaagcaagataccaattccagggtccctgcaaggagatt cttatggccgccgactgtttctggaacacttgggatgtgaaggtttcacacaggaatgttgactcttacactgaagtagagaaagtac gaatcaggaaacaatcgactgtagtagaactcattgttgatgaaaacagattctggttggaggagaagccgtgtccgtcccgtac agctctcagaacacttccatctactggcaagatggtgacatactgactacagccatcctacctgaagctctggtggtcaagttcaact tcaagcaactgctcgtcgtacatattagagatccattcgatggtaagacttgcggtatttgcggtaactacaaccaggatttcagtgat gattcttttgatgctgaaggagcctgtgatctgaccccaacccaccgggatgcaccgaagaacagaaacctgaagctgaacgac tctgcaatagtctcttcgccggtcaaagtgatcttgatcagaaatgtaacgtgtgccacaagcctgaccgtgtcgaacgatgcatgta -continued cgagtattgcctgagggacaacagggtttctgtgaccacgcatgggagttcaagaaagaatgctacataaagcatggagacac cctagaagtaccagatgaatgcaaa<u>gagagggac</u>gtgtctacctctcaggccgtacttccggacgacttccccagataccccgtggg caagttcttccaatatgacacctggagacagtccgcgggacgcctgcgcagaggcctgcctgccctcctgcgtgcccgccggggtcg catgcttgccaaagagctcaaagagttcagagaggccaaacgtcatcgtccctgatcgtgttaccacccaaagaccccgcccacggg ggagcctcttcggagatgtccagcaaccatcagtga Insulin-like growth hormone 2 (IGF-2) Human (nucleic acid sequence):

(SEQ ID NO: 288)

atgggaatcccaatggggaagtcgatgctggtgcttctcaccttcttggccttcgcctcgtgctgcattgctgcttaccgccccagtgag accctgtgcggcggggagctggtggacaccctccagttcgtctgtggggaccgcggcttctacttcagcaggccgcaagccgtgt gagccgtcgcagccgtggcatcgttgaggagtgctgtttccgcagctgtgacctggccctcctggagacgtactgtgctacccccgc caagtcc<u>gagagggac</u>Tactgcgccactgttcattgccaggactgtccttacgaacctgatccaccaaacacagttccaacttcctg tgaagctaaagaaggagaatgtattgatagcagctgtggcacctgcacgagagacatactatcagatggactgtgtgaaaataaa ccaggaaaaacatgttgccgaatgtgtcagtatgtaattgaatgcagagtagaggccgcaggatggtttagaacattctatggaaa gagattccagttccaggaacctggtacatacgtgtgggtcaaggaaccaagggcggcgactggaaggtgtccatcaccctggag aacctggatggaaccaaggggctgtgctgaccaagacaagactggaagtggctggagacatcattgacatcgctcaagctact gagaatcccatcactgtaaacggtggagctgaccctatcatcgccaacccgtacaccatcggcgaggtcaccatcgctgttgttga gatgccaggcttcaacatcaccgtcattgagttcttcaaactgatcgtgatcgacatcctcggaggaagatctgtaagaatcgcccc agacacagcaaaaaggaatgatctctggcctctgtggagatcttaaaatgatggaagatacagacttcacttcagatccagaa caactcgctattcagcctaagatcaaccaggagtttgacggttgtccactctatggaaatcctgatgacgttgcatactgcaaaggtc ttctggagccgtacaaggacagctgccgcaacccccatcaacttctactactacaccatctcctgcgccttcgcccgctgtatgggtgg agacgagcgagcctcacacgtgctgcttgactacaggggagacgtgcgctgctcccgaaactagaggaacctgcgttttgtctggac atactttctacgatacatttgacaaagcaagataccaattccagggtccctgcaaggagattcttatggccgccgactgtttctggaa cacttgggatgtgaaggtttcacacaggaatgttgactcttacactgaagtagagaaagtacgaatcaggaaacaatcgactgtag tagaactcattgttgatggaaaacagattctggttggaggagaagccgtgtccgtcccgtacagctctcagaacacttccatctactg gcaagatggtgacatactgactacagccatcctacctgaagctctggtggtcaagttcaacttcaagcaactgctcgtcgtacatatt agagatccattcgatgtaagacttgcggtatttgcggtaactacaaccaggatttcagtgatgattcttttgatgctgaaggagcctg tgatctgaccccaacccaccgggatgcaccgaagaacagaaacctgaagctgaacgactctgcaatagtctcttcgccggtcaa agtgatcttgatcagaaatgtaacgtgtgccacaagcctgaccgtgtcgaacgatgcatgtacgagtattgcctgaggggacaaca gggtttctgtgaccacgcatgggagttcaagaaagaatgctacataaagcatggagacaccctagaagtaccagatgaatgcaa a<u>gagagggac</u>gtgtcgaccctccgaccgtgcttccggacaacttccccagataccccgtgggcaagttcttccaatatgacacctgg aagcagtccacccagcgcctgcgcaggggcctgcctgccctcctgcgtgcccgccggggtcacgtgctcgccaaggagctcgagg cgttcagggaggccaaacgtcaccgtccctgattgctctacccacccaagaccccgcccacggggcgcccccccagagatggcc agcaatcggaagtga Parathyroid hormone (PTH) Mouse (nucleic acid sequence):

(SEQ ID NO: 289)

atgatgtctgcaaacaccgtggctaaagtgatgatcatcatgctggcagtctgtcttcttacccaaacggatgggaaacccgtgagg<u>aag</u>

<u>aga</u>Tactgcgccactgttcattgccaggactgtccttacgaacctgatccaccaaacacagttccaacttcctgtgaagctaaagaa ggagaatgtattgatagcagctgtggcacctgcacgagagacatactatcagatggactgtgtgaaaataaaccaggaaaaaca tgttgccgaatgtgtcagtatgtaattgaatgcagagtagaggccgcaggatggtttagaacattctatggaaagagattccagttcc aggaacctggtacatacgtgtgggtcaaggaaccaagggcggcgactggaaggtgtccatcaccctggagaacctggatggaa ccaagggggctgtgctgaccaagacaagactggaagtggctggagacatcattgacatcgctcaagctactgagaatcccatca ctgtaaacggtggagctgaccctatcatcgccaacccgtacaccatcggcgaggtcaccatcgctgttgttgagatgccaggcttca -continued

```
acatcaccgtcattgagttcttcaaactgatcgtgatcgacatcctcggaggaagatctgtaagaatcgccccagacacagcaaac aaaggaatgatctctggcctctgtggagatcttaaaatgatggaagatacagacttcacttcagatccagaacaactcgctattcag cctaagatcaaccaggagtttgacggttgtccactctatggaaatcctgatgacgttgcatactgcaaaggtcttctggagccgtaca aggacagctgccgcaacccatcaacttctactactacaccatctcctgcgccttcgcccgctgtatgggtggagacgagcgagcct cacacgtgctgcttgactacagggagacgtgcgctgctcccgaaactagaggaacctgcgttttgtctggacatactttctacgatac atttgacaaagcaagataccaattccagggtccctgcaaggagattcttatggccgccgactgtttctggaacactttgggatgtgaa ggtttcacacaggaatgttgactcttacactgaagtagagaaagtacgaatcaggaaacaatcgactgtagtagaactcattgttga tggaaaacagattctggttggaggagaagccgtgtccgtcccgtacagctctcagaacacttccatctactggcaagatggtgacat actgactacagccatcctacctgaagctctggtggtcaagttcaacttcaagcaactgctcgtcgtacatattagagatccattcgatg gtaagacttgcggtatttgcggtaactacaaccaggatttcagtgatgattcttttgatgctgaaggagcctgtgatctgacccccaac ccaccgggatgcaccgaagaacagaaacctgaagctgaacgactctgcaatagtctcttcgccggtcaaagtgatcttgatcaga aatgtaacgtgtgccacaagcctgaccgtgtcgaacgatgcatgtacgagtattgcctgaggggacaacagggtttctgtgaccac gcatgggagttcaagaaagaatgctacataaagcatggagacaccctagaagtaccagatgaatgcaaaaagagagctgtcagt gaaatacagcttatgcacaacctgggcaaacacctggcctccatggagaggatgcaatggctgagaaggaagctgcaagatatgcac aattttgttagtcttggagtccaaatggctgccagagatggcagtcaccagaagccaccaagaaggaggaaaatgtccttgttgatggc aatccaaaaagtcttggtgagggagacaaagctgatgtggatgtattagttaaatcaaaatctcagtaa
```

Parathyroid hormone (PTH) Human (nucleic acid sequence):

(SEQ ID NO: 290)

```
atgatacctgcaaaagacatggctaaagttatgattgtcatgttggcaatttgttttcttacaaaatcggatgggaaatctgttaagaagaga Tactgcgccactgttcattgccaggactgtccttacgaacctgatccaccaaacacagttccaacttcctgtgaagctaaagaagga gaatgtattgatagcagctgtggcacctgcacgagagacatactatcagatggactgtgtgaaaataaaccaggaaaaacatgtt gccgaatgtgtcagtatgtaattgaatgcagagtagaggccgcaggatggtttagaacattctatggaaagagattccagttccagg aacctggtacatacgtgttgggtcaaggaaccaagggcggcgactggaaggtgtccatcaccctggagaacctggatggaacca agggggctgtgctgaccaagacaagactggaagtggctgagacatcattgacatcgctcaagctactgagaatcccatcactgt aaacggtggagctgaccctatcatcgccaacccgtacaccatcggcgaggtcaccatcgctgttgttgagatgccaggcttcaaca tcaccgtcattgagttcttcaaactgatcgtgatcgacatcctcggaggaagatctgtaagaatcgccccagacacagcaaacaaa ggaatgatctctggcctctgtggagatcttaaaatgatggaagatacagacttcacttcagatccagaacaactcgctattcagccta agatcaaccaggagtttgacggttgtccactctatggaaatcctgatgacgttgcatactgcaaaggtcttctggagccgtacaagg acagctgccgcaacccatcaacttctactactacaccatctcctgcgccttcgcccgctgtatgggtggagacgagcgagcctcac acgtgctgcttgactacagggagacgtgcgctgctcccgaaactagaggaacctgcgttttgtctggacatactttctacgatacattt gacaaagcaagataccaattccagggtccctgcaaggagattcttatggccgccgactgtttctggaacactttgggatgtgaaggtt tcacacaggaatgttgactcttacactgaagtagagaaagtacgaatcaggaaacaatcgactgtagtagaactcattgttgatgg aaaacagattctggttggaggagaagccgtgtccgtcccgtacagctctcagaacacttccatctactggcaagatggtgacatact gactacagccatcctacctgaagctctggtggtcaagttcaacttcaagcaactgctcgtcgtacatattagagatccattcgatggta agacttgcggtatttgcggtaactacaaccaggatttcagtgatgattcttttgatgctgaaggagcctgtgatctgacccccaaccca ccgggatgcaccgaagaacagaaacctgaagctgaacgactctgcaatagtctcttcgccggtcaaagtgatcttgatcagaaat gtaacgtgtgccacaagcctgaccgtgtcgaacgatgcatgtacgagtattgcctgaggggacaacagggtttctgtgaccacgca tgggagttcaagaaagaatgctacataaagcatggagacaccctagaagtaccagatgaatgcaaaaagagatctgtgagtgaa atacagcttatgcataacctgggaaaacatctgaactcgatggagagagtagaatggctgcgtaagaagctgcaggatgtgcacaattttt gttgcccttggagctcctctagctcccagagatgctggttcccagaggccccgaaaaaggaagacaatgtcttggttgagagccatga aaaaagtcttggagaggcagacaaagctgatgtgaatgtattaactaaagctaaatcccagtga
```

-continued

Parathyroid hormone-related protein (PTHrP) Mouse (nucleic acid sequence):

(SEQ ID NO: 291)

atgctgcggaggctggttcagcagtggagtgtcctggtattcctgctcagctactccgtgccctcccgcgggcgttcggtggaggggct tggccgcaggctcaaacgcTactgcgccactgttcattgccaggactgtccttacgaacctgatccaccaaacacagttccaacttc ctgtgaagctaaagaaggagaatgtattgatagcagctgtggcacctgcacgagagacatactatcagatggactgtgtgaaaat aaaccaggaaaaacatgttgccgaatgtgtcagtatgtaattgaatgcagagtagaggccgcaggatggtttagaacattctatgg aaagagattccagttccaggaacctggtacatacgtgttgggtcaaggaaccaagggcggcgactggaaggtgtccatcaccctg gagaacctggatggaaccaaggggctgtgctgaccaagacaagactggaagtggctggagacatcattgacatcgctcaagct actgagaatcccatcactgtaaacggtggagctgaccctatcatcgccaacccgtacaccatcggcgaggtcaccatcgctgttgtt gagatgccaggcttcaacatcaccgtcattgagttcttcaaactgatcgtgatcgacatcctcggaggaagatctgtaagaatcgcc ccagacacagcaaacaaaggaatgatctctggcctctgtggagatcttaaaatgatggaagatacagacttcacttcagatccag aacaactcgctattcagcctaagatcaaccaggagtttgacggttgtccactctatggaaatcctgatgacgttgcatactgcaaag gtcttctggagccgtacaaggacagctgccgcaacccatcaacttctactactacaccatctcctgcgccttcgcccgctgtatggg tggagacgagcgagcctcacacgtgctgcttgactacagggagacgtgcgctgctcccgaaactagaggaacctgcgttttgtctg gacatactttctacgatacatttgacaaagcaagataccaattccagggtccctgcaaggagattcttatggccgccgactgtttctg gaacacttgggatgtgaaggtttcacacaggaatgttgactcttacactgaagtagagaaagtacgaatcaggaaacaatcgact gtagtagaactcattgttgatggaaaacagattctggttggaggagaagccgtgtccgtcccgtacagctctcagaacacttccatct actggcaagatggtgacatactgactacagccatcctacctgaagctctggtggtcaagttcaacttcaagcaactgctcgtcgtac atattagagatccattcgatggtaagacttgcggtatttgcggtaactacaaccaggatttcagtgatgattcttttgatgctgaaggag cctgtgatctgaccccaacccaccgggatgcaccgaagaacagaaacctgaagctgaacgactctgcaatagtctcttcgccgg tcaaagtgatcttgatcagaaatgtaacgtgtgccacaagcctgaccgtgtcgaacgatgcatgtacgagtattgcctgaggggac aacagggtttctgtgaccacgcatgggagttcaagaaagaatgctacataaagcatggagacaccctagaagtaccagatgaat gcaaaaaacgcgctgtgtctgaacatcagctactgcatgacaagggcaagtccatccaagacttgcgccgccgtttcttcctccaccat ctgatcgcggagatccacacagccgaaatcagagctacctcggaggtgtcccccaactccaaacctgctcccaacaccaaaaaccac cccgtgcggtttgggtcagacgatgagggcagatacctaactcaggaaaccaacaaggtggagacgtacaaagaacagccactcaa gacacccggaagaagaagaaaggcaagcctgggaaacgcagagaacaggagaaaaagaagcgaaggactcggtctgcctggc caagcacagctgcgagtggcctgcttgaggaccccctgccccacacctccaggccctcgctggagcccagcttaaggacgcattga Parathyroid hormone-related protein (PTHrP) Human (nucleic acid sequence):

(SEQ ID NO: 292)

atgcagcggagactggttcagcagtggagcgtcgcggtgttcctgctgagctacgcggtgccctcctgcgggcgctcggtggaggt ctcagccgccgcctcaaaagaTactgcgccactgttcattgccaggactgtccttacgaacctgatccaccaaacacagttccaactt cctgtgaagctaaagaaggagaatgtattgatagcagctgtggcacctgcacgagagacatactatcagatggactgtgtgaaaa taaaccaggaaaaacatgttgccgaatgtgtcagtatgtaattgaatgcagagtagaggccgcaggatggtttagaacattctatg gaaagagattccagttccaggaacctggtacatacgtgttgggtcaaggaaccaagggcggcgactggaaggtgtccatccct ggagaacctggatggaaccaaggggctgtgctgaccaagacaagactggaagtggctggagacatcattgacatcgctcaag ctactgagaatcccatcactgtaaacggtggagctgaccctatcatcgccaacccgtacaccatcggcgaggtcaccatcgctgttg ttgagatgccaggcttcaacatcaccgtcattgagttcttcaaactgatcgtgatcgacatcctcggaggaagatctgtaagaatcgc cccagacacagcaaacaaaggaatgatctctggcctctgtggagatcttaaaatgatggaagatacagacttcacttcagatccag aacaactcgctattcagcctaagatcaaccaggagtttgacggttgtccactctatggaaatcctgatgacgttgcatactgcaaag gtcttctggagccgtacaaggacagctgccgcaacccatcaacttctactactacaccatctcctgcgccttcgcccgctgtatggg tggagacgagcgagcctcacacgtgctgcttgactacagggagacgtgcgctgctcccgaaactagaggaacctgcgttttgtctg gacatactttctacgatacatttgacaaagcaagataccaattccagggtccctgcaaggagattcttatggccgccgactgtttctg -continued gaacacttgggatgtgaaggtttcacacaggaatgttgactcttacactgaagtagagaaagtacgaatcaggaaacaatcgact
gtagtagaactcattgttgatggaaaacagattctggttggaggagaagccgtgtccgtcccgtacagctctcagaacacttccatct
actggcaagatggtgacatactgactacagccatcctacctgaagctctggtggtcaagttcaacttcaagcaactgctcgtcgtac
atattagagatccattcgatggtaagacttgcggtatttgcggtaactacaaccaggatttcagtgatgattcttttgatgctgaaggag
cctgttgatctgaccccaacccaccgggatgcaccgaagaacagaaacctgaagctgaacgactctgcaatgtctcttcgccgg
tcaaagtgatcttgatcagaaatgtaacgtgtgccacaagcctgaccgtgtcgaacgatgcatgtacgagtattgcctgagggac
aacagggtttctgtgaccacgcatgggagttcaagaaagaatgctacataaagcatggagacaccctagaagtaccagatgaat
gcaaa<u>aaaag</u>agctgtgtctgaacatcagctcctccatgacaaggggaagtccatccaagatttacggcgacgattcttccttcaccatc
tgatcgcagaaatccacacagctgaaatcagagctacctcggaggtgtccctaactccaagccctctcccaacacaaagaaccaccc
cgtccgatttgggtctgatgatgagggcagatacctaactcaggaaactaacaaggtggaagacgtacaaagagcagccgctcaagac
acctgggaagaaaagaaaggcaagcccgggaaacgcaaggagcaggaaaagaaaaaacggcgaactcgctctgcctggttaga
ctctggagtgactgggagtgggctagaaggggaccacctgtctgacacctccacaacgtcgctggagctcgattcacggaggcattga Osteocalcin Mouse (nucleic acid sequence):

(SEQ ID NO: 293)
atgaggaccatctttctgctcactctgctgaccctggctgcgctctgtctctctgacctcacagatgccaagcccagcggccctgagtctg
acaaagccttcatgtccaagcaggagggcaataaggtagtgaacagactc<u>cggcgc</u>Tactgcgccactgttcattgccaggactgtc
cttacgaacctgatccaccaaacacagttccaacttcctgtgaagctaaagaaggagaatgtattgatagcagctgtggcacctgc
acgagagacatactatcagatggactgtgtgaaaataaaccaggaaaaacatgttgccgaatgtgtcagtatgtaattgaatgcag
agtagaggccgcaggatggtttagaacattctatggaaagagattccagttccaggaacctggtacatacgtgtttgggtcaaggaa
ccaagggcggcgactggaaggtgtccatcaccctggagaacctggatggaaccaaggggctgtgctgaccaagacaagactg
gaagtggctggagacatcattgacatcgctcaagctactgagaatcccatcactgtaaacggtggagctgaccctatctcgccaa
cccgtacaccatcggcgaggtcaccatcgctgttgttgagatgccaggcttcaacatcaccgtcattgagttcttcaaactgatcgtga
tcgacatcctcggaggaagatctgtaagaatcgccccagacacagcaaacaaaggaatgatctctggcctctgtggagatcttaa
aatgatggaagatacagacttcacttcagatccagaacaactcgctattcagcctaagatcaaccaggagtttgacggttgtccact
ctatggaaatcctgatgacgttgcatactgcaaaggtcttctggagccgtacaaggacagctgccgcaacccccatcaacttctacta
ctacaccatctcctgcgccttcgcccgctgtatgggtggagacgagcagcctcacacgtgctgcttgactacagggagacgtgcg
ctgctcccgaaactagaggaacctgcgttttgtctggacatactttctacgatacatttgacaaagcaagataccaattccagggtcc
ctgcaaggagattcttatggccgccgactgtttctgaacacttgggatgtgaaggtttcacacaggaatgttgactcttacactgaa
gtagagaaagtacgaatcaggaaacaatcgactgtagtagaactcattgttgatggaaaacagattctggttggaggagaagccg
tgtccgtcccgtacagctctcagaacacttccatctactggcaagatggtgacatactgactacagccatcctacctgaagctctggt
ggtcaagttcaacttcaagcaactgctcgtcgtacatattagagatccattcgatggtaagacttgcggtatttgcggtaactacaacc
aggatttcagtgatgattcttttgatgctgaaggagcctgtgatctgaccccaacccaccgggatgcaccgaagaacagaaacct
gaagctgaacgactctgcaatagtctcttcgccggtcaaagtgatcttgatcagaaatgtaacgtgtgccacaagcctgaccgtgtc
gaacgatgcatgtacgagtattgcctgagggacaacagggtttctgtgaccacgcatgggagttcaagaaagaatgctacataa
agcatggagacaccctagaagtaccagatgaatgcaaa<u>cggcgc</u>taccttggagcctcagtcccagcccagatcccctggagcc
cacccgggagcagtgtgagcttaaccctgcttgtgacgagctatcagaccagtatggcttgaagaccgcctacaaacgcatctatggtat
cactatttag Osteocalcin Human (nucleic acid sequence):

(SEQ ID NO: 294)
atgagagccctcacactcctcgccctattggccctggccgcacttttgcatcgctggccaggcaggtgcgaagcccagcggtgcagagt
ccagcaaaggtgcagcctttgtgtccaagcaggagggcagcgaggtagtgaagagaccc<u>aggcgc</u>Tactgcgccactgttcattgc
caggactgtccttacgaacctgatccaccaaacacagttccaacttcctgtgaagctaaagaaggagaatgtattgatagcagctgt
ggcacctgcacgagagacatactatcagatggactgtgtgaaaataaaccaggaaaaacatgttgccgaatgtgtcagtatgtaa -continued ttgaatgcagagtagaggccgcaggatggtttagaacattctatggaaagagattccagttccaggaacctggtacatacgtgttgg gtcaaggaaccaagggcggcgactggaaggtgtccatcaccctggagaacctggatggaaccaaggggggctgtgctgaccaa gacaagactggaagtggctggagacatcattgacatcgctcaagctactgagaatcccatcactgtaaacggtggagctgaccct atcatcgccaacccgtacaccatcggcgaggtcaccatcgctgttgttgagatgccaggcttcaacatcaccgtcattgagttcttca aactgatcgtgatcgacatcctcggaggaagatctgtaagaatcgccccagacacagcaaacaaaggaatgatctctggcctctg tggagatcttaaaatgatggaagatacagacttcacttcagatccagaacaactcgctattcagcctaagatcaaccaggagtttga cggttgtccactctatggaaatcctgatgacgttgcatactgcaaaggtcttctggagccgtacaaggacagctgccgcaacccat caacttctactactacaccatctcctgcgccttcgcccgctgtatgggtggagacgagcgagcctcacacgtgctgcttgactacagg gagacgtgcgctgctcccgaaactagaggaacctgcgttttgtctggacatactttctacgatacatttgacaaagcaagataccaa ttccagggtccctgcaaggagattcttatggccgccgactgtttctggaacacttgggatgtgaaggtttcacacaggaatgttgactc ttacactgaagtagagaaagtacgaatcaggaaacaatcgactgtagtagaactcattgttgatggaaaacagattctggttggag gagaagccgtgtccgtcccgtacagctctcagaacacttccatctactggcaagatggtgacatactgactacagccatcctacctg aagctctggtggtcaagttcaacttcaagcaactgctcgtcgtacatattagagatccattcgatggtaagacttgcggtatttgcggt aactacaaccaggatttcagtgatgattcttttgatgctgaaggagcctgtgatctgaccccaacccaccgggatgcaccgaaga acagaaacctgaagctgaacgactctgcaatagtctcttcgccggtcaaagtgatcttgatcagaaatgtaacgtgtgccacaagc ctgaccgtgtcgaacgatgcatgtacgagtattgcctgaggggacaacagggtttctgtgaccacgcatgggagttcaagaaaga atgctacataaagcatggagacaccctagaagtaccagatgaatgcaaaaggcgctacctgtatcaatggctgggagccccagtc ccctacccggatcccctggagcccaggagggaggtgtgtgagctcaatccggactgtgacgagttggctgaccacatcggctttcagg aggcctatcggcgcttctacggcccggtctag Urocortin-3 Mouse (nucleic acid sequence):

(SEQ ID NO: 295)
atgctgatgcccacctacttcctgctgctgccacttctgctgctcctaggaggtccaaggacaagcctctcccacaagttctacaacactg gaccagtcttcagctgcctcaacacagccctatctgaggtcaagaagaacaagctggaagatgtgcccttgctgagcaagaaga gctttggccacctgcccacacaagaccctcaggggaagaagatgacaaccaaacgcacctccagatcaaaagaactttctcag gtgccgcgggtgggaatggagctgggagcacccggtacagataccaatcccaggcacagcacaaggggaagctgtacccaga caagcccaaaagcgaccggggcaccaagTactgcgccactgttcattgccaggactgtccttacgaacctgatccaccaaacac agttccaacttcctgtgaagctaaagaaggagaatgtattgatagcagctgtggcacctgcacgagagacatactatcagatggac tgtgtgaaaataaaccaggaaaaacatgttgccgaatgtgtcagtatgtaattaatgcagagtagaggccgcaggatggtttaga acattctatggaaagagattccagttccaggaacctggtacatacgtgttgggtcaaggaaccaagggcggcgactggaaggtgt ccatcaccctggagaacctggatggaaccaaggggggctgtgctgaccaagacaagactggaagtggctggagacatcattgac atcgctcaagctactgagaatcccatcactgtaaacggtggagctgaccctatcatcgccaacccgtacaccatcggcgaggtcac catcgctgttgttgagatgccaggcttcaacatcaccgtcattgagttcttcaaactgatcgtgatcgacatcctcggaggaagatctg taagaatcgccccagacacagcaaacaaaggaatgatctctggcctctgtggagatcttaaaatgatggaagatacagacttcac ttcagatccagaacaactcgctattcagcctaagatcaaccaggagtttgacggttgtccactctatggaaatcctgatgacgttgca tactgcaaaggtcttctggagccgtacaaggacagctgccgcaacccatcaacttctactactacaccatctcctgcgccttcgccc gctgtatgggtggagacgagcgagcctcacacgtgctgcttgactacagggagacgtgcgctgctcccgaaactagaggaacct gcgttttgtctggacatactttctacgatacatttgacaaagcaagataccaattccagggtccctgcaaggagattcttatggccgcc gactgtttctggaacacttgggatgtgaaggtttcacacaggaatgttgactcttacactgaagtagagaaagtacgaatcaggaaa caatcgactgtagtagaactcattgttgatggaaaacagattctggttggaggagaagccgtgtccgtcccgtacagctctcagaac acttccatctactggcaagatggtgacatactgactacagccatcctacctgaagctctggtggtcaagttcaacttcaagcaactgc tcgtcgtacatattagagatccattcgatggtaagacttgcggtatttgcggtaactacaaccaggatttcagtgatgattcttttgatgc -continued tgaaggagcctgtgatctgacccccaacccaccgggatgcaccgaagaacagaaacctgaagctgaacgactctgcaatagtct cttcgccggtcaaagtgatcttgatcagaaatgtaacgtgtgccacaagcctgaccgtgtcgaacgatgcatgtacgagtattgcct gaggggacaacaggggtttctgtgaccacgcatgggagttcaagaaagaatgctacataaagcatggagacaccctagaagtac cagatgaatgcaaacggggcaccaagttcacccctttcccttgatgttcccactaacatcatgaacatcctcttcaacatcgacaaggcca agaatttgcgagccaaggcagctgccaatgctcagctcatggcacagattgggaagaagaagtaa Urocortin-3 Human (nucleic acid sequence):
(SEQ ID NO: 296)

Atgctgatgccggtccacttcctgctgctcctgctgctgctcctggggggcccccaggacaggcctcccccacaagttctacaaagcc aagcccatcttcagctgcctcaacaccgccctgtctgaggctgagaagggccagtgggaggatgcatccctgctgagcaagagg agcttccactacctgcgcagcagagacgcctcttcgggagaggaggaggaggggcaaagagaaaaagactttccccatctctggg gccaggggtggagccagaggcacccgtacagatacgtgtcccaagcacagcccaggggaaagccacgccaggacacggcc aagagtccccaccgcTactgcgccactgttcattgccaggactgtccttacgaacctgatccaccaaacacagttccaacttcctgt gaagctaaagaaggagaatgtattgatagcagctgtggcacctgcacgagagacatactatcagatggactgtgtgaaaataaa ccaggaaaaacatgttgccgaatgtgtcagtatgtaattgaatgcagagtagaggccgcaggatggtttagaacattctatggaaa gagattccagttccaggaacctggtacatacgtgttgggtcaaggaaccaagggcggcgactggaaggtgtccatcaccctggag aacctggatggaaccaaggggggctgtgctgaccaagacaagactggaagtggctggagacatcattgacatcgctcaagctact gagaatcccatcactgtaaacggtggagctgaccctatcatcgccaacccgtacaccatcggcgaggtcaccatcgctgttgttga gatgccaggcttcaacatcaccgtcattgagttcttcaaactgatcgtgatcgacatcctcggaggaagatctgtaagaatcgcccc agacacagcaaacaaggaatgatctctggcctctgtggagatcttaaaatgatggaagatacagacttcacttcagatccagaa caactcgctattcagcctaagatcaaccaggagtttgacggttgtccactctatggaaatcctgatgacgttgcatactgcaaaggtc ttctggagccgtacaaggacagctgccgcaacccccatcaacttctactactacaccatctcctgcgccttcgcccgctgtatgggtgg agacgagcgagcctcacacgtgctgcttgactacaggagacgtgcgctgctcccgaaactagaggaacctgcgttttgtctggac atactttctacgatacatttgacaaagcaagataccaattccagggtccctgcaaggagattcttatggccgccgactgtttctggaa cactggatgtgaaggtttcacacaggaatgttgactcttacactgaagtagagaaagtacgaatcaggaaacaatcgactgtag tagaactcattgttgatggaaaacagattctggttggaggagaagccgtgtccgtcccgtacagctctcagaacacttccatctactg gcaagatggtgacatactgactacagccatcctacctgaagctctggtggtcaagttcaacttcaagcaactgctcgtcgtacatatt agagatccattcgatggtaagacttgcggtatttgcggtaactacaaccaggatttcagtgatgattcttttgatgctgaaggagcctg tgatctgacccccaacccaccgggatgcaccgaagaacagaaacctgaagctgaacgactctgcaatagtctcttcgccggtcaa agtgatcttgatcagaaatgtaacgtgtgccacaagcctgaccgtgtcgaacgatgcatgtacgagtattgcctgagggggacaaca gggtttctgtgaccacgcatgggagttcaagaaagaatgctacataaagcatggagacaccctagaagtaccagatgaatgcaa acaccgcaccaagttcaccctgtccctcgacgtccccaccaacatcatgaacctcctcttcaacatcgccaaggccaagaacctgcgtg cccaggcggccgccaatgcccacctgatggcgcaaattgggaggaagaagtag Urocortin-2 Mouse (nucleic acid sequence):
(SEQ ID NO: 297)

Atgatgaccaggtgggcactggtggtgttcgtggtcctgatgttggataggatcctatttgtcccaggaactcctatccccaccttccagc tcctccctcagaactctctggagacaactcctagctctgtgacctcagagagctcctcaggtaccaccacaggaccctcagcttcctgga gcaactctaaagccagcccttacctagacacccgtgtcTactgcgccactgttcattgccaggactgtccttacgaacctgatccacca aacacagttccaacttcctgtgaagctaaagaaggagaatgtattgatagcagctgtggcacctgcacgagagacatactatcag atggactgtgtgaaaataaaccaggaaaaacatgttgccgaatgtgtcagtatgtaattgaatgcagagtagaggccgcaggatg gtttagaacattctatggaaagagattccagttccaggaacctggtacatacgtgttgggtcaaggaaccaagggcggcgactgga aggtgtccatcaccctggagaacctggatggaaccaaggggggctgtgctgaccaagacaagactggaagtggctggagacatc attgacatcgctcaagctactgagaatcccatcactgtaaacggtggagctgaccctatcatcgccaacccgtacaccatcggcga ggtcaccatcgctgttgttgagatgccaggcttcaacatcaccgtcattgagttcttcaaactgatcgtgatcgacatcctcggaggaa -continued gatctgtaagaatcgccccagacacagcaaacaaaggaatgatctctggcctctgtggagatcttaaaatgatggaagatacaga cttcacttcagatccagaacaactcgctattcagcctaagatcaaccaggagtttgacggttgtccactctatgaaatcctgatgac gttgcatactgcaaaggtcttctggagccgtacaaggacagctgccgcaaccccatcaacttctactactacaccatctcctgcgcct tcgcccgctgtatgggtggagacgagcgagcctcacacgtgctgcttgactacagggagacgtgcgctgctcccgaaactagagg aacctgcgttttgtctggacatactttctacgatacatttgacaaagcaagataccaattccagggtccctgcaaggagattcttatgg ccgccgactgtttctggaacacttgggatgtgaaggtttcacacaggaatgttgactcttacactgaagtagagaaagtacgaatca ggaaacaatcgactgtagtagaactcattgttgatgaaaacagattctggttggaggagaagccgtgtccgtcccgtacagctctc agaacacttccatctactggcaagatggtgacatactgactacagccatcctacctgaagctctggtggtcaagttcaacttcaagc aactgctcgtcgtacatattagagatccattcgatggtaagacttgcggtatttgcggtaactacaaccaggatttcagtgatgattcttt tgatgctgaaggagcctgtgatctgaccccaacccaccgggatgcaccgaagaacagaaacctgaagctgaacgactctgcaa tagtctcttcgccggtcaaagtgatcttgatcagaaatgtaacgtgtgccacaagcctgaccgtgtcgaacgatgcatgtacgagtat tgcctgaggggacaacagggtttctgtgaccacgcatgggagttcaagaaagaatgctcataaagcatggagacaccctagaa gtaccagatgaatgcaaa<u>acccgtgtc</u>atactctccctggatgttcccattggcctcctacggatcttactggaacaggctcgttacaag gctgccaggaatcaggctgccactaatgctcaaatactagcccatgttggccgccgctga Urocortin-2 Human (nucleic acid sequence):

(SEQ ID NO: 298)

atgaccaggtgtgctctgctgttgctgatggtcctgatgttgggcagagtcctggttgtcccagtgaccccta tcccaaccttccagctccg ccctcagaattctccccagaccactccccgacctgcggcctcagagagcccctcagctgctcccacatggccgtgggctgcccagag ccactgcagccccaccgccaccctggc<u>tcgcgcatt</u>Tactgcgccactgttcattgccaggactgtccttacgaacctgatccacca aacacagttccaacttcctgtgaagctaaagaaggagaatgtattgatagcagctgtggcacctgcacgagagacatactatcag atggactgtgtgaaaataaaccaggaaaaacatgttgccgaatgtgtcagtatgtaattgaatgcagagtagaggccgcaggatg gtttagaacattctatggaaagagattccagttccaggaacctggtacatacgtgtgggtcaaggaaccaagggcggcgactgga aggtgtccatcaccctggagaacctggatggaaccaaggggggctgtgctgaccaagacaagactggaagtggctggagacatc attgacatcgctcaagctactgagaatcccatcactgtaaacggtggagctgacctatcatcgccaacccgtacaccatcggcga ggtcaccatcgctgttgttgagatgccaggcttcaacatcaccgtcattgagttcttcaaactgatcgtgatcgacatcctcggaggaa gatctgtaagaatcgccccagacacagcaaacaaaggaatgatctctggcctctgtggagatcttaaaatgatggaagatacaga cttcacttcagatccagaacaactcgctattcagcctaagatcaaccaggagtttgacggttgtccactctatgaaatcctgatgac gttgcatactgcaaaggtcttctggagccgtacaaggacagctgccgcaaccccatcaacttctactactacaccatctcctgcgcct tcgcccgctgtatgggtggagacgagcgagcctcacacgtgctgcttgactacagggagacgtgcgctgctcccgaaactagagg aacctgcgttttgtctggacatactttctacgatacatttgacaaagcaagataccaattccagggtccctgcaaggagattcttatgg ccgccgactgtttctggaacacttgggatgtgaaggtttcacacaggaatgttgactcttacactgaagtagagaaagtacgaatca ggaaacaatcgactgtagtagaactcattgttgatgaaaacagattctggttggaggagaagccgtgtccgtcccgtacagctctc agaacacttccatctactggcaagatggtgacatactgactacagccatcctacctgaagctctggtggtcaagttcaacttcaagc aactgctcgtcgtacatattagagatccattcgatggtaagacttgcggtatttgcggtaactacaaccaggatttcagtgatgattcttt tgatgctgaaggagcctgtgatctgaccccaacccaccgggatgcaccgaagaacagaaacctgaagctgaacgactctgcaa tagtctcttcgccggtcaaagtgatcttgatcagaaatgtaacgtgtgccacaagcctgaccgtgtcgaacgatgcatgtacgagtat tgcctgaggggacaacagggtttctgtgaccacgcatgggagttcaagaaagaatgctcataaagcatggagacaccctagaa gtaccagatgaatgcaaa<u>tcgcgcatt</u>gtcctatcgctggatgtcccatcggcctcttgcagatcttactggagcaagcccgggccag ggctgccagggagcaggccaccaccaacgcccgcatcctggcccgtgtcggccactgctga -continued Urocortin-1 Mouse (nucleic acid sequence):
(SEQ ID NO: 299)
Atgatacagaggggacgcgctacgctcctggtggcgttgctgctcttggcacagcttcgcccggagagcagccagtggagcccagc ggctgcggcggcaactggggtccaggatccgaatctgcgatggagccctggagtgcggaatcagggcggcggcgtccgcgcgctc ctcttgctgttagcggagcgcttcccgcgccgcgcaggatctgagcctgcgggcgagcggcag<u>cgacgg</u>Tactgcgccactgttcat tgccaggactgtccttacgaacctgatccaccaaacacagttccaacttcctgtgaagctaaagaaggagaatgtattgatagcag ctgtggcacctgcacgagagacatactatcagatggactgtgtgaaaataaaccaggaaaaacatgttgccgaatgtgtcagtatg taattgaatgcagagtagaggccgcaggatggtttagaacattctatggaaagagattccagttccaggaacctggtacatacgtgt tgggtcaaggaaccaagggcggcgactggaaggtgtccatcaccctgagaacctggatggaaccaaggggctgtgctgacc aagacaagactggaagtggctggagacatcattgacatcgctcaagctactgagaatcccatcactgtaaacggtggagctgacc ctatcatcgccaacccgtacaccatcggcgaggtcaccatcgctgttgttgagatgccaggcttcaacatcaccgtcattgagttcttc aaactgatcgtgatcgacatcctcggaggaagatctgtaagaatcgccccagacacagcaaacaaaggaatgatctctggcctct gtggagatcttaaaatgatggaagatacagacttcacttcagatccagaacaactcgctattcagcctaagatcaaccaggagtttg acggttgtccactctatggaaatcctgatgacgttgcatactgcaaaggtcttctggagccgtacaaggacagctgccgcaacccca tcaacttctactactacaccatctcctgcgccttcgcccgctgtatgggtggagacgagcgagcctcacacgtgctgcttgactacag ggagacgtgcgctgctcccgaaactagaggaacctgcgttttgtctggacatactttctacgatacatttgacaaagcaagatacca attccagggtccctgcaaggagattcttatggccgccgactgtttctggaacacttgggatgtgaaggtttcacacaggaatgttgact cttacactgaagtagagaaagtacgaatcaggaaacaatcgactgtagtagaactcattgttgatggaaaacagattctggttgga ggagaagccgtgtccgtcccgtacagctctcagaacacttccatctactggcaagatggtgacatactgactacagccatcctacct gaagctctggtggtcaagttcaacttcaagcaactgctcgtcgtacatattagagatccattcgatggtaagacttgcggtatttgcgg taactacaaccaggatttcagtgatgattcttttgatgctgaaggagcctgtgatctgaccccaacccaccgggatgcaccgaaga acagaaacctgaagctgaacgactctgcaatagtctcttcgccggtcaaagtgatcttgatcagaaatgtaacgtgtgccacaagc ctgaccgtgtcgaacgatgcatgtacgagtattgcctgaggggacaacagggtttctgtgaccacgcatgggagttcaagaaaga atgctacataaagcatggagacaccctagaagtaccagatgaatgcaaa<u>cgacgg</u>gacgaccctccactgtccatcgacctcacc ttccacctgctgcggaccctgctggagctagctcggacacagagccagcgcgagcgcgcagagcagaaccgcatcatattcgattcg gtgggcaagtga Urocortin-1 Human (nucleic acid sequence):
(SEQ ID NO: 300)
atgaggcaggcgggacgcgcagcgctgctggccgcgctgctgctcctggtacagctgtgccctgggagcagccagaggagccccg aggcggccggggtccaggacccgagtctgcgctggagccccggggcacggaaccagggtggcggggcccgcgcgctcctcttgc tgctggcggagcgcttcccgcgccgcgcggggcccggccgattgggactcgggacggcaggcgagcggccg<u>cggcgg</u>Tactgc gccactgttcattgccaggactgtccttacgaacctgatccaccaaacacagttccaacttcctgtgaagctaaagaaggagaatgt attgatagcagctgtggcacctgcacgagagacatactatcagatggactgtgtgaaaataaaccaggaaaaacatgttgccgaa tgtgtcagtatgtaattgaatgcagagtagaggccgcaggatggtttagaacattctatggaaagagattccagttccaggaacctg gtacatacgtgttgggtcaaggaaccaagggcggcgactggaaggtgtccatcaccctgagaacctggatggaaccaagggg gctgtgctgaccaagacaagactggaagtggctggagacatcattgacatcgctcaagctactgagaatcccatcactgtaaacg gtggagctgaccctatcatcgccaacccgtacaccatcggcgaggtcaccatcgctgttgttgagatgccaggcttcaacatcaccg tcattgagttcttcaaactgatcgtgatcgacatcctcggaggaagatctgtaagaatcgccccagacacagcaaacaaaggaatg atctctggcctctgtggagatcttaaaatgatggaagatacagacttcacttcagatccagaacaactcgctattcagcctaagatca accaggagtttgacggttgtccactctatggaaatcctgatgacgttgcatactgcaaaggtcttctggagccgtacaaggacagct gccgcaaccccatcaacttctactactacaccatctcctgcgccttcgcccgctgtatgggtggagacgagcgagcctcacacgtgc tgcttgactacagggagacgtgcgctgctcccgaaactagaggaacctgcgttttgtctggacatactttctacgatacatttgacaa -continued agcaagataccaattccagggtccctgcaaggagattcttatggccgccgactgtttctggaacacttgggatgtgaaggtttcaca caggaatgttgactcttacactgaagtagagaaagtacgaatcaggaaacaatcgactgtagtagaactcattgttgatggaaaac agattctggttggaggagaagccgtgtccgtcccgtacagctctcagaacacttccatctactggcaagatggtgacatactgacta cagccatcctacctgaagctctggtggtcaagttcaacttcaagcaactgctcgtcgtacatattagagatccattcgatggtaagact tgcggtatttgcggtaactacaaccaggatttcagtgatgattcttttgatgctgaaggagcctgtgatctgaccccaacccaccgg gatgcaccgaagaacagaaacctgaagctgaacgactctgcaatagtctcttcgccggtcaaagtgatcttgatcagaaatgtaac gtgtgccacaagcctgaccgtgtcgaacgatgcatgtacgagtattgcctgaggggacaacagggtttctgtgaccacgcatggga gttcaagaagaatgctacataaagcatggagacaccctagaagtaccagatgaatgcaaacggcgggacaaccc ttctctgtcc attgacctcacctttcacctgctgcggaccctgctggagctggcgcggacgcagagccagcgggagcgcgccgagcagaaccgcat catattcgactcggtgggcaagtga FGF23 Mouse (nucleic acid sequence):
(SEQ ID NO: 301)
Atgctagggacctgccttagactcctggtgggcgtgctctgcactgtctgcagcttgggcactgctagagcctatccggacacttcccc attgcttggctccaactggggaagcctgacccacctgtacacggctacagccaggaccagctatcacctacagatccatagggatggtc atgtagatggcaccccccatcagaccatctacagtgccctgatgattacatcagaggacgccggctctgtggtgataacaggagccatg actcgaaggttcctttgtatggatctccacggcaacatttttggatcgcttcacttcagcccagagaattgcaagttccgccagtggacgct ggagaatggctatgacgtctacttgtcgcagaagcatcactacctggtgagcctgggccgcgccaagcgcatcttccagccgggcacc aacccgccgcccttctcccagttcctggctcgcaggaacgaggtcccgctgctgcatttctacactgttcgcccacggcgccacacgcg cagctactgcgccactgttcattgccaggactgtccttacgaacctgatccaccaaacacagttccaacttcctgtgaagctaaagaa ggagaatgtattgatagcagctgtggcacctgcacgagagacatactatcagatggactgtgtgaaaataaaccaggaaaaaca tgttgccgaatgtgtcagtatgtaattgaatgcagagtagaggccgcaggatggtttagaacattctatggaaagagattccagttcc aggaacctggtacatacgtgttgggtcaaggaaccaagggcggcgactggaaggtgtccatcaccctggagaacctggatggaa ccaaggggctgtgctgaccaagacaagactggaagtggctggagacatcattgacatcgctcaagctactgagaatcccatca ctgtaaacggtggagctgaccctatcatcgccaacccgtacaccatcggcgaggtcaccatcgctgttgttgagatgccaggcttca acatcaccgtcattgagttcttcaaactgatcgtgatcgacatcctcggaggaagatctgtaagaatcgccccagacacagcaaac aaaggaatgatctctggcctctgtggagatcttaaaatgatggaagatacagacttcacttcagatccgaacaactcgctattcag cctaagatcaaccaggagtttgacggttgtccactctatggaaatcctgatgacgttgcatactgcaaaggtcttctggagccgtaca aggacagctgccgcaacccccatcaacttctactactacaccatctcctgcgccttcgcccgctgtatgggtggagacgagcgagcct cacacgtgctgcttgactacagggagacgtgcgctgctcccgaaactagaggaacctgcgttttgtctggacatactttctacgatac atttgacaaagcaagataccaattccagggtccctgcaaggagattcttatggccgccgactgtttctggaacacttgggatgtgaa ggtttcacacaggaatgttgactcttacactgaagtagagaaagtacgaatcaggaaacaatcgactgtagtagaactcattgttga tggaaaacagattctggttggaggagaagccgtgtccgtcccgtacagctctcagaacacttccatctactggcaagatggtgacat actgactacagccatcctacctgaagctctggtggtcaagttcaacttcaagcaactgctcgtcgtacatattagagatccattcgatg gtaagacttgcggtatttgcggtaactacaaccaggatttcagtgatgattcttttgatgctgaaggagcctgtgatctgaccccaac ccaccgggatgcaccgaagaacagaaacctgaagctgaacgactctgcaatagtctcttcgccggtcaaagtgatcttgatcaga aatgtaacgtgtgccacaagcctgaccgtgtcgaacgatgcatgtacgagtattgcctgaggggacaacagggtttctgtgaccac gcatgggagttcaagaagaatgctacataaagcatggagacaccctagaagtaccagatgaatgcaaacgcagcgccgagg acccaccggagcgcgacccactgaacgtgctcaagccgcggccccgcgccacgcctgtgcctgtatcctgctctcgcgagctgccg agcgcagaggaaggtgggccccgcagccagcgatcctctgggggtgctgcgcagaggccgtggagatgctcgcgggggcgcggg aggcgcggataggtgtcgcccctttccaggttcgtctag -continued FGF23 Human (nucleic acid sequence):

(SEQ ID NO: 302)

Atgttgggggcccgcctcaggctctgggtctgtgccttgtgcagcgtctgcagcatgagcgtcctcagagcctatcccaatgcctccc cactgctcggctccagctggggtggcctgatccacctgtacacagccacagccaggaacagctaccacctgcagatccacaaga atggccatgtggatggcgcaccccatcagaccatctacagtgccctgatgatcagatcagaggatgctggctttgtggtgattacag gtgtgatgagcagaagatacctctgcatggatttcagaggcaacattttttggatcacactatttcgacccggagaactgcaggttcca acaccagacgctggaaaacgggtacgacgtctaccactctcctcagtatcacttcctggtcagtctgggccgggcgaagagagcct tcctgccaggcatgaacccaccccgtactcccagttcctgtcccggaggaacgagatccccctaattcacttcaacacccccatac cacggcggcacaccc<u>cggagc</u>tactgcgccactgttcattgccaggactgtccttacgaacctgatccaccaaacacagttccaactt cctgtgaagctaaagaaggagaatgtattgatagcagctgtggcacctgcacgagagacatactatcagatggactgtgtgaaaa taaaccaggaaaaacatgttgccgaatgtgtcagtatgtaattgatgcagagtagaggccgcaggatggtttagaacattctatg gaaagagattccagttccaggaacctggtacatacgtgttgggtcaaggaaccaagggcggcgactggaaggtgtccatcaccct ggagaacctggatggaaccaagggggctgtgctgaccaagacaagactggaagtggctggagacatcattgacatcgctcaag ctactgagaatccatcactgtaaacggtggagctgacctatcatcgccaacccgtacaccatcggcgaggtcaccatcgctgttg ttgagatgccaggcttcaacatcaccgtcattgagttcttcaaactgatcgtgatcgacatcctcggaggaagatctgtaagaatcgc cccagacacagcaaacaaaggaatgatctctggcctctgtggagatcttaaaatgatggaagatacagacttcacttcagatccag aacaactcgctattcagcctaagatcaaccaggagtttgacggttgtccactctatggaaatcctgatgacgttgcatactgcaaag gtcttctggagccgtacaaggacagctgccgcaacccccatcaacttctactactacaccatctcctgcgccttcgcccgctgtatggg tggagacgagcgagcctcacacgtgctgcttgactacagggagacgtgcgctgctcccgaaactagaggaacctgcgttttgtctg gacatactttctacgatacatttgacaaagcaagataccaattccagggtccctgcaaggagattcttatggccgccgactgtttctg gaacacttgggatgtgaaggtttcacaaggaatgttgactcttacactgaagtagagaaagtacgaatcaggaaacaatcgact gtagtagaactcattgttgatggaaaacagattctggttggaggagaagccgtgtccgtcccgtacagctctcagaacacttccatct actggcaagatggtgacatactgactacagccatcctacctgaagctctggtggtcaagttcaacttcaagcaactgctcgtcgtac atattagagatccattcgatggtaagacttgcggtatttgcggtaactacaaccaggatttcagtgatgattcttttgatgctgaaggag cctgtgatctgaccccaacccaccgggatgcaccgaagaacagaaacctgaagctgaacgactctgcaatagtctcttcgccgg tcaaagtgatcttgatcagaaatgtaacgtgtgccacaagcctgaccgtgtcgaacgatgcatgtacgagtattgcctgaggggac aacagggtttctgtgaccacgcatgggagttcaagaaagaatgctacataaagcatggagacaccctagaagtaccagatgaat gcaaac<u>cggagc</u>gccgaggacgactcggagcgggaccccctgaacgtgctgaagcccgggcccggatgaccccgccccggcc tcctgttcacaggagctcccgagcgccgaggacaacagcccgatggccagtgacccattaggggtggtcaggggcggtcgagtgaa cacgcacgctggggaacgggccggaaggctgccgccccttcgccaagttcatctag IL1B Mouse (nucleic acid sequence):

(SEQ ID NO: 303)

Atggcaactgttcctgaactcaactgtgaaatgccacctttttgacagtgatgagaatgacctgttctttgaagttgacgacccaaaaga tgaagggctgcttccaaacctttgacctgggctgtcctgatgagagcatccagcttcaaatctcgcagcagcacatcaacaagagcttca ggcaggcagtatcactcattgtggctgtgagaagctgtggcagctacctgtgtctttcccgtggaccttccaggatgaggacatgagca ccttcttttccttcatctttgaagaagagcccatcctctgtgactcatgggatgatgatgataacctgctggtgtgt<u>gacgtt</u>ccctactgcgc cactgttcattgccaggactgtccttacgaacctgatccaccaaacacagttccaacttcctgtgaagctaaagaaggagaatgtatt gatagcagctgtggcacctgcacgagagacatactatcagatggactgtgtgaaaataaaccaggaaaaacatgttgccgaatgt gtcagtatgtaattgaatgcagagtagaggccgcaggatggtttagaacattctatggaaagagattccagttccaggaacctggta catacgtgttgggtcaaggaaccaagggcggcgactggaaggtgtccatcaccctggagaacctggatggaaccaagggggct gtgctgaccaagacaagactggaagtggctggagacatcattgacatcgctcaagctactgagaatccatcactgtaacggtg gagctgacctatcatcgccaacccgtacaccatcggcgaggtcaccatcgctgttgttgagatgccaggcttcaacatcaccgtca -continued ttgagttcttcaaactgatcgtgatcgacatcctcggaggaagatctgtaagaatcgccccagacacagcaaacaaaggaatgatc tctggcctctgtggagatcttaaaatgatggaagatacagacttcacttcagatccagaacaactcgctattcagcctaagatcaacc aggagtttgacggttgtccactctatggaaatcctgatgacgttgcatactgcaaaggtcttctggagccgtacaaggacagctgcc gcaaccccatcaacttctactactacaccatctcctgcgccttcgccgctgtatgggtggagacgagcgagcctcacacgtgctgct tgactacagggagacgtgcgctgctcccgaaactagaggaacctgcgttttgtctggacatactttctacgatacatttgacaaagc aagataccaattccagggtccctgcaaggagattcttatggccgccgactgtttctggaacacttgggatgtgaaggtttcacacag gaatgttgactcttacactgaagtagagaaagtacgaatcaggaaacaatcgactgtagtagaactcattgttgatggaaaacaga ttctggttggaggagaagccgtgtccgtcccgtacagctctcagaacacttccatctactggcaagatggtgacatactgactacag ccatcctacctgaagctctggtggtcaagttcaacttcaagcaactgctcgtcgtacatattagagatccattcgatggtaagacttgc ggtatttgcggtaactacaaccaggatttcagtgatgattcttttgatgctgaaggagcctgtgatctgaccccaacccaccgggat gcaccgaagaacagaaacctgaagctgaacgactctgcaatagtctcttcgccggtcaaagtgatcttgatcagaaatgtaacgtg tgccacaagcctgaccgtgtcgaacgatgcatgtacgagtattgcctgaggggacaacagggtttctgtgaccacgcatgggagtt caagaaagaatgctacataaagcatggagacaccctagaagtaccagatgaatgcaaactggtgtgt<u>gacgtt</u>cccgttcccatta gacaactgcactacaggctccgagatgaacaacaaaaagcctcgtgctgtcggacccatatgagctgaaagctctccacctcaatgg acagaatatcaaccaacaagtgatattctccatgagctttgtacaaggagaaccaagcaacgacaaaatacctgtggccttgggcctcaa aggaaagaatctatacctgtcctgtgtaatgaaagacggcacaccccacctgcagctggagagtgtggatcccaagcaatacccaaag aagaagatggaaaaacggtttgtcttcaacaagatagaagtcaagagcaaagtggagtttgagtctgcagagttccccaactggtacatc agcacctcacaagcagagcacaagcctgtcttcctgggaaacaacagtggtcaggacataattgacttcaccatggaatccgtgtcttcc taa IL1B Human (nucleic acid sequence):

(SEQ ID NO: 304)

Atggcagaagtacctgagctcgccagtgaaatgatggcttattacagtggcaatgaggatgacttgttctttgaagctgatggccctaaa cagatgaagtgctccttccaggacctggacctctgccctctggatggcggcatccagctacgaatctccgaccaccactacagcaagg gcttcaggcaggccgcgtcagttgttgtggccatggacaagctgaggaagatgctggttccctgcccacagaccttccaggagaatga cctgagcaccttctttcccttcatctttgaagaagaacctatcttcttcgacacatgggataacgaggcttatgtgcac<u>gatgca</u>ccttactg cgccactgttcattgccaggactgtccttacgaacctgatccaccaaacacagttccaacttcctgtgaagctaaagaaggagaatg tattgatagcagctgtggcacctgcacgagagacatactatcagatggactgtgtgaaaataaaccaggaaaaacatgttgccga atgtgtcagtatgtaattgaatgcagagtagaggccgcaggatggtttagaacattctatggaaagagattccagttccaggaacct ggtacatacgtgttgggtcaaggaaccaagggcggcgactggaaggtgtccatcaccctggagaacctggatggaaccaaggg ggctgtgctgaccaagacaagactggaagtggctggagacatcattgacatcgctcaagctactgagaatcccatcactgtaaac ggtggagctgacccctatcatcgccaacccgtacaccatcggcgaggtcaccatcgctgttgttgagatgccaggcttcaacatcacc gtcattgagttcttcaaactgatcgtgatcgacatcctcggaggaagatctgtaagaatcgccccagacacagcaaacaaaggaat gatctctggcctctgtggagatcttaaaatgatggaagatacagacttcacttcagatccagaacaactcgctattcagcctaagatc aaccaggagtttgacggttgtccactctatggaaatcctgatgacgttgcatactgcaaaggtcttctggagccgtacaaggacagc tgccgcaaccccatcaacttctactactacaccatctcctgcgccttcgccgctgtatgggtggagacgagcgagcctcacacgtg ctgcttgactacagggagacgtgcgctgctcccgaaactagaggaacctgcgttttgtctggacatactttctacgatacatttgaca aagcaagataccaattccagggtccctgcaaggagattcttatggccgccgactgtttctggaacacttgggatgtgaaggtttcac acaggaatgttgactcttacactgaagtagagaaagtacgaatcaggaaacaatcgactgtagtagaactcattgttgatggaaaa cagattctggttggaggagaagccgtgtccgtcccgtacagctctcagaacacttccatctactggcaagatggtgacatactgact acagccatcctacctgaagctctggtggtcaagttcaacttcaagcaactgctcgtcgtacatattagagatccattcgatggtaaga cttgcggtattttgcggtaactacaaccaggatttcagtgatgattcttttgatgctgaaggagcctgtgatctgaccccaacccaccg ggatgcaccgaagaacagaaacctgaagctgaacgactcgtcaatagtctcttcgccggtcaaagtgatcttgatcagaaatgta -continued acgtgtgccacaagcctgaccgtgtcgaacgatgcatgtacgagtattgcctgaggggacaacagggtttctgtgaccacgcatgg gagttcaagaaagaatgctacataaagcatggagacaccctagaagtaccagatgaatgcaaaTatgtgcacgatgcacctgta cgatcactgaactgcacgctccgggactcacagcaaaaaagcttggtgatgtctggtccatatgaactgaaagctctccacctccaggg acaggatatggagcaacaagtggtgttctccatgtcctttgtacaaggagaagaaagtaatgacaaaatacctgtggccttgggcctcaa ggaaaagaatctgtacctgtcctgcgtgttgaaagtgataagcccactctacagctggagagtgtagatcccaaaaattacccaaagaa gaagatggaaaagcgatttgtcttcaacaagatagaaatcaataacaagctggaatttgagtctgcccagttccccaactggtacatcag caccctctcaagcagaaaacatgcccgtcttcctgggagggaccaaaggcggccaggatataactgacttcaccatgcaatttgtgtcttc ctaa TNFA Mouse (nucleic acid sequence):
(SEQ ID NO: 305)
Atgagcacagaaagcatgatccgcgacgtggaactggcagaagaggcactcccccaaaagatggggggcttccagaactccaggc ggtgcctatgtctcagcctcttctcattcctgcttgtggcaggggccaccacgctcttctgtctactgaacttcggggtgatcggtccccaa agggatgagaagttcccaaatggcctccctctcatcagttctatggcccagaccctcacactcagatactgcgccactgttcattgccag gactgtccttacgaacctgatccaccaaacacagttccaacttcctgtgaagctaaagaaggagaatgtattgatagcagctgtggc acctgcacgagacatactatcagatggactgtgtgaaaataaacccaggaaaaacatgttgccgaatgtgtcagtatgtaattga atgcagagtagaggccgcaggatggtttagaacattctatggaaagagattccagttccaggaacctggtacatacgtgttgggtc aaggaaccaagggcggcgactggaaggtgtccatcaccctggagaacctggatggaaccaaggggggctgtgctgaccaagac aagactggaagtggctggagacatcattgacatcgctcaagctactgagaatcccatcactgtaaacggtggagctgaccctatca tcgccaacccgtacaccatcggcgaggtcaccatcgctgttgttgagatgccaggcttcaacatcaccgtcattgagttcttcaaact gatcgtgatcgacatcctcggaggaagatctgtaagaatcgcccagacacagcaaacaaaggaatgatctctggcctctgtgga gatcttaaaatgatggaagatacagacttcacttcagatccagaacaactcgctattcagcctaagatcaaccaggagtttgacggt tgtccactctatggaaatcctgatgacgttgcatactgcaaaggtcttctggagccgtacaaggacagctgccgcaacccccatcaac ttctactactacaccatctcctgcgccttcgcccgctgtatgggtggagacgagcgagcctcacacgtgctgcttgactacaggag acgtgcgctgctcccgaaactagaggaacctgcgttttgtctggacatactttctacgatacatttgacaaagcaagataccaattcc agggtccctgcaaggagattcttatggccgccgactgtttctggaacactttgggatgtgaaggtttcacacaggaatgttgactcttac actgaagtagagaaagtacgaatcaggaaacaatcgactgtagtagaactcattgttgatggaaaacagattctggttggaggag aagccgtgtccgtcccgtacagctctcagaacacttccatctactggcaagatggtgacatactgactacagccatcctacctgaag ctctggtggtcaagttcaacttcaagcaactgctcgtcgtacatattagagatccattcgatggtaagacttgcggtatttgcggtaact acaaccaggatttcagtgatgattcttttgatgctgaggagcctgtgatctgaccccaacccaccgggatgcaccgaagaacag aaacctgaagctgaacgactctgcaatagtctcttcgccggtcaaagtgatcttgatcagaaatgtaacgtgtgccacaagcctgac cgtgtcgaacgatgcatgtacgagtattgcctgagggggacaacagggtttctgtgaccacgcatgggagttcaagaaagaatgcta cataaagcatggagacaccctagaagtaccagatgaatgcaaactcagatcatcttctcaaaattcgagtgacaagcctgtagccca cgtcgtagcaaaccaccaagtggaggagcagctggagtggctgagccagcgcgccaacgccctcctggccaacggcatggatctca aagacaaccaactagtggtgccagccgatgggttgtaccttgtctactcccaggttctcttcaagggacaaggctgccccgactacgtgc tcctcacccacaccgtcagccgatttgctatctcataccaggagaaagtcaacctcctctctgccgtcaagagccctgccccaaggac acccctgaggggctgagctcaaaccctggtatgagcccatatacctgggaggagtcttccagctggagaaggggaccaactcagc gctgaggtcaatctgcccaagtacttagactttgcggagtccgggcaggtctactttggagtcattgctctgtga TNFA Human (nucleic acid sequence):
(SEQ ID NO: 306)
Atgagcactgaaagcatgatccgggacgtggagctggccgaggaggcgctccccaagaagacaggggggccccagggctccag gcggtgcttgttcctcagcctcttctccttcctgatcgtggcaggcgccaccacgctcttctgcctgctgcactttggagtgatcggcccc agagggaagagttccccagggacctctctctaatcagccctctggcccaggcagtcagatactgcgccactgttcattgccaggactgt -continued ccttacgaacctgatccaccaaacacagttccaacttcctgtgaagctaaagaaggagaatgtattgatagcagctgtggcacctg cacgagagacatactatcagatggactgtgtgaaaataaaccaggaaaaacatgttgccgaatgtgtcagtatgtaattgaatgca gagtagaggccgcaggatggtttagaacattctatggaaagagattccagttccaggaacctggtacatacgtgtttgggtcaagga accaagggcggcgactggaaggtgtccatcaccctggagaacctggatggaaccaaggggggctgtgctgaccaagacaagact ggaagtggctggagacatcattgacatcgctcaagctactgagaatcccatcactgtaaacggtggagctgaccctatcatcgcca acccgtacaccatcggcgaggtcaccatcgctgttgttgagatgccaggcttcaacatcaccgtcattgagttcttcaaactgatcgtg atcgacatcctcggaggaagatctgtaagaatcgccccagacacagcaaacaaaggaatgatctctggcctctgtggagatctta aaatgatggaagatacagacttcacttcagatccagaacaactcgctattcagcctaagatcaaccaggagtttgacggttgtccac tctatggaaatcctgatgacgttgcatactgcaaaggtcttctggagccgtacaaggacagctgccgcaacccccatcaacttctacta ctacaccatctcctgcgccttcgcccgctgtatgggtggagacgagcgagcctcacacgtgctgcttgactacagggagacgtgcg ctgctcccgaaactagaggaacctgcgttttgtctggacatactttctacgatacatttgacaaagcaagataccaattccagggtcc ctgcaaggagattcttatggccgccgactgtttctggaacacttgggatgtgaaggtttcacacaggaatgttgactcttacactgaa gtagagaaagtacgaatcaggaaacaatcgactgtagtagaactcattgttgatggaaaacagattctggttggaggagaagccg tgtccgtcccgtacagctctcagaacacttccatctactggcaagatggtgacatactgactacagccatcctacctgaagctctggt ggtcaagttcaacttcaagcaactgctcgtcgtacatattagagatccattcgatggtaagacttgcggtatttgcggtaactacaacc aggatttcagtgatgattcttttgatgctgaaggagcctgtgatctgaccccaacccaccgggatgcaccgaagaacagaaacct gaagctgaacgactctgcaatagtctcttcgccggtcaaagtgatcttgatcagaaatgtaacgtgtgccacaagcctgaccgtgtc gaacgatgcatgtacgagtattgcctgaggggacaacagggtttctgtgaccacgcatgggagttcaagaaagaatgctacataa agcatggagacaccctagaagtaccagatgaatgcaaa<u>gtcagat</u>catcttctcgaaccccgagtgacaagcctgtagcccatgttg tagcaaaccctcaagctgaggggcagctccagtggctgaaccgccgggccaatgccctcctggccaatggcgtggagctgagagat aaccagctggtggtgccatcagagggcctgtacctcatctactcccaggtcctcttcaagggccaaggctgcccctccacccatgtgct cctcacccacaccatcagccgcatcgccgtctcctaccagaccaaggtcaacctcctctctgccatcaagagcccctgccagagggag accccagaggggctgaggccaagccctggtatgagcccatctatctgggaggggtcttccagctggagaagggtgaccgactcag cgctgagatcaatcggcccgactatctcgactttgccgagtctgggcaggtctactttgggatcattgccctgtga IFNG Mouse (nucleic acid sequence):

(SEQ ID NO: 307)

Atgaacgctacacactgcatcttggctttgcagctcttcctcatggctgtttctggctgttactgccacggcacagtcattgaaagcctaga aagtctgaataactattttaactcaagtggcatagatgtggaagaaaagagtctcttcttggatatctggaggaactggcaaaaggatggt gacatgaaaatcctgcagagccagattatctctttctacctcagactcttttgaagtcttgaaagacaatcaggccatcagcaacaacataa gcgtcattgaatcacacctgattactaccttcttcagcaacagcaaggcgaaaaaggatgcattcatgagtattgccaagtttgaggtcaa caacccacaggtccagcgccaagcattcaatgagctcatccgagtggtccaccagctgttgccggaatccagcctc<u>aggaag</u>tactgc gccactgttcattgccaggactgtccttacgaacctgatccaccaaacacagttccaacttcctgtgaagctaaagaaggagaatgt attgatagcagctgtggcacctgcacgagagacatactatcagatggactgtgtgaaaataaaccaggaaaaacatgttgccgaa tgtgtcagtatgtaattgatgcagagtagaggccgcaggatggtttagaacattctatggaaagagattccagttccaggaacctg gtacatacgtgtttgggtcaaggaaccaaggcggcgactggaaggtgtccatcaccctggagaacctggatggaaccaagggg gctgtgctgaccaagacaagactggaagtggctggagacatcattgacatcgctcaagctactgagaatcccatcactgtaaacg gtggagctgaccctatcatcgccaacccgtacaccatcggcgaggtcaccatcgctgttgttgagatgccaggcttcaacatcaccg tcattgagttcttcaaactgatcgtgatcgacatcctcggaggaagatctgtaagaatcgccccagacacagcaaacaaaggaatg atctctggcctctgtggagatcttaaaatgatggaagatacagacttcacttcagatccagaacaactcgctattcagcctaagatca accaggagtttgacggttgtccactctatggaaatcctgatgacgttgcatactgcaaaggtcttctggagccgtacaaggacagct gccgcaacccccatcaacttctactactacaccatctcctgcgccttcgcccgctgtatgggtggagacgagcgagcctcacacgtgc tgcttgactacagggagacgtgcgctgctcccgaaactagaggaacctgcgttttgtctggacatactttctacgatacatttgacaa agcaagataccaattccagggtccctgcaaggagattcttatggccgccgactgtttctggaacacttgggatgtgaaggtttcaca
caggaatgttgactcttacactgaagtagagaaagtacgaatcaggaaacaatcgactgtagtagaactcattgttgatggaaaac
agattctggttggaggagaagccgtgtccgtcccgtacagctctcagaacacttccatctactggcaagatggtgacatactgacta
cagccatcctacctgaagctctggtggtcaagttcaacttcaagcaactgctcgtcgtacatattagagatccattcgatggtaagact
tgcggtatttgcggtaactacaaccaggatttcagtgatgattcttttgatgctgaaggagcctgtgatctgacccccaacccaccgg
gatgcaccgaagacagaaacctgaagctgaacgactctgcaatagtctcttgccggtcaaagtgatcttgatcagaaatgtaac
gtgtccacaagcctgaccgtgtcgaacgatgcatgtacgagtattgcctgaggggacaacagggtttctgtgaccacgcatggga
gttcaagaaagaatgctacataaagcatggagacaccctagaagtaccagatgaatgcaaa<u>cggaaa</u>aggagtcgctgctga IFNG Human (nucleic acid sequence):

(SEQ ID NO: 308)

Atgaaatatacaagttatatcttggcttttcagctctgcatcgttttgggttctcttggctgttactgccaggacccatatgtaaaagaag
cagaaaaaccttaagaaatatttttaatgcaggtcattcagatgtagcggataatggaactcttttcttaggcattttgaagaattggaaa
gaggagagtgacagaaaaataatgcagagccaaattgtctccttttacttcaaactttttaaaaactttaaagatgaccagagcatc
caaagagtgtggagaccatcaaggaagacatgaatgtcaagttttttcaatagcaacaaaagaaacgagatgacttcgaaaa
gctgactaattattcggtaactgacttgaatgtccaacgcaaagcaatacatgaactcatccaagtgatggctgaactgtcgccagc
agctaaaacagggaagcgaaaaggagtcagatgctgtttcgaggt<u>cgaaga</u>tactgcgccactgttcattgccaggactgtcctt
acgaacctgatccaccaaacacagttccaacttcctgtgaagctaaagaaggagaatgtattgatagcagctgtggcacctgcac
gagagacatactatcagatggactgtgtgaaaataaaccaggaaaaacatgttgccgaatgtgtcagtatgtaattgaatgcaga
gtagaggccgcaggatggtttagaacattctatggaaagagattccagttccaggaacctggtatacgtgttgggtcaaggaac
caagggcggcgactggaaggtgtccatcaccctggagaacctggatggaaccaagggggctgtgctgaccaagacaagactg
gaagtggctggagacatcattgacatcgctcaagctactgagaatcccatcactgtaaacggtggagctgacctatcatcgccaa
cccgtacaccatcggcgaggtcaccatcgctgttgttgagatgccaggcttcaacataccgtcattgagttcttcaaactgatcgtga
tcgacatcctcggaggaagatctgtaagaatcgccccagacacagcaaacaaaggaatgatctctggcctctgtggagatcttaa
aatgatggaagatacagacttcacttcagatccgaacaactcgctattcagcctaagatcaaccaggagtttgacggttgtccact
ctatggaaatcctgatgacgttgcatactgcaaaggtcttctggagccgtacaaggacagctgccgcaaccccatcaacttctacta
ctacaccatctcctgcgccttcgcccgctgtatgggtggagacgagcgagcctcacacgtgctgcttgactacagggagacgtgcg
ctgctcccgaaactagaggaacctgcgttttgtctggacatactttctacgatacatttgacaaagcaagataccaattccagggtcc
ctgcaaggagattcttatggccgccgactgtttctggaacacttgggatgtgaaggtttcacacaggaatgttgactcttacactgaa
gtagagaaagtacgaatcaggaaacaatcgactgtagtagaactcattgttgatggaaaacagattctggttggaggagaagccg
tgtccgtcccgtacagctctcagaacacttccatctactggcaagatggtgacatactgactacagccatcctacctgaagctctggt
ggtcaagttcaacttcaagcaactgctcgtcgtacattagagatccattcgatggtaagacttgcggtatttgcggtaactacaacc
aggatttcagtgatgattcttttgtgctgaaggagcctgtgatctgaccccaacccaccgggatgcaccgaagaacagaaacct
gaagctgaacgactctgcaatagtctcttcgccggtcaaagtgatcttgatcagaaatgtaacgtgtgccacaagcctgaccgtgtc
gaacgatgcatgtacgagtattgcctgaggggacaacagggtttctgtaccacgcatgggagttcaagaaagaatgctacataa
agcatggagacaccctagaagtaccagatgaatgcaaaggt<u>cgaagag</u>catcccagtaa Sortilin Mouse (nucleic acid sequence):

(SEQ ID NO: 309)

Atggagcggccccggggagctgcggacggccttttgcgctggcccctcggcctcctcctgctccttcaactgctgcctcctgccgccg
tcggccaggaccggctggacgcgccgccgccgccgcgcctcctctgctgcgctgggccggtccggtcggggtgagctggggct
gcgcgccgccgcgcccggggcccgtcccccgcgctggccgttgg<u>cgccgc</u>tactgcgccactgttcattgccaggactgtcctt
acgaacctgatccaccaaacacagttccaacttcctgtgaagctaaagaaggagaatgtattgatagcagctgtggcacctgcac
gagagacatactatcagatggactgtgtgaaaataaaccaggaaaaacatgttgccgaatgtgtcagtatgtaattgaatgcaga -continued

```
gtagaggccgcaggatggtttagaacattctatggaaagagattccagttccaggaacctggtactacgtgttgggtcaaggaac
caagggcggcgactggaaggtgtccatcaccctggagaacctggatggaaccaaggggctgtgctgaccaagacaagactg
gaagtggctggagacatcattgacatcgctcaagctactgagaatcccatcactgtaaacggtggagctgaccctatcatcgccaa
cccgtacaccatcggcgaggtcaccatcgctgttgttgagatgccaggcttcaacatcaccgtcattgagttcttcaaactgatcgtga
tcgacatcctcggaggaagatctgtaagaatcgccccagacacagcaaacaaaggaatgatctctggcctctgtggagatcttaa
aatgatggaagatacagacttcacttcagatccagaacaactcgctattcagcctaagatcaaccaggagtttgacgttgtccact
ctatggaaatcctgatgacgttgcatactgcaaaggtcttctggagccgtacaaggacagctgccgcaacccatcaacttctacta
ctacaccatctcctgcgccttcgcccgctgtatgggtggagacgagcagcctcacacgtgctgcttgactacagggagacgtgcg
ctgctcccgaaactagaggaacctgcgttttgtctggacatactttctacgatacatttgacaaagcaagataccaattccagggtcc
ctgcaaggagattcttatggccgccgactgtttctggaacacttgggatgtgaaggtttcacacaggaatgttgactcttacactgaa
gtagagaaagtacgaatcaggaaacaatcgactgtagtagaactcattgttgatggaaaacagattctggttggaggagaagccg
tgtccgtcccgtacagctctcagaacacttccatctactggcaagatggtgacatactgactacagccatcctacctgaagctctggt
ggtcaagttcaacttcagcaactgctcgtcgtacatattagagatccattcgatggtaagacttgcggtatttgcggtaactacaacc
aggatttcagtgatgattcttttgatgctgaaggagcctgtgatctgaccccaacccaccgggatgcaccgaagaacagaaacct
gaagctgaacgactctgcaatagtctcttcgccggtcaaagtgatcttgatcagaaatgtaacgtgtgccacaagcctgaccgtgtc
gaacgatgcatgtacgagtattgcctgaggggacaacagggtttctgtgaccacgcatgggagttcaagaaagaatgctacataa
agcatggagacaccctagaagtaccagatgaatgcaaacgccgcggcgcgcccgccgaggaccaagactgcggccgcctccc
ggacttcatcgccaagctgaccaacaatacgcaccagcatgtctttgatgacctcagtggctcagtgtccttgtcctgggttggagacag
cactggggttattctcgtcctgaccactttccaagtgcctctggtaattgtgagctttggacagtccaagttgtatcgaagtgaggattatgg
aaagaactttaaggatattacaaatctcatcaataacaccttcattcggacggaatttggcatggctattggtcctgagaactctggaaagg
tgatactaacagcggaggtgtccggggaagccgaggcggaagagtgttcaggtcatcagactttgccaagaactttgtgcaaacaga
tctccccttcatcctctgacgcagatgatgtacagccctcagaattctgattacctgttagctctcagcaccgaaaatggcctgtgggtgtc
caagaattttggggaaaaatgggaagaaatccacaaagcagtatgtttggccaaatggggaccaaacaacatcatcttctttaccaccca
tgtgaatggctcctgcaaagctgatcttggtgccctggaattatggagaacatccgacttgggaaaaaccttcaaaaccattggtgtgaaa
atctactcctttggtcttgggggccgtttccttttttgcctctgtgatggctgataaggacacaacaagaaggatccatgtgtcaacagacca
gggggacacatggagcatggcacaacttccttctgtgggacaggaacagttctactccatcctggcagccaatgaggacatggtcttca
tgcatgtagatgaacctggagataccgggtttggcaccaatctttacctctgatgatcgaggcattgtctactccaagtctctggacagacat
ctctataccaccacaggcggggagacggactttaccaacgtgacttccctccgtggggtctatataacaagcacgctctcagaagataa
ctctattcagagcatgatcactttgaccagggaggacggtgggagcacctgcggaagccggagaacagcaagtgcgacgctaccgc
aaagaacaagaacgagtgcagccttcatatccatgcttcttatagcatctcccagaagctaaacgttccaatggcccacttccgagccc
aatgctgtgggcatagtcatcgctcacggtagtgtgggagatgccatctcggtgatggtcccagatgtgtacatctcagatgatgggggt
tactcctgggcgaagatgctagaaggaccacattactataccatcctggactctggaggcatcattgtggccattgagcacagcaaccgt
cctatcaatgtgattaagtctccacagatgaaggccagtgctggcagagctatgtgttcacacaggagcccatctacttcactgggcttg
cttccgagcctggagccaggtccatgaacatcagcatctggggattcacagagtctttcattacccgccagtgggtctcctacacagtcg
atttcaaagacatccttgagcggaattgtgaagaggatgactataccacgtggctggcacactccacagaccctggagattacaaagac
ggctgcattttgggctataaagaacagttcctacggctacgaagtcatccgtctgtcagaatggtcgagactatgttgtggccaagcag
ccatccgtctgtccgtgttccctggaggacttcctctgtgactttggctacttccgtccggagaacgcctcagagtgcgtggagcagcctg
aactgaaggggcatgagttagagttctgtctgtacggcaaggaggagcacctgacaacaaatgggtaccggaaaatcccaggagaca
aatgccaaggtgggatgaatcccgccagagaagtaaaagacttgaaaaagaaatgcacaagcaacttcttgaaccccacaaagcagg
actcccgcccacagggacacagcttgtcccagaatccagctccgcctcctcttggatacactgaaaacacacacttcctatctcctaccc
agaagcagaattccaagtcaaattctgtccctattatcctggccatcgtgggactgatgcttgtcacagtcgtagcaggagtcctcattgtg
``` aagaaatatgtctgtggcggaaggttcctggtgcaccggtactcggtgctacagcagcacgcagaggctgacggcgtagaggctttgg attcaacctcccacgctaaaagcggatatcacgacgactcagatgaggacctcctggaatag Sortilin Human (nucleic acid sequence):

(SEQ ID NO: 310)

Atggagcggccctggggagctgcggacggcctctcgcgctggccccatggcctcggcctcctcctcctcctgcagctgctgccgcc gtcgaccctcagccaggaccggctggacgcgccgccgccgcccgctgcgccgctgccgcgctggtctggccccatcggggtgagc tgggggctgcgggcggccgcagccgggggcgcgtttccccgcggcggccgttggcgtcgctactgcgccactgttcattgccagg actgtccttacgaacctgatccaccaaacacagttccaacttcctgtgaagctaaagaaggagaatgtattgatagcagctgtggca cctgcacgagagacatactatcagatggactgtgtgaaaataaaccaggaaaaacatgttgccgaatgtgtcagtatgtaattgaa tgcagagtagaggccgcaggatggtttagaacattctatggaaagagattccagttccaggaacctggtacatacgtgttgggtca aggaaccaagggcggcgactggaaggtgtccatcaccctggagaacctggatggaaccaagggggctgtgctgaccaagaca agactggaagtggctggagacatcattgacatcgctcaagctactgagaatcccatcactgtaaacggtggagctgacccctatcat cgccaacccgtacaccatcggcgaggtcaccatcgctgttgttgagatgccaggcttcaacatcaccgtcattgagttcttcaaactg atcgtgatcgacatcctcggaggaagatctgtaagaatcgcccagacacagcaaacaaaggaatgatctctggcctctgtggag atcttaaaatgatggaagatacagacttcacttcagatccagaacaactcgctattcagcctaagatcaaccaggagtttgacggtt gtccactctatggaaatcctgatgacgttgcatactgcaaaggtcttctggagccgtacaaggacagctgccgcaaccccatcaact tctactactacaccatctcctgcgccttcgcccgctgtatgggtggagacgagcgagcctcacacgtgctgcttgactacaggaga cgtgcgctgctcccgaaactagaggaacctgcgttttgtctggacatactttctacgatacatttgacaaagcaagataccaattcca gggtccctgcaaggagattcttatggccgccgactgtttctggaacacttgggatgtgaaggtttcacacaggaatgttgactcttaca ctgaagtagagaaagtacgaatcaggaaacaatcgactgtagtagaactcattgttgatggaaaacagattctggttggaggaga agccgtgtccgtcccgtacagctctcagaacacttccatctactggcaagatggtgacatactgactacagccatcctacctgaagct ctggtggtcaagttcaacttcaagcaactgctcgtcgtacatattagagatccattcgatggtaagacttgcggtatttgcggtaacta caaccaggatttcagtgatgattcttttgatgctgaaggagcctgtgatctgaccccaacccaccgggatgcaccgaagaacaga aacctgaagctgaacgactctgcaatagtctcttcgccggtcaaagtgatcttgatcagaaatgtaacgtgtgccacaagcctgacc gtgtcgaacgatgcatgtacgagtattgcctgaggggacaacagggtttctgtgaccacgcatgggagttcaagaaagaatgctac ataaagcatggagacacccctagaagtaccagatgaatgcaaacgtcgcagcgcgccgggcgaggacgaggagtgcggccggg tccgggacttcgtcgccaagctggccaacaacacgcaccagcatgtgtttgatgatctcagaggctcagtatccttgtcctgggttggag atagcactggggtcattctagtcttgactaccttccatgtaccactggtaattatgacttttggacagtccaagctatatcgaagtgaggatta tgggaagaactttaaggatattacagatctcatcaataacacctttattcggactgaatttggcatggctattggtcctgagaactctggaaa ggtggtgttaacagcagaggtgtctggaggaagtcgtggaggaagaatctttagatcatcagattttgcgaagaattttgtgcaaacagat ctcccttttcatcctctcactcagatgatgtatagccctcagaattctgattatcttttagctctcagcactgaaaatggcctgtgggtgtccaa gaatttgggggaaaatgggaagaaatccacaaagcagtatgtttggccaaatggggatcagacaacaccatcttctttacaacctatgc aaatggctcctgcaaagctgaccttggggctctggaattatggagaacttcagacttgggaaaaagcttcaaaactattggtgtgaaaatc tactcatttggtcttggggaacgtttcctttttgcctctgtgatggctgataaggatacaacaagaaggatccacgtttcaacagatcaagg ggacacatggagcatggcccagctcccctccgtgggacaggaacagttctattctattctggcagcaaatgatgacatggtattcatgca tgtagatgaacctggagacactgggtttggcacaatcttacctcagatgatcgaggcattgtctattccaagtctttggaccgacatctcta cactaccacaggcggagagacggactttaccaacgtgacctccctccgcggcgtctacataacaagcgtgctctccgaagataattcta tccagaccatgatcactttttgaccaaggaggaaggtggacgcacctgaggaagcctgaaaacagtgaatgtgatgctacagcaaaaaa caagaatgagtgcagccttcatattcatgcttcctacagcatctcccagaaactgaatgttccaatggcccactctcagagccgaatgcc gtaggcattgtcattgctcatggtagcgtgggggatgccatctcagtgatggttccagatgtgtacatctcagatgatgggggttactcctg gacaaagatgctggaaggaccccactattacaccatcctggattctggaggcatcattgtggccattgagcacagcagccgtcctatca -continued atgtgattaagttctccacagacgaaggtcaatgctggcaaacctacacgttccaggggaccccatctatttcactggcctagcttcaga
acctggagctaggtccatgaatatcagcatttggggcttcacagaatctttcctgaccagccagtgggtctcctacaccattgattttaaag
atatccttgaaaggaactgtgaagagaaggactataccatatggctggcacactccacagaccctgaagattatgaagatggctgcatttt
gggctacaaagaacagtttctgcggctacgcaagtcatccgtgtgtcagaatggtcgagactatgttgtgaccaagcagccctccatctg
cctctgttccctggaggactttctctgtgattttggctactaccgtccagaaaatgactccaagtgtgtggaacagccagaactgaagggc
cacgacctggagttttgtctgtacggaagagaagaacacctaacaacaaatgggtaccggaaaattccaggggacaaatgccagggt
ggggtaaatccagttcgagaagtaaaagacttgaaaaagaaatgcacaagcaacttttttgagtccggaaaaacagaattccaagtcaaa
ttctgttccaattatcctggccatcgtgggattgatgctggtcacagtcgtagcaggagtgctcattgtgaagaaatatgtctgtgggggaa
ggttcctggtgcatcgatactctgtgctgcagcagcatgcagaggccaatggtgtggatggtgtggatgctttggacacagcctcccaca
ctaataaaagtggttatcatgatgactcagatgaggacctcttggaatag Neuropeptide W Mouse (nucleic acid sequence):
(SEQ ID NO: 311)
Ctggcgtctaacagagaagtgcggggccctgggcccgggactcccaggaaccggccctgctgccctgctgctgcttctgctcttg
ctaccgctgcccgccagcgcctggtataagcacgtggcgagtcccgctatcacacagtgggtcgtgcctccgggctgctcatgggg
ctgcgccgctcgccctaccagtggcgccgttactgcgccactgttcattgccaggactgtccttacgaacctgatccaccaaacaca
gttccaacttcctgtgaagctaaagaaggagaatgtattgatagcagctgtggcacctgcacgagagacatactatcagatggact
gtgtgaaaataaaccaggaaaaacatgttgccgaatgtgtcagtatgtaattgaatgcagagtagaggccgcaggatggtttaga
acattctatggaaagagattccagttccaggaacctggtacatacgtgtgggtcaaggaaccaagggcggcgactggaaggtgt
ccatcaccctggagaacctggatggaaccaaggggctgtgctgaccaagacaagactggaagtggctggagacatcattgac
atcgctcaagctactgagaatccatcactgtaaacggtggagctgaccctatcatcgccaacccgtacaccatcggcgaggtcac
catcgctgttgttgagatgccaggcttcaacatcaccgtcattgagttcttcaaactgatcgtgatcgacatcctcggaggaagatctg
taagaatcgccccagacacagcaaacaaggaatgatctctggcctctgtggagatcttaaaatgatggaagatacagacttcac
ttcagatccagaacaactcgctattcagcctaagatcaaccaggagtttgacggttgtccactctatggaaatcctgatgacgttgca
tactgcaaaggtcttctggagccgtacaaggacagctgccgcaaccccatcaacttctactactacaccatctcctgcgccttcgccc
gctgtatgggtggagacgagcgagcctcacacgtgctgcttgactacaggggagacgtgcgctgctcccgaaactagaggaacct
gcgttttgtctggacatactttctacgatacatttgacaaagcaagataccaattccagggtccctgcaaggagattcttatggccgcc
gactgtttctggaacacttgggatgtgaaggtttcacacaggaatgttgactcttacactgaagtagagaaagtacgaatcaggaaa
caatcgactgtagtagaactcattgttgatggaaaacagattctggttggaggagaagccgtgtccgtcccgtacagctctcagaac
acttccatctactggcaagatggtgacatactgactacagccatcctacctgaagctctggtggtcaagttcaacttcaagcaactgc
tcgtcgtacatattagagatccattcgatggtaagacttgcggtatttgcggtaactacaaccaggatttcagtgatgattcttttgatgc
tgaaggagcctgtgatctgaccccaacccaccgggatgcaccgaagaacagaaacctgaagctgaacgactctgcaatagtct
cttcgccggtcaaagtgatcttgatcagaaatgtaacgtgtgccacaagcctgaccgtgtcgaacgatgcatgtacgagtattgcct
gagggacaacaggttcgtgaccacgcatgggagttcaagaaagaatgctacataaagcatggagacaccctagaagtac
cagatgaatgcaaacgccgtgccctgggcggggctgctggaccctctcccggctcccaggaccggtcgcccgcggcgctctcct
gcttccttcctcagggcaggagctgtgggaggtacgaagcaggagctcacctgcagggcttcccgtccatgcaccctggagtccgcg
ggacctggagggagtccgccaaccggagcagtcgctaagccttcactcctggatctcagaggagcccgctgctagagccttcggaga
gacgcttcgtgcccagccatggttcctgcagcaagtcatctttgccgatcctgtcaggcccaagaaccgatggcgcccccatgcttga Neuropeptide W Human (nucleotide acid sequence):
(SEQ ID NO: 312)
Ctggcgtggcgcccaggggagcgggggctcccgcgagcggccgcggctggcactgctgctgcttctgctcctgctgccgctgc
cctccggcgcgtggtacaagcacgtggcgagtcccgctaccacacggtggggccgcgccgctggcctgctcatgggggctgcgtcgc
tcacctatctgtggcgccgctactgcgccactgttcattgccaggactgtccttacgaacctgatccaccaaacacagttccaacttc
ctgtgaagctaaagaaggagaatgtattgatagcagctgtggcacctgcacgagagacatactatcagatggactgtgtgaaaat -continued aaaccaggaaaaacatgttgccgaatgtgtcagtatgtaattgaatgcagagtagaggccgcaggatggtttagaacattctatgg aaagagattccagttccaggaacctggtacatacgtgttgggtcaaggaaccaagggcggcgactggaaggtgtccatcaccctg gagaacctggatggaaccaaggggctgtgctgaccaagacaagactggaagtggctggagacatcattgacatcgctcaagct actgagaatcccatcactgtaaacggtggagctgaccctatcatcgccaacccgtacaccatcggcgaggtcaccatcgctgttgtt gagatgccaggcttcaacatcaccgtcattgagttcttcaaactgatcgtgatcgacatcctcggaggaagatctgtaagaatcgcc ccagacacagcaaacaaaggaatgatctctggcctctgtggagatcttaaaatgatggaagatacagacttcacttcagatccag aacaactcgctattcagcctaagatcaaccaggagtttgacggttgtccactctatggaaatcctgatgacgttgcatactgcaaag gtcttctggagccgtacaaggacagctgccgcaaccccatcaacttctactactacaccatctctgcgccttcgcccgctgtatggg tggagacgagcgagcctcacacgtgctgcttgactacaggagacgtgcgctgctcccgaaactagaggaacctgcgttttgtctg gacatactttctacgatacatttgacaaagcaagataccaattccaggtccctgcaaggagattcttatggccgccgactgtttctg gaacacttgggatgtgaaggtttcacacaggaatgttgactcttacactgaagtagagaaagtacgaatcaggaaacaatcgact gtagtagaactcattgttgatggaaaacagattctggttggaggagaagccgtgtccgtcccgtacagctctcagaacacttccatct actggcaagatggtgacatactgactacagccatcctacctgaagctctggtggtcaagttcaacttcaagcaactgctcgtcgtac atattagagatccattcgatggtaagacttgcggtatttgcggtaactacaaccaggatttcagtgatgattcttttgatgctgaaggag cctgtgatctgaccccaacccaccgggatgcaccgaagaacagaaacctgaagctgaacgactctgcaatagtctcttcgccgg tcaaagtgatcttgatcagaaatgtaacgtgtgccacaagcctgaccgtgtcgaacgatgcatgtacgagtattgcctgaggggac aacagggtttctgtgaccacgcatgggagttcaagaaagaatgctacataaagcatggagacaccctagaagtaccagatgaat gcaaa<u>cgccgc</u>gcgctgcgcggccgccgggcccctggccaggacaccctctccccgaacccgcagcccgcgaggctcctc tcctgctgccctcgtgggttcaggagctgtgggagacgcgacgcaggagctcccaggcagggatcccgtccgtgcgccccggagc ccgcgcgccccagagcctgcgctggaaccggagtccctggacttcagcggagctggccagagacttcggagagacgtctcccgccc agcggtggaccccgcagcaaaccgccttggcctgccctgcctggcccccggaccgttctga CART Mouse (nucleic acid sequence):

(SEQ ID NO: 313)

Atggagagctcccgcctgcggctgctaccccctcctgggcgccgccctgctgctactgctaccttgctgggtgcccgtgcccaggagg acgccgagctgcagccccgagccctggacatctactctgccgtggatgatgcgtcccacgagaaggagctgatcgaagcgttgcaag aagtcctgaagaagctcaagagtaaacgctactgcgccactgttcattgccaggactgtccttacgaacctgatccaccaaacacagt tccaacttcctgtgaagctaaagaaggagaatgtattgatagcagctgtggcacctgcacgagagacatactatcagatggactgt gtgaaaataaaccaggaaaaacatgttgccgaatgtgtcagtatgtaattgaatgcagagtagaggccgcaggatggtttagaac attctatggaaagagattccagttccaggaacctggtacatacgtgttgggtcaaggaaccaagggcggcgactggaaggtgtcc atcaccctggagaacctggatggaaccaaggggctgtgctgaccaagacaagactggaagtggctggagacatcattgacatc gctcaagctactgagaatcccatcactgtaaacggtggagctgaccctatcatcgccaacccgtacaccatcggcgaggtcaccat cgctgttgttgagatgccaggcttcaacatcaccgtcattgagttcttcaaactgatcgtgatcgacatcctcggaggaagatctgtaa gaatcgccccagacacagcaaacaaaggaatgatctctggcctctgtggagatcttaaaatgatggaagatacagacttcacttca gatccagaacaactcgctattcagcctaagatcaaccaggagtttgacggttgtccactctatggaaatcctgatgacgttgcatact gcaaaggtcttctggagccgtacaaggacagctgccgcaaccccatcaacttctactactacaccatctcctgcgccttcgcccgct gtatgggtggagacgagcgagcctcacacgtgctgcttgactacaggagacgtgcgctgctcccgaaactagaggaacctgcg ttttgtctggacatactttctaacgatacatttgacaaagcaagataccaattccaggtccctgcaaggagattcttatggccgccgac tgtttctggaacacttgggatgtgaaggtttcacacaggaatgttgactcttacactgaagtagagaaagtacgaatcaggaaacaa tcgactgtagtagaactcattgttgatggaaaacagattctggttggaggagaagccgtgtccgtcccgtacagctctcagaacactt ccatctactggcaagatggtgacatactgactacagccatcctacctgaagctctggtggtcaagttcaacttcaagcaactgctcgt cgtacatattagagatccattcgatggtaagacttgcggtatttgcggtaactacaaccaggaatttcagtgatgattcttttgatgctga aggagcctgtgatctgaccccccaacccaccgggatgcaccgaagaacagaaacctgaagctgaacgactctgcaatagtctcttc gccggtcaaagtgatcttgatcagaaatgtaacgtgtgccacaagcctgaccgtgtcgaacgatgcatgtacgagtattgcctgag gggacaacagggtttctgtgaccacgcatgggagttcaagaaagaatgctacataaagcatggagacaccctagaagtaccag atgaatgcaaa<u>aaacgc</u>attccgatctacgaagaagtacggccaagtccccatgtgtgacgctggagagcagtgcgcagtgagg aaaggggccaggatcgggaagctgtgtgactgtccccgaggaacttcctgcaattctttcctcttgaagtgcttgtga CART Human (nucleic acid sequence):

(SEQ ID NO: 314)

Atggagagctcccgcgtgaggctgctgcccctcctgggcgccgccctgctgctgatgctacctctgtttgggtacccgtgcccaggag gacgccgagctccagccccgagccctggacatctactctgccgtggatgatgcctcccacgagaaggagctgatcgaagcgctgcaa gaagtcttgaagaagctcaagagtaaacgttactgcgccactgttcattgccaggactgtccttacgaacctgatccaccaaacacag ttccaacttcctgtgaagctaaagaaggagaatgtattgatagcagctgtggcacctgcacgagagacatactatcagatggactgt gtgaaaataaaccaggaaaaacatgttgccgaatgtgtcagtatgtaattgaatgcagagtagaggccgcaggatggtttagaac attctatggaaagagattccagttccaggaacctggtacatacgtgtttgggtcaaggaaccaagggcggcgactggaaggtgtcc atcaccctggagaacctggatggaaccaagggggctgtgctgaccaagacaagactggaagtggctggagacatcattgacatc gctcaagctactgagaatcccatcactgtaaacggtggagctgaccctatcatcgccaacccgtacaccatcggcgaggtcaccat cgctgttgttgagatgccaggcttcaacatcaccgtcattgagttcttcaaactgatcgtgatcgacatcctcggaggaagatctgtaa gaatcgccccagacacagcaaacaaggaatgatctctggcctctgtggagatcttaaaatgatggaagatacagacttcacttca gatccagaacaactcgctattcagcctaagatcaaccaggagtttgacggttgtccactctatgaaatcctgatgacgttgcatact gcaaaggtcttctggagccgtacaaggacagctgccgcaaccccatcaacttctactactacaccatctcctgcgccttcgcccgct gtatgggtggagacgagcgagcctcacacgtgctgcttgactacagggagacgtgcgctgctcccgaaactagaggaacctgcg ttttgtctggacatactttctacgatacatttgacaaagcaagataccaattccagggtccctgcaaggagattcttatggccgccgac tgtttctggaacacttgggatgtgaaggtttcacacaggaatgttgactcttacactgaagtagagaaagtacgaatcaggaaacaa tcgactgtagtagaactcattgttgatggaaaaacagattctggttggaggagaagccgtgtccgtcccgtacagctctcagaacactt ccatctactggcaagatggtgacatactgactacagccatcctacctgaagctctggtggtcaagttcaacttcaagcaactgctcgt cgtacatattagagatccattcgatggtaagacttgcggtatttgcggtaactacaaccaggatttcagtgatgattcttttgatgctga aggagcctgtgatctgaccccccaacccaccgggatgcaccgaagacagaaacctgaagctgaacgactctgcaatagtctcttc gccggtcaaagtgatcttgatcagaaatgtaacgtgtgccacaagcctgaccgtgtcgaacgatgcatgtacgagtattgcctgag gggacaacagggtttctgtgaccacgcatgggagttcaagaaagaatgctacataaagcatggagacaccctagaagtaccag atgaatgcaaa<u>aaacgt</u>gttcccatctatgaagaagtatggccaagtccccatgtgtgacgccggtgagcagtgtgcagtgaggaa aggggcaaggatcgggaagctgtgtgactgtccccgaggaacctcctgcaattccttcctcctgaagtgcttatga TGFB1 Mouse (nucleic acid sequence):

(SEQ ID NO: 315)

Atgccgcctcggggctgcggctactgccgcttctgctcccactcccgtggcttctagtgctgacgcccgggaggccagccgcggga ctctccacctgcaagaccatcgacatggagctggtgaaacggaagcgcatcgaagccatccgtgccagatcctgtccaaactaagg ctcgccagtcccccaagccaggggaggtaccgcccggcccgctgcccgaggcggtgctcgctttgtacaacagcacccgcgacc gggtggcaggcgagagcgccgacccagagccggagcccgaagcggactactatgctaaagaggtcacccgcgtgctaatggtgga ccgcaacaacgccatctatgagaaaaccaaagacatctcacacagtatatatatgttcttcaatacgtcagacattcgggaagcagtgcc cgaacccccattgctgtcccgtgcagagctgcgcttgcagagattaaaatcaagtgtggagcaacatgtggaactctaccagaaatata gcaacaattcctggcgttaccttggtaaccggctgctgaccccccactgatacgcctgagtggctgtcttttgacgtcactggagttgtacg gcagtggctgaaccaaggagacggaatacagggctttcgattcagcgctcactgctcttgtgacagcaaagataacaaactccacgtg gaaatcaacgggatcagccccaaacgtcggggcgacctgggcaccatccatgacatgaaccggcccttcctgctcctcatggccacc cccctggaaaggggcccagcacctgcacagctcacggcac<u>cggaga</u>tactgcgccactgttcattgccaggactgtccttacgaacct gatccaccaaacacagttccaacttcctgtgaagctaaagaaggagaatgtattgatagcagctgtggcacctgcacgagagaca -continued

```
tactatcagatggactgtgtgaaaataaaccaggaaaaacatgttgccgaatgtgtcagtatgtaattgaatgcagagtagaggcc
gcaggatggtttagaacattctatggaaagagattccagttccaggaacctggtacatacgtgttgggtcaaggaaccaagggcg
gcgactggaaggtgtccatcaccctggagaacctggatggaaccaaggggctgtgctgaccaagacaagactggaagtggct
ggagacatcattgacatcgctcaagctactgagaatcccatcactgtaaacggtggagctgaccctatcatcgccaacccgtacac
catcggcgaggtcaccatcgctgttgttgagatgccaggcttcaacatcaccgtcattgagttcttcaaactgatcgtgatcgacatcc
tcggaggaagatctgtaagaatcgccccagacacagcaaacaaaggaatgatctctggcctctgtggagatcttaaaatgatgga
agatacagacttcacttcagatccagaacaactcgctattcagcctaagatcaaccaggagtttgacggttgtccactctatggaaat
cctgatgacgttgcatactgcaaaggtcttctggagccgtacaaggacagctgccgcaaccccatcaacttctactactacaccatct
cctgcgccttcgcccgctgtatgggtggagacgagcgagcctcacacgtgctgcttgactacaggagacgtgcgctgctcccgaa
actagaggaacctgcgttttgtctggacatactttctacgatacatttgacaaagcaagataccaattccaggtcccctgcaaggag
attcttatggccgccgactgtttctggaacacttgggatgtgaaggtttcacacaggaatgttgactcttacactgaagtagagaaagt
acgaatcaggaaacaatcgactgtagtagaactcattgttgatggaaaacagattctggttggaggagaagccgtgtccgtcccgt
acagctctcagaacacttccatctactggcaagatggtgacatactgactacagccatcctacctgaagctctggtggtcaagttcaa
cttcaagcaactgctcgtcgtacatattagagatccattcgatggtaagacttgcggtatttgcggtaactacaaccaggatttcagtg
atgattcttttgatgctgaaggagcctgtgatctgaccccccaacccaccgggatgcaccgaagaacagaaacctgaagctgaacg
actctgcaatagtctcttcgccggtcaaagtgatcttgatcagaaatgtaacgtgtgccacaagcctgaccgtgtcgaacgatgcatg
tacgagtattgcctgaggggacaacagggtttctgtgaccacgcatgggagttcaagaaagaatgctacataaagcatggagaca
ccctagaagtaccagatgaatgcaaacggagagccctggataccaactattgcttcagctccacagagaagaactgctgtgtgcggc
agctgtacattgactttaggaaggacctgggttggaagtggatccacgagcccaagggctaccatgccaacttctgtctgggaccctgc
ccctatatttggagcctggacacacagtacagcaaggtccttgccctctacaaccaacacaacccgggcgcttcggcgtcaccgtgctg
cgtgccgcaggctttggagccactgcccatcgtctactacgtgggtcgcaagcccaaggtggagcagttgtccaacatgattgtgcgct
cctgcaagtgcagctga
```

TGFB1 Human (nucleic acid sequence):

(SEQ ID NO: 316)
```
Atgccgccctccgggctgcggctgctgccgctgctgctaccgctgctgtggctactggtgctgacgcctggccggccggccgcggg
actatccacctgcaagactatcgacatggagctggtgaagcggaagcgcatcgaggccatccgcggccagatcctgtccaagctgcg
gctcgccagccccccgagccaggggaggtgccgcccggcccgctgcccgaggccgtgctcgccctgtacaacagcacccgcga
ccgggtggccggggagagtgcagaaccggagcccgagcctgaggccgactactacgccaaggaggtcacccgcgctgctaatggtg
gaaacccacaacgaaatctatgacaagttcaagcagagtacacacagcatatatatgttcttcaacacatcagagctccgagaagcggt
acctgaacccgtgttgctctcccgggcagagctgcgtctgctgaggctcaagttaaaagtggagcagcacgtggagctgtaccagaaa
tacagcaacaattcctggcgatacctcagcaaccggctgctggcacccagcgactcgccagagtggttatcttttgatgtcaccggagtt
gtgcggcagtggttgagccgtggagggaaattgagggctttcgccttagcgcccactgctcctgtgacagcagggataacacactgc
aagtggacatcaacgggttcactaccggccgccgaggtgacctggccaccattcatggcatgaaccggcctttcctgcttctcatggcc
accccgctggagagggcccagcatctgcaaagctcccggcaccgcccgatactgcgccactgttcattgccaggactgtccttacgaa
cctgatccaccaaacacagttccaacttcctgtgaagctaaagaaggagaatgtattgatagcagctgtggcacctgcacgagag
acatactatcagatggactgtgtgaaaataaaccaggaaaaacatgttgccgaatgtgtcagtatgtaattgaatgcagagtagag
gccgcaggatggtttagaacattctatggaaagagattccagttccaggaacctggtacatacgtgttgggtcaaggaaccaaggg
cggcgactggaaggtgtccatcaccctggagaacctggatggaaccaaggggctgtgctgaccaagacaagactggaagtgg
ctggagacatcattgacatcgctcaagctactgagaatcccatcactgtaaacggtggagctgaccctatcatcgccaacccgtac
accatcggcgaggtcaccatcgctgttgttgagatgccaggcttcaacatcaccgtcattgagttcttcaaactgatcgtgatcgacat
cctcggaggaagatctgtaagaatcgccccagacacagcaaacaaaggaatgatctctggcctctgtggagatcttaaaatgatg
```

-continued gaagatacagacttcacttcagatccagaacaactcgctattcagcctaagatcaaccaggagtttgacggttgtccactctatgga aatcctgatgacgttgcatactgcaaaggtcttctggagccgtacaaggacagctgccgcaaccccatcaacttctactactacacc atctcctgcgccttcgcccgctgtatgggtggagacgagcgagcctcacacgtgctgcttgactacagggagacgtgcgctgctccc gaaactagaggaacctgcgttttgtctggacatactttctacgatacatttgacaaagcaagataccaattccagggtccctgcaag gagattcttatggccgccgactgtttctggaacacttgggatgtgaaggtttcacacaggaatgttgactcttacactgaagtagaga aagtacgaatcaggaaacaatcgactgtagtagaactcattgttgatggaaaacagattctggttggaggagaagccgtgtccgtc ccgtacagctctcagaacacttccatctactggcaagatggtgacatactgactacagccatcctacctgaagctctggtggtcaagt tcaacttcaagcaactgctcgtcgtacatattagagatccattcgatggtaagacttgcggtatttgcggtaactacaaccaggatttc agtgatgattcttttgatgctgaaggagcctgtgatctgaccccaacccaccgggatgcaccgaagaacagaaacctgaagctg aacgactctgcaatagtctcttcgccggtcaaagtgatcttgatcagaaatgtaacgtgtgccacaagcctgaccgtgtcgaacgat gcatgtacgagtattgcctgaggggacaacagggtttctgtgaccacgcatgggagttcaagaaagaatgctacataaagcatgg agacacctagaagtaccagatgaatgcaaacgccgagccctggacaccaactattgcttcagctccacggagaagaactgctgcg tgcggcagctgtacattgacttccgcaaggacctcggctggaagtggatccacgagcccaagggctaccatgccaacttctgcctcgg gccctgccctacattggagcctggacacgcagtacagcaaggtcctggccctgtacaaccagcataacccgggcgcctcggcggc gccgtgctgcgtgccgcaggcgctggagccgctgcccatcgtgtactacgtgggccgcaagcccaaggtggagcagctgtccaaca tgatcgtgcgctcctgcaagtgcagctga TGFB2 Mouse (nucleic acid sequence):

(SEQ ID NO: 317)

Atgcactactgtgtgctgagcaccttttgctcctgcatctggtcccggtggcgctcagtctgtctacctgcagcaccctcgacatggatc agtttatgcgcaagaggatcgaggccatccgcggcagatcctgagcaagctgaagctcaccagcccccggaagactatccggag ccggatgaggtcccccggaggtgatttccatctacaacagtaccagggacttactgcaggagaaggcaagccggagggcagccgc ctgcgagcgcgagcggagcgacgaggagtactacgccaaggaggtttataaaatcgacatgccgtcccacctcccctccgaaaatgc catcccgcccactttctacagaccctacttcagaatcgtccgctttgatgtctcaacaatggagaaaaatgcttcgaatctggtgaaggca gagttcagggtcttccgcttgcaaaaccccaaagccagagtggccgagcagcggattgaactgtatcagatccttaaatccaaagactt aacatctcccacccagcgctacatcgatagcaaggttgtgaaaaccagagcggagggtgaatggctctccttcgacgtgacagacgct gtgcaggagtggcttcaccacaaagacaggaacctggggtttaaaataagtttacactgcccctgctgtaccttcgtgccgtctaataatt acatcatcccgaataaaaagcgaagagctcgaggcgagatttgcaggtattgatggcacctctacatatgccagtggtgatcagaaaact ataaagtccactaggaaaaaaaccagtgggaagaccccacatctcctgctaatgttgttgccctcctacagactggagtcacaacagtcc agccggcggtactgcgccactgttcattgccaggactgtccttacgaacctgatccaccaaacacagttccaacttcctgtgaagcta aagaaggagaatgtattgatagcagctgtggcacctgcacgagagacatactatcagatggactgtgtgaaaataaaccaggaa aaacatgttgccgaatgtgtcagtatgtaattgaatgcagagtagaggccgcaggatggtttagaacattctatggaaagagattcc agttccaggaacctggtacatacgtgttgggtcaaggaaccaagggcggcgactggaagtgtccatcaccctggagaacctgg atggaaccaagggggctgtgctgaccaagacaagactggaagtggctggagacatcattgacatcgctcaagctactgagaatc ccatcactgtaaacggtggagctgaccctatcatcgccaacccgtacaccatcggcgaggtcaccatcgctgttgttgagatgccag gcttcaacatcaccgtcattgagttcttcaaactgatcgtgatcgacatcctcggaggaagatctgtaagaatcgccccagacacag caaacaaaggaatgatctctggcctctgtggagatcttaaaatgatggaagatacagacttcacttcagatccagaacaactcgct attcagcctaagatcaaccaggagtttgacggttgtccactctatggaaatcctgatgacgttgcatactgcaaaggtcttctggagc cgtacaaggacagctgccgcaaccccatcaacttctactactacaccatctcctgcgccttcgcccgctgtatgggtggagacgagc gagcctcacacgtgctgcttgactacagggagacgtgcgctgctcccgaaactagaggaacctgcgttttgtctggacatactttcta cgatacatttgacaaagcaagataccaattccagggtccctgcaaggagattcttatggccgccgactgtttctggaacacttggga tgtgaaggtttcacacaggaatgttgactcttacactgaagtagagaaagtacgaatcaggaaacaatcgactgtagtagaactca ttgttgatggaaaacagattctggttggaggagaagccgtgtccgtcccgtacagctctcagaacacttccatctactggcaagatg -continued gtgacatactgactacagccatcctacctgaagctctggtggtcaagttcaacttcaagcaactgctcgtcgtacatattagagatcc
attcgatggtaagacttgcggtatttgcggtaactacaaccaggatttcagtgatgattcttttgatgctgaaggagcctgtgatctgac
ccccaacccaccgggatgcaccgaagaacagaaacctgaagctgaacgactctgcaatagtctcttcgccggtcaaagtgatctt
gatcagaaatgtaacgtgtgccacaagcctgaccgtgtcgaacgatgcatgtacgagtattgcctgaggggacaacagggtttctg
tgaccacgcatgggagttcaagaaagaatgctacataaagcatggagacaccctagaagtaccagatgaatgcaaa<u>cggcgg</u>a
agaagcgcgctttggatgctgcctactgctttagaaatgtgcaggataattgctgccttcgcccctcttttacattgattttaagagggatcttgg
atggaaatggatccatgaacccaaagggtacaatgctaacttctgtgctggggcatgcccatatctatggagttcagacactcaacacac
caaagtcctcagcctgtacaacaccataaatcccgaagcttccgcttccccttgctgtgtgtcccaggatctggaaccactgaccattctct
attacattggaaatacgcccaagatcgaacagcttttccaatatgattgtcaagtcttgtaaatgcagctaa TGFB2 Human (nucleic acid sequence):

(SEQ ID NO: 318)
Atgcactactgtgtgctgagcgcttttctgatcctgcatctggtcacggtcgcgctcagcctgtctacctgcagcacactcgatatggacc
agttcatgcgcaagaggatcgaggcgatccgcgggcagatcctgagcaagctgaagctcaccagtccccagaagactatcctgagc
ccgaggaagtccccggaggtgatttccatctacaacagcaccagggacttgctccaggagaaggcgagccggagggcggccgc
ctgcgagcgcgagaggagcgacgaagagtactacgccaaggaggtttacaaaatagacatgccgcccttcttccctccgaaactgtc
tgcccagttgttacaacaccctctggctcagtgggcagcttgtgctccagacagtcccaggtgctctgtgggtaccttgatgccatcccgc
ccactttctacagaccctacttcagaattgttcgatttgacgtctcagcaatggagaagaatgcttccaatttggtgaaagcagagttcaga
gtctttcgtagcagaacccaaaagccagagtgcctgaacaacggattgagctatatcagattctcaagtccaaagatttaacatctccaac
ccagcgctacatcgacagcaaagttgtgaaaacaagagcagaaggcgaatggctctccttcgatgtaactgatgctgttcatgaatggct
tcaccataaagacaggaacctgggatttaaaataagcttacactgtccctgctgcactttttgtaccatctaataattacatcatcccaaataa
aagtgaagaactagaagcaagatttgcaggtattgatggcacctccacatataccagtggtgatcagaaaaactataaagtccactaggaa
aaaaaacagtgggaagaccccacatctcctgctaatgttattgccctcctacagacttgagtcacaacagaccaac<u>cggcgg</u>tactgcg
ccactgttcattgccaggactgtccttacgaacctgatccaccaaacacagttccaacttcctgtgaagctaaagaaggagaatgta
ttgatagcagctgtggcacctgcacgagagacatactatcagatggactgtgtgaaaataaaccaggaaaaacatgttgccgaat
gtgtcagtatgtaattgaatgcagagtagaggccgcaggatggtttagaacattctatggaaagagattccagttccaggaacctgg
tacatacgtgttgggtcaaggaaccaagggcggcgactggaaggtgtccatcaccctggagaacctggatgaaccaaggggg
ctgtgctgaccaagacaagactggaagtggctggagacatcattgacatcgctcaagctactgagaatcccatcactgtaaacggt
ggagctgacccatcatcgccaacccgtacaccatcggcgaggtcaccatcgctgttgttgagatgccaggcttcaacatcaccgtc
attgagttcttcaaactgatcgtgatcgacatcctcggaggaagatctgtaagaatcgccccagacacagcaaacaaaggaatga
tctctggcctctgtggagatcttaaaatgatggaagatacagacttcacttcagatccgaacaactcgctattcagcctaagatcaa
ccaggagtttgacggttgtccactctatggaaatcctgatgacgttgcatactgcaaaggtcttctggagccgtacaaggacagctg
ccgcaacccccatcaacttctactactacaccatctcctgcgccttcgcccgctgtatgggtggagacgagcgagcctcacacgtgct
gcttgactacagggagacgtgcgctgctcccgaaactagaggaacctgcgttttgtctggacatactttctacgatacatttgacaaa
gcaagataccaattccagggtccctgcaaggagattcttatggccgccgactgtttctgaacacttgggatgtgaaggtttcacac
aggaatgttgactcttacactgaagtagagaaagtacgaatcaggaaacaatcgactgtagtagaactcattgttgatggaaaaca
gattctggttggaggagaagccgtgtccgtcccgtacagctctcagaacacttccatctactggcaagatggtgacatactgactac
agccatcctacctgaagctctggtggtcaagttcaacttcaagcaactgctcgtcgtacatattagagatccattcgatggtaagactt
gcggtatttgcggtaactacaaccaggatttcagtgatgattcttttgatgctgaaggagcctgtgatctgaccccaacccaccggg
atgcaccgaagaacagaaacctgaagctgaacgactctgcaatagtctcttcgccggtcaaagtgatcttgatcagaaatgtaacg
tgtgccacaagcctgaccgtgtcgaacgatgcatgtacgagtattgcctgaggggacaacagggtttctgtgaccacgcatgggag
ttcaagaaagaatgctacataaagcatggagacaccctagaagtaccagatgaatgcaaa<u>cggcgg</u>aagaagcgtgctttggat -continued gcggcctattgctttagaaatgtgcaggataattgctgcctacgtccactttacattgatttcaagagggatctagggtggaaatggataca cgaacccaaagggtacaatgccaacttctgtgctggagcatgcccgtatttatggagttcagacactcagcacagcagggtcctgagctt atataataccataaatccagaagcatctgcttctccttgctgcgtgtcccaagatttagaacctctaaccattctctactacattggcaaaaca cccaagattgaacagctttctaatatgattgtaaagtcttgcaaatgcagctaa TGFB3 Mouse (nucleic acid sequence):

(SEQ ID NO: 319)

Atgaagatgcacttgcaaagggctctggtagtcctggccctgctgaacttggccacaatcagcctctctctgtccacttgcaccacgttg gacttcggccacatcaagaagaagagggtggaagccattaggggacagatcttgagcaagctcaggctcaccagcccccctgagcc atcggtgatgacccacgtcccctatcaggtcctggcactttacaacagcacccgggagttgctggaagagatgcacggggagaggga ggaaggctgcactcaggagacctcggagtctgagtactatgccaaagagatccataaattcgacatgatccagggactggcggagca caatgaactggccgtctgccccaaaggaattacctctaaggttttttcgtttcaatgtgtcctcagtggagaaaaatggaaccaatctgttcc gggcagagttccgggtcttgcgggtgcccaaccccagctccaagcgcacagagcagagaattgagctcttccagatacttcgaccgg atgagcacatagccaagcagcgctacataggtggcaagaatctgcccacaaggggcaccgctgaatggctgtctttcgatgtcactga cactgtgcgcgagtggctgttgaggagagagtccaacttgggtctgaaatcagcatccactgtccatgtcacacctttcagcccaatgg agacatactggaaaatgttcatgaggtgatggaaatcaaattcaaaggagtggacaatgaagatgaccatggccgtggagacctgggg cgtctcaagaagcaaaaggatcaccacaacccacacctgatcctcatgatgatcccccacaccgactggacagcccaggccagggc agtcag<u>aaggaag</u>tactgcgccactgttcattgccaggactgtccttacgaacctgatccaccaaacacagttccaacttcctgtgaag ctaaagaaggagaatgtattgatagcagctgtggcacctgcacgagagacatactatcagatggactgtgtgaaaataaaccag gaaaaacatgttgccgaatgtgtcagtatgtaattgaatgcagagtagaggccgcaggatggtttagaacattctatggaaagaga ttccagttccaggaacctggtacatacgtgtgggtcaaggaaccaagggcggcgactggaaggtgtccatcaccctggagaacc tggatggaaccaagggggctgtgctgaccaagacaagactggaagtggctggagacatcattgacatcgctcaagctactgaga atcccatcactgtaaacggtggagctgacccatcatcgccaacccgtacaccatcggcgaggtcaccatcgctgttgttgagatgc caggcttcaacatcaccgtcattgagttcttcaaactgatcgtgatcgacatcctcggaggaagatctgtaagaatcgccccagaca cagcaaacaaggaatgatctctggcctctgtggagatcttaaaatgatggaagatacagacttcacttcagatccagaacaactc gctattcagcctaagatcaaccaggagtttgacggttgtccactctatggaaatcctgatgacgttgcatactgcaaaggtcttctgga gccgtacaaggacagctgccgcaacccccatcaacttctactactacaccatctcctgcgccttcgcccgctgtatgggtggagacga gcgagcctcacagtgctgcttgactacagggagacgtgcgctgctcccgaaactagaggaacctgcgttttgtctggacatactttc tacgatacatttgacaaagcaagataccaattccagggtccctgcaaggagattcttatggccgccgactgtttctggaacacttgg gatgtgaaggtttcacacaggaatgttgactcttacaactgaagtagagaaagtacgaatcaggaaacaatcgactgtagtagaact cattgttgatggaaaacagattctggttggaggagaagccgtgtccgtcccgtacagctctcagaacacttccatctactggcaaga tggtgacatactgactacagccatcctacctgaagctctggtggtcaagttcaacttcaagcaactgctcgtcgtacatattagagatc cattcgatggtaagacttgcggtatttgcggtaactacaaccaggatttcagtgatgattcttttgatgctgaaggagcctgtgatctga cccccaacccaccgggatgcaccgaagaacagaaacctgaagctgaacgactctgcaatagtctcttcgccggtcaaagtgatct tgatcagaaatgtaacgtgtgccacaagcctgaccgtgtcgaacgatgcatgtacgagtattgcctgagggacaacagggtttct gtgaccacgcatgggagttcaagaaagaatgctacataaagcatggagacaccctagaagtaccgatgaatgcaaa<u>aggaag</u> aagagggccctggacaccaattactgcttccgcaacctggaggagaactgctgtgtacgccccctttatattgacttccggcaggatcta ggctggaaatgggtccacgaacctaagggttactatgccaacttctgctcaggcccttgcccataccctcgcagcgcagacacaaccc atagcacggtgcttggactatacaaccccctgaacccagaggcgtctgcctcgccatgctgcgtccccaggacctggagcccctgac catcttgtactatgtgggcagaaccccaaggtggagcagctgtccaacatggtggtgaagtcgtgtaagtgcagctga TGFB3 Human (nucleic acid sequence):

(SEQ ID NO: 320)

Atgaagatgcacttgcaaagggctctggtggtcctggccctgctgaactttgccacggtcagcctctctctgtccacttgcaccaccttg gacttcggccacatcaagaagaagagggtggaagccattaggggacagatcttgagcaagctcaggctcaccagcccccctgagcc -continued aacggtgatgacccacgtcccctatcaggtcctggccctttacaacagcacccgggagctgctggaggagatgcatggggagaggga ggaaggctgcacccaggaaaacaccgagtcggaatactatgccaaagaaatccataaattcgacatgatccaggggctggcggagc acaacgaactggctgtctgccctaaaggaattacctccaaggttttccgcttcaatgtgtcctcagtggagaaaaatagaaccaacctatt ccgagcagaattccgggtcttgcgggtgcccaaccccagctctaagcggaatgagcagaggatcgagctcttccagatccttcggcca gatgagcacattgccaaacagcgctatatcggtggcaagaatctgcccacacggggcactgccgagtggctgtcctttgatgtcactga cactgtgcgtgagtggctgttgagaagagagtccaacttaggtctagaaatcagcattcactgtccatgtcacacctttcagcccaatgga gatatcctggaaaacattcacgaggtgatggaaatcaaattcaaaggcgtggacaatgaggatgaccatggccgtggagatctgggc gcctcaagaagcagaaggatcaccacaaccctcatctaatcctcatgatgattccccacaccggctcgacaacccgggccaggggg gtcagaggaagtactgcgccactgttcattgccaggactgtccttacgaacctgatccaccaaacacagttccaacttcctgtgaagc taaagaaggagaatgtattgatagcagctgtggcacctgcacgagagacatactatcagatggactgtgtgaaaataaaccagg aaaaacatgttgccgaatgtgtcagtatgtaattgaatgcagagtagaggccgcaggatggtttagaacattctatggaaagagatt ccagttccaggaacctggtacatacgtgttgggtcaaggaaccaagggcggcgactggaaggtgtccatcaccctggagaacct ggatggaaccaaggggctgtgctgaccaagacaagactggaagtggctggagacatcattgacatcgctcaagctactgaga atcccatcactgtaaacggtggagctgaccctatcatcgccaacccgtacaccatcggcgaggtcaccatcgctgttgttgagatgc caggcttcaacatcaccgtcattgagttcttcaaactgatcgtgatcgacatcctcggaggaagatctgtaagaatcgccccagaca cagcaaacaaggaatgatctctggcctctgtggagatcttaaaatgatggaagatacagacttcacttcagatccagaacaactc gctattcagcctaagatcaaccaggagtttgacggttgtccactctatggaaatcctgatgacgttgcatactgcaaaggtcttctgga gccgtacaaggacagctgccgcaaccccatcaacttctactactacaccatctcctgcgccttcgcccgctgtatgggtggagacga gcgagcctcacacgtgctgcttgactacagggagacgtgcgctgctcccgaaactagaggaacctgcgttttgtctggacatactttc tacgatacatttgacaaagcaagataccaattccagggtccctgcaaggagattcttatggccgccgactgtttctggaacacttgg gatgtgaaggtttcacacaggaatgttgactcttacactgaagtagagaaagtacgaatcaggaaacaatcgactgtagtagaact cattgttgatgaaaacagattctggttgaggagaagccgtgtccgtcccgtacagctctcagaacacttccatctactggcaaga tggtgacatactgactacagccatcctacctgaagctctggtggtcaagttcaacttcaagcaactgctcgtcgtacatattagagatc cattcgatggtaagacttgcggtatttgcggtaactacaaccaggatttcagtgatgattcttttgatgctgaaggagcctgtgatctga ccccaacccaccgggatgcaccgaagaacagaaacctgaagctgaacgactctgcaatagtctcttcgccggtcaaagtgatct tgatcagaaatgtaacgtgtgccacaagcctgaccgtgtcgaacgatgcatgtacgagtattgcctgaggggacaacagggtttct gtgaccacgcatgggagttcaagaaagaatgctcataaagcatggagacacctagaagtaccagatgaatgcaaaaggaag aagcgggctttggacaccaattactgcttccgcaacttggaggagaactgctgtgtgcgccccctctacattgacttccgacaggatctg ggctggaagtgggtccatgaacctaagggctactatgccaacttctgctcaggcccttgccatacctccgcagtgcagacacaaccca cagcacggtgctgggactgtacaacactctgaaccctgaagcatctgcctcgccttgctgcgtgccccaggacctggagcccctgacc atcctgtactatgttgggaggaccccccaaagtggagcagctctccaacatggtggtgaagtcttgtaaatgtagctga PDGFA Mouse (nucleic acid sequence):

(SEQ ID NO: 321)

Atgaggacctgggcttgctgctgctcctcggctgcggatacctcgcccatgccctggccgaggaagccgagataccccgggagttg atcgagcggctggctcgaagtcagatccacagcatccgggacctccagcgactcttggagatagactccgtaggggctgaggatgcc ttggagacaagtctgagagcccatgggtcccatgccattaaccatgtgcccgagaagcggcctgtgcccatt cgcaggtactgcgcca ctgttcattgccaggactgtccttacgaacctgatccaccaaacacagttccaacttcctgtgaagctaaagaaggagaatgtattga tagcagctgtggcacctgcacgagagacatactatcagatggactgtgtgaaaataaaccaggaaaaacatgttgccgaatgtgt cagtatgtaattgaatgcagagtagaggccgcaggatggtttagaacattctatggaaagagattccagttccaggaacctggtac atacgtgttgggtcaaggaaccaagggcggcgactggaaggtgtccatcaccctggagaacctggatggaaccaaggggctgt gctgaccaagacaagactggaagtggctggagacatcattgacatcgctcaagctactgagaatcccatcactgtaaacggtgga -continued gctgaccctatcatcgccaacccgtacaccatcggcgaggtcaccatcgctgttgttgagatgccaggcttcaacatcaccgtcattg agttcttcaaactgatcgtgatcgacatcctcggaggaagatctgtaagaatcgccccagacacagcaaacaaaggaatgatctct ggcctctgtggagatcttaaaatgatggaagatacagacttcacttcagatccagaacaactcgctattcagcctaagatcaaccag gagtttgacggttgtccactctatggaaatcctgatgacgttgcatactgcaaaggtcttctggagccgtacaaggacagctgccgc aaccccatcaacttctactactacaccatctcctgcgccttcgcccgctgtatgggtggagacgagcgagcctcacacgtgctgcttg actacagggagacgtgcgctgctcccgaaactagaggaacctgcgttttgtctggacatactttctacgatacatttgacaaagcaa gataccaattccagggtccctgcaaggagattcttatggccgccgactgtttctggaacacttgggatgtgaaggtttcacacagga atgttgactcttacactgaagtagagaaagtacgaatcaggaaacaatcgactgtagtagaactcattgttgatggaaaacagattc tggttggaggagaagccgtgtccgtcccgtacagctctcagaacacttccatctactggcaagatggtgacatactgactacagcca tcctacctgaagctctggtggtcaagttcaacttcaagcaactgctcgtcgtacatattagagatccattcgatggtaagacttgcggt atttgcggtaactacaaccaggatttcagtgatgattcttttgatgctgaaggagcctgtgatctgaccccaacccaccgggatgca ccgaagaacagaaacctgaagctgaacgactctgcaatagtctcttcgccggtcaaagtgatcttgatcagaaatgtaacgtgtgc cacaagcctgaccgtgtcgaacgatgcatgtacgagtattgcctgaggggacaacagggtttctgtgaccacgcatgggagttcaa gaaagaatgctacataaagcatggagacaccctagaagtaccagatgaatgcaaa<u>cgcagg</u>aagagaagtattgaggaagccat tcctgcagtttgcaagaccaggacggtcatttacgagatacctcggagccaggtggaccccacatcggccaacttcctgatctggcccc cagtgtgtggaggtgaagcgctgcactggctgttgtaacaccagcagcgtcaagtgccagccttcacgggtccaccaccgcagtgtcaa ggtggccaaagtggagtatgtcaggaagaagccaaaattgaaagaggtccaggtgaggttagaggaacacctggagtgtgcatgtgc gacctccaacctgaacccagaccatcgggaggaggagacagatgtgaggtga PDGFA Human (nucleic acid sequence):

(SEQ ID NO: 322)

Atgaggaccttggcttgcctgctgctcctcggctgcggataccctcgcccatgttctggccgaggaagccgagatcccccgcgaggtga tcgagaggctggcccgcagtcagatccacagcatccgggacctccagcgactcctggagatagactccgtagggagtgaggattcttt ggacaccagcctgagagctcacggggtccatgccactaagcatgtgcccgagaagcggcccctgcccatt<u>cggagg</u>tactgcgcca ctgttcattgccaggactgtccttacgaacctgatccaccaaacacagttccaacttcctgtgaagctaaagaaggagaatgtattga tagcagctgtggcacctgcacgagagacatactatcagatggactgtgtgaaaataaaccaggaaaaacatgttgccgaatgtgt cagtatgtaattgaatgcagagtagaggccgcaggatggtttagaacattctatggaaagagattccagttccaggaacctggtac atacgtgttgggtcaaggaaccaagggcggcgactggaaggtgtccatcaccctggagaacctggatggaaccaagggggctgt gctgaccaagacaagactggaagtggctggagacatcattgacatcgctcaagctactgagaatcccatcactgtaaacggtgga gctgaccctatcatcgccaacccgtacaccatcggcgaggtcaccatcgctgttgttgagatgccaggcttcaacatcaccgtcattg agttcttcaaactgatcgtgatcgacatcctcggaggaagatctgtaagaatcgccccagacacagcaaacaaaggaatgatctct ggcctctgtggagatcttaaaatgatggaagatacagacttcacttcagatccagaacaactcgctattcagcctaagatcaaccag gagtttgacggttgtccactctatggaaatcctgatgacgttgcatactgcaaaggtcttctggagccgtacaaggacagctgccgc aaccccatcaacttctactactacaccatctcctgcgccttcgcccgctgtatgggtggagacgagcgagcctcacacgtgctgcttg actacagggagacgtgcgctgctcccgaaactagaggaacctgcgttttgtctggacatactttctacgatacatttgacaaagcaa gataccaattccagggtccctgcaaggagattcttatggccgccgactgtttctggaacacttgggatgtgaaggtttcacacagga atgttgactcttacactgaagtagagaaagtacgaatcaggaaacaatcgactgtagtagaactcattgttgatggaaaacagattc tggttggaggagaagccgtgtccgtcccgtacagctctcagaacacttccatctactggcaagatggtgacatactgactacagcca tcctacctgaagctctggtggtcaagttcaacttcaagcaactgctcgtcgtacatattagagatccattcgatggtaagacttgcggt atttgcggtaactacaaccaggatttcagtgatgattcttttgatgctgaaggagcctgtgatctgaccccaacccaccgggatgca ccgaagaacagaaacctgaagctgaacgactctgcaatagtctcttcgccggtcaaagtgatcttgatcagaaatgtaacgtgtgc cacaagcctgaccgtgtcgaacgatgcatgtacgagtattgcctgaggggacaacagggtttctgtgaccacgcatgggagttcaa gaaagaatgctacataaagcatggagacaccctagaagtaccagatgaatgcaaa<u>cggagg</u>aagagaagcatcgaggaagctg -continued tccccgctgtctgcaagaccaggacggtcatttacgagattcctcggagtcaggtcgaccccacgtccgccaacttcctgatctggccc ccgtgcgtggaggtgaaacgctgcaccggctgctgcaacacgagcagtgtcaagtgccagccctcccgcgtccaccaccgcagcgt caaggtggccaaggtggaatacgtcaggaagaagccaaaattaaaagaagtccaggtgaggttagaggagcatttggagtgcgcctg cgcgaccacaagcctgaatccggattatcgggaagaggacacgggaaggcctagggagtcaggtaaaaaacggaaaagaaaaag gttaaaacccacctaa BDNF Mouse (nucleic acid sequence):

(SEQ ID NO: 323)

Atgttccaccaggtgagaagagtgatgaccatccttttccttactatggttatttcatacttcggttgcatgaaggcggcgcccatgaaaga agtaaacgtccacggacaaggcaacttggcctacccaggtgtgcggacccatgggactctggagagcgtgaatgggcccagggcag gttcgagaggtctgacgacgacatcactggctgacacttttgagcacgtcatcgaagagctgctggatgaggaccagaaggttcggcc caacgaagaaaaccataaggacgcggacttgtacacttcccgggtgatgctcagcagtcaagtgcctttggagcctcctctactctttctg ctggaggaatacaaaaattacctggatgccgcaaacatgtctatgagggttcggcgctactgcgccactgttcattgccaggactgtcct tacgaacctgatccaccaaacacagttccaacttcctgtgaagctaaagaaggagaatgtattgatagcagctgtggcacctgcac gagagacatactatcagatggactgtgtgaaaataaaccaggaaaaacatgttgccgaatgtgtcagtatgtaattgaatgcaga gtagaggccgcaggatggtttagaacattctatggaaagagattccagttccaggaacctggtacatacgtgttgggtcaaggaac caagggcggcgactggaaggtgtccatcaccctggagaacctggatggaaccaaggggggctgtgctgaccaagacaagactg gaagtggctggagacatcattgacatcgctcaagctactgagaatcccatcactgtaaacggtggagctgacccctatcatcgccaa cccgtacaccatcggcgaggtcaccatcgctgttgttgagatgccaggcttcaacatcaccgtcattgagttcttcaaactgatcgtga tcgacatcctcggaggaagatctgtaagaatcgcccccagacacagcaaacaaaggaatgatctctggcctctgtggagatcttaa aatgatggaagatacagacttcacttcagatccagaacaactcgctattcagcctaagatcaaccaggagtttgacggttgtccact ctatggaaatcctgatgacgttgcatactgcaaaggtcttctggagccgtacaaggacagctgccgcaaccccatcaacttctacta ctacaccatctcctgcgccttcgcccgctgtatgggtggagacgagcgagcctcacacgtgctgcttgactacagggagacgtgcg ctgctcccgaaactagaggaacctgcgttttgtctggacatactttctacgatacatttgacaaagcaagataccaattccagggtcc ctgcaaggagattcttatggccgccgactgtttctggaacacttgggatgtgaaggtttcacacaggaatgttgactcttacactgaa gtagagaaagtacgaatcaggaaacaatcgactgtagtagaactcattgttgatggaaaacagattctggttggaggagaagccg tgtccgtcccgtacagctctcagaacacttccatctactggcaagatggtgacatactgactacagccatcctacctgaagctctggt ggtcaagttcaacttcaagcaactgctcgtcgtacatattagagatccattcgatggtaagacttgcggtatttgcggtaactacaacc aggatttcagtgatgattcttttgatgctgaaggagcctgtgatctgaccccaacccaccgggatgcaccgaagaacagaaacct gaagctgaacgactctgcaatagtctcttcgccggtcaaagtgatcttgatcagaaatgtaacgtgtgccacaagcctgaccgtgtc gaacgatgcatgtacgagtattgcctgaggggacaacaggggtttctgtgaccacgcatgggagttcaagaaagaatgctacataa agcatggagacacccctagaagtaccagatgaatgcaaacggcgccactccgaccctgcccgccgtggggagctgagcgtgtgtg acagtattagcgagtgggtcacagcggcagataaaaagactgcagtggacatgtctggcgggacggtcacagtcctagagaaagtcc cggtatccaaaggccaactgaagcagtatttctacgagaccaagtgtaatcccatgggttacaccaaggaaggctgcaggggcataga caaaaggcactggaactcgcaatgccgaactaccaatcgtatgttcgggcccttactatggatagcaaaaagagaattggctggcgat tcataaggatagacacttcctgtgtatgtacactgaccattaaaaggggaagatag BDNF Human (nucleic acid sequence):

(SEQ ID NO: 324)

Atgaccatccttttccttactatggttatttcatactttggttgcatgaaggctgcccccatgaaagaagcaaacatccgaggacaaggtgg cttggcctacccaggtgtgcggacccatgggactctggagagcgtgaatgggcccaaggcaggttcaagaggcttgacatcattggct gacactttcgaacacgtgatagaagagctgttggatgaggaccagaaagttcggcccaatgaagaaaacaataaggacgcagacttgt acacgtccagggtgatgctcagtagtcaagtgcctttggagcctcctcttctctttctgctggaggaatacaaaaattacctagatgctgca aacatgtccatgagggtccggcgcgccactctgacccctgcccgccgatactgcgccactgttcattgccaggactgtccttacgaacctg -continued atccaccaaacacagttccaacttcctgtgaagctaaagaaggagaatgtattgatagcagctgtggcacctgcacgagagacat actatcagatggactgtgtgaaaataaaccaggaaaaacatgttgccgaatgtgtcagtatgtaattgaatgcagagtagaggccg caggatggtttagaacattctatggaaagagattccagttccaggaacctggtacatacgtgtttgggtcaaggaaccaagggcggc gactggaaggtgtccatcaccctggagaacctggatggaaccaagggggctgtgctgaccaagacaagactggaagtggctgg agacatcattgacatcgctcaagctactgagaatcccatcactgtaaacggtggagctgaccctatcatcgccaacccgtacaccat cggcgaggtcaccatcgctgttgttgagatgccaggcttcaacatcaccgtcattgagttcttcaaactgatcgtgatcgacatcctcg gaggaagatctgtaagaatcgccccagacacagcaaacaaggaatgatctctggcctctgtggagatcttaaaatgatggaag atacagacttcacttcagatccagaacaactcgctattcagcctaagatcaaccaggagtttgacggttgtccactctatggaaatcc tgatgacgttgcatactgcaaaggtcttctggagccgtacaaggacagctgccgcaaccccatcaacttctactactacaccatctcc tgcgccttcgcccgctgtatgggtggagacgagcgagcctcacacgtgctgcttgactacagggagacgtgcgctgctcccgaaac tagaggaacctgcgttttgtctggacatactttctacgatacatttgacaaagcaagataccaattccagggtcctgcaaggagatt cttatggccgccgactgtttctggaacacttgggatgtgaaggtttcacacaggaatgttgactcttacactgaagtagagaaagtac gaatcaggaaacaatcgactgtagtagaactcattgttgatggaaaacagattctggttggaggagaagccgtgtccgtcccgtac agctctcagaacacttccatctactggcaagatggtgacatactgactacagccatcctacctgaagctctggtggtcaagttcaact tcaagcaactgctcgtcgtacatattagagatccattcgatggtaagacttgcggtatttgcggtaactacaaccaggatttcagtgat gattcttttgatgctgaaggagcctgtgatctgaccccccaacccaccgggatgcaccgaagaacagaaacctgaagctgaacgac tctgcaatagtctcttcgccggtcaaagtgatcttgatcagaaatgtaacgtgtgccacaagcctgaccgtgtcgaacgatgcatgta cgagtattgcctgaggggacaacagggtttctgtgaccacgcatgggagttcaagaaagaatgctacataaagcatggagacac cctagaagtaccagatgaatgcaaa<u>cgccg</u>aggggagctgagcgtgtgtgacagtattagtgagtgggtaacggcggcagacaaa aagactgcagtggacatgtcgggcgggacggtcacagtccttgaaaaggtccctgtatcaaaaggccaactgaagcaatacttctacg agaccaagtgcaatcccatgggttacacaaaagaaggctgcaggggcatagacaaaaggcattggaactcccagtgccgaactaccc agtcgtacgtgcgggccccttaccatggatagcaaaagagaattggctggcgattcataaggatagacacttcttgtgtatgtacattgac cattaaaaggggaagatag NGF Mouse (nucleic acid sequence):

(SEQ ID NO: 325)

Atgtccatgttgttctacactctgatcactgcgttttttgatcggcgtacaggcagaaccgtacacagatagcaatgtcccagaaggagact ctgtccctgaagcccactggactaaacttcagcattcccttgacacagccctccgcagagcccgcagtgcccctactgcaccaatagct gcccgagtgacagggcagaccccgcaacatcactgtagaccccagactgtttaagaaacggagactccactcaccccgtgtgctgttca gcacccagcctccaccaccctcttcagacactctggatctagacttccaggcccatggtacaatccctttcaacaggactcaccggagc <u>aagcgc</u>tactgcgccactgttcattgccaggactgtccttacgaacctgatccaccaaacacagttccaacttcctgtgaagctaaag aaggagaatgtattgatagcagctgtggcacctgcacgagagacatactatcagatggactgtgtgaaaataaaccaggaaaaa catgttgccgaatgtgtcagtatgtaattgaatgcagagtagaggccgcaggatggtttagaacattctatggaaagagattccagtt ccaggaacctggtacatacgtgtttgggtcaaggaaccaagggcggcgactggaaggtgtccatcaccctggagaacctggatgg aaccaagggggctgtgctgaccaagacaagactggaagtggctggagacatcattgacatcgctcaagctactgagaatccat cactgtaaacggtggagctgaccctatcatcgccaacccgtacaccatcggcgaggtcaccatcgctgttgttgagatgccaggctt caacatcaccgtcattgagttcttcaaactgatcgtgatcgacatcctcggaggaagatctgtaagaatcgccccagacacagcaa acaaggaatgatctctggcctctgtggagatcttaaaatgatggaagatacagacttcacttcagatccagaacaactcgctattc agcctaagatcaaccaggagtttgacggttgtccactctatggaaatcctgatgacgttgcatactgcaaaggtcttctggagccgta caaggacagctgccgcaaccccatcaacttctactactacaccatctcctgcgccttcgcccgctgtatgggtggagacgagcgag cctcacacgtgctgcttgactacagggagacgtgcgctgctcccgaaactagaggaacctgcgttttgtctggacatactttctacga tacatttgacaaagcaagataccaattccagggtcctgcaaggagattcttatggccgccgactgtttctggaacacttgggatgtg aaggtttcacacaggaatgttgactcttacactgaagtagagaaagtacgaatcaggaaacaatcgactgtagtagaactcattgtt

```
gatggaaaacagattctggttggaggagaagccgtgtccgtcccgtacagctctcagaacacttccatctactggcaagatggtga
catactgactacagccatcctacctgaagctctggtggtcaagttcaacttcaagcaactgctcgtcgtacatattagagatccattcg
atggtaagacttgcggtatttgcggtaactacaaccaggatttcagtgatgattcttttgatgctgaaggagcctgtgatctgacccccc
aacccaccgggatgcaccgaagaacagaaacctgaagctgaacgactctgcaatagtctcttcgccggtcaaagtgatcttgatc
agaaatgtaacgtgtgccacaagcctgaccgtgtcgaacgatgcatgtacgagtattgcctgaggggacaacagggtttctgtgac
cacgcatgggagttcaagaaagaatgctacataaagcatggagacacctagaagtaccagatgaatgcaaaaagcgctcatcc
acccacccagtcttccacatgggggagttctcagtgtgtgacagtgtcagtgtgtgggttggagataagaccacagccacagacatcaa
gggcaaggaggtgacagtgctggccgaggtgaacattaacaacagtgtattcagacagtactttttgagaccaagtgccgagcctcca
atcctgttgagagtgggtgccggggcatcgactccaaacactggaactcatactgcaccacgactcacaccttcgtcaaggcgttgaca
acagatgagaagcaggctgcctggaggttcatccggatagacacagcctgtgtgtgtgtgctcagcaggaaggctacaagaagaggc
tga
```

NGF Human (nucleic acid sequence):

(SEQ ID NO: 326)

```
Atgtccatgttgttctacactctgatcacagcttttctgatcggcatacaggcggaaccacactcagagagcaatgtccctgcaggacac
aaccatcccccaagcccactggactaaacttcagcattcccttgacactgcccttcgcagagcccgcagcgccccggcagcggcgata
gctgcacgcgtggcggggcagacccgcaacattactgtggaccccaggctgtttaaaaagcggcgactccgttcacccgtgtgctgt
ttagcacccagcctccccgtgaagctgcagacactcaggatctggacttcgaggtcggtggtgctgccccttcaacaggactcacag
gagcaagcggtactgcgccactgttcattgccaggactgtccttacgaacctgatccaccaaacacagttccaacttcctgtgaagct
aaagaaggagaatgtattgatagcagctgtggcacctgcacgagagacatactatcagatggactgtgtgaaaataaaccagga
aaaacatgttgccgaatgtgtcagtatgtaattgaatgcagagtagaggccgcaggatggtttagaacattctatggaaagagattc
cagttccaggaacctggtacatacgtgttgggtcaaggaaccaagggcggcgactggaaggtgtccatcaccctggagaacctg
gatggaaccaaggggctgtgctgaccaagacaagactggaagtggctggagacatcattgacatcgctcaagctactgagaat
cccatcactgtaaacggtggagctgacccctatcatcgccaacccgtacaccatcggcgaggtcaccatcgctgttgttgagatgcca
ggcttcaacatcaccgtcattgagttcttcaaactgatcgtgatcgacatcctcggaggaagatctgtaagaatcgcccagacaca
gcaaacaaaggaatgatctctggcctctgtggagatcttaaactgatggaagatacagacttcacttcagatccagaacaactcgc
tattcagcctaagatcaaccaggagtttgacggttgtccactctatggaaatcctgatgacgttgcatactgcaaaggtcttctggagc
cgtacaaggacagctgccgcaacccatcaacttctactactacaccatctcctgcgccttcgcccgctgtatgggtggagacgagc
gagcctcacacgtgctgcttgactacagggagacgtgcgctgctcccgaaactagaggaacctgcgttttgtctggacatactttcta
cgatacatttgacaaagcaagataccaattccagggtccctgcaaggagattcttatggccgccgactgtttctggaacacttggga
tgtgaaggtttcacacaggaatgttgactcttacactgaagtagagaaagtacgaatcaggaaacaatcgactgtagtagaactca
ttgttgatggaaaacagattctggttggaggagaagccgtgtccgtcccgtacagctctcagaacacttccatctactggcaagatg
gtgacatactgactacagccatcctacctgaagctctggtggtcaagttcaacttcaagcaactgctcgtcgtacatattagagatcc
attcgatggtaagacttgcggtatttgcggtaactacaaccaggatttcagtgatgattcttttgatgctgaaggagcctgtgatctgac
ccccaacccaccgggatgcaccgaagaacagaaacctgaagctgaacgactctgcaatagtctcttcgccggtcaaagtgatctt
gatcagaaatgtaacgtgtgccacaagcctgaccgtgtcgaacgatgcatgtacgagtattgcctgaggggacaacagggtttctg
tgaccacgcatgggagttcaagaaagaatgctacataaagcatggagacacctagaagtaccagatgaatgcaaaaagcggt
catcatccatcccatcttccacaggggcgaattctcggtgtgtgacagtgtcagcgtgtgggttggggataagaccaccgccacagac
atcaagggcaaggaggtgatggtgttgggagaggtgaacattaacaacagtgtattcaaacagtactttttgagaccaagtgccggga
cccaaatcccgttgacagcgggtgccggggcattgactcaaagcactggaactcatattgtaccacgactcacacctttgtcaaggcgc
tgaccatggatggcaagcaggctgcctggcggtttatccggatagacacggcctgtgtgtgtgtgctcagcaggaaggctgtgagaag
agcctga
```

-continued

Albumin Mouse (nucleic acid sequence):

(SEQ ID NO: 327)

Atgaagtgggtaacctttctcctcctcctcttcgtctccggctctgcttttttccaggggtgtgttt<u>cgccga</u>tactgcgccactgttcattgcc
aggactgtccttacgaacctgatccaccaaacacagttccaacttcctgtgaagctaaagaaggagaatgtattgatagcagctgt
ggcacctgcacgagagacatactatcagatggactgtgtgaaaataaaccaggaaaaacatgttgccgaatgtgtcagtatgtaa
ttgaatgcagagtagaggccgcaggatggtttagaacattctatggaaagagattccagttccaggaacctggtacatacgtgttgg
gtcaaggaaccaagggcggcgactggaaggtgtccatcaccctggagaacctggatggaaccaaggggctgtgctgaccaa
gacaagactggaagtggctggagacatcattgacatcgctcaagctactgagaatcccatcactgtaaacggtggagctgaccct
atcatcgccaacccgtacaccatcggcgaggtcaccatcgctgttgttgagatgccaggcttcaacatcaccgtcattgagttcttca
aactgatcgtgatcgacatcctcggaggaagatctgtaagaatcgccccagacacagcaaacaaaggaatgatctctggcctctg
tggagatcttaaaatgatggaagatacagacttcacttcagatccagaacaactcgctattcagcctaagatcaaccaggagtttga
cggttgtccactctatggaaatcctgatgacgttgcatactgcaaaggtcttctggagccgtacaaggacagctgccgcaacccat
caacttctactactacaccatctcctgcgccttcgcccgctgtatgggtggagacgagcgagcctcacacgtgctgcttgactacagg
gagacgtgcgctgctcccgaaactagaggaacctgcgttttgtctggacatactttctacgacatttgacaaagcaagataccaa
ttccagggtccctgcaaggagattcttatggccgccgactgtttctggaacacttgggatgtgaaggtttcacacaggaatgttgactc
ttacactgaagtagagaaagtacgaatcaggaaacaatcgactgtagtagaactcattgttgatggaaaacagattctggttggag
gagaagccgtgtccgtcccgtacagctctcagaacacttccatctactggcaagatggtgacatactgactacagccatcctacctg
aagctctggtggtcaagttcaacttcaagcaactgctcgtcgtacatattagagatccattcgatggtaagacttgcggtatttgcggt
aactacaaccaggatttcagtgatgattcttttgatgctgaaggagcctgtgatctgaccccaacccaccgggatgcaccgaaga
acagaaacctgaagctgaacgactctgcaatagtctcttcgccggtcaaagtgatcttgatcagaaatgtaacgtgtgccacaagc
ctgaccgtgtcgaacgatgcatgtacgagtattgcctgaggggacaacagggtttctgtgaccacgcatgggagttcaagaaaga
atgctacataaagcatggagacacccctagacgtaccagatgaatgcaaa<u>cgccga</u>gaagcacacaagagtgagatcgcccatcg
gtataatgatttgggagaacaacatttcaaaggcctagtcctgattgccttttcccagtatctccagaaatgctcatacgatgagcatgcca
aattagtgcaggaagtaacagactttgcaaagacgtgtgttgccgatgagtctgccgccaactgtgacaaatcccttcacactctttttgga
gataagttgtgtgccattccaaacctccgtgaaaactatggtgaactggctgactgctgtacaaaacaagagcccgaaagaaacgaatg
tttcctgcaacacaaagatgacaaccccagcctgccaccatttgaaaggccagaggctgaggccatgtgcacctcctttaaggaaaacc
caaccacctttatgggacactatttgcatgaagttgccagaagacatccttatttctatgccccagaacttctttactatgctgagcagtacaa
tgagattctgacccagtgttgtgcagaggctgacaaggaaagctgcctgaccccgaagcttgatggtgtgaaggagaaagcattggtct
catctgtccgtcagagaatgaagtgctccagtatgcagaagtttggagagagagcttttaaagcatgggcagtagctcgtctgagccag
acattccccaatgctgactttgcagaaatcaccaaattggcaacagaccgaccaaagtcaacaaggagtgctgccatggtgacctgct
ggaatgcgcagatgacagggcggaacttgccaagtacatgtgtgaaaaccaggcgactatctccagcaaactgcagacttgctgcgat
aaaccactgttgaagaaagccactgtcttagtgaggtggagcatgacaccatgcctgctgatctgcctgccattgctgctgattttgttga
ggaccaggaagtgtgcaagaactatgctgaggccaaggatgtcttcctgggcacgttcttgtatgaatattcaagaagacaccctgatta
ctctgtatccctgttgctgagacttgctaagaaatatgaagccactctggaaaagtgctgcgctgaagccaatcctcccgcatgctacggc
acagtgcttgctgaatttcagcctcttgtagaagagcctaagaacttggtcaaaaccaactgtgatcttacgagaagcttggagaatatgg
attccaaaatgccattctagttcgctacacccagaaagcacctcaggtgtcaacccaactctcgtggaggctgcaagaaacctaggaa
gagtgggcaccaagtgttgtacacttcctgaagatcagagactgccttgtgtggaagactatctgtctgcaatcctgaaccgtgtgtgtct
gctgcatgagaagacccccagtgagtgagcatgttaccaagtgctgtagtggatccctggtggaaaggcggccatgcttctctgctctga
cagttgatgaaacatatgtccccaaagagtttaaagctgagaccttcaccttccactctgatatctgcacacttccagagaaggagaagca
gattaagaaacaaacggctcttgctgagctggtgaagcacaagcccaaggctacagcggagcaactgaagactgtcatggatgacttt
gcacagttcctggatacatgttgcaaggctgctgacaaggacacctgcttctcgactgagggtccaaaccttgtcactagatgcaaagac
gccttagcctaa -continued Albumin Human (nucleic acid sequence):

(SEQ ID NO: 328)

atgaagtgggtaacctttatttcccttcttttttctctttagctcggcttattccaggggggtgtgttt<u>cgtcga</u>tactgcgccactgttcattg ccaggactgtccttacgaacctgatccaccaaacacagttccaacttcctgtgaagctaaagaaggagaatgtattgatagcagctgtggc acctgcacgagagacatactatcagatggactgtgtgaaaataaaccaggaaaaacatgttgccgaatgtgtcagtatgtaattga atgcagagtagaggccgcaggatggtttagaacattctatggaaagagattccagttccaggaacctggtacatacgtgttgggtc aaggaaccaagggcggcgactggaaggtgtccatcaccctggagaacctggatgaaccaaggggggctgtgctgaccaagac aagactggaagtggctggagacatcattgacatcgctcaagctactgagaatcccatcactgtaaacggtggagctgaccctatca tcgccaacccgtacaccatcggcgaggtcaccatcgctgttgttgagatgccaggcttcaacatcaccgtcattgagttcttcaaact gatcgtgatcgacatcctcggaggaagatctgtaagaatcgccccagacacagcaaacaaaggaatgatctctggcctctgtgga gatcttaaaatgatggaagatacagacttcacttcagatccagaacaactcgctattcagcctaagatcaaccaggagtttgacggt tgtccactctatggaaatcctgatgacgttgcatactgcaaaggtcttctggagccgtacaaggacagctgccgcaacccatcaac ttctactacacaccatctcctgcgccttcgcccgctgtatgggtggagacgagcgagcctcacacgtgctgcttgactacaggag acgtgcgctgctcccgaaactagaggaacctgcgttttgtctggacatactttctacgatacatttgacaaagcaagataccaattcc agggtccctgcaaggagattcttatgccgccgactgtttctggaacacttgggatgtgaaggtttcacacaggaatgttgactcttac actgaagtagagaaagtacgaatcaggaaacaatcgactgtagtagaactcattgttgatggaaaacagattctggttggaggag aagccgtgtccgtcccgtacagctctcagaacacttccatctactggcaagatggtgacatactgactacagccatcctacctgaag ctctggtggtcaagttcaacttcaagcaactgctcgtcgtacatattagagatcfcattcgatggtaagacttgcggtatttgcggtaact acaaccaggatttcagtgatgattcttttgatgctgaaaggagcctgtgatctgaccccaaccccacgggatgcaccgaagaacag aaacctgaagctgaacgactctgcaatagtctcttcgccggtcaaagtgatcttgatcagaaatgtaacgtgtgccacaagcctgac cgtgtcgaacgatgcatgtacgagtattgcctgaggggacaacagggtttctgtgaccacgcatgggagttcaagaaagaatgcta cataaagcatggagacaccctagaagtaccagatgaatgcaaa<u>cgtcga</u>gatgcacacaagagtgaggttgctcatcggtttaaag atttgggagaagaaaatttcaaagccttggtgttgattgcctttgctcagtatcttcagcagtgtccatttgaagatcatgtaaaattagtgaat gaagtaactgaatttgcaaaaacatgtgttgctgatgagtcagctgaaaattgtgacaaatcacttcatacccttttttggagacaaattatgc acagttgcaactcttcgtgaaacctatggtgaaatggctgactgctgtgcaaaacaagaacctgagagaaatgaatgcttcttgcaacac aaagatgacaacccaaacctcccccgattggtgagaccagagagggttgatgtgatgtgcactgcttttcatgacaatgaagagacatttttga aaaaatacttatatgaaattgccagaagacatccttactttttatgccccggaactcctttctttttgctaaaaggtataaagctgcttttacagaa tgttgccaagctgctgataaagctgcctgcctgttgccaaagctcgatgaacttcgggatgaagggaaggcttcgtctgccaaacagag actcaagtgtgccagtctccaaaaatttggagaaagagctttcaaagcatgggcagtagctcgcctgagccagagatttcccaaagctg agtttgcagaagtttccaagttagtgacagatcttaccaaagtccacacggaatgctgccatggagatctgcttgaatgtgctgatgacag ggcggaccttgccaagtatatctgtgaaaatcaagattcgatctccagtaaactgaaggaatgctgtgaaaacctctgttggaaaaatcc cactgcattgccgaagtggaaaatgatgagatgcctgctgacttgccttcattagctgctgattttgttgaaagtaaggatgtttgcaaaaac tatgctgaggcaaaggatgtcttcctgggcatgttttttgtatgaatatgcaagaaggcatcctgattactctgtcgtgctgctgctgagactt gccaagacatatgaaaccactctagaagtgctgtgccgctgcagatcctcatgaatgctatgccaaagtgttcgatgaatttaaacctc ttgtggaagagcctcagaatttaatcaaacaaaattgtgagcttttttgagcagcttggagagtacaaattccagaatgcgctattagttcgtt acaccaagaaagtaccccaagtgtcaactccaactcttgtagaggtctcaagaaacctaggaaagtgggcagcaaatgttgtaaacat cctgaagcaaaaagatgccctgtgcagaagactatctatccgtggtcctgaaccagttatgtgtgttgcatgagaaaacgccagtaagt gacagagtcaccaaatgctgcacagaatccttggtgaacaggcgaccatgctttcagctctggaagtcgatgaaacatacgttcccaaa gagtttaatgctgaaacattcaccttccatgcagatatatgcacactttctgagaaggagagacaaatcaagaaacaaactgcacttgttg agctcgtgaaacacaagcccaaggcaacaaaagagcaactgaaagctgttatggatgatttcgcagcttttgtagagaagtgctgcaag gctgacgataaggagacctgctttgccgaggagggtaaaaaaacttgttgctgcaagtcaagctgccttaggcttataa -continued Calcitonin Mouse (nucleic acid sequence):

(SEQ ID NO: 329)

Atgggcttcctgaagttctccccttcctggttgtcagcatcttgctcctgtaccaggcatgcagcctccaggcagtgcctttgaggtcaat
cttggaaagcagcccaggcatggccactctcagtgaagaagaagttcgcctgctggctgcactggtgcaggactatatgcagatgaaa
gccagggagctggagcaggaggaagagcaggaggctgagggctctagcttgagacagccccagatct<u>aagcgg</u>tactgcgccactg
ttcattgccaggactgtccttacgaacctgatccaccaaacacagttccaacttcctgtgaagctaaagaaggagaatgtattgata
gcagctgtggcacctgcacgagagacatactatcagatggactgtgaaaataaaccaggaaaaacatgttgccgaatgtgtca
gtatgtaattgaatgcagagtagaggccgcaggatggtttagaacattctatggaaagagattccagttccaggaacctggtacata
cgtgttgggtcaaggaaccaagggcggcgactggaaggtgtccatcaccctggagaacctggatggaaccaaggggctgtgct
gaccaagacaagactggaagtggctggagacatcattgacatcgctcaagctactgaggaatcccatcactgtaaacggtggagct
gaccctatcatcgccaacccgtacaccatcggcgaggtcaccatcgctgttgttgagatgccaggcttcaacatcaccgtcattgagt
tcttcaaactgatcgtgatcgacatcctcggaggaagatctgtaagaatcgccccagacacagcaaacaaaggaatgatctctgg
cctctgtggagatcttaaaatgatggaagatacagacttcacttcagatccagaacaactcgctattcagcctaagatcaaccagga
gtttgacggttgtccactctatggaaatcctgatgacgttgcatactgcaaaggtcttctggagccgtacaaggacagctgccgcaac
cccatcaacttctactactacaccatctcctgcgccttcgcccgctgtatgggtggagacgagcgagcctcacacgtgctgcttgact
acagggagacgtgcgctgctcccgaaactagaggaacctgcttttgtctggacatactttctacgatacatttgacaaagcaagat
accaattccagggtccctgcaaggagattcttatggccgccgactgtttctggaacactttgggatgtgaaggtttcacacaggaatgt
tgactcttacactgaagtagagaaagtacgaatcaggaaacaatcgactgtagtagaactcattgttgatgaaaacagattctggt
tggaggagaagccgtgtccgtcccgtacagctctcagaacacttccatctactggcaagatggtgacatactgactacagccatcct
acctgaagctctggtggtcaagttcaacttcaagcaactgctcgtcgtacatattagagatccattcgatggtaagacttgcggtatt
gcggtaactacaaccaggatttcagtgatgattctttttgatgctgaaggagcctgtgatctgacccccaacccaccggatgcaccg
aagaacagaaacctgaagctgaacgactctgcaatagtctcttcgccggtcaaagtgatcttgatcagaaatgtaacgtgtgccac
aagcctgaccgtgtcgaacgatgcatgtacgagtattgcctgaggggacaacagggtttctgtgaccacgcatgggagttcaaga
aagaatgctacataaagcatggagacaccctagaagtaccagatgaatgcaaa<u>aagcgg</u>tgtgggaatctgagtacctgcatgct
gggcacgtacacacaagacctcaacaagtttcacaccttcccccaaacttcaattgggggttgaagcacctggcaagaaaagggatgtg
gccaaggacttggagacaaaccaccaatcccatttttggcaactaa Calcitonin Human (nucleic acid sequence):

(SEQ ID NO: 330)

Atgggcttccaaaagttctccccttcctggctctcagcatcttggtcctgttgcaggcaggcagcctccatgcagcaccattcaggtctg
ccctggagagcagcccagcagacccggccacgctcagtgaggacgaagcgcgcctcctgctggctgcactggtgcaggactatgtg
cagatgaaggccagtgagctggagcaggagcaagagagagagggctccagcctggacagccccagatct<u>aagcgg</u>tactgcgcc
actgttcattgccaggactgtccttacgaacctgatccaccaaacacagttccaacttcctgtgaagctaaagaaggagaatgtattg
atagcagctgtggcacctgcacgagagacatactatcagatggactgtgaaaataaaccaggaaaaacatgttgccgaatgtg
tcagtatgtaattgaatgcagagtagaggccgcaggatggtttagaacattctatggaaagagattccagttccaggaacctggtac
atacgtgttgggtcaaggaaccaagggcggcgactggaaggtgtccatcaccctggagaacctggatggaaccaaggggctgt
gctgaccaagacaagactggaagtggctggagacatcattgacatcgctcaagctactgagaatcccatcactgtaaacggtgga
gctgaccctatcatcgccaacccgtacaccatcggcgaggtcaccatcgctgttgttgagatgccaggcttcaacatcaccgtcattg
agttcttcaaactgatcgtgatcgacatcctcggaggaagatctgtaagaatcgccccagacacagcaaacaaaggaatgatctct
ggcctctgtggagatcttaaaatgatggaagatacagacttcacttcagatccagaacaactcgctattcagcctaagatcaaccag
gagtttgacggttgtccactctatggaaatcctgatgacgttgcatactgcaaaggtcttctggagccgtacaaggacagctgccgc
aaccccatcaacttctactactacaccatctcctgcgccttcgcccgctgtatgggtggagacgagcgagcctcacacgtgctgcttg
actacagggagacgtgcgctgctcccgaaactagaggaacctgcttttgtctggacatactttctacgatacatttgacaaagcaa
gataccaattccagggtccctgcaaggagattcttatggccgccgactgtttctggaacactttgggatgtgaaggtttcacacagga -continued

```
atgttgactcttacactgaagtagagaaagtacgaatcaggaaacaatcgactgtagtagaactcattgttgatggaaaacagattc tggttggaggagaagccgtgtccgtcccgtacagctctcagaacacttccatctactggcaagatggtgacatactgactacagcca tcctacctgaagctctggtggtcaagttcaacttcaagcaactgctcgtcgtacatattagagatccattcgatggtaagacttgcggt atttgcggtaactacaaccaggatttcagtgatgattcttttgatgctgaaggagcctgtgatctgaccccaacccaccgggatgca ccgaagaacagaaacctgaagctgaacgactctgcaatagtctcttcgccggtcaaagtgatcttgatcagaaatgtaacgtgtgc cacaagcctgaccgtgtcgaacgatgcatgtacgagtattgcctgagggggacaacagggtttctgtgaccacgcatgggagttcaa gaaagaatgctacataaagcatggagacaccctagaagtaccagatgaatgcaaaaagcggtgcggtaatctgagtacttgcatg ctgggcacatacacgcaggacttcaacaagtttcacacgttccccaaactgcaattggggttggagcacctggaaagaaaagggatat gtccagcgacttggagagagaccatcgccctcatgttagcatgccccagaatgccaactaa
```

Due to the redundancy of the genetic code, any fusion protein of the present invention could be specified by any number of nucleic acid sequences in which synonymous base changes have been incorporated. Therefore, the nucleic acid sequences listed should be taken as case examples of one such instance for each propeptide-luciferase fusion protein, rather than the only tolerated nucleic acid sequence. The amino acid sequence of each construct ultimately determines the function of the fusion protein, though many possible nucleic acid sequences can specify each the sequence of each peptide.

The nucleic acid sequences of SEQ ID NOs: 139-330 can be introduced into cells for expression. After transcription of these sequences into RNA and subsequent translation into a peptide, the peptide is processed. For example, for those propeptides of the present invention in which the mature peptide is secreted, cleavage will occur at the cleavage sites by the appropriate protease, thereby freeing the bioluminescent protein from the mature peptide. Then, both the bioluminescent protein and the mature peptide are secreted from the cell simultaneously. In other embodiments, for those propeptides of the present invention in which the mature peptide is a transmembrane protein expressed at the cell surface, the cleavage occurs at the cleavage sites before or after the mature peptide is expressed on the cell surface. The sequences outlined in SEQ ID NO: 139 through SEQ ID NO: 330 encode an amino acid sequence, or a propeptide-luciferase fusion protein. Exemplary fusion proteins encoded by SEQ ID NO: 139-204 are listed below by example, and are not to be construed as limiting the present invention to the fusion peptides disclosed below. One of ordinary skill in the art would readily be able to determine the amino acid sequences of any of SEQ ID NO: 139-330.

```
Proamylin-luciferase Mouse (amino acid sequence)
                                           (SEQ ID NO: 331)
MMCISKLPAVLLILSVALNHLRATPVRSGSNPQMDKRKCNTATCATQRLANFLVRSSNN

LGPVLPPTNVGSNTYGKRNAKPTENNEDFNIVAVASNFATTDLDADRGKLPGKKLPLEV

LKEMEANARKAGCTRGCLICLSHIKCTPKMKKFIPGRCHTYEGDKESAQGGIGEAIVDIP

EIPGFKDLEPMEQFIAQVDLCVDCTTGCLKGLANVQCSDLLKKWLPQRCATFASKIQGQ

VDKIKGAGGDKRNAAGDPNRESLDFLLV

Proamylin-luciferase Human (amino acid sequence)
                                           (SEQ ID NO: 332)
MGILKLQVFLIVLSVALNHLKATPIESHQVEKRKCNTATCATQRLANFLVHSSNNFGAIL

SSTNVGSNTYGKRNAKPTENNEDFNIVAVASNFATTDLDADRGKLPGKKLPLEVLKEME

ANARKAGCTRGCLICLSHIKCTPKMKKFIPGRCHTYEGDKESAQGGIGEAIVDIPEIPGFK

DLEPMEQFIAQVDLCVDCTTGCLKGLANVQCSDLLKKWLPQRCATFASKIQGQVDKIKG

AGGDKRNAVEVLKREPLNYLPL

Proinsulin-luciferase Mouse (amino acid sequence)
                                           (SEQ ID NO: 333)
MALWMRFLPLLALLFLWESHPTQAFVKQHLCGSHLVEALYLVCGERGFFYTPMSRREV

EDPQVAQLELGGGPGAGDLQTLALEVAQQKRKPTENNEDFNIVAVASNFATTDLDADR

GKLPGKKLPLEVLKEMEANARKAGCTRGCLICLSHIKCTPKMKKFIPGRCHTYEGDKES

AQGGIGEAIVDIPEIPGFKDLEPMEQFIAQVDLCVDCTTGCLKGLANVQCSDLLKKWLPQ

RCATFASKIQGQVDKIKGAGGDKRGIVDQCCTSICSLYQLENYCN
```

```
Proinsulin-luciferase Human (amino acid sequence)
                                                   (SEQ ID NO: 334)
MALWMRLLPLLALLALWGPDPAAAFVNQHLCGSHLVEALYLVCGERGFFYTPKTRREA

EDLQVGQVELGGGPGAGSLQPLALEGSLQKRKPTENNEDFNIVAVASNFATTDLDADRG

KLPGKKLPLEVLKEMEANARKAGCTRGCLICLSHIKCTPKMKKFIPGRCHTYEGDKESA

QGGIGEAIVDIPEIPGFKDLEPMEQFIAQVDLCVDCTTGCLKGLANVQCSDLLKKWLPQR

CATFASKIQGQVDKIKGAGGDKRGIVEQCCTSICSLYQLENYCN

Proglucagon (includes GRPP, glucagon, GLP-1, GLP-2)
Mouse (amino acid sequence)
                                                   (SEQ ID NO: 335)
MKTIYFVAGLLIMLVQGSWQHALQDTEENPRSFPASQTEAHEDPDEMNEDKRHSQGTFT

SDYSKYLDSRRAQDFVQWLMNTKRNRNNIAKRHDEFERHAEGTFTSDVSSYLEGQAAK

EFIAWLVKGRGRRDFPEEVAIAEELGRKRRKPTENNEDFNIVAVASNFATTDLDADRGK

LPGKKLPLEVLKEMEANARKAGCTRGCLICLSHIKCTPKMKKFIPGRCHTYEGDKESAQ

GGIGEAIVDIPEIPGFKDLEPMEQFIAQVDLCVDCTTGCLKGLANVQCSDLLKKWLPQRC

ATFASKIQGQVDKIKGAGGDKRGRRHADGSFSDEMSTILDNLATRDFINWLIQTKITDKK

Proglucagon (includes GRPP, glucagon, GLP-1, GLP-2)
Human (amino acid sequence)
                                                   (SEQ ID NO: 336)
MKSIYFVAGLFVMLVQGSWQRSLQDTEEKSRSFSASQADPLSDPDQMNEDKRHSQGTFT

SDYSKYLDSRRAQDFVQWLMNTKRNRNNIAKRHDEFERHAEGTFTSDVSSYLEGQAAK

EFIAWLVKGRGRRDFPEEVAIVEELGRKRRKPTENNEDFNIVAVASNFATTDLDADRGK

LPGKKLPLEVLKEMEANARKAGCTRGCLICLSHIKCTPKMKKFIPGRCHTYEGDKESAQ

GGIGEAIVDIPEIPGFKDLEPMEQFIAQVDLCVDCTTGCLKGLANVQCSDLLKKWLPQRC

ATFASKIQGQVDKIKGAGGDKRGRRHADGSFSDEMNTILDNLAARDFINWLIQTKITDRK

Peptide YY Mouse (amino acid sequence)
                                                   (SEQ ID NO: 337)
MVAVRRPWPVTVAMLLILLACLGALVDAYPAKPEAPGEDASPEELSRYYASLRHYLNL

VTRQRYGKRKPTENNEDFNIVAVASNFATTDLDADRGKLPGKKLPLEVLKEMEANARK

AGCTRGCLICLSHIKCTPKMKKFIPGRCHTYEGDKESAQGGIGEAIVDIPEIPGFKDLEPME

QFIAQVDLCVDCTTGCLKGLANVQCSDLLKKWLPQRCATFASKIQGQVDKIKGAGGDK

RRDVPAALFSKLLFTDDSDSENLPFRPEGLDQW

Peptide YY Human (amino acid sequence)
                                                   (SEQ ID NO: 338)
MVFVRRPWPALTTVLLALLVCLGALVDAYPIKPEAPGEDASPEELNRYYASLRHYLNLV

TRQRYGKRKPTENNEDFNIVAVASNFATTDLDADRGKLPGKKLPLEVLKEMEANARKA

GCTRGCLICLSHIKCTPKMKKFIPGRCHTYEGDKESAQGGIGEAIVDIPEIPGFKDLEPMEQ

FIAQVDLCVDCTTGCLKGLANVQCSDLLKKWLPQRCATFASKIQGQVDKIKGAGGDKR

RDGPDTLLSKTFFPDGEDRPVRSRSEGPDLW

Neuropeptide Y Mouse (amino acid sequence)
                                                   (SEQ ID NO: 339)
MLGNKRMGLCGLTLALSLLVCLGILAEGYPSKPDNPGEDAPAEDMARYYSALRHYINLI

TRQRYGKRKPTENNEDFNIVAVASNFATTDLDADRGKLPGKKLPLEVLKEMEANARKA

GCTRGCLICLSHIKCTPKMKKFIPGRCHTYEGDKESAQGGIGEAIVDIPEIPGFKDLEPMEQ

FIAQVDLCVDCTTGCLKGLANVQCSDLLKKWLPQRCATFASKIQGQVDKIKGAGGDKR

RSSPETLISDLLMKESTENAPRTRLEDPSMW
```

-continued

Neuropeptide Y Human (amino acid sequence)
(SEQ ID NO: 340)
MLGNKRLGLSGLTLALSLLVCLGALAEAYPSKPDNPGEDAPAEDMARYYSALRHYINLI

TRQRYGKRKPTENNEDFNIVAVASNFATTDLDADRGKLPGKKLPLEVLKEMEANARKA

GCTRGCLICLSHIKCTPKMKKFIPGRCHTYEGDKESAQGGIGEAIVDIPEIPGFKDLEPMEQ

FIAQVDLCVDCTTGCLKGLANVQCSDLLKKWLPQRCATFASKIQGQVDKIKGAGGDKR

RSSPETLISDLLMRESTENVPRTRLEDPAMW

Pancreatic polypeptide Mouse (amino acid sequence)
(SEQ ID NO: 341)
MAVAYCCLSLFLVSTWVALLLQPLQGTWGAPLEPMYPGDYATPEQMAQYETQLRRYIN

TLTRPRYGKRKPTENNEDFNIVAVASNFATTDLDADRGKLPGKKLPLEVLKEMEANARK

AGCTRGCLICLSHIKCTPKMKKFIPGRCHTYEGDKESAQGGIGEAIVDIPEIPGFKDLEPME

QFIAQVDLCVDCTTGCLKGLANVQCSDLLKKWLPQRCATFASKIQGQVDKIKGAGGDK

RRAEEENTGGLPGVQLSPCTSPPVGLIPCSAPWS

Pancreatic polypeptide Human (amino acid sequence)
(SEQ ID NO: 342)
MAAARLCLSLLLLSTCVALLLQPLLGAQGAPLEPVYPGDNATPEQMAQYAADLRRYIN

MLTRPRYGKRKPTENNEDFNIVAVASNFATTDLDADRGKLPGKKLPLEVLKEMEANAR

KAGCTRGCLICLSHIKCTPKMKKFIPGRCHTYEGDKESAQGGIGEAIVDIPEIPGFKDLEP

MEQFIAQVDLCVDCTTGCLKGLANVQCSDLLKKWLPQRCATFASKIQGQVDKIKGAGG

DKRRHKEDTLAFSEWGSPHAAVPRELSPLDL

Somatostatin Mouse (amino acid sequence)
(SEQ ID NO: 343)
MLSCRLQCALAALCIVLALGGVTGAPSDPRLRQFLQKSLAAATGKQELAKYFLAELRKK

PTENNEDFNIVAVASNFATTDLDADRGKLPGKKLPLEVLKEMEANARKAGCTRGCLICL

SHIKCTPKMKKFIPGRCHTYEGDKESAQGGIGEAIVDIPEIPGFKDLEPMEQFIAQVDLCV

DCTTGCLKGLANVQCSDLLKKWLPQRCATFASKIQGQVDKIKGAGGDRKLSEPNQTEN

DALEPEDLPQAAEQDEMRLELQRSANSNPAMAPRERKAGCKNFFWKTFTSC

Somatostatin Human (amino acid sequence)
(SEQ ID NO: 345)
MLSCRLQCALAALSIVLALGCVTGAPSDPRLRQFLQKSLAAAAGKQELAKYFLAELRKK

PTENNEDFNIVAVASNFATTDLDADRGKLPGKKLPLEVLKEMEANARKAGCTRGCLICL

SHIKCTPKMKKFIPGRCHTYEGDKESAQGGIGEAIVDIPEIPGFKDLEPMEQFIAQVDLCV

DCTTGCLKGLANVQCSDLLKKWLPQRCATFASKIQGQVDKIKGAGGDRKLSEPNQTEN

DALEPEDLSQAAEQDEMRLELQRSANSNPAMAPRERKAGCKNFFWKTFTSC

GHRH Mouse (amino acid sequence)
(SEQ ID NO: 346)
MLLWVLFVILILTSGSHCSLPPSPPFRMQRHVDAIFTTNYRKLLSQLYARKVIQDIMNKQ

GERIQEQRARLSRQEDSMWTEDKQMTLESIRRKPTENNEDFNIVAVASNFATTDLDADR

GKLPGKKLPLEVLKEMEANARKAGCTRGCLICLSHIKCTPKMKKFIPGRCHTYEGDKES

AQGGIGEAIVDIPEIPGFKDLEPMEQFIAQVDLCVDCTTGCLKGLANVQCSDLLKKWLPQ

RCATFASKIQGQVDKIKGAGGDRRLQGFPRMKPSADA

GHRH Human (amino acid sequence)
(SEQ ID NO: 347)
MPLWVFFFVILTLSNSSHCSPPPPLTLRMRRYADAIFTNSYRKVLGQLSARKLLQDIMSR

QQGESNQERGARARLGRQVDSMWAEQKQMELESILVALRRKPTENNEDFNIVAVASNF

ATTDLDADRGKLPGKKLPLEVLKEMEANARKAGCTRGCLICLSHIKCTPKMKKFIPGRC

-continued

HTYEGDKESAQGGIGEAIVDIPEIPGFKDLEPMEQPIAQVDLCVDCTTGCLKGLANVQCS

DLLKKWLPQRCATFASKIQGQVDKIKGAGGDRRLQKHRNSQG

POMC (ACTH, MSH) Mouse (amino acid sequence)
(SEQ ID NO: 348)
MPRFCYSRSGALLLALLLQTSIDVWSWCLESSQCQDLTTESNLLACIRACKLDLSLETPV

FPGNGDEQPLTENPRKYVMGHFRWDRFGPRNSSSAGSAAQRRAEEEAVWGDGSPEPSP

REGKRKPTENNEDFNIVAVASNFATTDLDADRGKLPGKKLPLEVLKEMEANARKAGCT

RGCLICLSHIKCTPKMKKFIPGRCHTYEGDKESAQGGIGEAIVDIPEIPGFKDLEPMEQFIA

QVDLCVDCTTGCLKGLANVQCSDLLKKWLPQRCATFASKIQGQVDKIKGAGGDKRSYS

MEHFRWGKPVGKKRRPVKVYPNVAENESAEAFPLEFKRELEGERPLGLEQVLESDAEK

DDGPYRVEHFRWSNPPKDKRYGGFMTSEKSQTPLVTLFKNAIIKNAHKKGQ

POMC (ACTH, MSH) Human (amino acid sequence)
(SEQ ID NO: 349)
MPRSCCSRSGALLLALLLQASMEVRGWCLESSQCQDLTTESNLLECIRACKPDLSAETPM

FPGNGDEQPLTENPRKYVMGHFRWDRFGRRNSSSSGSSGAGQKREDVSAGEDCGPLPE

GGPEPRSDGAKPGPREGKRKPTENNEDFNIVAVASNFATTDLDADRGKLPGKKLPLEVL

KEMEANARKAGCTRGCLICLSHIKCTPKMKKFIPGRCHTYEGDKESAQGGIGEAIVDIPEI

PGFKDLEPMEQFIAQVDLCVDCTTGCLKGLANVQCSDLLKKWLPQRCATFASKIQGQV

DKIKGAGGDKRSYSMEHFRWGKPVGKKRRPVKVYPNGAEDESAEAFPLEFKRELTGQR

LREGDGPDGPADDGAGAQADLEHSLLVAAEKKDEGPYRMEHFRWGSPPKDKRYGGFM

TSEKSQTPLVTLFKNAIIKNAYKKGE

Oxytocin Mouse (amino acid sequence)
(SEQ ID NO: 350)
MACPSLACCLLGLLALTSACYIQNCPLGGKRKPTENNEDFNIVAVASNFATTDLDADRG

KLPGKKLPLEVLKEMEANARKAGCTRGCLICLSHIKCTPKMKKFIPGRCHTYEGDKESA

QGGIGEAIVDIPEIPGFKDLEPMEQFIAQVDLCVDCTTGCLKGLANVQCSDLLKKWLPQR

CATFASKIQGQVDKIKGAGGDKRAVLDLDMRKCLPCGPGGKGRCFGPSICCADELGCFV

GTAEALRCQEENYLPSPCQSGQKPCGSGGRCAATGICCSPDGCRTDPACDPESAFSER

Oxytocin Human (amino acid sequence)
(SEQ ID NO: 351)
MAGPSLACCLLGLLALTSACYIQNCPLGGKRKPTENNEDFNIVAVASNFATTDLDADRG

KLPGKKLPLEVLKEMEANARKAGCTRGCLICLSHIKCTPKMKKFIPGRCHTYEGDKESA

QGGIGEAIVDIPEIPGFKDLEPMEQFIAQVDLCVDCTTGCLKGLANVQCSDLLKKWLPQR

CATFASKIQGQVDKIKGAGGDKRAAPDLDVRKCLPCGPGGKGRCFGPNICCAEELGCFV

GTAEALRCQEENYLPSPCQSGQKACGSGGRCAVLGLCCSPDGCHADPACDAEATFSQR

Vasopressin-Neurophysin-2 Mouse (amino acid sequence)
(SEQ ID NO: 352)
MLARMLNTTLSACFLSLLAFSSACYFQNCPRGGKRKPTENNEDFNIVAVASNFATTDLD

ADRGKLPGKKLPLEVLKEMEANARKAGCTRGCLICLSHIKCTPKMKKFIPGRCHTYEGD

KESAQGGIGEAIVDIPEIPGFKDLEPMEQFIAQVDLCVDCTTGCLKGLANVQCSDLLKKW

LPQRCATFASKIQGQVDKIKGAGGDKRAISDMELRQCLPCGPGGKGRCFGPSICCADELG

CFVGTAEALRCQEENYLPSPCQSGQKPCGSGGRCAAVGICCSDESCVAEPECHDGFFRLT

RAREPSNATQLDGPARALLLRLVQLAGTRESVDSAKPRVY

Vasopressin-Neurophysin-2 Human (amino acid sequence)
(SEQ ID NO: 353)
MPDTMLPACFLGLLAFSSACYFQNCPRGGKRKPTENNEDFNIVAVASNFATTDLDADRG

KLPGKKLPLEVLKEMEANARKAGCTRGCLICLSHIKCTPKMKKFIPGRCHTYEGDKESA

-continued

QGGIGEAIVDIPEIPGFKDLEPMEQFIAQVDLCVDCTTGCLKGLANVQCSDLLKKWLPQR

CATFASKIQGQVDKIKGAGGDKRAMSDLELRQCLPCGPGGKGRCFGPSICCADELGCFV

GTAEALRCQEENYLPSPCQSGQKACGSGGRCAAFGVCCNDESCVTEPECREGFHRRARA

SDRSNATQLDGPAGALLLRLVQLAGAPEPFEPAQPDAY

Gonadotropin-releasing hormone (GnRH)
Mouse (amino acid sequence)
(SEQ ID NO: 354)
MILKLMAGILLLTVCLEGCSSQHWSYGLRPGGKRKPTENNEDFNIVAVASNFATTDLDA

DRGKLPGKKLPLEVLKEMEANARKAGCTRGCLICLSHIKCTPKMKKFIPGRCHTYEGDK

ESAQGGIGEAIVDIPEIPGFKDLEPMEQFIAQVDLCVDCTTGCLKGLANVQCSDLLKKWL

PQRCATFASKIQGQVDKIKGAGGDKRNTEHLVESFQEMGKEVDQMAEPQHFECTVHWP

RSPLRDLRGALESLIEEEARQKKM

Gonadotropin-releasing hormone (GnRH)
Human (amino acid sequence)
(SEQ ID NO: 355)
MKPIQKLLAGLILLLTWCVEGCSSQHWSYGLRPGGKRKPTENNEDFNIVAVASNFATTDL

DADRGKLPGKKLPLEVLKEMEANARKAGCTRGCLICLSHIKCTPKMKKFIPGRCHTYEG

DKESAQGGIGEAIVDIPEIPGFKDLEPMEQFIAQVDLCVDCTTGCLKGLANVQCSDLLKK

WLPQRCATFASKIQGQVDKIKGAGGDKRDAENLIDSFQEIVKEVGQLAETQRFECTTHQ

PRSPLRDLKGALESLIEEETGQKKI

Thyroid-stimulating hormone, beta subunit
(TSHB) Mouse (amino acid sequence)
(SEQ ID NO: 356)
MSAAVLLSVLFALACGQAASFCIPTEYTMYVDRRECAYCLTINTTICAGYCMTRDINGK

LFLPKYALSQDVCTYRDFIYRTVEIPGCPHHVTPYFSFPVAISCKCGKCNTDNSDCIHEAV

RTNYCTKPQSFYLKPTENNEDFNIVAVASNFATTDLDADRGKLPGKKLPLEVLKEMEAN

ARKAGCTRGCLICLSHIKCTPKMKKFIPGRCHTYEGDKESAQGGIGEAIVDIPEIPGFKDL

EPMEQFIAQVDLCVDCTTGCLKGLANVQCSDLLKKWLPQRCATFASKIQGQVDKIKGA

GGDYLGGFSV

Thyroid-stimulating hormone, beta subunit (TSHB)
Human (amino acid sequence)
(SEQ ID NO: 334)
MTALFLMSMLFGLTCGQAMSFCIPTEYTMHIERRECAYCLTINTTICAGYCMTRDINGKL

FLPKYALSQDVCTYRDFIYRTVEIPGCPLHVAPYFSYPVALSCKCGKCNTDYSDCIHEAIK

TNYCTKPQKSYLKPTENNEDFNIVAVASNFATTDLDADRGKLPGKKLPLEVLKEMEANA

RKAGCTRGCLICLSHIKCTPKMKKFIPGRCHTYEGDKESAQGGIGEAIVDIPEIPGFKDLEP

MEQFIAQVDLCVDCTTGCLKGLANVQCSDLLKKWLPQRCATFASKIQGQVDKIKGAGG

DYLVGFSV

Cortisol-releasing factor (CRF) Mouse (amino acid sequence)
(SEQ ID NO: 357)
MRLRLLVSAGMLLVALSSCLPCRALLSRGSVPRAPRAPQPLNFLQPEQPQQPQPVLIRMG

EEYFLRLGNLNRSPAARLSPNSTPLTAGRGSRPSHDQAAANFFRVLLQQLQMPQRSLDSR

AEPAERGAEDALGGHQGALERERRKPTENNEDFNIVAVASNFATTDLDADRGKLPGKK

LPLEVLKEMEANARKAGCTRGCLICLSHIKCTPKMKKFIPGRCHTYEGDKESAQGGIGEA

IVDIPEIPGFKDLEPMEQFIAQVDLCVDCTTGCLKGLANVQCSDLLKKWLPQRCATFASK

IQGQVDKIKGAGGDRRSEEPPISLDLTFHLLREVLEMARAEQLAQQAHSNRKLMEIIGK

Cortisol-releasing factor (CRF) Human (amino acid sequence)
(SEQ ID NO: 358)
MRLPLLVSAGVLLVALLPCPPCRALLSRGPVPGARQAPQHPQPLDFFQPPPQ

SEQPQQPQARPVLLRMGEEYFLRLGNLNKSPAAPLSPASSLLAGGSGSRPSPEQATANFF

RVLLQQLLLPRRSLDSPAALAERGARNALGGHQEAPERERRKPTENNEDFNIVAVASNF

ATTDLDADRGKLPGKKLPLEVLKEMEANARKAGCTRGCLICLSHIKCTPKMKKFIPGRC

HTYEGDKESAQGGIGEAIVDIPEIPGFKDLEPMEQPIAQVDLCVDCTTGCLKGLANVQCS

DLLKKWLPQRCATFASKIQGQVDKIKGAGGDRRSEEPPISLDLTFHLLREVLEMARAEQL

AQQAHSNRKLMEIIGK

Atrial natriuretic peptide (ANP) Mouse (amino acid sequence)
(SEQ ID NO: 359)
MGSFSITLGFFLVLAFWLPGHIGANPVYSAVSNTDLMDFKNLLDHLEEKMPVEDEVMPP

QALSEQTEEAGAALSSLPEVPPWTGEVNPPLRDGSALGRSPWDPSDRSALLKSKLRALLA

GPRSKPTENNEDFNIVAVASNFATTDLDADRGKLPGKKLPLEVLKEMEANARKAGCTR

GCLICLSHIKCTPKMKKFIPGRCHTYEGDKESAQGGIGEAIVDIPEIPGFKDLEPMEQFIAQ

VDLCVDCTTGCLKGLANVQCSDLLKKWLPQRCATFASKIQGQVDKIKGAGGDRSLRRS

SCFGGRIDRIGAQSGLGCNSFRYRR

Atrial natriuretic peptide (ANP) Human (amino acid sequence)
(SEQ ID NO: 360)
MSSFSTTTVSFLLLLAFQLLGQTRANPMYNAVSNADLMDFKNLLDHLEEKMPLEDEVVP

PQVLSEPNEEAGAALSPLPEVPPWTGEVSPAQRDGGALGRGPWDSSDRSALLKSKLRAL

LTAPRSKPTENNEDFNIVAVASNFATTDLDADRGKLPGKKLPLEVLKEMEANARKAGCT

RGCLICLSHIKCTPKMKKFIPGRCHTYEGDKESAQGGIGEAIVDIPEIPGFKDLEPMEQFIA

QVDLCVDCTTGCLKGLANVQCSDLLKKWLPQRCATFASKIQGQVDKIKGAGGDRSLRR

SSCFGGRMDRIGAQSGLGCNSFRY

Brain natriuretic peptide (BNP) Human (amino acid sequence)
(SEQ ID NO: 361)
MDPQTAPSRALLLLLFLHLAFLGGRSHPLGSPGSASDLETSGLQEQRNHLQGKLSELQVE

QTSLEPLQESPRPTGVWKSREVATEGIRGHRKMVLYTLRAPRSKPTENNEDFNIVAVASN

FATTDLDADRGKLPGKKLPLEVLKEMEANARKAGCTRGCLICLSHIKCTPKMKKFIPGR

CHTYEGDKESAQGGIGEAIVDIPEIPGFKDLEPMEQFIAQVDLCVDCTTGCLKGLANVQC

SDLLKKWLPQRCATFASKIQGQVDKIKGAGGDRSRSPKMVQGSGCFGRKMDRISSSSGL

GCKVLRRH

Renin Mouse (amino acid sequence)
(SEQ ID NO: 362)
MDRRRMPLWALLLLWSPCTFSLPTRTATFERIPLKKMPSVREILEERGVDMTRLSAEWG

VFTKRKPTENNEDFNIVAVASNFATTDLDADRGKLPGKKLPLEVLKEMEANARKAGCT

RGCLICLSHIKCTPKMKKFIPGRCHTYEGDKESAQGGIGEAIVDIPEIPGFKDLEPMEQFIA

QVDLCVDCTTGCLKGLANVQCSDLLKKWLPQRCATFASKIQGQVDKIKGAGGDKRPSL

TNLTSPVVLTNYLNTQYYGEIGIGTPPQTFKVIFDTGSANLWVPSTKCSRLYLACGIHSLY

ESSDSSSYMENGSDFTIHYGSGRVKGFLSQDSVTVGGITVTQTFGEVTELPLIPFMLAKFD

GVLGMGFPAQAVGGVTPVFDHILSQGVLKEEVFSVYYNRGSHLLGGEVVLGGSDPQHY

QGNFHYVSISKTDSWQITMKGVSVGSSTLLCEEGCAVVVDTGSSFISAPTSSLKLIMQAL

GAKEKRIEEYVVNCSQVPTLPDISFDLGGRAYTLSSTDYVLQYPNRRDKLCTLALHAMDI

PPPTGPVWVLGATFIRKFYTEFDRHNNRIGFALAR

-continued

Renin Human (amino acid sequence)
(SEQ ID NO: 363)
MDGWRRMPRWGLLLLLWGSCTFGLPTDTTTFKRKPTENNEDFNIVAVASNFATTDLDA

DRGKLPGKKLPLEVLKEMEANARKAGCTRGCLICLSHIKCTPKMKKFIPGRCHTYEGDK

ESAQGGIGEAIVDIPEIPGFKDLEPMEQFIAQVDLCVDCTTGCLKGLANVQCSDLLKKWL

PQRCATFASKIQGQVDKIKGAGGDKRIFLKRMPSIRESLKERGVDMARLGPEWSQPMKR

LTLGNTTSSVILTNYMDTQYYGEIGIGTPPQTFKVVFDTGSSNVWVPSSKCSRLYTACVY

HKLFDASDSSSYKHNGTELTLRYSTGTVSGFLSQDIITVGGITVTQMFGEVTEMPALPFM

LAEFDGVVGMGFIEQAIGRVTPIFDNIISQGVLKEDVFSFYYNRDSENSQSLGGQIVLGGS

DPQHYEGNFHYINLIKTGVWQIMKGVSVGSSTLLCEDGCLALVDTGASYISGSTSSIEK

LMEALGAKKRLFDYVVKCNEGPTLPDISFHLGGKEYTLTSADYVFQESYSSKKLCTLAIH

AMDIPPPTGPTWALGATFIRKFYTEFDRRNNRIGFALAR

Galanin Mouse (amino acid sequence)
(SEQ ID NO: 364)
MARGSVILLGWLLLVVTLSATLGLGMPAKEKRGKPTENNEDFNIVAVASNFATTDLDA

DRGKLPGKKLPLEVLKEMEANARKAGCTRGCLICLSHIKCTPKMKKFIPGRCHTYEGDK

ESAQGGIGEAIVDIPEIPGFKDLEPMEQFIAQVDLCVDCTTGCLKGLANVQCSDLLKKWL

PQRCATFASKIQGQVDKIKGAGGDKRGWTLNSAGYLLGPHAIDNHRSFSDKHGLTGKRE

LQLEVEERRPGSVDVPLPESNIVRTIMEFLSFLHLKEAGALDSLPGIPLATSSEDLEKS

Galanin Human (amino acid sequence)
(SEQ ID NO: 365)
MARGSALLLASLLLAAALSASAGLWSPAKEKRGKPTENNEDFNIVAVASNFATTDLDAD

RGKLPGKKLPLEVLKEMEANARKAGCTRGCLICLSHIKCTPKMKKFIPGRCHTYEGDKE

SAQGGIGEAIVDIPEIPGFKDLEPMEQFIAQVDLCVDCTTGCLKGLANVQCSDLLKKWLP

QRCATFASKIQGQVDKIKGAGGDKRGWTLNSAGYLLGPHAVGNHRSFSDKNGLTSKRE

LRPEDDMKPGSFDRSIPENNIMRTIIEFLSFLHLKEAGALDRLLDLPAAASSEDIERS

Orexin Mouse (amino acid sequence)
(SEQ ID NO: 366)
MNFPSTKVPWAAVTLLLLLLLPPALLSLGVDAQPLPDCCRQKTCSCRLYELLHGAGNHA

AGILTLGKRRPGPPGLQGRLQRLLQANGNHAAGILTMGRRKPTENNEDFNIVAVASNFA

TTDLDADRGKLPGKKLPLEVLKEMEANARKAGCTRGCLICLSHIKCTPKMKKFIPGRCH

TYEGDKESAQGGIGEAIVDIPEIPGFKDLEPMEQFIAQVDLCVDCTTGCLKGLANVQCSD

LLKKWLPQRCATFASKIQGQVDKIKGAGGDRRAGAELEPHPCSGRGCPTVTTTALAPR

GGSGV

Orexin Human (amino acid sequence)
(SEQ ID NO: 367)
MNLPSTKVSWAAVTLLLLLLLLPPALLSSGAAAQPLPDCCRQKTCSCRLYELLHGAGNH

AAGILTLGKRRSGPPGLQGRLQRLLQASGNHAAGILTMGRRKPTENNEDFNIVAVASNF

ATTDLDADRGKLPGKKLPLEVLKEMEANARKAGCTRGCLICLSHIKCTPKMKKFIPGRC

HTYEGDKESAQGGIGEAIVDIPEIPGFKDLEPMEQFIAQVDLCVDCTTGCLKGLANVQCS

DLLKKWLPQRCATFASKIQGQVDKIKGAGGDRRAGAEPAPRPCLGRRCSAPAAASVA

PGGQSGI

Ghrelin-Obestatin Mouse (amino acid sequence)
(SEQ ID NO: 368)
MLSSGTICSLLLLSMLWMDMAMAGSSFLSPEHQKAQQRKESKKPPAKLQPRAKPTENN

EDFNIVAVASNFATTDLDADRGKLPGKKLPLEVLKEMEANARKAGCTRGCLICLSHIKC

TPKMKKFIPGRCHTYEGDKESAQGGIGEAIVDIPEIPGFKDLEPMEQFIAQVDLCVDCTTG

CLKGLANVQCSDLLKKWLPQRCATFASKIQGQVDKIKGAGGDPRALEGWLHPEDRGQA

EETEEELEIRFNAPFDVGIKLSGAQYQQHGRALGKFLQDILWEEVKEAPADK

Ghrelin-Obestatin Human (amino acid sequence)
(SEQ ID NO: 369)
MPSPGTVCSLLLLGMLWLDLAMAGSSFLSPEHQRVQRKESKKPPAKLQPRAKPTENNED

FNIVAVASNFATTDLDADRGKLPGKKLPLEVLKEMEANARKAGCTRGCLICLSHIKCTP

KMKKFIPGRCHTYEGDKESAQGGIGEAIVDIPEIPGFKDLEPMEQFIAQVDLCVDCTTGCL

KGLANVQCSDLLKKWLPQRCATFASKIQGQVDKIKGAGGDPRALAGWLRPEDGGQAE

GAEDELEVRFNAPFDVGIKLSGVQYQQHSQALGKFLQDILWEEAKEAPADK

Cholecystokinin Mouse (amino acid sequence)
(SEQ ID NO: 370)
MKSGVCLCVVMAVLAAGALAQPVVPAEATDPVEQRAQEAPRRQLRAKPTENNEDFNIV

AVASNFATTDLDADRGKLPGKKLPLEVLKEMEANARKAGCTRGCLICLSHIKCTPKMK

KFIPGRCHTYEGDKESAQGGIGEAIVDIPEIPGFKDLEPMEQFIAQVDLCVDCTTGCLKGL

ANVQCSDLLKKWLPQRCATFASKIQGQVDKIKGAGGDRRQLRAVLRTDGEPRARLGAL

LARYIQQVRKAPSGRMSVLKNLQSLDPSHRISDRDYMGWMDFGRRSAEDYEYPS

Cholecystokinin Human (amino acid sequence)
(SEQ ID NO: 371)
MNSGVCLCVLMAVLAAGALTQPVPPADPAGSGLQRAEEAPRRQLRVKPTENNEDFNIV

AVASNFATTDLDADRGKLPGKKLPLEVLKEMEANARKAGCTRGCLICLSHIKCTPKMK

KFIPGRCHTYEGDKESAQGGIGEAIVDIPEIPGFKDLEPMEQFIAQVDLCVDCTTGCLKGL

ANVQCSDLLKKWLPQRCATFASKIQGQVDKIKGAGGDRRQLRVSQRTDGESRAHLGAL

LARYIQQARKAPSGRMSIVKNLQNLDPSHRISDRDYMGWMDFGRRSAEEYEYPS

Gastrin Mouse (amino acid sequence)
(SEQ ID NO: 372)
MPRLCVYMLVLVLALATFSEASWKPRSQLQDASSGPGTNEDLEQRQFNKLGSASHHRR

QLGPQGPQHFIADLSKKQRPRMEEEEEAYGWMDFGRRSKPTENNEDFNIVAVASNFATT

DLDADRGKLPGKKLPLEVLKEMEANARKAGCTRGCLICLSHIKCTPKMKKFIPGRCHTY

EGDKESAQGGIGEAIVDIPEIPGFKDLEPMEQPIAQVDLCVDCTTGCLKGLANVQCSDLL

KKWLPQRCATFASKIQGQVDKIKGAGGDRRSAEEDQ

Gastrin Human (amino acid sequence)
(SEQ ID NO: 373)
MQRLCVYVLIFALALAAFSEASWKPRSQQPDAPLGTGANRDLELPWLEQQGPASHHRR

QLGPQGPPHLVADPSKKQGPWLEEEEEAYGWMDFGRRSKPTENNEDFNIVAVASNFAT

TDLDADRGKLPGKKLPLEVLKEMEANARKAGCTRGCLICLSHIKCTPKMKKFIPGRCHT

YEGDKESAQGGIGEAIVDIPEIPGFKDLEPMEQFIAQVDLCVDCTTGCLKGLANVQCSDL

LKKWLPQRCATFASKIQGQVDKIKGAGGDRRSAEDEN

Protachykinin-1 (Substance P, Neurokinin A, Neuropeptide K,
Neuropeptide gamma) Mouse (amino acid sequence)
(SEQ ID NO: 374)
MKILVAVAVFFLVSTQLFAEEIDANDDLNYWSDWSDSDQIKEAMPEPFEHLLQRIARRK

PTENNEDFNIVAVASNFATTDLDADRGKLPGKKLPLEVLKEMEANARKAGCTRGCLICL

SHIKCTPKMKKFIPGRCHTYEGDKESAQGGIGEAIVDIPEIPGFKDLEPMEQFIAQVDLCV

DCTTGCLKGLANVQCSDLLKKWLPQRCATFASKIQGQVDKIKGAGGDRRPKPQQFFGL

MGKRDADSSVEKQVALLKALYGHGQISHKRHKTDSFVGLMGKRALNSVAYERSAMQN

YERRRK

-continued

Protachykinin-1 (Substance P, Neurokinin A, Neuropeptide K, Neuropeptide gamma) Human (amino acid sequence)
(SEQ ID NO: 375)
MKILVALAVFFLVSTQLFAEEIGANDDLNYWSDWYDSDQIKEELPEPFEHLLQRIARRKP

TENNEDFNIVAVASNFATTDLDADRGKLPGKKLPLEVLKEMEANARKAGCTRGCLICLS

HIKCTPKMKKFIPGRCHTYEGDKESAQGGIGEAIVDIPEIPGFKDLEPMEQFIAQVDLCVD

CTTGCLKGLANVQCSDLLKKWLPQRCATFASKIQGQVDKIKGAGGDRRPKPQQFFGLM

GKRDADSSIEKQVALLKALYGHGQISHKRHKTDSFVGLMGKRALNSVAYERSAMQNYE

RRR

Proenkephalin-A Mouse (amino acid sequence)
(SEQ ID NO: 376)
MARFLRLCTWLLALGSCLLATVQAECSQDCAKCSYRLVRPGDINFLACTLECEGQLPSF

KIWETCKDLLQVSRPEFPWDNIDMYKDSSKQDESHLLAKKYGGFMKRYGGFMKKMDE

LYPMEPEEEANGGEILAKRYGGFMKKDADEGDTLANSSDLLKELLGTGDNRAKDSHQQ

ESTNNDEDMSKRYGGFMRSLKRSPQLEDEAKELQKRYGGFMRRKPTENNEDFNIVAVA

SNFATTDLDADRGKLPGKKLPLEVLKEMEANARKAGCTRGCLICLSHIKCTPKMKKFIP

GRCHTYEGDKESAQGGIGEAIVDIPEIPGFKDLEPMEQFIAQVDLCVDCTTGCLKGLANV

QCSDLLKKWLPQRCATFASKIQGQVDKIKGAGGDRRVGRPEWWMDYQKRYGGFLKRF

AESLPSDEEGENYSKEVPEIEKRYGGFMRF

Proenkephalin-A Human (amino acid sequence)
(SEQ ID NO: 377)
MARFLTLCTWLLLLGPGLLATVRAECSQDCATCSYRLVRPADINFLACVMECEGKLPSL

KIWETCKELLQLSKPELPQDGTSTLRENSKPEESHLLAKRYGGFMKRYGGFMKKMDEL

YPMEPEEEANGSEILAKRYGGFMKKDAEEDDSLANSSDLLKELLETGDNRERSHHQDGS

DNEEEVSKRYGGFMRGLKRSPQLEDEAKELQKRYGGFMRRKPTENNEDFNIVAVASNF

ATTDLDADRGKLPGKKLPLEVLKEMEANARKAGCTRGCLICLSHIKCTPKMKKFIPGRC

HTYEGDKESAQGGIGEAIVDIPEIPGFKDLEPMEQFIAQVDLCVDCTTGCLKGLANVQCS

DLLKKWLPQRCATFASKIQGQVDKIKGAGGDRRVGRPEWWMDYQKRYGGFLKRFAEA

LPSDEEGESYSKEVPEMEKRYGGFMRF

Proenkephalin-B Mouse (amino acid sequence)
(SEQ ID NO: 378)
MAWSRLMLAACLLVMPSNVMADCLSLCSLCAVRIQDGPRPINPLICSLECQDLVPPSEE

WETCRGFSSFLTLTVSGLRGKDDLEDEVALEEGYSALAKLLEPVLKELEKSRLLTSVPEE

KFRGLSSSFGNGKESELAGADRMNDEAAQAGTLHFNEEDLRKQAKRYGGFLRKYPKRK

PTENNEDFNIVAVASNFATTDLDADRGKLPGKKLPLEVLKEMEANARKAGCTRGCLICL

SHIKCTPKMKKFIPGRCHTYEGDKESAQGGIGEAIVDIPEIPGFKDLEPMEQFIAQVDLCV

DCTTGCLKGLANVQCSDLLKKWLPQRCATFASKIQGQVDKIKGAGGDKRSSEMARDED

GGQDGDQVGHEDLYKRYGGFLRRIRPKLKWDNQKRYGGFLRRQFKVVTRSQENPNTY

SEDLDV

Proenkephalin-B Human (amino acid sequence)
(SEQ ID NO: 379)
MAWQGLVLAACLLMFPSTTADCLSRCSLCAVKTQDGPKPINPLICSLQCQAALLPSEEW

ERCQSFLSFFTPSTLGLNDKEDLGSKSVGEGPYSELAKLSGSFLKELEKSKFLPSISTKENT

LSKSLEEKLRGLSDGFREGAESELMRDAQLNDGAMETGTLYLAEEDPKEQVKRKPTEN

NEDFNIVAVASNFATTDLDADRGKLPGKKLPLEVKEMEANARKAGCTRGCLICLSHIK

CTPKMKKFIPGRCHTYEGDKESAQGGIGEAIVDIPEIPGFKDLEPMEQFIAQVDLCVDCTT

```
GCLKGLANVQCSDLLKKWLPQRCATFASKIQGQVDKIKGAGGDKRYGGFLRKYPKRSS

EVAGEGDGDSMGHEDLYKRYGGFLRRIRPKLKWDNQKRYGGFLRRQFKVVTRSQEDP

NAYSGELFDA

Insulin-like growth hormone 1 (IGF-1)
Mouse (amino acid sequence)
                                                    (SEQ ID NO: 380)
MGKISSLPTQLFKICLCDFLKIKIHIMSSSHLFYLALCLLTFTSSTTAGPETLCGAELVDAL

QFVCGPRGFYFNKPTGYGSSIRRKPTENNEDFNIVAVASNFATTDLDADRGKLPGKKLPL

EVLKEMEANARKAGCTRGCLICLSHIKCTPKMKKFIPGRCHTYEGDKESAQGGIGEAIVD

IPEIPGFKDLEPMEQFIAQVDLCVDCTTGCLKGLANVQCSDLLKKWLPQRCATFASKIQG

QVDKIKGAGGDSSIRRAPQTGIVDECCFRSCDLRRLEMYCAPLKPTKAARSIRAQRHTD

MPKTQKSPSLSTNKKTLQRRRKGSTFEEHK

Insulin-like growth hormone 1 (IGF-1)
Human (amino acid sequence)
                                                    (SEQ ID NO: 381)
MGKISSLPTQLFKCCFCDFLKVKMHTMSSSHLFYLALCLLTFTSSATAGPETLCGAELVD

ALQFVCGDRGFYFNKPTGYGSSSRRKPTENNEDFNIVAVASNFATTDLDADRGKLPGKK

LPLEVLKEMEANARKAGCTRGCLICLSHIKCTPKMKKFIPGRCHTYEGDKESAQGGIGEA

IVDIPEIPGFKDLEPMEQFIAQVDLCVDCTTGCLKGLANVQCSDLLKKWLPQRCATFASK

IQGQVDKIKGAGGDSSRRAPQTGIVDECCFRSCDLRRLEMYCAPLKPAKSARSVRAQRH

TDMPKTQKYQPPSTNKNTKSQRRKGSTFEERK

Insulin-like growth hormone 2 (IGF-2)
Mouse (amino acid sequence)
                                                    (SEQ ID NO: 382)
MGGSVAGFQVPMGIPVGKSMLVLLISLAFALCCIAAYGPGETLCGGELVDTLQFVCSDR

GFYFSRPSSRANRRSRGIVEECCFRSCDLALLETYCATPAKSERDKPTENNEDFNIVAVAS

NFATTDLDADRGKLPGKKLPLEVLKEMEANARKAGCTRGCLICLSHIKCTPKMKKFIPG

RCHTYEGDKESAQGGIGEAIVDIPEIPGFKDLEPMEQFIAQVDLCVDCTTGCLKGLANVQ

CSDLLKKWLPQRCATFASKIQGQVDKIKGAGGDERDVSTSQAVLPDDFPRYPVGKFFQY

DTWRQSAGRLRRGLPALLRARRGRMLAKELKEFREAKRHRPLIVLPPKDPAHGGASSE

MSSNHQ

Insulin-like growth hormone 2 (IGF-2)
Human (amino acid sequence)
                                                    (SEQ ID NO: 383)
MGIPMGKSMLVLLTFLAFASCCIAAYRPSETLCGGELVDTLQFVCGDRGFYFSRPASRVS

RRSRGIVEECCFRSCDLALLETYCATPAKSERDKPTENNEDFNIVAVASNFATTDLDADR

GKLPGKKLPLEVLKEMEANARKAGCTRGCLICLSHIKCTPKMKKFIPGRCHTYEGDKES

AQGGIGEAIVDIPEIPGFKDLEPMEQFIAQVDLCVDCTTGCLKGLANVQCSDLLKKWLPQ

RCATFASKIQGQVDKIKGAGGDERDVSTPPTVLPDNFPRYPVGKFFQYDTWKQSTQRLR

RGLPALLRARRGHVLAKELEAFREAKRHRPLIALPTQDPAHGGAPPEMASNRK

Parathyroid hormone (PTH) Mouse (amino acid sequence)
                                                    (SEQ ID NO: 384)
MMSANTVAKVMIIMLAVCLLTQTDGKPVRKRKPTENNEDFNIVAVASNFATTDLDADR

GKLPGKKLPLEVLKEMEANARKAGCTRGCLICLSHIKCTPKMKKFIPGRCHTYEGDKES

AQGGIGEAIVDIPEIPGFKDLEPMEQFIAQVDLCVDCTTGCLKGLANVQCSDLLKKWLPQ

RCATFASKIQGQVDKIKGAGGDKRAVSEIQLMHNLGKHLASMERMQWLRRKLQDMHN

FVSLGVQMAARDGSHQKPTKKEENVLVDGNPKSLGEGDKADVDVLVKSKSQ
```

-continued

Parathyroid hormone (PTH) Human (amino acid sequence)
(SEQ ID NO: 385)
MIPAKDMAKVMIVMLAICFLTKSDGKSVKKRKPTENNEDFNIVAVASNFATTDLDADR

GKLPGKKLPLEVLKEMEANARKAGCTRGCLICLSHIKCTPKMKKFIPGRCHTYEGDKES

AQGGIGEAIVDIPEIPGFKDLEPMEQFIAQVDLCVDCTTGCLKGLANVQCSDLLKKWLPQ

RCATFASKIQGQVDKIKGAGGDKRSVSEIQLMHNLGKHLNSMERVEWLRKKLQDVHNF

VALGAPLAPRDAGSQRPRKKEDNVLVESHEKSLGEADKADVNVLTKAKSQ

Parathyroid hormone-related protein (PTHrP)
Mouse (amino acid sequence)
(SEQ ID NO: 386)
MLRRLVQQWSVLVFLLSYSVPSRGRSVEGLGRRLKRKPTENNEDFNIVAVASNFATTDL

DADRGKLPGKKLPLEVLKEMEANARKAGCTRGCLICLSHIKCTPKMKKFIPGRCHTYEG

DKESAQGGIGEAIVDIPEIPGFKDLEPMEQFIAQVDLCVDCTTGCLKGLANVQCSDLLKK

WLPQRCATFASKIQGQVDKIKGAGGDKRAVSEHQLLHDKGKSIQDLRRRFFLHHLIAEIH

TAEIRATSEVSPNSKPAPNTKNHPVRFGSDDEGRYLTQETNKVETYKEQPLKTPGKKKK

GKPGKRREQEKKKRRTRSAWPSTAASGLLEDPLPHTSRPSLEPSLRTH

Parathyroid hormone-related protein (PTHrP)
Human (amino acid sequence)
(SEQ ID NO: 387)
MQRRLVQQWSVAVFLLSYAVPSCGRSVEGLSRRLKRKPTENNEDFNIVAVASNFATTDL

DADRGKLPGKKLPLEVLKEMEANARKAGCTRGCLICLSHIKCTPKMKKFIPGRCHTYEG

DKESAQGGIGEAIVDIPEIPGFKDLEPMEQFIAQVDLCVDCTTGCLKGLANVQCSDLLKK

WLPQRCATFASKIQGQVDKIKGAGGDKRAVSEHQLLHDKGKSIQDLRRRFFLHHLIAEIH

TAEIRATSEVSPNSKPSPNTKNHPVRFGSDDEGRYLTQETNKVETYKEQPLKTPGKKKKG

KPGKRKEQEKKKRRTRSAWLDSGVTGSGLEGDHLSDTSTTSLELDSRRH

Osteocalcin Mouse (amino acid sequence)
(SEQ ID NO: 388)
MRTIFLLTLLTLAALCLSDLTDAKPSGPESDKAFMSKQEGNKVVNRLRRKPTENNEDFNI

VAVASNFATTDLDADRGKLPGKKLPLEVLKEMEANARKAGCTRGCLICLSHIKCTPKM

KKFIPGRCHTYEGDKESAQGGIGEAIVDIPEIPGFKDLEPMEQFIAQVDLCVDCTTGCLKG

LANVQCSDLLKKWLPQRCATFASKIQGQVDKIKGAGGDRRYLGASVPSPDPLEPTREQC

ELNPACDELSDQYGLKTAYKRIYGITI

Osteocalcin Human (amino acid sequence)
(SEQ ID NO: 389)
MRALTLLALLALAALCIAGQAGAKPSGAESSKGAAFVSKQEGSEVVKRPRRKPTENNED

FNIVAVASNFATTDLDADRGKLPGKKLPLEVLKEMEANARKAGCTRGCLICLSHIKCTP

KMKKFIPGRCHTYEGDKESAQGGIGEAIVDIPEIPGFKDLEPMEQHAQVDLCVDCTTGCL

KGLANVQCSDLLKKWLPQRCATFASKIQGQVDKIKGAGGDRRYLYQWLGAPVPYPDPL

EPRREVCELNPDCDELADHIGFQEAYRRFYGPV

Urocortin-3 Mouse (amino acid sequence)
(SEQ ID NO: 390)
MLMPTYFLLPLLLLLGGPRTSLSHKFYNTGPVFSCLNTALSEVKKNKLEDVPLLSKKSFG

HLPTQDPSGEEDDNQTHLQIKRTFSGAAGGNGAGSTRYRYQSQAQHKGKLYPDKPKSD

RGTKKPTENNEDFNIVAVASNFATTDLDADRGKLPGKKLPLEVLKEMEANARKAGCTR

GCLICLSHIKCTPKMKKFIPGRCHTYEGDKESAQGGIGEAIVDIPEIPGFKDLEPMEQFIAQ

VDLCVDCTTGCLKGLANVQCSDLLKKWLPQRCATFASKIQGQVDKIKGAGGDRGTKFT

LSLDVPTNIMNILFNIDKAKNLRAKAAANAQLMAQIGKKK

```
Urocortin-3 Human (amino acid sequence)
                                                   (SEQ ID NO: 391)
MLMPVHFLLLLLLLLGGPRTGLPHKFYKAKPIFSCLNTALSEAEKGQWEDASLLSKRSFH

YLRSRDASSGEEEEGKEKKTFPISGARGGARGTRYRYVSQAQPRGKPRQDTAKSPHRKP

TENNEDFNIVAVASNFATTDLDADRGKLPGKKLPLEVLKEMEANARKAGCTRGCLICLS

HIKCTPKMKKFIPGRCHTYEGDKESAQGGIGEAIVDIPEIPGFKDLEPMEQFIAQVDLCVD

CTTGCLKGLANVQCSDLLKKWLPQRCATFASKIQGQVDKIKGAGGDHRTKFTLSLDVPT

NIMNLLFNIAKAKNLRAQAAANAHLMAQIGRKK

Urocortin-2 Mouse (amino acid sequence)
                                                   (SEQ ID NO: 392)
MMTRWALVVFVVLMLDRILFVPGTPIPTFQLLPQNSLETTPSSVTSESSSGTTTGPSASWS

NSKASPYLDTRVKPTENNEDFNIVAVASNFATTDLDADRGKLPGKKLPLEVLKEMEANA

RKAGCTRGCLICLSHIKCTPKMKKFIPGRCHTYEGDKESAQGGIGEAIVDIPEIPGFKDLEP

MEQFIAQVDLCVDCTTGCLKGLANVQCSDLLKKWLPQRCATFASKIQGQVDKIKGAGG

DTRVILSLDVPIGLLRILLEQARYKAARNQAATNAQILAHVGRR

Urocortin-2 Human (amino acid sequence)
                                                   (SEQ ID NO: 393)
MTRCALLLLMVLMLGRVLVVPVTPIPTFQLRPQNSPQTTPRPAASESPSAAPTWPWAAQ

SHCSPTRHPGSRIKPTENNEDFNIVAVASNFATTDLDADRGKLPGKKLPLEVLKEMEANA

RKAGCTRGCLICLSHIKCTPKMKKFIPGRCHTYEGDKESAQGGIGEAIVDIPEIPGFKDLEP

MEQFIAQVDLCVDCTTGCLKGLANVQCSDLLKKWLPQRCATFASKIQGQVDKIKGAGG

DSRIVLSLDVPIGLLQILLEQARARAAREQATTNARILARVGHC

Urocortin-1 Mouse (amino acid sequence)
                                                   (SEQ ID NO: 394)
MIQRGRATLLVALLLLAQLRPESSQWSPAAAAATGVQDPNLRWSPGVRNQGGGVRALL

LLLAERFPRRAGSEPAGERQRRKPTENNEDFNIVAVASNFATTDLDADRGKLPGKKLPLE

VLKEMEANARKAGCTRGCLICLSHIKCTPKMKKFIPGRCHTYEGDKESAQGGIGEAIVDI

PEIPGFKDLEPMEQFIAQVDLCVDCTTGCLKGLANVQCSDLLKKWLPQRCATFASKIQG

QVDKIKGAGGDRRDDPPLSIDLTFHLLRTLLELARTQSQRERAEQNRIIFDSVGK

Urocortin-1 Human (amino acid sequence)
                                                   (SEQ ID NO: 395)
MRQAGRAALLAALLLLVQLCPGSSQRSPEAAGVQDPSLRWSPGARNQGGGARALLLLL

AERFPRRAGPGRLGLGTAGERPRRKPTENNEDFNIVAVASNFATTDLDADRGKLPGKKL

PLEVLKEMEANARKAGCTRGCLICLSHIKCTPKMKKFIPGRCHTYEGDKESAQGGIGEAI

VDIPEIPGFKDLEPMEQFIAQVDLCVDCTTGCLKGLANVQCSDLLKKWLPQRCATFASKI

QGQVDKIKGAGGDRRDNPSLSIDLTFHLLRTLLELARTQSQRERAEQNRIIFDSVGK
```

Multiplexing Luciferase Reporters for Tracking Multiple Proteins and/or for Normalization The nucleic acid constructs and propeptide-luciferase fusion proteins described herein can be used either in isolation to track the secretion of a single protein, or in a multiplexed format to track the secretion of multiple proteins simultaneously. The nucleic acid constructs and propeptide-luciferase fusion proteins described herein can be used either in isolation to track the expression of a single protein at the cell surface, or in a multiplexed format to track the expression of multiple proteins at the cell surface simultaneously. As *Gaussia* luciferase and *Cypridina* luciferase act on different substrates to create luminescence, one could use a "Propeptide.A—*Gaussia* luciferase" fusion protein to track secretion of Protein.A, and a "Propeptide.B—*Cypridina* luciferase" fusion protein to track secretion of Protein.B, if each fusion protein were expressed in the same cells, or if each were expressed separately but in a mixed pool of cells. The ability to multiplex the luciferase reporters has added advantage and utility in chemical and genetic screening assays. Similarly, one could track the cell surface expression of Protein A and Protein B, as described herein.

For example, one skilled in the art could use the multiplex format for screening compounds that affect inflammation. In this example, two nucleic acid constructs encoding propeptide-luciferase fusion proteins can be utilized, the first comprises a propeptide that is an anti-inflammatory cytokine and the *Gaussia* luciferase and the second comprises a propeptide that is a pro-inflammatory cytokine and the *Cypridina* luciferase. The nucleic acid constructs are introduced into the same cell, or a population of cells, such that each cell expresses both constructs. The cells are contacted by test compounds and the bioluminescence is detected, for example by luminometer. Luminescence resulting from activation of the *Gaussia* or *Cypridina* luciferase indicates that the test compound stimulates anti-inflammatory signaling or pro-inflammatory signaling, respectively. In this manner, more than one biological readout (in this case, mature secreted cytokine) can be detected at one time, granting increased utility to the invention described herein for use in chemical and genetic screens.

In another embodiment, a control luciferase that acts on different substrates to create luminescence from the propeptide-luciferase reporter can be used as an internal reference. For example, as Firefly luciferase acts on a third substrate to produce luminescence, one could use this bioluminescent protein to normalize for expression differences across cells, for example by expressing it constitutively within the cells expressing the propeptide-luciferase fusion reporters described. In such a manner, one could assemble kits to monitor the activity of multiple biologic pathways and/or secreted proteins, with or without normalization to a control luciferase signal, for use in basic science research, as well as chemical and genetic screening projects.

High Throughput Screening Assays

Traditional methods of investigating peptide secretion are time-intensive and expensive. ELISA tests are accurate only within a limited range of detection, and as such, results often need to be verified by using serial dilution assays to verify that the signal detected is within the linear range.

The present invention provides methods that are more efficient, cost-effective, sensitive, accurate, and therefore more amenable to large-scale high throughput chemical and genetic screens than the standard methods known in the art to date. The present invention is highly sensitive and accurate as the detection of the luminescence, for example, by a luminometer, is highly sensitive, requires no dilution, and has a very broad range of signal detection. As an example, up to a thousand-fold dilution of sample still results in a signal within the linear range of the assay.

The present invention contemplates methods for identifying specific modulators, such as chemical compounds or genes, of peptide secretion or cell surface expression using various screening assays known in the art. The present invention also contemplates methods for identifying specific compounds that differentiate a embryonic or iPS stem cell to a mature, or differentiated cell using various screening assays known in the art. For example, the mature or differentiated cell is a hormone-secreting cell, a neuropeptide-secreting cell, a cytokine-secreting cell, or a cell that can no longer differentiate into more than one cell type.

Any screening technique known in the art can be used to screen modulators of peptide secretion or cell surface expression. For example, natural products libraries can be screened using assays of the invention. The present invention contemplates screens for synthetic small molecule agents, chemical compounds, chemical complexes, and salts thereof. Other molecules that can be identified using the screens of the invention include proteins and peptide fragments, peptides, nucleic acids and oligonucleotides, carbohydrates, phospholipids and other lipid derivatives. Other modulators of peptide secretion can also include genes that are involved in regulating the pathways that control hormone secretion. Other modulators of cell surface expression can also include genes that are involved in regulating the pathways that control cell surface expression.

In another aspect, synthetic libraries (Needels et al., Proc. Natl. Acad. Sci. USA 90:10700-4, 1993; Ohlmeyer et al., Proc. Natl. Acad. Sci. USA 90:10922-10926, 1993; Lam et al., International Patent Publication No. WO 92/00252; Kocis et al., International Patent Publication No. WO 9428028) and the like can be used to screen for compounds that modulate peptide secretion.

Test compounds are screened from large libraries of synthetic or natural compounds. Numerous means are currently used for random and directed synthesis of saccharide, peptide, and nucleic acid based compounds. Synthetic compound libraries are commercially available from Maybridge Chemical Co. (Trevillet, Cornwall, UK), Comgenex (Princeton, N.J.), Brandon Associates (Merrimack, N.H.), and Microsource (New Milford, Conn.). A rare chemical library is available from Aldrich (Milwaukee. Wis.). Alternatively, libraries of natural compounds in the form of bacterial, fungal, plant and animal extracts are available from e.g. Pan Laboratories (Bothell, Wash.) or MycoSearch (N.C.), or are readily producible. Additionally, natural and synthetically produced libraries and compounds are readily modified through conventional chemical, physical, and biochemical means (Blondelle et al., Tib Tech, 14:60, 1996).

RNAi and open reading frame (ORF) libraries, such as those of the RNAi Consortium at the Broad Institute, can be used to screen for genes that increase or decrease peptide secretion, or increase or decrease cell surface expression.

The sensitivity and accuracy of the luminescence detection allows for screening at the level of single cell detection. Single cell analysis may be particularly useful in RNAi screens, where pools of RNAi molecules can be tested. For example, a pool of unique short hairpins targeting different genes that each contain an unique "barcode" that designates the target gene, would be introduced to a population of cells that express a prohormone fusion protein of the present invention. The bioluminescence signal and the unique hairpin can be detected using various single cell analysis methods known in the art. For example, the population of cells can be separated and analyzed using various well-, trap-, pattern-, and droplet-based microfluidic devices and platforms. The luminescence signal and the shRNA "barcode" can be determined concurrently or sequentially to identify the genes responsible for modulating hormone secretion.

Once genetic variants that have altered peptide secretion or cell surface expression are identified, additional compound screens can be performed to identify those compounds that reverse or augment the genetic effect.

According to the present invention, a host cell containing a fusion construct between a propeptide and a bioluminescent protein is constructed. Candidate agents are added to in vitro cell cultures of host cells, prepared by known methods in the art, and the activity of the bioluminescent protein is measured within the cellular supernatant. Various in vitro systems can be used to analyze the effects of a new compound on bioluminescent protein expression. For example, light emission is detected by known methods, such as detection with suitable instrumentation (such as a luminometer or CCD camera) in vivo or in vitro, such as in a living cell or intact organism, a cell culture system, a tissue section, or an array. Preferably, the luminescence is detected by luminometer. Preferably, the luminometer is in a plate-reader format.

Vectors and Kits

The present invention also provides a nucleic acid expression vector comprising a nucleic acid sequence encoding a bioluminescent protein, wherein the bioluminescent protein lacks a native signal peptide; a nucleic acid sequence encoding two cleavage sites, wherein the cleavage sites flank the bioluminescent protein such that when the vector is expressed by a cell, the bioluminescent protein is cleaved from the remaining peptide; and at least one insertion site for insertion of a nucleic acid sequence encoding a propeptide such that the inserted nucleic acid sequence is in-frame with the bioluminescent protein. The insertion site is a restriction enzyme site, multiple cloning site containing multiple restriction enzyme sites, or a site recognized by a recombinase. Optionally, the nucleic acid expression vector comprises a promoter, wherein the promoter is operatively linked to the nucleic acid sequence encoding the bioluminescent protein. Optionally, the nucleic acid expression vector comprises a selective marker operatively linked to a second promoter. The selective marker can be an antibiotic resistance gene, drug resistance gene, toxin resistance gene or a cell surface marker.

Alternatively, a nucleic acid expression vector may comprise any nucleic acid construct described herein operatively linked to a promoter and a selective marker operatively linked to a second promoter.

The vectors of the present invention can be expressed in any of the cells described herein.

The present invention further provides a kit. The kit includes any or at least one of the nucleic acid expression vectors described herein, at least one luciferase substrate and instructions for use. The luciferase substrate will be selected according to the nucleic acid expression vector of the kit, such that the luciferase of the expression vector will dictate the luciferase substrate included in the kit. For example, a kit containing a nucleic acid expression vector that encodes *Gaussia* luciferase will also include the *Gaussia* luciferase substrate. For those kits that include more than one nucleic acid expression vector, the corresponding luciferase substrates to each nucleic acid expression vector will also be included in the kit.

The present invention further provides a kit that contains any one of the cells that express a propeptide-luciferase fusion protein as described herein.

Any kit of the present invention further comprises a control nucleic acid construct that encodes a control luciferase or cells expressing the control luciferase for use as an internal control. Importantly, the control luciferase is different from the luciferase(s) of the nucleic acid expression vectors; such that the detected luminescence can be easily distinguished from the luminescence signal of the *Gaussia* and/or *Cypridina* reporters. For example, the control luciferase is Firefly luciferase.

Definitions

"Compound" as used herein encompasses all types of organic or inorganic molecules, including but not limited to proteins, peptides, polysaccharides, lipids, nucleic acids, small organic molecules, inorganic compounds, and derivatives thereof.

"Polypeptide," "Protein," and "Peptide" are used interchangeably to refer to amino acid chains in which the amino acid residues are linked by covalent peptide bonds. The amino acid chains can be of any length of at least two amino acids, including full-length proteins. Unless otherwise specified, the terms "polypeptide," "protein," and "peptide" also encompass various modified forms thereof, including but not limited to glycosylated forms, phosphorylated forms, etc.

"Test agent" or "Test compound" means a chemical compound, preferably an organic compound, to be tested in the present invention to determine its ability to interact with another chemical compound. Test agents may include various forms of organic compounds, or combinations or conjugates thereof. In one embodiment, the test agents preferably are polypeptides, in which case the test agents are termed "test polypeptides" or "test proteins."

"Fusion construct" refers to a non-naturally occurring hybrid or chimeric construct having two or more distinct portions covalently linked together, each portion being or being derived from a specific molecule. When two or more portions in a fusion construct as defined above are polypeptides and are linked together by peptide bonds, the fusion construct is conveniently referred to as "fusion protein."

"Preprohormone" is the precursor protein to one or more prohormones, which are in turn precursors to peptide hormones. The protein generally consists of the amino acid chain that is created by the hormone secreting cell, before any changes have been made to it. It contains a signal peptide, the hormone(s) itself (themselves), and intervening amino acids. Before the hormone is released from the cell, the signal peptide and other amino acids are removed.

"Prohormone" is a substance that is a precursor to a hormone.

"Propeptide" is a peptide precursor to a mature peptide. In some embodiments, the propeptide is processed to become a mature peptide, i.e. by cleavage and/or transport through the secretory pathway to be either secreted or expressed at the cell surface.

"Peptide hormones" are a class of peptides that are secreted into the blood stream and have endocrine functions in living animals "Light-generating" or "luminescent" includes the property of generating light through a chemical reaction or through the absorption of radiation, including phosphorescence, fluorescence, and bioluminescence.

"Bioluminescent proteins" include any light-generating polypeptides, including fluorescent proteins such as green fluorescent protein (GFP) and luminescent proteins such as luciferase.

"Bioluminescent" molecules or moieties include luminescent substances such as proteins that utilize chemical energy to produce light.

"Fluorescent" molecules or moieties include those that are luminescent via a single electronically excited state, which is of very short duration after removal of the source of radiation. The wavelength of the emitted fluorescence light is longer than that of the exciting illumination (Stokes' Law), because part of the exciting light is converted into heat by the fluorescent molecule.

"Light" includes electromagnetic radiation having a wavelength of between about 300 nm and about 1100 nm, but can be of longer or shorter wavelength.

"Light-generating gene product" includes any protein known to those of ordinary skill in the art to provide a readily detectable source of light when present in stable form. Non-limiting examples include light-generating proteins described in U.S. Pat. Nos. 5,683,888, 5,958,713, and 5,650,135, e.g., ferredoxin IV, green fluorescent protein, red fluorescent protein, yellow fluorescent protein, blue fluorescent protein, the luciferase family (see, e.g., WO 03/016839), and the aequorin family. In a preferred embodiment, the light-generating polypeptide moiety is a protein such as green fluorescent protein, red fluorescent protein, yellow fluorescent protein and blue fluorescent protein. Light-generating gene products include light-generating polypeptide moieties.

"Light-generating fusion protein" or "fusion protein' includes proteins of the invention having a light-generating or luminescent portion, i.e., a light-generating polypeptide such as luciferase and preprohormone.

"Small molecule" includes compositions that have a molecular weight of less than about 5 kD and most preferably less than about 4 kD. Small molecules is, e.g., nucleic acids, peptides, polypeptides, peptidomimetics, carbohydrates, lipids or other organic or inorganic molecules.

"Heterologous gene" includes a gene that has been transfected into a host organism. Typically, a heterologous gene refers to a gene that is not originally derived from the transfected or transformed cells' genomic DNA.

"Recombinant nucleic acid molecules" include nucleic acid sequences not naturally present in the cell, tissue or organism into which they are introduced.

The term "operably linked" relates to the orientation of polynucleotide elements in a functional relationship. Operably linked means that the DNA sequences being linked are generally contiguous and, where necessary to join two protein coding regions, contiguous and in the same reading frame. However, since enhancers generally function when separated from the promoter by several kilobases, some nucleic acids is operably linked but not contiguous.

The terms "polynucleotide" and "nucleic acid molecule" are used interchangeably to refer to polymeric forms of nucleotides of any length. The polynucleotides may contain deoxyribonucleotides, ribonucleotides and/or their analogs. Nucleotides may have any three-dimensional structure, and may perform any function, known or unknown. The term "polynucleotide" includes single-, double-stranded and triple helical molecules. "Oligonucleotide" refers to polynucleotides of between 5 and about 100 nucleotides of single- or double-stranded DNA. Oligonucleotides are also known as oligomers or oligos and are isolated from genes, or chemically synthesized by methods known in the art. A "primer" refers to an oligonucleotide, usually single-stranded, that provides a 3'-hydroxyl end for the initiation of enzyme-mediated nucleic acid synthesis. The following are non-limiting embodiments of polynucleotides: a gene or gene fragment, exons, introns, mRNA, tRNA, rRNA, ribozymes, cDNA, recombinant polynucleotides, branched polynucleotides, plasmids, vectors, isolated DNA of any sequence, isolated RNA of any sequence, nucleic acid probes and primers. A nucleic acid molecule may also comprise modified nucleic acid molecules, such as methylated nucleic acid molecules and nucleic acid molecule analogs. Analogs of purines and pyrimidines are known in the art, and include, but are not limited to, aziridinycytosine, 4-acetylcytosine, 5-fluorouracil, 5-bromouracil, 5-carboxymethylaminomethyl-2-thiouracil, 5-carboxymethylaminomethyluracil, inosine, N6-isopentenyladenine, 1-methyladenine, 1-methylpseudouracil, 1-methylguanine, 1-methylinosine, 2,2-dimethylguanine, 2-methyladenine, 2-methylguanine, 3-methylcytosine, 5-methylcytosine, pseudouracil, 5-pentylnyluracil and 2,6-diaminopurine. The use of uracil as a substitute for thymine in a deoxyribonucleic acid is also considered an analogous form of pyrimidine.

A "fragment" of a polynucleotide is a polynucleotide comprised of at least 9 contiguous nucleotides, preferably at least 15 contiguous nucleotides and more preferably at least 45 nucleotides, of coding or non-coding sequences.

The term "homologous recombination" refers to the exchange of DNA fragments between two DNA molecules or chromatids at the site of homologous nucleotide sequences.

The term "homologous" as used herein denotes a characteristic of a DNA sequence having at least about 70 percent sequence identity as compared to a reference sequence, typically at least about 85 percent sequence identity, preferably at least about 95 percent sequence identity, and more preferably about 98 percent sequence identity, and most preferably about 100 percent sequence identity as compared to a reference sequence. Homology is determined using, for example, a "BLASTN" algorithm. It is understood that homologous sequences can accommodate insertions, deletions and substitutions in the nucleotide sequence. Thus, linear sequences of nucleotides are essentially identical even if some of the nucleotide residues do not precisely correspond or align. The reference sequence is a subset of a larger sequence, such as a portion of a gene or flanking sequence, or a repetitive portion of a chromosome.

The term "transgenic cell" refers to a cell containing within its genome a nucleic acid encoding a preprohormone operably linked to a nucleic acid encoding a bioluminescent protein introduced by the method of gene targeting.

The term "proliferating cell" includes any cell undergoing cell division.

As used herein, the terms "selectable marker" and "positive selection marker" refer to a gene encoding a product that enables only the cells that carry the gene to survive and/or grow under certain conditions. For example, plant and animal cells that express the introduced neomycin resistance (Neo (r)) gene are resistant to the compound G418. Cells that do not carry the Neo (r) gene marker are killed by G418. Other positive selection markers are known to or are within the purview of those of ordinary skill in the art.

A "host cell" includes an individual cell or cell culture that is or has been a recipient for vector(s) or for incorporation of nucleic acid molecules and/or proteins. Host cells include progeny of a single host cell, and the progeny may not necessarily be completely identical (in morphology or in total DNA complement) to the original parent due to natural, accidental, or deliberate mutation. A host cell includes cells transfected with the constructs of the present invention.

The term "modulates" as used herein refers to the decrease, inhibition, reduction, increase, or enhancement of a gene function, expression, or activity.

EXAMPLES

Example 1: General Methods

Cell Culture

MIN6 cells (Miyazaki, J. et al *Endocrinology* 127:126-132 (1990)) were maintained in DMEM with 4.5 g/L glucose, supplemented with 10% heat-inactivated fetal bovine serum and 55 µM beta-mercaptoethanol (Sigma®, St. Louis, Mo.). INS-1E cells (Merglen, A et al. *Endocrinology* 145: 667-678 (2004)) were maintained in RPMI with 2 g/L glucose, supplemented with 10% heat-inactivated fetal bovine serum, 1 mM sodium pyruvate, 2 mM L-glutamine, 10 mM HEPES and 55 µM beta-mercaptoethanol (Invitrogen®, Grand Island, N.Y.). Cells were grown on standard tissue culture-treated plastic (Becton Dickenson®, Waltham, Mass.) and all dissociation steps were performed using TrypLE (Invitrogen®).

Prohormone-Luciferase Constructs

The proinsulin-luciferase fusion construct was created by Gibson Assembly® (fusion construct method) in the pUC19 vector (NEB®, Ipswich, Mass.) using two gBlocks (IDT®, Coralville, Iowa) encoding the protein and Gibson Assembly® Master Mix (NEB®). Mouse proamylin was subcloned from the vector pT7T3D-PacI (clone MmCD00310704, DF/HCC DNA Resource Core, Boston, Mass.) into the pCI-Neo vector (Promega®, Madison, Wis.). *Gaussia* luciferase was amplified from pCMV-GLuc (NEB®) using oligonucleotide primers (IDT®) designed to exclude the start codon, signal peptide and stop codon, and to add a prohormone convertase 2 site to the c-terminus and flanking BsmI sites. pCI-Neo-proamylin was then digested with BsmI (NEB®) and ligated to the BsmI digest of the *Gaussia* luciferase PCR product. The proinsulin-luciferase and proamylin-luciferase fusion constructs were subsequently PCR-amplified with primers to add attB1 and attB2 sites, inserted by BP Clonase® II into the Gateway® Entry vector pDONR223 (Invitrogen®), and then shuttled by LR Clonase® II into the Gateway® Destination vector pLX304 (David Root lab, Addgene plasmid 25890) (Yang, X. et al. Nat Methods 8:659-661 (2011)). Other prohormone-luciferase constructs, such as the preproglucagon-luciferase construct, were generated in a similar manner.

Lentivirus Production

Lentivirus expressing each prohormone-luciferase fusion protein was produced as described (Yang, X. et al. Nat Methods 8:659-661 (2011)). Briefly, 2 µg of pLX304 expression plasmid containing the fusion construct, 1.8 µg of psPAX2 packaging plasmid (Didier Trono lab, Addgene plasmid 12260), 200 ng of pMD2.G envelope plasmid (Didier Trono lab, Addgene plasmid 12259) and 12 µL TransIT-LT1 (Minis Bio™, Madison, Wis.) were used to transfect a 10 cm dish of HEK293T packaging cells (ATCC™, Manassas, Va.). Virus was pooled from harvests at 48 and 72 hours and passed through 0.2 µm cellulose acetate filters (VWR™, Radnor, Pa.) prior to use.

Virus Infection

MIN6 and INS-1E cells were plated in their respective growth media with the addition of 8 µg/mL polybrene (Sigma®). Virus was then added and the cells were spun at 800 g for 1 hour at 30° C. After 24 hours in the presence of virus, the cells were placed in fresh growth media for 24 hours, then selection was performed using 5 µg/mL blasticidin (Invitrogen®). Cells were assessed for luciferase localization and secretion after 1 week of antibiotic selection.

Immunofluorescence

Staining of cells was performed as described (Walpita D. et al. *J Biomol Screen* 17:509-518 (2012)). Briefly, cultures were fixed for 15 min at room temperature using 3% paraformaldehyde and washed twice with PBS. Cells were permeabilized for 20 min at room temperature in PBS containing 0.1% saponin and blocked overnight at 4° C. with 2% bovine serum albumin (BSA) in PBS. Primary antibodies to *Gaussia* luciferase (#401P, Nanolight™, Pinetop, Ariz.) and insulin (#18510. Sigma™) were diluted 1:1000 in antibody dilution buffer (ADB; 1% BSA in PBS) and incubated overnight at 4° C., followed by three washes in ADB. Cultures were then incubated in secondary antibodies (Alexa Fluor™-conjugated anti-rabbit and anti-guinea pig; Invitrogen®) diluted 1:1000 in ADB for 1 hour at room temperature, followed by five washes with PBS. Images were acquired using a Zeiss® Axiovert® 200M inverted fluorescent microscope and AxioCam™ MRm camera (Zeiss®, Thornwood, N.Y.).

Secretion Assays

For standard secretion assays, MIN6 and INS-1E cells were plated in 96-well format at a density of $4 \times 10^4$ cells per well in 100 µL of their respective growth media and incubated overnight at 37° C. in 5% $CO_2$ to allow attachment. Cells were washed once with PBS and incubated for 1 hour at 37° C. in sterile, 0.45 µm-filtered Krebs Ringer Buffer (KRB) containing 138 mM NaCl, 5.4 mM KCl, 2.6 mM $MgCl_2$, 2.6 mM $CaCl_2$, 5 mM NaHCO3, 10 mM HEPES and 5 g/L bovine serum albumin (Sigma®). The cells were then washed in KRB once and stimulated for 1 hour in 100 µL of fresh KRB containing varying amounts of glucose and compounds. The insulin concentration was determined using an insulin ELISA (ALPCO®) with the supplied protocol. Luciferase activity was determined from the same samples by adding the coelenterazine substrate (Nanolight®) to the supernatant to a final concentration of 20 µM and reading on a standard plate reader (Biotek™, Winooski, Vt.).

High-Throughput Screens

MIN6 and INS-1E cells were expanded to 80% confluence in their respective growth media, washed once in PBS and incubated for 1 hour at 37° C. in KRB without glucose. Cells were then dissociated, spun at 300 g×2 minutes, resuspended in fresh KRB without glucose and filtered through 40 µm mesh (Becton Dickenson®). Next, the cells were counted and diluted in KRB to $1 \times 10^6$ cells per mL, and glucose was added as required for each experiment. Cells were then seeded in 384-well format, $3 \times 10^4$ cells in 30 µL per well, using a Multidrop™ Combi device (Thermo Scientific®, Billerica, Mass.). Compounds from the Pharmakon 1600 Collection (Microsource Discovery Systems™, Gaylordsville, Conn.) were pinned into each well using a CyBio® Vario (CyBio®, Jena, Germany) to a final concentration of 30 µM, and the plates were then incubated for 1 hour at 37° C. The plates were then spun at 300 g×2 minutes and the supernatant transferred to a new 384-well plate. Coelenterazine substrate was then added to a final concentration of 20 µM and luciferase activity determined using a standard plate reader (Biotek®).

Data Analysis

For the high-throughput screens, the Z-score of each test compound was calculated using the formula:

$$Z-\text{score} = \frac{x - \mu}{\sigma}$$

where x is the log-transformed, signal decay-adjusted luciferase signal from a compound-treated well, µ is the mean of the log-transformed luciferase signals from the DMSO-treated wells on the same plate, and a is the standard deviation of the log-transformed luciferase signals of the DMSO-treated wells across all plates (to allow for cross-plate comparison of compounds). Prior to calculating the Z-score, a row-based correction factor was applied to all luciferase readings to adjust for the rapid signal decay occurring during the course of each 384-well plate read. The signal decay was modeled as a logarithmic function (Microsoft® Excel) and then used to adjust each well's luciferase reading based on the corresponding row within the plate.

Human Islet Cell Culture

Human islets were obtained through the Integrated Islet Distribution Program (iidp.coh.org). Specific donor information is reported in Supplemental Table S2. Islets were maintained and dissociated in 96-well format as described.sup.4. To test compounds for their effects on insulin secretion, the dissociated islets were washed gently in KRB and incubated for 1 hour at 37° C. in KRB without glucose. The cells were then washed twice with KRB and placed in 100 µL of fresh KRB with 50 mg/dL glucose. Compounds were added to a final concentration of 50 µM and the cells were treated for 1 hour at 37° C. Thereafter, the supernatant was removed and the insulin concentration measured using an insulin ELISA (ALPCO®) according to the manufacturer's instructions.

Example 2: Construction of Proamylin Fusion Proteins to Measure Amylin Secretion The key concept of our creation is that luciferase, when appropriately targeted to the secretory granule of a beta cell, can be used as a close proxy for insulin in a secretion assay. To target luciferase to the secretory granule of the beta cell, we created novel fusion proteins in which the sequence encoding *Gaussia* luciferase was placed within the open reading frame of proamylin, a peptide hormone that are normally co-secreted from the beta cell. *Gaussia* luciferase was chosen rather than a more commonly used luciferase because of its smaller size and more intense luminescence characteristics (1000 times brighter than Firefly luciferase). The construct showed robust luciferase response without any detrimental effect on beta cell viability or replication.

Amylin comprises about 1% of the protein in each secretory vesicle of the beta cell, and it is derived from a prohormone that undergoes cleavage by the same enzymes that convert proinsulin to mature insulin within these vesicles. Amylin differs from insulin in its smaller size, simplified protein structure and fewer cysteine residues involved in disulfide bridge formation. In our construct, we selected the mouse isoform of proamylin because it does not form toxic amyloid protein aggregates, unlike the human isoform. As shown in FIG. 1A, the luciferase was placed near the C-terminal end of the proamylin peptide, adjacent to an existing "prohormone convertase 2" (PC2) cleavage site. To increase the likelihood that the luciferase would function well after its release from the proamylin peptide, we added 6 bases encoding an additional PC2 cleavage site to the 3'-end of the luciferase sequence. As a result, the cleaved luciferase protein differed from the wildtype luciferase by only 3 additional amino acids located on its N-terminus, with no additional amino acids on its C-terminus.

Figure 1B:
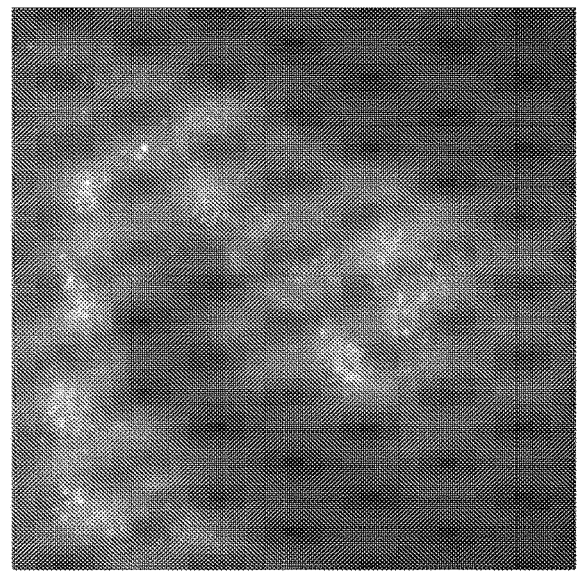
Figure 2B:
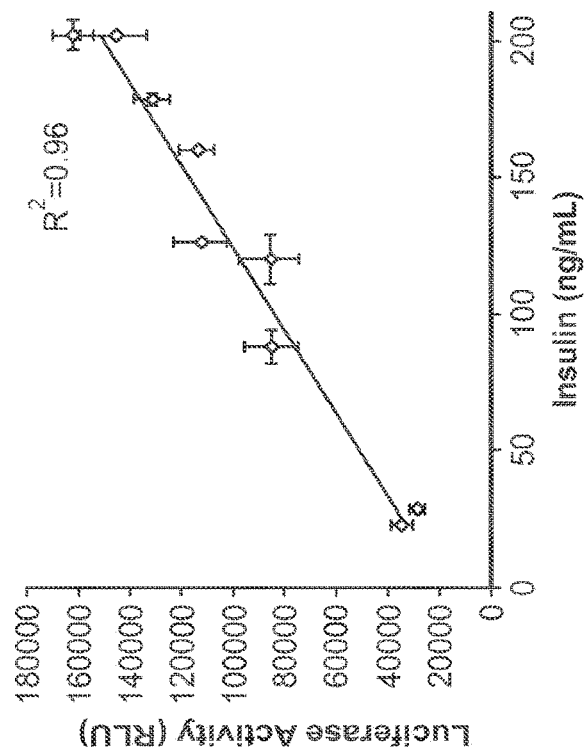
FIG. 2A-2B is two graphs showing the validation of proamylin-luciferase reporter in MIN6 cells. Luciferase activity tracks closely with insulin concentration (as measured by ELISA) during glucose stimulation ($R^2$=0.96).
Figure 2A:
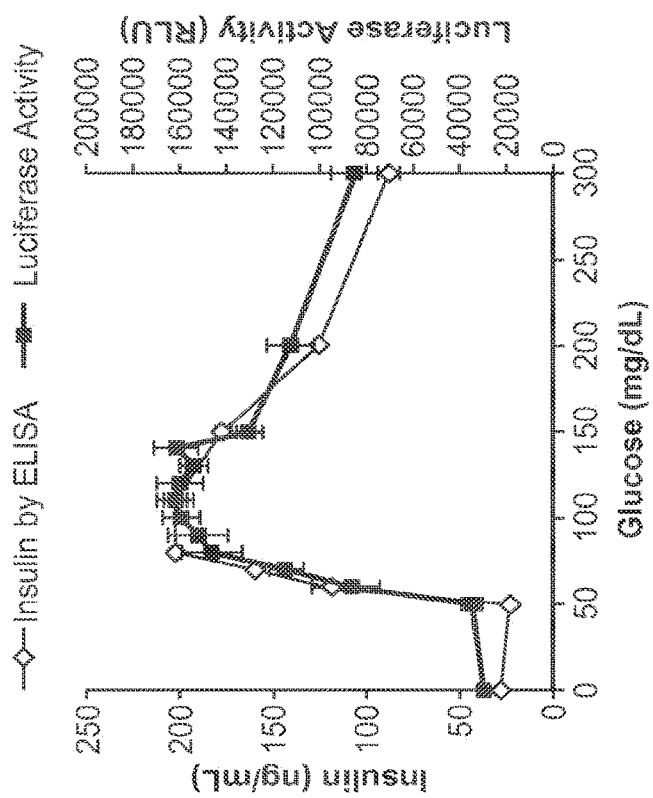
Figures 3A, 3B:
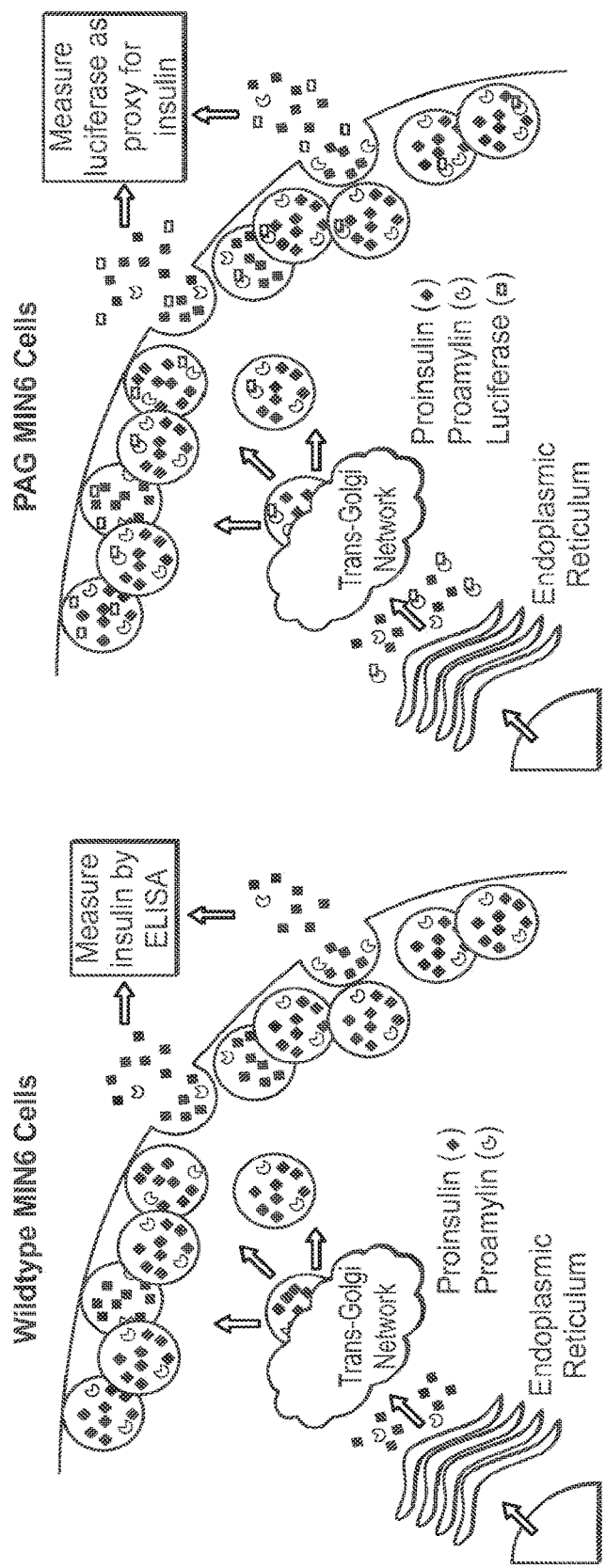
FIG. 3A-3B is two schematics illustrating (A) wildtype MIN6 beta cells and (B) "PAG" containing MIN6 beta cells. Luciferase travels within proamylin from ER, through the Golgi and to the secretory vesicles, where it is cleaved out and co-secreted with endogenous insulin and amylin.
Figure 4:
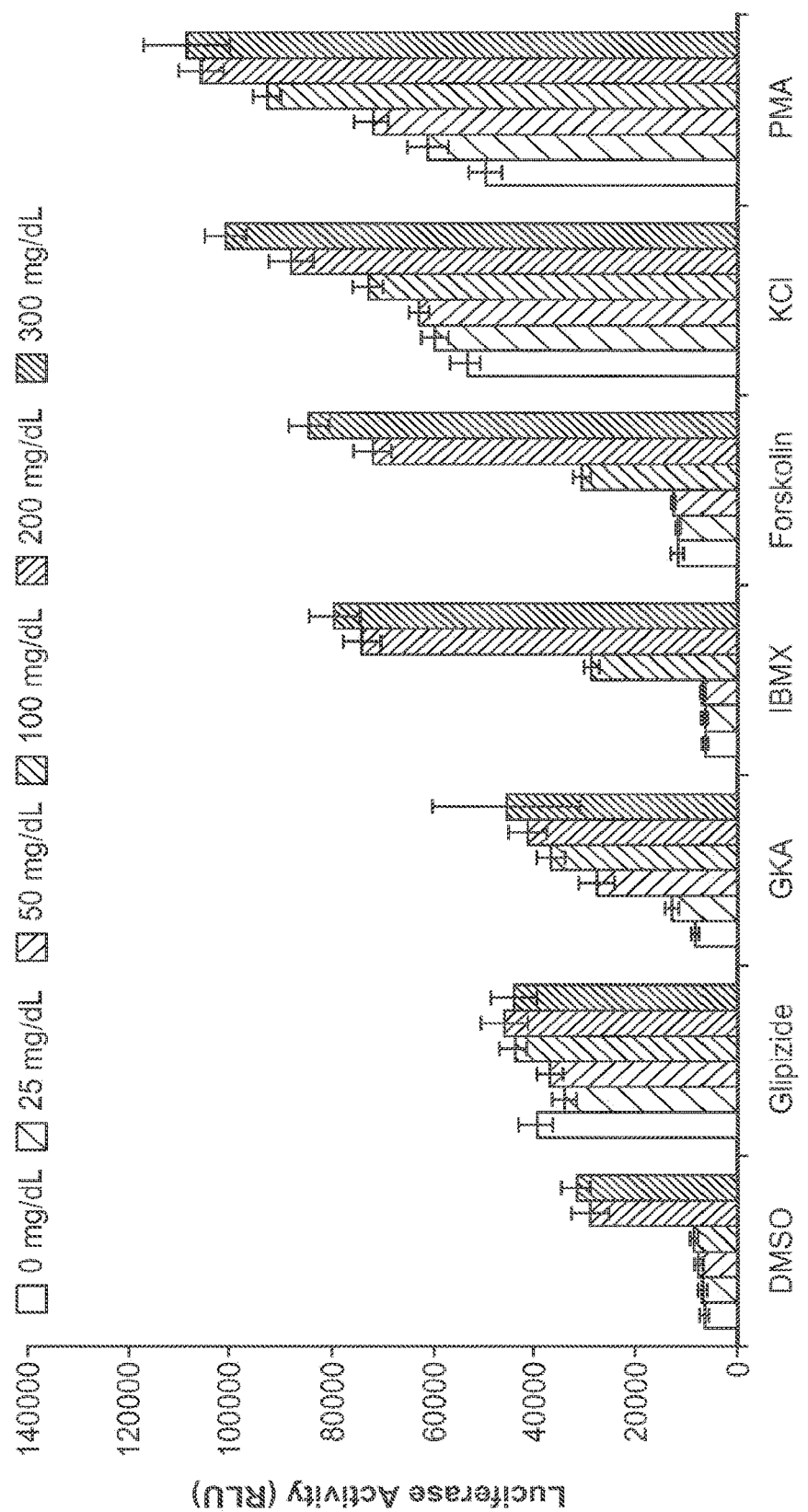
FIG. 4 is a graph showing the pre-proamylin-luciferase reporter in MIN6 cells responds as predicted to known insulin secretagogues. Cells were treated for 1 hour at the indicated glucose concentrations with either DMSO, 25 uM glipizide, 2.5 uM glucokinase activator (GKA), 50 uM 3-isobutyl-1-methylxanthine (IBMX), 20 uM forskolin, 40 mM potassium chloride (KCl), or 20 uM phorbol myristate acetate (PMA).

Example 3: Measurement of Insulin Secretion Using Preproamlyin Fusion Constructs The preproamlyin constructs was introduced into the MIN6 mouse beta cell line (FIGS. 3A and 3B). High magnification imaging studies by immunohistochemistry shows co-localization the luciferase protein with insulin in the secretory granules, as expected (FIG. 1B). Cells containing the reporter secreted luciferase in response to glucose and other secretagogues in close correlation with insulin, as measured by the standard ELISA (FIG. 2). In studies performed to date, the secreted luciferase appears to serve as a close proxy for secreted insulin (FIG. 4). Specifically, negative controls show treatment with DMSO and glipizide even at high concentrations did not increase luciferase activity. Stimulation of cells with IBMX, forskolin, KCl, and PMA increased luminescence in a dose-dependent manner, indicating that the secreted luciferase can be used as an accurate readout of amylin or insulin secretion.

Figure 5:
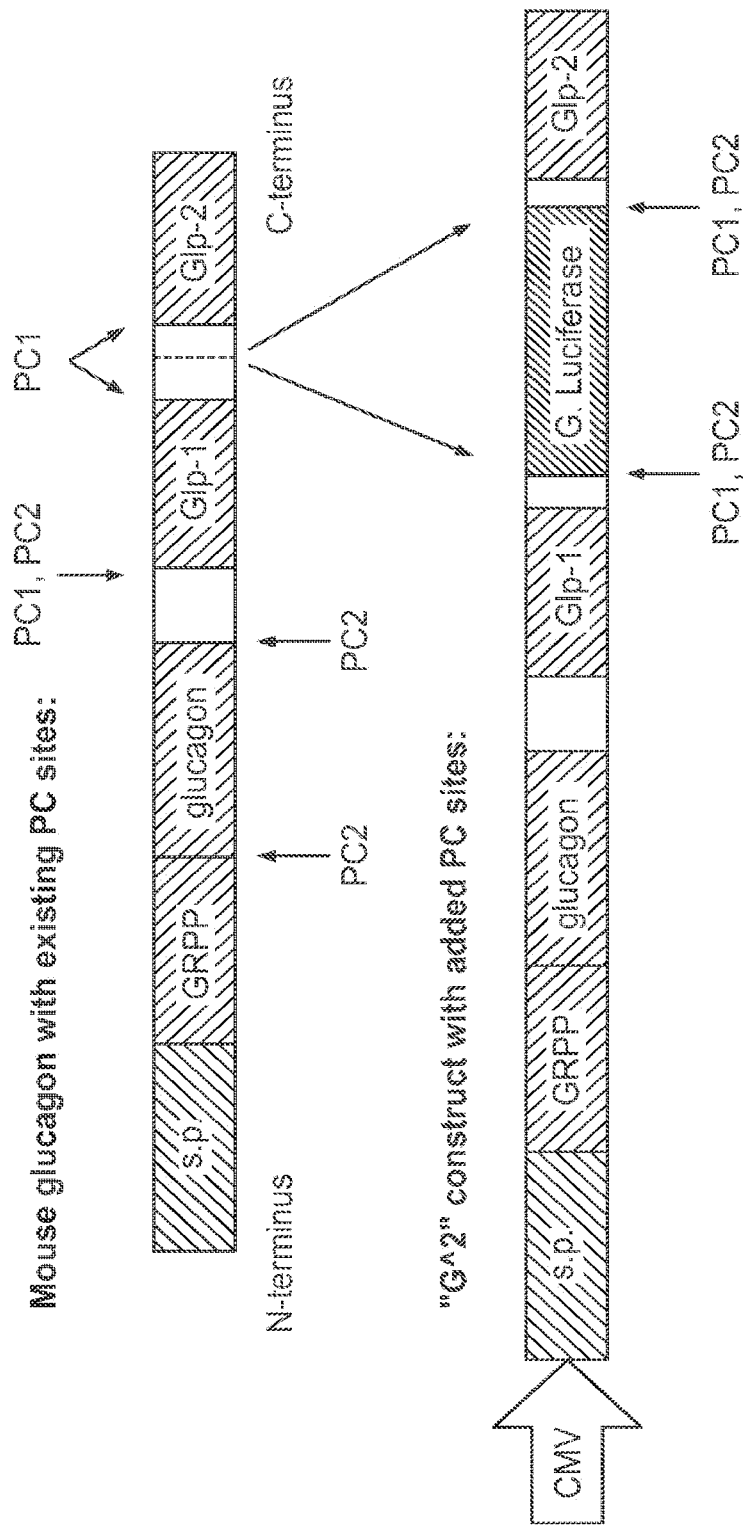
FIG. 5 depicts the structure of proglucagon-Gaussia luciferase (G2) construct. The luciferase was placed between the Glp-1 and the Glp-2 peptides; flanked by PC1 and PC2 cleavage sites on the N and C-terminal ends. s.p. stands for signal peptide.

Example 4: Construction of Proglucagon Fusion Protein to Measure Glucagon and Glp-1 Secretion The glucagon gene contains sequences encoding 4 peptide hormones: (a) Grpp, (b) glucagon, (c) Glp-1, and (d) Glp-2 (FIG. 5). Preglucagon processing results result in glucagon or Glp-1 secretion. The construct described herein allows for detection of glucagon or Glp-1 secretion. A preproglucagon-luciferase (G2) reporter was constructed using mouse glucagon, which contains endogenous PC1 and PC2 sites that are utilized to produce glucagon or Glp-1. The $G^2$ construct was constructed similarly to the proinsulin and proamylin constructs described supra. The *Gaussia* luciferase gene was inserted near the C-terminal end of the proglucagon peptide, between the Glp-1 and Glp-2-encoding peptides. Importantly, both PC1 and PC2 cleavage sites were added to the N-terminal and C-terminal ends of the *Gaussia* luciferase. The cellular context determines which cleavage sites are utilized for glucagon processing. For example, introduction of the $G^2$ construct into PC1-expressing L cells would result in cleavage at the PC1 sites for Glp-1 secretion, while introduction of the $G^2$ construct into PC2-expressing alpha cells would result in cleavage at the PC2 sites for glucagon secretion.

Example 5: Measuring Glucagon and Glp-1 Secretion

Figure 6:
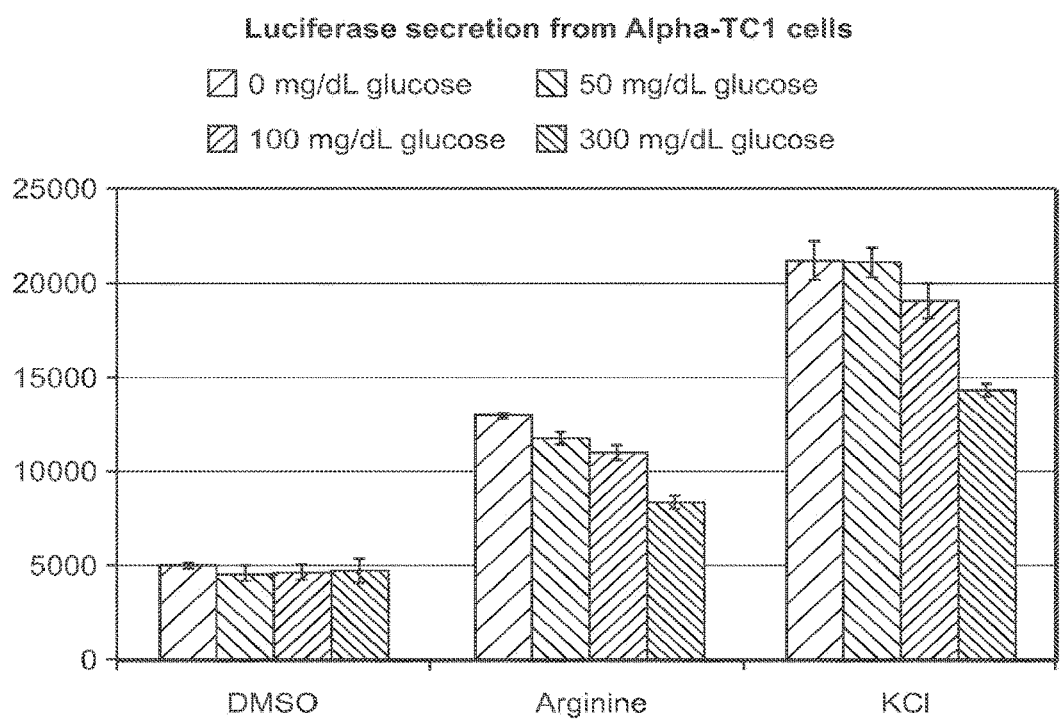
FIG. 6 is a graph establishing that the secreted luciferase serves as a close proxy for secreted glucagon. The G2 construct was transfected into mouse alpha cells. Luciferase secretion was measured by luciferase activity in response to stimulation with arginine or KCl and varying dosages of glucose (DMSO was used as control).

The preglucagon $G^2$ construct was introduced into the Alpha TC1 mouse alpha cell line. Cells were stimulated with IBMX, arginine, or potassium chloride (KCl) and varying amounts of glucose in the range of 0-300 mg/dL (0-16.7 mM). Luciferase activity of the supernatant was determined (FIG. 6). As expected, the $G^2$-expressing alpha cells secreted luciferase in response to arginine and KCl1 in a glucose-dependent manner. There was no secretion of luciferase in response to IBMX, also as expected. This assay demonstrates that the secreted luciferase appears to serve as a close proxy for secreted glucagon.

Figure 7B:
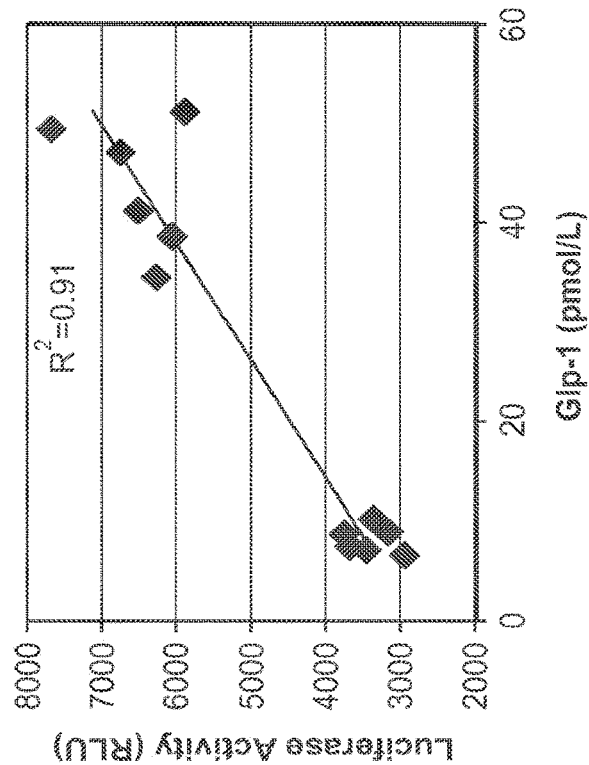
FIG. 7A-7B is two graphs establishing that the secreted luciferase serves as a close proxy for secreted Glp-1. The G2 construct was transfected into mouse L cells. A) Luciferase secretion was measured by luciferase activity in response to stimulation with forskolin/IBMX, KCl, glipizide, PMA or L-glutamine. B) The correlation of luciferase secretion (signal) with secreted Glp-1 concentration was very high.
Figure 7A:
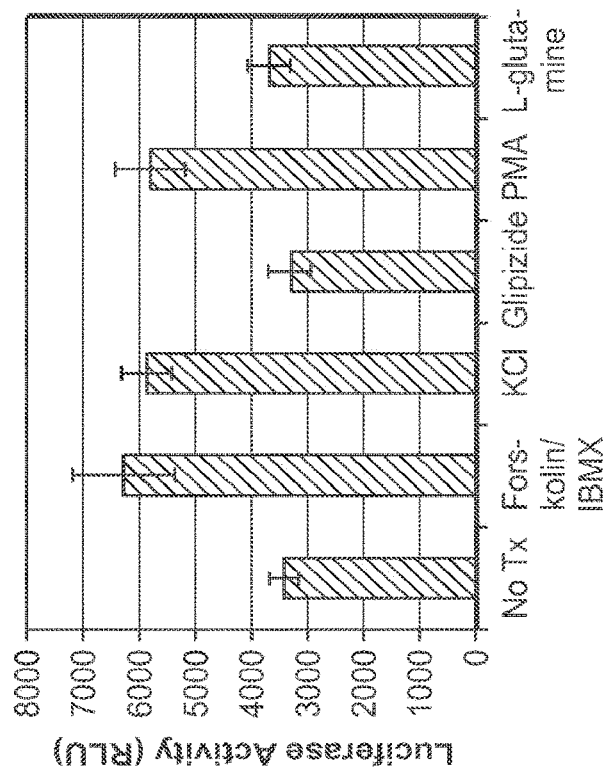

The proglucagon $G^2$ construct was also introduced into the GLUTag mouse L-cell line. Cells were stimulated with Forskolin/IBMX, KCl, glipizide, PMA, and L-glutamine. Luciferase activity of the supernatant was determined. As expected, the $G^2$-expressing L-cells secreted luciferase in response to forskolin/IBMX, Kcl and PMA; and also as expected, there was no secretion of luciferase in response to glipizide or L-glutamine (FIG. 7A). Glp-1 secretion was measured by standard ELISA and results show that luciferase secretion is closely correlated with Glp-1 secretion (FIG. 7B). Taken together, these assay results demonstrate that the secreted luciferase serves as a close proxy for secreted Glp-1. The $G^2$ reporter was also tested in L-cells in 384-well format, to demonstrate the amenability of the reporter in a high throughput format.

Example 6: Construction of Proinsulin Fusion Proteins to Measure Insulin Secretion To enable high-throughput investigation of genes and compounds affecting insulin secretion, a simple, reproducible, and much less expensive assay was needed. We reasoned that luciferase could be used to create such an assay, if the enzyme could be properly targeted to secretory vesicles in the beta cell via the natural proinsulin processing pathway. To test this hypothesis, we constructed a proinsulin-luciferase fusion protein in which we placed the sequence of *Gaussia* luciferase within the C-peptide portion of proinsulin (FIG. 8A), a fragment that is normally cleaved by prohormone convertases and co-secreted with mature insulin during exocytosis (Oyer, P. E. et al. J Biol Chem 246:1375-1386 (1971)).

Figure 8A:
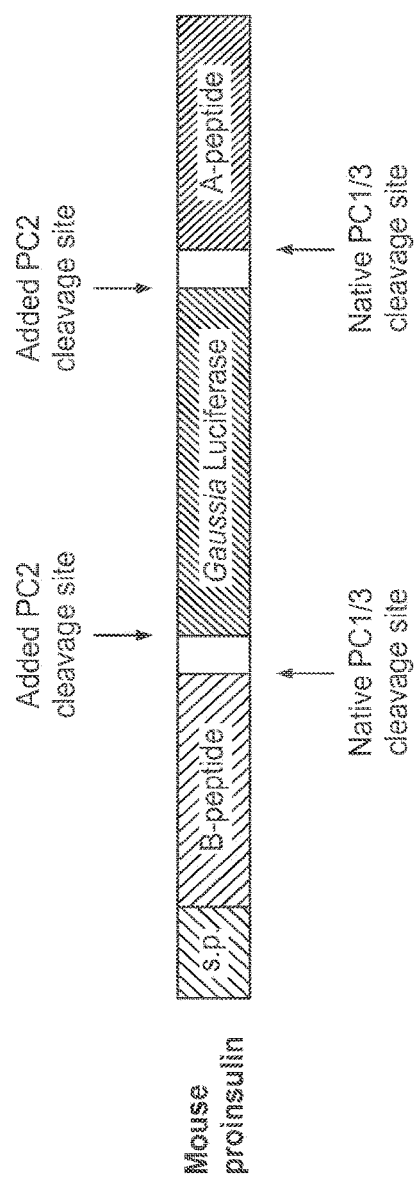
FIG. 8A-8F shows characterization of the proinsulin-luciferase fusion protein. (A) Diagram of proinsulin-luciferase fusion construct, showing Gaussia luciferase within the C-peptide portion of proinsulin. The natural secretory signal peptide of Gaussia luciferase was removed to prevent unregulated secretion; the luciferase sequence was flanked with recognition sites for prohormone convertase 2 (PC2) to minimize carryover of extraneous amino acids after processing within the secretory vesicles. (B) Immunohistochemistry of INS-1E cells expressing the proinsulin-luciferase reporter, stained for luciferase (green, left), insulin (red, middle), or both (merged, right). (C-D) Glucose-stimulated secretion of luciferase (red) and insulin (blue) from MIN6 cells expressing the fusion construct (C). Correlation between insulin concentration and luciferase activity (D). (E-F) Assessment of luciferase secretion induced by known insulin secretagogues. Cells were treated for 1 hour at the indicated glucose concentrations with either DMSO, 25 uM glipizide, 2.5 uM glucokinase activator (GKA), 20 mM arginine, 1 nM glucagon-like peptide-1 (GLP-1), 50 uM 3-isobutyl-1-methylxanthine (IBMX), 20 uM forskolin, 40 mM potassium chloride (KCl), or 20 uM phorbol myristate acetate (PMA). Correlation between insulin and luciferase secretion for all samples (F).

As shown in FIG. 8A we placed the luciferase within the c-peptide portion of proinsulin, and near the C-terminal end of the proamylin peptide adjacent to an existing "prohormone convertase 2" (PC2) cleavage site. To increase the likelihood that the luciferase would function well after its release from each prohormone, we added PC2 cleavage sites to both ends of the luciferase using in the proinsulin construct, and to the 3'-end of the luciferase used in the proamylin construct. After cleavage, the luciferase protein will therefore differ only minimally from the wildtype luciferase protein.

We envisioned that luciferase would remain trapped within proinsulin until cleavage of the fusion protein by pH-sensitive prohormone convertases resident in secretory vesicles, enabling its co-secretion with mature insulin after stimulation of the beta cell.

Figure 8B:
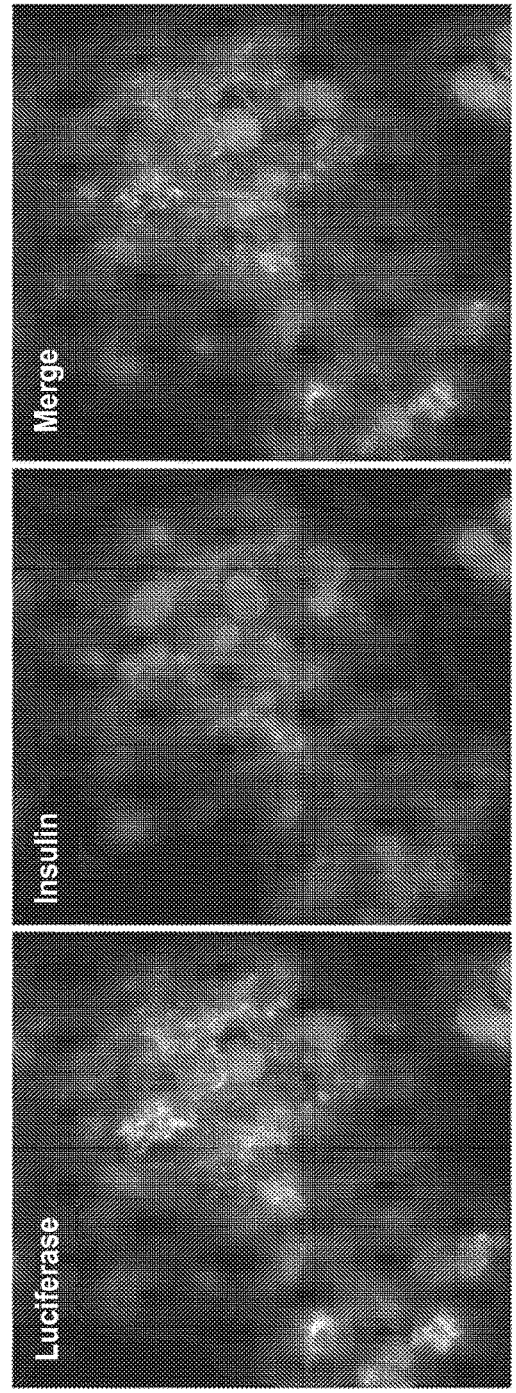
Figure 8D:
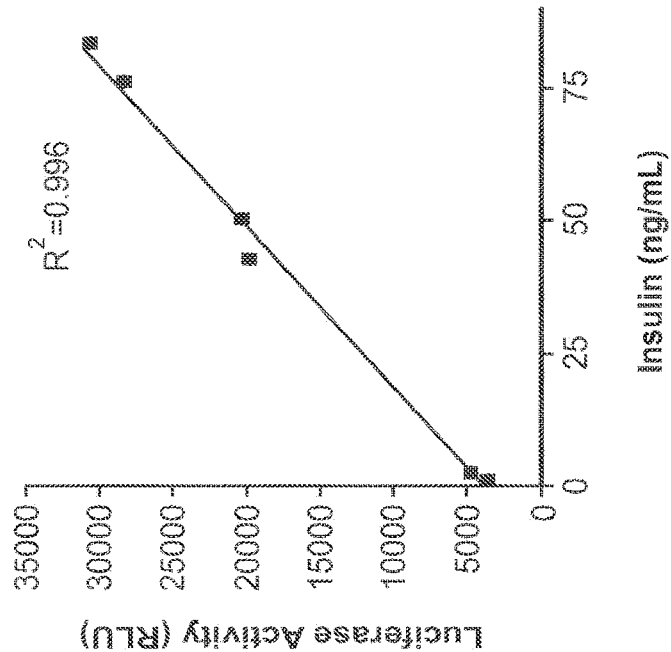
Figure 8C:
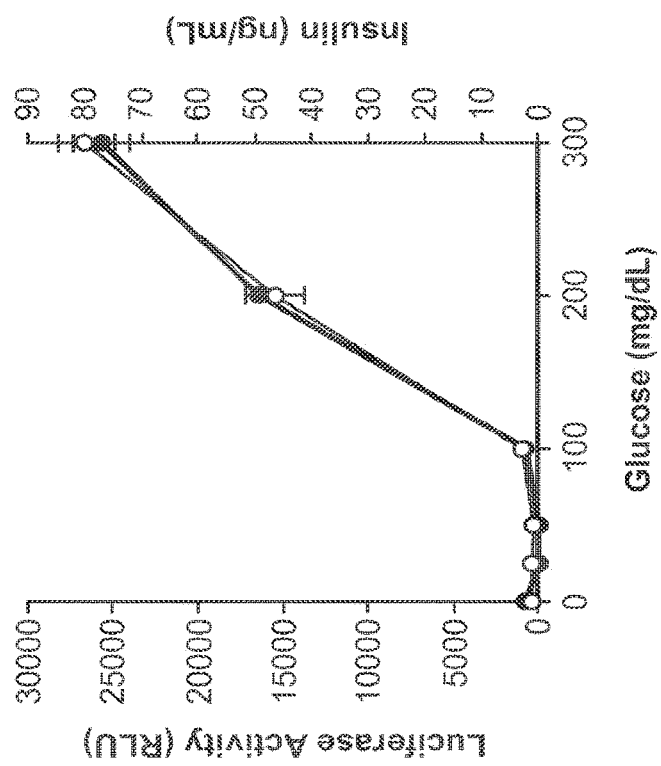
Figures 8E, 8F:
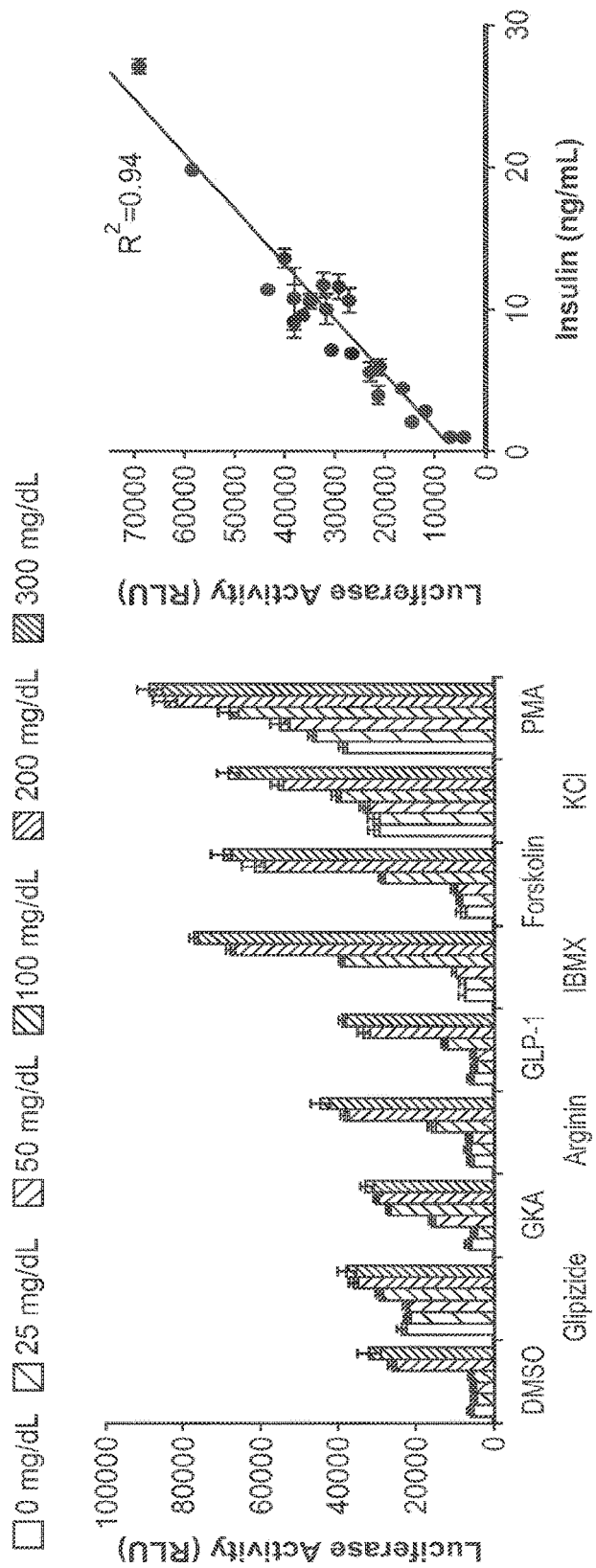

Upon expression of the construct under the control of a constitutive promoter in rodent beta-cell lines (Miyazaki, J. et al. *Endocrinology* 127:126-132 (1990); Merglen, A. et al. *Endocrinology* 145:667-678 (2004)), we observed strong co-localization of insulin and luciferase within the secretory granules of most cells (FIG. 8B). Challenging the cells with increasing glucose concentrations induced secretion of both luciferase and insulin, as measured by ELISA, in close correlation ($r^2$=0.996) (FIG. 8C). Furthermore, upon treatment of the cells with established insulin secretagogues, luciferase secretion tracked closely with insulin in each instance (FIG. 8D).

Example 7: High Throughput Screening Using the Proinsulin Fusion Protein

Figure 9A:
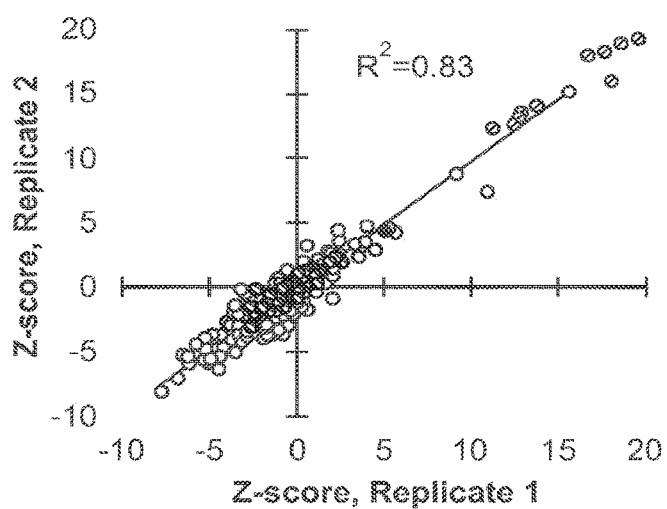
FIG. 9A-9E shows the application of proinsulin-luciferase reporter to high-throughput chemical screen. (A) Scatter plot of the results of high-throughput screening of 1600 compounds for luciferase secretion using MIN6 cells expressing proinsulin-luciferase construct. The screen was performed in duplicate in the presence of sub-stimulatory 100 mg/dL glucose, and Z-scores were calculated based on the DMSO control distribution. DMSO controls shown in red, glipizide in green, KCl in yellow, test compounds in blue. (B) Insulin secretion induced by the top-scoring compounds in MIN6 cells in the presence of sub-stimulatory 100 mg/dL glucose, as measured using a standard insulin ELISA. (C) Effect of same eight compounds on insulin secretion from dissociated human islets, in the presence of sub-stimulatory 50 mg/dL glucose. (D) Scatter plot comparing results of high-throughput screening for luciferase secretion in presence and absence of glucose. DMSO controls shown in red, glipizide in green, glucokinase activator in yellow, test compounds in blue. (E) Measurement of insulin secretion induced by hit compounds in MIN6 cells, in presence (100 mg/dL, in red) and absence (0 mg/dL, in blue) of glucose. Data represent the average±standard deviation of 2 replicates.

We next sought to determine the potential of the proinsulin-luciferase reporter cell line for high-throughput screening by optimizing the assay for 384-well format, where it exhibited tight reproducibility (CV<5%) and excellent separation between positive and negative controls (Z' factor 0.6) (Zhang, J. H. et al. *J Biomol Screen* 4:67-73 (1999)). We performed a pilot chemical screen at a substimulatory glucose concentration (100 mg/dL) in MIN6 cells using a collection of 1600 known bioactive small molecules, with the sulfonylurea glipizide included as a positive control. Each compound was tested in duplicate, and we observed high reproducibility within experimental replicates ($R^2$=0.80) (FIG. 9A). Several commonly used drugs without known links to beta-cell function caused significant increases in luciferase secretion in our assay (compounds summarized in Table 1).

TABLE 1

Top insulin secretagogues from 1600 compound screen, active in both the presence and absence of glucose.

| Compound | Z-score | Annotation |
|---|---|---|
| Triamterene | 76.3 | Potassium-sparing diuretic |
| Tyrothricin | 52.4 | Topical antibiotic |
| Trihexyphenidyl | 50.5 | Anticholinergic |
| Levosimendan | 40.7 | Calcium sensitizer used in CHF |
| Tacrine | 38.8 | Cholinesterase inhibitor |
| Monobenzone | 38.7 | Decreases melanin excretion |
| (S)-chlorpheniramine | 31.8 | Antihistamine |
| Orphenadrine | 27.4 | Anticholinergic |
| Nafronyl | 25.4 | Serotonin-R antagonist |
| Camylofine | 23.8 | Anticholinergic |

Figure 9B:
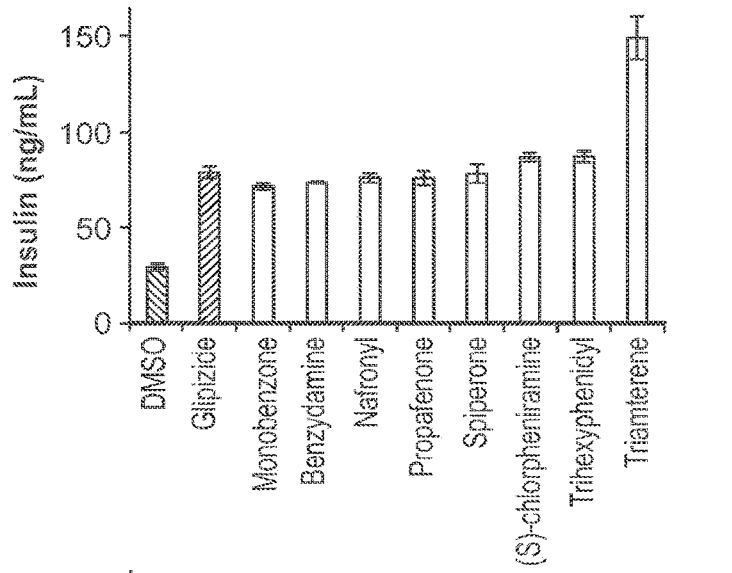

To confirm that the results from the luminescent assay were reflective of insulin secretion, we treated MIN6 cells with the top hits from the primary screen and measured insulin secretion using the standard ELISA. All top-scoring compounds increased insulin secretion, some to a level higher than that of our positive control, glipizide (FIG. 9B). Next, to determine if our assay could identify compounds with relevance to human beta-cell function, we tested the top compounds for effects on insulin secretion at 50 mg/dL glucose using dissociated human pancreatic islet cells (Table 2) (Walpita. D. et al. *J Biomol Screen* 17:509-518 (2012)).

TABLE 2

Summary of human islet information.

| | |
|---|---|
| Age: | 54 years-old |
| Gender: | male |
| Height: | 77 inches |
| Weight: | 278 pounds |
| BMI: | 33 |
| Islet purity: | 85% |
| Islet viability: | 93% |
| Cause of death: | cerebrovascular accident (stroke) |

Figure 9C:
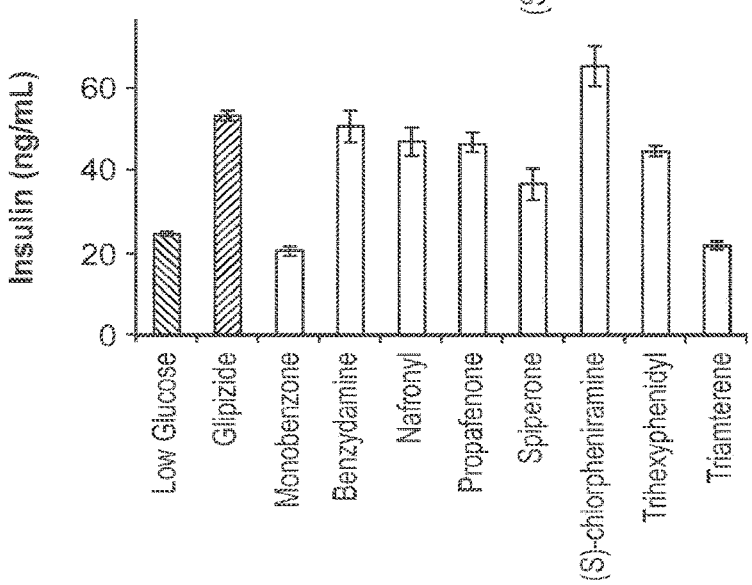

Six of the eight compounds augmented insulin secretion from human beta cells to a similar extent as glipizide (FIG. 9C).

Figure 9D:
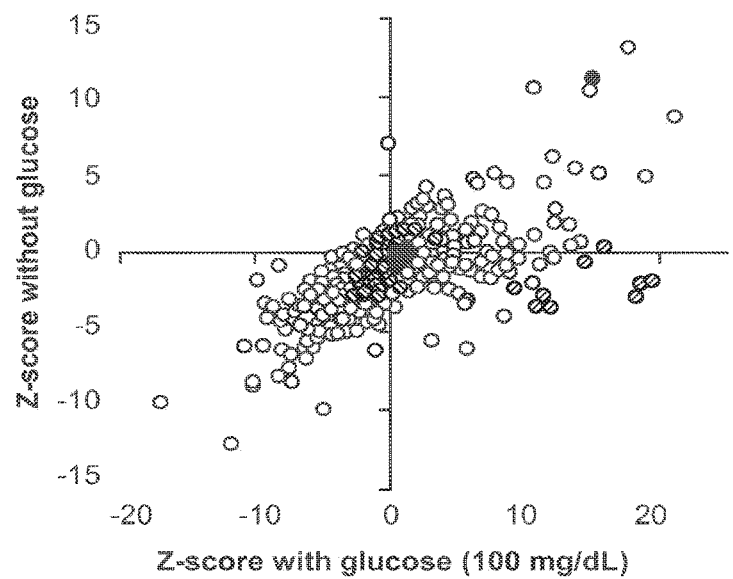
Figure 9E:
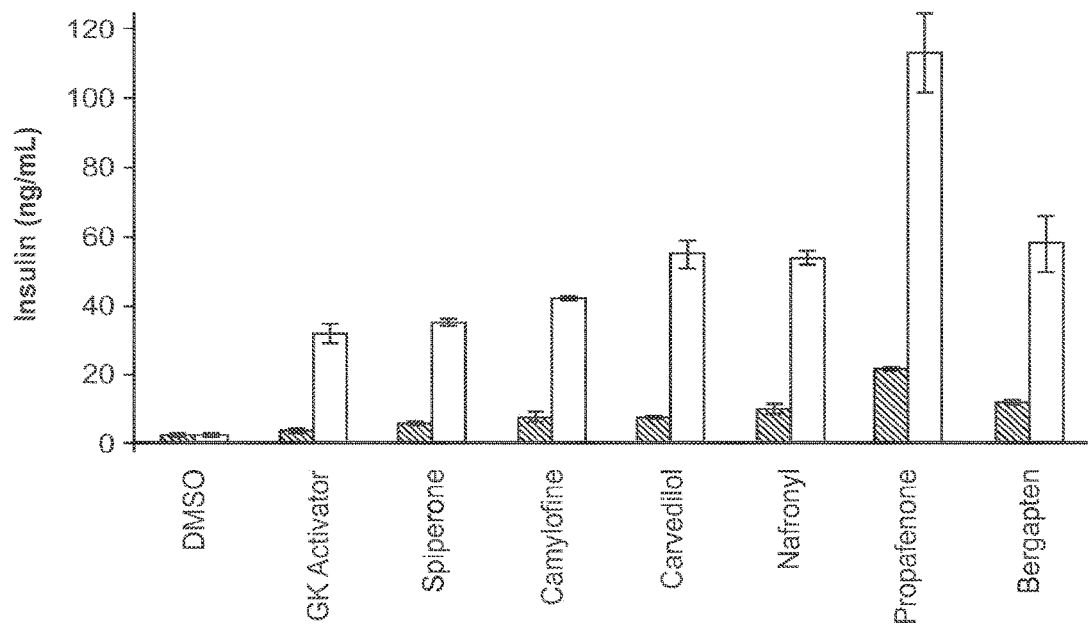

As there is a well-recognized need for glucose-dependent small-molecule agonists of insulin secretion, we subsequently evaluated whether our assay could be adapted to find such secretagogues. We repeated the 1600-compound screen in the presence and absence of a substimulatory glucose concentration (100 mg/dL). As expected, the sulfonylurea glipizide caused luciferase secretion regardless of the ambient glucose level, while several compounds appeared to have the desired property of increasing luciferase secretion only in the presence of glucose (FIG. 9D). We confirmed that these compounds augment insulin secretion only in the presence of glucose using the standard ELISA in MIN6 cells (FIG. 9E). Notably, none of the top-scoring compounds in this screen have been previously reported to affect insulin secretion (Table 3).

TABLE 3

Top glucose-dependent insulin secretagogues from 1600 compound screen, active only in the presence of a permissive glucose environment.

| | Z-score | | | |
|---|---|---|---|---|
| | With Glucose | Without Glucose | Δ | Annotation |
| Monobenzone | 31.8 | 5.6 | 26.2 | Decreases melanin secretion |
| Bergapten | 20.9 | 2.9 | 18 | Citrus product, alters K currents |
| Hydroxyprogesterone | 18.3 | 2.7 | 15.6 | Steroid hormone |
| Nafronyl | 17.8 | 3.4 | 14.4 | Serotonin-R antagonist |
| Clemizole | 12.2 | 0.4 | 11.8 | Antihistamine |
| Spiperone | 9.0 | −2.8 | 11.8 | Serotonin-R, DA-R antagonist |
| Propafenone | 10.5 | 1.5 | 9 | Na-channel, beta blocker |
| Carvedilol | 10.2 | 1.5 | 8.7 | Alpha-1, beta blocker |
| Camylofine | 4.7 | 0.2 | 4.5 | Antimuscarinic |

As compared to the standard ELISA, our luminescent insulin secretion reporter assay has the advantages of simplicity, at least a 50-fold decrease in cost, and reproducibility in high-throughput screening applications. After stimulation of beta cells expressing the fusion protein, luciferase activity in the supernatant is determined by simply adding the luciferase substrate coelenterazine and measuring the resulting luminescence with a plate reader. No wash steps are required and the procedure takes less than one minute to complete per 384-well plate.

Much like an ELISA, our assay detects changes in the secretion of insulin rather than in its expression. Other groups have described reporters in which a luciferase is placed under the control of the insulin promoter (Olansky, L. et al. J Clin Invest 89:1596-1602 (1992)), and while these are useful for tracking gene transcription, they are not applicable to screens of insulin release as the transcriptional activity of insulin correlates poorly with its secretion.

In summary, we have created a fast and inexpensive luminescent assay to accurately and reproducibly detect insulin secretion in high-throughput screening applications. In addition to chemical screening, this reporter should prove useful for investigating (1) genes impacting beta-cell function, (2) physiologic stressors relevant to diabetes, and (3) culture conditions promoting differentiation of stem cells into insulin-secreting beta cells. More generally, our prohormone-luciferase fusion design may prove useful to monitor the secretion of other disease-relevant peptide hormones for which ELISA-based methods are even more limited, including glucagon, GLP-1, and peptide YY. Such luminescent hormone secretion reporters would represent valuable tools in the search for drugs to treat metabolic and endocrine disorders.

As described supra, high throughput screening of compounds that modulate other hormone secretion can also be performed. For example, screening of compounds that modulate, increase, or decrease secretion of amylin, glucagon, or Glp-1 can be performed using the fusion protein constructs described herein and the methods described supra.

Furthermore, the methods demonstrated supra can also be used for high throughput screening of compounds that modulate peptide secretion. For example, screening of compounds that modulate, increase, or decrease secretion of peptides such as neuropeptides and cytokines can be performed using the fusion protein constructs described herein. The methods demonstrated supra can also be used for high throughput screening of compounds that modulate cell surface expression of transmembrane proteins or peptides. For example, screening of compounds that modulate, increase, or decrease the cell surface expression of transmembrane proteins can be performed using the fusion protein constructs described herein.

Example 8: Screening for Genes that Modulate Peptide Secretion or Cell Surface Expression The hormone-luciferase constructs of the invention can be used in high throughput screens to find genes that significantly alter the secretion of hormones of interest, for example insulin (in response to glucose), amylin, glucagon or Glp-1.

We are currently using our proinsulin construct in the MIN6 and INS-1E beta cell lines to perform a pilot RNAi screen of genes known to impact insulin secretion. The effect of silencing the expression of these positive control genes will be assessed using the luciferase readout. Ample negative control hairpins will also be included in this pilot study to characterize the baseline variability of luciferase secretion. Once the assay is validated for use with RNAi constructs, a targeted RNAi screen can be performed against genes recently implicated by human genetics in the pathogenesis of type 2 diabetes and intermediate traits, such as fasting glucose.

Genome wide association studies have identified over 40 sequence variants linked to this disease, many of which affect insulin levels after a glucose challenge, yet in most cases the risk polymorphism is non-coding and thought to impart risk for disease through changes in the expression of a nearby gene. We will cast a wide net by testing RNAi constructs against all genes within +/-300 kilobases from each risk variant, or about 120 genes in total. The RNAi Consortium at the Broad has created 5-10 hairpins targeting each of these genes, and we will test each available construct for an effect on insulin secretion using our luciferase-based assay. "Hits" from this primary screen will be confirmed through repeat testing with our assay, and then validated in an independent assay using a commercially available insulin ELISA.

Pending the results from this targeted RNAi screen, we anticipate performing an unbiased genome wide RNAi screen to comprehensively explore the genes regulating insulin secretion in the beta cell. Should a human beta cell line become available, we will validate our construct in this line and then use it to perform the RNAi screen using the Broad's human lentiviral shRNA library.

Other propeptide-luciferase constructs of the present invention can also be utilized in assays to determine genes that modulate peptide secretion or cell surface expression of the peptide.

Example 9: Screening for Compounds that Modulate Peptide Secretion or Cell Surface Expression Our invention allows for the high throughput measurement of hormone secretion in the setting of genetic and chemical perturbations, and as such is well suited to screens for compounds impacting this physiologic process. The hormone-luciferase constructs of the invention can be used in small molecule cell-based screens to find compounds that significantly alter the secretion of hormones of interest, for example insulin (in response to glucose), amylin, glucagon or Glp-1.

As described in Example 7, we have performed a pilot screen using the proinsulin fusion protein to screen 1600 known bioactive small molecules, which identified several compounds that increase insulin secretion in a glucose-dependent manner. Based on these results, we were selected to participate in the NIH MLPCN program, which will allow us to screen >350,000 compounds for similar effects on insulin secretion.

Similarly, any of the fusion proteins of the present invention can be used in screens for compounds that modulate hormone secretion. Pilot screens will be performed involving 6 plates of compounds enriched for known bioactive molecules. Based on the results from this initial screen, we anticipate testing a larger collection of compounds to fully explore the interaction of small molecules with the pathways regulating insulin secretion. Targets of any compounds identified in these screens will be sought using the tools of the Chemical Biology and Proteomics groups at the Broad, so as to determine the relevant molecular pathways.

As described in Example 8, genes that regulate hormone secretion can be identified using the described invention. Once genetic variants are identified that adversely affect insulin secretion, we will screen small molecules for their ability to reverse or modulate this genetic effect, so as to increase our understanding of the underlying biology.

Furthermore, genes that regulate secretion of other peptides, such as neuropeptides and cytokines can also be identified using the described invention. Similarly, genes that regulated the cell surface expression of transmembrane proteins can also be identified using the described invention. Similarly, once genetic variants are identified that adversely affect peptide secretion or cell surface expression, small molecules can then be screened for their ability to reverse or modulate the genetic effect.

Example 10: Screening for Factors that Differentiate Cells

Figure 10:
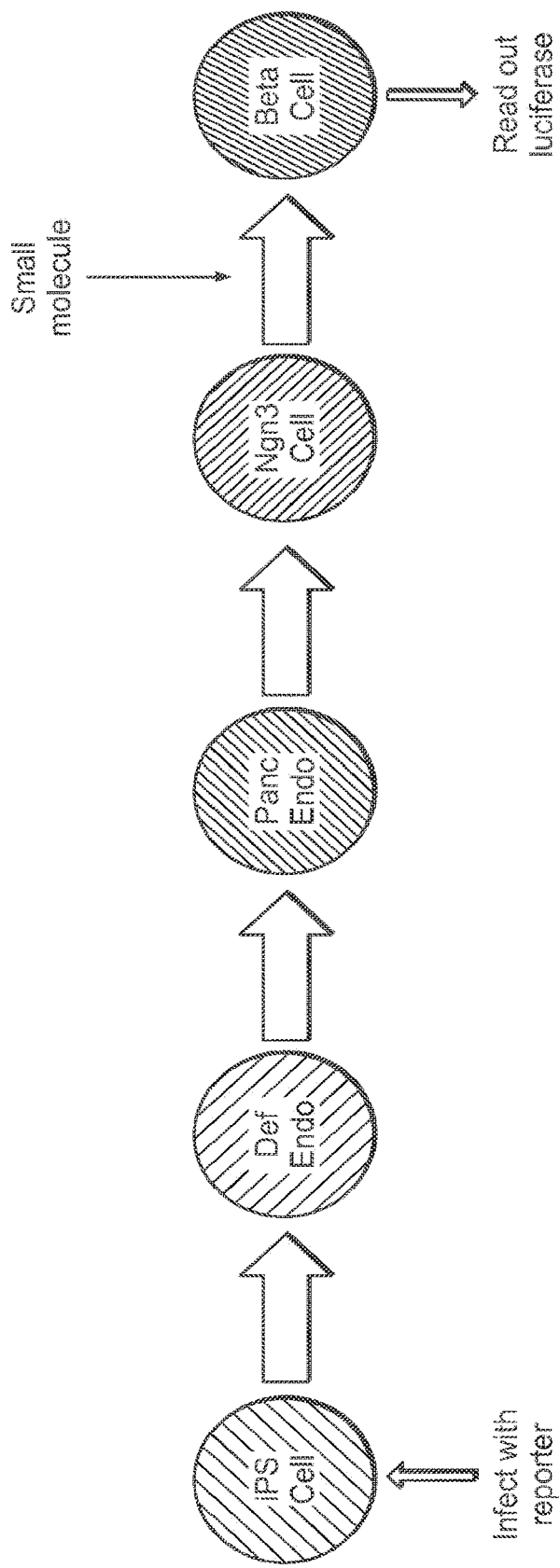
FIG. 10 is a schematic depicting an assay to screen for beta cell differentiation from iPS cells using luciferase secretion as the readout as a marker for beta cell maturation.
Figure 11:
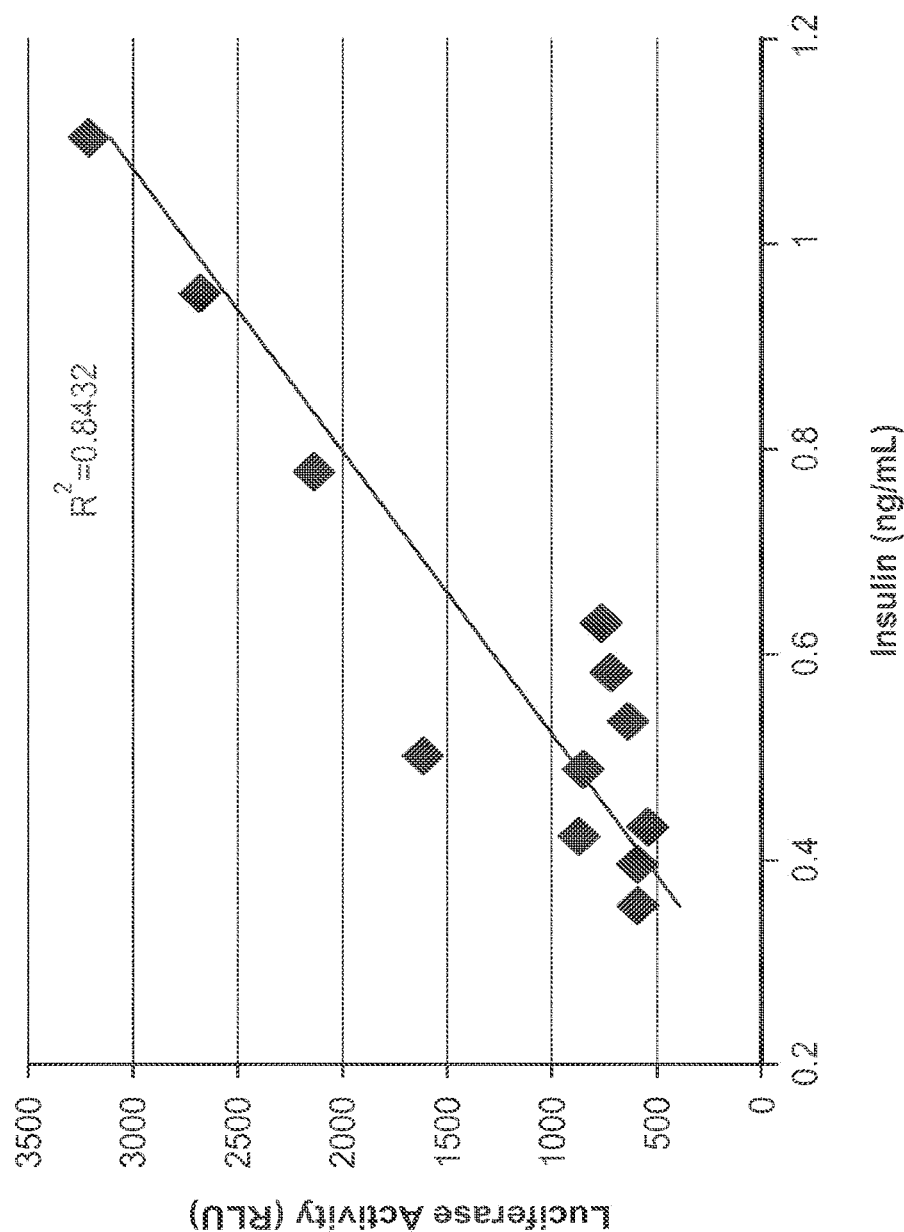
FIG. 11 is a graph depicting the correlation between secreted luciferase and secreted insulin from proinsulin reporter-expressing human beta-like cells.

In addition to using the hormone reporter constructs for screening compounds or genes that modulate and peptide secretion, the present invention provides a method for screening for factors that can differentiate iPS cells or ES cells into pancreatic beta cells competent for hormone secretion (FIG. 10). The present invention also provides a method for screening for factors that can differentiate iPS or ES cells into any differentiated or mature cell that is capable of peptide-secretion or cell surface expression of the particular peptide of interest. ES or iPS cells are infected with any of the reporter constructs of the present invention, and can be differentiated using methods known in the art. Luciferase secretion is used as a marker of cell maturation in screens to identify compounds (such as small molecules) or other factors that induce cell differentiation and maturation. As an initial experiment, human beta-like cells were infected with the proinsulin reporter construct. Luciferase activity was detected as described supra, and insulin secretion was measured by standard ELISA (FIG. 11). Results indicate that the luciferase signal and secreted insulin were closely correlated, therefore demonstrating that the reporter construct can be used as a marker for beta cell maturation.

One of ordinary skill in the art can use this example as guidance to screen factors that differentiate iPS or ES cells into a differentiated or mature cell.

SEQUENCE LISTING

The patent contains a lengthy "Sequence Listing" section. A copy of the "Sequence Listing" is available in electronic form from the USPTO web site (http://seqdata.uspto.gov/?pageRequest=docDetail&DocID=US10370697B2). An electronic copy of the "Sequence Listing" will also be available from the USPTO upon request and payment of the fee set forth in 37 CFR 1.19(b)(3).

We claim:

1. A method for screening for compounds that modulate peptide secretion or localization at the surface of a cell having a cell surface and a secretory pathway comprising:
   a) contacting a cell culture with a test compound, wherein the cell culture comprises a cell comprising a nucleic acid construct encoding a fusion protein comprising a propeptide linked to a bioluminescent protein, wherein the bioluminescent protein is flanked by two cleavage sites, the first of which is positioned 0, 1, 2, 3 or 4 amino acids from the N-terminal end of the bioluminescent protein and the second of which is positioned 0, 1, 2, 3 or 4 amino acids from the C-terminal end of the bioluminescent protein, such that when the fusion protein is expressed by the cell, the fusion protein is transported through the secretory pathway and the bioluminescent protein is cleaved from the propeptide within a secretory vesicle and wherein the cleaved bioluminescent protein is secreted simultaneously with secretion or cell surface localization of the mature form of the propeptide and
   b) determining bioluminescence activity in the cell culture, wherein a difference in bioluminescence from the cell culture that has been contacted with the test compound compared to bioluminescence from a control cell culture indicates that the test compound modulates peptide secretion or localization at the cell surface.

2. The method of claim 1, wherein the propeptide is selected from the group consisting of a prohormone, a preprohormone, a cytokine precursor and a neuropeptide precursor.

3. The method of claim 2, wherein the preprohormone is preproinsulin and the bioluminescent protein is within the C-peptide component of preproinsulin.

4. The method of claim 2, wherein the preprohormone is preproamylin, wherein the preproamylin has a signal peptide and comprises a mature amylin hormone sequence within preproamylin, wherein the bioluminescent protein is inserted between regions encoding the signal peptide and the mature amylin hormone sequence or at the C-terminus of the mature amylin hormone sequence.

5. The method of claim 2, wherein the preprohormone is preproglucagon comprising a signal peptide, glicentin-related polypeptide (GRPP), glucagon, glucagon-like peptide 1 (GLP-1), and glucagon-like peptide 2 (GLP-2), wherein the bioluminescent protein is inserted between the regions encoding the GRPP and glucagon, glucagon and GLP-1, or GLP-1 and GLP-2.

6. The method of claim 1, wherein the bioluminescent protein comprises less than 200 amino acids.

7. The method of claim 1, wherein the nucleic acid construct comprises a nucleotide sequence selected from the group consisting of SEQ ID NOs: 5-100.

8. The method of claim 1, wherein the nucleic acid construct encoding the first or second cleavage site or the first and second cleavage sites has a sequence selected from the group consisting of SEQ ID NOs: 101-138.

9. The method of claim 1, wherein the nucleic acid construct further comprises a sequence encoding an additional cleavage site in the fusion protein at the N-terminal or C-terminal end of the bioluminescent protein, or at both the N-terminal and C-terminal ends of the bioluminescent protein.

10. The method of claim 1, wherein the nucleic acid construct further comprises at least 3 additional nucleotides flanking the nucleic acid sequence encoding at least one cleavage site.

11. The method of claim 1, wherein the nucleic acid construct further comprises a promoter.

12. The method of claim 1, wherein the bioluminescent protein is a luciferase, optionally a *Gaussia* luciferase, optionally wherein the *Gaussia* luciferase lacks a native signal sequence, optionally wherein the *Gaussia* luciferase comprises SEQ ID NO: 1.

13. The method of claim 12, wherein the luciferase is a *Cypridina* luciferase, optionally wherein the *Cypridina* luciferase lacks a native signal sequence, optionally wherein the *Cypridina* luciferase comprises SEQ ID NO: 3.

14. The method of claim 1, wherein the cell is selected from the group consisting of an endocrine cell, an immune cell, a neuron, a hepatocyte, a myocyte, a kidney cell, an adipocyte, and an osteocyte.

15. The method of claim 14, wherein the cell is an endocrine cell selected from the group consisting of a beta cell, an alpha cell, an L cell, a K cell, and another endocrine cell.

16. The method of claim 14, wherein the immune cell is selected from the group consisting of a B cell, a T cell, a monocyte, a macrophage, a dendritic cell, a mast cell, and a neutrophil.

17. The method of claim 1, wherein the cell comprises at least two nucleic acid constructs encoding a fusion protein comprising a propeptide linked to a bioluminescent protein, wherein the cell is capable of expressing the encoded fusion proteins and wherein the bioluminescent proteins of the at least two nucleic acid constructs are different.

18. The method of claim 17, wherein the cell comprises a first nucleic acid construct and a second nucleic acid construct, wherein the first nucleic acid construct comprises a *Gaussia* luciferase and wherein the second nucleic acid construct comprises a *Cypridina* luciferase.

19. The method of claim 1, wherein the cell further comprises a control nucleic acid construct encoding a control luciferase as an internal reference, wherein the cell is capable of expressing the control luciferase.

20. The method of claim 1, wherein the nucleic acid construct:
comprises any one of the nucleotide sequences of SEQ ID NO: 139-330, or
encodes any one of the propeptide-bioluminescent fusion protein sequences of SEQ ID NO: 331-395.

21. The method of claim 1, wherein the cell is of the same species as that of the propeptide sequence of the nucleic acid construct.

22. A method for screening for compounds that modulate peptide secretion or localization at the surface of a cell having a cell surface and a secretory pathway comprising:
a) contacting a population of cells in cell culture media with a test compound, wherein the population of cells comprises a cell comprising a nucleic acid construct encoding a fusion protein comprising a propeptide linked to a bioluminescent protein, wherein the bioluminescent protein is flanked by two cleavage sites, the first of which is positioned 0, 1, 2, 3 or 4 amino acids from the N-terminal end of the bioluminescent protein and the second of which is positioned 0, 1, 2, 3 or 4 amino acids from the C-terminal end of the bioluminescent protein, such that when the fusion protein is expressed by the cell, the fusion protein is transported through the secretory pathway and the bioluminescent protein is cleaved from the propeptide within a secretory vesicle and wherein the cleaved bioluminescent protein is secreted into the cell culture media simultaneously with secretion or cell surface localization of the mature form of the propeptide;
b) separating the population of cells into single cells; and
c) determining bioluminescence activity of cell culture media of a single cell of the population of cells, wherein a difference in bioluminescence between cell culture media of a single cell that has been contacted with the test compound and cell culture media of a control cell culture indicates that the test compound modulates peptide secretion or localization at the cell surface.

23. The method of claim 22, wherein the separating of the population of cells into single cells is performed by a microfluidic device.

24. The method of claim 22, wherein the test compound is a test nucleic acid and further comprising determining the identity of the test nucleic acid using single cell nucleic acid amplification methods.

25. A method for screening for compounds that differentiate embryonic stem cells or iPS cells into mature pancreatic beta cells comprising:
a) contacting a cell culture with a test compound, wherein the cell culture comprises a cell comprising a nucleic acid construct encoding a fusion protein comprising a propeptide linked to a bioluminescent protein, wherein the bioluminescent protein is flanked by two cleavage sites, the first of which is positioned 0, 1, 2, 3 or 4 amino acids from the N-terminal end of the bioluminescent protein and the second of which is positioned 0, 1, 2, 3 or 4 amino acids from the C-terminal end of the bioluminescent protein, such that when the fusion protein is expressed by the cell, the fusion protein is transported through the secretory pathway and the bioluminescent protein is cleaved from the propeptide within a secretory vesicle, and wherein the cleaved bioluminescent protein is secreted simultaneously with secretion or cell surface localization of the mature form of the propeptide and
b) determining bioluminescence in the cell culture, wherein an increase of bioluminescence from the cell culture that has been contacted with the test compound compared to bioluminescence from a control cell culture indicates that the test compound differentiates embryonic stem cells or iPS cells into mature pancreatic beta cells.

26. The method of claim 25, wherein the test compound is a nucleic acid or a small molecule.

27. The method of claim 26, wherein the nucleic acid is an RNAi molecule.

* * * * *